United States Patent
Vendeville et al.

(10) Patent No.: US 10,875,876 B2
(45) Date of Patent: Dec. 29, 2020

(54) CYCLIZED SULFAMOYLARYLAMIDE DERIVATIVES AND THE USE THEREOF AS MEDICAMENTS FOR THE TREATMENT OF HEPATITIS B

(71) Applicant: Janssen Sciences Ireland UC, Co Cork (IE)

(72) Inventors: Sandrine Marie Helene Vendeville, Woluwe-Saint-Pierre (BE); Stefaan Julien Last, Lint (BE); Samuël Dominique Demin, Antwerpen (BE); Sandrine Céline Grosse, Beerse (BE); Geerwin Yvonne Paul Haché, Kapellan (BE); Lili Hu, Mechelen (BE); Serge Maria Aloysius Pieters, Hulst (NL); Geert Rombouts, Barsbeek (BE); Koen Vandyck, Paal-Beringen (BE); Wim Gaston Verschueren, Berchem (BE); Pierre Jean-Marie Bernard Raboisson, Rosieres (BE)

(73) Assignee: JANSSEN SCIENCES IRELAND UC, County Cork (IE)

( * ) Notice: Subject to any disclaimer, the term of this patent is extended or adjusted under 35 U.S.C. 154(b) by 0 days.

(21) Appl. No.: 15/195,809

(22) Filed: Jun. 28, 2016

(65) Prior Publication Data
US 2017/0002025 A1  Jan. 5, 2017

(30) Foreign Application Priority Data

Jul. 2, 2015 (EP) .................................... 15175021
Oct. 15, 2015 (EP) .................................... 15189903
Dec. 18, 2015 (EP) .................................... 15201332
Feb. 26, 2016 (EP) .................................... 16157726

(51) Int. Cl.

| | | |
|---|---|---|
| C07D 267/02 | (2006.01) |
| C07D 267/22 | (2006.01) |
| C07D 513/00 | (2006.01) |
| A61K 31/553 | (2006.01) |
| C07D 513/04 | (2006.01) |
| C07D 513/20 | (2006.01) |
| C07D 515/04 | (2006.01) |
| C07D 515/20 | (2006.01) |
| C07D 291/08 | (2006.01) |
| A61P 31/20 | (2006.01) |
| A61K 31/407 | (2006.01) |
| A61K 31/542 | (2006.01) |
| A61K 31/554 | (2006.01) |
| A61K 45/06 | (2006.01) |
| C07D 515/10 | (2006.01) |

(52) U.S. Cl.
CPC .......... *C07D 513/04* (2013.01); *A61K 31/407* (2013.01); *A61K 31/542* (2013.01); *A61K 31/554* (2013.01); *A61K 45/06* (2013.01); *A61P 31/20* (2018.01); *C07D 291/08* (2013.01); *C07D 513/20* (2013.01); *C07D 515/04* (2013.01); *C07D 515/10* (2013.01); *C07D 515/20* (2013.01)

(58) Field of Classification Search
CPC ........................ C07D 513/04; A61K 31/554
USPC ...... 540/552, 546, 467; 544/48; 514/211.09, 514/211.1
See application file for complete search history.

(56) References Cited

U.S. PATENT DOCUMENTS

| | | |
|---|---|---|
| 3,843,662 A | 10/1974 | Holland |
| 4,569,940 A | 2/1986 | Watts |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson |

(Continued)

FOREIGN PATENT DOCUMENTS

| | | |
|---|---|---|
| CA | 2950807 A1 | 12/2013 |
| CN | 1390201 A | 1/2003 |

(Continued)

OTHER PUBLICATIONS

Hughes et al. "Hepatitis Delta Virus" Lancet 2011 vol. 378 pp. 73-85.

(Continued)

*Primary Examiner* — Shengjun Wang

(57) ABSTRACT

Inhibitors of HBV replication of Formula (I-A)

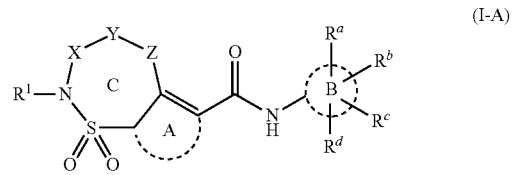

including stereochemically isomeric forms, and salts, hydrates, solvates thereof, wherein $R^a$ to $R^d$, and $R^1$ to $R^8$ have the meaning as defined herein.

The present invention also relates to processes for preparing said compounds, pharmaceutical compositions containing them and their use, alone or in combination with other HBV inhibitors, in HBV therapy.

18 Claims, No Drawings

(56) References Cited

U.S. PATENT DOCUMENTS

| | | |
|---|---|---|
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Duplantier et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien |
| 7,384,967 B2 | 6/2008 | Polisetti et al. |
| 7,541,373 B2 | 6/2009 | Polisetti et al. |
| 7,544,700 B2 | 6/2009 | Halazy et al. |
| 7,576,688 B2 | 8/2009 | Lehtinen |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev |
| 8,207,195 B2 | 6/2012 | Navratil et al. |
| 8,227,489 B2 | 7/2012 | Dubois et al. |
| 8,273,754 B2 | 9/2012 | Ali et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,141 B2 | 4/2013 | Murata et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,722,742 B2 | 5/2014 | Reyes |
| 8,808,702 B2 | 8/2014 | Reddy et al. |
| 8,889,716 B2 | 11/2014 | Prime et al. |
| 8,993,771 B2 | 3/2015 | Hartman |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 10,071,961 B2 | 9/2018 | Vandyck et al. |
| 2002/0049236 A1 | 4/2002 | Duplantier et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto et al. |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0113421 A1 | 5/2010 | Williams |
| 2010/0204210 A1 | 8/2010 | Sorensen |
| 2011/0009622 A1 | 1/2011 | Makoto et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1 | 10/2015 | Vandyck et al. |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | |
|---|---|---|
| CN | 101039919 A | 9/2007 |
| CN | 102093320 A | 6/2011 |
| CN | 102206172 A | 10/2011 |
| EP | 0232067 A2 | 8/1987 |
| EP | 0742200 A1 | 11/1996 |
| EP | 2280001 A4 | 1/2012 |
| JP | 62142164 | 6/1987 |

(56) References Cited

FOREIGN PATENT DOCUMENTS

| | | |
|---|---|---|
| JP | 2008179621 A | 7/2008 |
| JP | 2008525406 A | 7/2008 |
| JP | 2010535172 A | 11/2010 |
| WO | 198403281 A1 | 8/1984 |
| WO | 199207835 A1 | 5/1992 |
| WO | 1998023285 A1 | 6/1998 |
| WO | 199909022 A1 | 2/1999 |
| WO | 1999038845 A1 | 8/1999 |
| WO | 199948492 A1 | 9/1999 |
| WO | 199965906 A1 | 12/1999 |
| WO | 200105390 A2 | 1/2001 |
| WO | 200119788 A2 | 3/2001 |
| WO | 2001025200 A1 | 4/2001 |
| WO | 2001051487 A1 | 7/2001 |
| WO | 200155121 A1 | 8/2001 |
| WO | 200185694 A2 | 11/2001 |
| WO | 2002051410 | 7/2002 |
| WO | 2002064618 A2 | 8/2002 |
| WO | 2003002518 A1 | 1/2003 |
| WO | 2003007955 A2 | 1/2003 |
| WO | 2003044016 A1 | 5/2003 |
| WO | 2003101961 A1 | 12/2003 |
| WO | 2004010943 A2 | 2/2004 |
| WO | 2004011427 A2 | 2/2004 |
| WO | 2004022060 A2 | 3/2004 |
| WO | 2004058709 A2 | 7/2004 |
| WO | 2004086865 A1 | 10/2004 |
| WO | 2004099192 A2 | 11/2004 |
| WO | 2004100947 A2 | 11/2004 |
| WO | 2005016922 A1 | 2/2005 |
| WO | 2005000231 A3 | 5/2005 |
| WO | 2005044797 A1 | 5/2005 |
| WO | 2005087217 A1 | 9/2005 |
| WO | 2005105785 A2 | 11/2005 |
| WO | 2005115374 A1 | 12/2005 |
| WO | 2006002133 A1 | 1/2006 |
| WO | 2006012642 A2 | 2/2006 |
| WO | 2006024834 A1 | 3/2006 |
| WO | 2006053109 A1 | 5/2006 |
| WO | 2006067445 A2 | 6/2006 |
| WO | 2006067446 A1 | 6/2006 |
| WO | 2006123257 A2 | 11/2006 |
| WO | 2006128129 A2 | 11/2006 |
| WO | 2006128172 A2 | 11/2006 |
| WO | 2007031791 A1 | 3/2007 |
| WO | 2007070556 A2 | 6/2007 |
| WO | 2008011476 A2 | 1/2008 |
| WO | 2008022171 A1 | 2/2008 |
| WO | 2008054605 A2 | 7/2008 |
| WO | 2008093614 A1 | 8/2008 |
| WO | 2008137794 A1 | 11/2008 |
| WO | 2008154819 A1 | 12/2008 |
| WO | 2009016088 A1 | 2/2009 |
| WO | 2009018219 A2 | 2/2009 |
| WO | 2009062402 A1 | 5/2009 |
| WO | 2009086303 A2 | 7/2009 |
| WO | 2009131065 A1 | 10/2009 |
| WO | 2009146013 A1 | 12/2009 |
| WO | 2010018113 A2 | 2/2010 |
| WO | 2010043592 A1 | 4/2010 |
| WO | 2010059658 A1 | 5/2010 |
| WO | 2010088000 A2 | 8/2010 |
| WO | 2010123139 A1 | 10/2010 |
| WO | 2010138758 A1 | 12/2010 |
| WO | 2011002635 A1 | 1/2011 |
| WO | 2011035143 A2 | 3/2011 |
| WO | 2011088015 A1 | 7/2011 |
| WO | 2011088561 A1 | 7/2011 |
| WO | 2011109237 A1 | 9/2011 |
| WO | 2011112191 A1 | 9/2011 |
| WO | 2011123609 A1 | 10/2011 |
| WO | 2011140324 A1 | 11/2011 |
| WO | 2011155898 A1 | 12/2011 |
| WO | 2012016133 A2 | 2/2012 |
| WO | 2012018635 A2 | 2/2012 |
| WO | 2012033956 A1 | 3/2012 |
| WO | 2012049277 A1 | 4/2012 |
| WO | 2012075235 A1 | 6/2012 |
| WO | 2012080050 A1 | 6/2012 |
| WO | 2012117216 A1 | 9/2012 |
| WO | 2012136834 A1 | 10/2012 |
| WO | WO 2013/006394 A1 | 1/2013 |
| WO | WO 2013/096744 A1 | 6/2013 |
| WO | WO 2013/102655 A1 | 7/2013 |
| WO | 2013130703 A2 | 9/2013 |
| WO | WO 2013/144129 A1 | 10/2013 |
| WO | WO 2013/174962 A1 | 11/2013 |
| WO | 2013181584 A2 | 12/2013 |
| WO | 2013184757 A1 | 12/2013 |
| WO | WO 2014/033167 A1 | 3/2014 |
| WO | WO 2014/033170 A1 | 3/2014 |
| WO | WO 2014/033176 A1 | 3/2014 |
| WO | WO 2014/037480 A1 | 3/2014 |
| WO | 2014106019 A2 | 7/2014 |
| WO | 2014151958 A1 | 9/2014 |
| WO | WO 2014/131847 A1 | 9/2014 |
| WO | WO 2014/161888 A1 | 10/2014 |
| WO | WO 2014/165128 A1 | 10/2014 |
| WO | WO 2014/184328 A1 | 11/2014 |
| WO | WO 2014/184350 A1 | 11/2014 |
| WO | WO 2014/184365 A1 | 11/2014 |
| WO | 2014191301 A1 | 12/2014 |
| WO | 2014191726 A1 | 12/2014 |
| WO | 2014198880 A1 | 12/2014 |
| WO | WO 2015/011281 A1 | 1/2015 |
| WO | 2015055764 A1 | 4/2015 |
| WO | 2015057945 A1 | 4/2015 |
| WO | WO 2015/059212 A1 | 4/2015 |
| WO | WO 2015/073774 A1 | 5/2015 |
| WO | WO 2015/109130 A1 | 7/2015 |
| WO | 2015116923 A1 | 8/2015 |
| WO | WO 2015/118057 A1 | 8/2015 |
| WO | 2015138895 A1 | 9/2015 |
| WO | WO 2015/132276 A1 | 9/2015 |
| WO | WO 2015/144093 A1 | 10/2015 |
| WO | WO 2015/180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |
| WO | 2019011323 A1 | 1/2019 |

OTHER PUBLICATIONS

Weber et al. "Inhibition of Human Hepatitis B Virus (HBV) by a Novel Non-Nucleosidic Compound in a Transgenic Mouse Model" Antiviral Research 2002 vol. 43 pp. 69-78.
International Search Report and Written Opinion for International Application No. PCT/EP2016/065488 dated Aug. 10, 2016.
Extended European Search Report for EP Application No. 15175021.3 dated Sep. 9, 2015.
Online Registry Via STN Dec. 22, 2008, RN 1088200-12-7.
Online Registry Via STN, Mar. 2, 2007, RN 924514-21-6.
Online Registry Via STN, Sep. 2, 2003, RN 577752-12-6.
Bennes, et al., "Recognition-induced control and acceleration of a pyroole Diels-Alder reaction", Tetrahedron Letters, vol. 42 : pp. 2377-2380 (2001).
Berke, et al, "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-21 (Feb. 2016).
Brezillon, et al., "Antiviral Activity of Bay 41-4109 on Hepatitis B Virus in Humanized Alb-uPA/SCID Mice", PLos One, vol. 6 (12): pp. e25096 (1-6) (Dec. 2011).
Cai, et al, "Identification of disubstituted sulfonamide compounds as specific inhibitors of hepatitis B virus covalently dosed circular

(56) References Cited

OTHER PUBLICATIONS

DNA formuation, Antimicrobial agents and chemotherapy", pp. vol. 56(8): pp. 4277-4288 (May 29, 2012).
Campagna et al., "Sulfamoylbenzamide Derivatives Inhibit the Assembly of Hepatitis B Virus Nucleocapsids", Journal of Virology, ),vol. 87 (12): pp. 6931-6942 (Jun. 2013).
Campagna, "Sulfamoylbenzamide Derivatives are a Novel Class of Hepatities B Virus Inhibitors Targeting PGRNA Encapsidation", 2011 International Meeting on Molecular Biology of Hepatitis B Viruses, Poster Presentation, (Oct. 9-12, 2011).
Carver, et al, Polyfunctionalisation of Imidazole via Sequential Imidazolyl Anion Formation, Tetrahedron, 1997, pp. 14481-14496, vol. 53 Issue 42.
Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).
Cho, et al, "2-Amino-N-(2,6-dichloropyridin-3-yl)acetamide derivatives as a novel class of HBV capsid assembly inhibitor", Journal of Viral Hepatitis, vol. 21: pp. 843-852 (2014).
Cowie, et al., "Mortality due to viral hepatitis in the Global Burden of Disease Study 2010: new evidence of an urgent global public health priority demanding action", Antiviral Therapy,vol. 18: pp. 953-954 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Duan, et al., 2-Phenylquinazolin-4(3H)-one, a class of potent PDE5 Inhibitors with High Selectivity Versus PDE6, Bioorganic & Medicinal Chemistry Letter, vol. 19: pp. 2777-2779 (2009).
El-Sayed, et al, "A Comparative Study of the 1-9 Reactions of Thiophene-2-Carboxanilides and related Compounds", Chemistry of Heterocyclic Compounds, vol. 34 (7): pp. 796-801 (Jan. 1, 1998).(XP000881506).
El-Sharief, et al., "Synthesis of Different Types of Chlorinated Sulphonamides with Expected Insecticidal and Bactericidal Activities", Proceedings of the Indian National Science Academy, vol. 53(1): pp. 179-188 (1987).
Ermann, et al, "Arylsulfonamide CB2 Receptor Agonists: SAR and Optimization of CB2 Selectivity", Bioorganic & Medicinal Chemistry Letters, vol. 18: pp. 1725-1729 (2008).
Foley, "An Effecient Synthesis of 2-Chloro-3-carboethoxy or 2-Chloro-3-cyano-4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Geies, et al, Synthesis of some Thiazolo-[3,2-a]Pyrimidines, Phosphorus, Sulfur and Silicon, vol. 56: pp. 87-93 (1991).
Geng et al, "Small-Molecule Inhibitors for the Treatment of Hepatitis B Virus Documented in Patents", Mini-Reviews in Medicinal Chemistry, Apr. 1, 2013, pp. 749-776 (XP055105561-XP009176654), vol. 13.
Goodman, et al, "Discovery of potent, selective sulfonylfuran urea endothelial lipase inhibitors", Bioorganic & Medicinal Chemistry Letters, vol. 19:pp. 27-30 (2009).
Guo et al., "HBc binds to the CpG island of HBV cccDNA and promotes an epigenetic permissive state", Epigenetics, vol. 6 (6): pp. 720-26 (Jun. 2011).
Hogan, et al, "Aqueous Process Chemistry: The Preparation of Aryl Sulfonyl Chlorides", Organic Process Research & Development, vol. 13: pp. 875-879 (2009).
Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, (Oct. 2016).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al, "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Kim, et al, "Discovery of novel HCV polymerase inhibitors using pharmacophore-based virtual screening", Bioorganic & Medicinal Chemistry Letters, vol. 21 (11): pp. 3329-3334 (Apr. 4, 2011). (XP028211474).
Klumpp, et al., "High Antiviral Activity of the HBV Core Inhibitor NVR 3-778 in the Humanized UPA/SCID Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Lambeng, et al, "Arylsulfonamides as a new class of cannabinoid CB1 receptor ligands:identification of a lead and initial SAR studies", Bioorganic & Medicinal Chemistry Letters, vol. 17(1) pp. 272-277 (Dec. 22, 2006).
Lau, et al., "Peginterferon Alfa-2a, Lamivudine, and the Combination for HBeAg-Positive Chronic Hepatitis B", New England Journal of Medicine, vol. 352(26): pp. 2682-2695 (Jun. 30, 2005).
Li Bing, et al., Progress in anti Hepatitus B Virus non-nucleosidic drugs, J. Liaoning Medical University, vol. 30(1): pp. 88-91 (Dec. 31, 2009).
Liaw, et al., "Hepatitis B Virus Infection", Lancet, vol. 373: pp. 582-592 (Feb. 14, 2009).
Lucifora, et al., "Specific and Nonhepatotoxic Degradation of Nuclear Hepatitis B Virus cccDNA", Science, vol. 343: pp. 1221-1228 (Mar. 14, 2014).
Mabrouk, "Discovering best candidates for Hepatocellular Carcinoma (HCC) by in-silico techniques and tools", Int. J. Bioinformatics Research and Applications, vol. 8 (1/2): pp. 141-152 (Jan. 1, 2012).
Manzoor, et al., "Hepatitis B Virus Therapy: What's the future holding for us?", World Journal of Gastroenterology, vol. 21(44): pp. 12558-12575 (Nov. 28, 2015).
Marcellin, et al, "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Mohamed, et al, "Synthesis of Different Types of Chlorinated Sulphonamides with Expected Insecticidal and Antimicrobial Activities", Acta Pharmaceutica Jugoslavica, vol. 36 (3): pp. 301-310, (1986).
Online Registr Via STN, Dec. 28, 2008, RN 1090750-88-1.
Online Registry Via STN, Aug. 13, 2012, RN 1390589-54-4.
Online Registry Via STN Feb. 2, 2007, RN 919040-39-4.
Online Registry Via STN Feb. 2, 2007, RN 919040-53-2.
Online Registry Via STn Feb. 2, 2007, RN 919040-55-4.
Online Registry Via STN Aug. 6, 2012. RN 1386725-02-5.
Online Registry Via STN Jun. 7, 2012, RN 1375909-37-7.
Online Registry Via STN Dec. 8, 2012, RN 1389720-57-3.

(56) References Cited

OTHER PUBLICATIONS

Online Registry Via STN Oct. 10, 2001, RN 361373-90-2.
Online Registry Via STN Dec. 11, 2007, RN 957487-45-5.
Online Registry Via STN Dec. 11, 2007, RN 957487-49-9.
Online Registry Via STN Aug. 12, 2012, RN 1389686-79-6.
Online Registry Via STN Aug. 13, 2012, RN 1390500-09-0.
Online Registry Via STN Jan. 16, 2001, RN 314043-17-9.
Online Registry Via STN Mar. 17, 2013, RN 1424462-66-7.
Online Registry Via STN Sep. 18, 2012, RN 1394742-82-5.
Online Registry Via STN 2010, RN 1253220-91-5.
Online Registry Via STN Aug. 30, 2011, RN 1325664-90-1.
Online Registry Via STN, Jan. 24, 2008, RN 296790-26-6.
Online Registry Via STN, Feb. 2, 2007, RN 9019040-48-5.
Online Registry Via STN, Feb. 2, 2007, RN 919040-37-2.
Online Registry Via STN, May 6, 2011, RN 1291044-81-9.
Online Registry Via STN, Sep. 6, 2011, RN 1328738-57-3.
Online Registry Via STN, Oct. 7, 2008, RN 1057788-44-9.
Online Registry Via STN, Oct. 7, 2008, RN 1057871-39-2.
Online Registry Via STN, Jan. 9, 2001, RN 313253-89-3.
Online Registry Via STN, Mar. 10, 2010, RN 1208400-27-4.
Online Registry Via STN, Feb. 15, 2007, RN 921179-95-5.
Online Registry Via STN, Aug. 15, 2011, RN 1317923-24-2.
Online Registry Via STN, Aug. 15, 2011, RN 1318022-74-0.
Online Registry Via STN, Mar. 17, 2003, RN 499189-09-2.
Online Registry Via STN, May 18, 2011, RN 1296380-95-4.
Online Registry Via STN, Oct. 18, 2000, RN 296894-70-7.
Online Registry Via STN, Sep. 20, 2013, RN 1452780-00-5.
Online Registry Via STN, Apr. 24, 2002, RN 406926-60-1.
Online Registry Via STN, Apr. 28, 2011, RN 1286906-97-5.
Online Registry Via STN. Apr. 19, 2008, RN 930914-71-9.
Patani, et al., "Bioisoterism: A rational Approach in Drug Design", Chem. Rev., vol. 96: pp. 3147-3176 (1996).
Patel, et al., "Synthesis N-Ethylpiperazinyl Sulfonyl Group Incorporated Benzamides", Indian Journal of Heterocyclic Chemistry, vol. 15: pp. 201-202 (Oct.-Dec. 2005).
Qidong You et al, Pharmaceutical Chemistry, Chemical Industry Press, Jan. 31, 2014, pp. 32-33, /.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Schroder, et al., "Arzneimittelchemie Passage", Arzneimittelchemei Grundlagen Nerven Musklen und Gewebe, vol. XX (XX): pp. 30-33 (Jan. 1, 1976).
Shi, et al., "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (RO5212773)", Bioorganic & Medicinal Chemistry Letters, vol. 21: pp. 1227-1231 (Dec. 21, 2010).
Stray, et al., "A Heteroaryldihydropyrimidine Activates and Can Misdirect Hepatitis B Virus Capsid Assembly", PNAS, vol. 102(23): pp. 8138-8143 (Jun. 7, 2005).
Stray, et al., "Bay 41-4109 has multiple effects on Hepatitis B virus capsid assembly", Journal of Molecular Recognition,vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
Taylor, et al., "A Brain-Permeable Small Molecule Reduces Neuronal Cholesterol by Inhibiting Activity of Sirtuin 2 Deacetylase", ASC Chemical Biology, vol. 6: pp. 540-546 (2011).
The Merk Index "Infliximab", An Encyclopedia of Chemicals, Drugs and Biologicals, 14th Ed., p. 924 (2013).

The Merk Index, "Zidovudine", An Encyclopedia of Chemicals, Drugs and Biologicals, 14th Ed., p. 1885 (2013).
Thompson et al., "Toll-like receptors, RIG-I-like RNA Helicases and the Antiviral Innate Immune Response", Immunology and Cell Biology, vol. 85: pp. 435-445 (2007).
Wang, et al., "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al., "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber et al., "Inhibition of Human Hepatitis B Virus (HBV) by a Novel Non-Nucleosidic Compound in a Transgenic Mouse Model", Antiviral Research, vol. 54: pp. 69-78 (2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yarmolchuk et al., "Synthesis of beta-fluoro-beta-proline", Tetrahedron Letters, vol. 52: pp. 1300-1302, (2011).
Yogaratnam, et al., "Safety, Tolerability and Pharmacokentics of JNJ 56136379, a Novel HBV Capsid Assembly Modulator in Healthy Subjects", the Abstracts of the Liver Meeting 2016 (AASLD), Abstract 1881: pp. 930A-931A, Boston, MA (Oct. 2016).
Yuen, et al., "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al., "NVR 3-778, a first-in-class HBV core inhibitor, alone and in combination with PEG-Interferon (PEGIFN), in treatment-naive HBEAG-positive patients: early reductions in HBV DNA and HBEAG", The Abstracts of the International Liver Congress (EASL), Abstract LB-06: pp. S210-S211 (Oct. 2016).
Zhang, et al., "A Potent Small Molecule Inhibits Polyglutamine Aggregation in Huntington's Disease Neurons and Suppresses Neurodegeneration in Vivo", PNAS, vol. 102 (3): pp. 892-897 (2005).
Zlotnick, et al., "Core Protein: A pleiotropic Keystone in the HBV Lifecycle", Antiviral Research, vol. 121: pp. 32-93 (2015).
Zoulim, et al., "Current Treatments for Chronic Hepatitis B Virus Infections", Current Opinion in Virology, vol. 18: pp. 109-116 (2016).
Horig, et al., from bemnch to Clinic and back: Perspective on the 1st IQPC translational Research conference, Journal of translational medicine, Dec. 20, 2004, pp. 1-8, vol. 2 Issue 44.
Mohebbi, et al., An Overview of Hepatitis B Virus Surface Antigen Secreation Inhibitors, Frontier in Microbiology, Apr. 5, 2018, pp. 1-9, vol. 9.
Schafer, et al., Failure Is option: learning from unsuccessful proof-ofconcepts trails, Drug Discovery Today, 2008, pp. 913-916, vol. 13 Issue 21/22.
Online Registry Via STN Feb. 3, 2012, RN 1359583-56-4.
Online Registry Via STN Feb. 3, 2012, RN 1359596-55-6.
Nijampatnam et al., "Recent advances in the development of HBV capsid assembly modulators", Current Opinion in Chemical Biology, vol. 50; pp. 73-79 (2019).
Online Registry Via STN Aug. 24, 2019, RN 1275589-30-4.
Online Registry Via STN Aug. 24, 2019, RN 312756-74-4.

(56) References Cited

OTHER PUBLICATIONS

Online Registry Via STN Aug. 24, 2019, RN 312756-75-5.
Online Registry Via STN Aug. 24, 2019, RN 313225_30_8.
Online Registry Via STN Aug. 24, 2019, RN 313254-27-2.
Basarab et al., Design of Helicobacter pylon glutamate racemase inhibitors as selective antibacterial agents : a novel pro-drug approach to increase exposure, Bioorg. Med. Chem. Lett., vol. 18; pp. 4716-4722 (Aug. 15, 2008).
Moranta et al., "Synthesis and properties of 1-alkyl-2-methyl-3-sulfonylpyrroles and 1-alkyl-2-methyl-3-sulfonylpyrrole-5-carboxylic acid derivates", J. Chem. Soc. Perkin Trans., vol. 19: pp. 3285-3292 (1998).
Online Registry Via STN Aug. 24, 2019, RN 311800-19-8.
Online Registry via STN Mar. 18, 2010, RN 1211415-65-4.

CYCLIZED SULFAMOYLARYLAMIDE DERIVATIVES AND THE USE THEREOF AS MEDICAMENTS FOR THE TREATMENT OF HEPATITIS B

CROSS-REFERENCE TO RELATED APPLICATIONS

This application claims priority to European Patent Application No. 15175021.3 filed Jul. 2, 2015, European Patent Application No. 15189903.6 filed Oct. 15, 2015, European Patent Application No. 15201332.2 filed Dec. 18, 2015, and European Patent Application No. 16157726.7 filed Feb. 26, 2016, the contents of which are hereby incorporated herein by reference for all purposes.

FIELD OF THE INVENTION

The present invention relates to inhibitors of HBV replication. The invention also relates to processes for preparing said compounds, pharmaceutical compositions containing them and their use, alone or in combination with other HBV inhibitors, in HBV therapy.

BACKGROUND OF THE INVENTION

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma. Additionally, HBV acts as a helper virus to hepatitis delta virus (HDV), and it is estimated that more than 15 million people may be HBV/HDV co-infected worldwide, with an increased risk of rapid progression to cirrhosis and increased hepatic decompensation, than patients suffering from HBV alone (Hughes, S. A. et al. Lancet 2011, 378, 73-85).

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO2013/006394, published on Jan. 10, 2013, relates to a subclass of sulfamoyl-arylamides active against HBV.

WO2013/096744, published on Jun. 26, 2013 relates to compounds active against HBV.

Amongst the problems which HBV direct antivirals may encounter are toxicity, mutagenicity, lack of selectivity, poor efficacy, poor bioavailability, low solubility and difficulty of synthesis.

There is a need for additional HBV inhibitors that may overcome at least one of these disadvantages or that have additional advantages such as increased potency or an increased safety window.

SUMMARY OF THE INVENTION

The present invention relates to a compound of Formula (I-A)

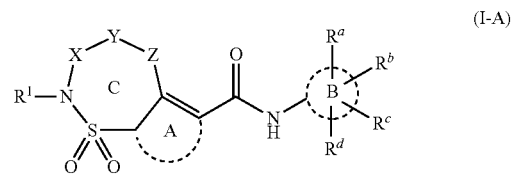

or a stereoisomer or tautomeric form thereof, wherein

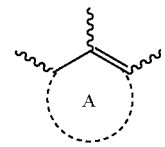

represents a monocyclic 5 or 6 membered aryl optionally containing one or two heteroatoms, such aryl optionally being substituted with one or more substituents each independently selected from the group consisting of $C_1$-$C_3$alkyl, in particular methyl, $C_3$-$C_4$cycloalkyl, —CN and halogen;

represents a 6 membered aryl optionally containing one nitrogen atom;

X represents —$CR^2R^3$—;

Y represents $C_1$-$C_7$alkanediyl or $C_2$-$C_7$alkenediyl, each optionally substituted with one or more substituents each independently selected from the group consisting of $C_1$-$C_4$alkyl, fluoro, and —OH;

Z represents a heteroatom, preferably NH or oxygen and more preferably oxygen, or a single bond;

$R^a$, $R^b$, $R^c$ and $R^d$ are each independently selected from the group consisting of hydrogen, halogen, —$CHF_2$, —$CF_2$-methyl, —$CH_2F$, —$CF_3$, —$OCF_3$, —CN, $C_3$-$C_4$cycloalkyl and —$C_1$-$C_4$alkyl;

$R^1$ is hydrogen or $C_1$-$C_{10}$alkyl optionally substituted with one or more substituents each independently selected from the group consisting of —OH, fluoro, and oxo;

$R^2$ is selected from the group consisting of hydrogen; $C_1$-$C_{10}$alkyl optionally substituted with one or more substituents each independently selected from the group consisting of —OH, fluoro, methoxy, oxo, and —C(=O)O$C_1$-$C_4$alkyl; $C_1$-$C_3$alkyl-$R^7$; $C_2$-$C_4$alkynyl;

a 3-7 membered saturated ring optionally containing one or more heteroatoms each independently selected from the group consisting of O, S and N; and monocyclic aryl optionally containing one or two heteroatoms; wherein the $C_1$-$C_3$alkyl-$R^7$, 3-7 membered saturated ring or the monocyclic aryl are each optionally substituted with one or more $R^8$ substituents;

$R^3$ is hydrogen or $C_{1-6}$alkyl optionally substituted with —OH; in particular, hydrogen or methyl;

or $R^2$ and $R^3$ taken together with the carbon atom to which they are attached form a 3-7 membered saturated ring optionally containing one or more heteroatoms each independently selected from the group consisting of O, S and N, and optionally being substituted with one or more substituents each independently selected from the group consisting of —OH, fluoro, methoxy, oxo, —C(=O)O$C_1$-$C_4$alkyl, benzyl, and $C_1$-$C_4$alkyl optionally substituted with one or more substituents each independently selected from fluoro and/or —OH;

$R^7$ represents a monocyclic aryl optionally containing one or two heteroatoms, and optionally being substituted with one or two substituents each independently selected from the group consisting of halo and $C_{1-3}$alkyl; a 3-7 membered saturated ring optionally containing one or more heteroatoms each independently selected from the group consisting of O, S and N; or —$NR^9R^{10}$;

wherein $R^9$ and $R^{10}$ are each independently selected from hydrogen and $C_1$-$C_3$alkyl optionally substituted with one or more fluoro substituents;

each $R^8$ is independently selected from the group consisting of —OH, fluoro, methoxy, oxo, —C(=O)O$C_1$-$C_4$alkyl, $C_1$-$C_4$alkyloxy$C_1$-$C_4$alkyloxy, and $C_1$-$C_4$alkyl optionally substituted with one or more substituents each independently selected from fluoro and/or —OH;

or a pharmaceutically acceptable salt or a solvate thereof.

The invention further relates to a pharmaceutical composition comprising a compound of Formula (I-A), and a pharmaceutically acceptable carrier.

The invention also relates to the compounds of Formula (I-A) for use as a medicament, preferably for use in the prevention or treatment of an HBV infection in a mammal.

In a further aspect, the invention relates to a combination of a compound of Formula (I-A), and another HBV inhibitor.

DETAILED DESCRIPTION OF THE INVENTION

The present invention relates to a compound of Formula (I-A) as defined hereinbefore.

More in particular, the present invention relates to a compound of Formula (I-A)

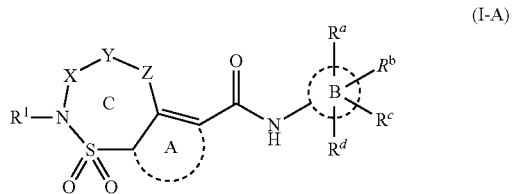

(I-A)

or a stereoisomer or tautomeric form thereof, wherein

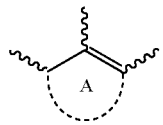

represents a monocyclic 5 or 6 membered aryl optionally containing one or two heteroatoms, such aryl optionally being substituted with one or more substituents each independently selected from the group consisting of $C_1$-$C_3$alkyl, in particular methyl, $C_3$-$C_4$cycloalkyl, —CN and halogen;

represents a 6 membered aryl optionally containing one nitrogen atom;

X represents —$CR^2R^3$—;

Y represents $C_1$-$C_7$alkanediyl or $C_2$-$C_7$alkenediyl each optionally being substituted with one or more substituents each independently selected from $C_1$-$C_4$alkyl and —OH;

Z represents a heteroatom, preferably oxygen, or a single bond;

$R^a$, $R^b$, $R^c$ and $R^d$ are each independently selected from the group consisting of Hydrogen, halogen, —$CHF_2$, —$CF_2$-methyl, —$CH_2F$, —$CF_3$, —$OCF_3$, —CN, $C_3$-$C_4$cycloalkyl and —$C_1$-$C_4$alkyl;

$R^1$ is Hydrogen or $C_1$-$C_6$alkyl, such $C_1$-$C_6$alkyl optionally being substituted with one or more substituents each independently selected from the group consisting of —OH, Fluoro, oxo, and $C_1$-$C_4$alkyl optionally substituted with one or more Fluoro and/or —OH;

$R^2$ is selected from the group consisting of hydrogen, $C_1$-$C_6$alkyl, $C_1$-$C_3$alkyl-$R^7$, a 3-7 membered saturated ring optionally containing one or more heteroatoms each independently selected from the group consisting of O, S and N, and monocyclic aryl optionally containing one or two heteroatoms, such $C_1$-$C_6$alkyl, $C_1$-$C_3$alkyl-$R^7$, 3-7 membered saturated ring or monocyclic aryl optionally being substituted with one or more $R^8$;

$R^3$ is hydrogen or $C_{1-6}$alkyl; in particular, hydrogen or methyl;

or $R^2$ and $R^3$ taken together form together with the carbon atom to which they are attached a 3-7 membered saturated ring optionally containing one or more heteroatoms each independently selected from the group consisting of O, S and N, such 3-7 membered saturated ring optionally being substituted with one or more $R^8$;

$R^7$ represents a monocyclic aryl optionally containing one or two heteroatoms; a 3-7 membered saturated ring optionally containing one or more heteroatoms each independently selected from the group consisting of O, S and N; or —$NR^9R^{10}$;

wherein $R^9$ and $R^{10}$ are each independently selected from Hydrogen and $C_1$-$C_3$alkyl;

each $R^8$ independently is selected from the group consisting of —OH, Fluoro, methoxy, oxo, —C(=O)O$C_1$-$C_4$alkyl and $C_1$-$C_4$alkyl optionally substituted with one or more substituents each independently selected from Fluoro and/or —OH;

or a pharmaceutically acceptable salt or a solvate thereof.

In a particular embodiment, the invention relates to a compound of Formula (I-A)

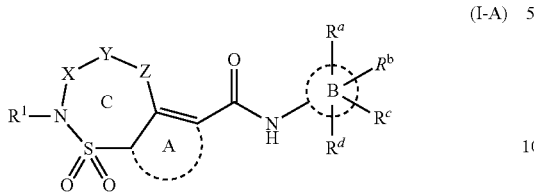

(I-A)

or a stereoisomer or tautomeric form thereof, wherein:

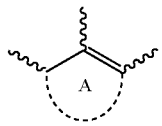

represents a monocyclic 5 or 6 membered aryl optionally containing one or two heteroatoms, such aryl optionally being substituted with one or more substituents each independently selected from the group consisting of $C_1$-$C_3$alkyl, in particular methyl, $C_3$-$C_4$cycloalkyl, —CN and halogen;

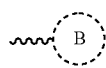

represents a 6 membered aryl optionally containing one nitrogen atom;

X represents —$CR^2R^3$—;
Y represents $C_1$-$C_7$alkanediyl or $C_2$-$C_7$alkenediyl each optionally being substituted with one or more substituents each independently selected from $C_1$-$C_4$alkyl and —OH;
Z represents a heteroatom, preferably oxygen, or a single bond;
$R^a$, $R^b$, $R^c$ and $R^d$ are each independently selected from the group consisting of hydrogen, halogen, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^1$ is hydrogen or $C_1$-$C_6$alkyl, such $C_1$-$C_6$alkyl optionally being substituted with one or more substituents each independently selected from the group consisting of —OH, Fluoro, oxo, and $C_1$-$C_4$alkyl optionally substituted with one or more Fluoro and/or —OH;
$R^2$ is selected from the group consisting of hydrogen, $C_1$-$C_6$alkyl, $C_1$-$C_3$alkyl-$R^7$, a 3-7 membered saturated ring optionally containing one or more heteroatoms each independently selected from the group consisting of O, S and N, and monocyclic aryl optionally containing one or two heteroatoms, such $C_1$-$C_6$alkyl, $C_1$-$C_3$alkyl-$R^7$, 3-7 membered saturated ring or monocyclic aryl optionally being substituted with one or more $R^8$;
$R^3$ is hydrogen;
or $R^2$ and $R^3$ taken together form together with the carbon atom to which they are attached a 3-7 membered saturated ring optionally containing one or more heteroatoms each independently selected from the group consisting of O, S and N, such 3-7 membered saturated ring optionally being substituted with one or more $R^8$;

$R^7$ represents a monocyclic aryl optionally containing one or two heteroatoms; a 3-7 membered saturated ring optionally containing one or more heteroatoms each independently selected from the group consisting of O, S and N; or —$NR^9R^{10}$;
wherein $R^9$ and $R^{10}$ are each independently selected from hydrogen and $C_1$-$C_3$alkyl;
each $R^8$ independently is selected from the group consisting of —OH, Fluoro, methoxy, oxo, —C(=O)O$C_1$-$C_4$alkyl and $C_1$-$C_4$alkyl optionally substituted with one or more substituents each independently selected from Fluoro and/or —OH;
or a pharmaceutically acceptable salt or a solvate thereof.

In a further particular embodiment, the invention relates to a compound of Formula (I-A) as defined herein, or a stereoisomer or tautomeric form thereof, wherein:

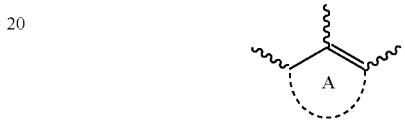

represents a monocyclic 5 or 6 membered aryl optionally containing one or two heteroatoms, such aryl optionally being substituted with one or more substituents each independently selected from the group consisting of $C_1$-$C_3$alkyl, in particular methyl, $C_3$-$C_4$cycloalkyl, —CN and halogen;

represents a 6 membered aryl optionally containing one nitrogen atom;

X represents —$CR^2R^3$—;
Y represents a $C_1$-$C_7$alkanediyl or $C_2$-$C_7$alkenediyl each optionally substituted with one or more $C_1$-$C_4$alkyl or —OH;
Z represents a heteroatom, preferably oxygen, or a single bond;
$R^a$, $R^b$, $R^c$ and $R^d$ are independently selected from the group consisting of Hydrogen, halogen, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^1$ is Hydrogen or $C_1$-$C_6$alkyl, such $C_1$-$C_6$alkyl optionally being substituted with one or more substituents each independently selected from the group consisting of —OH, Fluoro, oxo, and $C_1$-$C_4$alkyl optionally substituted with one or more Fluoro and/or —OH;
$R^2$ is selected from the group consisting of hydrogen, $C_1$-$C_6$alkyl, $C_1$-$C_3$alkyl-$R^7$, a 3-7 membered saturated ring optionally containing one or more heteroatoms each independently selected from the group consisting of O, S and N, and monocyclic aryl optionally containing one or two heteroatoms, such $C_1$-$C_6$alkyl, $C_1$-$C_3$alkyl-$R^7$, 3-7 membered saturated ring or monocyclic aryl optionally being substituted with one or more $R^8$;
$R^3$ is hydrogen;
or $R^2$ and $R^3$ taken together form together with the carbon atom to which they are attached a 3-7 membered saturated ring optionally containing one or more heteroatoms each independently selected from the group consisting of O, S and N, such 3-7 membered saturated ring optionally substituted with one or more $R^8$;

$R^7$ represents a monocyclic aryl optionally containing one or two heteroatoms;

each $R^8$ independently is selected from the group consisting of —OH, Fluoro, methoxy, oxo, —C(=O)OC$_1$-C$_4$alkyl and C$_1$-C$_4$alkyl optionally substituted with one or more Fluoro and/or —OH;

or a pharmaceutically acceptable salt or a solvate thereof.

In a further embodiment, the invention relates to a compound of Formula (I-A) as defined herein, or a stereoisomer or tautomeric form thereof, wherein:

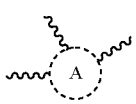

represents

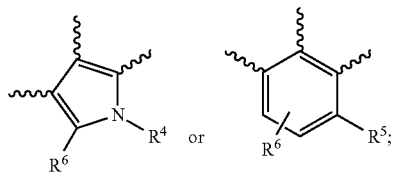

wherein $R^4$ is hydrogen, —C$_1$-C$_3$alkyl or C$_3$-C$_4$cycloalkyl; in particular methyl;

$R^5$ is hydrogen or halogen; in particular fluoro;

and wherein $R^6$ is selected from hydrogen, methyl, —CN and halogen; in particular, hydrogen or methyl; in particular, hydrogen or fluoro, in particular hydrogen;

and all other variables are as defined in Formula (I-A);

or a pharmaceutically acceptable salt or a solvate thereof.

The present invention further relates in particular to a compound of Formula (A)

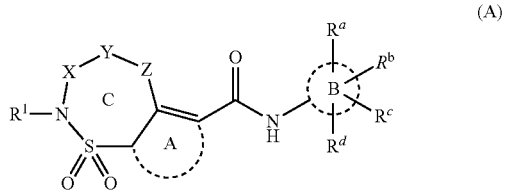

or a stereoisomer or tautomeric form thereof, wherein:

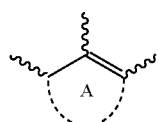

represents a monocyclic 5 or 6 membered aryl optionally containing one or two heteroatoms, such aryl optionally substituted with one or more methyl, —CN or halogen;

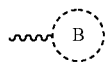

represents a 6 membered aryl optionally containing one nitrogen atom;

X represents —CR$^2$R$^3$—;

Y represents a C$_1$-C$_7$alkanediyl or C$_2$-C$_7$alkenediyl each optionally substituted with one or more C$_1$-C$_4$alkyl or —OH;

Z represents a heteroatom, preferably oxygen, or a single bond;

$R^a$, $R^b$, $R^c$ and $R^d$ are independently selected from the group consisting of Hydrogen, halogen, —CHF$_2$, —CF$_2$-methyl, —CH$_2$F, —CF$_3$, —OCF$_3$, —CN, C$_3$-C$_4$cycloalkyl and —C$_1$-C$_4$alkyl;

$R^1$ is Hydrogen or C$_1$-C$_6$alkyl, such C$_1$-C$_6$alkyl optionally being substituted with one or more substituents each independently selected from the group consisting of —OH, Fluoro, oxo, and C$_1$-C$_4$alkyl optionally substituted with one or more Fluoro and/or —OH;

$R^2$ is selected from the group consisting of hydrogen, C$_1$-C$_6$alkyl, C$_1$-C$_3$alkyl-$R^7$, a 3-7 membered saturated ring optionally containing one or more heteroatoms each independently selected from the group consisting of O, S and N, and monocyclic aryl optionally containing one or two heteroatoms, such C$_1$-C$_6$alkyl, C$_1$-C$_3$alkyl-$R^7$, 3-7 membered saturated ring or monocyclic aryl optionally being substituted with one or more $R^8$;

$R^3$ is hydrogen;

or $R^2$ and $R^3$ taken together form together with the carbon atom to which they are attached a 3-7 membered saturated ring optionally containing one or more heteroatoms each independently selected from the group consisting of O, S and N, such 3-7 membered saturated ring optionally substituted with one or more $R^8$;

$R^7$ represents a monocyclic aryl optionally containing one or two heteroatoms;

Each $R^8$ independently is selected from the group consisting of —OH, Fluoro, methoxy, oxo, —C(=O)OC$_1$-C$_4$alkyl and C$_1$-C$_4$alkyl optionally substituted with one or more Fluoro and/or —OH;

or a pharmaceutically acceptable salt or a solvate thereof.

The invention further relates to a pharmaceutical composition comprising a compound of Formula (A), and a pharmaceutically acceptable carrier.

The invention also relates to the compounds of Formula (A) for use as a medicament, preferably for use in the prevention or treatment of an HBV infection in a mammal.

In a further aspect, the invention relates to a combination of a compound of Formula (A), and another HBV inhibitor.

Whenever used hereinafter, the term "compounds of Formula (I-A)" or "compounds of Formula (A)",

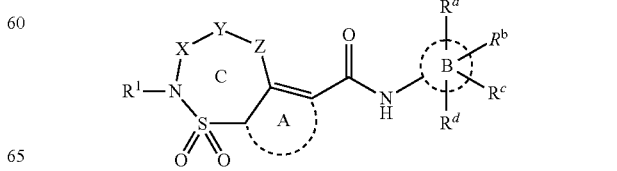

or "the present compounds" or similar term is meant to include all compounds of general Formula (I-A), (A), (A*), (B), or (C), salts, stereoisomeric forms and racemic mixtures or any subgroups thereof.

The present invention relates in particular to compounds of Formula (A)

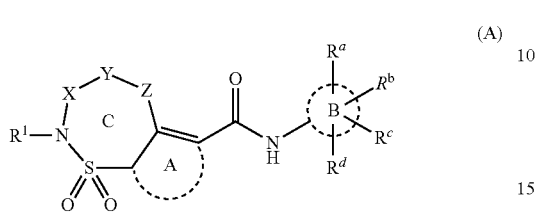

or a stereoisomer or tautomeric form thereof, wherein:

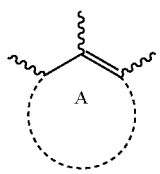

represents a monocyclic 5 or 6 membered aryl optionally containing one or two heteroatoms, such aryl optionally substituted with one or more methyl, —CN or halogen;

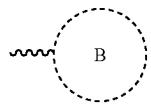

represents a 6 membered aryl optionally containing one nitrogen atom;

X represents —CR$^2$R$^3$—;

Y represents a C$_1$-C$_7$alkanediyl or C$_2$-C$_7$alkenediyl each optionally substituted with one or more C$_1$-C$_4$alkyl or —OH;

Z represents a heteroatom, preferably oxygen, or a single bond;

R$^a$, R$^b$, R$^c$ and R$^d$ are independently selected from the group consisting of Hydrogen, halogen, —CHF$_2$, —CF$_2$-methyl, —CH$_2$F, —CF$_3$, —OCF$_3$, —CN, C$_3$-C$_4$cycloalkyl and —C$_1$-C$_4$alkyl;

R$^1$ is Hydrogen or C$_1$-C$_6$alkyl, such C$_1$-C$_6$alkyl optionally being substituted with one or more substituents each independently selected from the group consisting of —OH, Fluoro, oxo, and C$_1$-C$_4$alkyl optionally substituted with one or more Fluoro and/or —OH;

R$^2$ is selected from the group consisting of hydrogen, C$_1$-C$_6$alkyl, C$_1$-C$_3$alkyl-R$^7$, a 3-7 membered saturated ring optionally containing one or more heteroatoms each independently selected from the group consisting of O, S and N, and monocyclic aryl optionally containing one or two heteroatoms, such C$_1$-C$_6$alkyl, C$_1$-C$_3$alkyl-R$^7$, 3-7 membered saturated ring or monocyclic aryl optionally being substituted with one or more R$^8$;

R$^3$ is hydrogen;

or R$^2$ and R$^3$ taken together form together with the carbon atom to which they are attached a 3-7 membered saturated ring optionally containing one or more heteroatoms each independently selected from the group consisting of O, S and N, such 3-7 membered saturated ring optionally substituted with one or more R$^8$;

R$^7$ represents a monocyclic aryl optionally containing one or two heteroatoms;

Each R$^8$ independently is selected from the group consisting of —OH, Fluoro, methoxy, oxo, —C(=O)OC$_1$-C$_4$alkyl and C$_1$-C$_4$alkyl optionally substituted with one or more Fluoro and/or —OH;

or a pharmaceutically acceptable salt or a solvate thereof.

In one embodiment, the present invention relates to compounds of Formula (A)

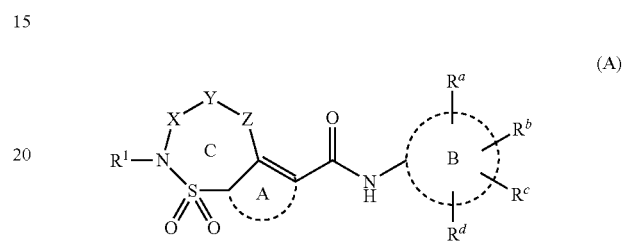

or a stereoisomer or tautomeric form thereof, wherein:

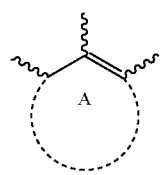

represents a monocyclic 5 or 6 membered aryl optionally containing one or two heteroatoms, such aryl optionally substituted with one or more methyl, —CN or halogen;

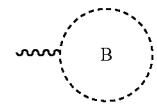

represents a 6 membered aryl optionally containing one nitrogen atom;

X represents —CR$^2$R$^3$—;

Y represents a C$_1$-C$_7$alkanediyl or C$_2$-C$_7$alkenediyl each optionally substituted with one or more C$_1$-C$_4$alkyl;

Z represents a heteroatom, preferably oxygen, or a single bond;

R$^a$, R$^b$, R$^c$ and R$^d$ are independently selected from the group consisting of Hydrogen, halogen, —CHF$_2$, —CF$_2$-methyl, —CH$_2$F, —CF$_3$, —OCF$_3$, —CN, C$_3$-C$_4$cycloalkyl and —C$_1$-C$_4$alkyl;

R$^1$ is Hydrogen or C$_1$-C$_6$alkyl, such C$_1$-C$_6$alkyl optionally being substituted with one or more substituents each independently selected from the group consisting of —OH, Fluoro, oxo, and C$_1$-C$_4$alkyl optionally substituted with one or more Fluoro and/or —OH;

R$^2$ is selected from the group consisting of hydrogen, C$_1$-C$_6$alkyl, C$_1$-C$_3$alkyl-R$^7$ and monocyclic aryl optionally containing one or two heteroatoms, such C$_1$-C$_6$alkyl, C$_1$-C$_3$alkyl-R$^7$ or monocyclic aryl optionally being substituted with one or more R$^8$;

$R^3$ is hydrogen;

or $R^2$ and $R^3$ taken together form together with the carbon atom to which they are attached a 3-7 membered saturated ring optionally containing one or more heteroatoms each independently selected from the group consisting of O, S and N, such 3-7 membered saturated ring optionally substituted with one or more Fluoro and/or —OH, or $C_1$-$C_4$alkyl optionally substituted with one or more Fluoro and/or —OH;

$R^7$ represents a monocyclic aryl optionally containing one or two heteroatoms;

Each $R^8$ independently is selected from the group consisting of —OH, Fluoro, methoxy, oxo, and $C_1$-$C_4$alkyl optionally substituted with one or more Fluoro and/or —OH;

or a pharmaceutically acceptable salt or a solvate thereof.

In one embodiment, the invention relates to compounds of Formula (B)

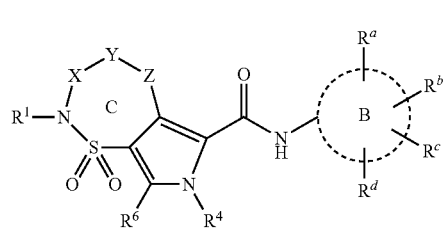

(B)

or Formula (C)

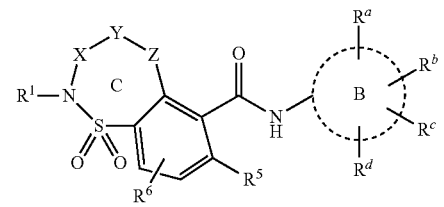

(C)

wherein $R^a$, $R^b$, $R^c$ and $R^d$ are independently selected from the group consisting of Hydrogen, halogen, —CHF$_2$, —CF$_2$-methyl, —CH$_2$F, —CF$_3$, —OCF$_3$, —CN, $C_3$-$C_4$cycloalkyl and —$C_1$-$C_4$alkyl;

$R^1$ is Hydrogen or $C_1$-$C_6$alkyl, such $C_1$-$C_6$alkyl optionally being substituted with one or more substituents each independently selected from the group consisting of —OH, Fluoro, oxo, and $C_1$-$C_4$alkyl optionally substituted with one or more Fluoro and/or —OH;

$R^2$ is selected from the group consisting of hydrogen, $C_1$-$C_6$alkyl, $C_1$-$C_3$alkyl-$R^7$ and monocyclic aryl optionally containing one or two heteroatoms, such $C_1$-$C_6$alkyl, $C_1$-$C_3$alkyl-$R^7$ or monocyclic aryl optionally being substituted with one or more $R^8$;

$R^3$ is hydrogen;

or $R^2$ and $R^3$ taken together form together with the carbon atom to which they are attached a 3-7 membered saturated ring optionally containing one or more heteroatoms each independently selected from the group consisting of O, S and N, such 3-7 membered saturated ring optionally substituted with one or more Fluoro and/or —OH, or $C_1$-$C_4$alkyl optionally substituted with one or more Fluoro and/or —OH;

$R^4$ is Hydrogen, —$C_1$-$C_3$alkyl or $C_3$-$C_4$cycloalkyl, preferably methyl;

$R^5$ is Hydrogen or Halogen, preferably Fluoro;

$R^6$ is selected from hydrogen, methyl, —CN and halogen;

$R^7$ represents a monocyclic aryl optionally containing one or two heteroatoms;

And each $R^8$ independently is selected from the group consisting of —OH, Fluoro, methoxy, oxo, and $C_1$-$C_4$alkyl optionally substituted with one or more Fluoro and/or —OH;

or a pharmaceutically acceptable salt or a solvate thereof.

In an additional embodiment, the invention relates to compounds of Formula (I-A), (A), (A*), (B) or (C) as described herein, wherein $R^1$ is Hydrogen or $C_1$-$C_6$alkyl optionally substituted with one or more substituents, in particular 1-3 substituents, each independently selected from the group consisting of —OH, and Fluoro.

An additional embodiment of the present invention relates to compounds of Formula (I-A) having, in particular, Formula (I-AA1) or Formula (I-AA2)

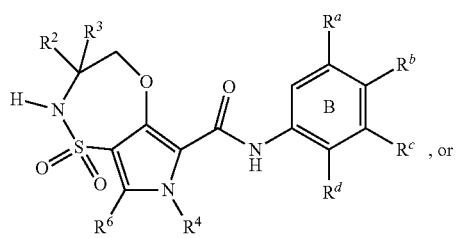

(I-AA1)

, or

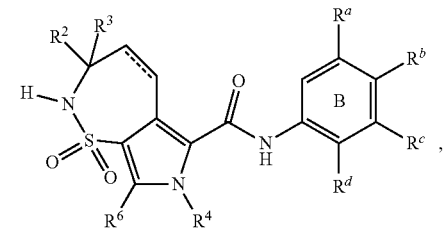

(I-AA2)

wherein

Ring B represents phenyl or 4-pyridyl;

wherein in Formula (I-AA2) represents a single or a double bond;

$R^2$ is selected from the group consisting of hydrogen, $C_1$-$C_6$alkyl, $C_1$-$C_3$alkyl-$R^7$, a 3-7 membered saturated ring optionally containing one or more heteroatoms each independently selected from the group consisting of O, S and N, and monocyclic aryl optionally containing one or two heteroatoms, such $C_1$-$C_6$alkyl, $C_1$-$C_3$alkyl-$R^7$, 3-7 membered saturated ring or monocyclic aryl optionally being substituted with one or more $R^8$;

$R_3$ is hydrogen or $C_1$-$C_6$alkyl, in particular hydrogen or methyl;

$R^4$ is $C_1$-$C_3$alkyl, in particular methyl;

$R^6$ is hydrogen or methyl;

$R^7$ is selected from the group consisting of a monocyclic aryl optionally containing one or two heteroatoms; a 3-7 membered saturated ring optionally containing one or more heteroatoms each independently selected from the group consisting of O, S and N; or —NR$^9$R$^{10}$;

wherein $R^9$ and $R^{10}$ are each independently selected from hydrogen and $C_1$-$C_3$alkyl; each $R^8$ independently is selected from the group consisting of —OH, fluoro, methoxy, oxo, —C(=O)OC$_1$-$C_4$alkyl and $C_1$-$C_4$alkyl optionally substituted with one or more substituents each independently selected from fluoro and/or —OH;
$R^a$ is selected from hydrogen and halogen, in particular hydrogen;
$R^b$ is absent when ring B is pyridyl or is hydrogen or a halogen, in particular a halogen, when ring B is phenyl;
$R^c$ is selected from halogen, $CH_3$, $CHF_2$, $CF_3$, and —CN;
$R^d$ is selected from hydrogen and halogen, in particular hydrogen;
or a pharmaceutically acceptable salt or a solvate thereof.

A further embodiment the present invention relates to compounds of Formula (I-A) having, in particular, Formula (I-A1) or Formula (I-A2)

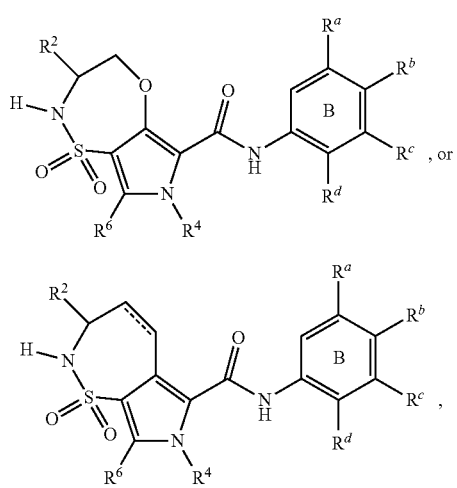

(I-A1)

(I-A2)

wherein
Ring B represents phenyl or 4-pyridyl;
wherein in Formula (I-A2) represents a single or a double bond;
$R^2$ is selected from the group consisting of hydrogen, $C_1$-$C_6$alkyl, $C_1$-$C_3$alkyl-$R^7$, a 3-7 membered saturated ring optionally containing one or more heteroatoms each independently selected from the group consisting of O, S and N, and monocyclic aryl optionally containing one or two heteroatoms, such $C_1$-$C_6$alkyl, $C_1$-$C_3$alkyl-$R^7$, 3-7 membered saturated ring or monocyclic aryl optionally being substituted with one or more $R^8$;
$R^4$ is $C_1$-$C_3$alkyl, in particular methyl;
$R^6$ is hydrogen or methyl;
$R^7$ is selected from the group consisting of a monocyclic aryl optionally containing one or two heteroatoms; a 3-7 membered saturated ring optionally containing one or more heteroatoms each independently selected from the group consisting of O, S and N; or —$NR^9R^{10}$;
wherein $R^9$ and $R^{10}$ are each independently selected from hydrogen and $C_1$-$C_3$alkyl;
each $R^8$ independently is selected from the group consisting of —OH, fluoro, methoxy, oxo, —C(=O)O$C_1$-$C_4$alkyl and $C_1$-$C_4$alkyl optionally substituted with one or more substituents each independently selected from fluoro and/or —OH;
$R^a$ is selected from hydrogen and halogen, in particular hydrogen;
$R^b$ is absent when ring B is pyridyl or is hydrogen or a halogen, in particular a halogen, when ring B is phenyl;
$R^c$ is selected from halogen, $CH_3$, $CHF_2$, $CF_3$, and —CN;
$R^d$ is selected from hydrogen and halogen, in particular hydrogen;
or a pharmaceutically acceptable salt or a solvate thereof.

In a further embodiment the present invention relates to compounds of Formula (I-A) having, in particular, Formula (I-A1') or Formula (I-A2')

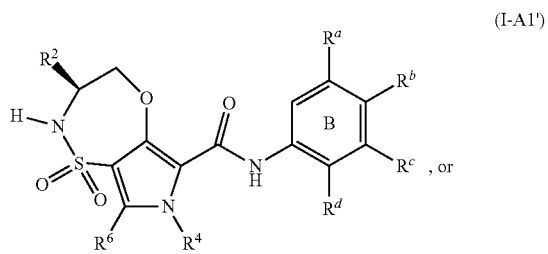

(I-A1')

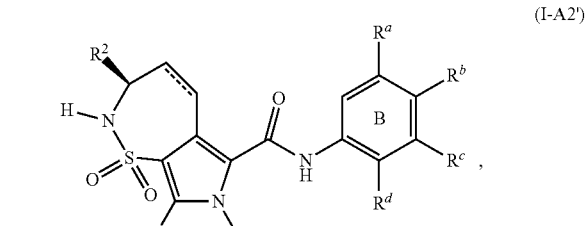

(I-A2')

wherein
Ring B represents phenyl or 4-pyridyl;
wherein in Formula (I-A2) represents a single or a double bond;
$R^2$ is selected from the group consisting of $C_1$-$C_6$alkyl, $C_1$-$C_3$alkyl-$R^7$, a 3-7 membered saturated ring optionally containing one or more heteroatoms each independently selected from the group consisting of O, S and N, and monocyclic aryl optionally containing one or two heteroatoms, such $C_1$-$C_6$alkyl, $C_1$-$C_3$alkyl-$R^7$, 3-7 membered saturated ring or monocyclic aryl optionally being substituted with one or more $R^8$;
$R^4$ is $C_1$-$C_3$alkyl, in particular methyl;
$R^6$ is hydrogen or methyl;
$R^7$ is selected from the group consisting of a monocyclic aryl optionally containing one or two heteroatoms; a 3-7 membered saturated ring optionally containing one or more heteroatoms each independently selected from the group consisting of O, S and N; or —$NR^9R^{10}$;
wherein $R^9$ and $R^{10}$ are each independently selected from hydrogen and $C_1$-$C_3$alkyl;
each $R^8$ independently is selected from the group consisting of —OH, fluoro, methoxy, oxo, —C(=O)O$C_1$-$C_4$alkyl and $C_1$-$C_4$alkyl optionally substituted with one or more substituents each independently selected from fluoro and/or —OH;
$R^a$ is selected from hydrogen and halogen, in particular hydrogen;
$R^b$ is absent when ring B is pyridyl or is hydrogen or a halogen, in particular a halogen, when ring B is phenyl;
$R^c$ is selected from halogen, $CH_3$, $CHF_2$, $CF_3$, and —CN;
$R^d$ is selected from hydrogen and halogen, in particular hydrogen;
or a pharmaceutically acceptable salt or a solvate thereof.

In a further embodiment the present invention relates to compounds of Formula (I-A) having, in particular, Formula (I-A1') or Formula (I-A2'), as defined herein wherein $R^2$ is $C_1$-$C_6$alkyl optionally substituted with 1-4 substituents each independently selected from the group consisting of —OH, fluoro, and methoxy, in particular —OH and fluoro; Ring B represents phenyl; $R^a$ is selected from hydrogen and halogen;

$R^b$ is hydrogen or a halogen, in particular a halogen; and $R^c$ is selected from halogen, $CH_3$, $CHF_2$, $CF_3$, and CN; and the rest of the variables are as defined herein.

Another embodiment of the present invention relates to those compounds of Formula (I-A), Formula (I-AA1), Formula (I-AA2), Formula (I-A1), Formula (I-A2), Formula (I-A1'), Formula (I-A2'), Formula (A), Formula (B), or Formula (C) or any subgroup thereof as mentioned in any of the other embodiments wherein one or more of the following restrictions apply:

(a) Ring C consists of 6 to 8 atoms, preferably 7 atoms.
(b) Y represents linear $C_1$-$C_7$alkanediyl or $C_2$-$C_7$alkenediyl, each optionally substituted with 1-3 substituents each independently selected from the group consisting of fluoro and —OH.
(c) Y represents linear $C_1$-$C_7$alkanediyl or $C_2$-$C_7$alkenediyl, each optionally substituted with —OH.
(d) $R^2$ is $C_1$-$C_6$alkyl optionally substituted with one or more Fluoro and/or —OH substituents, each independently selected. Preferably, $R^2$ is a branched $C_1$-$C_6$alkyl substituted with one or more Fluoro substituents.
(e) $R^2$ is $C_1$-$C_6$alkyl optionally substituted with one or more —OH substituents. In particular, $R^2$ is $C_{1-6}$alkyl substituted with one —OH.
(f) $R^2$ is $C_1$-$C_4$alkyl optionally substituted with one or more fluoro substituents.
(g) $R^2$ is $C_3$-$C_6$alkyl optionally substituted with one or more fluoro substituents.
(h) $R^3$ is $C_1$-$C_4$alkyl, in particular methyl.
(i) $R^3$ is $C_1$-$C_4$alkyl, in particular methyl; and $R^2$ is selected from the group consisting of $C_1$-$C_6$alkyl, and monocyclic aryl optionally containing one or two heteroatoms, such $C_1$-$C_6$alkyl or monocyclic aryl optionally being substituted with one or more $R^8$, wherein $R^8$ is as defined herein.
(j) $R^4$ is $C_1$-$C_3$alkyl, preferably methyl.
(k) $R^b$ is Hydrogen or Fluoro.
(l) $R^b$ and $R^c$ are independently selected from hydrogen, fluoro and CN.
(m) $R^b$ and $R^c$ are independently selected from Hydrogen or Fluoro.
(n) $R^b$ and $R^c$ are independently selected from fluoro and CN.
(o) $R^a$ and/or $R^d$ is Hydrogen
(p) $R^b$ and $R^d$ are both Hydrogen.
(q) $R^b$ and/or $R^c$ are Fluoro.
(r) $R^1$ is hydrogen or $C_1$-$C_6$alkyl optionally substituted with one or more substituents, in particular 1-4 substituents, each independently selected from the group consisting of —OH and fluoro.
(s) $R^1$ is hydrogen.

(t)
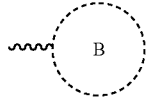

represents phenyl.

(u)
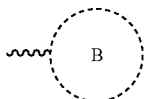

represents phenyl substituted with one or more halogen substituents.

(v)
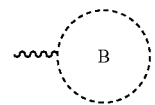

represents phenyl substituted with at least one Halogen, more preferably at least one Fluoro, even more preferably 2 Fluoro.

(w) $R^7$ is a 3-7 membered saturated ring, in particular cyclopropyl.

(x) $R^2$ is selected from the group consisting of methyl, ethyl, isopropyl,

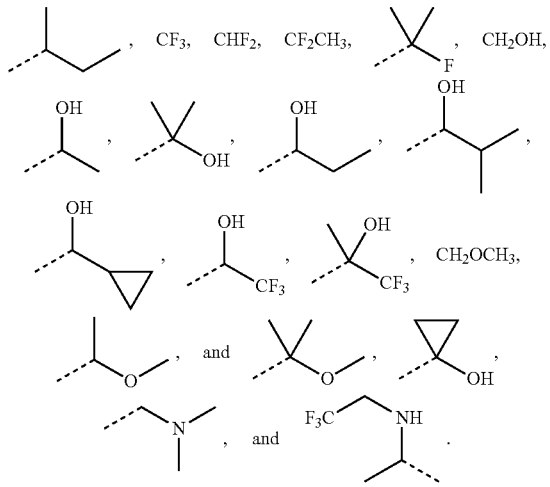

(y) $R^2$ is selected from the group consisting of methyl, ethyl, isopropyl,

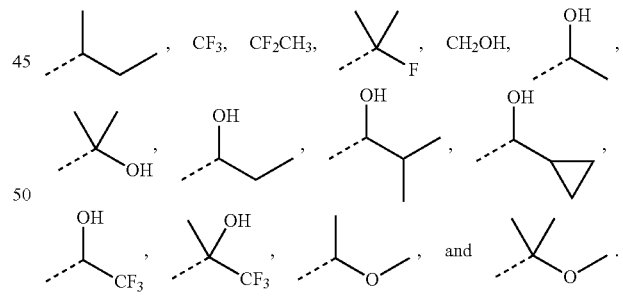

(z)
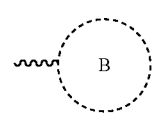

represents phenyl, and $R^a$, $R^b$, $R^c$ and $R^d$ are each independently selected from the group consisting of hydrogen, halogen, —$CHF_2$, —$CF_2$-methyl, —$CF_3$, —$OCF_3$, —CN, $C_3$-$C_4$cycloalkyl and —$C_1$-$C_4$alkyl.

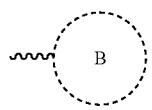

(aa)

represents phenyl, and $R^a$ is selected from hydrogen and halogen; $R^b$ is hydrogen or a halogen, in particular a halogen; $R^c$ is selected from halogen, $CH_3$, $CHF_2$, $CF_3$, and —CN; and $R^d$ is selected from hydrogen and halogen, in particular hydrogen.

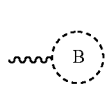

(bb)

represents phenyl, and $R^a$ is selected from hydrogen and halogen; $R^b$ is hydrogen or a halogen, in particular a halogen; $R^c$ is selected from halogen, $CH_3$, $CF_3$, and —CN; and $R^d$ is selected from hydrogen and halogen, in particular hydrogen.

Further combinations of any of the embodiments are also envisioned to be in the scope of the present invention.

In an additional embodiment, the present invention relates to a compound of Formula (I-A) as defined herein, or a stereoisomer or tautomeric form thereof, wherein

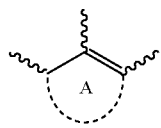

represents a monocyclic 5 or 6 membered aryl or heteroaryl selected from the group consisting of pyrrolyl, thiophenyl, pyrazolyl, phenyl, and pyridyl, each optionally substituted with one or two substituents each independently selected from the group consisting of $C_1$-$C_3$alkyl, in particular methyl, $C_3$-$C_4$cycloalkyl, —CN and halogen;

represents phenyl or pyridyl;
X represents —$CR^2R^3$—;
Y represents linear $C_1$-$C_7$alkanediyl or $C_2$-$C_7$alkenediyl, each optionally substituted with one, two or three substituents each independently selected from the group consisting of fluoro and —OH;
Z represents oxygen, or a single bond;
$R^a$, $R^b$, $R^c$ and $R^d$ are each independently selected from the group consisting of hydrogen, halogen, —$CHF_2$, —$CF_2$-methyl, —$CH_2F$, —$CF_3$, —$OCF_3$, —CN, $C_3$-$C_4$cycloalkyl and —$C_1$-$C_4$alkyl;
$R^1$ is hydrogen or $C_1$-$C_6$alkyl optionally substituted with one, two, three or four substituents each independently selected from the group consisting of —OH and fluoro;
$R^2$ is selected from the group consisting of hydrogen; $C_1$-$C_6$alkyl optionally substituted with 1-4 substituents each independently selected from the group consisting of —OH, fluoro, methoxy, oxo, and —C(=O)O$C_1$-$C_4$alkyl; $C_1$-$C_3$alkyl-$R^7$; $C_2$-$C_4$alkynyl; a 3-7 membered saturated ring optionally containing one or two heteroatoms each independently selected from the group consisting of O, S and N; and monocyclic aryl optionally containing one or two heteroatoms; wherein the $C_1$-$C_3$alkyl-$R^7$, 3-7 membered saturated ring or the monocyclic aryl are each optionally substituted with one or more $R^8$ substituents;
$R^3$ is hydrogen or $C_{1-6}$alkyl optionally substituted with —OH; in particular, hydrogen or methyl;
or $R^2$ and $R^3$ taken together with the carbon atom to which they are attached form a 3-7 membered saturated ring optionally containing one or more heteroatoms each independently selected from the group consisting of O, S and N, and optionally being substituted with one or more substituents each independently selected from the group consisting of —OH, fluoro, methoxy, oxo, benzyl, and $C_1$-$C_4$alkyl;
$R^7$ represents a monocyclic aryl optionally containing one or two heteroatoms, and optionally being substituted with one or two substituents each independently selected from the group consisting of halo and $C_{1-3}$alkyl; a 3-7 membered saturated ring optionally containing one or more heteroatoms each independently selected from the group consisting of O, S and N; or —$NR^9R^{10}$;
wherein $R^9$ and $R^{10}$ are each independently selected from hydrogen and $C_1$-$C_3$alkyl optionally substituted with one or more fluoro substituents;
each $R^8$ is independently selected from the group consisting of —OH, fluoro, methoxy, oxo, —C(=O)O$C_1$-$C_4$alkyl, $C_1$-$C_4$alkyloxy$C_1$-$C_4$alkyloxy, and $C_1$-$C_4$alkyl optionally substituted with one or more substituents each independently selected from fluoro and/or —OH;
or a pharmaceutically acceptable salt or a solvate thereof.

In an additional embodiment, the present invention relates to a compound of Formula (I-A) as defined herein, or a stereoisomer or tautomeric form thereof, wherein

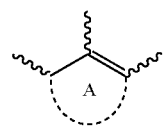

represents a monocyclic 5 membered heteroaryl selected from the group consisting of pyrrolyl, thiophenyl and pyrazolyl, each optionally substituted with one or two substituents each independently selected from the group consisting of $C_1$-$C_3$alkyl, in particular methyl;

represents phenyl or pyridyl;
X represents —$CR^2R^3$—;
Y represents linear $C_1$-$C_7$alkanediyl or $C_2$-$C_7$alkenediyl, each optionally substituted with one or two substituents each independently selected from the group consisting of fluoro and —OH;
Z represents oxygen, or a single bond;
$R^a$, $R^b$, $R^c$ and $R^d$ are each independently selected from the group consisting of hydrogen, halogen, —$CHF_2$, —CF$_2$-methyl, —CH$_2$F, —CF$_3$, —OCF$_3$, —CN, C$_3$-C$_4$cycloalkyl and —C$_1$-C$_4$alkyl;

R$^1$ is hydrogen or C$_1$-C$_3$alkyl optionally substituted with one, two or three substituents each independently selected from the group consisting of —OH and fluoro; more in particular, hydrogen;

R$^2$ is selected from the group consisting of hydrogen; C$_1$-C$_6$alkyl optionally substituted with one, two, three or four substituents each independently selected from the group consisting of —OH, fluoro, and methoxy; C$_1$-C$_3$alkyl-R$^7$; C$_2$-C$_4$alkynyl; 3-7 membered saturated ring optionally containing one or two heteroatoms each independently selected from the group consisting of O, S and N selected from the group consisting of cyclopropyl, tetrahydropyranyl and piperidinyl; and monocyclic aryl optionally containing one or two heteroatoms selected from the group consisting of phenyl, pyridyl, pyrimidinyl, pyrazinyl, pyrazolyl, imidazolyl, and oxazolyl; wherein the C$_1$-C$_3$alkyl-R$^7$, 3-7 membered saturated ring or the monocyclic aryl are each optionally substituted with one or more R$^8$ substituents;

R$^3$ is hydrogen or C$_{1-3}$alkyl optionally substituted with —OH; in particular, hydrogen or methyl;

or R$^2$ and R$^3$ taken together with the carbon atom to which they are attached form a cyclopropyl, oxetanyl, tetrahydrofuranyl, tetrahydropyranyl, pyrrolidinyl or piperidinyl ring, each optionally being substituted with benzyl;

R$^7$ is selected from the group consisting of phenyl, pyridyl, pyrazolyl, imidazolyl, and oxazolyl, each optionally substituted with one or two substituents each independently selected from the group consisting of halo and C$_{1-3}$alkyl; cyclopropyl; and —NR$^9$R$^{10}$;

wherein R$^9$ and R$^{10}$ are each independently selected from hydrogen and C$_1$-C$_3$alkyl optionally substituted with one or more fluoro substituents;

each R$^8$ is independently selected from the group consisting of —OH, fluoro, methoxy, oxo, —C(=O)OC$_1$-C$_4$alkyl, C$_1$-C$_4$alkyloxyC$_1$-C$_4$alkyloxy, and C$_1$-C$_4$alkyl optionally substituted with one or more substituents each independently selected from fluoro and/or —OH;

or a pharmaceutically acceptable salt or a solvate thereof.

In a further embodiment, the invention relates to compounds of Formula (I-A), (A) or (A*), as defined herein, wherein

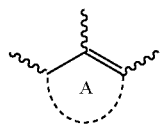

is selected from the group consisting of pyrrolyl, thienyl and pyrazolyl, each optionally substituted with one or two substituents each independently selected from the group consisting of C$_1$-C$_3$alkyl, in particular methyl, —CN and halo.

In an additional embodiment, the invention relates to compounds of the invention, as defined herein, wherein R$^2$ is selected from the group consisting of hydrogen, C$_1$-C$_6$alkyl optionally substituted with 1-4 substituents each independently selected from the group consisting of —OH, fluoro and methoxy; C$_1$-C$_3$alkyl-R$^7$ optionally substituted with —OH; a heterocyclyl selected from piperidinyl and tetrahydropyranyl, each optionally substituted with C$_1$-C$_4$alkyl, which may be optionally substituted with 1-3 fluoro substituents; and aryl or heteroaryl selected from the group consisting of phenyl, pyridyl, pyrazinyl, pyrimidinyl, and oxazolyl, each optionally substituted with methyl; wherein R$^7$ is selected from the group consisting of cyclopropyl, phenyl, pyridyl, oxazolyl, pyrazolyl and imidazolyl, each optionally substituted with 1-3 substituents each independently selected from halo and methyl; and —NR$^9$R$^{10}$, wherein R$^9$ and R$^{10}$ are each independently selected from hydrogen, C$_1$-C$_3$alkyl and C$_1$-C$_3$alkyl substituted with 1-3 fluoro substituents;

R$^3$ is hydrogen or C$_{1-6}$alkyl optionally substituted with —OH; in particular, hydrogen or methyl;

or R$^2$ and R$^3$ taken together with the carbon atom to which they are attached form a cyclopropyl, an oxetanyl, a tetrahydrofuranyl or a pyrrolidinyl ring optionally substituted with benzyl, in particular an oxetanyl or a tetrahydrofuranyl ring.

In an additional embodiment, the invention relates to compounds of the invention, as defined herein, wherein R$^2$ is selected from the group consisting of C$_1$-C$_6$alkyl optionally substituted with 1-4 substituents each independently selected from the group consisting of —OH and fluoro; C$_1$-C$_3$alkyl-R$^7$; optionally substituted with —OH;

piperidinyl or tetrahydropyranyl, each of which may be optionally substituted with C$_1$-C$_4$alkyl, which may be optionally substituted with 1-3 fluoro substituents;

phenyl, pyridyl, pyrazinyl, pyrimidinyl, oxazolyl, each of which optionally being substituted with methyl;

wherein R$^7$ is selected from cyclopropyl, phenyl, pyridyl, oxazolyl, pyrazolyl and imidazolyl, each of which optionally being substituted with 1-3 substituents each independently selected from halo and methyl; and —NR$^9$R$^{10}$, wherein R$^9$ and R$^{10}$ are each independently selected from hydrogen and C$_1$-C$_3$alkyl;

R$^3$ is hydrogen or C$_{1-6}$alkyl; in particular, hydrogen or methyl;

or R$^2$ and R$^3$ taken together with the carbon atom to which they are attached form a cyclopropyl, an oxetanyl or a tetrahydrofuranyl, in particular an oxetanyl or a tetrahydrofuranyl ring.

Preferred compounds according to the invention are compound or a stereoisomer or tautomeric form thereof with a Formula as represented in the synthesis of compounds section and of which the activity is displayed in Table 1.

Definitions

The term "aryl" means a monocyclic or polycyclic aromatic ring comprising carbon atoms, and hydrogen atoms. If indicated, such aromatic ring may include one or more heteroatoms (then also referred to as heteroaryl), preferably, 1 to 3 heteroatoms, independently selected from nitrogen, oxygen, and sulfur, preferably nitrogen. As is well known to those skilled in the art, heteroaryl rings have less aromatic character than their all-carbon counter parts. Thus, for the purposes of the present invention, a heteroaryl group need only have some degree of aromatic character. Illustrative examples of aryl groups are optionally substituted phenyl. Illustrative examples of heteroaryl groups according to the invention include optionally substituted pyrrole, pyridine, and imidazole. Thus, the term monocyclic aryl optionally containing one or more heteroatoms, for example one or two heteroatoms, refers for example, to a 5- or 6-membered aryl or heteroaryl group such as, but not limited to, phenyl, pyridyl, pyrimidinyl, pyrazinyl, pyridazinyl, pyrrolyl, thienyl, pyrazolyl, imidazolyl and oxazolyl.

The terms "$C_{1-x}$alkyl" and $C_1$-$C_x$alkyl can be used interchangeably.

The term "$C_{1-10}$alkyl", "$C_{1-6}$alkyl", "$C_{1-3}$alkyl" as a group or part of a group refers to a hydrocarbyl radical of Formula $C_nH_{2n+1}$ wherein n is a number ranging from 1 to 10, from 1 to 6, or from 1 to 3. For example, in the case that $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

$C_{1-4}$alkyl as a group or part of a group defines straight or branched chain saturated hydrocarbon radical having from 1 to 4 carbon atoms such as the group defined for $C_{1-3}$alkyl and butyl and the like.

$C_{1-6}$alkyl and $C_{2-6}$alkyl as a group or part of a group defines straight or branched chain saturated hydrocarbon radicals having from 1 to 6 carbon atoms, or from 2 to 6 carbon atoms such as the groups defined for $C_{1-4}$alkyl and pentyl, hexyl, 2-methylbutyl and the like.

The term "$C_{1-7}$alkanediyl" as a group or part of a group defines bivalent straight or branched chained saturated hydrocarbon radicals having from 1 to 7 carbon atoms such as, for example, methanediyl, ethanediyl, propanediyl, butanediyl, pentanediyl, hexanediyl and heptanediyl.

The term "$C_{2-7}$alkenediyl" as a group or part of a group defines straight or branched chain bivalent hydrocarbon radicals having from 2 to 7 carbon atoms and having at least one double bond, preferably one double bond, such as ethenediyl, propenediyl, butenediyl, pentenediyl, hexenediyl and heptenediyl and the like.

The term "$C_3$-$C_4$cycloalkyl" is generic to cyclopropyl and cyclobutyl.

As used herein, the term "3-7 membered saturated ring" means saturated cyclic hydrocarbon (cycloalkyl) with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms (also referred to as heterocyclyl), such that at least one carbon atom is replaced by a heteroatom selected from N, O and S, in particular from N and O. Examples include oxetanyl, tetrahydro-2H-pyranyl, piperidinyl, tetrahydrofuranyl, morpholinyl, thiolane 1,1-dioxide and pyrrolidinyl. Preferred are saturated cyclic hydrocarbons with 3 or 4 carbon atoms and 1 oxygen atom. Examples include oxetanyl, and tetrahydrofuranyl.

It should be noted that different isomers of the various heterocycles may exist within the definitions as used throughout the specification. For example, pyrrolyl may be 1H-pyrrolyl or 2H-pyrrolyl.

The term halo and halogen are generic to Fluoro, Chloro, Bromo or Iodo. Preferred halogens are Bromo, Fluoro and Chloro.

The term "heteroatom" refers to an atom other than carbon or hydrogen in a ring structure or a saturated backbone as defined herein. Typical heteroatoms include N(H), O, S.

The term *R and *S depicted in a structural formula indicate that a racemic mixture of the compound is separated into its 2 enantiomers. The first eluting enantiomer is indicated with *R and the second eluting enantiomer is indicated with *S. Both *R and *S therefore indicate a specific separated enantiomer, but the stereocenter conformation is not established.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

The term

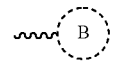

or ring B represents a 6 membered aryl optionally containing one nitrogen atom. Ring B can therefore be referred to as phenyl or pyridyl.

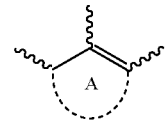

represents a monocyclic 5 or 6 membered aryl optionally containing one or two heteroatoms, such aryl optionally being substituted with one or more substituents each independently selected from the group consisting of $C_1$-$C_3$alkyl, in particular methyl, $C_3$-$C_4$cycloalkyl, —CN and halogen. Such monocyclic 5 or 6 membered aryl or heteroaryl groups, as defined herein, include, but are not limited to phenyl, pyridyl, pyrimidinyl, pyrazinyl, pyridazinyl, pyrrolyl, thienyl, pyrazolyl, imidazolyl and oxazolyl. Ring A can alternatively be depicted bearing the optional substituents $C_1$-$C_3$alkyl, $C_3$-$C_4$cycloalkyl, —CN and halogen at particular positions, as defined herein, by referring to such substituents as $R^4$, $R^5$ and $R^6$, as applicable.

Lines drawn from substituents into ring systems indicate that the bond may be attached to any of the suitable ring atoms.

Positions indicated on ring B (e.g. ortho, meta and/or para) are indicated relative to the bond connecting aryl B to the main structure. An example with regard to the position of meta $R^a$, location is indicated relative to the nitrogen (*) connected to the main structure as shown in Formula (A*).

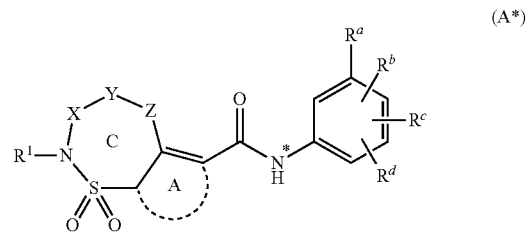

(A*)

When any variable (e.g. halogen or $C_{1-4}$alkyl) occurs more than one time in any constituent, each definition is independent.

The expression "one or more substituents" refers in particular to 1, 2, 3, 4, or more substituents, in particular to 1, 2, 3, or 4 substituents, more in particular, to 1, 2, or 3 substituents.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

For therapeutic use, the salts of the compounds of Formula (I-A), (A), (B), (C), are those wherein the counter ion is pharmaceutically or physiologically acceptable. However, salts having a pharmaceutically unacceptable counter ion may also find use, for example, in the preparation or purification of a pharmaceutically acceptable compound of Formula (I-A), (A), (B), (C). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid, sulfuric, hemisulphuric, nitric, phosphoric and the like acids; or organic acids such as, for example, acetic, aspartic, dodecyl-sulphuric, heptanoic, hexanoic, nicotinic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "solvate" comprises the solvent addition forms as well as the salts thereof, which the compounds of the present invention are able to form. Examples of such solvent addition forms are, e.g. hydrates, alcoholates and the like.

The present compounds may also exist in their tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in a mixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereo-isomeric excess of 97% up to 100%. The terms 'enantiomerically pure' and 'diastereomerically pure' should be understood in a similar way, but then having regard to the enantiomeric excess or the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The stereometric forms of compounds of Formula (I-A), (A), (B), or (C), can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, Hydrogen includes the tritium and deuterium isotopes. Carbon includes the C-13 and C-14 isotopes.

In a further aspect, the present invention concerns a pharmaceutical composition comprising a therapeutically or prophylactically effective amount of a compound of Formula (I-A), or of Formula (A), (B) or (C) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of Formula (I-A), (A) (B) or (C), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or solvate form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (I-A), (A), (B), or (C) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma. HBV acts as a helper virus to HDV, which infects only subjects suffering from HBV infection. Therefore, in a particular embodiment, said compounds of Formula (I-A), (A), (B), or (C) can be used in the treatment and/or prophylaxis of HBV/HDV co-infection, or diseases associated with HBV/HDV co-infection.

Due to their antiviral properties, particularly their anti-HBV properties, the compounds of Formula (I-A), (A), (B), or (C), or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular a human, infected by HBV, or being at risk of infection by HBV, said method comprising the administration of a therapeutically effective amount of a compound of Formula (I-A), (A), (B), or (C). In a particular embodiment, the warm-blooded animal, in particular the human, may be HBV/HDV co-infected, or be at risk of HBV/HDV co-infection.

The compounds of Formula (I-A), (A), (B), or (C), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection. In a particular embodiment, said HBV infection is in particular HBV/HDV co-infection.

The present invention also relates to the use of the present compounds in the manufacture of a medicament. The present invention also relates to the use of the present compounds in the manufacture of a medicament for the treatment or the prevention of HBV infection. In a particular embodiment, the invention relates to the use of the present compounds in the manufacture of a medicament for the treatment or the prevention of HBV/HDV co-infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of Formula (I-A), (A), (B), or (C), or any subgroup thereof, as specified herein with other anti-HBV agents. The term "combination" may relate to a product or kit containing (a) a compound of Formula (I-A), (A), (B), or (C), as specified above, and (b) at least one other compound/agent capable of treating HBV infection (herein designated as anti-HBV agent), as a combined preparation for simultaneous, separate or sequential use in treatment of HBV infections. In an embodiment, the invention concerns a combination of a compound of Formula (I-A), (A), (B), or (C), or any subgroup thereof with at least one anti-HBV agent. In a particular embodiment, the invention concerns a combination of a compound of Formula (I-A), (A), (B), or (C), or any subgroup thereof with at least two anti-HBV agents. In a particular embodiment, the invention concerns a combination of a compound of Formula (I-A), (A), (B), or (C), or any subgroup thereof with at least three anti-HBV agents. In a particular embodiment, the invention concerns a combination of a compound of Formula (I-A), (A), (B), or (C), or any subgroup thereof with at least four anti-HBV agents.

The term anti-HBV agent also includes compounds that are therapeutic nucleic acids, antibodies or proteins either in their natural form or chemically modified and/or stabilized. The term therapeutic nucleic acid includes but is not limited to nucleotides and nucleosides, oligonucleotides, polynucleotides, of which non limiting examples are antisense oligonucleotides, miRNA, siRNA, shRNA, therapeutic vectors and DNA/RNA editing components.

The term anti-HBV agent also includes compounds capable of treating HBV infection via immunomodulation. Examples of immunomodulators are interferon-α (IFN-α), pegylated interferon-α or stimulants of the innate immune system such as Toll-like receptor 7 and/or 8 agonists and therapeutic or prophylactic vaccines. One embodiment of the present invention relates to combinations of a compound of Formula (I-A), (A), (B), or (C), or any subgroup thereof, as specified herein, with an immunomodulating compound, more specifically a Toll-like receptor 7 and/or 8 agonist.

The additional HBV antiviral(s) can be selected for example, from therapeutic vaccines; RNA interference therapeutic/antisense oligonucleotides (siRNA, ddRNA, shRNA); immunomodulators (TLR agonists (TLR7, TLR8 or TLR9 agonists); STING agonists; RIG-I modulators; NKT modulators; IL agonists; Interleukin or other immune active proteins, therapeutic and prophylactic vaccines and immune checkpoint modulators); HBV entry inhibitors; cccDNA modulators; capsid assembly inhibitors/modulators; core or X protein targeting agents; nucleotide analogues; nucleoside analogues; interferons or modified interferons; HBV antivirals of distinct or unknown mechanism; cyclophilin inhibitors; and sAg release inhibitors.

In particular, the combination of previously known anti-HBV agents, such as interferon-α (IFN-α), pegylated interferon-α, 3TC, tenofovir, lamivudine, entecavir, telbivudine, and adefovir or a combination thereof, and, a compound of Formula (I-A), (A), (B), or (C), or any subgroup thereof can be used as a medicine in a combination therapy.

Particular examples of such HBV antiviral(s) include, but are not limited to:

RNA interference (RNAi) therapeutics: TKM-HBV (also known as ARB-1467), ARB-1740, ARC-520, ARC-521, BB-HB-331, REP-2139, ALN-HBV, ALN-PDL, LUNAR-HBV, GS3228836, and GS3389404;

HBV entry inhibitors: Myrcludex B, IVIG-Tonrol, GC-1102;

HBV capsid inhibitor/modulators, core or X targeting agents, direct cccDNA inhibitors, cccDNA formation inhibitors or cccDNA epigenetic modifiers: BAY 41-4109, NVR 3-778, GLS-4, NZ-4 (also known as W28F), Y101, ARB-423, ARB-199, ARB-596, JNJ-56136379, ASMB-101 (also known as AB-V102), ASMB-103, CHR-101, CC-31326; AT-130

HBV polymerase inhibitors: entecavir (Baraclude, Entavir), lamivudine (3TC, Zeffix, Heptovir, Epivir, and Epivir-HBV), telbivudine (Tyzeka, Sebivo), clevudine, besifovir, adefovir (hepsera), tenofovir (in particular tenofovir disoproxil fumarate (Viread), tenofovir alafenamide fumarate (TAF)), tenofovir disoproxil orotate (also known as DA-2802), tenofovir disopropxil aspartate (also known as CKD-390), AGX-1009, and CMX157);

Zidovudine, Didanosine, Zalcitabine, Stavudine, and Abacavir;

cyclophilin inhibitors: OCB-030 (also known as NVP-018), SCY-635, SCY-575, and CPI-431-32;

dinucleotides: SB9200;

compounds of distinct or unknown mechanism, such as but not limited to AT-61 ((E)-N-(1-chloro-3-oxo-1-phenyl-3-(piperidin-1-yl)prop-1-en-2-yl)benzamide), ((E)-N-(1-bromo-1-(2-methoxyphenyl)-3-oxo-3-(piperidin-1-yl)prop-1-3n-2-yl)-4-nitrobenzamide), and similar analogs; REP-9AC (also known as REP-2055), REP-9AC' (also known as REP-2139), REP-2165 and HBV-0259;

TLR agonists (TLR7, 8 and/or 9): RG7795 (also known as RO-6864018), GS-9620, SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-pyrin-9-yl)propyl][3-(4-morpholinyl)propyl]amino}methyl)phenyl]acetate); ARB-1598;

RIG-I modulators: SB-9200;

SMAC inhibitor: Birinapant

Check Point inhibitors: BMS-936558 (Opdivo (nivolumab)), KEYTRUDA® (pembrolizumab);

therapeutic vaccines: HBsAG-HBIG, HB-Vac, ABX203, NASVAC, GS-4774, GX-110 (also known as HB-110E), CVI-HBV-002, RG7944 (also known as INO-1800), TG-1050, FP-02 (Hepsyn-B), AIC649, VGX-6200, KW-2, TomegaVax-HBV, ISA-204, NU-500, INX-102-00557 HBV MVA, PepTcell;

IL agonists and immune acting proteins: INO-9112; recombinant IL12;

interferons: interferon alpha (IFN-α), interferon alpha-2a, recombinant interferon alpha-2a, peginterferon alpha-2a (Pegasys), interferon alpha-2b (Intron A), recombinant interferon alpha-2b, interferon alpha-2b XL, peginterferon alpha-2b, glycosylated interferon alpha-2b, interferon alpha-2c, recombinant interferon alpha-2c, interferon beta, interferon beta-1a, peginterferon beta-1a, interferon delta, interferon lambda (IFN-λ), peginterferon lambda-1, interferon omega, interferon tau, interferon gamma (IFN-γ), interferon alfacon-1, interferon alpha-n1, interferon alpha-n3, albinterferon alpha-2b, BLX-883, DA-3021, P1101 (also known as AOP2014), PEG-infergen, Belerofon, INTEFEN-IFN, albumin/interferon alpha 2a fusion protein, rHSA-IFN alpha 2a, rHSA-IFN alpha 2b, PEG-IFN-SA, interferon alpha biobetter; in particular, peginterferon alpha-2a, peginterferon alpha-2b, glycosylated interferon alpha-2b, peginterferon beta-1a, and peginterferon lambda-1; more in particular, peginterferon alpha-2a;

HDV targeting agent: Lonafamib.

In a further embodiment, the additional HBV antiviral compound is selected from the compounds disclosed in WO2013102655, WO2013174962, WO2014033167, WO2014033170, WO2014033176, WO2014131847, WO2014161888, WO2014184350, WO2014184365, WO2015011281, WO2015059212, WO2015118057, WO2013/096744, WO2014/165128, WO2015/073774, WO2015/109130.

In a further embodiment, the additional HBV antiviral compound is selected from the compounds based on the HAP scaffold, in particular those disclosed in Roche US20160083383, in particular compounds 19, 21, 22, 25, 27, 30, 34, 36; 38, 42, 43, 54, 55, 59, 62, 73, 76, 82B, 86B, 87B, 88B and 91B WO2014184328, WO2014037480, US20150252057, WO2015132276(A1), WO 2013144129.

Medshine Discovery Inc
WO 2015180631
Sunshine lake pharma co
WO 2015144093

Generic Synthesis

The substituents represented by $R^{a,b,c,d}$ or $R^1$ in this general synthesis section are meant to include any substituent or reactive species that is suitable for transformation into any $R^{a,b,c,d}$ or $R^1$ substituent according to the present invention without undue burden for the person skilled in the art.

A possible synthesis of compound of general formula (I) is described in schemes 1, 2, 3 and 4.

Compound of general formula (II) can be reacted with an amine of general formula (III), wherein X has the meaning as defined in the claims, for example a $C_1$-$C_6$alkanediyl optionally being substituted with one or more substituents each independently selected from the group consisting of —OH, Fluoro, and oxo, for example in an organic solvent like acetonitrile or DCM possibly in the presence of an organic base like for example triethylamine or DIPEA, or an inorganic base like for example sodium bicarbonate. The formed compound of general formula (IV) can be ring closed under Heck conditions with a ligand like bis(tri-tert-butylphosphine)palladium(0) to a compound of general formula (V). Compound of general formula (IV) can also be reacted with potassium allyltrifluoroborate under Suzuki conditions with a ligand like bis(tri-tert-butylphosphine) palladium(0) in the presence of an inorganic base like $Cs_2CO_3$ to give a mixture of compound of general formula (VII) and compound of general formula (VIII). Compound of general formula (VII) or compound of general formula (VIII) can be ring closed under metathesis conditions with a catalyst like Grubbs catalyst $2^{nd}$ generation, resulting in the formation of a compound of general formula (V). The compound of general formula (V) can be reacted with an amine of general formula (VI) in the presence of a base like for example lithium bis(trimethylsilyl)amide, in a solvent like for example THF, resulting in the formation of a compound of general formula (Ia), wherein Y* represents an alkenediyl and Z a single bond. Hydrogenation of the double bond forms a compound of general formula (Ib), wherein Y** represents an alkanediyl and Z a single bond. Alternatively the amide can be formed via the classical routes known by the person skilled in the art like—without any limitations—via the acid and a coupling reagent like HATU or via activation to the acid chloride and reaction with an amine of general formula (VI). Compound of general formula (IV) can also be reacted with an amine of general formula (VI) in the presence of a base like for example lithium bis(trimethylsilyl)amide, in a solvent like for example THF, resulting in the formation of a compound of general formula (XXXIV). The formed compound of general formula (XXXIV) can be ring closed under Heck conditions with a ligand like bis(tri-tert-butylphosphine) palladium(0) to a compound of general formula (Ia), wherein Y* represents an alkenediyl and Z a single bond.

Compound of general formula (II) can be reacted with an aminoalcohol of general formula (XXXI), wherein X has the meaning as defined in the claims, for example a $C_1$-$C_6$alkanediyl optionally being substituted with one or more substituents each independently selected from the group consisting of —OH, Fluoro, and oxo, for example in an organic solvent like acetonitrile or DCM possibly in the presence of an organic base like for example triethylamine or DIPEA, or an inorganic base like for example sodium bicarbonate. The formed compound of general formula (XXXII) can be oxidized in a solvent like THF with an oxidant like 2-iodoxybenzoic acid resulting in a compound of general formula (XXXIII). Compound of general formula (XXXIII) can be reacted under Wittig conditions to a compound of general formula (IV).

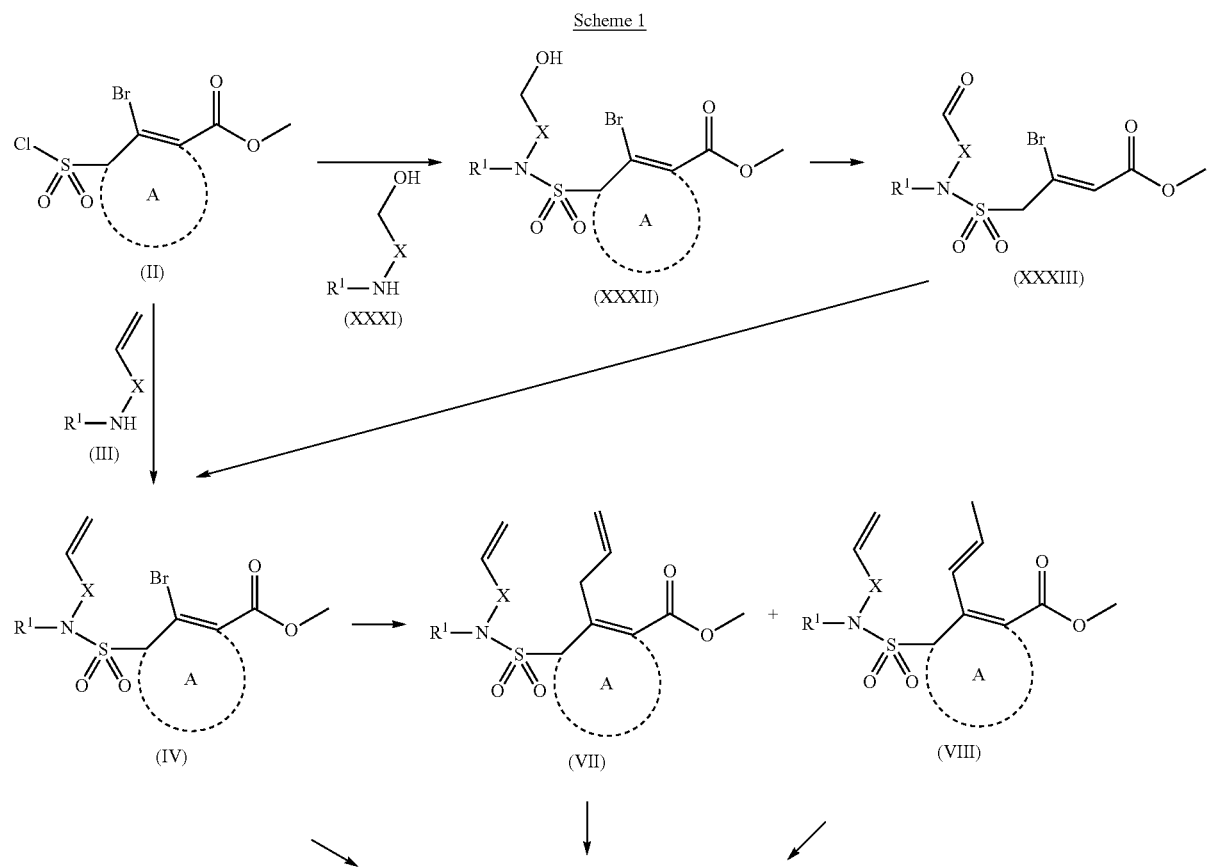

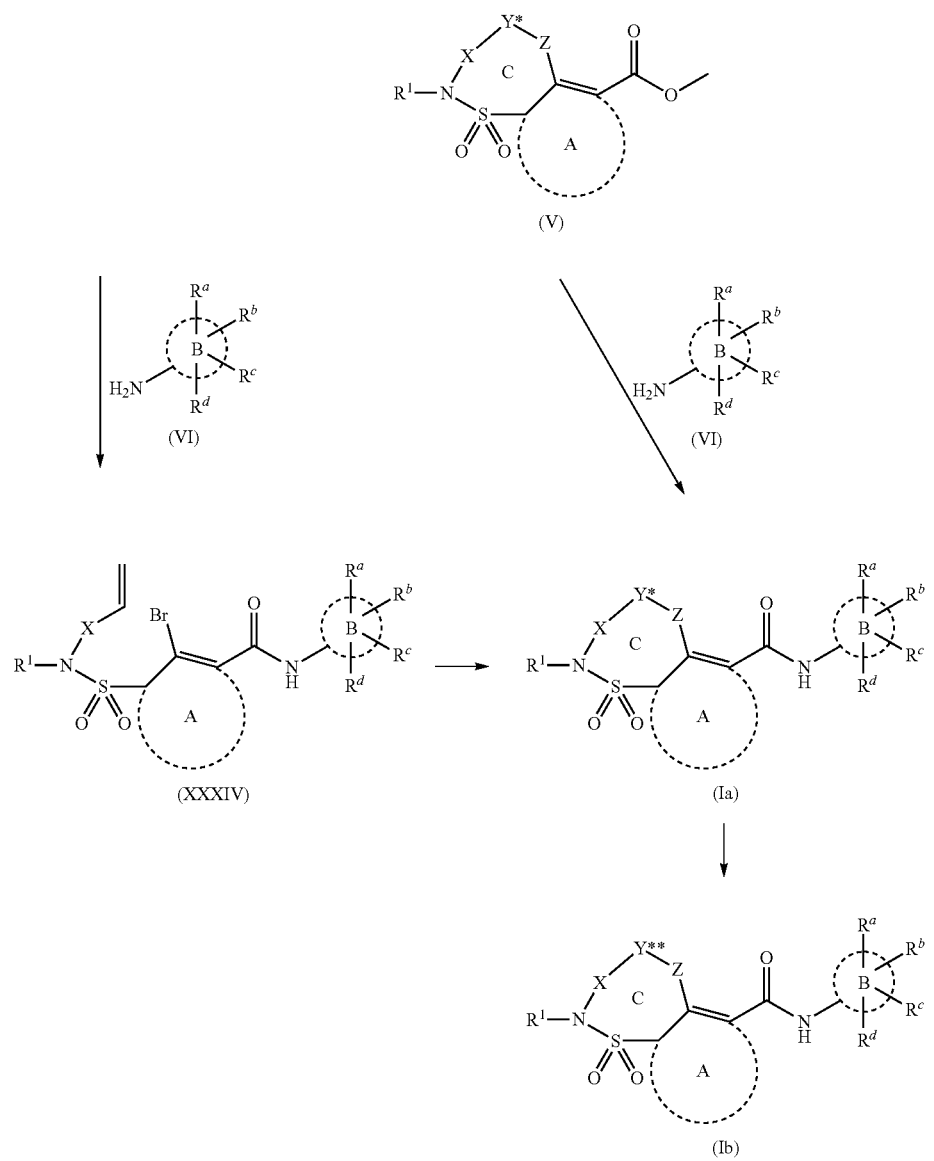

Alternatively, as described in Scheme 2, a compound of formula (II) can be reacted with an amine of general formula (IX), for example in an organic solvent like acetonitrile or DCM possibly in the presence of an organic base like for example triethylamine or DIPEA, or an inorganic base like for example sodium bicarbonate. The formed compound of general formula (X) can be reacted with potassium allyltrifluoroborate under Suzuki conditions with a ligand like bis(tri-tert-butylphosphine)palladium(0) in the presence of an inorganic base like $Cs_2CO_3$ to give a mixture of compound of general formula (XI) and compound of general formula (XII). A compound of general formula (XI) or a compound of general formula (XII) can be reacted with an amine of general formula (VI) in the presence of a base like for example lithium bis(trimethylsilyl)amide, in a solvent like for example THF, results in the formation of a compound of general formula (XIII) or general formula (XV). A compound of general formula (XIII) or a compound of general formula (XV) can be reacted under Mitsonobu conditions with an alcohol of general formula (XVII), wherein X has the meaning as defined in the claims, for example a $C_1$-$C_6$alkanediyl optionally being substituted with one or more substituents each independently selected from the group consisting of —OH, Fluoro, and oxo, and results in a compound of general formula (XIV) or a compound of general formula (XVI). A compound of general formula (XIV) or a compound of general formula (XVI) can be ring closed under metathesis conditions with a catalyst like Grubbs catalyst $2^{nd}$ generation, resulting in the formation of a compound of general Formula (Ia), wherein Y* represents an alkenediyl and Z a single bond. Hydrogenation of the double bond forms a compound of general formula (Ib), wherein Y** represents an alkanediyl and Z a single bond.

Scheme 2
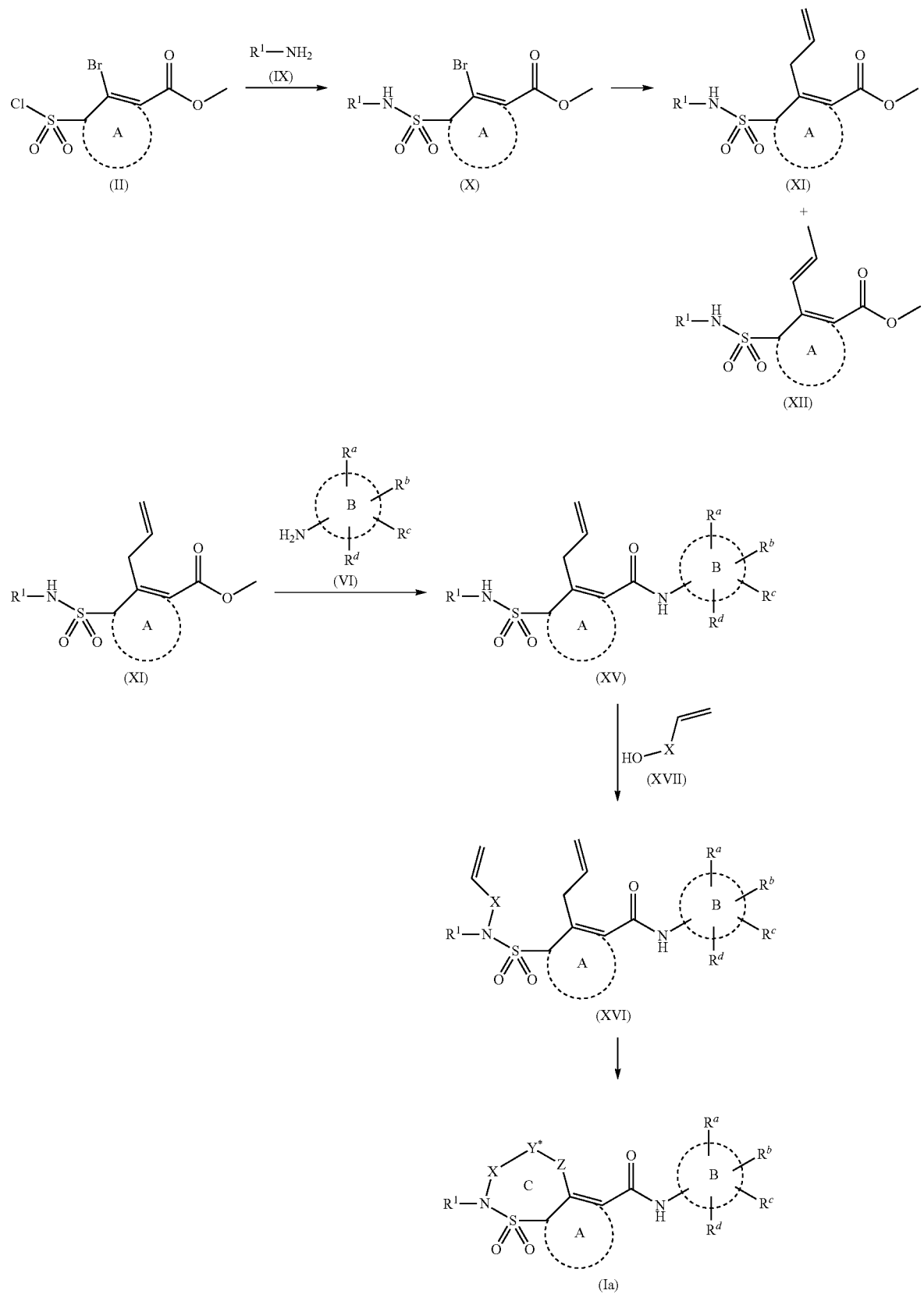

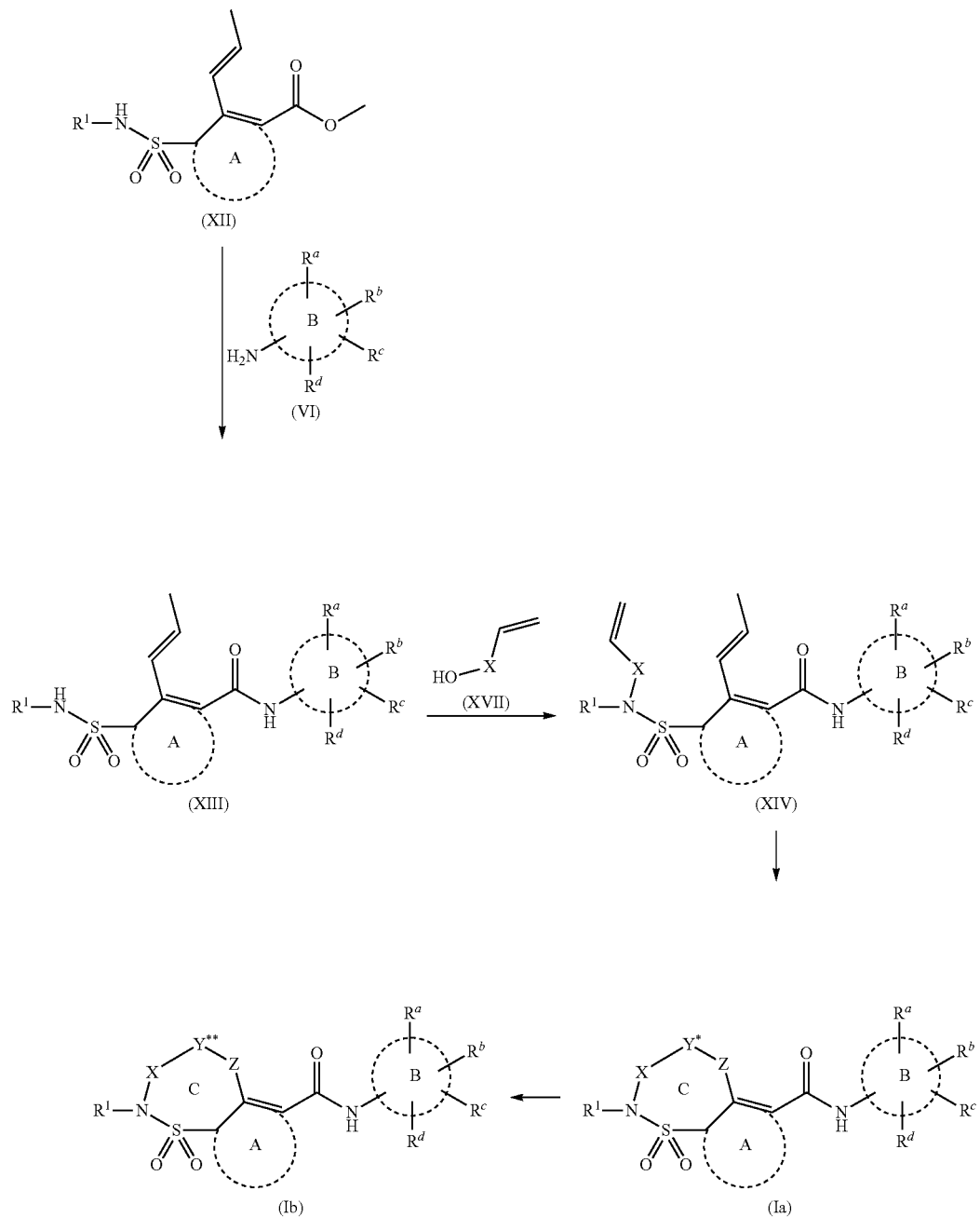

Alternatively, as described in Scheme 3, a compound of formula (XVIII) can be reacted with an alcohol of general formula (XIX), for example in an organic solvent like THF or DCM possibly in the presence of an organic base like for example triethylamine or DIPEA, or an inorganic base like for example sodium bicarbonate. The formed compound of general formula (XX) can be coupled with an amine of general formula (VI) in the presence of a base like for example lithium bis(trimethylsilyl)amide, in a solvent like for example THF. The formed compound of general formula (XXI) can be ring closed in the presence of a base like CsF, resulting in a compound of general formula (Ic) wherein Z is oxygen.

A compound of formula (XXII) can be reacted with an alcohol of general formula (XIX), for example in a mixture of an organic solvent like THF or DCM with water, possibly in the presence of an organic base like for example triethylamine or DIPEA, or an inorganic base like for example sodium carbonate. The formed compound of general formula (XXIII) can be coupled with an amine of general formula (VI) in the presence of an activating reagent like for example HATU and an organic base like triethylamine or DIPEA, resulting in a compound of general formula (XXI).

Scheme 3

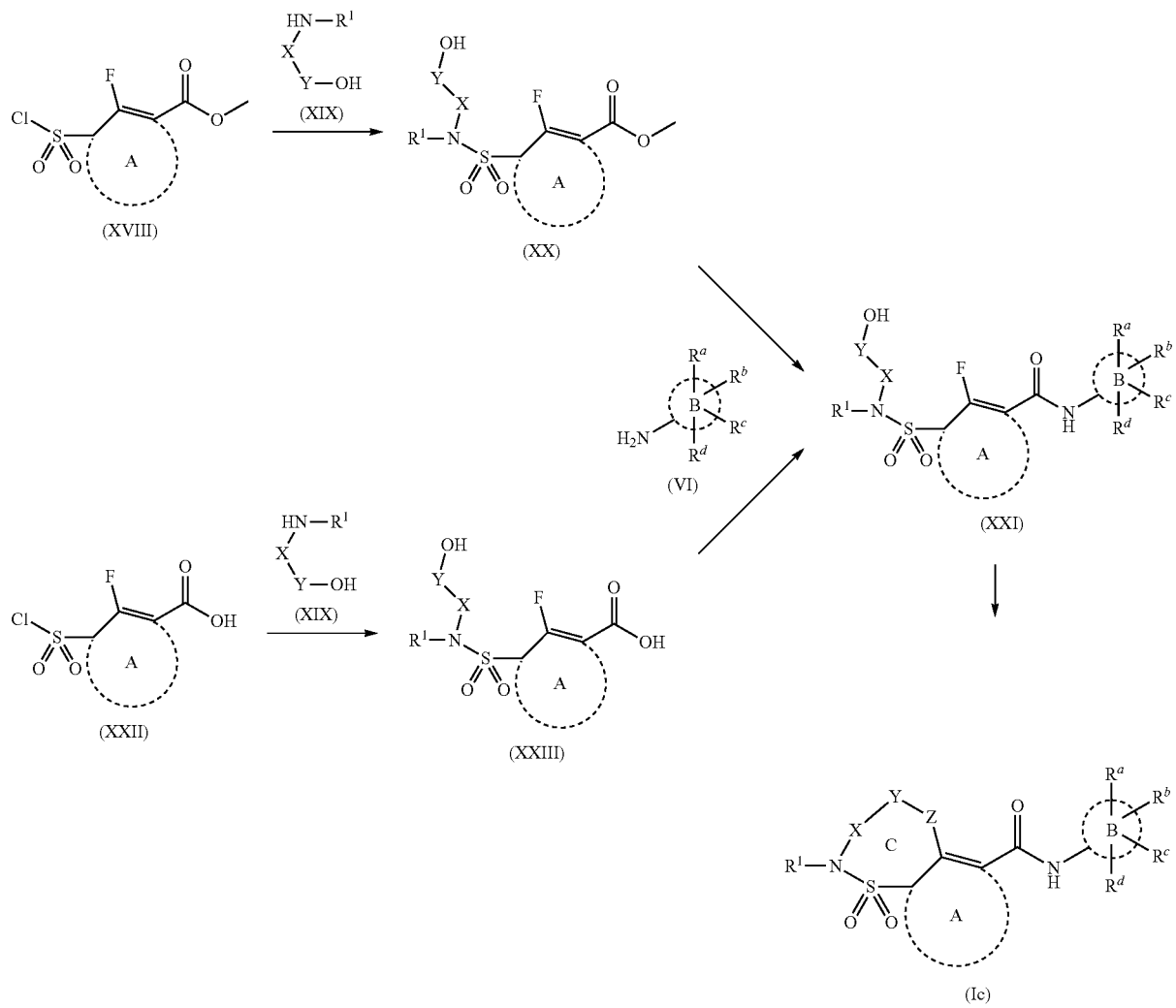

Alternatively, as described in Scheme 4, a compound of formula (II) can be treated with ammonia in a solvent like dioxane, resulting in a compound of general formula (XXIV). The formed compound (XXIV) can either be coupled with a 1-3-diketoalkane like pentane-2,4-dione or heptane-3,5-dione resulting in a compound of general formula (XXV) wherein Ry is a $C_1$-$C_4$alkyl or under Stille conditions with a stannane like (Z)-1-ethoxy-2-(tributylstannyl)ethene resulting in a compound of general formula (XXIX). Compounds of general formula's (XXV) can be ring closed under acidic conditions using an acid like TFA to a compound of general formula (XXVI) wherein Rz is a $C_1$-$C_4$alkyl. Compounds of general formula's (XXIX) can be ring closed under acidic conditions using an acid like TFA to a compound of general formula (XXVI) where Rz is hydrogen. The formed compound of general formula (XXVI) can either be hydrogenated to form a compound of general formula (XXVII) or coupled with and amine of general formula (VI) in the presence of a base like for example lithium bis(trimethylsilyl)amide, in a solvent like for example THF, resulting in a compound of general formula (XXX). The compound of general formula (XXVII) can be alkylated for example with an alkylbromide, followed by a coupling with and amine of general formula (VI) in the presence of a base like for example lithium bis(trimethylsilyl)-amide, in a solvent like for example THF, resulting in a compound of general formula (Ib), wherein Y represents an alkanediyl and Z a single bond. Compound of general formula (XXX) can be hydrogenated to a compound of general formula (Id), wherein Y represents an alkanediyl and Z a single bond. A compound of general formula (XXVII) can be coupled with an amine of general formula (VI) in the presence of a base like for example lithium bis(trimethylsilyl)amide, in a solvent like for example THF, resulting in a compound of general formula (Id), wherein Y** represents an alkanediyl and Z a single bond.

Scheme 4
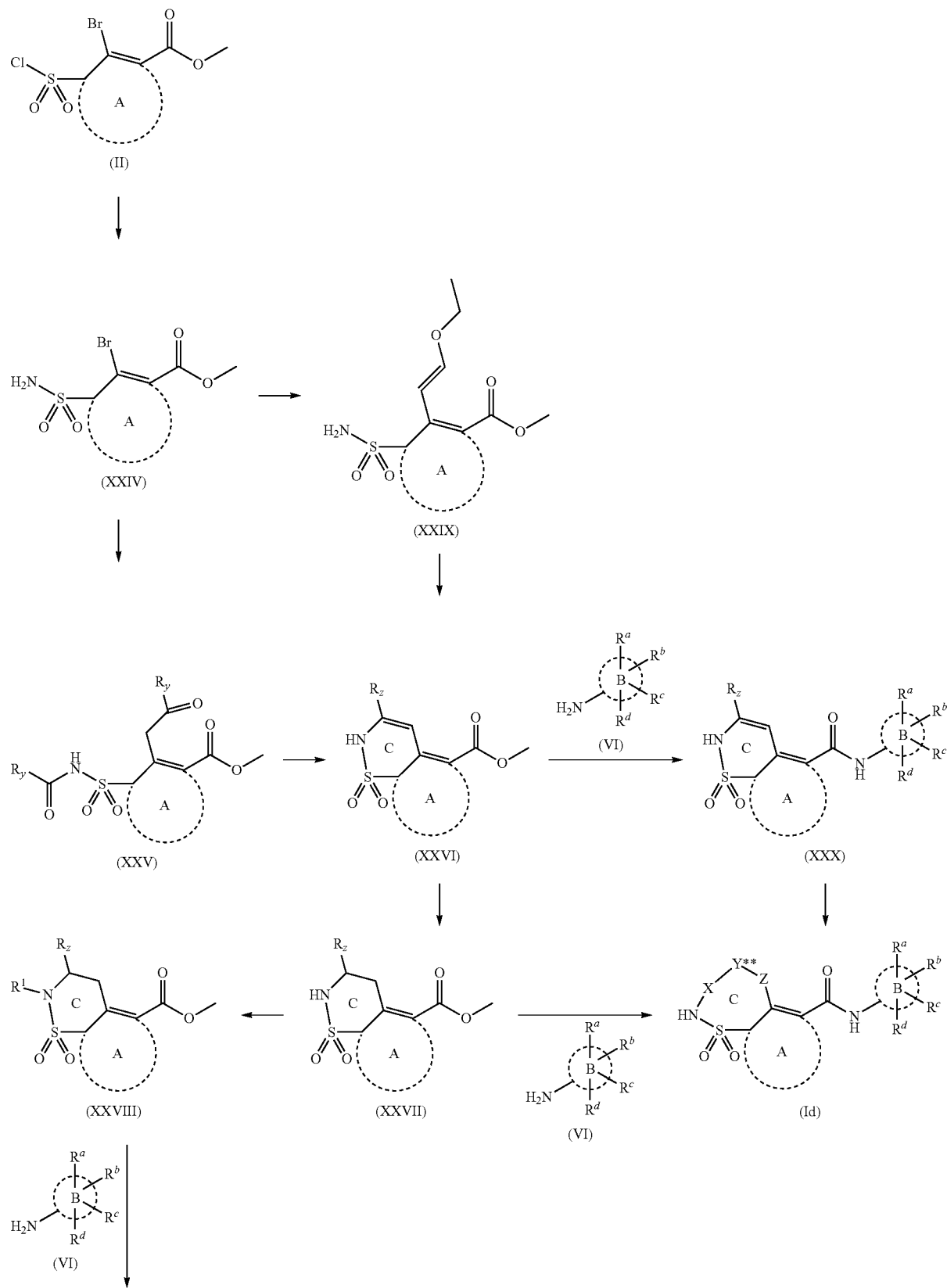

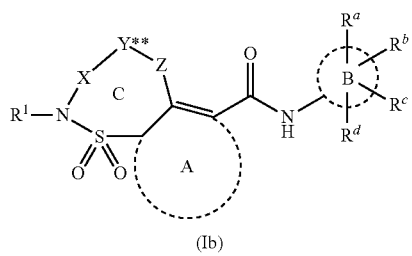

(Ib)

Alternatively, as described in Scheme 5, a compound of formula (XXXV) can be reacted with a compound of general formula (XXXVI), wherein X has the meaning as defined in the claims, for example a $C_1$-$C_6$alkanediyl optionally being substituted with one or more substituents each independently selected from the group consisting of —OH, Fluoro, and oxo, for example in a solvent like DMF under Suzuki conditions with a ligand like bis(tri-tert-butylphosphine)palladium(0) in the presence of an organic base like Hunigs' base. The formed compound of general formula (XXXVII) can be reduced under catalytic conditions using palladium on carbon under a hydrogen gas atmosphere. The formed compound of general formula (XXXVIII) can be deprotected with a reagent like ethylenediamine in a solvent like n-butanol to form a compound of general formula (XXXIX). A compound of general formula (XXXIX) can be chlorosulfonated in the presence of chlorosulfonic acid and thionyl chloride and then ring closed via quenching in a saturated aqueous solution of an inorganic base like $NaHCO_3$ or $Na_2CO_3$ to a compound of general formula (XXXX) wherein Y** represents an alkanediyl and Z a single bond. Compound of general formula (XXXX) can be reacted with an amine of general formula (VI) in the presence of a base like for example lithium bis(trimethylsilyl)amide, in a solvent like for example THF, resulting in the formation of a compound of general formula (Ib).

Scheme 5

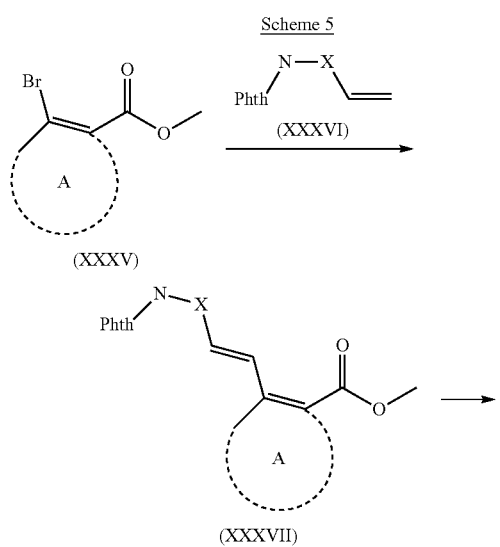

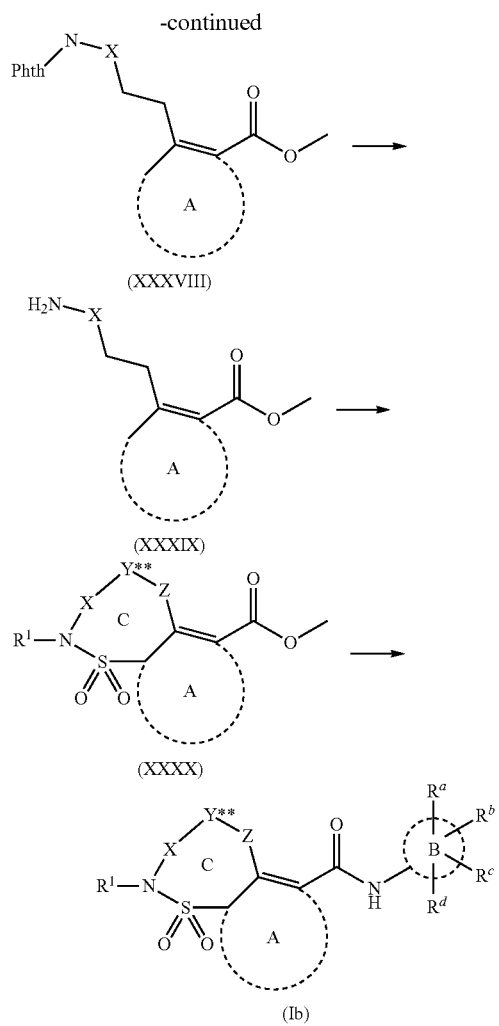

Alternatively, as described in Scheme 6, a compound of formula (XXXXI) can be reacted with a compound of general formula (XXXXII), wherein X has the meaning as defined in the claims, for example a $C_1$-$C_6$alkanediyl optionally being substituted with one or more substituents each independently selected from the group consisting of —OH, Fluoro, and oxo, for example in a solvent like ACN in the presence of an organic base like Hunigs' base. The formed compound of general formula (XXXXIII) can be ring closed via Mitsunobu conditions. After deprotection of the formed compound of general formula (XXXXIV) and reaction with an amine of general formula (VI) in the presence of a base like for example lithium bis(trimethylsilyl)amide, in a solvent like for example THF, a compound of general formula (Ic) can be formed.

Scheme 6

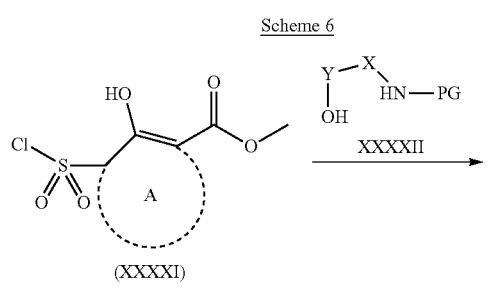

(XXXXI)

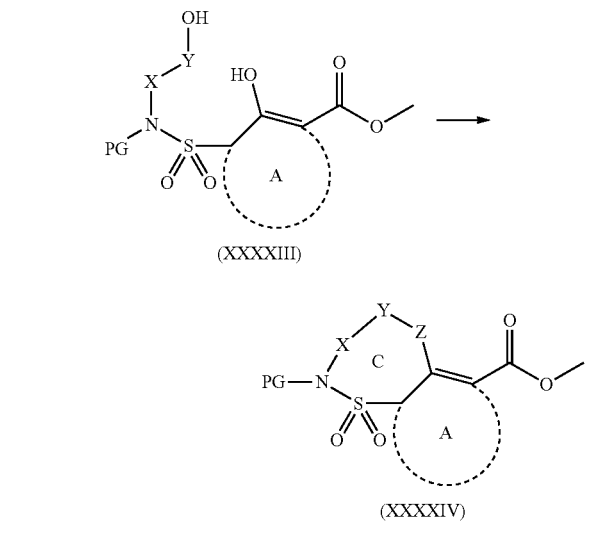

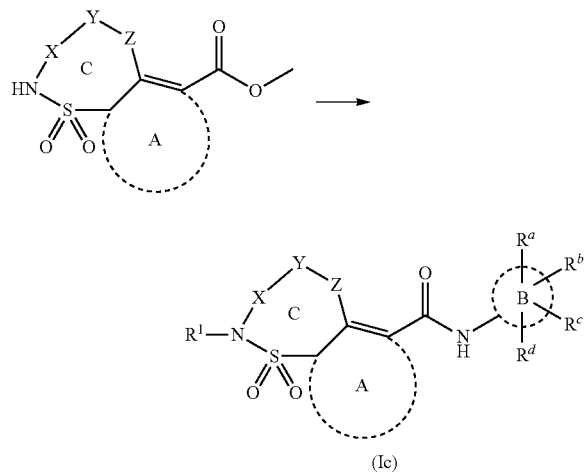

Alternatively, as described in Scheme 7, a compound of formula (XXXXV) can be reacted with a compound of general formula (XXXXVI), for example in a solvent like dioxane in the presence of silver carbonate. The tert-butyl ester of the formed compound of general formula (XXXXVII) can be cleaved using TFA in a solvent like DCM. Consecutive esterification in a solvent like DMF with methyliodide in the presence of an inorganic base like $Cs_2CO_3$ can result in a compound of general formula (XXXXVIII). A compound of general formula (XXXXVIII) can be chlorosulfonated in the presence of chlorosulfonic acid and thionyl chloride and then ring closed via quenching in a saturated aqueous solution of an inorganic base like $NaHCO_3$ or $Na_2CO_3$. The resulting compound of formula (XXXXIX) can be reacted with a Grignard reagent like methylmagnesium bromide in a solvent like THF to form a compound of general formula (XXXXX) The formed compound of general formula) (XXXXX) can be reacted with an amine of general formula (VI) in the presence of a base like for example lithium bis(trimethylsilyl)amide, in a solvent like for example THF, resulting in the formation of a compound of general formula (XXXXXI).

Scheme 7

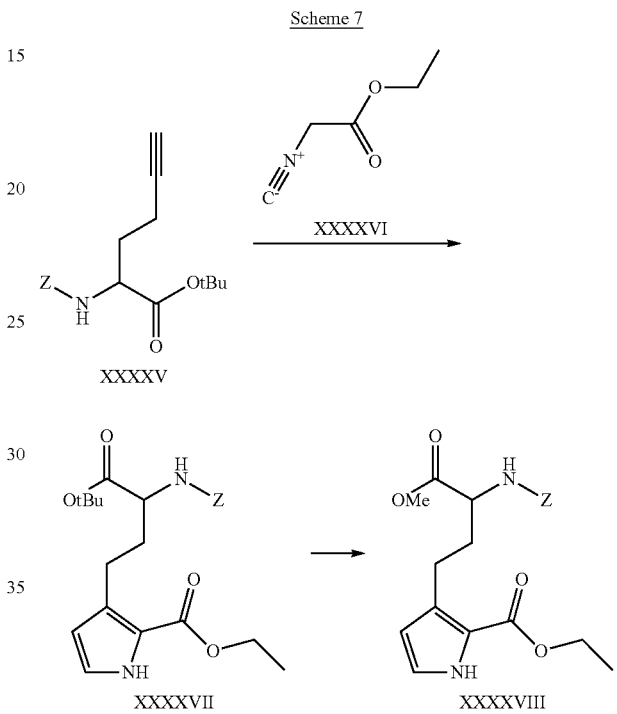

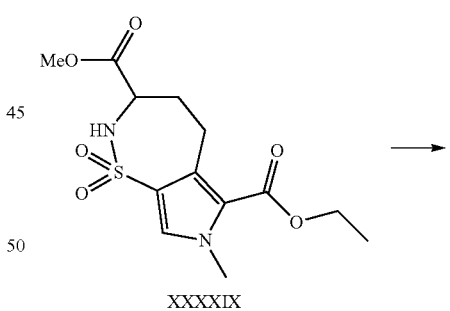

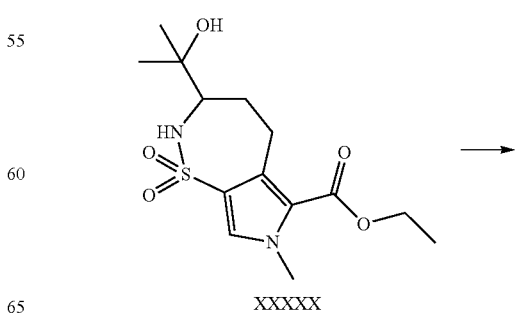

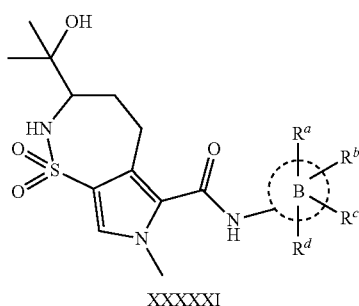

XXXXXI

General Procedure LCMS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the [M+H]$^+$ (protonated molecule) and/or [M−H]$^−$ (deprotonated molecule). In case the compound was not directly ionizable the type of adduct is specified (i.e. [M+NH$_4$]$^+$, [M+HCOO]$^−$, etc. . . . ). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof" Quadrupole Time-of-flight mass spectrometers, "CLND", ChemiLuminescent Nitrogen Detector, "ELSD" Evaporative Light Scanning Detector, LCMS Methods (Flow expressed in mL/min; column temperature (T) in ° C.; Run time in minutes).

| Method code | Instrument | Column | Mobile phase | Gradient | Flow / Col T | Run time |
|---|---|---|---|---|---|---|
| A | Waters: Acquity ® UPLC ® - DAD and SQD | Waters: HSS T3 (1.8 µm, 2.1*100 mm) | A: 10 mM CH3COONH4 in 95% H2O + 5% CH3CN B: CH3CN | From 100% A to 5% A in 2.10 min, to 0% A in 0.90 min, to 5% A in 0.5 min | 0.8 55 | 3.5 |
| B | Waters: Acquity ® UPLC ® - DAD and SQD | Waters: BEH C18 (1.7 µm, 2.1*50 mm) | A: 10 mM CH3COONH4 in 95% H2O + 5% CH3CN B: CH3CN | From 95% A to 5% A in 1.3 min, held for 0.7 min. | 0.8 55 | 2 |
| C | Waters: Acquity ® UPLC ® - DAD and SQD | Waters: HSS T3 (1.8 µm, 2.1*100 mm) | A: 10 mM CH3COONH4 in 95% H2O + 5% CH3CN B: CH3CN | From 95% A to 0% A in 2.5 min, to 5% A in 0.5 min | 0.8 55 | 3 |
| D | Waters: Acquity ® UPLC ® - DAD and SQD | Waters: HSS T3 (1.8 µm, 2.1*100 mm) | A: 10 mM CH3COONH4 in 95% H2O + 5% CH3CN B: CH3CN | From 100% A to 5% A in 2.10 min, to 0% A in 0.90 min, to 5% A in 0.5 min | 0.7 55 | 3.5 |
| Z | Waters: Alliance ®- DAD - ZMD and CLND 8060 Antek | Atlantis T3 column (5 µm, 4.6 × 100 mm) | A: 70% CH3OH, 30% H2O B: 0.1 formic acid in H2O/ CH3OH 95/5 | 100% B to 5% B in 9 min, hold 3.0 min to 100% B in 1 min and hold 0.5 min | 1.5 45 | 13.5 |

General Procedure for SFC-MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC-MS Methods (Flow expressed in mL/min; column temperature (T) in ° C.; Run time in minutes, Backpressure (BPR) in bars).

| Method code | column | mobile phase | gradient | Flow / Col T | Run time / BPR |
|---|---|---|---|---|---|
| E | Daicel Chiralpak ® AD-H column (5.0 μm, 250 × 4.6 mm) | A: $CO_2$<br>B: EtOH + 0.2% $iPrNH_2$ | 25% B hold 4 min, to 50% in 1 min hold 2 min | 5 / 40 | 7 / 110 |
| F | Daicel Chiralpak ® AD-H column (5.0 μm, 250 × 4.6 mm) | A: $CO_2$<br>B: EtOH + 0.2% $iPrNH_2$ | 30% B hold 4 min, to 50% in 1 min hold 2 min | 5 / 40 | 7 / 110 |
| G | Whelk ®-O-(R,R) column (5.0 μm, 250 × 4.6 mm) | A: $CO_2$<br>B: MeOH + 0.2% $iPrNH_2$ | 35% B hold 4 min, to 50% in 1 min hold 2 min | 5 / 40 | 7 / 110 |
| H | Daicel Chiralpak ® AD-H column (5.0 μm, 250 × 4.6 mm) | A: $CO_2$<br>B: EtOH + 0.2% $iPrNH_2$ | 10% B hold 4 min, to 50% in 1 min hold 2 min | 5 / 40 | 7 / 110 |
| I | Daicel Chiralpak ® AD-H column (5.0 μm, 250 × 4.6 mm) | A: $CO_2$<br>B: EtOH + 0.2% $iPrNH_2$ | 20% B hold 4 min, to 50% in 1 min hold 2 min | 5 / 40 | 7 / 110 |
| J | Daicel Chiralpak ® AD-H column (5.0 μm, 250 × 4.6 mm) | A: $CO_2$<br>B: EtOH + 0.2% $iPrNH_2$ | 45% B hold 4 min, to 50% in 1 min hold 2 min | 5 / 40 | 7 / 110 |
| K | Daicel Chiralpak ® AD-H column (5.0 μm, 250 × 4.6 mm) | A: $CO_2$<br>B: EtOH + 0.2% $iPrNH_2$ | 40% B hold 4 min, to 50% in 1 min hold 2 min | 5 / 40 | 7 / 110 |
| L | Whelk ®-O-(R,R) column (5.0 μm, 250 × 4.6 mm) | A: $CO_2$<br>B: EtOH + 0.2% $iPrNH_2$ | 40% B hold 4 min, to 50% in 1 min hold 2 min | 5 / 40 | 7 / 110 |
| M | Whelk ®-O-(R,R) column (5.0 μm, 250 × 4.6 mm) | A: $CO_2$<br>B: iPrOH + 0.2% $iPrNH_2$ | 40% B hold 4 min, to 50% in 1 min hold 2 min | 5 / 40 | 7 / 110 |
| N | Daicel Chiralpak ® AD-H column (5.0 μm, 250 × 4.6 mm) | A: $CO_2$<br>B: EtOH + 0.2% $iPrNH_2$ | 35% B hold 4 min, to 50% in 1 min hold 2 min | 5 / 40 | 7 / 110 |
| O | Daicel Chiralpak ® ID-H column (5.0 μm, 250 × 4.6 mm) | A: $CO_2$<br>B: EtOH + 0.2% $iPrNH_2$ | 35% B hold 4 min, to 50% in 1 min hold 2 min | 5 / 40 | 7 / 110 |
| P | Daicel Chiralpak ® AD-H column (5.0 μm, 250 × 4.6 mm) | A: $CO_2$<br>B: EtOH-iPrOH + 0.2% $iPrNH_2$ | 35% B hold 4 min, to 50% in 1 min hold 2 min | 5 / 40 | 7 / 110 |
| Q | Daicel Chiralpak ® AD-H column (5.0 μm, 250 × 4.6 mm) | A: $CO_2$<br>B: EtOH + 0.2% $iPrNH_2$ | 5% B hold 4 min, to 50% in 1 min hold 2 min | 5 / 40 | 7 / 110 |
| R | Daicel Chiralpak ® AD3 column (3.0 μm, 150 × 4.6 mm) | A: $CO_2$<br>B: EtOH + 0.2% $iPrNH_2$ | 10%-50% B in 6 min, hold 3.5 min | 2.5 / 40 | 9.5 / 110 |
| S | Whelk ®-O-(R,R) column (5.0 μm, 250 × 4.6 mm) | A: $CO_2$<br>B: EtOH-iPrOH + 0.2% $iPrNH_2$ | 35% B hold 4 min, to 50% in 1 min hold 2 min | 5 / 40 | 7 / 110 |
| T | Daicel Chiralpak ® AS3 column (3.0 μm, 150 × 4.6 mm) | A: $CO_2$<br>B: EtOH + 0.2% $iPrNH_2$ + 3% $H_2O$ | 10%-50% B in 6 min, hold 3.5 min | 2.5 / 40 | 9.5 / 110 |
| U | Daicel Chiralpak ® ID-H column (3.0 μm, 150 × 4.6 mm) | A: $CO_2$<br>B: EtOH + 0.2% $iPrNH_2$ + 3% $H_2O$ | 10%-50% B in 6 min, hold 3.5 min | 2.5 / 40 | 9.5 / 110 |

| Method code | column | mobile phase | gradient | Flow Col T | Run time BPR |
|---|---|---|---|---|---|
| V | Daicel Chiralpak ® AD-H column (3.0 μm, 150 × 4.6 mm) | A: $CO_2$ B: MeOH + 0.2% $iPrNH_2$ + 3% $H_2O$ | 10%-50% B in 6 min, hold 3.5 min | 2.5 40 | 9.5 110 |
| W | Daicel Chiralpak ® AD-H column (3.0 μm, 150 × 4.6 mm) | A: $CO_2$ B: iPrOH + 0.2% $iPrNH_2$ + 3% $H_2O$ | 10%-50% B in 6 min, hold 3.5 min | 2.5 40 | 9.5 110 |
| X | Whelk ®-O- (R,R) column (5.0 μm, 250 × 4.6 mm) | A: $CO_2$ B: EtOH + 0.2% $iPrNH_2$ | 10%-50% B in 6 min, hold 3.5 min | 2.5 40 | 9.5 110 |
| Y | Daicel Chiralpak ® OD-H column (3.0 μm, 150 × 4.6 mm) | A: $CO_2$ B: EtOH + 0.2% $iPrNH_2$ + 3% $H_2O$ | 10%-50% B in 6 min, hold 3.5 min | 2.5 40 | 9.5 110 |
| AA | Daicel Chiralpak ® IC-H column (3.0 μm, 150 × 4.6 mm) | A: $CO_2$ B: EtOH + 0.2% $iPrNH_2$ + 3% $H_2O$ | 10%-50% B in 6 min, hold 3.5 min | 2.5 40 | 9.5 110 |
| AB | Daicel Chiralpak ® AS3 column (3.0 μm, 150 × 4.6 mm) | A: $CO_2$ B: MeOH + 0.2% $iPrNH_2$ | 10%-50% B in 6 min, hold 3.5 min | 2.5 40 | 9.5 110 |
| AC | Daicel Chiralpak ® AS3 column (3.0 μm, 150 × 4.6 mm) | A: $CO_2$ B: iPrOH + 0.2% $iPrNH_2$ | 10%-50% B in 6 min, hold 3.5 min | 2.5 40 | 9.5 110 |
| AD | Daicel Chiralpak ® AD-H column (3.0 μm, 150 × 4.6 mm) | A: $CO_2$ B: EtOH-iPrOH + 0.2% $iPrNH_2$ | 10%-50% B in 6 min, hold 3.5 min | 2.5 40 | 9.5 110 |

Melting points (MP) reported in ° C. are referring to the peak observed in differential scanning calorimetry (DSC): From 30 to 300° C. at 10° C./min.

Synthesis of Compounds

Compound 1: (9E)-N-(3,4-difluorophenyl)-4,14-dimethyl-2,2-dioxo-2λ[6]-thia-3,14-diazabicyclo[10.3.0]pentadeca-1(15),9,12-triene-13-carboxamide

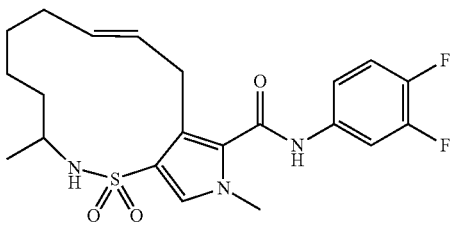 [SMILES: CC1CCCC/C=C/Cc2c(cn(C)c2C(=O)Nc2ccc(F)c(F)c2)S(=O)(=O)N1]

Methyl 3-bromo-4-chlorosulfonyl-1-methyl-pyrrole-2-carboxylate (500 mg, 1.58 mmol), oct-7-en-2-amine (221 mg, 1.74 mmol) and Hunig's base (0.82 mL, 0.75 g/mL, 4.74 mmol) were dissolved in THF (5 mL) and stirred overnight at room temperature. The volatiles were removed under reduced pressure and the residue was purified on silica using a heptane to EtOAc gradient yielding methyl 3-bromo-1-methyl-4-(1-methylhept-6-enylsulfamoyl)pyrrole-2-carboxylate (507 mg) as an oil which solidified on standing. $^1$H NMR (400 MHz, CHLOROFORM-d) δ ppm 1.09 (d, J=6.6 Hz, 3H), 1.22-1.36 (m, 4H), 1.37-1.50 (m, 2H), 1.89-2.06 (m, 2H), 3.11-3.38 (m, 1H), 3.91 (s, 3H), 3.92-3.95 (m, 3H), 4.53 (d, J=7.7 Hz, 1H), 4.89-5.01 (m, 2H), 5.76 (ddt, J=17.1, 10.3, 6.7, 6.7 Hz, 1H), 7.35 (s, 1H).

Methyl 3-bromo-1-methyl-4-(1-methylhept-6-enylsulfamoyl)pyrrole-2-carboxylate (100 mg, 0.25 mmol), potassium allyltrifluoroborate (109 mg, 0.74 mmol), bis(tri-tert-butylphosphine)palladium(0) (12.6 mg, 0.025 mmol) and $Cs_2CO_3$ (240 mg, 0.74 mmol) were dissolved in a mixture of DME (5 mL) and water (1 mL) and heated in the microwave oven at 120° C. for 30 minutes. The volatiles were removed under reduced pressure and the residue was purified on silica using a heptane to EtOAc gradient yielding methyl 3-allyl-1-methyl-4-(1-methylhept-6-enylsulfamoyl)pyrrole-2-carboxylate (62 mg) as a clear oil.

Methyl 3-allyl-1-methyl-4-(1-methylhept-6-enylsulfamoyl)pyrrole-2-carboxylate (62 mg, 0.17 mmol) was dissolved in DCE (50 mL) and heated to 80° C. while bubbling $N_2$ through the reaction mixture. Grubbs catalyst $2^{nd}$ generation (14.3 mg, 0.017 mmol) was added and heating was continued for 2 hours. The volatiles were removed under reduced pressure and the residue was purified on silica using a heptane to EtOAc gradient yielding methyl (9Z)-4,14-dimethyl-2,2-dioxo-2-thia-3,14-diazabicyclo-[10.3.0]pentadeca-1(15),9,12-triene-13-carboxylate (35 mg). Method B; Rt: 1.19 min. m/z: 341 (M+H)$^+$ Exact mass: 340.1.

Methyl (9Z)-4,14-dimethyl-2,2-dioxo-2-thia-3,14-diazabicyclo[10.3.0]pentadeca-1(15),9,12-triene-13-carboxylate (35 mg, 0.1 mmol) and 3,4-difluoroaniline (12.4 μL, 1.29 g/mL, 0.12 mmol) were dissolved in THF (5 mL). Lithium bis(trimethylsilyl)-amide (0.31 mL, 1 M in THF, 0.31 mmol) was added and the reaction mixture was stirred overnight at room temperature. The reaction mixture was quenched with $NH_4Cl$ (aq., sat., 5 mL). The organic layer was removed and the aqueous layer extracted with DCM (2×5 mL). The combined organic layers were evaporated to dryness and the residue purified on silica using a heptane to EtOAc gradient. The obtained product was crystallized from a DCM:DIPE mixture yielding compound 1 as an off-white powder. $^1$H NMR (600 MHz, CHLOROFORM-d) δ ppm 1.15-1.21 (m, 1H) 1.22 (d, J=6.5 Hz, 3H) 1.23-1.30 (m, 1H) 1.41-1.49 (m, 3H) 1.66-1.73 (m, 1H) 2.02-2.10 (m, 1H) 2.32 (br d, J=13.5 Hz, 1H) 3.27 (dt, J=12.3, 6.2 Hz, 1H) 3.64 (br d, J=18.5 Hz, 1H) 3.85 (br dd, J=18.3, 5.0 Hz, 1H) 3.91 (s, 3H) 4.24 (d, J=6.2 Hz, 1H) 5.28-5.36 (m, 1H) 5.93 (br d, J=15.6 Hz, 1H) 7.01-7.06 (m, 1H) 7.06-7.12 (m, 1H) 7.31 (s, 1H) 7.58 (ddd, J=12.0, 7.1, 2.6 Hz, 1H) 7.94 (br s, 1H). Method B; Rt: 1.17 min. m/z: 438 (M+H)$^+$ Exact mass: 437.2.

Compounds 2a and 2b: 8Z—N-(3,4-difluorophenyl)-4,13-dimethyl-2,2-dioxo-2λ$^6$-thia-3,13-diazabicyclo[9.3.0]tetradeca-1(14),8,11-triene-12-carboxamide and 8E-N-(3,4-difluorophenyl)-4,13-dimethyl-2,2-dioxo-2λ$^6$-thia-3,13-diazabicyclo[9.3.0]tetradeca-1(14),8,11-triene-12-carboxamide

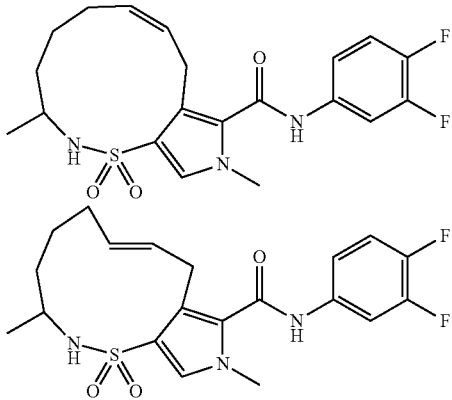

Methyl 3-bromo-1-methyl-4-(1-methylhept-6-enylsulfamoyl)pyrrole-2-carboxylate (420 mg, 1.03 mmol), potassium allyltrifluoroborate (458 mg, 3.09 mmol), bis(tri-tert-butylphosphine)palladium(0) (52.7 mg, 0.1 mmol) and Cs$_2$CO$_3$ (1008 mg, 3.09 mmol) were dissolved in a mixture of DME (5 mL) and water (1 mL) and heated in the microwave oven at 120° C. for 30 minutes. The volatiles were removed under reduced pressure and the residue was purified on silica using a heptane to EtOAc gradient yielding methyl 3-allyl-1-methyl-4-[[(E)-1-methylhept-5-enyl]sulfamoyl]pyrrole-2-carboxylate (258 mg) as a clear oil.

Methyl 3-allyl-1-methyl-4-[[(E)-1-methylhept-5-enyl]sulfamoyl]pyrrole-2-carboxylate (258 mg, 0.7 mmol) was dissolved in DCE (50 mL) and N$_2$ was bubbled through the reaction mixture. Grubbs catalyst 2$^{nd}$ generation (38.7 mg, 0.046 mmol) was added and the reaction mixture was heated for 5 hours. The volatiles were removed under reduced pressure and the residue was purified on silica using a heptane to EtOac gradient yielding methyl (8Z)-4,13-dimethyl-2,2-dioxo-2-thia-3,13-diazabicyclo[9.3.0]tetradeca-1(14),8,11-triene-12-carboxylate as an off-white powder.

Methyl (8Z)-4,13-dimethyl-2,2-dioxo-2-thia-3,13-diazabicyclo[9.3.0]tetradeca-1(14),-8,11-triene-12-carboxylate (22 mg, 0.067 mmol) and 3,4-difluoroaniline (8.2 µL, 1.29 g/mL, 0.081 mmol) were dissolved in THF (5 mL). Lithium bis(trimethylsilyl)-amide (1M in THF) (202 µL, 1 M in THF, 0.2 mmol) was added and the reaction mixture was stirred overnight at room temperature. The reaction mixture was quenched with NH4Cl (aq., sat., 5 mL). The organic layer was removed and the aqueous layer extracted with DCM (2×5 mL). The combined organic layers were evaporated to dryness and the residue purified on silica using a heptane to EtOAc gradient. The obtained product was purified via Prep HPLC (Stationary phase: RP XBridge Prep C18 ODB-5 µm, 30×250 mm, Mobile phase: 0.25% NH$_4$HCO$_3$ solution in water, ACN) yielding compound 2a (7.2 mg) $^1$H NMR (400 MHz, CHLOROFORM-d) δ ppm 1.30 (d, J=6.4 Hz, 3H), 1.36-1.48 (m, 4H), 1.84 (br dd, 5.1 Hz, 1H), 1.93-2.10 (m, 1H), 3.30-3.41 (m, 1H), 3.56-3.68 (m, 1H), 3.77-3.84 (m, 1H), 3.85 (s, 3H), 4.02-4.26 (m, 1H), 5.54-5.74 (m, 2H), 7.09-7.19 (m, 2H), 7.26 (s, 1H), 7.65-7.72 (m, 1H), 8.11 (br s, 1H). Method D; Rt: 2.05 min. m/z: 424 (M+H)$^+$ Exact mass: 423.1 and compound 2b (18.2 mg) $^1$H NMR (400 MHz, CHLOROFORM-d) δ ppm −0.05-0.05 (m, 1H), 1.25 (d, J=6.2 Hz, 3H), 1.36-1.45 (m, 1H), 1.47-1.65 (m, 3H), 2.00-2.27 (m, 2H), 3.05 (br s, 1H), 3.48-3.69 (m, 2H), 3.75-3.90 (m, 3H), 4.34 (br s, 1H), 5.34 (dt, J=15.6, 7.5 Hz, 1H), 5.84 (dt, J=15.7, 4.1 Hz, 1H), 7.08-7.22 (m, 2H), 7.63-7.72 (m, 1H), 7.91 (br s, 1H). Method D; Rt: 2.09 min. m/z: 424 (M+H)$^+$ Exact mass: 423.1.

Compound 3: (5Z)—N-(3,4-difluorophenyl)-8-methyl-1,1-dioxo-2-[(1R)-2,2,2-trifluoro-1-methylethyl]-3,4-dihydropyrrolo[3,4-g]thiazocine-7-carboxamide

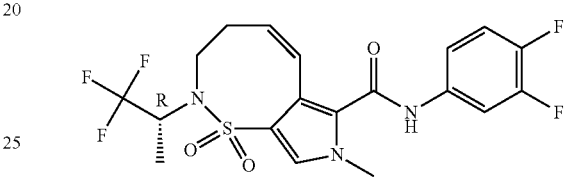

Methyl 3-bromo-4-chlorosulfonyl-1-methyl-pyrrole-2-carboxylate (5 g, 15.79 mmol), (R)-1,1,1-trifluoro-2-propylamine (2.68 g, 23.7 mmol), NaHCO$_3$ (3.98 g, 47.4 mmol) and molecular sieves (10 g) were dispensed in ACN (75 mL) in a 150 mL pressure vessel. This suspension was stirred overnight at 80° C. The reaction mixture was filtered and the volatiles were removed under reduced pressure. The residue was purified on silica using a heptane to EtOAc gradient. The fractions containing the product were evaporated to dryness yielding methyl 3-bromo-1-methyl-4-[[(1R)-2,2,2-trifluoro-1-methyl-ethyl]sulfamoyl]pyrrole-2-carboxylate (4.89 g) as a white powder.

Methyl 3-bromo-1-methyl-4-[[(1R)-2,2,2-trifluoro-1-methyl-ethyl]sulfamoyl]pyrrole-2-carboxylate (2 g, 5.09 mmol), potassium allyltrifluoroborate (2.26 g, 15.3 mmol), bis(tri-tert-butylphosphine)palladium(0) (260 mg, 0.51 mmol) and Cs$_2$CO$_3$ (4.97 g, 15.3 mmol) were dissolved in a mixture of DME (15 mL) and water (3 mL) and heated in the microwave oven at 100° C. for 30 minutes. The volatiles were removed under reduced pressure and the residue was purified on silica using a heptane to EtOAc gradient yielding methyl 1-methyl-3-[(E)-prop-1-enyl]-4-[[(1R)-2,2,2-trifluoro-1-methyl-ethyl]sulfamoyl]pyrrole-2-carboxylate (1.18 g) as a light brown powder.

Methyl 1-methyl-3-[(E)-prop-1-enyl]-4-[[(1R)-2,2,2-trifluoro-1-methyl-ethyl]-sulfamoyl]pyrrole-2-carboxylate (1.18 g, 3.33 mmol) and 3,4-difluoroaniline (404 µL, 1.29 g/mL, 4 mmol) were dissolved in THF (25 mL). Lithium bis(trimethylsilyl)amide (10 mL, 1 M in THF, 10 mmol) was added and the reaction mixture was stirred overnight at room temperature. The reaction mixture was quenched with NH$_4$Cl (aq., sat., 10 mL). The organic layer was removed and the aqueous layer extracted with DCM (2×5 mL). The combined organic layers were evaporated to dryness and the residue purified on silica using a heptane to EtOAc gradient yielding N-(3,4-difluoro-phenyl)-1-methyl-3-[(E)-prop-1- enyl]-4-[[(1R)-2,2,2-trifluoro-1-methyl-ethyl]sulfamoyl]
pyrrole-2-carboxamide (1.08 g) as a brown powder.

DIAD (0.12 mL, 1.04 g/mL, 0.6 mmol) was added to a solution of N-(3,4-difluoro-phenyl)-1-methyl-3-[(E)-prop-1-enyl]-4-[[(1R)-2,2,2-trifluoro-1-methyl-ethyl]sulfamoyl]pyrrole-2-carboxamide (180 mg, 0.4 mmol), 3-buten-1-ol (31.6 mg, 0.44 mmol) and triphenylphosphine (157 mg, 0.6 mmol) in THF (5 mL). The reaction mixture was stirred overnight at room temperature. LCMS showed 60% conversion to the desired product. 3-buten-1-ol (31.6 mg, 0.44 mmol), triphenylphosphine (157 mg, 0.6 mmol) and DIAD (0.12 mL, 1.04 g/mL, 0.6 mmol) were added and the reaction mixture was stirred for 1 hour. The volatiles were removed under reduced pressure and the residue was purified on silica using a heptane to EtOAc gradient yielding 4-[but-3-enyl-[(1R)-2,2,2-trifluoro-1-methyl-ethyl]sulfamoyl]-N-(3,4-difluorophenyl)-1-methyl-3-[(E)-prop-1-enyl]pyrrole-2-carboxamide (120 mg) as a clear oil.

4-[but-3-enyl-[(1R)-2,2,2-trifluoro-1-methyl-ethyl]sulfamoyl]-N-(3,4-difluorophenyl)-1-methyl-3-[(E)-prop-1-enyl]pyrrole-2-carboxamide (120 mg, 0.24 mmol) was dissolved in DCE (150 mL) and N$_2$ was bubbled through the reaction mixture. Grubbs catalyst 2$^{nd}$ generation (20.2 mg, 0.024 mmol) was added and the reaction mixture was heated at 80° C. overnight. The volatiles were removed under reduced pressure and the residue was purified on silica using a heptane to EtOAc gradient yielding compound 3 (92 mg) as a white powder. $^1$H NMR (400 MHz, CHLOROFORM-d) δ ppm 1.37 (br d, J=7.0 Hz, 3H), 2.39 (br s, 2H), 3.49-3.61 (m, 2H), 3.99 (s, 3H), 4.71 (dt, 7.6 Hz, 1H), 6.24 (dt, J=10.6, 8.8 Hz, 1H), 6.75 (d, J=10.8 Hz, 1H), 7.07-7.17 (m, 2H), 7.30 (s, 1H), 7.60-7.70 (m, 2H); Method B; Rt: 1.13 min. m/z: 464 (M+H)$^+$ Exact mass: 463.1.

Compound 4: N-(3,4-difluorophenyl)-8-methyl-1,1-dioxo-2-[(1R)-2,2,2-trifluoro-1-methyl-ethyl]-3,4,5,6-tetrahydropyrrolo[3,4-g]thiazocine-7-carboxamide

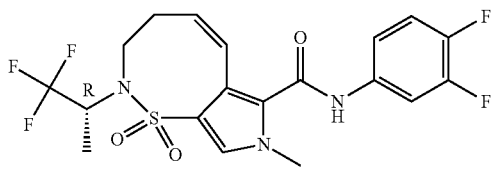

Compound 3 (80 mg, 0.17 mmol) was dissolved in MeOH (20 mL), Pd/C (10%) (18 mg, 0.017 mmol) was added and the reaction mixture was stirred overnight under a hydrogen atmosphere. The volatiles were removed under reduced pressure and the residue was purified on silica using a heptane to EtOac gradient yielding compound 4 (63.1 mg) as a white powder after crystallisation from DCM:DIPE. $^1$H NMR (400 MHz, CHLOROFORM-d) δ ppm 1.36 (d, J=7.0 Hz, 3H), 1.63-1.73 (m, 2H), 1.73-1.86 (m, 2H), 3.13-3.34 (m, 2H), 3.51-3.60 (m, 2H), 3.84 (s, 3H), 4.76 (dt, J=15.1, 7.5 Hz, 1H), 7.08-7.20 (m, 3H), 7.53 (s, 1H), 7.67 (ddd, J=12.0, 7.2, 2.4 Hz, 1H); Method B; Rt: 1.18 min. m/z: 466 (M+H)$^+$ Exact mass: 465.1; MP: 137.3° C.

Compound 5: (4Z)—N-(3,4-difluorophenyl)-3,8-dimethyl-1,1-dioxo-3,6-dihydro-2H-pyrrolo[3,4-g]thiazocine-7-carboxamide

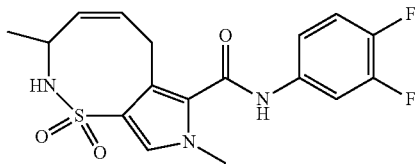 [SMILES: CC1/C=C\Cc2c(cn(C)c2C(=O)Nc2ccc(F)c(F)c2)S(=O)(=O)N1]

Methyl 3-bromo-4-chlorosulfonyl-1-methyl-pyrrole-2-carboxylate (1000 mg, 3.16 mmol) and 3-buten-2-amine, hydrochloride (374 mg, 3.47 mmol) were dissolved in THF (5 mL). Hunig's base (1.63 mL, 0.75 g/mL, 9.48 mmol) was added and the reaction mixture was stirred overnight at room temperature. NH$_4$Cl (sat., aq., 5 mL) was added and the organic layer was removed. The aqueous layer was extracted with DCM (2×5 mL) and the combined organic layers were evaporated to dryness. The residue was purified on silica using a heptane to EtOAc gradient yielding methyl 3-bromo-1-methyl-4-(1-methylallylsulfamoyl)pyrrole-2-carboxylate (981 mg) as a white powder.

Methyl 3-bromo-1-methyl-4-(1-methylallylsulfamoyl)pyrrole-2-carboxylate (200 mg, 0.57 mmol), potassium allyltrifluoroborate (253 mg, 1.71 mmol), bis(tri-tert-butylphosphine)palladium(0) (29 mg, 0.057 mmol) and Cs$_2$CO$_3$ (557 mg, 1.71 mmol) were dissolved in a mixture of DME (5 mL) and water (1 mL) and heated in the microwave oven at 80° C. for 30 minutes. The volatiles were removed under reduced pressure and the residue was purified on silica using a heptane to EtOAc gradient yielding methyl 3-allyl-1-methyl-4-(1-methylallylsulfamoyl)pyrrole-2-carboxylate (47 mg) and methyl 3,7-di methyl-1,1-dioxo-2,3-dihydropyrrolo[3,4-f]thiazepine-6-carboxylate (79 mg).

Methyl 3-allyl-1-methyl-4-(1-methylallylsulfamoyl)pyrrole-2-carboxylate (47 mg, 0.15 mmol) was dissolved in DCE (100 mL) and N$_2$ was bubbled through the reaction mixture. Grubbs catalyst 2$^{nd}$ generation (26 mg, 0.03 mmol) was added and the reaction mixture was heated at 80° C. overnight. The volatiles were removed under reduced pressure and the residue was purified on silica using a heptane to EtOAc gradient yielding methyl (4Z)-3,8-dimethyl-1,1-dioxo-3,6-dihydro-2H-pyrrolo[3,4-g]thiazocine-7-carboxylate (31 mg).

Methyl (4Z)-3,8-dimethyl-1,1-dioxo-3,6-dihydro-2H-pyrrolo[3,4-g]thiazocine-7-carboxylate (31 mg, 0.11 mmol) and 3,4-difluoroaniline (13.2 μL, 1.29 g/mL, 0.13 mmol) were dissolved in THF (5 mL). Lithium bis(trimethylsilyl)amide (0.33 mL, 1 M in THF, 0.33 mmol) was added and the reaction mixture was stirred overnight at room temperature. The reaction mixture was quenched with NH$_4$Cl (aq., sat., 5 mL). The organic layer was removed and the aqueous layer extracted with DCM (2×5 mL). The combined organic layers were evaporated to dryness and the residue purified on silica using a heptane to EtOAc gradient. The obtained product was purified via prep. HPLC (Stationary phase: RP XBridge Prep C18 OBD-10 μm, 30×150 mm, Mobile phase: 0.25% NH$_4$HCO$_3$ solution in water, MeOH) yielding compound 5 (9.7 mg) as a white powder. $^1$H NMR (400 MHz, DMSO-d$_6$) δ ppm 1.23 (d, J=6.8 Hz, 3H), 3.16-3.29 (m, 1H), 3.58 (dd, J=13.5, 10.2 Hz, 1H), 3.68 (s, 3H), 4.37-4.48 (m, 1H), 5.30 (dd, J=10.0, 7.6 Hz, 1H), 5.69 (q, J=9.1 Hz, 1H), 7.28 (br d, J=9.9 Hz, 1H), 7.39 (s, 1H), 7.40-7.46 (m, 2H), 7.81-7.90 (m, 1H), 10.56 (s, 1H); Method B; Rt: 0.97 min. m/z: 382 (M+H)+ Exact mass: 381.1.

Compound 6: N-(3,4-difluorophenyl)-7-methyl-1,1-dioxo-2-[(1R)-2,2,2-trifluoro-1-methyl-ethyl]-3H-pyrrolo[3,4-f]thiazepine-6-carboxamide

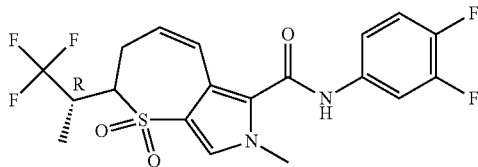

DIAD (0.16 mL, 1.04 g/mL, 0.8 mmol) was added to a solution of N-(3,4-difluoro-phenyl)-1-methyl-3-[(E)-prop-1-enyl]-4-[[(1R)-2,2,2-trifluoro-1-methyl-ethyl]sulfamoyl] pyrrole-2-carboxamide (180 mg, 0.4 mmol), 2-propen-1-ol (25.5 mg, 0.44 mmol) and triphenylphosphine (209 mg, 0.8 mmol) in THF (5 mL). The reaction mixture was stirred overnight at room temperature. The volatiles were removed under reduced pressure and the residue was purified on silica using a heptane to EtOAc gradient. The obtained residue was purified via prep. HPLC (Stationary phase: RP XBridge Prep C18 OBD-10 μm, 30×150 mm, Mobile phase: 0.25% NH4HCO3 solution in water, MeOH) yielding 4-[allyl-[(1R)-2,2,2-trifluoro-1-methyl-ethyl]sulfamoyl]-N-(3,4-difluoro-phenyl)-1-methyl-3-[(E)-prop-1-enyl]pyrrole-2-carboxamide (81 mg). 4-[allyl-[(1R)-2,2,2-trifluoro-1-methyl-ethyl]sulfamoyl]-N-(3,4-difluorophenyl)-1-methyl-3-[(E)-prop-1-enyl]pyrrole-2-carboxamide (81 mg, 0.16 mmol) was dissolved in DCE (100 mL) and N2 was bubbled through the reaction mixture. Grubbs catalyst 2nd generation (28 mg, 0.033 mmol) was added and the reaction mixture was heated at 80° C. overnight. The volatiles were removed under reduced pressure and the residue was purified via prep. HPLC (Stationary phase: RP)(Bridge Prep C18 OBD-10 μm, 30×150 mm, Mobile phase: 0.25% NH4HCO3 solution in water, MeOH) yielding compound 6 (50.1 mg) as a white powder after crystallization from DCM:DIPE. 1H NMR (360 MHz, DMSO-d6) δ ppm 1.17 (d, J=7.0 Hz, 3H), 3.74 (s, 3H), 4.10 (dd, J=21.2, 4.8 Hz, 1H), 4.28-4.37 (m, 1H), 4.37-4.45 (m, 1H), 5.68-5.75 (m, 1H), 6.57 (br d, J=12.8 Hz, 1H), 7.40-7.49 (m, 2H), 7.67 (s, 1H), 7.81-7.89 (m, 1H), 10.76 (s, 1H); Method B; Rt: 1.13 min. m/z: 450 (M+H)+ Exact mass: 449.1.

Compound 7: N-(3,4-difluorophenyl)-3,7-dimethyl-1,1-dioxo-2,3-dihydropyrrolo-[3,4-f]thiazepine-6-carboxamide

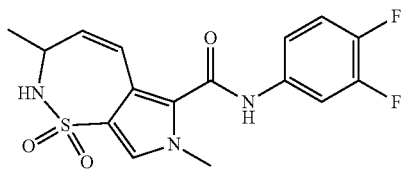 [SMILES: CC1C=Cc2c(cn(C)c2C(=O)Nc2ccc(F)c(F)c2)S(=O)(=O)N1]

Methyl 3,7-dimethyl-1,1-dioxo-2,3-dihydropyrrolo[3,4-f] thiazepine-6-carboxylate (79 mg, 0.29 mmol) and 3,4-difluoroaniline (36 μL, 1.29 g/mL, 0.35 mmol) were dissolved in THF (5 mL). Lithium bis(trimethylsilyl)amide (0.88 mL, 1 M in THF, 0.88 mmol) was added and the reaction mixture was stirred overnight at room temperature. The reaction mixture was quenched with NH4Cl (aq., sat., 5 mL). The organic layer was removed and the aqueous layer extracted with DCM (2×5 mL). The combined organic layers were evaporated to dryness and the residue purified on silica using a heptane to EtOAc gradient. The resulting product was purified via prep. HPLC (Stationary phase: RP XBridge Prep C18 ODB-5 μm, 30×250 mm, Mobile phase: 0.25% NH4HCO3 solution in water, ACN) yielding compound 7. 1H NMR (360 MHz, CHLOROFORM-d) δ ppm 1.41 (d, J=7.3 Hz, 3H), 3.71 (q, J=7.0 Hz, 1H), 3.76 (s, 3H), 4.40 (br s, 1H), 5.61 (dd, J=12.4, 2.6 Hz, 1H), 6.53 (dd, J=12.4, 2.2 Hz, 1H), 7.10-7.26 (m, 3H), 7.71 (ddd, J=12.0, 7.2, 2.4 Hz, 1H), 8.20 (br s, 1H); Method D; Rt: 1.72 min. m/z: 368 (M+H)+ Exact mass: 367.1. This racemic mixture was separated in enantiomers 7a (19.5 mg) and 7b (13.4 mg) by preparative SFC (Stationary phase: Chiralpak Diacel AD 20×250 mm, Mobile phase: CO2, EtOH with 0.4% iPrNH2). Method E; Rt: 7a: 1.80 min, 7b: 2.33 min.

Compound 8: N-(3,4-difluorophenyl)-7-methyl-1,1-dioxo-3-(trifluoromethyl)-2,3-dihydropyrrolo[3,4-f] thiazepine-6-carboxamide

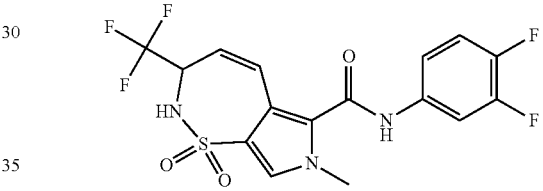

Methyl 3-bromo-4-chlorosulfonyl-1-methyl-pyrrole-2-carboxylate (1000 mg, 3.16 mmol), 1,1,1-trifluorobut-3-en-2-ylamine (612 mg, 3.79 mmol), NaHCO3 (1062 mg, 12.64 mmol) and molecular sieves (2 g) were dispensed in ACN (30 mL) and the reaction mixture was stirred 4 days at 80° C. The reaction mixture was filtered and the filtrate was evaporated to dryness. The residue was purified on silica using a heptane to EtOAc gradient yielding methyl 3-bromo-1-methyl-4-[1-(trifluoromethyl)-allylsulfamoyl]pyrrole-2-carboxylate (894 mg) as a white powder.

Methyl 3-bromo-1-methyl-4-[1-(trifluoromethyl)allylsulfamoyl]pyrrole-2-carboxylate (837 mg, 2.07 mmol), bis(tri-tert-butylphosphine)palladium(0) (211 mg, 0.41 mmol) and TEA (286 μL, 0.73 g/mL, 2.07 mmol) were dissolved in DMF (5 mL). The reaction mixture was heated in the microwave oven for 30 minutes at 120° C. The volatiles were removed under reduced pressure and the residue was purified on silica using a heptane to EtOac gradient yielding methyl 7-methyl-1,1-dioxo-3-(trifluoromethyl)-2,3-dihydropyrrolo[3,4-f]thiazepine-6-carboxylate (470 mg).

Methyl 7-methyl-1,1-dioxo-3-(trifluoromethyl)-2,3-dihydropyrrolo[3,4-f]thiazepine-6-carboxylate (470 mg, 1.45 mmol) and 3,4-difluoroaniline (176 μL, 1.29 g/mL, 1.74 mmol) were dissolved in THF (5 mL). Lithium bis(trimethylsilyl)amide (4.35 mL, 1 M in THF, 4.35 mmol) was added and the reaction mixture was stirred overnight at room temperature. The reaction mixture was quenched with NH4Cl (aq., sat., 5 mL). The organic layer was removed and the aqueous layer extracted with DCM (2×5 mL). The combined organic layers were evaporated to dryness and the residue purified via Prep HPLC (Stationary phase: RP XBridge Prep C18 OBD-10 μm, 30×150 mm, Mobile phase: 0.25% NH$_4$HCO$_3$ solution in water, MeOH) yielding compound 8 (28.1 mg) as a white powder. $^1$H NMR (360 MHz, DMSO-d$_6$) δ ppm 3.75 (s, 3H), 4.88 (br s, 1H), 5.80 (dd, J=12.2, 3.0 Hz, 1H), 6.77-6.83 (m, 1H), 7.41-7.49 (m, 2H), 7.73 (s, 1H), 7.81-7.89 (m, 1H), 8.64 (br d, J=10.1 Hz, 1H), 10.83 (s, 1H); Method D; Rt: 1.89 min. m/z: 420 (M−H)$^-$ Exact mass: 421.1; MP: 245.6° C.

Compound 9: N-(3,4-difluorophenyl)-7-methyl-1,1-dioxo-2,3-dihydropyrrolo[3,4-f]-thiazepine-6-carboxamide

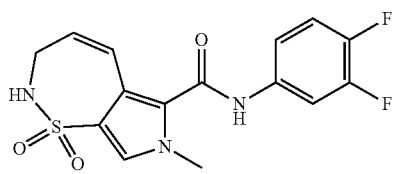 [SMILES: Cn1cc2c(c1C(=O)Nc1ccc(F)c(F)c1)C=CCNS2(=O)=O]

Methyl 3-bromo-4-chlorosulfonyl-1-methyl-pyrrole-2-carboxylate (500 mg, 1.58 mmol) and allylamine (223 mg, 3.79 mmol) were dissolved in THF (5 mL). Hunig's base (1.63 mL, 0.75 g/mL, 9.48 mmol) was added and the reaction mixture was stirred overnight at room temperature. NH$_4$Cl (sat., aq., 5 mL) was added and the organic layer was removed. The aqueous layer was extracted with DCM (2×5 mL) and the combined organic layers were evaporated to dryness. The residue was purified on silica using a heptane to EtOAc gradient yielding methyl 4-(allylsulfamoyl)-3-bromo-1-methyl-pyrrole-2-carboxylate (488 mg) as a white powder.

Methyl 4-(allylsulfamoyl)-3-bromo-1-methyl-pyrrole-2-carboxylate (430 mg, 1.28 mmol), bis(tri-tert-butylphosphine)palladium(0) (130 mg, 0.26 mmol) and TEA (177 μL, 0.73 g/mL, 1.28 mmol) were dissolved in DMF (5 mL) and heated in the microwave for 30 minutes at 140° C. The reaction mixture was directly purified via Prep HPLC (Stationary phase: RP XBridge Prep C18 OBD-10 μm, 30×150 mm, Mobile phase: 0.25% NH$_4$HCO$_3$ solution in water, ACN) yielding methyl 7-methyl-1,1-dioxo-2,3-dihydropyrrolo[3,4-f]thiazepine-6-carboxylate (75 mg).

Methyl 7-methyl-1,1-dioxo-2,3-dihydropyrrolo[3,4-f]thiazepine-6-carboxylate (75 mg, 0.29 mmol) and 3,4-difluoroaniline (36 μL, 1.29 g/mL, 0.35 mmol) were dissolved in THF (5 mL). Lithium bis(trimethylsilyl)amide (0.88 mL, 1 M in THF, 0.88 mmol) was added and the reaction mixture was stirred overnight at room temperature. The reaction mixture was quenched with NH$_4$Cl (aq., sat., 5 mL). The organic layer was removed and the aqueous layer extracted with DCM (2×5 mL). The combined organic layers were evaporated to dryness and the residue purified on silica using a heptane to EtOac gradient yielding compound 9 as a light brown powder after crystallization from a DCM:DIPE mixture. $^1$H NMR (360 MHz, DMSO-d$_6$) δ ppm 3.71 (s, 3H), 3.89 (ddd, J=6.4, 3.9, 1.8 Hz, 2H), 5.65 (dt, J=12.5, 4.0 Hz, 1H), 6.52 (dt, J=12.8, 1.7 Hz, 1H), 7.39-7.48 (m, 2H), 7.55 (s, 1H), 7.62 (t, J=6.5 Hz, 1H), 7.82-7.89 (m, 1H), 10.76 (s, 1H); Method B; Rt: 0.84 min. m/z: 352 (M−H)$^-$ Exact mass: 353.1; MP: 221.9° C.

Compound 10: N-(3,4-difluorophenyl)-3,7-dimethyl-1,1-dioxo-2,3,4,5-tetrahydropyrrolo[3,4-f]thiazepine-6-carboxamide

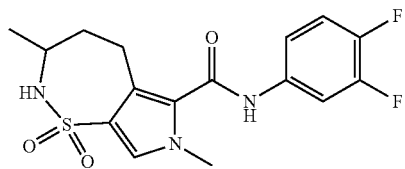 [SMILES: CC1CCc2c(cn(C)c2C(=O)Nc2ccc(F)c(F)c2)S(=O)(=O)N1]

Compound 7a (120 mg, 0.33 mmol) and Pd/C (10%) (35 mg, 0.033 mmol) were dispensed in MeOH (20 mL). The reaction mixture was set under a hydrogen atmosphere and stirred for 2 hours. The reaction mixture was filtered and evaporated to dryness yielding compound 10a (111 mg) as a white powder. $^1$H NMR (400 MHz, DMSO-d$_6$) δ ppm 1.13 (d, J=6.8 Hz, 3H), 1.23-1.40 (m, 1H), 1.84 (br dd, 6.5 Hz, 1H), 2.78-3.01 (m, 2H), 3.58-3.66 (m, 1H), 3.69 (s, 3H), 6.89-7.17 (m, 1H), 7.37-7.45 (m, 3H), 7.81-7.89 (m, 1H), 10.49 (br s, 1H); Method B; Rt: 0.90 min. m/z: 368 (M−H)$^-$ Exact mass: 369.1; MP: 231.6° C.

Compound 10b (35.6 mg) was prepared similarly as described for compound 10a, using compound 7b instead of compound 7a. $^1$H NMR (400 MHz, DMSO-d$_6$) δ ppm 1.13 (d, J=6.8 Hz, 3H), 1.29-1.40 (m, 1H), 1.84 (br dd, 6.5 Hz, 1H), 2.78-3.02 (m, 2H), 3.58-3.66 (m, 1H), 3.69 (s, 3H), 7.01 (br s, 1H), 7.36-7.44 (m, 3H), 7.81-7.88 (m, 1H), 10.48 (br s, 1H); Method B; Rt: 0.90 min. m/z: 368 (M−H)$^-$ Exact mass: 369.1; MP: 229.8° C.

Compound 11: N-(3,4-difluorophenyl)-3,6-dimethyl-1,1-dioxo-3,4-dihydro-2H-pyrrolo-[3,4-e]thiazine-5-carboxamide

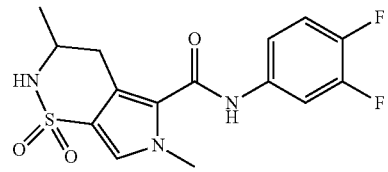 [SMILES: CC1Cc2c(cn(C)c2C(=O)Nc2ccc(F)c(F)c2)S(=O)(=O)N1]

Methyl 3-bromo-4-chlorosulfonyl-1-methyl-pyrrole-2-carboxylate (2.2 g, 6.95 mmol) was dissolved in ammonia (60 mL, 0.5 M in dioxane, 30 mmol). The reaction mixture was stirred at 4 days at room temperature. The volatiles were removed and the residue was dissolved in 2-Me-THF and washed with water. The organic layer was dried (MgSO$_4$), filtered, and evaporated to dryness to afford methyl 3-bromo-1-methyl-4-sulfamoyl-pyrrole-2-carboxylate (2 g) as a white powder. Method B; Rt: 0.55 min. m/z: 295 (M−H)$^-$ Exact mass: 296.

A mixture of methyl 3-bromo-1-methyl-4-sulfamoyl-pyrrole-2-carboxylate (1.20 g, 3.92 mmol), pentane-2,4-dione (1.18 g, 11.8 mmol), copper(I) iodide (74.6 mg, 0.39 mmol) and potassium phosphate tribasic (1.66 g, 7.83 mmol) in DMSO (18 mL) was stirred under a N$_2$ atmosphere at 90° C. overnight. The mixture was quenched with HCl (aq., 1M, 20 mL), the solution was extracted with EtOAc (3×50 mL). The organic layers were combined, dried over sodium sulfate and evaporated to dryness. The brown residue was purified using silica gel column chromatography (EtOAc in heptane from 0 to 100%) to afford methyl 3-acetonyl-4-(acetylsulfamoyl)-1-methyl-pyrrole-2-carboxylate (1.22 g) as light brown powder. Method B; Rt: 0.41 min. m/z: 315 (M−H)$^-$ Exact mass: 316.0.

Methyl 3-acetonyl-4-(acetylsulfamoyl)-1-methyl-pyrrole-2-carboxylate (1.22 g, 3.86 mmol) was dissolved in TFA and heated at reflux for 2 hours. The reaction mixture was concentrated. The residue was dissolved in DCM (20 mL) and washed with NaHCO$_3$ (aq., sat., 2×5 mL), dried (Na$_2$SO$_4$), filtered, the filtrate concentrated in vacuo and the crude residue was purified using silica gel column chromatography (EtOAc in heptane from 0 to 100%) to afford methyl 3,6-dimethyl-1,1-dioxo-2H-pyrrolo[3,4-e]thiazine-5-carboxylate (203 mg). $^1$H NMR (360 MHz, DMSO-d$_6$) δ ppm 2.02 (d, J=1.1 Hz, 3H), 3.81 (s, 3H), 3.92 (s, 3H), 6.24 (br s, 1H), 7.86 (s, 1H), 10.52 (br s, 1H); Method B; Rt: 0.59 min. m/z: 255 (M−H)$^-$ Exact mass: 256.0. To a solution of methyl 3,6-dimethyl-1,1-dioxo-2H-pyrrolo[3,4-e]thiazine-5-carboxylate (203 mg, 0.79 mmol) and 3,4-difluoroaniline (123 mg, 0.95 mmol) in THF (5 mL) was added lithium bis(trimethylsilyl)amide (3.17 mL, 1 M in THF, 3.17 mmol). The reaction mixture was stirred at room temperature for 40 minutes and quenched with NH$_4$Cl (aq., sat., 5 mL). The aqueous layer was extracted with DCM (3×50 mL). The combined organic layers were dried (Na$_2$SO$_4$), concentrated and the residue was purified on silica using a heptane to EtOAc gradient yielding a brown powder which was triturated in methanol. The precipitation was filtered and the solids were washed with methanol to afford N-(3,4-difluorophenyl)-3,6-dimethyl-1,1-dioxo-2H-pyrrolo-[3,4-e]thiazine-5-carboxamide (33 mg) as a white powder. Method B; Rt: 0.80 min. m/z: 354 (M+H)$^+$ Exact mass: 353.0.

N-(3,4-difluorophenyl)-3,6-dimethyl-1,1-dioxo-2H-pyrrolo[3,4-e]thiazine-5-carboxamide (33 mg, 0.093 mmol) was dissolved in THF (40 mL) and under a nitrogen atmosphere Pd/C (10%) (56 mg, 0.053 mmol) was added. The reaction mixture was hydrogenated for 1 hour. The reaction mixture was filtered over decalite. The filter was washed with THF (3×50 mL). The filtrate was evaporated to dryness and the residue was purified using silica gel column chromatography (EtOAc in heptane from 0 to 100%) to afford compound 11 (18 mg) as a white powder. $^1$H NMR (400 MHz, DMSO-d$_6$) δ ppm 1.26 (d, J=6.6 Hz, 3H), 2.51-2.58 (m, 1H), 2.83 (dd, 3.5 Hz, 1H), 3.55-3.70 (m, 1H), 3.77 (br s, 3H), 7.08 (br d, J=10.9 Hz, 1H), 7.37-7.46 (m, 2H), 7.61 (s, 1H), 7.77-7.85 (m, 1H), 10.15 (s, 1H); Method B; Rt: 0.87 min. m/z: 354 (M−H)$^-$ Exact mass: 355.0.

Compound 12: N-(3,4-difluorophenyl)-7-fluoro-3-methyl-1,1-dioxo-3,4-dihydro-2H-5,1λ$^6$,2-benzoxathiazepine-6-carboxamide

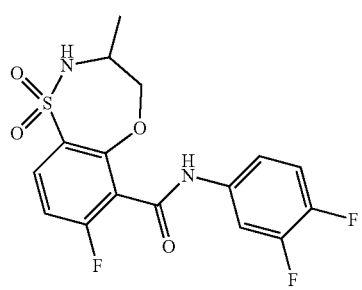 [SMILES: CC1COc2c(ccc(F)c2C(=O)Nc2ccc(F)c(F)c2)S(=O)(=O)N1]

Na$_2$CO$_3$ (2.06 g, 19.5 mmol) was dissolved in water (30 mL). To this was added DL-alaninol (2.93 g, 39.0 mmol) at once followed by THF (30 mL). The obtained solution was stirred and cooled in an ice bath. 3-(chlorosulfonyl)-2,6-difluorobenzoic acid (5.00 g, 19.5 mmol) was dissolved in THF (40 mL) and this was added drop wise to the stirring solution. The resulting mixture was stirred for 30 minutes while cooling was continued. Then the mixture was stirred for 3 hours at room temperature. The mixture was concentrated in vacuo until only water remained. Then 20 mL of water was added and the mixture was acidified with exactly 20 mL HCl (aq., 1M). This was extracted using 2-Me-THF (3×50 mL). The combined organics were washed with brine (50 mL), dried (Na$_2$SO$_4$), filtered and concentrated in vacuo yielding 2,6-difluoro-3-[(2-hydroxy-1-methyl-ethyl)sulfamoyl]benzoic acid as a yellow powder (4.9 g).

Method D; Rt: 0.75 min. m/z: 294 (M−H)$^-$ Exact mass: 295.0. 2,6-difluoro-3-[(2-hydroxy-1-methyl-ethyl)sulfamoyl]benzoic acid (1.00 g, 3.18 mmol), 3,4-difluoroaniline (623 mg, 4.78 mmol), HATU (1.33 mg, 3.5 mmol) and DIPEA (1.65 mL, 0.75 g/mL, 9.55 mmol) were dissolved in DMF (2 mL) and stirred at room temperature for 2 hours. This mixture was injected directly onto a silica plug and purified using silica gel column chromatography (gradient elution: EtOAc:heptane 0:100 to 100:0) yielding N-(3,4-difluorophenyl)-2,6-difluoro-3-[(2-hydroxy-1-methylethyl)sulfamoyl]benzamide (987 mg) as an oil.

N-(3,4-difluorophenyl)-2,6-difluoro-3-[(2-hydroxy-1-methyl-ethyl)sulfamoyl]-benzamide (887 mg, 2.18 mmol) in DMF (8 mL) was treated with NaH (437 mg, 60% dispersion in mineral oil, 10.9 mmol) at room temperature and this was stirred for 2 minutes. Then it was heated under microwave irradiation to 110° C. for 40 minutes. The reaction mixture was poured into ice water (100 mL) and this was extracted using EtOAc (3×100 mL). The combined extracts were washed with brine (100 mL), dried (Na$_2$SO$_4$), filtered and concentrated in vacuo. The crude was purified using silica gel column chromatography (gradient elution: EtOAc:heptane 0:100 to 30:70) yielding an oil which was crystallised out of boiling diisopropylether/acetonitrile yielding compound 12 (191 mg) as a white powder. $^1$H NMR (400 MHz, DMSO-d$_6$) δ ppm 1.10 (d, J=7.04 Hz, 3H) 3.66 (dd, J=12.32, 9.68 Hz, 1H) 3.77-3.88 (m, 1H) 4.45 (dd, J=12.43, 2.31 Hz, 1H) 7.32 (t, J=8.69 Hz, 1H) 7.35-7.50 (m, 2H) 7.79-7.91 (m, 3H) 10.97 (s, 1H); Method B; Rt: 0.89 min. m/z: 387 (M+H)$^+$ Exact mass: 386.1.

Compound 13: N-(3,4-difluorophenyl)-6-methyl-1,1-dioxo-3,4-dihydro-2H-pyrrolo-[3,4-e]thiazine-5-carboxamide

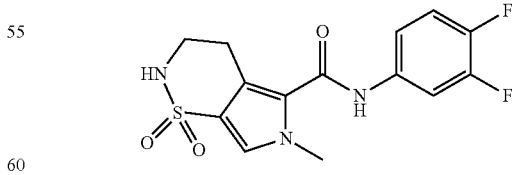

To a solution of methyl 3-bromo-1-methyl-4-sulfamoyl-pyrrole-2-carboxylate (300 mg, 0.98 mmol) in DMF (10 mL) was added (Z)-1-ethoxy-2-(tributylstannyl)ethene (490 µL, 1.08 g/mL, 1.47 mmol). The reaction mixture was purged with nitrogen for 5 minutes and bis(tri-tert-butylphosphine)palladium(0) (150 mg, 0.29 mmol) was added. The reaction mixture was heated at 140° C. for 20 minutes. The reaction mixture was poured into water and extracted with EtOAc (3×30 mL). The combined organic layers were washed with brine, dried (Na$_2$SO$_4$) and concentrated to give a brown oil. This oil was dissolved in acetonitrile and washed with heptane. The solution was concentrated to dryness to afford methyl 3-[(E)-2-ethoxyvinyl]-1-methyl-4-sulfamoyl-pyrrole-2-carboxylate (707 mg) as a brown oil. Method B; Rt: 0.63 min. m/z: 289 (M+H)$^+$ Exact mass: 288.0.

Methyl 3-[(Z)-2-ethoxyvinyl]-1-methyl-4-sulfamoyl-pyrrole-2-carboxylate (707 mg, 1.15 mmol) was dissolved TFA (5 mL) and stirred at room temperature for 1 hour. The reaction mixture was concentrated and dissolved in THF (50 mL) and concentrated to methyl 6-methyl-1,1-dioxo-2H-pyrrolo[3,4-e]thiazine-5-carboxylate (600 mg) as a brown oil. Method D; Rt: 1.10 min. m/z: 243 (M+H)$^+$ Exact mass: 242.0.

Methyl 6-methyl-1,1-dioxo-2H-pyrrolo[3,4-e]thiazine-5-carboxylate (70 mg, 0.29 mmol) was dissolved in THF (20 mL) and under a nitrogen atmosphere Pd/C (10%) (26.4 mg, 0.025 mmol) was added. The reaction mixture was hydrogenated for 18 hours. The reaction mixture was filtered over decalite. The filter was washed with THF (3×20 mL). The combined filtrates were evaporated to dryness. The residue was purified using silica gel column chromatography (EtOAc in heptane from 0 to 100%) to afford methyl 6-methyl-1,1-dioxo-3,4-dihydro-2H-pyrrolo[3,4-e]thiazine-5-carboxylate (73 mg) as a white powder. Method B; Rt: 0.62 min. m/z: 243 (M−H)$^-$ Exact mass: 244.0.

To a solution of methyl 6-methyl-1,1-dioxo-3,4-dihydro-2H-pyrrolo[3,4-e]thiazine-5-carboxylate (20 mg, 0.078 mmol) and 3,4-difluoroaniline (12.1 mg, 0.093 mmol) in THF (2 mL) was added lithium bis(trimethylsilyl)amide (0.31 mL, 1 M in THF, 0.31 mmol). The reaction mixture was stirred at room temperature for 30 minutes and quenched with NH$_4$Cl (aq., sat., 2 mL). The aqueous layer was extracted with DCM (3×5 mL) and ethyl acetate (15 mL). The combined organic layers were concentrated and the residue was purified twice on silica (EtOAc in heptane from 0 to 100%) and via Prep HPLC (Stationary phase: RP XBridge Prep C18 OBD-10 μm, 30×150 mm, Mobile phase: 0.25% NH$_4$HCO$_3$ solution in water, ACN) yielding compound 13 (15 mg) as a white powder. $^1$H NMR (360 MHz, DMSO-d$_6$) δ ppm 2.72-2.79 (m, 2H), 3.42-3.50 (m, 2H), 3.78 (br s, 3H), 7.18 (br s, 1H), 7.37-7.47 (m, 2H), 7.63 (s, 1H), 7.78-7.85 (m, 1H), 10.21 (br s, 1H); Method B; Rt: 0.82 min. m/z: 340 (M−H)$^-$ Exact mass: 341.0.

Compound 14: N-(3,4-difluorophenyl)-3,7-dimethyl-1,1-dioxo-3,4-dihydro-2H-pyrrolo-[3,4-b][1,4,5]oxathiazepine-6-carboxamide

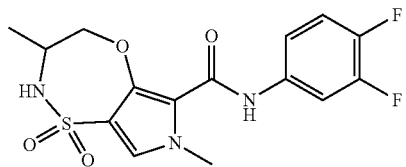 [SMILES: CC1COc2c(cn(C)c2C(=O)Nc2ccc(F)c(F)c2)S(=O)(=O)N1]

Ethyl 4-chlorosulfonyl-3-fluoro-1-methyl-pyrrole-2-carboxylate (500 mg, 1.85 mmol), DL-alaninol (209 mg, 2.78 mmol) and Hunig's base (0.96 mL, 0.75 g/mL, 5.56 mmol) were dissolved in THF and stirred overnight at room temperature. The formed precipitate was filtered off and the filtrate was evaporated to dryness. The residue was purified on silica using a heptane to EtOAc gradient yielding ethyl 3-fluoro-4-[(2-hydroxy-1-methyl-ethyl)sulfamoyl]-1-methyl-pyrrole-2-carboxylate (513 mg) as a white powder.

Ethyl 3-fluoro-4-[(2-hydroxy-1-methyl-ethyl)sulfamoyl]-1-methyl-pyrrole-2-carboxylate (240 mg, 0.78 mmol) and 3,4-difluoroaniline (0.094 mL, 1.29 g/mL, 0.93 mmol) were dissolved in THF (5 mL). Lithium bis(trimethylsilyl)amide (2.34 mL, 1 M in THF, 2.34 mmol) was added and the reaction mixture was stirred overnight at room temperature. Lithium bis(trimethylsilyl)amide (0.5 mL, 1 M in THF, 0.5 mmol) was added and the reaction mixture was stirred 1 hour. NH$_4$Cl (sat., aq., 5 mL) was added and the organic layer was removed. The aqueous layer was extracted with DCM (2×5 mL) and the combined organic layers were evaporated to dryness. The residue was purified on silica using a heptane to EtOac gradient yielding N-(3,4-difluorophenyl)-3-fluoro-4-[(2-hydroxy-1-methyl-ethyl)sulfamoyl]-1-methyl-pyrrole-2-carboxamide (225 mg) as a white powder after crystallization from a DCM:DIPE mixture.

N-(3,4-difluorophenyl)-3-fluoro-4-[(2-hydroxy-1-methyl-ethyl)sulfamoyl]-1-methyl-pyrrole-2-carboxamide (183 mg, 0.47 mmol) and cesium fluoride (15.5 mg, 0.94 mmol) were dispensed in DMF (3 mL). The reaction mixture was heated in the microwave oven for 2 hours at 140° C. The reaction mixture was purified via prep. HPLC (Stationary phase: RP XBridge Prep C18 OBD-10 μm, 30×150 mm, Mobile phase: 0.25% NH$_4$HCO$_3$ solution in water, ACN) yielding compound 14 (130 mg). $^1$H NMR (400 MHz, DMSO-d$_6$) δ ppm 1.10-1.20 (m, 3H), 3.78-3.86 (m, 5H), 4.51-4.59 (m, 1H), 7.36-7.48 (m, 3H), 7.61 (br s, 1H), 7.85 (ddd, J=13.1, 7.4, 2.3 Hz, 1H), 9.44 (s, 1H); Method D; Rt: 1.82 min. m/z: 372 (M+H)$^+$ Exact mass: 371.1. This racemic mixture was separated in enantiomers 14a (40.6 mg) and 14b (36.9 mg) by preparative SFC (Stationary phase: Chiralpak Diacel AD 20×250 mm, Mobile phase: CO$_2$, EtOH with 0.4% iPrNH$_2$). Method F; Rt: 14a: 1.52 min, 14b: 2.14 min.

Compound 15: (5Z)—N-(3,4-difluorophenyl)-3,8-dimethyl-1,1-dioxo-3,4-dihydro-2H-pyrrolo[3,4-g]thiazocine-7-carboxamide

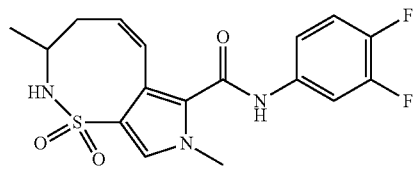 [SMILES: CC1C/C=C\c2c(cn(C)c2C(=O)Nc2ccc(F)c(F)c2)S(=O)(=O)N1]

Methyl 3-bromo-4-chlorosulfonyl-1-methyl-pyrrole-2-carboxylate (1000 mg, 3.16 mmol) and pent-4-en-2-ylamine hydrochloride (423 mg, 3.47 mmol) were dissolved in THF (5 mL). Hunig's base (1.63 mL, 0.75 g/mL, 9.48 mmol) was added and the reaction mixture was stirred overnight at room temperature. NH$_4$Cl (sat., aq., 5 mL) was added and the organic layer was removed. The aqueous layer was extracted with DCM (2×5 mL) and the combined organic layers were evaporated to dryness. The residue was purified on silica using a heptane to EtOAc gradient yielding methyl 3-bromo-1-methyl-4-(1-methylbut-3-enylsulfamoyl)pyrrole-2-carboxylate (965 mg) as a white powder.

Methyl 3-bromo-1-methyl-4-(1-methylbut-3-enylsulfamoyl)pyrrole-2-carboxylate (97 mg, 0.28 mmol), bis(tritert-butylphosphine)palladium(0) (13.6 mg, 0.027 mmol) and TEA (36.8 μL, 0.73 g/mL, 0.27 mmol) were dissolved in DMF (5 mL) and heated in the microwave oven at 150° C. for 30 minutes. The reaction mixture was purified via Prep HPLC (Stationary phase: RP XBridge Prep C18 OBD-10 μm, 30×150 mm, Mobile phase: 0.25% NH$_4$HCO$_3$ solution in water, ACN) yielding methyl (5Z)-3,8-dimethyl-1,1-dioxo-3,4-dihydro-2H-pyrrolo[3,4-g]thiazocine-7-carboxylate (41 mg).

Methyl (5Z)-3,8-dimethyl-1,1-dioxo-3,4-dihydro-2H-pyrrolo[3,4-g]thiazocine-7-carboxylate (41 mg, 0.14 mmol) and 3,4-difluoroaniline (17.5 μL, 1.29 g/mL, 0.17 mmol) were dissolved in THF (5 mL). Lithium bis(trimethylsilyl)amide (433 μL, 1 M in THF, 0.43 mmol) was added and the reaction mixture was stirred overnight at room temperature. The reaction mixture was quenched with NH$_4$Cl (aq., sat., 5 mL). The organic layer was removed and the aqueous layer extracted with DCM (2×5 mL). The combined organic layers were evaporated to dryness and the residue purified via Prep HPLC (Stationary phase: RP XBridge Prep C18 OBD-10 μm, 30×150 mm, Mobile phase: 0.25% NH$_4$HCO$_3$ solution in water, MeOH) yielding compound 15. $^1$H NMR (400 MHz, DMSO-d$_6$) δ ppm 1.32 (d, J=7.0 Hz, 3H), 2.08-2.16 (m, 1H), 2.46 (ddd, J=13.6, 8.6, 1.8 Hz, 1H), 3.51 (quind, J=6.9, 6.9, 6.9, 6.9, 1.8 Hz, 1H), 3.92 (s, 3H), 6.08 (dt, J=11.0, 8.8 Hz, 1H), 6.77 (d, J=11.0 Hz, 1H), 7.31 (dt, J=10.4, 9.0 Hz, 1H), 7.38-7.44 (m, 2H), 7.89 (ddd, J=13.0, 7.4, 2.6 Hz, 1H); Method D; Rt: 1.78 min. m/z: 382 (M+H)$^+$ Exact mass: 381.1. This racemic mixture was separated in enantiomers 15a (4.7 mg) and 15b (4.2 mg) by preparative SFC (Stationary phase: Kromasil (R,R) Whelk-O 1 10/100, Mobile phase: CO2, MeOH+0.4 iPrNH$_2$). Method G; Rt: 15a: 2.31 min, 15b: 2.75 min.

Compound 16: N-(3,4-difluorophenyl)-2-isopropyl-6-methyl-1,1-dioxo-3,4-dihydropyrrolo[3,4-e]thiazine-5-carboxamide

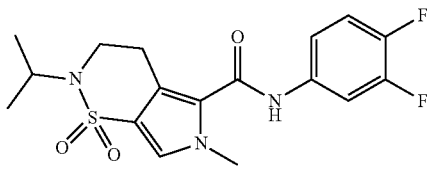 [SMILES: CC(C)N1CCc2c(cn(C)c2C(=O)Nc2ccc(F)c(F)c2)S1(=O)=O]

Methyl 6-methyl-1,1-dioxo-3,4-dihydro-2H-pyrrolo[3,4-e]thiazine-5-carboxylate (40 mg, 0.11 mmol) was dissolved in DMF (1 mL) and 2-bromopropane (17.2 μL, 2.28 g/mL, 0.32 mmol) was added. The reaction mixture was stirred at room temperature for 66 hours. The reaction mixture was diluted with water and extracted with EtOAc (3×10 mL). The combined organic layers were dried and concentrated to dryness. The white solid was purified using silica gel column chromatography (EtOAc in heptane from 0 to 100%) to afford methyl 2-isopropyl-6-methyl-1,1-dioxo-3,4-dihydro-pyrrolo[3,4-e]thiazine-5-carboxylate (20 mg) as a white powder. Method B; Rt: 0.84 min. m/z: 287 (M+H)$^+$ Exact mass: 286.0.

To a solution of methyl 2-isopropyl-6-methyl-1,1-dioxo-3,4-dihydropyrrolo-[3,4-e]thiazine-5-carboxylate (20 mg, 0.07 mmol) and 3,4-difluoroaniline (10.82 mg, 0.084 mmol) in THF (2 mL) was added lithium bis(trimethylsilyl)amide (0.28 mL, 1 M in THF, 0.28 mmol) and the reaction mixture was stirred 1 hour at room temperature. Lithium bis(trimethylsilyl)amide (0.28 mL, 1 M in THF, 0.28 mmol) was added and the reaction mixture was stirred 5 minutes at room temperature and quenched with NH$_4$Cl (aq., sat., 2 mL). The aqueous layer was extracted with DCM (3×5 mL). The combined organic layers were concentrated and the residue was purified on silica (EtOAc in heptane from 0 to 100%) to afford a brown powder. This was triturated in hot methanol. The white suspension was filtered to afford compound 16 (18 mg) as an off white solid. $^1$H NMR (400 MHz, DMSO-d$_6$) δ ppm 1.16 (d, J=6.8 Hz, 6H), 2.83-2.90 (m, 2H), 3.58-3.65 (m, 2H), 3.78 (s, 3H), 4.09-4.21 (m, 1H), 7.36-7.46 (m, 2H), 7.63 (s, 1H), 7.77-7.83 (m, 1H), 10.08 (br s, 1H); Method B; Rt: 0.98 min. m/z: 384 (M+H)$^+$ Exact mass: 383.0.

Compound 17: N-(3,4-difluorophenyl)-3-ethyl-6-methyl-1,1-dioxo-3,4-dihydro-2H-pyrrolo[3,4-e]thiazine-5-carboxamide

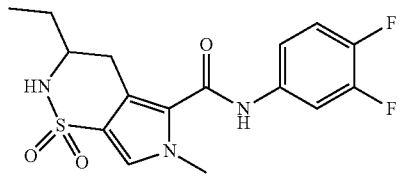 [SMILES: CCC1Cc2c(cn(C)c2C(=O)Nc2ccc(F)c(F)c2)S(=O)(=O)N1]

Methyl 3-ethyl-6-methyl-1,1-dioxo-2H-pyrrolo[3,4-e]thiazine-5-carboxylate was prepared similarly as described for methyl 3,6-dimethyl-1,1-dioxo-2H-pyrrolo[3,4-e]-thiazine-5-carboxylate, using heptane-3,5-dione instead of pentane-2,4-dione. Methyl 3-ethyl-6-methyl-1,1-dioxo-2H-pyrrolo [3,4-e]thiazine-5-carboxylate (128 mg, 0.18 mmol) was dissolved in MeOH (10 mL) and under a nitrogen atmosphere Pd/C (10%) (20 mg, 0.018 mmol) was added. The reaction mixture was hydrogenated for 18 hours. Pd/C (10%) (20 mg, 0.018 mmol) was added under nitrogen atmosphere. The reaction mixture was hydrogenated for 18 hours at 50° C. The reaction mixture was filtered over decalite. The filter cake was washed with MeOH (3×20 mL). The filtrate was evaporated to dryness and the residue was purified using silica gel column chromatography (EtOAc in heptane from 0 to 100%) to afford methyl 3-ethyl-6-methyl-1,1-dioxo-3,4-dihydro-2H-pyrrolo[3,4-e]thiazine-5-carboxylate (20 mg). Method B; Rt: 0.74 min. m/z: 271 (M−H)$^-$ Exact mass: 272.0.

To a solution of methyl 3-ethyl-6-methyl-1,1-dioxo-3,4-dihydro-2H-pyrrolo-[3,4-e]thiazine-5-carboxylate (20 mg, 0.073 mmol) and 3,4-difluoroaniline (9.5 mg, 0.073 mmol) in THF (2 mL) was added lithium bis(trimethylsilyl)amide (0.29 mL, 1 M in THF, 0.29 mmol). The reaction mixture was stirred at room temperature for 30 minutes and quenched with NH$_4$Cl (aq., sat., 2 mL). The aqueous layer was extracted with DCM (3×5 mL). The combined organic layers were concentrated and the residue was purified via Prep HPLC (Stationary phase: RP XBridge Prep C18 OBD-10 μm, 30×150 mm, Mobile phase: 0.25% NH$_4$HCO$_3$ solution in water, ACN) yielding compound 17 (4.5 mg) as an off white powder. $^1$H NMR (400 MHz, DMSO-d$_6$) δ ppm 0.96 (tt, J=7.3, 1.0 Hz, 3H), 1.54-1.63 (m, 2H), 2.45-2.55 (m, 1H), 2.80-2.92 (m, 1H), 3.16-3.44 (m, 1H), 3.77 (s, 3H), 6.92-7.05 (m, 1H), 7.37-7.46 (m, 2H), 7.60 (s, 1H), 7.77-7.84 (m, 1H), 10.09-10.19 (m, 1H); Method B; Rt: 0.91 min. m/z: 368 (M−H)$^-$ Exact mass: 369.1.

Compound 18: N-(3,4-difluorophenyl)-2,3,7-trimethyl-1,1-dioxo-3H-pyrrolo-[3,4-f]thiazepine-6-carboxamide

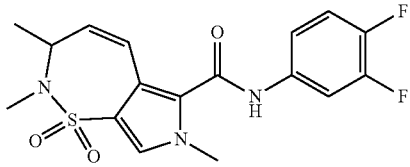 [SMILES: CC1C=Cc2c(cn(C)c2C(=O)Nc2ccc(F)c(F)c2)S(=O)(=O)N1C]

Trimethylsulfoxonium iodide (123 mg, 0.56 mmol) and potassium tert-butoxide (58 mg, 0.52 mmol) were dissolved in DMSO (5 mL) at 50° C. Compound 7 (100 mg, 0.27 mmol) dissolved in DMSO (5 mL) was added dropwise and the reaction mixture was stirred overnight at 50° C. Trimethylsulfoxonium iodide (123 mg, 0.56 mmol) and potassium tert-butoxide (58 mg, 0.52 mmol) were dissolved in DMSO (5 mL) and this was added to the reaction mixture which was stirred for another hour. The reaction mixture was purified via prep HPLC (Stationary phase: RP)(Bridge Prep C18 OBD-10 μm, 30×150 mm, Mobile phase: 0.25% $NH_4HCO_3$ solution in water, MeOH) yielding compound 18 (23.7 mg). $^1$H NMR (400 MHz, ACETONE-$d_6$) δ ppm 1.41 (d, J=7.5 Hz, 3H), 2.53 (s, 3H), 3.86 (s, 3H), 4.88 (qt, J=7.5, 2.6 Hz, 1H), 5.40 (dd, 2.5 Hz, 1H), 6.67 (dd, J=12.5, 2.9 Hz, 1H), 7.34 (dt, J=10.4, 9.0 Hz, 1H), 7.44 (s, 1H), 7.47-7.56 (m, 1H), 7.94 (ddd, 7.5, 2.6 Hz, 1H), 9.84 (br s, 1H); Method B; Rt: 0.99 min. m/z: 382 $(M+H)^+$ Exact mass: 381.1.

Compound 19: N-(3,4-difluorophenyl)-7-methyl-1,1-dioxo-spiro[2,4-dihydropyrrolo-[3,4-b][1,4,5]oxathiazepine-3,1'-cyclopropane]-6-carboxamide

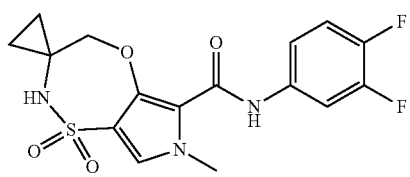 [SMILES: Cn1cc2c(c1C(=O)Nc1ccc(F)c(F)c1)OCC1(CC1)NS2(=O)=O]

Compound 19 (18.1 mg) was prepared similarly as described for compound 14, using 1-amino-cyclopropanemethanol instead of DL-alaninol. $^1$H NMR (400 MHz, DMSO-$d_6$) δ ppm 0.91-1.04 (m, 4H), 3.83 (s, 3H), 4.15 (s, 2H), 7.36-7.47 (m, 2H), 7.49 (s, 1H), 7.84 (ddd, 7.5, 2.2 Hz, 1H), 8.23 (s, 1H), 9.51 (s, 1H); Method B; Rt: 0.94 min. m/z: 384 $(M+H)^+$ Exact mass: 383.1.

Compound 20: (3R)—N-(3,4-difluorophenyl)-3-ethyl-7-methyl-1,1-dioxo-3,4-dihydro-2H-pyrrolo[3,4-b][1,4,5]oxathiazepine-6-carboxamide

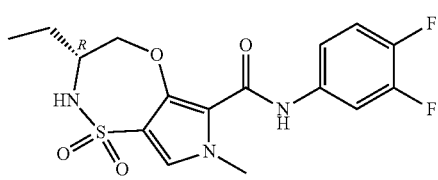

Compound 20 (36.6 mg) was prepared similarly as described for compound 14, using (R)-(−)-2-amino-1-butanol instead of DL-alaninol. $^1$H NMR (400 MHz, DMSO-$d_6$) δ ppm 0.98 (t, J=7.4 Hz, 3H), 1.37-1.55 (m, 2H), 3.47-3.59 (m, 1H), 3.82 (s, 3H), 3.83-3.89 (m, 1H), 4.56-4.62 (m, 1H), 7.36-7.49 (m, 3H), 7.54 (br d, J=8.4 Hz, 1H), 7.85 (ddd, 7.5, 2.4 Hz, 1H), 9.43 (s, 1H); Method B; Rt: 0.99 min. m/z: 386 $(M+H)^+$ Exact mass: 385.1.

Compound 21: N-(3,4-difluorophenyl)-3,8-dimethyl-1,1-dioxo-2,3,4,5-tetrahydropyrrolo[3,4-b][1,4,5]oxathiazocine-7-carboxamide

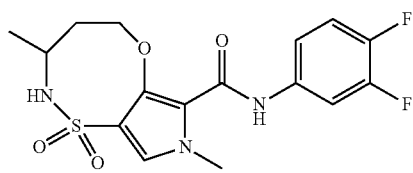 [SMILES: CC1CCOc2c(cn(C)c2C(=O)Nc2ccc(F)c(F)c2)S(=O)(=O)N1]

Compound 21 (137.3 mg) was prepared similarly as described for compound 14, using 3-aminobutan-1-ol instead of DL-alaninol. $^1$H NMR (400 MHz, DMSO-$d_6$) δ ppm 1.04 (d, J=5.9 Hz, 3H), 1.21 (d, J=6.6 Hz, 3H), 1.66-1.76 (m, 1H), 1.97-2.05 (m, 1H), 3.78-3.85 (m, 4H), 4.21 (ddd, J=11.8, 8.4, 3.2 Hz, 1H), 4.31-4.38 (m, 1H), 7.36-7.48 (m, 3H), 7.63 (d, J=9.2 Hz, 1H), 7.86 (ddd, J=13.3, 7.4, 2.4 Hz, 1H), 9.54 (s, 1H); Method B; Rt: 0.96 min. m/z: 386 $(M+H)^+$ Exact mass: 385.1.

Compound 22: (3S)—N-(3,4-difluorophenyl)-3-isopropyl-7-methyl-1,1-dioxo-3,4-dihydro-2H-pyrrolo[3,4-b][1,4,5]oxathiazepine-6-carboxamide

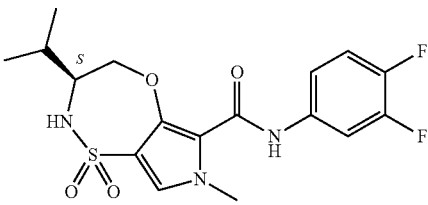

Compound 22 (46.5 mg) was prepared similarly as described for compound 14, using (S)-(+)-2-amino-3-methyl-1-butanol instead of DL-alaninol. $^1$H NMR (400 MHz, DMSO-$d_6$) δ ppm 0.94 (d, J=6.8 Hz, 3H), 0.97 (d, J=6.6 Hz, 3H), 1.85 (dq, J=13.4, 6.8 Hz, 1H), 3.46 (br s, 1H), 3.83 (s, 3H), 3.94 (dd, J=12.7, 9.1 Hz, 1H), 4.70 (dd, J=12.5, 1.5 Hz, 1H), 7.36-7.55 (m, 4H), 7.86 (ddd, J=13.1, 7.4, 2.5 Hz, 1H), 9.42 (s, 1H); Method B; Rt: 1.05 min. m/z: 400 $(M+H)^+$ Exact mass: 399.1.

Compound 23: (3 S)—N-(3,4-difluorophenyl)-7-methyl-3-[(1S)-1-methylpropyl]-1,1-dioxo-3,4-dihydro-2H-pyrrolo[3,4-b][1,4,5]oxathiazepine-6-carboxamide

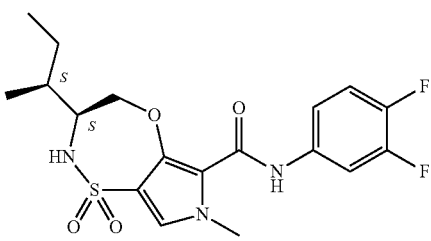

Compound 23 (30.8 mg) was prepared similarly as described for compound 14, using L-isoleucinol instead of DL-alaninol. $^1$H NMR (400 MHz, DMSO-$d_6$) δ ppm 0.87 (t, J=7.4 Hz, 3H), 0.94 (d, J=6.8 Hz, 3H), 1.22-1.33 (m, 1H), 1.46-1.56 (m, 1H), 1.56-1.65 (m, 1H), 3.53 (br s, 1H), 3.83 (s, 3H), 3.94 (dd, J=12.8, 9.0 Hz, 1H), 4.71 (d, J=11.0 Hz, 1H), 7.36-7.45 (m, 1H), 7.45-7.52 (m, 2H), 7.56 (br s, 1H), 7.86 (ddd, J=13.2, 7.4, 2.5 Hz, 1H), 9.42 (s, 1H); Method B; Rt: 1.10 min. m/z: 414 (M+H)$^+$ Exact mass: 413.1.

Compound 24: N-(3,4-difluorophenyl)-7-methyl-1,1-dioxo-spiro[2,4-dihydropyrrolo-[3,4-b][1,4,5]oxathiazepine-3,3'-oxetane]-6-carboxamide

Compound 24 (51.6 mg) was prepared similarly as described for compound 14, using (3-aminooxetan-3-yl)methanol instead of DL-alaninol. $^1$H NMR (400 MHz, DMSO-$d_6$) δ ppm 3.82 (s, 3H), 4.47 (d, J=6.8 Hz, 2H), 4.65 (d, J=6.8 Hz, 2H), 4.76 (s, 2H), 7.38-7.46 (m, 1H), 7.49 (s, 1H), 7.50-7.54 (m, 1H), 7.89 (ddd, J=13.1, 7.4, 2.5 Hz, 1H), 8.47 (s, 1H), 9.46 (s, 1H); Method B; Rt: 0.88 min. m/z: 400 (M+H)$^+$ Exact mass: 399.1.

Compound 25: (3R)—N-(3,4-difluorophenyl)-7-methyl-1,1-dioxo-3-phenyl-3,4-dihydro-2H-pyrrolo[3,4-b][1,4,5]oxathiazepine-6-carboxamide

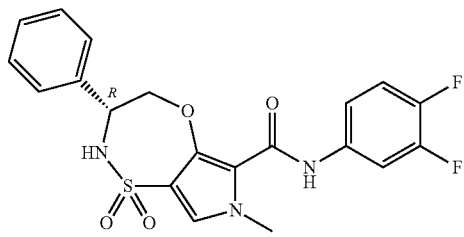

Compound 25 (5 mg) was prepared similarly as described for compound 14, using (D)-beta-aminophenethyl alcohol instead of DL-alaninol. $^1$H NMR (400 MHz, DMSO-$d_6$) δ ppm 3.86 (br s, 3H), 4.15-4.26 (m, 1H), 4.74 (br d, J=11.7 Hz, 1H), 4.92 (br d, J=9.2 Hz, 1H), 7.28-7.44 (m, 4H), 7.48 (br s, 3H), 7.58 (s, 1H), 7.85 (br s, 1H), 9.43 (br s, 1H); Method B; Rt: 1.07 min. m/z: 432 (M–H)$^-$ Exact mass: 433.1.

Compound 26: (3S)—N-(3,4-difluorophenyl)-7-methyl-1,1-dioxo-3-phenyl-3,4-dihydro-2H-pyrrolo[3,4-b][1,4,5]oxathiazepine-6-carboxamide

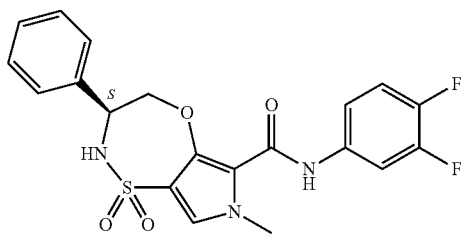

Compound 26 (8.8 mg) was prepared similarly as described for compound 14, using (S)-(+)-2-phenylglycinol instead of DL-alaninol. $^1$H NMR (400 MHz, DMSO-$d_6$) δ ppm 3.86 (s, 3H), 4.20 (dd, J=12.8, 9.7 Hz, 1H), 4.74 (dd, 2.0 Hz, 1H), 4.92 (br d, J=8.1 Hz, 1H), 7.31-7.44 (m, 4H), 7.44-7.51 (m, 3H), 7.56 (s, 1H), 7.85 (ddd, 7.5, 2.4 Hz, 1H), 8.24 (br s, 1H), 9.43 (br s, 1H); Method B; Rt: 1.07 min. m/z: 432 (M–H)$^-$ Exact mass: 433.1.

Compound 27: (3R)—N-(3,4-difluorophenyl)-3-isopropyl-7-methyl-1,1-dioxo-3,4-dihydro-2H-pyrrolo[3,4-b][1,4,5]oxathiazepine-6-carboxamide

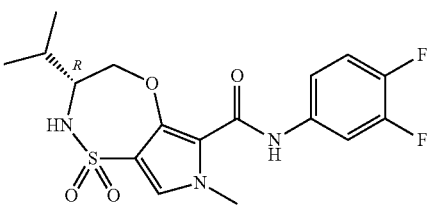

Compound 27 (22.7 mg) was prepared similarly as described for compound 14, D-valinol instead of DL-alaninol. $^1$H NMR (400 MHz, DMSO-$d_6$) δ ppm 0.96 (dd, J=12.1, 6.8 Hz, 6H), 1.85 (dq, J=13.3, 6.7 Hz, 1H), 3.46 (br d, J=6.8 Hz, 1H), 3.83 (s, 3H), 3.94 (dd, J=12.8, 9.2 Hz, 1H), 4.69 (dd, 1.5 Hz, 1H), 7.36-7.54 (m, 4H), 7.86 (ddd, J=13.2, 7.4, 2.5 Hz, 1H), 9.42 (s, 1H); Method D; Rt: 2.00 min. m/z: 400 (M+H)$^+$ Exact mass: 399.1.

Compound 28: N-(3,4-difluorophenyl)-3,4,7-trimethyl-1,1-dioxo-3,4-dihydro-2H-pyrrolo[3,4-b][1,4,5]oxathiazepine-6-carboxamide

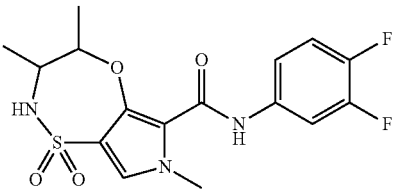 [SMILES: CC1NS(=O)(=O)c2cn(C)c(C(=O)Nc3ccc(F)c(F)c3)c2OC1C]

Compound 28 (18.1 mg) was prepared similarly as described for compound 14, using 3-amino-2-butanol instead of DL-alaninol. Method B; Rt: 0.94 min. m/z: 384 (M+H)+ Exact mass: 383.1.

Compound 29: (*S)-3,7-dimethyl-1,1-dioxo-N-(3,4,5-trifluorophenyl)-2,3-dihydropyrrolo[3,4-f]thiazepine-6-carboxamide

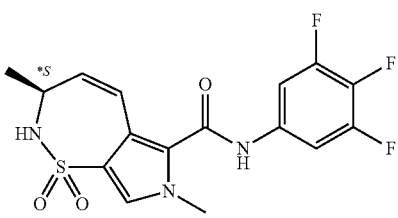 [SMILES: C[C@H]1C=Cc2c(cn(C)c2C(=O)Nc2cc(F)c(F)c(F)c2)S(=O)(=O)N1]

3-chloro-1-butene (88.1 g, 973 mmol) was added to an overhead stirred suspension of potassium phthalimide (157 g, 848 mmol) and $K_2CO_3$ (23.5 g, 170 mmol) in DMF (1.3 L). The reaction mixture was heated to 120° C. for 5 hours. The reaction mixture was allowed to cool to room temperature and stirred overnight at room temperature. The reaction mixture was quenched in ice cold water (6 L) and filtered. The filter cake was washed with cold water (300 mL) and dried on the air for one hour and then in the vacuum oven for 3 days yielding 2-(1-methylallyl)isoindoline-1,3-dione (148 g) as a white powder. $^1$H NMR (400 MHz, DMSO-$d_6$) δ ppm 1.51 (d, J=7.0 Hz, 3H), 4.79-4.87 (m, 1H), 5.10-5.20 (m, 2H), 6.11 (ddd, 10.5, 5.7 Hz, 1H), 7.82-7.89 (m, 4H). This racemic mixture was separated in enantiomers (*R)-2-(1-methylallyl)isoindoline-1,3-dione (43.6 g) and (*S)-2-(1-methylallyl)isoindoline-1,3-dione (48 g) by preparative Chiral HPLC (Stationary phase: Chiralpak Diacel AD 20 microhm 2000 gr, Mobile phase: Isocratic 100% MeOH), where *R means first eluting enantiomer and *S means second eluting enantiomer.

To a solution of (*S)-2-(1-methylallyl)isoindoline-1,3-dione (5.03 g, 25 mmol) in EtOH (10 mL) was added ethanolamine (6.34 mL, 1.01 g/mL, 105 mmol). The mixture was heated at 45° C. for 20 h and allowed to reach room temperature and then at 90° C. for 5 hours. The flask was equipped with a short path distillation apparatus and the ethanol and free amine was distilled as an azeotrope at atmospheric pressure. The pot temperature was 120° C. and the boiling point of the ethanol+amine distillate was 80° C. To the distillate (6.8 mol % in ethanol) was added a solution of methyl 3-bromo-4-chlorosulfonyl-1-methyl-pyrrole-2-carboxylate (5.00 g, 15.8 mmol) in DCM (100 mL) and Hunig's base (5.44 mL, 0.75 g/mL, 31.6 mmol). The reaction mixture was stirred at room temperature for 18 h. The reaction mixture was concentrated to dryness and the residue was dissolved in DCM (100 mL) and washed with saturated aqueous ammonium chloride solution. The organic layer was separated and dried ($Na_2SO_4$), filtered and concentrated to dryness. The residue was purified using silica gel column chromatography (EtOAc in heptane from 0 to 100%) to afford methyl 3-bromo-1-methyl-4-[[(1*S)-1-methylallyl]sulfamoyl]pyrrole-2-carboxylate (4.08 g) as a white powder.

Compound 29 (139 mg) was prepared similarly as described for compound 8, using methyl 3-bromo-1-methyl-4-[[(1*S)-1-methylallyl]sulfamoyl]pyrrole-2-carboxylate instead of methyl 3-bromo-1-methyl-4-[1-(trifluoromethyl)allylsulfamoyl]pyrrole-2-carboxylate and heating 5 minutes instead of 30 minutes, using 3,4,5-trifluoroaniline instead of 3,4-difluoroaniline. $^1$H NMR (400 MHz, DMSO-$d_6$) δ ppm 1.31 (d, J=7.3 Hz, 3H), 3.71 (s, 3H), 4.20-4.33 (m, 1H), 5.59 (dd, J=12.6, 2.4 Hz, 1H), 6.43 (dd, J=12.6, 2.6 Hz, 1H), 7.48-7.68 (m, 4H), 10.86 (s, 1H); Method B; Rt: 0.97 min. m/z: 384 (M−H)− Exact mass: 385.1.

Compound 30: (*S)—N-[4-fluoro-3-(trifluoromethyl)phenyl]-3,7-dimethyl-1,1-dioxo-2,3-dihydropyrrolo[3,4-f]thiazepine-6-carboxamide

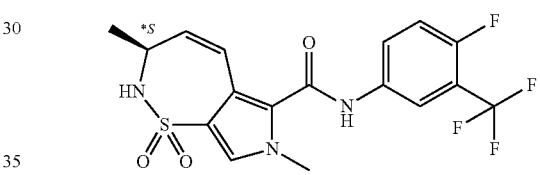

Compound 30 (126 mg) was prepared similarly as described for compound 29, using 4-fluoro-3-(trifluoromethyl)aniline instead of 3,4,5-trifluoroaniline. $^1$H NMR (400 MHz, DMSO-$d_6$) δ ppm 1.31 (d, J=7.3 Hz, 3H), 3.72 (s, 3H), 4.22-4.32 (m, 1H), 5.58 (dd, J=12.6, 2.4 Hz, 1H), 6.48 (dd, J=12.6, 2.6 Hz, 1H), 7.48-7.61 (m, 3H), 7.92-8.00 (m, 1H), 8.20 (dd, J=6.5, 2.7 Hz, 1H), 10.84 (br s, 1H); Method B; Rt: 1.00 min. m/z: 416 (M−H)− Exact mass: 417.1.

Compound 31: (*S)—N-(4-fluoro-3-methyl-phenyl)-3,7-dimethyl-1,1-dioxo-2,3-dihydropyrrolo[3,4-f]thiazepine-6-carboxamide

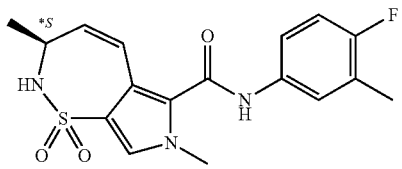

Compound 31 (106 mg) was prepared similarly as described for compound 29, using 4-fluoro-3-methylaniline instead of 3,4,5-trifluoroaniline. $^1$H NMR (400 MHz, DMSO-$d_6$) δ ppm 1.31 (d, J=7.3 Hz, 3H), 2.19-2.26 (m, 3H), 3.70 (s, 3H), 4.22-4.31 (m, 1H), 5.55 (dd, J=12.5, 2.4 Hz, 1H), 6.43 (dd, J=12.6, 2.6 Hz, 1H), 7.11 (t, J=9.2 Hz, 1H), 7.37-7.79 (m, 4H), 10.50 (br s, 1H); Method B; Rt: 0.92 min. m/z: 362 (M−H)− Exact mass: 363.1.

Compound 32: (*S)—N-(3-cyano-4-fluoro-phenyl)-3,7-dimethyl-1,1-dioxo-2,3-dihydropyrrolo[3,4-f]thiazepine-6-carboxamide

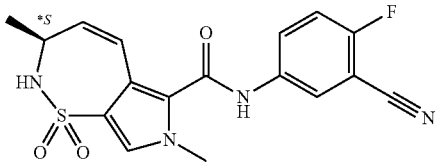 [SMILES: C[C@H]1C=Cc2c(cn(C)c2C(=O)Nc2ccc(F)c(C#N)c2)S(=O)(=O)N1]

Compound 32 (78 mg) was prepared similarly as described for compound 29, using 5-amino-2-fluorobenzonitrile instead of 3,4,5-trifluoroaniline. $^1$H NMR (400 MHz, DMSO-$d_6$) δ ppm 1.31 (d, J=7.5 Hz, 3H), 3.72 (s, 3H), 4.23-4.32 (m, 1H), 5.58 (dd, J=12.6, 2.4 Hz, 1H), 6.47 (dd, J=12.6, 2.6 Hz, 1H), 7.51-7.60 (m, 3H), 7.97 (ddd, J=9.2, 4.9, 2.7 Hz, 1H), 8.19 (dd, J=5.8, 2.7 Hz, 1H), 10.86 (br s, 1H); Method B; Rt: 0.84 min. m/z: 373 (M−H)$^-$ Exact mass: 374.1.

Compound 33: (3R)—N-(3,4-difluorophenyl)-3-[(1R)-1-hydroxyethyl]-7-methyl-1,1-dioxo-3,4-dihydro-2H-pyrrolo[3,4-b][1,4,5]oxathiazepine-6-carboxamide

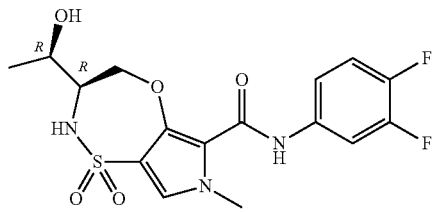

Compound 33 (44.1 mg) was prepared similarly as described for compound 14, using L-threoninol instead of DL-alaninol. $^1$H NMR (400 MHz, DMSO-$d_6$) δ ppm 1.10 (d, J=6.4 Hz, 3H), 3.60-3.70 (m, 1H), 3.83 (s, 3H), 3.85-4.00 (m, 2H), 4.74 (d, J=11.4 Hz, 1H), 4.96 (d, J=4.6 Hz, 1H), 7.35-7.44 (m, 2H), 7.44-7.50 (m, 2H), 7.87 (ddd, 7.5, 2.4 Hz, 1H), 9.44 (s, 1H); Method B; Rt: 0.87 min. m/z: 402 (M+H)$^+$ Exact mass: 401.1.

Compound 34: (3S)—N-(3,4-difluorophenyl)-3-[(1R)-1-hydroxyethyl]-7-methyl-1,1-dioxo-3,4-dihydro-2H-pyrrolo[3,4-b][1,4,5]oxathiazepine-6-carboxamide

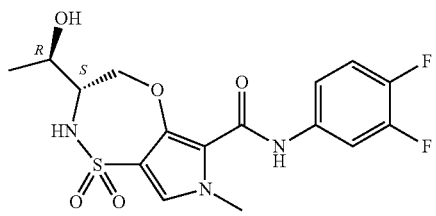

Compound 34 (93.6 mg) was prepared similarly as described for compound 14, using D-allo-threoninol instead of DL-alaninol. $^1$H NMR (400 MHz, DMSO-$d_6$) δ ppm 1.21 (d, J=6.2 Hz, 3H), 3.38-3.45 (m, 1H), 3.56-3.64 (m, 1H), 3.82 (s, 3H), 3.97 (dd, J=12.5, 9.0 Hz, 1H), 4.89 (dd, J=12.8, 2.0 Hz, 1H), 5.05 (d, J=5.9 Hz, 1H), 7.36-7.44 (m, 1H), 7.44-7.49 (m, 2H), 7.61 (d, J=9.7 Hz, 1H), 7.87 (ddd, 7.5, 2.4 Hz, 1H), 9.42 (s, 1H); Method B; Rt: 0.86 min. m/z: 402 (M+H)$^+$ Exact mass: 401.1.

Compound 35: (3R)—N-(3,4-difluorophenyl)-3-[(1S)-1-hydroxyethyl]-7-methyl-1,1-dioxo-3,4-dihydro-2H-pyrrolo[3,4-b][1,4,5]oxathiazepine-6-carboxamide

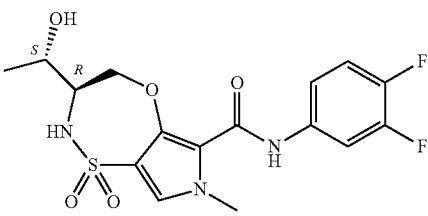

Compound 35 (68.5 mg) was prepared similarly as described for compound 14, using L-allo-threoninol instead of DL-alaninol. $^1$H NMR (400 MHz, DMSO-$d_6$) δ ppm 1.21 (d, J=6.2 Hz, 3H), 3.35-3.44 (m, 1H), 3.60 (dt, J=8.1, 6.1 Hz, 1H), 3.82 (s, 3H), 3.97 (dd, J=12.8, 9.0 Hz, 1H), 4.89 (dd, J=12.7, 1.9 Hz, 1H), 5.04 (d, J=5.9 Hz, 1H), 7.36-7.44 (m, 1H), 7.44-7.49 (m, 2H), 7.61 (d, J=9.7 Hz, 1H), 7.87 (ddd, 7.5, 2.4 Hz, 1H), 9.42 (s, 1H); Method B; Rt: 0.86 min. m/z: 402 (M+H)$^+$ Exact mass: 401.1.

Compound 36: (3R)—N-(3,4-difluorophenyl)-3-[(R)-hydroxy(phenyl)methyl]-7-methyl-1,1-dioxo-3,4-dihydro-2H-pyrrolo[3,4-b][1,4,5]oxathiazepine-6-carboxamide

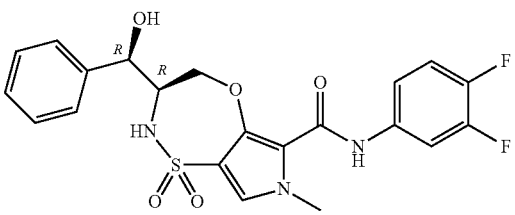

Compound 36 (81.4 mg) was prepared similarly as described for compound 14, using (1R,2R)-(−)-2-amino-1-phenyl-1,3-propanediol instead of DL-alaninol. Method B; Rt: 1.00 min. m/z: 464 (M+H)$^+$ Exact mass: 463.1.

Compound 37: (3S)—N-(3,4-difluorophenyl)-3-[(1S)-1-hydroxyethyl]-7-methyl-1,1-dioxo-3,4-dihydro-2H-pyrrolo[3,4-b][1,4,5]oxathiazepine-6-carboxamide

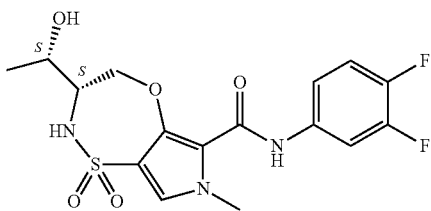

Compound 37 (105.5 mg) was prepared similarly as described for compound 14, using D-threoninol instead of DL-alaninol. $^1$H NMR (400 MHz, DMSO-d$_6$) δ ppm 1.10 (d, J=6.4 Hz, 3H), 3.61-3.70 (m, 1H), 3.82 (s, 3H), 3.85-3.99 (m, 2H), 4.74 (d, J=11.4 Hz, 1H), 4.96 (d, J=4.6 Hz, 1H), 7.36-7.44 (m, 2H), 7.44-7.50 (m, 2H), 7.87 (ddd, 7.5, 2.6 Hz, 1H), 9.44 (s, 1H); Method B; Rt: 0.87 min. m/z: 402 (M+H)$^+$ Exact mass: 401.1.

Compound 38: (3S)—N-(3,4-difluorophenyl)-7-methyl-1,1-dioxo-3-(3-pyridylmethyl)-3,4-dihydro-2H-pyrrolo[3,4-b][1,4,5]oxathiazepine-6-carboxamide

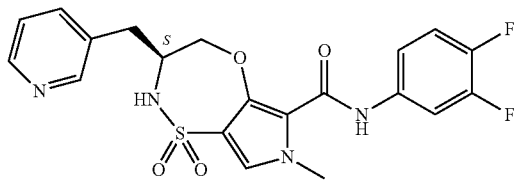

Compound 38 (7.1 mg) was prepared similarly as described for compound 14, using (2S)-2-amino-3-(3-pyridyl)propan-1-ol instead of DL-alaninol. $^1$H NMR (400 MHz, CHLOROFORM-d) δ ppm 2.86-3.10 (m, 2H), 3.94 (s, 3H), 4.13 (br s, 1H), 4.36 (dd, J=13.0, 9.0 Hz, 1H), 4.66 (dd, J=12.9, 3.0 Hz, 1H), 5.35 (br s, 1H), 7.03 (s, 1H), 7.06-7.16 (m, 2H), 7.27-7.34 (m, 1H), 7.61-7.70 (m, 2H), 8.45 (d, J=1.5 Hz, 1H), 8.51 (dd, J=4.8, 1.5 Hz, 1H), 8.66 (s, 1H); Method B; Rt: 0.91 min. m/z: 449 (M+H)$^+$ Exact mass: 448.1.

Compound 39: (3*S)-3,7-dimethyl-1,1-dioxo-N-(3,4,5-trifluorophenyl)-2,3,4,5-tetrahydropyrrolo[3,4-f]thiazepine-6-carboxamide

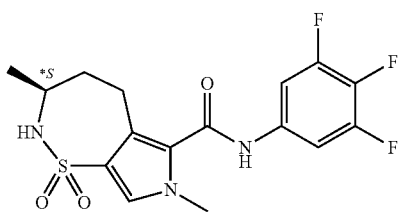

Compound 39 (41 mg) was prepared similarly as described for compound 10, using compound 29 instead of compound 7. $^1$H NMR (400 MHz, DMSO-d$_6$) δ ppm 1.13 (d, J=6.8 Hz, 3H), 1.34 (q, J=12.2 Hz, 1H), 1.84 (br dd, J=14.0, 6.4 Hz, 1H), 2.78-2.99 (m, 1H), 3.57-3.66 (m, 1H), 3.69 (s, 3H), 7.03 (d, J=9.6 Hz, 1H), 7.44 (s, 1H), 7.54-7.66 (m, 1H), 10.59 (s, 1H); Method B; Rt: 0.91 min. m/z: 386 (M−H)$^-$ Exact mass: 387.1.

Compound 40: (3*S)—N-[4-fluoro-3-(trifluoromethyl)phenyl]-3,7-dimethyl-1,1-dioxo-2,3,4,5-tetrahydropyrrolo[3,4-f]thiazepine-6-carboxamide

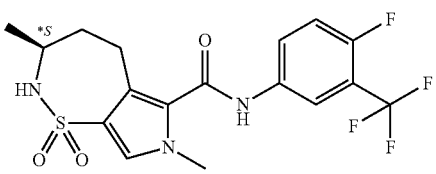

Compound 40 (49 mg) was prepared similarly as described for compound 10, using compound 30 instead of compound 7. $^1$H NMR (400 MHz, DMSO-d$_6$) δ ppm 1.13 (d, J=6.8 Hz, 3H), 1.27-1.41 (m, 1H), 1.81-1.88 (m, 1H), 2.80-2.89 (m, 1H), 2.94-3.02 (m, 1H), 3.59-3.67 (m, 1H), 3.69 (s, 3H), 7.02 (d, J=9.6 Hz, 1H), 7.43 (s, 1H), 7.51 (t, J=9.8 Hz, 1H), 7.91-7.96 (m, 1H), 8.20 (dd, J=6.6, 2.7 Hz, 1H), 10.58 (s, 1H); Method B; Rt: 1.01 min. m/z: 418 (M−H)$^-$ Exact mass: 419.1.

Compound 41: (3*S)—N-(4-fluoro-3-methyl-phenyl)-3,7-dimethyl-1,1-dioxo-2,3,4,5-tetrahydropyrrolo[3,4-f]thiazepine-6-carboxamide

Compound 41 (52 mg) was prepared similarly as described for compound 10, using compound 31 instead of compound 7. $^1$H NMR (400 MHz, DMSO-d$_6$) δ ppm 1.13 (d, J=6.8 Hz, 3H), 1.35 (q, J=12.3 Hz, 1H), 1.84 (br dd, J=14.0, 6.4 Hz, 1H), 2.20-2.24 (m, 3H), 2.78-2.98 (m, 2H), 3.59-3.73 (m, 4H), 7.00 (d, J=9.5 Hz, 1H), 7.10 (t, J=9.2 Hz, 1H), 7.39 (s, 1H), 7.45-7.52 (m, 1H), 7.62 (dd, J=7.1, 2.7 Hz, 1H), 10.23 (s, 1H); Method B; Rt: 0.92 min. m/z: 364 (M−H)$^-$ Exact mass: 365.1.

Compound 42: (3*S)-3,7-dimethyl-1,1-dioxo-N-[2-(trifluoromethyl)-4-pyridyl]-2,3-dihydropyrrolo[3,4-f]thiazepine-6-carboxamide

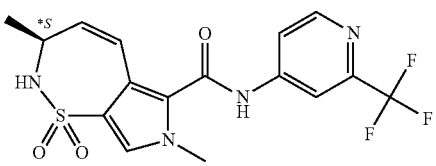

Compound 42 (115 mg) was prepared similarly as described for compound 29, using 4-amino-2-trifluoromethylpyridine instead of 3,4,5-trifluoroaniline. ¹H NMR (400 MHz, DMSO-d₆) δ ppm 1.32 (d, J=7.3 Hz, 3H), 3.74 (s, 3H), 4.22-4.34 (m, 1H), 5.61 (dd, J=12.6, 2.4 Hz, 1H), 6.49 (dd, J=12.6, 2.6 Hz, 1H), 7.56-7.63 (m, 2H), 7.89 (dd, J=5.5, 2.0 Hz, 1H), 8.20 (d, J=2.0 Hz, 1H), 8.67 (d, J=5.5 Hz, 1H), 11.21 (br s, 1H); Method B; Rt: 0.86 min. m/z: 401 (M+H)⁺ Exact mass: 400.1.

Compound 43: N-(3,4-difluorophenyl)-7-methyl-3-(1-methylpyrazol-4-yl)-1,1-dioxo-3,4-dihydro-2H-pyrrolo[3,4-b][1,4,5]oxathiazepine-6-carboxamide

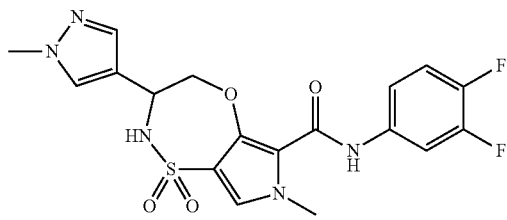 [SMILES: Cn1cc(C2COc3c(cn(C)c3C(=O)Nc3ccc(F)c(F)c3)S(=O)(=O)N2)cn1]

Compound 43 (53.6 mg) was prepared similarly as described for compound 14, using 2-amino-2-(1-methyl-1h-pyrazol-4-yl)ethan-1-ol instead of DL-alaninol. The ring closure was obtained after heating overnight at 140° C. in DMA and compound 43 was purified using a heptane to EtOAc:EtOH 3:1 gradient. ¹H NMR (400 MHz, DMSO-d₆) δ ppm 3.81 (s, 3H), 3.84 (s, 3H), 3.98-4.11 (m, 1H), 4.72 (dd, J=12.5, 2.2 Hz, 1H), 4.86 (td, J=9.6, 1.9 Hz, 1H), 7.36-7.44 (m, 1H), 7.44-7.51 (m, 2H), 7.53 (s, 1H), 7.72 (s, 1H), 7.82-7.89 (m, 1H), 8.02 (d, J=9.7 Hz, 1H), 9.46 (s, 1H); Method B; Rt: 0.90 min. m/z: 438 (M+H)⁺ Exact mass: 437.1.

Compound 44: (3S)—N-(3,4-difluorophenyl)-7-fluoro-3-isopropyl-1,1-dioxo-3,4-dihydro-2H-5,1λ⁶, 2-benzoxathiazepine-6-carboxamide

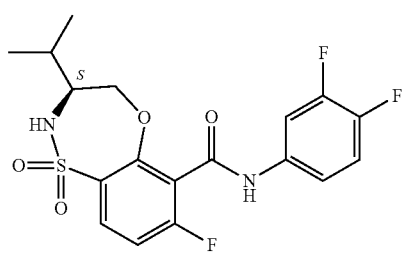

Compound 44 (11.5 mg) was prepared similarly as described for compound 12, using L-valinol instead of DL-alaninol. ¹H NMR (400 MHz, DMSO-d₆) δ ppm 0.94 (dd, J=6.71, 1.65 Hz, 6H) 1.80 (dq, J=13.70, 6.80 Hz, 1H) 3.43-3.56 (m, 1H) 3.80 (dd, J=12.43, 10.01 Hz, 1H) 4.55 (dd, J=12.54, 2.20 Hz, 1H) 7.31 (t, J=8.69 Hz, 1H) 7.35-7.51 (m, 2H) 7.70 (br d, J=8.58 Hz, 1H) 7.80-7.92 (m, 2H) 10.98 (s, 1H); Method B; Rt: 1.03 min. m/z: 413 (M–H)⁻ Exact mass: 414.1.

Compound 45: (3S)—N-(3-cyano-4-fluoro-phenyl)-7-fluoro-3-isopropyl-1,1-dioxo-3,4-dihydro-2H-5, 1λ⁶,2-benzoxathiazepine-6-carboxamide

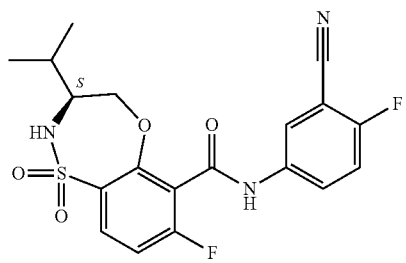

Compound 45 (378.5 mg) was prepared similarly as described for compound 44, using 5-amino-2-fluorobenzonitrile instead of 3,4-difluoroaniline. ¹H NMR (400 MHz, DMSO-d₆) δ ppm 0.94 (dd, J=6.82, 2.20 Hz, 6H) 1.80 (dq, J=13.78, 6.78 Hz, 1H) 3.48 (br s, 1H) 3.80 (dd, J=12.54, 10.12 Hz, 1H) 4.56 (dd, J=12.54, 2.20 Hz, 1H) 7.33 (t, J=8.69 Hz, 1H) 7.56 (t, J=9.13 Hz, 1H) 7.70 (br s, 1H) 7.85-7.98 (m, 2H) 8.20 (dd, J=5.72, 2.64 Hz, 1H) 11.14 (s, 1H); Method B; Rt: 0.98 min. m/z: 420 (M–H)⁻ Exact mass: 421.1.

Compound 46: (3R)-7-fluoro-N-(3-fluoro-4-methylphenyl)-3-isopropyl-1,1-dioxo-3,4-dihydro-2H-5, 1λ⁶,2-benzoxathiazepine-6-carboxamide

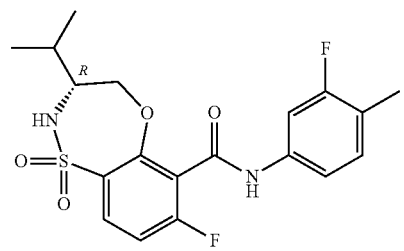

Compound 46 (155.1 mg) was prepared similarly as described for compound 44, using 4-fluoro-3-methylaniline instead of 3,4-difluoroaniline. ¹H NMR (400 MHz, DMSO-d₆) δ ppm 0.94 (dd, J=6.82, 1.98 Hz, 6H) 1.80 (dq, J=13.78, 6.78 Hz, 1H) 2.24 (d, J=1.54 Hz, 3H) 3.41-3.60 (m, 1H) 3.80 (dd, J=12.32, 9.90 Hz, 1H) 4.53 (dd, J=12.54, 2.20 Hz, 1H) 7.13 (t, J=9.24 Hz, 1H) 7.29 (t, J=8.58 Hz, 1H) 7.40-7.52 (m, 1H) 7.63 (dd, J=6.93, 2.53 Hz, 1H) 7.68 (br d, J=7.48 Hz, 1H) 7.87 (dd, J=8.80, 6.38 Hz, 1H) 10.70 (s, 1H); Method B; Rt: 1.04 min. m/z: 409 (M–H)⁻ Exact mass: 410.1.

Compound 47: N-(3,4-difluorophenyl)-7-methyl-1, 1-dioxo-3-(trifluoromethyl)-2,3,4,5-tetrahydropyrrolo[3,4-f]thiazepine-6-carboxamide

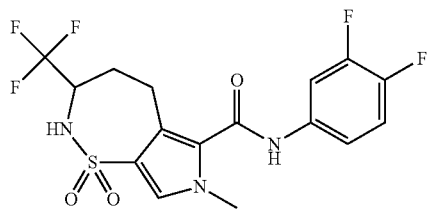 [SMILES: Cn1cc2c(c1C(=O)Nc1ccc(F)c(F)c1)CCC(C(F)(F)F)NS2(=O)=O]

1,1,1-trifluorobut-3-en-2-ylamine (306 mg, 1.90 mmol) was dissolved in pyridine (5 mL). Methyl 3-bromo-4-chlorosulfonyl-1-methyl-pyrrole-2-carboxylate (500 mg, 1.58 mmol) was added and the mixture stirred at room temperature for 16 hours. The reaction mixture was filtered and the filtrate was evaporated to dryness. The residue was purified by column chromatography using a gradient from 0 till 50% EtOAc in heptane over 15 column volumes. The product fractions were concentrated in vacuum to yield methyl 3-bromo-1-methyl-4-[1-(trifluoromethyl)allylsulfamoyl] pyrrole-2-carboxylate (385 mg) as a white powder. Method D; Rt: 1.74 min. m/z: 405 (M+H)⁺ Exact mass: 404.0.

Methyl 3-bromo-1-methyl-4-[1-(trifluoromethyl)allylsulfamoyl]pyrrole-2-carboxylate (385 mg), bis(tri-tert-butylphosphine)palladium(0) (211 mg, 0.41 mmol) and trimethylamine (286 μL, 2.07 mmol) were dissolved in DMF (5 mL). The reaction mixture was heated in the microwave oven for 30 minutes at 120° C. The volatiles were removed under reduced pressure and the residue was purified by column chromatography using a gradient from 0 till 50% EtOAc in heptane over 15 column volumes. The product fractions were concentrated in vacuo to yield methyl 7-methyl-1,1-dioxo-3-(trifluoromethyl)-2,3-dihydropyrrolo[3,4-f]thiazepine-6-carboxylate (152 mg) as a white solid. Method D; Rt: 1.64 min. m/z: 405 (M+H)⁺ Exact mass: 404.0.

Methyl 7-methyl-1,1-dioxo-3-(trifluoromethyl)-2,3-dihydropyrrolo[3,4-f]thiazepine-6-carboxylate (152 mg) and Pd/C (10%) (50 mg, 0.047 mmol) were dispensed in MeOH (50 mL). The reaction mixture was set under a hydrogen atmosphere and stirred for 2 hours. The reaction mixture was filtered and the volatiles were removed under reduced pressure yielding methyl 7-methyl-1,1-dioxo-3-(trifluoromethyl)-2,3,4,5-tetrahydropyrrolo[3,4-f]thiazepine-6-carboxylate (153 mg) as a white powder.

Methyl 7-methyl-1,1-dioxo-3-(trifluoromethyl)-2,3,4,5-tetrahydropyrrolo-[3,4-f]thiazepine-6-carboxylate (153 mg) and 3,4-difluoroaniline (57 μL, 0.56 mmol) were dissolved in THF (10 mL). Lithium bis(trimethylsilyl)amide (1.41 mL, 1 M in THF, 1.41 mmol) was added and the reaction mixture was stirred 4 hours at room temperature. NH₄Cl (sat., aq., 5 mL) was added and the organic layer was removed. The aqueous layer was extracted with DCM (2×5 mL) and the combined organic layers were evaporated to dryness. The residue was purified via prep. HPLC (Stationary phase: RP XBridge Prep C18 OBD-10 μm, 30×150 mm, mobile phase: 0.25% NH₄HCO₃ solution in water, MeOH) compound 47 (73 mg) as a white powder. ¹H NMR (400 MHz, DMSO-d₆) δ ppm 1.58-1.69 (m, 1H), 2.11 (br dd, J=13.8, 6.3 Hz, 1H), 2.84-2.95 (m, 1H), 3.12 (br dd, J=15.6, 6.2 Hz, 1H), 3.70 (s, 3H), 4.18-4.31 (m, 1H), 7.37-7.50 (m, 2H), 7.54 (s, 1H), 7.79-7.88 (m, 1H), 8.04 (d, J=10.4 Hz, 1H), 10.54 (s, 1H); Method D; Rt: 1.82 min. m/z: 422 (M–H)⁻ Exact mass: 423.1.

Compound 48: (3R)—N-(3,4-difluorophenyl)-7-fluoro-3-isopropyl-1,1-dioxo-3,4-dihydro-2H-5,1λ⁶,2-benzoxathiazepine-6-carboxamide

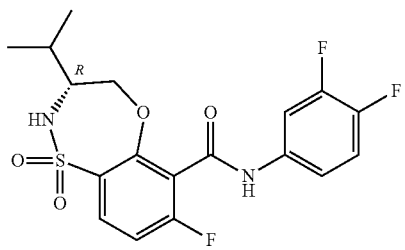

Compound 48 (75.5 mg) was prepared similarly as described for compound 12, using D-valinol instead of DL-alaninol. ¹H NMR (400 MHz, DMSO-d₆) δ ppm 0.94 (dd, J=6.71, 1.87 Hz, 6H) 1.66-1.94 (m, 1H) 3.48 (br t, J=7.59 Hz, 1H) 3.80 (dd, J=12.43, 10.01 Hz, 1H) 4.55 (dd, J=12.54, 2.20 Hz, 1H) 7.23-7.35 (m, 1H) 7.36-7.51 (m, 2H) 7.70 (s, 1H) 7.79-7.94 (m, 2H) 10.97 (s, 1H); Method B; Rt: 1.02 min. m/z: 413 (M–H)⁻ Exact mass: 414.1.

Compound 49: (3R)—N-(3-cyano-4-fluoro-phenyl)-7-fluoro-3-isopropyl-1,1-dioxo-3,4-dihydro-2H-5,1λ⁶,2-benzoxathiazepine-6-carboxamide

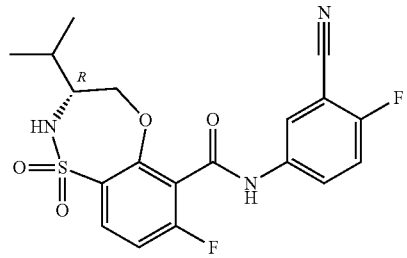

Compound 49 (39.7 mg) was prepared similarly as described for compound 48, using 5-amino-2-fluorobenzonitrile instead of 3,4-difluoroaniline. ¹H NMR (400 MHz, DMSO-d₆) δ ppm 0.94 (dd, J=6.82, 2.20 Hz, 6H) 1.80 (dq, J=13.64, 6.82 Hz, 1H) 3.43-3.54 (m, 1H) 3.81 (dd, J=12.43, 10.01 Hz, 1H) 4.56 (dd, J=12.54, 2.20 Hz, 1H) 7.32 (t, J=8.58 Hz, 1H) 7.56 (t, J=9.13 Hz, 1H) 7.71 (br s, 1H) 7.84-8.04 (m, 2H) 8.20 (dd, J=5.61, 2.75 Hz, 1H) 11.15 (br s, 1H); Method B; Rt: 0.97 min. m/z: 420 (M–H)⁻ Exact mass: 421.1.

Compound 50: (3*S)—N-(2-bromo-4-pyridyl)-3,7-dimethyl-1,1-dioxo-2,3-dihydropyrrolo[3,4-f]thiazepine-6-carboxamide

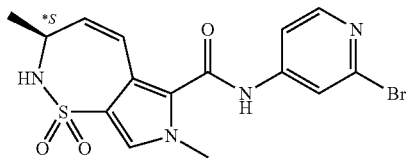

Compound 50 (42 mg) was prepared similarly as described for compound 29, using 4-amino-2-bromopyridine instead of 3,4,5-trifluoroaniline. ¹H NMR (400 MHz, DMSO-d₆) δ ppm 1.31 (d, J=7.5 Hz, 3H), 3.72 (s, 3H), 4.19-4.33 (m, 1H), 5.61 (dd, J=12.5, 2.4 Hz, 1H), 6.45 (dd, J=12.8, 2.6 Hz, 1H), 7.55-7.60 (m, 2H), 7.63 (dd, J=5.6, 1.9 Hz, 1H), 7.96 (d, J=1.8 Hz, 1H), 8.29 (d, J=5.6 Hz, 1H), 11.05 (s, 1H); Method D; Rt: 1.52 min. m/z: 411 (M+H)⁺ Exact mass: 410.0.

Compound 51: (3*S)—N-[3-(difluoromethyl)-4-fluoro-phenyl]-3,7-dimethyl-1,1-dioxo-2,3-dihydro-pyrrolo[3,4-f]thiazepine-6-carboxamide

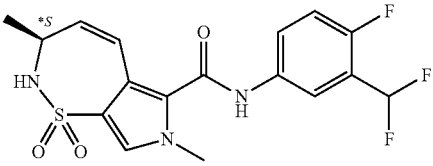

Compound 51 (46 mg) was prepared similarly as described for compound 29, using 3-(difluoromethyl)-4-fluoro-aniline instead of 3,4,5-trifluoroaniline. $^1$H NMR (400 MHz, DMSO-$d_6$) δ ppm 1.31 (d, J=7.5 Hz, 3H), 3.71 (s, 3H), 4.20-4.33 (m, 1H), 5.57 (dd, J=12.5, 2.4 Hz, 1H), 6.46 (dd, J=12.6, 2.6 Hz, 1H), 7.23 (br t, J=54.4 Hz, 1H), 7.38 (t, J=9.6 Hz, 1H), 7.51-7.58 (m, 2H), 7.77-7.87 (m, 1H), 8.06 (dd, J=6.3, 2.7 Hz, 1H), 10.75 (s, 1H); Method B; Rt: 0.90 min. m/z: 398 (M−H)$^-$ Exact mass: 399.1.

Compound 52: (3*S)—N-(3-chloro-2,4-difluoro-phenyl)-3,7-dimethyl-1,1-dioxo-2,3-dihydropyrrolo[3,4-f]thiazepine-6-carboxamide

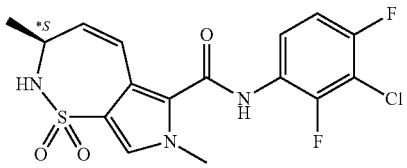 [SMILES: C[C@H]1C=Cc2c(cn(C)c2C(=O)Nc2ccc(F)c(Cl)c2F)S(=O)(=O)N1]

Compound 52 (40 mg) was prepared similarly as described for compound 29, using 3-chloro-2,4-difluoroaniline instead of 3,4,5-trifluoroaniline. $^1$H NMR (400 MHz, DMSO-$d_6$) δ ppm 1.31 (d, J=7.5 Hz, 3H), 3.73 (s, 3H), 4.20-4.33 (m, 1H), 5.60 (dd, J=12.5, 2.4 Hz, 1H), 6.58 (dd, J=12.7, 2.5 Hz, 1H), 7.36 (td, J=9.0, 2.0 Hz, 1H), 7.55 (s, 1H), 7.57 (d, J=9.3 Hz, 1H), 7.64 (td, J=8.7, 5.8 Hz, 1H), 10.45 (br s, 1H); Method B; Rt: 0.93 min. m/z: 400 (M−H)$^-$ Exact mass: 401.0.

Compound 53: (3*S)-3,7-dimethyl-1,1-dioxo-N-[2-(trifluoromethyl)-4-pyridyl]-2,3,4,5-tetrahydropyrrolo[3,4-f]thiazepine-6-carboxamide

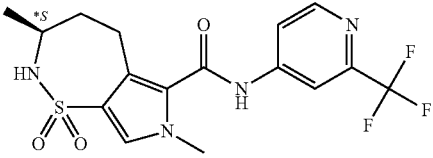 [SMILES: C[C@H]1CCc2c(cn(C)c2C(=O)Nc2ccnc(C(F)(F)F)c2)S(=O)(=O)N1]

To a solution of methyl 3-bromo-1-methyl-4-[[(1*S)-1-methylallyl]sulfamoyl]pyrrole-2-carboxylate (3.5 g, 10 mmol) in DMA (200 mL), in a pressure tube, purged with nitrogen, was added Hunig's base (1.89 mL, 0.75 g/mL, 11.0 mmol) and bis(tri-tert-butylphosphine)palladium(0) (0.76 g, 1.49 mmol). The reaction mixture was heated for 10 minutes at 140° C. The reaction mixture was poured into HCL (aq., 0.5 M, 150 mL). The resulting suspension was extracted with ethyl acetate (3×100 mL). The combined organic layers were dried (Na$_2$SO$_4$), concentrated and the residue (8 g) was purified using silica gel column chromatography (ethyl acetate in heptane from 0 to 40%). The desired fractions were combined and concentrated. This was purified via preparative HPLC (Stationary phase: RP XBridge Prep C18 OBD-10 μm, 30×150 mm, Mobile phase: 0.25% NH$_4$HCO$_3$ solution in water, MeOH) yielding methyl (3*S)-3,7-dimethyl-1,1-dioxo-2,3-dihydropyrrolo[3,4-f]thiazepine-6-carboxylate (640 mg) as a white powder. Method B; Rt: 0.74 min. m/z: 269 (M−H)$^-$ Exact mass: 270.1.

Methyl (3*S)-3,7-dimethyl-1,1-dioxo-2,3-dihydropyrrolo[3,4-f]thiazepine-6-carboxylate (400 mg, 1.48 mmol) was dissolved in MeOH (40 mL). Under a nitrogen atmosphere Pd/C (10%) (157 mg, 0.15 mmol) was added. The reaction mixture was hydrogenated for 30 minutes. The reaction mixture was filtered over decalite. The filtrate was evaporated to dryness to afford methyl (3S)-3,7-dimethyl-1,1-dioxo-2,3,4,5-tetrahydropyrrolo[3,4-f]thiazepine-6-carboxylate (360 mg) as a white powder.

To a solution of methyl (3S)-3,7-dimethyl-1,1-dioxo-2,3,4,5-tetrahydropyrrolo-[3,4-f]thiazepine-6-carboxylate (72 mg) and 4-amino-2-trifluoromethylpyridine (51 mg, 0.32 mmol in THF (5 mL) was added lithium bis(trimethylsilyl)amide (1.06 mL, 1 M in THF, 1.06 mmol) and the reaction mixture was stirred 1 hour at room temperature. NH$_4$Cl (sat., aq., 5 mL) was added and the organic layer was separated. The aqueous layer was extracted with DCM (2×5 mL) and the combined organic layers were evaporated to dryness. The residue was purified via prep. HPLC (Stationary phase: RP XBridge Prep C18 OBD-10 μm, 30×150 mm, Mobile phase: 0.25% NH$_4$HCO$_3$ solution in water, ACN) yielding compound 53 (60 mg) as a white powder. $^1$H NMR (400 MHz, DMSO-$d_6$) δ ppm 1.13 (d, J=6.8 Hz, 3H), 1.29-1.42 (m, 1H), 1.79-1.89 (m, 1H), 2.80-2.91 (m, 1H), 2.94-3.05 (m, 1H), 3.56-3.67 (m, 1H), 3.71 (s, 3H), 7.04 (d, J=9.6 Hz, 1H), 7.47 (s, 1H), 7.86 (dd, J=5.6, 2.0 Hz, 1H), 8.19 (d, J=2.0 Hz, 1H), 8.64 (d, J=5.5 Hz, 1H), 10.94 (br s, 1H); Method D; Rt: 1.63 min. m/z: 403 (M+H)$^+$ Exact mass: 402.1.

Compound 54: (3*S)—N-(3-chloro-2,4-difluoro-phenyl)-3,7-dimethyl-1,1-dioxo-2,3,4,5-tetrahydro-pyrrolo[3,4-f]thiazepine-6-carboxamide

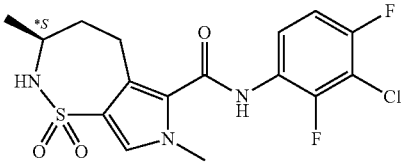 [SMILES: C[C@H]1CCc2c(cn(C)c2C(=O)Nc2ccc(F)c(Cl)c2F)S(=O)(=O)N1]

Compound 54 (24 mg) was prepared similarly as described for compound 53, using 3-chloro-2,4-difluoroaniline instead of 4-amino-2-trifluoromethylpyridine. $^1$H NMR (400 MHz, DMSO-$d_6$) δ ppm 1.14 (d, J=6.8 Hz, 3H), 1.38 (q, J=12.4 Hz, 1H), 1.87 (br dd, J=14.1, 6.6 Hz, 1H), 2.76-2.89 (m, 1H), 3.12 (br dd, J=15.5, 6.6 Hz, 1H), 3.56-3.68 (m, 1H), 3.69 (s, 3H), 7.02 (d, J=9.6 Hz, 1H), 7.35 (td, J=9.0, 2.0 Hz, 1H), 7.42 (s, 1H), 7.65 (td, J=8.8, 5.8 Hz, 1H), 10.18 (br s, 1H); Method B; Rt: 0.94 min. m/z: 402 (M−H)$^-$ Exact mass: 403.1.

Compound 55: (3*S)—N-[3-(difluoromethyl)-4-fluoro-phenyl]-3,7-dimethyl-1,1-dioxo-2,3,4,5-tetrahydropyrrolo[3,4-f]thiazepine-6-carboxamide

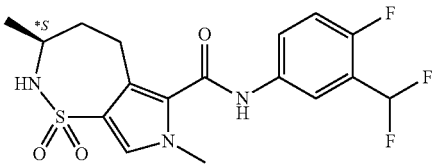 [SMILES: C[C@H]1CCc2c(cn(C)c2C(=O)Nc2ccc(F)c(C(F)F)c2)S(=O)(=O)N1]

Compound 55 (55 mg) was prepared similarly as described for compound 53, using 3-(difluoromethyl)-4-fluoro-aniline instead of 4-amino-2-trifluoromethylpyridine. $^1$H NMR (400 MHz, DMSO-$d_6$) δ ppm 1.13 (d, J=6.8 Hz, 3H), 1.36 (q, J=12.3 Hz, 1 H), 1.85 (br dd, J=13.9, 6.4 Hz, 1H), 2.76-2.90 (m, 1H), 2.92-3.02 (m, 1H), 3.57-3.74 (m, 4H), 7.01 (d, J=9.6 Hz, 1H), 7.22 (t, J=54.4 Hz, 1H), 7.33-7.40 (m, 1H), 7.41 (s, 1H), 7.74-7.86 (m, 1H), 8.06 (dd, J=6.4, 2.7 Hz, 1H), 10.48 (s, 1H); Method B; Rt: 0.91 min. m/z: 400 (M−H)$^-$ Exact mass: 401.1.

Compound 56: (3*S)—N-(3-cyano-4-fluoro-phenyl)-3,7-dimethyl-1,1-dioxo-2,3,4,5-tetrahydropyrrolo[3,4-f]thiazepine-6-carboxamide

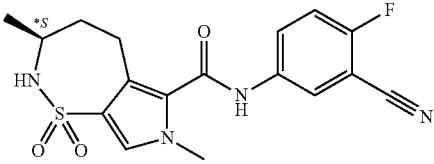 [SMILES: C[C@H]1CCc2c(cn(C)c2C(=O)Nc2ccc(F)c(C#N)c2)S(=O)(=O)N1]

Compound 56 (53 mg) was prepared similarly as described for compound 53, using 5-amino-2-fluorobenzonitrile instead of 4-amino-2-trifluoromethylpyridine. $^1$H NMR (400 MHz, DMSO-$d_6$) δ ppm 1.13 (d, J=6.8 Hz, 3H), 1.35 (br q, J=12.5 Hz, 1H), 1.84 (br dd, J=14.1, 6.4 Hz, 1H), 2.78-2.89 (m, 1H), 2.92-3.02 (m, 1H), 3.56-3.66 (m, 1H), 3.69 (s, 3H), 7.02 (d, J=9.5 Hz, 1H), 7.43 (s, 1H), 7.53 (t, J=9.1 Hz, 1H), 7.95 (ddd, J=9.2, 4.9, 2.7 Hz, 1H), 8.19 (dd, J=5.8, 2.7 Hz, 1H), 10.59 (s, 1H); Method B; Rt: 0.84 min. m/z: 375 (M−H)$^-$ Exact mass: 376.1.

Compound 57: (3*S)—N-(2-bromo-4-pyridyl)-3,7-dimethyl-1,1-dioxo-2,3,4,5-tetrahydropyrrolo[3,4-f]thiazepine-6-carboxamide

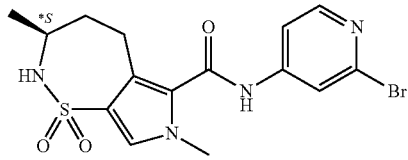 [SMILES: C[C@H]1CCc2c(cn(C)c2C(=O)Nc2ccnc(Br)c2)S(=O)(=O)N1]

Compound 57 (25 mg) was prepared similarly as described for compound 53, using 4-amino-2-bromopyridine instead of 4-amino-2-trifluoromethylpyridine. $^1$H NMR (400 MHz, DMSO-$d_6$) δ ppm 1.13 (d, J=6.8 Hz, 3H), 1.35 (q, J=12.3 Hz, 1H), 1.79-1.91 (m, 1H), 2.79-2.89 (m, 1H), 2.91-3.00 (m, 1H), 3.55-3.67 (m, 1H), 3.70 (s, 3H), 7.04 (d, J=9.6 Hz, 1H), 7.46 (s, 1H), 7.61 (dd, J=5.6, 1.9 Hz, 1H), 7.95 (d, J=1.8 Hz, 1H), 8.27 (d, J=5.6 Hz, 1H), 10.78 (s, 1H); Method B; Rt: 0.84 min. m/z: 411 (M−H)$^-$ Exact mass: 412.0.

Compound 58: 7-methyl-1,1-dioxo-3-(trifluoromethyl)-N-[2-(trifluoromethyl)-4-pyridyl]-2,3-dihydropyrrolo[3,4-f]thiazepine-6-carboxamide

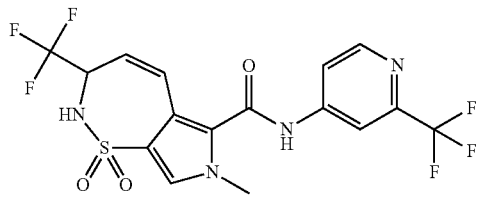 [SMILES: Cn1cc2c(c1C(=O)Nc1ccnc(C(F)(F)F)c1)C=CC(C(F)(F)F)NS2(=O)=O]

Methyl 7-methyl-1,1-dioxo-3-(trifluoromethyl)-2,3-dihydropyrrolo[3,4-f]thiazepine-6-carboxylate (200 mg) and 4-amino-2-trifluoromethylpyridine (102 mg, 0.62 mmol) were dissolved in THF (4 mL). Lithium bis(trimethylsilyl)amide (1.85 mL, 1 M in THF, 1.85 mmol) was added dropwise to the reaction mixture and stirred at room temperature for 2 hours. The reaction was quenched with NH$_4$Cl (sat., aq., 5 mL) and the organic layer was separated, dried (MgSO$_4$), filtered and concentrated in vacuum. The residue was purified via prep. HPLC (Stationary phase: RP XBridge Prep C18 OBD-10 μm, 30×150 mm, Mobile phase: 0.25% NH$_4$HCO$_3$ solution in water, ACN) yielding compound 58 (10 mg). $^1$H NMR (400 MHz, DMSO-$d_6$) δ ppm 3.78 (s, 3H), 4.89 (br dd, J=11.1, 8.2 Hz, 1H), 5.82 (dd, J=12.2, 3.0 Hz, 1H), 6.86 (dd, J=12.2, 2.7 Hz, 1H), 7.79 (s, 1H), 7.89 (dd, J=5.5, 2.0 Hz, 1H), 8.20 (d, J=1.9 Hz, 1H), 8.67 (d, J=5.2 Hz, 1H), 8.69 (s, 1H), 11.27-11.32 (m, 1H); Method D; Rt: 1.76 min. m/z: 455 (M+H)$^+$ Exact mass: 454.1.

Compound 59: 7-methyl-1,1-dioxo-3-(trifluoromethyl)-N-[2-(trifluoromethyl)-4-pyridyl]-2,3,4,5-tetrahydropyrrolo[3,4-f]thiazepine-6-carboxamide

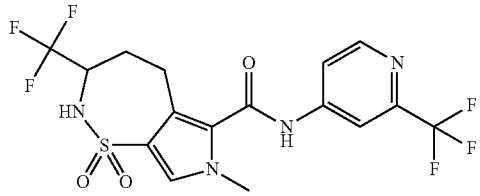 [SMILES: Cn1cc2c(c1C(=O)Nc1ccnc(C(F)(F)F)c1)CCC(C(F)(F)F)NS2(=O)=O]

Compound 59 (118 mg) was prepared similarly as described for compound 47, using 4-amino-2-trifluoromethylpyridine instead of 3,4-difluoroaniline. $^1$H NMR (400 MHz, DMSO-$d_6$) δ ppm 1.64 (q, J=12.2 Hz, 1H), 2.06-2.15 (m, 1H), 2.87-2.98 (m, 1H), 3.13-3.29 (m, 1H), 3.68-3.80 (m, 3H), 4.20-4.32 (m, 1H), 7.61 (s, 1H), 7.87 (dd, J=5.5, 2.0 Hz, 1H), 8.07 (br d, J=9.9 Hz, 1H), 8.19 (d, J=2.0 Hz, 1H), 8.66 (d, J=5.5 Hz, 1H), 11.03 (s, 1H); Method D; Rt: 1.75 min. m/z: 457 (M+H)$^+$ Exact mass: 456.1. This racemic mixture was separated in enantiomers 59a and 59b by preparative SFC (Stationary phase: Chiralpak Diacel AD

Compound 60: N-(3-cyano-4-fluoro-phenyl)-7-methyl-1,1-dioxo-3-(trifluoromethyl)-2,3,4,5-tetrahydropyrrolo[3,4-f]thiazepine-6-carboxamide

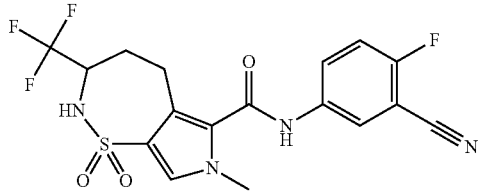 [SMILES: Cn1cc2c(c1C(=O)Nc1ccc(F)c(C#N)c1)CCC(C(F)(F)F)NS2(=O)=O]

Compound 60 (139 mg) was prepared similarly as described for compound 47, using 5-amino-2-fluorobenzonitrile instead of 3,4-difluoroaniline. $^1$H NMR (400 MHz, DMSO-d$_6$) δ ppm 1.59-1.70 (m, 1H), 2.06-2.16 (m, 1H), 2.84-2.96 (m, 1H), 3.10-3.21 (m, 1H), 3.66-3.78 (m, 3H), 4.19-4.32 (m, 1H), 7.51-7.58 (m, 2H), 7.96 (ddd, J=9.2, 4.8, 2.6 Hz, 1H), 8.05 (d, J=10.3 Hz, 1H), 8.19 (dd, J=5.8, 2.7 Hz, 1H), 10.61-10.71 (m, 1H); Method D; Rt: 1.73 min. m/z: 429 (M−H)$^-$ Exact mass: 430.1. This racemic mixture was separated in enantiomers 60a and 60b by preparative SFC (Stationary phase: Chiralpak Diacel AD 20×250 mm, Mobile phase: CO$_2$, EtOH with 0.4% iPrNH$_2$). Method I; Rt: 60a: 1.16 min, 60b: 1.61 min.

Compound 61: (3S)—N-(3,4-difluorophenyl)-7-methyl-1,1-dioxo-3-(trifluoromethyl)-3,4-dihydro-2H-pyrrolo[3,4-b][1,4,5]oxathiazepine-6-carboxamide

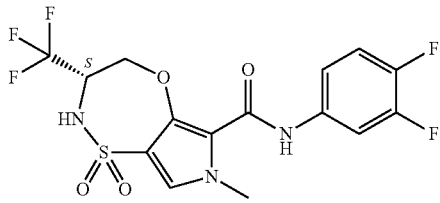

Ethyl 4-chlorosulfonyl-3-fluoro-1-methyl-pyrrole-2-carboxylate (250 mg) and (2S)-2-amino-3,3,3-trifluoropropan-1-ol hydrochloride (153 mg, 0.93 mmol) were dissolved in pyridine (2 mL) and stirred overnight at room temperature. The volatiles were removed under reduced pressure and the residue was purified on silica using a heptane to EtOAc gradient yielding ethyl 3-fluoro-1-methyl-4-[[(1S)-2,2,2-trifluoro-1-(hydroxymethyl)ethyl]sulfamoyl]pyrrole-2-carboxylate (254 mg).

Ethyl 3-fluoro-1-methyl-4-[[(1S)-2,2,2-trifluoro-1-(hydroxymethyl)ethyl]sulfamoyl]-pyrrole-2-carboxylate (254 mg) and 3,4-difluoroaniline (0.071 mL, 0.7 mmol) were dissolved in THF (5 mL). Lithium bis(trimethylsilyl)amide (2.8 mL, 1 M in THF, 2.8 mmol) was added and the reaction mixture was stirred overnight at room temperature. NH$_4$Cl (sat., aq., 50 mL) was added and the organic layer was removed. The aqueous layer was extracted with DCM (2×5 mL) and the combined organic layers were evaporated to dryness. The residue was purified on silica using a heptane to EtOAc:EtOH 3:1 gradient yielding N-(3,4-difluorophenyl)-3-fluoro-1-methyl-4-[[(1S)-2,2,2-trifluoro-1-(hydroxymethyl)ethyl]sulfamoyl]pyrrole-2-carboxamide (198 mg). Method B; Rt: 0.91 min. m/z: 446 (M+H)$^+$ Exact mass: 445.1.

N-(3,4-difluorophenyl)-3-fluoro-1-methyl-4-[[(1S)-2,2,2-trifluoro-1-(hydroxymethyl)-ethyl]sulfamoyl]pyrrole-2-carboxamide (198 mg) and cesium fluoride (173 mg, 1.14 mmol) were dissolved in DMF (5 mL) and heated overnight at 100° C. The reaction mixture was purified via prep. HPLC (Stationary phase: RP XBridge Prep C18 OBD-10 μm, 30×150 mm, Mobile phase: 0.25% NH$_4$HCO$_3$ solution in water, ACN) yielding compound 61 as a white powder. $^1$H NMR (400 MHz, DMSO-d$_6$) δ ppm 3.83 (s, 3H), 4.29 (dd, J=12.7, 9.4 Hz, 1H), 4.49-4.62 (m, 1H), 4.91 (dd, J=13.0, 2.0 Hz, 1H), 7.37-7.46 (m, 1H), 7.46-7.52 (m, 1H), 7.58 (s, 1H), 7.86 (ddd, J=13.2, 7.5, 2.4 Hz, 1H), 8.75 (br s, 1H), 9.47 (s, 1H); Method B; Rt: 0.99 min. m/z: 426 (M+H)$^+$ Exact mass: 425.1.

Compound 62: (3R)—N-(3,4-difluorophenyl)-3-[(1R)-1-methoxyethyl]-7-methyl-1,1-dioxo-3,4-dihydro-2H-pyrrolo[3,4-b][1,4,5]oxathiazepine-6-carboxamide

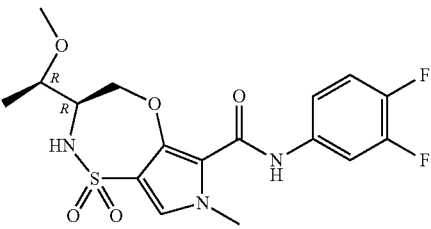

Ethyl 4-chlorosulfonyl-3-fluoro-1-methyl-pyrrole-2-carboxylate (250 mg), O-methyl-L-threonine (119 mg, 0.89 mmol) and Hunig's base (0.46 mL, 2.68 mmol) were dissolved in DCM (5 mL) and stirred overnight at room temperature. The reaction mixture was directly loaded on a silica cartridge and a gradient from heptane to EtOAc:EtOH:AcOH 3:1:0.1 was applied yielding (2S,3R)-2-[(5-ethoxycarbonyl-4-fluoro-1-methyl-pyrrol-3-yl)sulfonylamino]-3-methoxy-butanoic acid as an off-white powder (310 mg).

(2S,3R)-2-[(5-ethoxycarbonyl-4-fluoro-1-methyl-pyrrol-3-yl)sulfonylamino]-3-methoxy-butanoic acid (310 mg) and 3,4-difluoroaniline (86 μL, 0.85 mmol) were dissolved in THF (5 mL). Lithium bis(trimethylsilyl)amide (4.23 mL, 1 M in THF, 4.23 mmol) was added and the reaction mixture was stirred 2 hours at room temperature. NH$_4$Cl (sat., aq., 50 mL) was added and the organic layer was removed. The aqueous layer was extracted with DCM (2×5 mL) and the combined organic layers were evaporated to dryness. The residue was purified on silica using a gradient from heptane to EtOAc:EtOH:AcOH 3:1:0.1 yielding (2S,3R)-2-[[5-[(3,4-difluoro-phenyl)carbamoyl]-4-fluoro-1-methyl-pyrrol-3-yl]sulfonylamino]-3-methoxy-butanoic acid as an off-white powder (324 mg).

(2S,3R)-2-[[5-[(3,4-difluorophenyl)carbamoyl]-4-fluoro-1-methyl-pyrrol-3-yl]-sulfonylamino]-3-methoxy-butanoic acid was dissolved in THF (10 mL) and lithium aluminum hydride solution (1.44 mL, 1 M in THF, 1.44 mmol) was added dropwise and the reaction mixture was stirred overnight at room temperature. Sodium sulfate decahydrate (348 mg, 1.08 mmol) was added followed by Na$_2$SO$_4$. The reaction mixture was filtered and evaporated to dryness. The residue was purified using a heptane to EtOAc:EtOH 3:1 gradient yielding N-(3,4-difluorophenyl)-3-fluoro-4-[[(1R,2R)-1-(hydroxymethyl)-2-methoxy-propyl]sulfamoyl]-1-methyl-pyrrole-2-carboxamide (50 mg).

N-(3,4-difluorophenyl)-3-fluoro-4-[[(1R,2R)-1-(hydroxymethyl)-2-methoxy-propyl]-sulfamoyl]-1-methyl-pyrrole-2-carboxamide (50 mg) was dissolved in DMF (5 mL). Cesium fluoride (70 mg, 0.46 mmol) was added and the reaction mixture was heated overnight at 100° C. The reaction mixture was directly loaded on a silica cartridge and a gradient from heptane to EtOAc was applied yielding compound 62 (23.9 mg) as an off-white powder. $^1$H NMR (400 MHz, DMSO-d$_6$) δ ppm 1.13 (d, J=6.4 Hz, 3H), 3.28 (s, 3H), 3.55-3.65 (m, 1H), 3.77 (br dd, J=7.9, 3.3 Hz, 1H), 3.82 (s, 3H), 4.00 (dd, J=12.5, 9.0 Hz, 1H), 4.70 (dd, J=12.7, 1.2 Hz, 1H), 7.36-7.44 (m, 1H), 7.44-7.51 (m, 2H), 7.51-7.62 (m, 1H), 7.86 (ddd, J=13.3, 7.5, 2.5 Hz, 1H), 9.42 (s, 1H); Method B; Rt: 0.99 min. m/z: 416 (M+H)$^+$ Exact mass: 415.1.

Compound 63: (3S)—N-(3,4-difluorophenyl)-3-[(S)-hydroxy(phenyl)methyl]-7-methyl-1,1-dioxo-3,4-dihydro-2H-pyrrolo[3,4-b][1,4,5]oxathiazepine-6-carboxamide

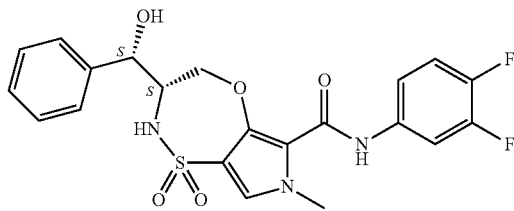

Compound 63 (32.7 mg) was prepared similarly as described for compound 14, using (1S,2S)-(+)-2-amino-1-phenyl-1,3-propanediol instead of DL-alaninol. The ring closure was obtained after heating overnight at 100° C. in DMF and compound 63 was purified via prep. HPLC (Stationary phase: RP XBridge Prep C18 OBD-10 μm, 30×150 mm, Mobile phase: 0.25% NH$_4$HCO$_3$ solution in water, ACN). $^1$H NMR (400 MHz, DMSO-d$_6$) δ ppm 3.80 (s, 3H), 3.85-3.96 (m, 1H), 4.01 (dd, J=12.4, 9.1 Hz, 1H), 4.72 (br d, J=11.9 Hz, 1H), 4.86 (t, J=4.3 Hz, 1H), 5.67 (d, J=4.6 Hz, 1H), 7.25-7.31 (m, 1H), 7.31-7.48 (m, 8H), 7.79-7.90 (m, 1H), 9.44 (s, 1H); Method B; Rt: 0.98 min. m/z: 462 (M−H)$^-$ Exact mass: 463.1.

Compound 64: (3R)—N-[3-(difluoromethyl)-4-fluoro-phenyl]-3-[(1S)-1-hydroxyethyl]-7-methyl-1,1-dioxo-3,4-dihydro-2H-pyrrolo[3,4-b][1,4,5]oxathiazepine-6-carboxamide

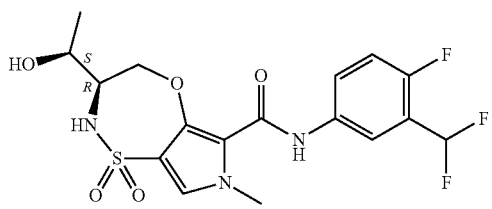

Compound 64 (124.8 mg) was prepared similarly as described for compound 35, using 3-(difluoromethyl)-4-fluoro-aniline instead of 3,4-difluoroaniline and heating overnight at 100° C. $^1$H NMR (400 MHz, DMSO-d$_6$) δ ppm 1.22 (d, J=6.2 Hz, 3H), 3.35-3.46 (m, 1H), 3.55-3.67 (m, 1H), 3.83 (s, 3H), 3.99 (dd, J=12.8, 9.0 Hz, 1H), 4.89 (dd, J=12.8, 1.8 Hz, 1H), 5.05 (br s, 1H), 7.21 (t, J=54.4 Hz, 1H), 7.35 (t, J=9.5 Hz, 1H), 7.47 (s, 1H), 7.61 (br s, 1H), 7.82 (dt, J=8.1, 4.1 Hz, 1H), 8.04 (dd, J=6.3, 2.5 Hz, 1H), 9.41-9.51 (m, 1H); Method B; Rt: 0.87 min. m/z: 432 (M−H)$^-$ Exact mass: 433.1.

Compound 65: (3R)—N-(3-cyano-4-fluoro-phenyl)-3-[(1S)-1-hydroxyethyl]-7-methyl-1,1-dioxo-3,4-dihydro-2H-pyrrolo[3,4-b][1,4,5]oxathiazepine-6-carboxamide

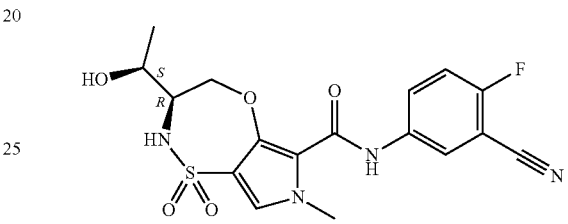

Compound 65 (29.2 mg) was prepared similarly as described for compound 64, using 5-amino-2-fluorobenzonitrile instead of 3-(difluoromethyl)-4-fluoro-aniline. $^1$H NMR (400 MHz, DMSO-d$_6$) δ ppm 1.21 (d, J=6.2 Hz, 3H), 3.41 (br t, J=8.0 Hz, 1H), 3.61 (br s, 1H), 3.83 (s, 3H), 3.97 (dd, J=12.9, 9.1 Hz, 1H), 4.88-4.96 (m, 1H), 5.06 (br s, 1H), 7.49 (s, 1H), 7.51 (t, J=9.2 Hz, 1H), 7.64 (br s, 1H), 8.05 (ddd, J=9.2, 4.9, 2.9 Hz, 1H), 8.20 (dd, J=5.7, 2.6 Hz, 1H), 9.51 (s, 1H); Method B; Rt: 0.81 min. m/z: 407 (M−H)$^-$ Exact mass: 408.1.

Compound 66: (3R)—N-(2-bromo-4-pyridyl)-3-[(1S)-1-hydroxyethyl]-7-methyl-1,1-dioxo-3,4-dihydro-2H-pyrrolo[3,4-b][1,4,5]oxathiazepine-6-carboxamide

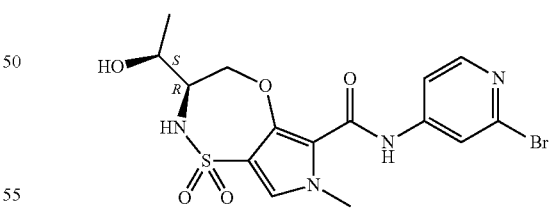

Compound 66 (82.9 mg) was prepared similarly as described for compound 64, using 4-amino-2-bromopyridine instead of 3-(difluoromethyl)-4-fluoro-aniline. $^1$H NMR (400 MHz, DMSO-d$_6$) δ ppm 1.21 (d, J=6.2 Hz, 3H), 3.34-3.46 (m, 1H), 3.56-3.66 (m, 1H), 3.83 (s, 3H), 4.01 (dd, J=12.8, 9.0 Hz, 1H), 4.92 (dd, J=12.7, 1.9 Hz, 1H), 5.07 (d, J=5.5 Hz, 1H), 7.54 (s, 1H), 7.61-7.70 (m, 1H), 7.72 (dd, J=5.6, 1.9 Hz, 1H), 8.02 (d, J=1.8 Hz, 1H), 8.24 (d, J=5.5 Hz, 1H), 9.65 (br s, 1H); Method B; Rt: 0.75 min. m/z: 443 (M−H)$^-$ Exact mass: 444.0.

Compound 67: N-(3,4-difluorophenyl)-3,7-dimethyl-1,1-dioxo-2,3,4,5-tetrahydropyrrolo[3,4-f][1,2,5]thiadiazepine-6-carboxamide

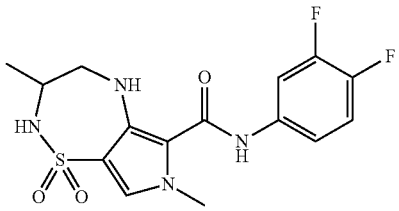 [SMILES: CC1CNc2c(cn(C)c2C(=O)Nc2ccc(F)c(F)c2)S(=O)(=O)N1]

Carbamic acid, n-(2-aminopropyl)-, 1,1-dimethylethyl ester (850 mg, 4.64 mmol) was dissolved in DCM (20 mL. Hunig's base (1.92 mL, 11.1 mmol) was added and then Ethyl 4-chlorosulfonyl-3-fluoro-1-methyl-pyrrole-2-carboxylate (1 g) was added. The mixture was stirred at room temperature for 2 hours. The mixture was washed with water and the organic layer was separated, dried (MgSO$_4$), filtered and concentrated in vacuo. The residue was purified by column chromatography using a gradient from 0 till 50% EtOAc in heptane over 15 column volumes. The product fractions were concentrated in vacuum to yield ethyl 4-[[2-(tert-butoxycarbonylamino)-1-methyl-ethyl]sulfamoyl]-3-fluoro-1-methyl-pyrrole-2-carboxylate (1.3 g) as a white powder.

Ethyl 4-[[2-(ter t-butoxycarbonylamino)-1-methyl-ethyl]sulfamoyl]-3-fluoro-1-methyl-pyrrole-2-carboxylate (1.3 g) was dissolved in 1,4-dioxane (15 mL). HCl (8 mL, 4 M in dioxane, 31.9 mmol) was added and the mixture was stirred at room temperature for 16 hours. The precipitated product was filtered off and dried under vacuum to yield ethyl 4-[(2-amino-1-methyl-ethyl)sulfamoyl]-3-fluoro-1-methyl-pyrrole-2-carboxylate hydrochloride (1 g) as a white solid. Method B; Rt: 0.50 min. m/z: 208 (M+H)$^+$ Exact mass: 307.1.

Ethyl 4-[(2-amino-1-methyl-ethyl)sulfamoyl]-3-fluoro-1-methyl-pyrrole-2-carboxylate hydrochloride (539 mg) and 3,4-difluoroaniline (0.19 mL, 1.88 mmol) were dissolved in THF (20 mL). Lithium bis(trimethylsilyl)amide (7.8 mL, (1M in THF), 7.8 mmol) was added dropwise to the reaction mixture. The mixture was stirred at room temperature for 1 hour. The mixture was quenched with NH$_4$Cl (sat., aq., 15 mL). The reaction mixture was diluted with 2-MeTHF and the organic layer was separated, dried (MgSO$_4$), filtered and concentrated in vacuum. The residue was triturated in DIPE, filtered off and dried under vacuum to yield 4-[(2-amino-1-methyl-ethyl)sulfamoyl]-N-(3,4-difluorophenyl)-3-fluoro-1-methyl-pyrrole-2-carboxamide (500 mg) as a pale brown solid.

A microwave vial was charged with 4-[(2-amino-1-methyl-ethyl)sulfamoyl]-N-(3,4-difluorophenyl)-3-fluoro-1-methyl-pyrrole-2-carboxamide (200 mg), water (15 mL) and 1,4-dioxane (3 mL). The vial was capped and the mixture was irradiated at 150° C. for 6 hours. The mixture was neutralized with HCl (aq., 1M). The mixture was extracted with DCM and the organic phase was separated, dried (MgSO4), filtered and concentrated in vacuo. The residue was purified via prep. HPLC (Stationary phase: RP XBridge Prep C18 OBD-10 µm, 30×150 mm, Mobile phase: 0.25% NH$_4$HCO$_3$ solution in water, MeOH) yielding compound 67 (16 mg). $^1$H NMR (400 MHz, DMSO-d$_6$) δ ppm 1.12 (d, J=6.9 Hz, 3H), 2.80 (dd, J=14.1, 8.5 Hz, 1H), 3.39 (dd, J=13.7, 1.6 Hz, 1H), 3.48-3.60 (m, 1H), 3.78 (s, 3H), 5.45 (br s, 1H), 7.26-7.31 (m, 1H), 7.31-7.35 (m, 1H), 7.35 (s, 1H), 7.36-7.43 (m, 1H), 7.78 (ddd, J=13.4, 7.4, 2.2 Hz, 1H), 10.45 (br s, 1H); Method B; Rt: 0.91 min. m/z: 369 (M−H)$^-$ Exact mass: 370.1.

Compound 68: N-(3,4-difluorophenyl)-4-hydroxy-7-methyl-1,1-dioxo-2,3,4,5-tetrahydropyrrolo[3,4-f]thiazepine-6-carboxamide

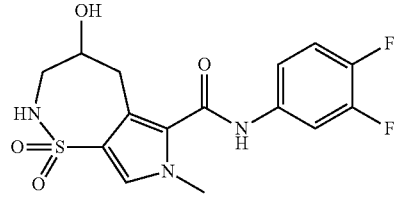 [SMILES: Cn1cc2c(c1C(=O)Nc1ccc(F)c(F)c1)CC(O)CNS2(=O)=O]

1-penten-4-yne (6.2 g) and ethyl isocyanoacetate (35.3 g, 297 mmol) dissolved in dioxane (100 mL) was added dropwise to a suspension of silver carbonate (3.88 g, 14.1 mmol) in dioxane (200 mL) between 80 and 90° C. during 45 minutes. The reaction mixture was stirred 2 hours at 80° C. The reaction mixture was filtered and concentrated. The residue was subjected to column chromatography using a gradient from 10 till 100% EtOAc in heptane over 10 column volumes yielding ethyl 3-allyl-1H-pyrrole-2-carboxylate (15.7 g) as an oil. $^1$H NMR (400 MHz, DMSO-d$_6$) δ ppm 1.28 (t, J=7.2 Hz, 3H), 3.48 (d, J=6.6 Hz, 2H), 4.22 (q, J=7.2 Hz, 2H), 4.93-4.98 (m, 1H), 4.98-5.06 (m, 1H), 5.93 (ddt, J=16.9, 10.1, 6.6, 6.6 Hz, 1H), 6.01 (t, J=2.4 Hz, 1H), 6.88 (t, J=2.9 Hz, 1H), 11.51 (br s, 1H); Method D; Rt: 1.83 min. m/z: 180 (M+H)$^+$ Exact mass: 179.1.

Ethyl 3-allyl-1H-pyrrole-2-carboxylate (15.7 g) and methyl iodide (14.3 g, 100 mmol) were dissolved in DMF (150 mL) and stirred in an ice bath. NaH (4.37 g, 60% dispersion in mineral oil, 109 mmol) was added portionwise during 10 minutes and the reaction mixture was stirred 1 hour. Another amount of NaH (2.27 g, 60% dispersion in mineral oil, 56.8 mmol) was added portionwise followed by methyl iodide (7.19 g, 50.6 mmol) and the reaction mixture was stirred 1 hour in an ice bath. The reaction mixture was quenched with ethanol (10 mL) and diluted with water (500 mL). The mixture was extracted with EtOAc (3×200 mL). The combined organic layers were dried (MgSO$_4$), filtered and concentrated. The residue was subjected to column chromatography using a gradient from 0 till 100% EtOAc in heptane over 10 column volumes yielding ethyl 3-allyl-1-methyl-pyrrole-2-carboxylate (13.2 g) as a light yellow oil. $^1$H NMR (400 MHz, DMSO-d$_6$) δ ppm 1.28 (t, J=7.2 Hz, 3H), 3.45 (d, J=6.6 Hz, 2H), 3.80 (s, 3H), 4.21 (q, J=7.1 Hz, 2H), 4.93-5.04 (m, 2H), 5.86-5.97 (m, 2H), 6.97 (d, J=2.4 Hz, 1H); Method D; Rt: 2.07 min. m/z: 194 (M+H)$^+$ Exact mass: 193.1.

Osmium tetroxide (2.43 g, 2.5% in t-butanol, 0.239 mmol) was added to ethyl 3-allyl-1-methyl-pyrrole-2-carboxylate (1156 mg, 5.982 mmol) in ACN (50 mL) and stirred 10 minutes. Water (10 mL) was added followed by benzyloxycarbonylamino 4-chlorobenzoate (1.83 g, 5.98 mmol). The reaction mixture was stirred 2 hours and then quenched with K$_2$S$_2$O$_5$ (aq., sat., 10 mL), diluted with water (100 mL) and extracted with EtOAc (2×100 mL). The combined organic layers were washed with saturated NaHCO$_3$ solution, dried (MgSO$_4$), filtered and concentrated. The residue was subjected to column chromatography using a gradient from 10 till 100% EtOAc in heptane over 10 column volumes yielding ethyl 3-[3-(benzyloxycarbonylamino)-2-hydroxy-propyl]-1-methyl-pyrrole-2-carboxylate (1.25 g) as a clear oil. $^1$H NMR (400 MHz, DMSO-d$_6$) δ ppm 1.27 (t, J=7.2 Hz, 3H), 2.67 (dd, J=14.0, 7.2 Hz, 1H), 2.81-2.96 (m, 2H), 3.00-3.08 (m, 1H), 3.60-3.75 (m, 1H), 3.78 (s, 3H), 4.19 (q, J=7.0 Hz, 2H), 4.57 (d, J=5.5 Hz, 1H), 5.00 (s, 2H), 6.01 (d, J=2.4 Hz, 1H), 6.94 (d, J=2.4 Hz, 1H), 7.06 (br t, J=5.6 Hz, 1H), 7.28-7.39 (m, 5H); Method D; Rt: 1.76 min. m/z: 361 (M+H)$^+$ Exact mass: 360.1.

Ethyl 3-[3-(benzyloxycarbonylamino)-2-hydroxy-propyl]-1-methyl-pyrrole-2-carboxylate (920 mg) was dissolved in EtOH (100 mL). Under a nitrogen atmosphere Pd/C (10%) (100 mg, 0.094 mmol) was added. The reaction mixture was hydrogenated for 3 hours. The reaction mixture was filtered over decalite. The filtrate was evaporated to dryness to afford ethyl 3-(3-amino-2-hydroxy-propyl)-1-methyl-pyrrole-2-carboxylate (549 mg) as an oil. Method D; Rt: 1.00 min. m/z: 227 (M+H)$^+$ Exact mass: 226.1.

Chlorosulfonic acid (2.06 g, 17.7 mmol) dissolved in dichloromethane (10 mL) was added to ethyl 3-(3-amino-2-hydroxy-propyl)-1-methyl-pyrrole-2-carboxylate (500 mg) in DCM (25 mL) in an ice bath and stirred for 1 hour. ACN (150 mL) was added and the reaction mixture was stirred 1 hour. Na$_2$CO$_3$ (2.58 g, 24.3 mmol) was added and the reaction mixture was stirred 1 hour. Na$_2$CO$_3$ (2.58 g, 24.3 mmol) was added and the reaction mixture was stirred for another 2 hours. 5 g Na$_2$CO$_3$ was added and the reaction mixture was stirred over weekend. The reaction mixture was filtered and concentrated. The residue was dissolved in DMF (5 mL), filtered and subjected as such to column chromatography using a gradient from 10 till 100% EtOAc in heptane over 10 column volumes yielding ethyl 4-hydroxy-7-methyl-1,1-dioxo-2,3,4,5-tetrahydropyrrolo-[3,4-f]thiazepine-6-carboxylate (51 mg) as a clear resin.

Lithium bis(trimethylsilyl)amide (1.4 mL, 1 M in THF, 1.4 mmol) was added to a solution of ethyl 4-hydroxy-7-methyl-1,1-dioxo-2,3,4,5-tetrahydropyrrolo-[3,4-f]thiazepine-6-carboxylate (51 mg) and 3,4-difluoroaniline (40 mg, 0.31 mmol) in THF (10 mL) and stirred for 1 hour. The reaction mixture was quenched with NH$_4$Cl (sat., aq., 25 mL) and extracted with EtOAc (50 mL). The organic layer was dried (Na$_2$SO$_4$), filtered and concentrated. The residue was subjected to column chromatography using a gradient from 10 till 100% EtOAc in heptane. The product fractions were concentrated and the residue was dissolved in methanol (5 mL), water was added until the product crystallized. Compound 68 (15.5 mg) was filtered off as beige crystals and dried in vacuo at 50° C. $^1$H NMR (400 MHz, DMSO-d$_6$) δ ppm 2.92-3.09 (m, 2H), 3.21-3.27 (m, 2H), 3.49-3.59 (m, 1H), 3.68 (s, 3H), 5.06 (d, J=4.4 Hz, 1H), 7.34 (br t, J=6.7 Hz, 1H), 7.38-7.47 (m, 3H), 7.82-7.90 (m, 1H), 10.48 (s, 1H); Method D; Rt: 1.76 min. m/z: 372 (M+H)$^+$ Exact mass: 371.1; MP: 229.0° C.

Compound 69: (3R)—N-(3,4-difluorophenyl)-3-[(1R)-1-hydroxyethyl]-7-methyl-1,1-dioxo-2,3-dihydropyrrolo[3,4-f]thiazepine-6-carboxamide

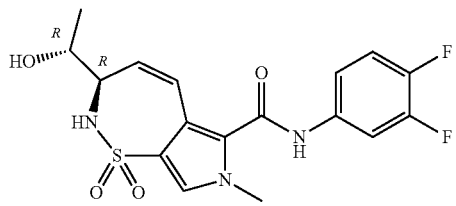

To a solution of N-(tert-butoxycarbonyl)-L-threonine methyl ester (10 g, 42.9 mmol) in CH$_2$Cl$_2$ (100 mL) was added 2-methoxypropene (8.22 mL, 85.7 mmol)) and camphorsulfonic acid (100 mg, 0.43 mmol)) at 0° C. under a nitrogen atmosphere. The resulting solution was stirred at room temperature for 2 hours. The reaction was then quenched with Et$_3$N (5 mL) and the organic solvents were removed in vacuo. Purification of the residue via flash chromatography (silica gel, 0 to 15% EtOAc in heptanes) afforded O3-tert-butyl O4-methyl (4S,5R)-2,2,5-trimethyl-oxazolidine-3,4-dicarboxylate (10.5 g) as a colorless oil. $^1$H NMR (400 MHz, DMSO-d$_6$) δ 1.25-1.54 (m, 18H), 3.66-3.72 (m, 3H), 3.86-3.91 (m, 1H), 4.06-4.13 (m, 1H) (rotamers).

To a stirred solution of methyltriphenylphosphonium bromide (27.4 g, 76.7 mmol) in THF (77 mL) at 0° C. was added KOtBu (8.39 g, 74.8 mmol) in one portion. The resulting mixture was stirred for one additional hour at the same temperature prior to use. To a stirred solution of O3-tert-butyl O4-methyl (4S,5R)-2,2,5-trimethyloxazolidine-3,4-dicarboxylate (10.5 g, 38.42 mmol) in CH$_2$Cl$_2$ (125 mL) was added DIBAL-H (1 M in hexanes, 77 mL) dropwise over 1 hour at −78° C. under a nitrogen atmosphere. After an additional 2 hours at the same temperature, the ylide THF suspension was added dropwise over 40 minutes. After an additional 15 minutes, the reaction mixture was warmed to room temperature, and after an additional 3 hours at the same temperature, the reaction mixture was warmed to 50° C. After an additional 14 hours at the same temperature, the reaction mixture was cooled to room temperature, diluted with H$_2$O (50 mL), then aqueous HCl (aq., 1 M, 150 mL), and the layers were separated. The aqueous residue was extracted with EtOAc (4×100 mL). The combined organic layers were washed with brine (1×250 mL), dried (Na$_2$SO$_4$), filtered, and concentrated under reduced pressure. The resulting residue was purified by flash chromatography (1 to 23% EtOAc in heptane) on silica gel to yield tert-butyl (4R,5R)-2,2,5-trimethyl-4-vinyl-oxazolidine-3-carboxylate (4.5 g). $^1$H NMR (400 MHz, CHLOROFORM-d) δ ppm 1.28 (d, J=6.0 Hz, 3H), 1.36-1.49 (m, 9H), 1.49-1.53 (m, 3H), 1.57-1.63 (m, 3H), 3.72 (br s, 1H), 3.78-3.89 (m, 1H), 5.08-5.29 (m, 2H), 5.44-5.92 (m, 1H).

Tert-butyl (4R,5R)-2,2,5-trimethyl-4-vinyl-oxazolidine-3-carboxylate (4.5 g) was dissolved in diethyl ether (150 mL) and HCl (47 mL, 4 M in dioxane, 186 mmol) was added. The reaction mixture was stirred at room temperature overnight and concentrated to dryness. The residue was triturated in diethyl ether and concentrated to dryness. To this residue was added a pre-mixed solution of 4.7 mL H$_2$O in 47 mL 4 M HCl in dioxane cooled to 0° C. using an ice/water bath and the resulting mixture was stirred for 2 hours allowing to warm to room temperature. The mixture was then diluted with toluene (50 mL) and concentrated to dryness under reduced pressure. The residue was then azeotroped with toluene (3×50 mL) to remove all traces of water to afford (2R,3R)-3-aminopent-4-en-2-ol hydrochloride (3.35 g). $^1$H NMR (400 MHz, DMSO-d$_6$) δ ppm 1.09 (d, J=6.3 Hz, 3H), 3.32-3.48 (m, 1H), 3.62-3.78 (m, 1H), 5.22-5.50 (m, 2H), 5.80 (ddd, J=17.3, 10.5, 7.9 Hz, 1H), 8.16 (br s, 3H).

Methyl 3-bromo-4-chlorosulfonyl-1-methyl-pyrrole-2-carboxylate (2.12 g) was dissolved in DCM (200 mL) and (2R,3R)-3-aminopent-4-en-2-ol (3.35 g, 32.1 mmol) and Hunig's base (13.9 mL, 80.4 mmol) were added. The reaction mixture was stirred at room temperature for 1 hour. The reaction was quenched with NH$_4$Cl (sat., aq., 40 mL). The layers were separated and the organics were dried (Na₂SO₄), filtered and concentrated to afford a brown residue which was purified using silica gel column chromatography (ethyl acetate in heptane from 0 to 100%) to afford methyl 3-bromo-4-[[(1R)-1-[(1R)-1-hydroxyethyl]allyl]sulfamoyl]-1-methyl-pyrrole-2-carboxylate (2.60 g) as an off white powder. ¹H NMR (400 MHz, DMSO-d₆) δ ppm 0.96 (d, J=6.0 Hz, 3H), 3.55-3.67 (m, 2H), 3.82 (s, 3H), 3.86 (s, 3H), 4.57-4.77 (m, 1H), 4.97-5.10 (m, 2H), 5.71 (ddd, J=17.3, 10.5, 5.7 Hz, 1H), 7.35 (br s, 1H), 7.70 (s, 1H); Method B; Rt: 0.70 min. m/z: 379 (M−H)⁻ Exact mass: 380.0.

To a solution of methyl 3-bromo-4-[[(1R)-1-[(1R)-1-hydroxyethyl]allyl]sulfamoyl]-1-methyl-pyrrole-2-carboxylate (600 mg) in DMA (5 mL) purged with nitrogen was added Hunig's base (0.3 mL, 1.73 mmol) and bis(tri-tert-butylphosphine)palladium(0) (0.16 g, 0.31 mmol). The reaction mixture was heated in the microwave for 5 minutes at 140° C. The reaction mixture was diluted with methanol (60 mL) and purified via prep. HPLC (Stationary phase: RP XBridge Prep C18 ODB-5 μm, 30×250 mm, Mobile phase: 0.25% NH₄HCO₃ solution in water, ACN) yielding methyl (3R)-3-[(1R)-1-hydroxyethyl]-7-methyl-1,1-dioxo-2,3-dihydropyrrolo[3,4-f]thiazepine-6-carboxylate (160 mg). ¹H NMR (400 MHz, DMSO-d₆) δ ppm 1.09 (d, J=6.4 Hz, 3H) 3.73-3.87 (m, 6H) 3.87-3.93 (m, 1H) 4.09 (br s, 1H) 4.94 (br d, J=4.0 Hz, 1H) 5.93 (dd, J=12.8, 2.6 Hz, 1H) 7.17 (dd, J=12.9, 2.8 Hz, 1H) 7.31 (br s, 1H) 7.69 (s, 1H); Method B; Rt: 0.60 min. m/z: 299 (M−H)⁻ Exact mass: 300.1.

Methyl (3R)-3-[(1R)-1-hydroxyethyl]-7-methyl-1,1-dioxo-2,3-dihydropyrrolo[3,4-f]-thiazepine-6-carboxylate (160 mg) and 3,4-difluoroaniline (76 mg, 0.59 mmol) were dissolved in THF (5 mL). Lithium bis(trimethylsilyl)amide (2.4 mL, 1 M in THF, 2.4 mmol) was added and the reaction mixture was stirred 60 minutes at room temperature. 3,4-difluoroaniline (21 mg, 0.16 mmol) was added followed by lithium bis(trimethylsilyl)amide (1 mL, 1 M in THF, 1 mmol). The reaction mixture was stirred at room temperature for 30 minutes. NH₄Cl (sat., aq., 5 mL) was added and the organic layer was separated. The aqueous layer was extracted with DCM (2×5 mL) and the combined organic layers were evaporated to dryness. The residue was purified using silica gel column chromatography twice (ethyl acetate in heptane from 0 to 100%) and then by prep. HPLC (Hypersyl C18 BDS-3 μm, 100×4.6 mm) Mobile phase (NH₄HCO₃ 0.2% in water, ACN) to yield compound 69 (68 mg). ¹H NMR (400 MHz, DMSO-d₆) δ ppm 1.10 (d, J=6.4 Hz, 3H), 3.71 (s, 3H), 3.85-3.94 (m, 1H), 4.11 (br s, 1H), 4.92 (br s, 1H), 5.81 (dd, J=12.7, 2.5 Hz, 1H), 6.59 (dd, J=12.5, 2.6 Hz, 1H), 7.22 (br s, 1H), 7.39-7.47 (m, 2H), 7.57 (s, 1H), 7.82-7.88 (m, 1H), 10.74 (br s, 1H); Method B; Rt: 0.79 min. m/z: 396 (M−H)⁻ Exact mass: 397.1.

Compound 70: (3R)—N-(3,4-difluorophenyl)-3-[(1R)-1-hydroxyethyl]-7-methyl-1,1-dioxo-2,3,4,5-tetrahydropyrrolo[3,4-f]thiazepine-6-carboxamide

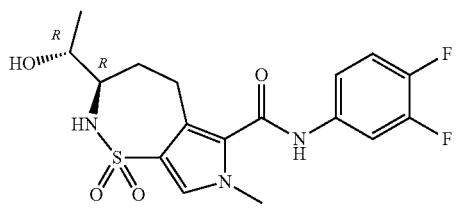

Compound 69 (32 mg) was dissolved in MeOH (40 mL). Under a nitrogen atmosphere Pd/C (10%) (24 mg, 0.022 mmol) was added. The reaction mixture was hydrogenated for 60 minutes. The reaction mixture was filtered over decalite and the filtrate was evaporated to dryness to afford a white residue which was purified using silica gel column chromatography (ethyl acetate in heptane from 0 to 100%) to yield compound 70 (23 mg) as a white powder. ¹H NMR (400 MHz, DMSO-d₆) δ ppm 1.04 (d, J=6.2 Hz, 3H), 1.44 (q, J=12.1 Hz, 1H), 1.90 (br dd, J=14.1, 6.6 Hz, 1H), 2.78 (br t, J=13.2 Hz, 1H), 3.02 (br dd, J=15.3, 5.4 Hz, 1H), 3.38-3.48 (m, 1H), 3.63-3.73 (m, 4H), 4.61 (br d, J=3.7 Hz, 1H), 6.69 (br d, J=8.6 Hz, 1H), 7.38-7.47 (m, 3H), 7.81-7.89 (m, 1H), 10.48 (br s, 1H); Method B; Rt: 0.79 min. m/z: 398 (M−H)⁻ Exact mass: 399.1

Compound 71: (3S)—N-(3-cyano-4-fluoro-phenyl)-7-methyl-1,1-dioxo-3-(3-pyridylmethyl)-3,4-dihydro-2H-pyrrolo[3,4-b][1,4,5]oxathiazepine-6-carboxamide

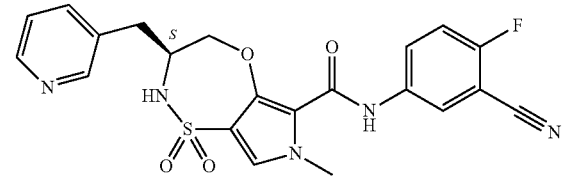

Compound 71 (11.2 mg) was prepared similarly as described for compound 38, using 5-amino-2-fluorobenzonitrile instead of 3,4-difluoroaniline. ¹H NMR (400 MHz, DMSO-d₆) δ ppm 2.66-2.76 (m, 1H) 2.88 (dd, J=14.1, 4.8 Hz, 1H) 3.82 (s, 3H) 3.86-3.98 (m, 1H) 4.03 (dd, J=12.7, 9.1 Hz, 1H) 4.67 (br d, J=12.3 Hz, 1H) 7.37 (dd, J=7.7, 4.8 Hz, 1H) 7.48-7.55 (m, 2H) 7.68-7.81 (m, 2H) 7.99-8.04 (m, 1H) 8.18 (dd, J=5.7, 2.6 Hz, 1H) 8.45-8.50 (m, 2H) 9.55 (s, 1H); Method B; Rt: 0.85 min. m/z: 456 (M+H)⁺ Exact mass: 455.1.

Compound 72: tert-butyl 4-[6-[(3,4-difluorophenyl)carbamoyl]-7-methyl-1,1-dioxo-3,4-dihydro-2H-pyrrolo[3,4-b][1,4,5]oxathiazepin-3-yl]piperidine-1-carboxylate

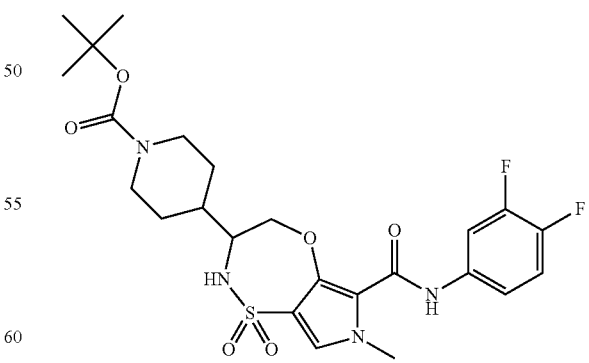

To a cooled (−78° C.) solution of tert-butyl 4-(1-amino-2-methoxy-2-oxoethyl)piperidine-1-carboxylate (1 g) in THF (50 mL) was added dropwise lithium aluminium hydride (3.56 mL, 1 M in THF, 3.562 mmol) at −78° C. The mixture was stirred at −78° C. for 3 hours and the mixture was allowed to rise to room temperature. The mixture was further stirred at room temperature for 16 hours. Sodium sulfate decahydrate (1.72 g, 5.34 mmol) was carefully added and the mixture was stirred at room temperature for 10 minutes. Na$_2$SO$_4$ was added and the mixture was filtered. The filtrate was concentrated in vacuum and the residue was purified by column chromatography using a gradient from 0 till 100% MeOH/NH$_3$ (90/10) in DCM over 10 column volumes. The product fractions were concentrated in vacuum to yield tert-butyl 4-(1-amino-2-hydroxy-ethyl)piperidine-1-carboxylate (513 mg) as an oil.

Compound 72 (127 mg) was prepared similarly as described for compound 14, using tert-butyl 4-(1-amino-2-hydroxy-ethyl)piperidine-1-carboxylate instead of DL-alaninol and heating 6 hours at 110° C. instead of 2 hours at 140° C. $^1$H NMR (400 MHz, DMSO-d$_6$) δ ppm 1.12-1.27 (m, 2H), 1.40 (s, 9H), 1.71 (br t, J=12.7 Hz, 3H), 2.67 (br s, 2H), 3.47-3.55 (m, 1H), 3.82 (s, 3H), 3.90-4.05 (m, 2H), 3.96-4.01 (m, 1H), 4.71 (d, J=10.9 Hz, 1H), 7.35-7.45 (m, 1H), 7.45-7.51 (m, 2H), 7.62 (d, J=9.7 Hz, 1H), 7.85 (ddd, J=13.2, 7.4, 2.4 Hz, 1H), 9.42 (s, 1H); Method B; Rt: 1.13 min. m/z: 539 (M−H)$^-$ Exact mass: 540.2.

Compound 73: N-(3,4-difluorophenyl)-7-methyl-1,1-dioxo-3-(4-piperidyl)-3,4-dihydro-2H-pyrrolo[3,4-b][1,4,5]oxathiazepine-6-carboxamide

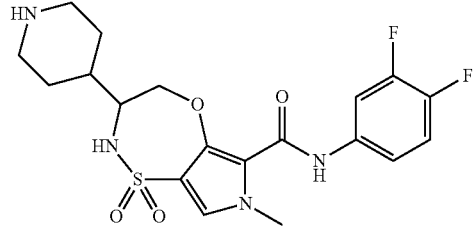 [SMILES: Cn1cc2c(c1C(=O)Nc1ccc(F)c(F)c1)OCC(C1CCNCC1)NS2(=O)=O]

Compound 72 (119 mg) was suspended in DCM (5 mL). TFA (0.25 mL, 3.30 mmol) was added and the mixture was stirred at room temperature for 1 hour. The mixture was washed with sat. NaHCO$_3$ solution. The organic layer was separated, dried (MgSO$_4$), filtered and concentrated in vacuo. The residue was purified via prep. HPLC (Stationary phase: RP XBridge Prep C18 OBD-10 µm, 30×150 mm, Mobile phase: 0.25% NH$_4$HCO$_3$ solution in water, ACN). The product fractions were collected to yield compound 73 (21 mg) as a white solid. $^1$H NMR (400 MHz, DMSO-d$_6$) δ ppm 1.10-1.25 (m, 2H), 1.51-1.71 (m, 3H), 1.75 (s, 1H), 2.34-2.45 (m, 2H), 2.89-2.97 (m, 2H), 3.39-3.49 (m, 1H), 3.80-3.85 (m, 3H), 3.95 (dd, J=12.8, 9.0 Hz, 1H), 4.72 (dd, J=12.9, 1.9 Hz, 1H), 7.36-7.57 (m, 4H), 7.86 (ddd, J=13.2, 7.5, 2.5 Hz, 1H), 9.34-9.48 (m, 1H); Method B; Rt: 0.72 min. m/z: 441 (M+H)$^+$ Exact mass: 440.1.

Compound 74: (3S)—N-(4-fluoro-3-methyl-phenyl)-7-methyl-1,1-dioxo-3-(3-pyridylmethyl)-3,4-dihydro-2H-pyrrolo[3,4-b][1,4,5]oxathiazepine-6-carboxamide

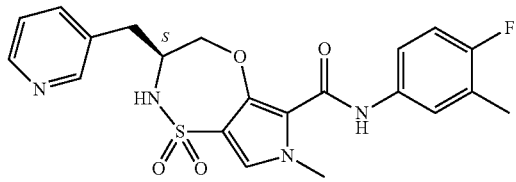

Compound 74 (29 mg) was prepared similarly as described for compound 38, using 4-fluoro-3-methylaniline instead of 3,4-difluoroaniline. $^1$H NMR (400 MHz, DMSO-d$_6$) δ ppm 2.23 (d, J=1.5 Hz, 3H), 2.66-2.75 (m, 1H), 2.85-2.92 (m, 1H), 3.82 (s, 3H), 3.93 (br s, 1H), 3.99-4.11 (m, 1H), 4.67 (dd, J=12.5, 2.0 Hz, 1H), 7.10 (t, J=9.1 Hz, 1H), 7.37 (dd, J=7.7, 5.1 Hz, 1H), 7.45 (s, 1H), 7.49 (br d, J=4.6 Hz, 1H), 7.53-7.58 (m, 1H), 7.70-7.80 (m, 2H), 8.46 (d, J=5.1 Hz, 1H), 8.49 (s, 1H), 9.24 (s, 1H); Method B; Rt: 0.91 min. m/z: 445 (M+H)$^+$ Exact mass: 444.1.

Compound 75: (3S)—N-[3-(difluoromethyl)-4-fluoro-phenyl]-7-methyl-1,1-dioxo-3-(3-pyridylmethyl)-3,4-dihydro-2H-pyrrolo[3,4-b][1,4,5]oxathiazepine-6-carboxamide

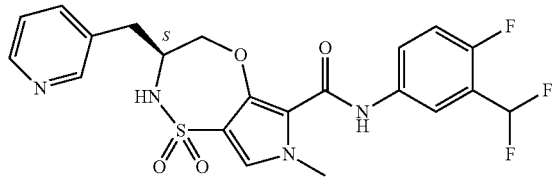

Compound 75 (5 mg) was prepared similarly as described for compound 38, using 3-(difluoromethyl)-4-fluoro-aniline instead of 3,4-difluoroaniline. $^1$H NMR (400 MHz, DMSO-d$_6$) δ ppm 2.65-2.76 (m, 1H), 2.87 (br dd, J=14.3, 4.8 Hz, 1H), 3.83 (s, 3H), 3.93 (br s, 1H), 4.00-4.08 (m, 1H), 4.65 (dd, J=12.8, 2.2 Hz, 1H), 7.20 (t, J=48.0 Hz, 1H), 7.35-7.40 (m, 2H), 7.47 (s, 1H), 7.70-7.83 (m, 3H), 8.02 (dd, J=6.3, 2.5 Hz, 1H), 8.46 (dd, J=4.8, 1.5 Hz, 1H), 8.49 (d, J=2.0 Hz, 1H), 9.49 (s, 1H); Method B; Rt: 0.90 min. m/z: 481 (M+H)$^+$ Exact mass: 480.1.

Compound 76: N-(3,4-difluorophenyl)-7-methyl-3-(1-methyl-4-piperidyl)-1,1-dioxo-3,4-dihydro-2H-pyrrolo[3,4-b][1,4,5]oxathiazepine-6-carboxamide

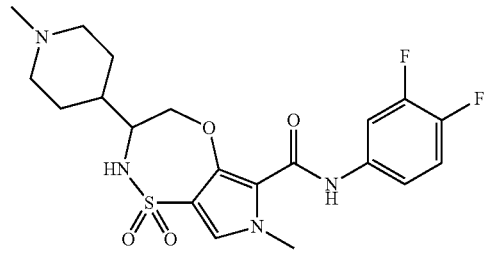 [SMILES: CN1CCC(C2COc3c(cn(C)c3C(=O)Nc3ccc(F)c(F)c3)S(=O)(=O)N2)CC1]

Compound 73 (109 mg) was dissolved in MeOH (1 mL) and DCE (2 mL). The mixture was cooled on a ice bath and formaldehyde (22 µL, 1.09 g/mL, 0.297 mmol) was added followed by sodium cyanoborohydride (33 mg, 0.50 mmol). The mixture was stirred at room temperature for 16 hours. The solvent was evaporated and the residue was partioned between NaOH (aq., 1M) and Me-THF. The organic layer was separated, dried (MgSO4), filtered and evaporated. The residue was purified by column chromatography using a gradient from 0 till 100% DCM/NH$_3$ sol. in MeOH (90/10) in DCM over 10 column volumes. The product fractions were concentrated in vacuo. The product was crystallized from water:MeOH to yield compound 76 (51 mg) as a white solid. ¹H NMR (400 MHz, DMSO-d₆) δ ppm 1.24-1.47 (m, 3H), 1.64-1.83 (m, 4H), 2.09-2.16 (m, 3H), 2.71-2.84 (m, 2H), 3.39-3.53 (m, 1H), 3.82 (s, 3H), 3.95 (dd, J=12.9, 9.1 Hz, 1H), 4.73 (dd, J=13.0, 2.0 Hz, 1H), 7.36-7.53 (m, 3H), 7.58 (d, J=9.7 Hz, 1H), 7.86 (ddd, J=13.2, 7.4, 2.5 Hz, 1H), 9.38-9.43 (m, 1H); Method B; Rt: 0.75 min. m/z: 455 (M+H)⁺ Exact mass: 454.1.

Compound 77: (3R)—N-[2-(difluoromethyl)-4-pyridyl]-3-[(1S)-1-hydroxyethyl]-7-methyl-1,1-dioxo-3,4-dihydro-2H-pyrrolo[3,4-b][1,4,5]oxathiazepine-6-carboxamide

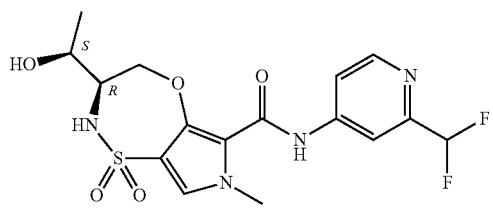

Compound 77 (72.7 mg) was prepared similarly as described for compound 64, using 2-(difluoromethyl)pyridin-4-amine instead of 3-(difluoromethyl)-4-fluoro-aniline. ¹H NMR (400 MHz, DMSO-d₆) δ ppm 1.43 (d, J=6.4 Hz, 3H), 2.12 (s, 1H), 3.85 (tdd, J=9.2, 9.2, 4.8, 2.4 Hz, 1H), 3.96 (s, 3H), 4.19 (quin, J=6.1 Hz, 1H), 4.35 (dd, J=13.0, 8.8 Hz, 1H), 4.90 (dd, J=13.0, 2.4 Hz, 1H), 5.18 (d, J=9.5 Hz, 1H), 6.62 (t, J=55.5 Hz, 1H), 7.10 (s, 1H), 7.71-7.73 (m, 1H), 7.74-7.75 (m, 1H), 8.53 (d, J=5.5 Hz, 1H), 9.05 (s, 1H); Method B; Rt: 0.71 min. m/z: 415 (M–H)⁻ Exact mass: 416.1.

Compound 78: N-(3,4-difluorophenyl)-7-methyl-1,1-dioxo-3-[1-(2,2,2-trifluoroethyl)-4-piperidyl]-3,4-dihydro-2H-pyrrolo[3,4-b][1,4,5]oxathiazepine-6-carboxamide

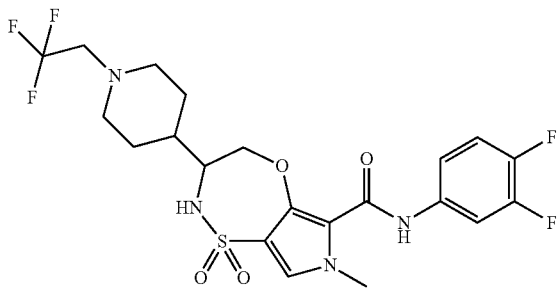 [SMILES: Cn1cc2c(c1C(=O)Nc1ccc(F)c(F)c1)OCC(C1CCN(CC(F)(F)F)CC1)NS2(=O)=O]

A microwave vial was charged with compound 73 (50 mg, 0.11 mmol), 2,2,2-trifluoroethyl trichloromethanesulfonate (34 mg, 0.11 mmol), K₂CO₃ (19 mg, 0.14 mmol) in acetone (1 mL). The vial was capped and the mixture was stirred at 60° C. for 16 hours. The mixture was concentrated and the residue was purified by column chromatography using a gradient from 0 till 100% EtOAc in Heptane over 10 column volumes. The product fractions were concentrated in vacuo. The product was triturated in DIPE, filtered off and dried under vacuum to give compound 78 (38 mg) as a white solid. ¹H NMR (400 MHz, DMSO-d₆) δ ppm 1.28-1.44 (m, 2H), 1.44-1.54 (m, 1H), 1.64-1.76 (m, 2H), 2.20-2.36 (m, 2H), 2.89-2.98 (m, 2H), 3.05-3.20 (m, 2H), 3.42-3.56 (m, 1H), 3.82 (s, 3H), 3.92-4.04 (m, 1H), 4.68-4.76 (m, 1H), 7.36-7.51 (m, 3H), 7.59 (d, J=9.8 Hz, 1H), 7.86 (ddd, J=13.2, 7.5, 2.5 Hz, 1H), 9.38-9.43 (m, 1H); Method D; Rt: 2.06 min. m/z: 521 (M+H)⁺ Exact mass: 522.1.

Compound 79: N-(3,4-difluorophenyl)-3-isopropyl-7-methyl-1,1-dioxo-2,3-dihydropyrrolo[3,4-f]thiazepine-6-carboxamide

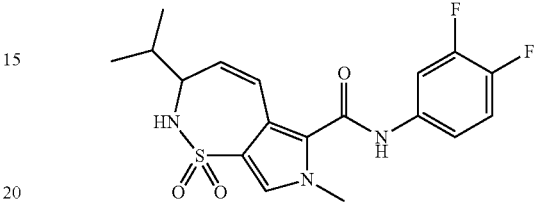

Methyl 3-bromo-4-chlorosulfonyl-1-methyl-pyrrole-2-carboxylate (2 g, 6.32 mmol) was dissolved in DCM (100 mL). To this was added Hunig's base (4.36 mL, 25.3 mmol). To this was added 4-methyl-1-penten-3-amine (1.71 g, 12.6 mmol) in DCM (100 mL). The resulting mixture was stirred overnight and concentrated in vacuo and the residue was purified using silica gel column chromatography (gradient elution: EtOAc:heptane 0:100 to 100:0) yielding methyl 3-bromo-4-(1-isopropylallylsulfamoyl)-1-methyl-pyrrole-2-carboxylate (1.88 g) as a beige powder which was used as such. Method B; Rt: 0.98 min. m/z: 379 (M+H)⁺ Exact mass: 378.0.

Methyl 3-bromo-4-(1-isopropylallylsulfamoyl)-1-methyl-pyrrole-2-carboxylate (1.70 g, 4.48 mmol) and TEA (0.62 mL, 0.73 g/mL, 4.48 mmol) in DMF (10 mL) was stirred and purged with nitrogen for 5 minutes. Then bis(tri-tert-butylphosphine)palladium(0) (458 mg, 0.90 mmol) was added and stirring and purging was continued for 5 more minutes. The mixture was heated under microwave irradiation to 100° C. for 75 minutes. The reaction mixture was cooled to room temperature and filtered through a pad of dicalite and rinsed with 150 mL of EtOAc. Then the filtrate was concentrated in vacuo and purified using silica gel column chromatography (gradient elution: EtOAc:heptane 0:100 to 100:0) yielding a mixture of 2 isomers. This mixture was purified via preparative HPLC (Stationary phase: RP XBridge Prep C18 OBD-10 μm, 30×150 mm, Mobile phase: 0.25% NH₄HCO₃ solution in water, ACN) yielding methyl 3-isopropyl-7-methyl-1,1-dioxo-2,3-dihydropyrrolo[3,4-f]thiazepine-6-carboxylate (203 mg). Method B; Rt: 0.88 min. m/z: 299 (M+H)⁺ Exact mass: 298.1.

A mixture of methyl 3-isopropyl-7-methyl-1,1-dioxo-2,3-dihydropyrrolo[3,4-f]-thiazepine-6-carboxylate (101 mg, 0.34 mmol) and 3,4-difluoroaniline (49 mg, 0.37 mmol) in THF (5 mL) was treated with LiHMDS (0.64 mL, 1.06 M in THF, 0.68 mmol) and this was stirred for 2 hours at room temperature. The resulting mixture was quenched with NH₄Cl (aq. sat., 5 mL). Then brine (5 mL) was added and the layers were separated. The water layer was extracted using EtOAc (2×10 mL). The combined extracts were concentrated in vacuo and the obtained crude was purified using silica gel column chromatography (gradient elution: EtOAc:heptane 0:100 to 100:0). The desired fractions were concentrated in vacuo and the obtained residue was purified via Prep HPLC (Stationary phase: RP XBridge Prep C18 OBD-10 μm, 30×150 mm, Mobile phase: 0.25% NH$_4$HCO$_3$ solution in water, ACN) yielding compound 79 as a bright white solid (60.3 mg). $^1$H NMR (400 MHz, DMSO-d$_6$) δ ppm 1.47-1.51 (m, 3H) 1.51-1.56 (m, 3H) 3.20-3.24 (m, 1H) 3.20-3.24 (m, 2H) 4.30 (s, 2H) 4.53-4.63 (m, 1H) 6.21 (dd, J=12.32, 2.86 Hz, 1H) 6.49 (d, J=10.56 Hz, 1H) 7.15 (dd, J=12.32, 2.64 Hz, 1H) 7.76-7.89 (m, 2H) 7.95-8.05 (m, 1H) 8.43 (ddd, J=12.87, 7.37, 2.64 Hz, 1H) 10.23 (br s, 1H); Method D; Rt: 1.90 min. m/z: 396 (M+H)$^+$ Exact mass: 395.1. This racemic mixture was separated in its enantiomers via preparative SFC (Stationary phase: Chiralpak Diacel AD 20×250 mm, Mobile phase: CO$_2$, EtOH+0.4 iPrNH$_2$) yielding compound 79a and 79b. Method E; Rt: 79a: 1.22 min, 79b: 2.09 min.

Compound 80: N-(3,4-difluorophenyl)-3-(1-methoxy-1-methyl-ethyl)-7-methyl-1,1-dioxo-3,4-dihydro-2H-pyrrolo[3,4-b][1,4,5]oxathiazepine-6-carboxamide

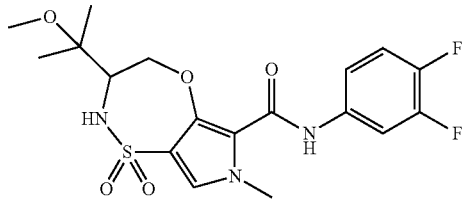 [SMILES: COC(C)(C)C1COc2c(cn(C)c2C(=O)Nc2ccc(F)c(F)c2)S(=O)(=O)N1]

Ethyl 4-chlorosulfonyl-3-fluoro-1-methyl-pyrrole-2-carboxylate (250 mg, 0.89 mmol), 2-amino-3-methoxy-3-methylbutanoic acid (131 mg, 0.89 mmol) and Hunig's base (0.46 mL, 0.75 g/mL, 2.68 mmol) were dissolved in DCM (5 mL) and stirred overnight at room temperature. The reaction mixture was directly loaded on a silica cartridge and a gradient from heptane to EtOAc:EtOH:AcOH 3:1:0.02 was applied yielding 2-[(5-ethoxycarbonyl-4-fluoro-1-methyl-pyrrol-3-yl)sulfonylamino]-3-methoxy-3-methyl-butanoic acid (143 mg).
2-[(5-ethoxycarbonyl-4-fluoro-1-methyl-pyrrol-3-yl) sulfonylamino]-3-methoxy-3-methyl-butanoic acid (143 mg, 0.38 mmol) and 3,4-difluoroaniline (38 μL, 1.29 g/mL, 0.38 mmol) were dissolved in THF (5 mL). Lithium bis(trimethylsilyl)amide (1.88 mL, 1 M in THF, 1.88 mmol) was added and the reaction mixture was stirred overnight at room temperature. NH$_4$Cl (sat., aq., 5 mL) was added and the organic layer was removed. The aqueous layer was extracted with DCM (2×5 mL) and the combined organic layers were evaporated to dryness. The residue was purified on silica using a heptane to EtOAc:EtOH:AcOH 3:1:0.02 gradient yielding 2-[[5-[(3,4-difluorophenyl)-carbamoyl]-4-fluoro-1-methyl-pyrrol-3-yl]sulfonylamino]-3-methoxy-3-methyl-butanoic acid (123 mg).
2-[[5-[(3,4-difluorophenyl)carbamoyl]-4-fluoro-1-methyl-pyrrol-3-yl]sulfonylamino]-3-methoxy-3-methyl-butanoic acid (123 mg, 0.27 mmol) was dissolved in THF (10 mL) and LAH (0.27 mL, 1 M in THF, 0.27 mmol) was added drop wise. The reaction mixture was stirred overnight at room temperature. LAH (0.27 mL, 1 M in THF, 0.27 mmol) was added and stirring was continued for 24 hours. The reaction mixture was quenched with sodium sulfate decahydrate (128 mg, 0.4 mmol) followed by addition of Na$_2$SO$_4$. After filtration and evaporation an oily residue was obtained which was purified on silica using a heptane to EtOAc:EtOH 3:1 gradient yielding N-(3,4-difluorophenyl)-3-fluoro-4-[[1-(hydroxymethyl)-2-methoxy-2-methyl-propyl]-sulfamoyl]-1-methyl-pyrrole-2-carboxamide (17 mg).
N-(3,4-difluorophenyl)-3-fluoro-4-[[1-(hydroxymethyl)-2-methoxy-2-methyl-propyl]sulfamoyl]-1-methyl-pyrrole-2-carboxamide (17 mg, 0.038 mmol) and cesium fluoride (23 mg, 0.15 mmol) were dispensed in DMF (5 mL) and heated to 100° C. for 4 hours. The reaction mixture was directly purified via prep. HPLC (Stationary phase: RP XBridge Prep C18 OBD-10 μm, 30×150 mm, Mobile phase: 0.25% NH$_4$HCO$_3$ solution in water, ACN) yielding compound 80 (6.3 mg) as a white powder. $^1$H NMR (400 MHz, DMSO-d$_6$) δ ppm 1.31-1.43 (m, 6H), 3.19 (s, 3H), 3.85 (br s, 1H), 3.95 (s, 3H), 4.04 (dd, J=12.8, 8.8 Hz, 1H), 4.82-4.93 (m, 2H), 7.05 (s, 1H), 7.08-7.14 (m, 2H), 7.62-7.69 (m, 1H), 8.81 (s, 1H); Method B; Rt: 1.04 min. m/z: 428 (M−H)$^−$ Exact mass: 429.1.

Compound 81: N-(3,4-difluorophenyl)-3-isopropyl-7-methyl-1,1-dioxo-2,3,4,5-tetrahydropyrrolo[3,4-f]thiazepine-6-carboxamide

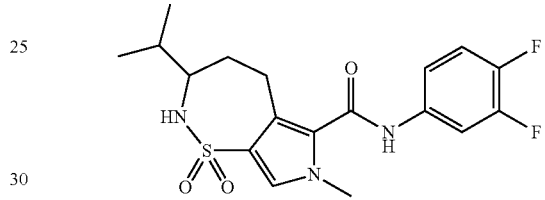

A hydrogenation flask was flushed with nitrogen and then charged with Pd/C (10%) (10 mg, 0.0094 mmol). To this was added under nitrogen compound 79 (50 mg, 0.13 mmol) in MeOH (30 mL). The resulting suspension was then stirred under a hydrogen atmosphere at room temperature for 90 minutes. Then the mixture was filtered over a pad of dicalite under a constant nitrogen flow and this pad was rinsed with MeOH (50 mL). The filtrate was concentrated in vacuo and the obtained residue was purified using silica gel column chromatography (gradient elution: EtOAc:heptane 0:100 to 100:0). The desired fractions were concentrated in vacuo and dried in a vacuum oven at 55° C. yielding compound 81 (36 mg) as a bright white powder. $^1$H NMR (400 MHz, DMSO-d$_6$) δ ppm 0.88 (d, J=3.74 Hz, 3H) 0.90 (d, J=3.52 Hz, 3H) 1.31-1.48 (m, 1H) 1.68 (dq, J=12.90, 6.56 Hz, 1H) 1.79-1.95 (m, 1H) 2.72-2.86 (m, 1H) 2.94-3.07 (m, 1H) 3.18-3.29 (m, 1H) 3.68 (s, 3H) 6.90 (d, J=10.12 Hz, 1H) 7.35-7.49 (m, 3H) 7.78-7.92 (m, 1H) 10.48 (s, 1H); Method B; Rt: 1.03 min. m/z: 396 (M−H)$^−$ Exact mass: 397.1.

Compound 82: N-[3-(difluoromethyl)-4-fluoro-phenyl]-3-isopropyl-7-methyl-1,1-dioxo-2,3-dihydropyrrolo[3,4-f]thiazepine-6-carboxamide

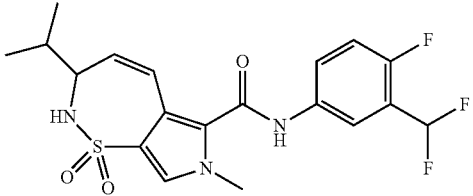 [SMILES: CC(C)C1C=Cc2c(cn(C)c2C(=O)Nc2ccc(F)c(C(F)F)c2)S(=O)(=O)N1]

Compound 82 (70.9 mg) was prepared similarly as described for compound 79, using 3-(difluoromethyl)-4-fluoro-aniline instead of 3,4-difluoroaniline. $^1$H NMR (400 MHz, DMSO-d$_6$) δ ppm 0.95 (d, J=6.82 Hz, 3H) 0.98 (d, J=6.60 Hz, 3H) 1.85-2.01 (m, 1H) 3.72 (s, 3H) 3.91-3.98 (m, 1H) 5.70 (dd, J=12.43, 2.75 Hz, 1H) 6.57 (dd, J=12.43, 2.75 Hz, 1H) 7.06-7.43 (m, 3H) 7.58 (s, 1H) 7.78-7.87 (m, 1H) 8.06 (dd, J=6.27, 2.53 Hz, 1H) 10.75 (s, 1H); Method B; Rt: 1.02 min. m/z: 426 (M–H)$^-$ Exact mass: 427.1.

Compound 83: N-(3,4-difluorophenyl)-3-(hydroxymethyl)-7-methyl-1,1-dioxo-3,4-dihydro-2H-pyrrolo[3,4-b][1,4,5]oxathiazepine-6-carboxamide

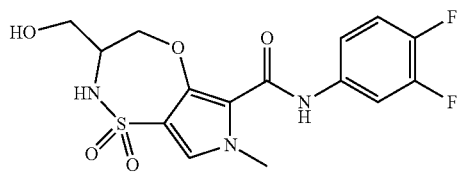 [SMILES: Cn1cc2c(c1C(=O)Nc1ccc(F)c(F)c1)OCC(CO)NS2(=O)=O]

Compound 83 (216 mg) was prepared similarly as described for compound 14, using 2-amino-1,3-propanediol instead of DL-alaninol. The ring closure was obtained after heating overnight at 100° C. in DMF and compound 83 was purified on silica using a gradient from heptane to EtOAc: EtOH 3:1. $^1$H NMR (400 MHz, DMSO-d$_6$) δ ppm 3.35-3.42 (m, 1H), 3.56 (dt, J=10.8, 5.2 Hz, 1H), 3.63-3.73 (m, 1H), 3.82 (s, 3H), 3.94 (dd, J=12.8, 8.8 Hz, 1H), 4.74 (dd, J=12.7, 1.9 Hz, 1H), 5.10 (dd, J=6.5, 5.0 Hz, 1H), 7.36-7.50 (m, 3H), 7.61 (d, J=9.7 Hz, 1H), 7.87 (ddd, J=13.2, 7.5, 2.6 Hz, 1H), 9.44 (s, 1H); Method B; Rt: 0.81 min. m/z: 386 (M–H)$^-$ Exact mass: 387.1.

Compound 84: (3R)—N-(3,4-difluorophenyl)-3-[(1S)-1-hydroxyethyl]-7-methyl-1,1-dioxo-2,3-dihydropyrrolo[3,4-f]thiazepine-6-carboxamide

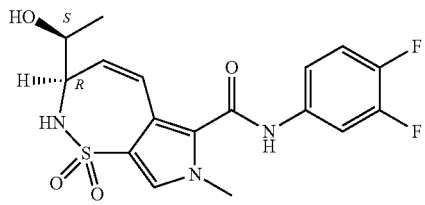

Methyl 3-bromo-4-chlorosulfonyl-1-methyl-pyrrole-2-carboxylate (10.8 g, 34.1 mmol) was dissolved in ACN (200 mL) and (2S,3R)-3-aminopent-4-en-2-ol hydrochloride (4.99 g, 36.2 mmol) and Hunig's base (14.7 mL, 0.75 g/mL, 85.3 mmol) were added. The reaction mixture was stirred at room temperature overnight. The reaction mixture was concentrated and the residue was purified using silica gel column chromatography (EtOAc in heptane from 0 to 100%) to afford methyl 3-bromo-4-[[(1R)-1-[(1S)-1-hydroxyethyl]allyl]sulfamoyl]-1-methyl-pyrrole-2-carboxylate (11.4 g) as an off white powder. $^1$H NMR (400 MHz, DMSO-d$_6$) δ ppm 0.99 (d, J=6.4 Hz, 3H), 3.41-3.50 (m, 1H), 3.53-3.63 (m, 1H), 3.81 (s, 3H), 3.85 (s, 3H), 4.62 (br d, J=5.1 Hz, 1H), 4.91-4.95 (m, 1H), 4.97 (d, J=0.7 Hz, 1H), 5.63-5.74 (m, 1H), 7.33 (br s, 1H), 7.69 (s, 1H); Method B; Rt: 0.68 min. m/z: 379 (M–H)$^-$ Exact mass: 380.0.

To a solution of methyl 3-bromo-4-[[(1R)-1-[(1S)-1-hydroxyethyl]allyl]sulfamoyl]-1-methyl-pyrrole-2-carboxylate (1.10 g, 2.89 mmol) in DMF (5 mL) purged with nitrogen was added Hunig's base (0.55 mL, 0.75 g/mL, 3.17 mmol) and bis(tri-tert-butylphosphine)palladium(0) (147 mg, 0.29 mmol). The reaction mixture was heated in the microwave for 10 minutes at 130° C. The reaction mixture was purified via preparative HPLC (Stationary phase: RP XBridge Prep C18 OBD-10 µm, 50×150 mm, Mobile phase: 0.25% NH$_4$HCO$_3$ solution in water, ACN) yielding methyl (3R)-3-[(1S)-1-hydroxyethyl]-7-methyl-1,1-dioxo-2,3-dihydropyrrolo[3,4-f]thiazepine-6-carboxylate (380 mg). $^1$H NMR (400 MHz, DMSO-d$_6$) δ ppm 1.19 (d, J=6.2 Hz, 3H), 3.62-3.72 (m, 1H), 3.76-3.88 (m, 7H), 4.98 (br d, J=3.7 Hz, 1H), 6.07 (dd, J=12.9, 2.8 Hz, 1H), 7.12 (dd, J=12.8, 2.6 Hz, 1H), 7.49 (br s, 1H), 7.69 (s, 1H); Method B; Rt: 0.59 min. m/z: 299 (M–H)$^-$ Exact mass: 300.1 and methyl 3-acetyl-7-methyl-1,1-dioxo-2,3,4,5-tetrahydropyrrolo[3,4-f]thiazepine-6-carboxylate. $^1$H NMR (400 MHz, DMSO-d$_6$) ppm 1.46-1.59 (m, 1H), 2.12-2.20 (m, 1H), 2.22 (s, 3H), 2.77-2.87 (m, 1H), 3.58 (br dd, J=15.7, 7.7 Hz, 1H), 3.80 (s, 3H), 3.79 (s, 3H), 4.19 (br t, J=9.5 Hz, 1H), 7.59 (s, 1H), 7.68 (br d, J=9.3 Hz, 1H); Method B; Rt: 0.67 min. m/z: 299 (M–H)$^-$ Exact mass: 300.1

Methyl (3R)-3-[(1S)-1-hydroxyethyl]-7-methyl-1,1-dioxo-2,3-dihydropyrrolo[3,4-f]-thiazepine-6-carboxylate (95 mg, 0.32 mmol) and 3,4-difluoroaniline (53 mg, 0.41 mmol) were dissolved in THF (5 mL). Lithium bis(trimethylsilyl)amide (2 mL, 1 M in THF, 2 mmol) was added and the reaction mixture was stirred at room temperature. The reaction was quenched after 1 hour with NH$_4$Cl (sat., aq., 5 mL) and the organic layer was separated. The aqueous layer was extracted with DCM (2×4 mL) and the combined organic layers were dried (Na$_2$SO$_4$) and evaporated to dryness. The residue was purified via preparative HPLC (Stationary phase: RP XBridge Prep C18 OBD-10 µm, 50×150 mm, Mobile phase: 0.25% NH$_4$HCO$_3$ solution in water, ACN). The obtained product was purified using silica gel column chromatography (EtOAc in heptane from 0 to 100%) to afford compound 84 (62 mg). $^1$H NMR (400 MHz, DMSO-d$_6$) δ ppm 1.20 (d, J=6.2 Hz, 3H), 3.60-3.77 (m, 4H), 3.77-3.87 (m, 1H), 4.97 (br d, J=5.7 Hz, 1H), 5.96 (dd, J=12.5, 2.6 Hz, 1H), 6.54 (dd, J=12.5, 2.6 Hz, 1H), 7.35-7.52 (m, 3H), 7.57 (s, 1H), 7.81-7.89 (m, 1H), 10.73 (br s, 1H); Method B; Rt: 0.78 min. m/z: 396 (M–H)$^-$ Exact mass: 397.1.

Compound 85: N-(3-cyano-4-fluoro-phenyl)-3-isopropyl-7-methyl-1,1-dioxo-2,3,4,5-tetrahydropyrrolo[3,4-f]thiazepine-6-carboxamide

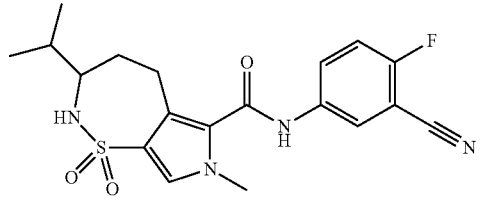 [SMILES: CC(C)C1CCc2c(cn(C)c2C(=O)Nc2ccc(F)c(C#N)c2)S(=O)(=O)N1]

Methyl 3-bromo-1-methyl-pyrrole-2-carboxylate (2.44 g, 11.1 mmol), tert-butyl N-(1-isopropylallyl)carbamate (2.65 g, 13.3 mmol) and TEA (3 mL, 0.73 g/mL, 22.2 mmol) in DMF (5 mL) was stirred and purged with nitrogen for 5 minutes. Then bis(tri-tert-butylphosphine)palladium(0) (1.13 g, 2.22 mmol) was added and stirring and purging was continued for 5 more minutes. The mixture was heated under microwave irradiation to 100° C. for 60 minutes. The reaction mixture was cooled to room temperature and filtered through a pad of dicalite and rinsed with EtOAc (150 mL). Then the filtrate was concentrated in vacuo and purified using silica gel column chromatography (gradient elution: EtOAc:heptane 0:100 to 100:0) yielding methyl 3-[(E)-3-(tert-butoxycarbonylamino)-4-methyl-pent-1-enyl]-1-methyl-pyrrole-2-carboxylate (3.31 g) as an oil. Method B; Rt: 1.18 min. m/z: 335 (M−H)⁻ Exact mass: 336.2.

A hydrogenation flask was flushed with nitrogen and then charged with Pd/C (10%) (733 mg, 0.69 mmol). To this was added under nitrogen methyl 3-[(E)-3-(tert-butoxycarbonylamino)-4-methyl-pent-1-enyl]-1-methyl-pyrrole-2-carboxylate (2.20 g, 6.54 mmol) in MeOH (35 mL). The resulting suspension was then stirred under a hydrogen atmosphere at room temperature for 90 minutes. Then the mixture was filtered over a pad of dicalite under a constant nitrogen flow and this pad was rinsed with MeOH (150 mL). The filtrate was concentrated in vacuo and the obtained residue was purified using silica gel column chromatography (gradient elution: EtOAc:heptane 0:100 to 100:0). The desired fractions were concentrated in vacuo yielding methyl 3-[3-(tert-butoxycarbonylamino)-4-methyl-pentyl]-1-methyl-pyrrole-2-carboxylate (2.16 g) as a bright white powder.

Methyl 3-[3-(tert-butoxycarbonylamino)-4-methyl-pentyl]-1-methyl-pyrrole-2-carboxylate (250 mg, 0.74 mmol) in DCM (10 mL) was treated with chlorosulfonic acid (246 μL, 1.75 g/mL, 3.69 mmol) in DCM (5 mL) at 0° C. Then it was allowed to reach room temperature and the stirred for another hour. The mixture was added dropwise to ice-water (20 mL) and this was extracted with 2-MeTHF (2×20 mL). The combined extracts were dried on Na₂SO₄, filtered and concentrated in vacuo yielding methyl 3-isopropyl-7-methyl-1,1-dioxo-2,3,4,5-tetrahydropyrrolo[3,4-f]thiazepine-6-carboxylate (80 mg).

Methyl 3-isopropyl-7-methyl-1,1-dioxo-2,3,4,5-tetrahydropyrrolo[3,4-f]thiazepine-6-carboxylate (80 mg, 0.27 mmol) and 5-amino-2-fluoro-benzonitrile (36 mg, 0.27 mmol) in dry THF (5 mL) was treated with lithium bis(trimethylsilyl)amide (1.3 mL, 1 M in THF, 1.3 mmol) and this was stirred for 2 hours at room temperature. The resulting mixture was quenched with NH₄Cl (aq. sat., 5 mL). Then brine (5 mL) was added and the layers were separated. The water layer was extracted using EtOAc (2×20 mL). The combined extracts were concentrated in vacuo and the obtained crude was purified using silica gel column chromatography (gradient elution: EtOAc:heptane 0:100 to 100:0). The desired fractions were concentrated in vacuo and the obtained residue was purified via preparative HPLC (Stationary phase: RP XBridge Prep C18 OBD-10 μm, 30×150 mm, Mobile phase: 0.25% NH₄HCO₃ solution in water, ACN) yielding compound 85 (17 mg) as a bright white solid. ¹H NMR (400 MHz, DMSO-d₆) δ ppm 0.88 (d, J=3.30 Hz, 3H) 0.90 (d, J=3.08 Hz, 3H) 1.32-1.47 (m, 1H) 1.69 (dq, J=12.96, 6.54 Hz, 1H) 1.79-1.93 (m, 1H) 2.72-2.85 (m, 1H) 2.98-3.11 (m, 1H) 3.19-3.28 (m, 1H) 3.69 (s, 3H) 6.91 (d, J=10.34 Hz, 1H) 7.44 (s, 1H) 7.54 (t, J=9.13 Hz, 1H) 7.95 (ddd, J=9.24, 4.84, 2.64 Hz, 1H) 8.18 (dd, J=5.83, 2.75 Hz, 1H) 10.59 (s, 1H); Method B; Rt: 0.97 min. m/z: 403 (M−H)⁻ Exact mass: 404.1.

Compound 86: N-[3-(difluoromethyl)-4-fluoro-phenyl]-3-isopropyl-7-methyl-1,1-dioxo-2,3,4,5-tetrahydropyrrolo[3,4-f]thiazepine-6-carboxamide

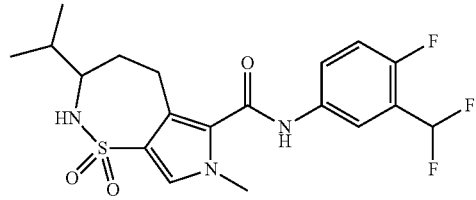 [SMILES: CC(C)C1CCc2c(cn(C)c2C(=O)Nc2ccc(F)c(C(F)F)c2)S(=O)(=O)N1]

Compound 86 (17 mg) was prepared similarly as described for compound 81, using compound 82 instead of compound 79. ¹H NMR (400 MHz, DMSO-d₆) δ ppm 0.88 (d, J=3.30 Hz, 3H) 0.90 (d, J=3.30 Hz, 3H) 1.32-1.46 (m, 1H) 1.69 (dq, J=13.04, 6.73 Hz, 1H) 1.79-1.95 (m, 1H) 2.71-2.88 (m, 1H) 2.95-3.11 (m, 1H) 3.19-3.28 (m, 1H) 3.69 (s, 3H) 6.89 (d, J=10.34 Hz, 1H) 7.22 (t, J=54.36 Hz, 1H) 7.36 (t, J=9.46 Hz, 1H) 7.42 (s, 1H) 7.76-7.85 (m, 1H) 8.02-8.08 (m, 1H) 10.49 (s, 1H); Method B; Rt: 1.02 min. m/z: 428 (M−H)⁻ Exact mass: 429.1.

Compound 87: (3R)—N-(3-cyano-4-fluoro-phenyl)-3-[(1S)-1-hydroxyethyl]-7-methyl-1,1-dioxo-2,3-dihydropyrrolo[3,4-f]thiazepine-6-carboxamide

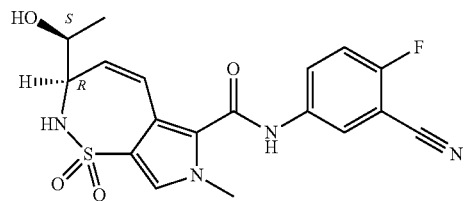

Compound 87 (55 mg) was prepared similarly as described for compound 84, using 5-amino-2-fluoro-benzonitrile instead of 3,4-difluoroaniline. ¹H NMR (400 MHz, DMSO-d₆) δ ppm 1.20 (d, J=6.2 Hz, 3H), 3.60-3.77 (m, 4H), 3.77-3.87 (m, 1H), 4.97 (d, J=5.7 Hz, 1H), 5.97 (dd, J=12.5, 2.6 Hz, 1H), 6.57 (dd, J=12.5, 2.4 Hz, 1H), 7.40 (br d, J=9.5 Hz, 1H), 7.55 (t, J=9.1 Hz, 1H), 7.59 (s, 1H), 7.98 (ddd, J=9.2, 4.8, 2.8 Hz, 1H), 8.20 (dd, J=5.7, 2.6 Hz, 1H), 10.85 (br s, 1H); Method B; Rt: 0.74 min. m/z: 403 (M−H)⁻ Exact mass: 404.1.

Compound 88: (3R)—N-(3,4-difluorophenyl)-3-[(1S)-1-hydroxyethyl]-7-methyl-1,1-dioxo-2,3,4,5-tetrahydropyrrolo[3,4-f]thiazepine-6-carboxamide

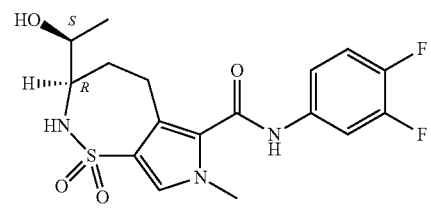

Methyl (3R)-3-[(1 S)-1-hydroxyethyl]-7-methyl-1,1-dioxo-2,3-dihydropyrrolo[3,4-f]-thiazepine-6-carboxylate (200 mg, 0.67 mmol) was dissolved in MeOH (30 mL). Under a nitrogen atmosphere Pd/C (10%) (71 mg, 0.067 mmol) was added. The reaction mixture was set under a hydrogen atmosphere for 60 minutes. The reaction mixture was filtered over decalite and the solids were washed with methanol (4×100 mL) and THF (4×100 mL). The filtrate was evaporated to dryness to afford methyl (3R)-3-[(1S)-1-hydroxyethyl]-7-methyl-1,1-dioxo-2,3,4,5-tetrahydropyrrolo[3,4-f]thiazepine-6-carboxylate (180 mg) as a white powder. Method B; Rt: 0.59 min. m/z: 301 (M–H)⁻ Exact mass: 302.1.

Methyl (3R)-3-[(1S)-1-hydroxy ethyl]-7-methyl-1,1-dioxo-2,3,4,5-tetrahydropyrrolo[3,4-f]thiazepine-6-carboxylate (90 mg, 0.24 mmol) and 3,4-difluoro-aniline (40 mg, 0.31 mmol) were dissolved in THF (5 mL). Lithium bis(trimethylsilyl)-amide (1.6 mL, 1 M in THF, 1.6 mmol) was added and the reaction mixture was stirred 1 hour at room temperature. The reaction was quenched with NH₄Cl (sat., aq., 5 mL) and the organic layer was separated. The aqueous layer was extracted with DCM (2×4 mL) and the combined organic layers were dried (Na₂SO₄) and evaporated to dryness. The residue was purified via preparative HPLC (Stationary phase: RP XBridge Prep C18 OBD-10 μm, 50×150 mm, Mobile phase: 0.25% NH₄HCO₃ solution in water, ACN). The obtained product was purified using silica gel column chromatography (ethyl acetate in heptane from 0 to 100%) yielding compound 88 (35 mg). ¹H NMR (400 MHz, DMSO-d₆) δ ppm 1.13 (d, J=6.2 Hz, 3H), 1.20-1.35 (m, 1H), 2.18 (br dd, J=14.3, 6.8 Hz, 1H), 2.67-2.80 (m, 1H), 3.02 (br dd, J=14.9, 6.5 Hz, 1H), 3.14-3.27 (m, 1H), 3.43-3.51 (m, 1H), 3.68 (s, 3H), 4.67 (d, J=5.9 Hz, 1H), 6.89 (d, J=10.1 Hz, 1H), 7.38-7.46 (m, 3H), 7.81-7.89 (m, 1H), 10.47 (s, 1H); Method B; Rt: 0.78 min. m/z: 398 (M–H)⁻ Exact mass: 399.1.

Compound 89: N-(3,4-difluorophenyl)-7-methyl-1,1-dioxo-3-tetrahydropyran-4-yl-3,4-dihydro-2H-pyrrolo[3,4-b][1,4,5]oxathiazepine-6-carboxamide

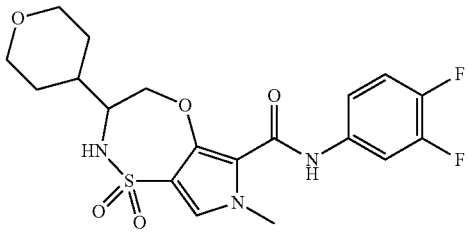 [SMILES: Cn1cc2c(c1C(=O)Nc1ccc(F)c(F)c1)OCC(C1CCOCC1)NS2(=O)=O]

Compound 89 (320 mg) was prepared similarly as described for compound 14, using 2-amino-2-(oxan-4-yl)ethan-1-ol hydrochloride instead of DL-alaninol. The ring closure was obtained after heating 90 minutes at 110° C. in DMF and compound 83 was purified on silica using a gradient from heptane to EtOAc. ¹H NMR (400 MHz, DMSO-d₆) δ ppm 1.24-1.44 (m, 2H), 1.60-1.79 (m, 3H), 3.20-3.29 (m, 2H), 3.42-3.51 (m, 1H), 3.81-4.04 (m, 6H), 4.72 (d, J=12.5 Hz, 1H), 7.36-7.50 (m, 3H), 7.62 (d, J=9.6 Hz, 1H), 7.86 (ddd, J=13.2, 7.5, 2.5 Hz, 1H), 9.42 (s, 1H); Method D; Rt: 1.80 min. m/z: 440 (M–H)⁻ Exact mass: 441.1. This racemic mixture was separated in enantiomers 89a (101 mg) and 89b (75 mg) by preparative SFC (Stationary phase: Chiralpak Diacel AD 20×250 mm, Mobile phase: CO2, EtOH+0.4 iPrNH₂). Method J; Rt: 89a: 1.39 min, 89b: 2.96 min.

Compound 90: (3R)—N-(3-cyano-4-fluoro-phenyl)-3-[(1S)-1-hydroxyethyl]-7-methyl-1,1-dioxo-2,3,4,5-tetrahydropyrrolo[3,4-f]thiazepine-6-carboxamide

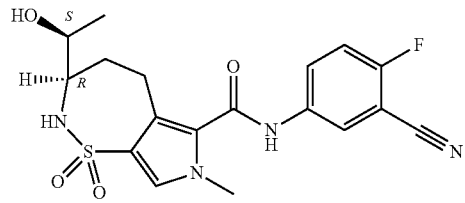

Compound 90 (38 mg) was prepared similarly as described for compound 88, using 5-amino-2-fluoro-benzonitrile instead of 3,4-difluoroaniline. ¹H NMR (400 MHz, DMSO-d₆) δ ppm 1.13 (d, J=6.2 Hz, 3H), 1.20-1.35 (m, 1H), 2.19 (br dd, J=14.2, 6.9 Hz, 1H), 2.71-2.81 (m, 1H), 3.05 (br dd, J=15.0, 6.4 Hz, 1H), 3.16-3.27 (m, 1H), 3.47 (sxt, J=6.4 Hz, 1H), 3.69 (s, 3H), 4.67 (d, J=5.7 Hz, 1H), 6.90 (d, J=10.1 Hz, 1H), 7.44 (s, 1H), 7.54 (t, J=9.1 Hz, 1H), 7.96 (ddd, J=9.1, 4.8, 2.8 Hz, 1H), 8.19 (dd, J=5.7, 2.6 Hz, 1H), 10.59 (s, 1H); Method B; Rt: 0.73 min. m/z: 405 (M–H)⁻ Exact mass: 406.1.

Compound 91: N-(3-cyano-4-fluoro-phenyl)-7-methyl-1,1-dioxo-3,4-dihydro-2H-pyrrolo[3,4-b][1,4,5]oxathiazepine-6-carboxamide

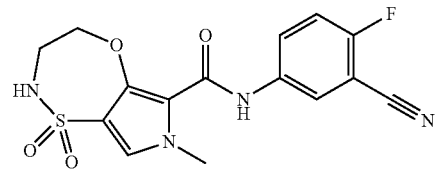 [SMILES: Cn1cc2c(c1C(=O)Nc1ccc(F)c(C#N)c1)OCCNS2(=O)=O]

Ethyl 3-hydroxy-1-methyl-pyrrole-2-carboxylate (200 mg, 1.0 mmol) was dissolved in THF (8 mL) under nitrogen and NaH (60% dispersion in mineral oil) (64 mg, 1.61 mmol) was added at room temperature and stirred for 10 minutes before 2-(tert-butoxycarbonylamino)ethyl methanesulfonate (361 mg, 1.51 mmol) was added. The solution was heated overnight at 80° C. The solution was quenched with ice water diluted with EtOAc, extracted twice with EtOAc, and the combined organics were dried with MgSO₄, filtered, and concentrated in vacuo. The residue was purified on silica using gradient elution (heptane/EtOAc from 100/0 to 50/50) to yield ethyl 3-[2-(tert-butoxycarbonylamino)ethoxy]-1-methyl-pyrrole-2-carboxylate (238 mg) as an oil.

Ethyl 3-[2-(tert-butoxycarbonylamino)ethoxy]-1-methyl-pyrrole-2-carboxylate (235 mg, 0.68 mmol) was dissolved in DCM (4 mL) and chlorosulfonic acid (0.090 mL, 1.75 g/mL, 1.354 mmol) was added under inert atmosphere at 0° C. and stirred for 2 hours. The solution was concentrated in vacuo to give 4-(2-aminoethoxy)-5-ethoxycarbonyl-1-methyl-pyrrole-3-sulfonic acid (197 mg).

4-(2-aminoethoxy)-5-ethoxycarbonyl-1-methyl-pyrrole-3-sulfonic acid (197 mg, 0.6 mmol) was dissolved in DCM (4 mL) and SOCl₂ (0.218 mL, 1.64 g/mL, 2.999 mmol) was added and the solution was heated for 2 hours at 70° C. The solution was coevaporated with toluene until dryness. The residue was redissolved in MeOH and quenched with NaHCO₃ (aq. sat.). The excess salts were filtered off and the residue concentrated in vacuo. The crude was then further purified on silica using a DCM/MeOH from 100/0 to 90/10 gradient to give ethyl 7-methyl-1,1-dioxo-3,4-dihydro-2H-pyrrolo[3,4-b][1,4,5]oxathiazepine-6-carboxylate (85 mg) as a yellow solid. $^1$H NMR (400 MHz, CHLOROFORM-d) δ ppm 1.36 (t, J=7.2 Hz, 3H) 3.62-3.70 (m, 2H) 3.83 (s, 3H) 4.28-4.36 (m, 4H) 4.87 (br s, 1H) 7.03 (s, 1H).

Ethyl 7-methyl-1,1-dioxo-3,4-dihydro-2H-pyrrolo[3,4-b][1,4,5]oxathiazepine-6-carboxylate (67 mg, 0.22 mmol) was dissolved in THF (4 mL) and 5-amino-2-fluoro-benzonitrile (33 mg, 0.24 mmol) was added followed by lithium bis(trimethylsilyl)-amide (0.87 mL, 1 M in THF, 0.87 mmol) at room temperature under an inert atmosphere and stirred for 2 hours. The solution was quenched with NH$_4$Cl (sat., aq.) and the organics were removed in vacuo, diluted with DCM, separated, dried with Na$_2$SO$_4$, filtered off, and concentrated in vacuo. The crude was then purified via preparative HPLC to give compound 91 (15 mg). $^1$H NMR (400 MHz, CHLOROFORM-d) δ ppm 3.77-3.83 (m, 2H), 3.97 (s, 3H), 4.43-4.47 (m, 2H), 4.72 (t, J=6.9 Hz, 1H), 7.11 (s, 1H), 7.18-7.22 (m, 1H), 7.72 (ddd, J=9.1, 4.5, 2.8 Hz, 1H), 7.96 (dd, J=5.4, 2.8 Hz, 1H), 8.86 (s, 1H); Method B; Rt: 0.82 min. m/z: 363 (M-H)$^-$ Exact mass: 364.1.

Compound 92: (3S)-3-[cyclopropyl(hydroxy)methyl]-N-(3,4-difluorophenyl)-7-methyl-1,1-dioxo-3,4-dihydro-2H-pyrrolo[3,4-b][1,4,5]oxathiazepine-6-carboxamide

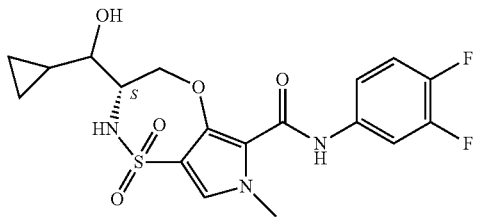

To a cooled solution of (S)-(−)-3-boc-2,2-dimethyloxazolidine-4-carboxaldehyde in dry THF (20 mL) at −78° C. was added cyclopropylmagnesium bromide (4.83 mL, 1M in THF, 4.83 mmol). The reaction mixture was warmed slowly to room temperature and stirred for 4 hours. The reaction mixture was quenched with water (20 ml) and then EtOAc was added (10 ml) to extract the product (some NaCl was added to get all THF out of the water layer). The water layer was extracted once more with EtOAc. The combined organic layers were dried over Na$_2$SO$_4$, filtered and evaporated to dryness and the crude oil was purified on silica (from 0% to 40% EtOAc in heptane). All pure fractions were collected and evaporated to get tert-butyl (4S)-4-[cyclopropyl(hydroxy)methyl]-2,2-dimethyl-oxazolidine-3-carboxylate (679 mg) as a clear yellow oil. $^1$H NMR (400 MHz, CHLOROFORM-d) δ ppm 0.20-0.65 (m, 4H), 0.75-0.99 (m, 1H), 1.38-1.78 (m, 15H), 2.98-3.57 (m, 2H), 3.87-4.35 (m, 3H).

HCl (2.35 mL, 4 M in dioxane, 9.41 mmol) was added to a solution of tert-butyl (4S)-4-[cyclopropyl(hydroxy)methyl]-2,2-dimethyl-oxazolidine-3-carboxylate (679 mg, 2.35 mmol) in 1,4-dioxane (10 mL). The reaction mixture was stirred at rt for 150 minutes. The reaction mixture was concentrated under reduced pressure to yield (2S)-2-amino-1-cyclopropyl-propane-1,3-diol hydrochloride (308 mg) which was used as such.

Ethyl 4-chlorosulfonyl-3-fluoro-1-methyl-pyrrole-2-carboxylate (667 mg, 2.47 mmol) was added to a solution of (2S)-2-amino-1-cyclopropyl-propane-1,3-diol hydrochloride (308.26 mg, 2.35 mmol) and Hunig's base (2.56 mL, 0.75 g/mL, 14.8 mmol) in DCM (15 mL) at room temperature under nitrogen atmosphere. The reaction mixture was stirred at room temperature overnight. A part of the DCM was concentrated and the reaction mixture was directly purified on silica (heptane/ethyl acetate 100/0 to 0/100) to afford ethyl 4-[[(1S)-2-cyclopropyl-2-hydroxy-1-(hydroxymethyl)ethyl]sulfamoyl]-3-fluoro-1-methyl-pyrrole-2-carboxylate (756 mg). Method B; Rt: 0.66 min. m/z: 363 (M-H)$^-$ Exact mass: 364.1.

Lithium bis(trimethylsilyl)amide (5.5 mL, 1 M in THF, 5.5 mmol) was added dropwise to a solution of ethyl 4-[[(1S)-2-cyclopropyl-2-hydroxy-1-(hydroxymethyl)ethyl]sulfamoyl]-3-fluoro-1-methyl-pyrrole-2-carboxylate (400 mg, 1.1 mmol) and 3,4-difluoroaniline (0.13 mL, 1.29 g/mL, 1.32 mmol) in THF (15 mL). The reaction mixture was stirred at room temperature for 30 min. The reaction mixture was quenched by adding water and diluted in ethyl acetate. The aqueous layer was extracted twice with ethyl acetate. The combined organic layers were dried over Na$_2$SO$_4$, filtered off and concentrated under reduced pressure. The residue was purified on silica (heptane/ethyl acetate 100/0 to 0/100) to afford 4-[[(1S)-2-cyclopropyl-2-hydroxy-1-(hydroxymethyl)ethyl]sulfamoyl]-N-(3,4-difluorophenyl)-3-fluoro-1-methyl-pyrrole-2-carboxamide (250 mg).

Cesium fluoride (272 mg, 1.79 mmol) was added to a solution of 4-[[(1S)-2-cyclopropyl-2-hydroxy-1-(hydroxymethyl)ethyl]sulfamoyl]-N-(3,4-difluorophenyl)-3-fluoro-1-methyl-pyrrole-2-carboxamide (200 mg, 0.45 mmol) in DMF (5 mL). The reaction mixture was stirred at 110° C. for 7 hours. The reaction mixture was concentrated and purified on silica (heptane/ethyl acetate 100/0 to 0/100). The obtained product was purified via preparative SFC (Stationary phase: Chiralpak Diacel AD 20×250 mm, Mobile phase: CO$_2$, EtOH-iPrOH (50-50)+0.4% iPrNH$_2$) to yield compound 92a (34 mg); $^1$H NMR (400 MHz, DMSO-d$_6$) δ ppm 0.25-0.50 (m, 4H), 0.98-1.10 (m, 1H), 3.03-3.14 (m, 1H), 3.56-3.67 (m, 1H), 3.83 (s, 3H), 4.00 (dd, J=12.8, 9.2 Hz, 1H), 4.91 (dd, J=12.8, 1.8 Hz, 1H), 5.00 (d, J=5.7 Hz, 1H), 7.35-7.50 (m, 3H), 7.60 (d, J=9.9 Hz, 1H), 7.87 (ddd, J=13.3, 7.5, 2.5 Hz, 1H), 9.43 (s, 1H); Method D; Rt: 1.78 min. m/z: 426 (M-H)$^-$ Exact mass: 427.1, and 92b (11 mg); $^1$H NMR (400 MHz, DMSO-d$_6$) δ ppm 0.17-0.47 (m, 4H), 0.95-1.08 (m, 1H), 3.04-3.18 (m, 1H), 3.82 (s, 4H), 3.93-4.10 (m, 1H), 4.74 (dd, J=12.7, 1.4 Hz, 1H), 5.00 (d, J=5.1 Hz, 1H), 7.34-7.49 (m, 4H), 7.86 (ddd, J=13.2, 7.5, 2.4 Hz, 1H), 9.35-9.48 (m, 1H); Method D; Rt: 1.77 min. m/z: 426 (M-H)$^-$ Exact mass: 427.1 being the 2 epimers of compound 92. Method P; Rt: 92a: 1.88 min, 92b: 2.27 min.

Compound 93: (3R)—N-(3,4-difluorophenyl)-3-(1-hydroxy-1-methyl-ethyl)-7-methyl-1,1-dioxo-3,4-dihydro-2H-pyrrolo[3,4-b][1,4,5]oxathiazepine-6-carboxamide

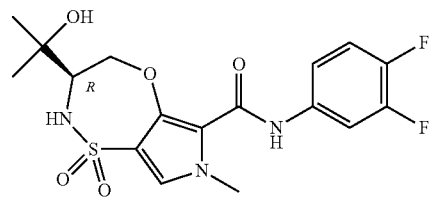

Methylmagnesium bromide (12.7 mL, 3 M, 38.2 mmol) was added to a solution of (R)-3-tert-butyl 4-methyl 2,2- dimethyloxazolidine-3,4-dicarboxylate (3 g, 1.08 g/mL, 11.6 mmol) in THF (100 mL) at −20° C. under a nitrogen atmosphere. The reaction mixture was stirred at 0° C. for 4 h and then the reaction mixture was quenched with NH$_4$Cl (sat., aq.) and diluted in EtOAc. The two layers were separated and the aqueous layer was extracted with EtOAc (twice). The combined organic layers were dried over Na$_2$SO$_4$, filtered and concentrated under reduced pressure. The residue was purified on silica (heptane/EtOAc 100/0 to 70/30 to afford tert-butyl (4R)-4-(1-hydroxy-1-methyl-ethyl)-2,2-dimethyl-oxazolidine-3-carboxylate (2.11 g) as a light yellow oil.

Compound 93 (188 mg) was prepared similarly as described for compound 92, using tert-butyl (4R)-4-(1-hydroxy-1-methyl-ethyl)-2,2-dimethyl-oxazolidine-3-carboxylate instead of tert-butyl (4S)-4-[cyclopropyl(hydroxy)methyl]-2,2-dimethyl-oxazolidine-3-carboxylate. $^1$H NMR (400 MHz, DMSO-d$_6$) δ ppm 1.13 (d, J=6.2 Hz, 3H), 1.20-1.35 (m, 1H), 2.19 (br dd, J=14.2, 6.9 Hz, 1H), 2.71-2.81 (m, 1H), 3.05 (br dd, J=15.0, 6.4 Hz, 1H), 3.16-3.27 (m, 1H), 3.47 (sxt, J=6.4 Hz, 1H), 3.69 (s, 3H), 4.67 (d, J=5.7 Hz, 1H), 6.90 (d, J=10.1 Hz, 1H), 7.44 (s, 1H), 7.54 (t, J=9.1 Hz, 1H), 7.96 (ddd, J=9.1, 4.8, 2.8 Hz, 1H), 8.19 (dd, J=5.7, 2.6 Hz, 1H), 10.59 (s, 1H); Method B; Rt: 0.73 min. m/z: 405 (M−H)$^−$ Exact mass: 406.1.

Compound 94: (3S)—N-(3,4-difluorophenyl)-3-(1-hydroxy-1-methyl-ethyl)-7-methyl-1,1-dioxo-3,4-dihydro-2H-pyrrolo[3,4-b][1,4,5]oxathiazepine-6-carboxamide

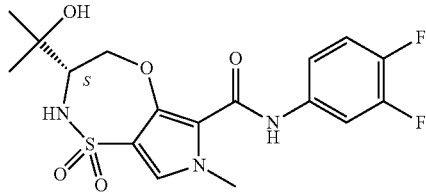

Compound 94 (300 mg) was prepared similarly as described for compound 93, using (S)-(−)-3-tert-butoxycarbonyl-4-methoxycarbonyl-2,2-dimethyl-1,3-oxazolidine instead of (R)-3-tert-butyl 4-methyl 2,2-dimethyloxazolidine-3,4-dicarboxylate. $^1$H NMR (400 MHz, DMSO-d$_6$) δ ppm 1.06 (s, 3H), 1.25 (s, 3H), 3.55 (t, J=9.4 Hz, 1H), 3.83 (s, 3H), 3.92 (dd, J=12.5, 9.0 Hz, 1H), 4.85 (s, 1H), 4.96 (d, J=11.4 Hz, 1H), 7.33-7.54 (m, 4H), 7.87 (ddd, J=13.2, 7.5, 2.4 Hz, 1H), 9.43 (s, 1H); Method B; Rt: 0.88 min. m/z: 414 (M−H)$^−$ Exact mass: 415.1. MP: 234.1° C.

Compound 95: N-(3,4-difluorophenyl)-3-[hydroxy(3-pyridyl)methyl]-7-methyl-1,1-dioxo-3,4-dihydro-2H-pyrrolo[3,4-b][1,4,5]oxathiazepine-6-carboxamide

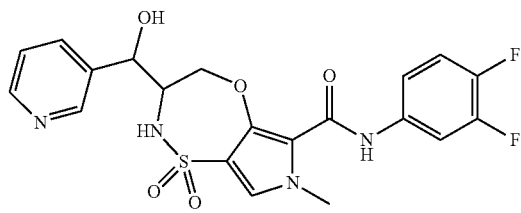 [SMILES: Cn1cc2c(c1C(=O)Nc1ccc(F)c(F)c1)OCC(C(O)c1cccnc1)NS2(=O)=O]

To a solution of KOH (2.48 g, 44.2 mmol) in EtOH (100 mL) at 0° C. was added 3-pyridinecarboxaldehyde (4.66 mL, 1.14 g/mL, 48.6 mmol) and ethyl isocyanoacetate (4.85 mL, 1.03 g/mL, 44.2 mmol). The reaction mixture was stirred for 3 hours and then concentrated to yield an oil. This was redissolved in HCl (37% in H$_2$O, 50 mL) and heated at 60° C. for 2 hours. The formed precipitate was filtered off to give 2-amino-3-hydroxy-3-(3-pyridyl)propanoic acid (8.3 g).

In a 250 mL flask 2-amino-3-hydroxy-3-(3-pyridyl)propanoic acid (8.3 g, 32.5 mmol) was dissolved in dry MeOH (50 mL) and cooled till 5° C. SOCl$_2$ (11.8 mL, 1.64 g/mL, 163 mmol) was added dropwise and after addition the reaction was heated at reflux for 3 hours. The reaction mixture was concentrated to dryness and partitioned between DCM and NaHCO$_3$ (sat., aq.). The organic layer was dried over MgSO$_4$ and evaporated to dryness yielding methyl 2-amino-3-hydroxy-3-(3-pyridyl)propanoate (8.76 g) as a light yellow oil.

Methyl 2-amino-3-hydroxy-3-(3-pyridyl)propanoate (8.76 g, 32.5 mmol), BOC-anhydride (7.32 g, 32.5 mmol) and Et$_3$N (22.6 mL, 0.73 g/mL, 163 mmol) were dissolved in THF (150 mL) and stirred 3 hours at room temperature. The volatiles were removed under reduced pressure and the residue was separated between water and 2-MeTHF. The organic layer was removed and concentrated under reduced pressure. The residue was purified on silica using a heptane to EtOAc:EtOH 3:1 gradient yielding methyl 2-(tert-butoxycarbonylamino)-3-hydroxy-3-(3-pyridyl)propanoate (3.3 g). Method B; Rt: 0.65 min. m/z: 295 (M−H)$^−$ Exact mass: 296.1.

Methyl 2-(tert-butoxycarbonylamino)-3-hydroxy-3-(3-pyridyl)propanoate (3.3 g, 11.1 mmol) was dispensed in dioxane (100 mL). LAH (12 mL, 1 M in THF, 12 mmol) was added and the reaction mixture was stirred overnight at 80° C. The reaction mixture was quenched with sodium sulfate decahydrate (550 mg, 1.7 mmol) and then dried with MgSO$_4$. The solids were filtered off and the filtrate was evaporated to dryness. The residue was purified on silica using a heptane to EtOAc:EtOH 3:1 gradient yielding tert-butyl N-[2-hydroxy-1-(hydroxymethyl)-2-(3-pyridyl)ethyl]carbamate (763 mg) as a white powder.

tert-butyl N-[2-hydroxy-1-(hydroxymethyl)-2-(3-pyridyl)ethyl]carbamate (350 mg, 1.3 mmol) was dissolved in DCM (10 mL). TFA (300 μL, 1.49 g/mL, 3.91 mmol) was added and the reaction mixture was stirred overnight. TFA (300 μL, 1.49 g/mL, 3.91 mmol) was added and the reaction mixture was stirred for 2 days at 40° C. Hunig's base (2.25 mL, 0.75 g/mL, 13.04 mmol) was added and this reaction mixture was used as such in the further synthesis.

Compound 95 (15.2 mg) was prepared similarly as described for compound 63, using the previously described reaction mixture instead of (1S,2S)-(+)-2-amino-1-phenyl-1,3-propanediol. $^1$H NMR (400 MHz, DMSO-d$_6$) δ ppm 3.80 (s, 3H), 3.91-3.97 (m, 1H), 3.97-4.06 (m, 1H), 4.82 (d, J=11.7 Hz, 1H), 4.99 (d, J=3.3 Hz, 1H), 5.91 (br s, 1H), 7.36-7.50 (m, 4H), 7.53 (br s, 1H), 7.78 (dt, J=7.7, 1.8 Hz, 1H), 7.82-7.90 (m, 1H), 8.48 (dd, J=4.8, 1.5 Hz, 1H), 8.59 (d, J=1.8 Hz, 1H), 9.49 (s, 1H); Method B; Rt: 0.84 min. m/z: 463 (M−H)$^−$ Exact mass: 464.1.

Compound 96: (3R)—N-[3-(difluoromethyl)-4-fluoro-phenyl]-3-[(1S)-1-hydroxyethyl]-7-methyl-1,1-dioxo-2,3-dihydropyrrolo[3,4-f]thiazepine-6-carboxamide

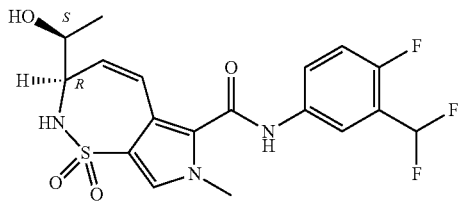

Compound 96 (177 mg) was prepared similarly as described for compound 84, using 3-(difluoromethyl)-4-fluoro-aniline instead of 3,4-difluoroaniline. $^1$H NMR (400 MHz, DMSO-d$_6$) δ ppm 1.20 (d, J=6.2 Hz, 3H), 3.64-3.76 (m, 4H), 3.76-3.88 (m, 1H), 4.96 (d, J=5.9 Hz, 1H), 5.96 (dd, J=12.5, 2.9 Hz, 1H), 6.56 (dd, J=12.5, 2.6 Hz, 1H), 7.23 (t, J=54.4 Hz, 1H), 7.32-7.44 (m, 2H), 7.57 (s, 1H), 7.80-7.85 (m, 1H), 8.07 (dd, J=6.4, 2.4 Hz, 1H), 10.75 (br s, 1H); Method B; Rt: 0.81 min. m/z: 428 (M−H)$^−$ Exact mass: 429.1. MP: 182.3° C.

Compound 97: (3R)—N-(2-bromo-4-pyridyl)-3-[(1S)-1-hydroxyethyl]-7-methyl-1,1-dioxo-2,3-dihydropyrrolo[3,4-f]thiazepine-6-carboxamide

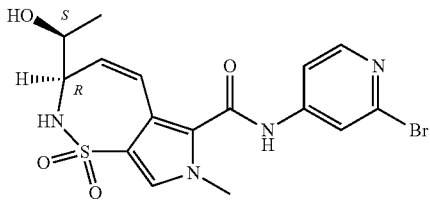

Compound 97 (134 mg) was prepared similarly as described for compound 84, using 4-amino-2-bromopyridine instead of 3,4-difluoroaniline. $^1$H NMR (400 MHz, DMSO-d$_6$) δ ppm 1.21 (d, J=6.2 Hz, 3H), 3.64-3.91 (m, 5H), 4.98 (d, J=5.7 Hz, 1H), 5.99 (dd, J=12.5, 2.9 Hz, 1H), 6.56 (dd, J=12.5, 2.6 Hz, 1H), 7.42 (d, J=10.3 Hz, 1H), 7.59-7.67 (m, 2H), 7.97 (d, J=1.8 Hz, 1H), 8.29 (d, J=5.7 Hz, 1H), 11.04 (s, 1H); Method B; Rt: 0.69 min. m/z: 439 (M−H)$^−$ Exact mass: 440.0.

Compound 98: (3R)-3-[(1S)-1-hydroxyethyl]-7-methyl-1,1-dioxo-N-(3,4,5-trifluorophenyl)-2,3-dihydropyrrolo[3,4-f]thiazepine-6-carboxamide

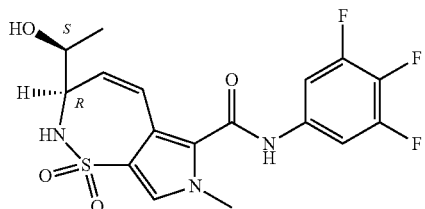

Compound 98 (146 mg) was prepared similarly as described for compound 84, using 3,4,5-trifluoroaniline instead of 3,4-difluoroaniline. $^1$H NMR (400 MHz, DMSO-d$_6$) δ ppm 1.21 (d, J=6.2 Hz, 3H), 3.54-3.74 (m, 4H), 3.76-3.90 (m, 1H), 4.98 (d, J=5.7 Hz, 1H), 5.98 (dd, J=12.5, 2.6 Hz, 1H), 6.54 (dd, J=12.5, 2.4 Hz, 1H), 7.40 (br d, J=10.1 Hz, 1H), 7.54-7.66 (m, 3H), 10.85 (br s, 1H); Method B; Rt: 0.86 min. m/z: 414 (M−H)$^−$ Exact mass: 415.1. MP: 244.0° C.

Compound 99: (3R)—N-(4-fluoro-3-methyl-phenyl)-3-[(1S)-1-hydroxyethyl]-7-methyl-1,1-dioxo-2,3-dihydropyrrolo[3,4-f]thiazepine-6-carboxamide

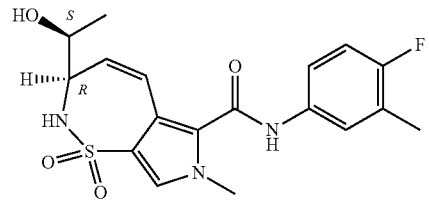

Compound 99 (134 mg) was prepared similarly as described for compound 84, using 4-fluoro-3-methylaniline instead of 3,4-difluoroaniline. $^1$H NMR (400 MHz, DMSO-d$_6$) δ ppm 1.20 (d, J=6.2 Hz, 3H), 2.23 (d, J=1.5 Hz, 3H), 3.64-3.76 (m, 4H), 3.76-3.88 (m, 1H), 4.96 (br d, J=5.5 Hz, 1H), 5.94 (dd, J=12.5, 2.6 Hz, 1H), 6.53 (dd, J=12.5, 2.6 Hz, 1H), 7.12 (t, J=9.2 Hz, 1H), 7.37 (br d, J=8.1 Hz, 1H), 7.48-7.53 (m, 1H), 7.54 (s, 1H), 7.63 (dd, J=6.9, 2.3 Hz, 1H), 10.49 (s, 1H); Method B; Rt: 0.80 min. m/z: 392 (M−H)$^−$ Exact mass: 393.1.

Compound 100: (3R)—N-[3-(difluoromethyl)-4-fluoro-phenyl]-3-(1-hydroxy-1-methyl-ethyl)-7-methyl-1,1-dioxo-3,4-dihydro-2H-pyrrolo[3,4-b][1,4,5]oxathiazepine-6-carboxamide

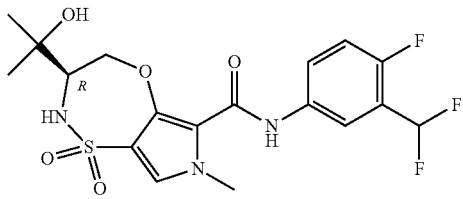

Compound 100 (216 mg) was prepared similarly as described for compound 93, using 3-(difluoromethyl)-4-fluoro-aniline instead of 3,4-difluoroaniline. $^1$H NMR (400 MHz, DMSO-d$_6$) δ ppm 1.06 (s, 3H), 1.25 (s, 3H), 3.55 (br t, J=9.5 Hz, 1H), 3.83 (s, 3H), 3.94 (dd, J=12.5, 8.8 Hz, 1H), 4.86 (s, 1H), 4.95 (d, J=11.4 Hz, 1H), 7.06-7.37 (m, 2H), 7.47-7.53 (m, 2H), 7.77-7.85 (m, 1H), 8.04 (dd, J=6.3, 2.5 Hz, 1H), 9.47 (s, 1H); Method B; Rt: 0.90 min. m/z: 446 (M−H)$^−$ Exact mass: 447.1.

Compound 101: (3S)—N-[3-(difluoromethyl)-4-fluoro-phenyl]-3-(1-hydroxy-1-methyl-ethyl)-7-methyl-1,1-dioxo-3,4-dihydro-2H-pyrrolo[3,4-b][1,4,5]oxathiazepine-6-carboxamide

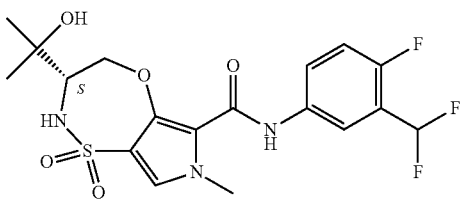

Compound 101 (132.8 mg) was prepared similarly as described for compound 94, using 3-(difluoromethyl)-4-fluoro-aniline instead of 3,4-difluoroaniline. $^1$H NMR (400 MHz, DMSO-$d_6$) δ ppm 1.06 (s, 3H), 1.25 (s, 3H), 3.55 (t, J=9.4 Hz, 1H), 3.83 (s, 3H), 3.93 (dd, J=12.5, 9.0 Hz, 1H), 4.86 (s, 1H), 4.95 (d, J=11.4 Hz, 1H), 7.05-7.39 (m, 2H), 7.45-7.55 (m, 2H), 7.77-7.85 (m, 1H), 8.04 (dd, J=6.3, 2.5 Hz, 1H), 9.47 (s, 1H); Method B; Rt: 0.89 min. m/z: 446 (M–H)$^-$ Exact mass: 447.1. MP: 214.4° C.

Compound 102: (3R)—N-(3,4-difluorophenyl)-3-(1-hydroxy-1-methyl-ethyl)-7-methyl-1,1-dioxo-2,3,4,5-tetrahydropyrrolo[3,4-f]thiazepine-6-carboxamide

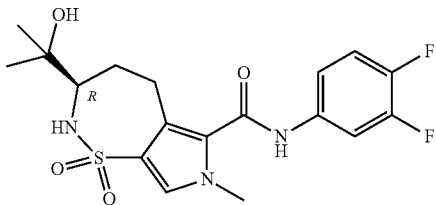

A solution of tert-butyl (2R)-2-(benzyloxycarbonylamino)hex-5-ynoate (5.03 g, 15.8 mmol) and ethyl isocyanoacetate (5.10 g, 42.8 mmol) in dioxane (15 mL) was added dropwise at 90° C. during 45 minutes to a solution of ethyl isocyanoacetate (1.50 g, 12.6 mmol) in dioxane (20 mL) wherein silver carbonate (947 mg, 3.44 mmol) was suspended. The reaction mixture was heated and stirred further at this temperature during 3 hours. The reaction mixture was filtered while still hot and concentrated. The residue was subjected to silica column chromatography using a gradient from 10 till 100% EtOAc in heptane resulting in ethyl 3-[(3R)-3-(benzyloxycarbonylamino)-4-tert-butoxy-4-oxo-butyl]-1H-pyrrole-2-carboxylate (1.98 g) as a clear oil.

TFA (5.3 mL, 1.49 g/mL, 69 mmol) was added to ethyl 3-[(3R)-3-(benzyloxycarbonylamino)-4-tert-butoxy-4-oxo-butyl]-1H-pyrrole-2-carboxylate (1.98 g, 4.6 mmol) in DCM (50 mL) and stirred for 3 hours. The reaction mixture was concentrated and redissolved in DMF (50 mL). MeI (6.24 mL, 2.28 g/mL, 100 mmol) and Cs$_2$CO$_3$ (13 g, 40 mmol) were added and the reaction mixture was stirred overnight. The reaction mixture was filtered and directly loaded on a silica cartridge. A gradient from 0 till 100% EtOAc in heptane was applied yielding ethyl 3-[(3R)-3-(benzyloxycarbonylamino)-4-methoxy-4-oxo-butyl]-1-methyl-pyrrole-2-carboxylate (1.70 g). $^1$H NMR (400 MHz, DMSO-$d_6$) δ ppm 1.26 (t, J=7.2 Hz, 3H), 1.76-1.87 (m, 1H), 1.87-2.00 (m, 1H), 2.67-2.78 (m, 2H), 3.62 (s, 3H), 3.78 (s, 3H), 3.94-4.06 (m, 1H), 4.19 (q, J=7.0 Hz, 2H), 5.05 (s, 2H), 5.93 (d, J=2.4 Hz, 1H), 6.96 (d, J=2.4 Hz, 1H), 7.27-7.42 (m, 5H), 7.77 (d, J=7.7 Hz, 1H); Method D; Rt: 2.07 min. m/z: 401 (M–H)$^-$ Exact mass: 402.2.

Chlorosulfonic acid (112 mg, 0.96 mmol) was added to a solution of ethyl 3-[(3R)-3-(benzyloxycarbonylamino)-4-methoxy-4-oxo-butyl]-1-methyl-pyrrole-2-carboxylate (193 mg, 0.48 mmol) in DCM (20 mL) and stirred for 1 hour. Thionyl chloride (285 mg, 2.4 mmol) was added and the reaction mixture was stirred and refluxed 2 hours and then cooled in an icebath and quenched with methanol (1 mL). The mixture was poured in NaHCO$_3$ (aq. sat., 100 mL). The mixture was extracted with DCM (2×50 mL) and the combined organic layers were dried over magnesium sulfate, filtered and concentrated. The residue was purified by column chromatography using a gradient from 0 till 100% EtOAc in heptane yielding O6-ethyl O3-methyl (3R)-7-methyl-1,1-dioxo-2,3,4,5-tetrahydropyrrolo[3,4-f]thiazepine-3,6-dicarboxylate (58.8 mg) as a white powder. $^1$H NMR (400 MHz, DMSO-$d_6$) δ ppm 1.29 (t, J=7.0 Hz, 3H), 1.61-1.74 (m, 1H), 2.16-2.26 (m, 1H), 2.81 (br dd, J=14.1, 12.1 Hz, 1H), 3.62-3.72 (m, 4H), 3.80 (s, 3H), 4.22-4.30 (m, 3H), 7.56 (s, 1H), 7.74 (d, J=9.9 Hz, 1H); Method D; Rt: 1.60 min. m/z: 329 (M–H)$^-$ Exact mass: 330.1.

Methylmagnesium chloride (0.12 mL, 3 M, 0.35 mmol) was added to O6-ethyl O3-methyl (3R)-7-methyl-1,1-dioxo-2,3,4,5-tetrahydropyrrolo[3,4-f]thiazepine-3,6-dicarboxylate (58.8 mg, 0.168 mmol) in THF (10 mL) at −78° C. The reaction mixture was allowed immediately to reach room temperature. Another equal amount methylmagnesium chloride (0.12 mL, 3 M, 0.35 mmol) was added at −78° C. and the reaction mixture allowed to reach room temperature. Methylmagnesium chloride (0.04 mL, 3 M, 0.12 mmol) was added at 20° C. and the reaction mixture was stirred for 15 minutes. The reaction mixture was quenched with HCl (aq., 1M, 30 mL) diluted with brine (50 mL) and extracted with EtOAc (3×50 mL). The combined organic layers were dried over MgSO$_4$, filtered and concentrated. The residue was subjected to silica gel column chromatography using a gradient from 0 till 100% EtOAc in heptane yielding ethyl (3R)-3-(1-hydroxy-1-methyl-ethyl)-7-methyl-1,1-dioxo-2,3,4,5-tetrahydropyrrolo[3,4-f]thiazepine-6-carboxylate (26 mg) as a clear oil. Method D; Rt: 1.46 min. m/z: 329 (M–H)$^-$ Exact mass: 330.1.

Lithium bis(trimethylsilyl)amide (0.32 mL, 1 M in THF, 0.32 mmol) was added to a solution of ethyl (3R)-3-(1-hydroxy-1-methyl-ethyl)-7-methyl-1,1-dioxo-2,3,4,5-tetrahydropyrrolo[3,4-f]thiazepine-6-carboxylate (26 mg, 0.0787 mmol) and 3,4-difluoro-aniline (21 mg, 0.16 mmol) in THF (2 mL) and stirred for 30 minutes. Another 3 times this amount of 3,4-difluoroaniline (21 mg, 0.16 mmol) and lithium bis(trimethylsilyl)amide (0.32 mL, 1 M in THF, 0.32 mmol) were added and the reaction mixture was stirred for 1 hour. The reaction mixture was quenched with NH$_4$Cl solution (aq. sat., 10 mL), diluted with brine (10 mL) and extracted with EtOAc (50 mL). The organic layer was dried over MgSO$_4$, filtered and concentrated. The residue was subjected to silica gel column chromatography using a gradient from 0 till 100% EtOAc in heptane. The product fractions were concentrated and the residue subjected to silica gel column chromatography using a gradient from 5 till 30% iPrOH in heptane yielding compound 102 (12 mg) as a beige resin. $^1$H NMR (400 MHz, DMSO-$d_6$) δ ppm 1.20-1.31 (m, 6H), 1.47-1.59 (m, 1H), 1.70 (br s, 1H), 2.09-2.18 (m, 1H), 2.89-2.99 (m, 1H), 3.17 (td, J=7.7, 5.5

Hz, 1H), 3.39-3.51 (m, 1H), 3.74 (s, 3H), 4.67 (d, J=10.3 Hz, 1H), 7.09-7.18 (m, 2H), 7.19-7.25 (m, 1H), 7.70 (ddd, J=12.0, 7.2, 2.4 Hz, 1H), 8.20 (s, 1H); Method D; Rt: 1.58 min. m/z: 412 (M−H)⁻ Exact mass: 413.1; MP: 218.2° C.

Compound 103: (3R)—N-[3-(difluoromethyl)-4-fluoro-phenyl]-3-[(1S)-1-hydroxyethyl]-7-methyl-1,1-dioxo-2,3,4,5-tetrahydropyrrolo[3,4-f]thiazepine-6-carboxamide

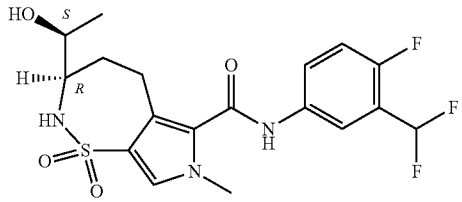

Compound 96 (109 mg, 0.25 mmol) was dissolved in MeOH (30 mL). Under a nitrogen atmosphere Pd/C (10%) (27 mg, 0.025 mmol) was added. The reaction mixture was hydrogenated for 60 minutes. The reaction mixture was filtered over decalite and the solids were washed with THF (4×80 mL). The filtrate was evaporated to dryness and the residue was purified using silica gel column chromatography (EtOAc in heptane from 0 to 100%) to afford compound 103 (70 mg) as a white powder. ¹H NMR (400 MHz, DMSO-d₆) δ ppm 1.13 (d, J=6.2 Hz, 3H), 1.19-1.37 (m, 1H), 2.19 (br dd, J=14.3, 6.8 Hz, 1H), 2.71-2.81 (m, 1H), 3.05 (br dd, J=15.3, 6.1 Hz, 1H), 3.16-3.29 (m, 1H), 3.40-3.54 (m, 1H), 3.69 (s, 3H), 4.67 (d, J=5.7 Hz, 1H), 6.89 (d, J=10.1 Hz, 1H), 7.22 (t, J=54.2 Hz, 1H), 7.37 (t, J=9.6 Hz, 1H), 7.42 (s, 1H), 7.78-7.84 (m, 1H), 8.04-8.09 (m, 1H), 10.48 (s, 1H); Method B; Rt: 0.80 min. m/z: 430 (M−H)⁻ Exact mass: 431.1. MP: 274.7° C.

Compound 104: (3R)-3-[(1S)-1-hydroxyethyl]-7-methyl-1,1-dioxo-N-(3,4,5-trifluorophenyl)-2,3,4,5-tetrahydropyrrolo[3,4-f]thiazepine-6-carboxamide

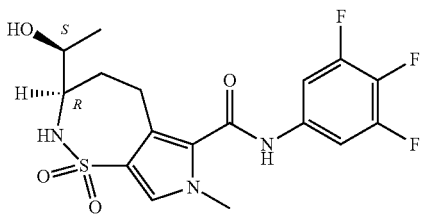

Compound 98 (75 mg, 0.18 mmol) was dissolved in MeOH (30 mL). Under a nitrogen atmosphere Pd/C (10%) (19 mg, 0.018 mmol) was added. The reaction mixture was hydrogenated for 60 minutes. The reaction mixture was filtered over decalite and the solids were washed with THF (4×80 mL). The filtrate was evaporated to dryness and the residue was purified using silica gel column chromatography (EtOAc in heptane from 0 to 100%) to afford compound 104 (37 mg) as a white powder. ¹H NMR (400 MHz, DMSO-d₆) δ ppm 1.13 (d, J=6.4 Hz, 3H), 1.19-1.36 (m, 1H), 2.18 (br dd, J=14.2, 7.2 Hz, 1H), 2.71-2.80 (m, 1H), 3.02 (br dd, J=15.4, 5.9 Hz, 1H), 3.16-3.28 (m, 1H), 3.33-3.54 (m, 1H), 3.68 (s, 3H), 4.67 (d, J=5.9 Hz, 1H), 6.90 (d, J=10.3 Hz, 1H), 7.44 (s, 1H), 7.56-7.64 (m, 2H), 10.58 (s, 1H); Method B; Rt: 0.85 min. m/z: 416 (M−H)⁻ Exact mass: 417.1.

Compound 105: (3R)-3-[cyclopropyl(hydroxy)methyl]-N-(3,4-difluorophenyl)-7-methyl-1,1-dioxo-3,4-dihydro-2H-pyrrolo[3,4-b][1,4,5]oxathiazepine-6-carboxamide

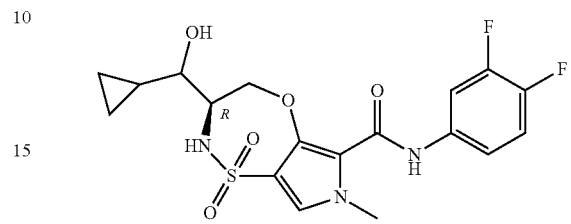

Compound 105 (310 mg) was prepared similarly as described for compound 92, using (R)-(−)-3-boc-2,2-dimethyloxazolidine-4-carboxaldehyde instead of (S)-(−)-3-boc-2,2-dimethyloxazolidine-4-carboxaldehyde. The obtained product was purified via preparative SFC (Stationary phase: Chiralpak Diacel AD 20×250 mm, Mobile phase: CO₂, EtOH+0.4% iPrNH₂) to yield compound 105a (60 mg); ¹H NMR (400 MHz, DMSO-d₆) δ ppm 0.16-0.27 (m, 1H), 0.27-0.36 (m, 1H), 0.36-0.48 (m, 2H), 0.94-1.09 (m, 1H), 3.13 (dt, J=7.5, 4.0 Hz, 1H), 3.72-3.80 (m, 1H), 3.83 (s, 3H), 4.04 (dd, J=12.8, 9.2 Hz, 1H), 4.75 (dd, J=12.7, 1.4 Hz, 1H), 5.01 (d, J=4.8 Hz, 1H), 7.33-7.52 (m, 4H), 7.86 (ddd, J=13.2, 7.5, 2.4 Hz, 1H), 9.45 (s, 1H); Method D; Rt: 1.77 min. m/z: 426 (M−H)⁻ Exact mass: 427.1; MP: 243.0° C., and 105b (203 mg); ¹H NMR (400 MHz, DMSO-d₆) δ ppm 0.22-0.41 (m, 3H), 0.41-0.53 (m, 1H), 0.98-1.11 (m, 1H), 3.03-3.14 (m, 1H), 3.56-3.70 (m, 1H), 3.83 (s, 3H), 4.00 (dd, J=12.8, 9.2 Hz, 1H), 4.91 (dd, J=12.8, 1.8 Hz, 1H), 5.01 (d, J=5.5 Hz, 1H), 7.34-7.51 (m, 3H), 7.61 (d, J=9.7 Hz, 1H), 7.87 (ddd, J=13.2, 7.5, 2.4 Hz, 1H), 9.43 (s, 1H); Method D; Rt: 1.77 min. m/z: 426 (M−H)⁻ Exact mass: 427.1; MP: 244.8° C., being the 2 epimers of compound 105. Method K; Rt: 105a: 1.98 min, 105b: 1.68 min.

Compound 106: (3R)—N-(3-cyano-4-fluoro-phenyl)-3-(1-hydroxy-1-methyl-ethyl)-7-methyl-1,1-dioxo-3,4-dihydro-2H-pyrrolo[3,4-b][1,4,5]oxathiazepine-6-carboxamide

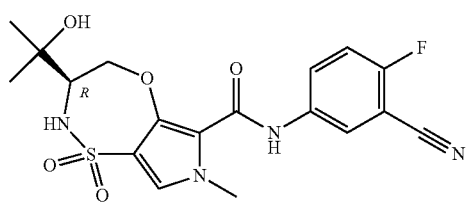

Compound 106 (134 mg) was prepared similarly as described for compound 93, using 5-amino-2-fluoro-benzonitrile instead of 3,4-difluoroaniline. ¹H NMR (400 MHz, DMSO-d₆) δ ppm 1.06 (s, 3H), 1.25 (s, 3H), 3.55 (br t, J=9.5 Hz, 1H), 3.84 (s, 3H), 3.93 (dd, J=12.5, 9.0 Hz, 1H), 4.86 (s, 1H), 4.99 (d, J=11.4 Hz, 1H), 7.46-7.56 (m, 3H), 8.06 (ddd, J=9.2, 4.8, 2.9 Hz, 1H), 8.21 (dd, J=5.7, 2.9 Hz, 1H), 9.52 (s, 1H); Method B; Rt: 0.83 min. m/z: 421 (M−H)⁻ Exact mass: 422.1; MP: 260.1° C.

Compound 107: (3S)—N-(3-cyano-4-fluoro-phenyl)-3-(1-hydroxy-1-methyl-ethyl)-7-methyl-1,1-dioxo-3,4-dihydro-2H-pyrrolo[3,4-b][1,4,5]oxathiazepine-6-carboxamide

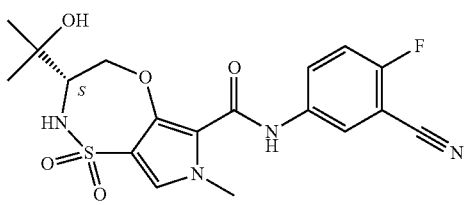

Compound 107 (111.4 mg) was prepared similarly as described for compound 94, using 5-amino-2-fluoro-benzonitrile instead of 3,4-difluoroaniline. $^1$H NMR (400 MHz, DMSO-$d_6$) δ ppm 1.06 (s, 3H), 1.25 (s, 3H), 3.55 (br t, J=7.6 Hz, 1H), 3.84 (s, 3H), 3.93 (dd, J=12.4, 8.9 Hz, 1H), 4.86 (s, 1H), 4.99 (d, J=11.4 Hz, 1H), 7.46-7.56 (m, 3H), 8.06 (ddd, J=9.2, 4.9, 2.9 Hz, 1H), 8.21 (dd, J=5.7, 2.9 Hz, 1H), 9.52 (s, 1H); Method B; Rt: 0.85 min. m/z: 421 (M−H)$^-$ Exact mass: 422.1. MP: 259.8° C.

Compound 108: N-[2-(difluoromethyl)-4-pyridyl]-3-isopropyl-7-methyl-1,1-dioxo-2,3,4,5-tetrahydropyrrolo[3,4-f]thiazepine-6-carboxamide

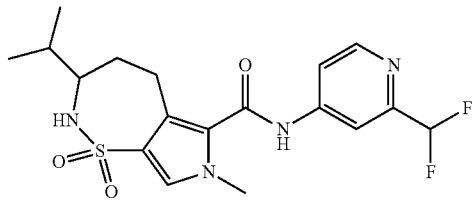 [SMILES: CC(C)C1CCc2c(cn(C)c2C(=O)Nc2ccnc(C(F)F)c2)S(=O)(=O)N1]

Compound 108 (10.8 mg) was prepared similarly as described for compound 85, using 2-(difluoromethyl)pyridin-4-amine instead of 5-amino-2-fluoro-benzonitrile. $^1$H NMR (400 MHz, DMSO-$d_6$) δ ppm 0.86-0.89 (m, 3H) 0.89-0.92 (m, 3H) 1.32-1.47 (m, 1H) 1.62-1.74 (m, 1H) 1.82-1.93 (m, 1H) 2.74-2.88 (m, 1H) 2.99-3.10 (m, 1H) 3.19-3.27 (m, 1H) 3.71 (s, 3H) 6.73-7.08 (m, 2H) 7.47 (s, 1H) 7.70-7.82 (m, 1H) 8.03 (d, J=1.76 Hz, 1H) 8.56 (d, J=5.72 Hz, 1H) 10.85 (s, 1H); Method B; Rt: 0.88 min. m/z: 411 (M−H)$^-$ Exact mass: 412.1.

Compound 109: N-(4-fluoro-3-methyl-phenyl)-3-isopropyl-7-methyl-1,1-dioxo-2,3,4,5-tetrahydropyrrolo[3,4-f]thiazepine-6-carboxamide

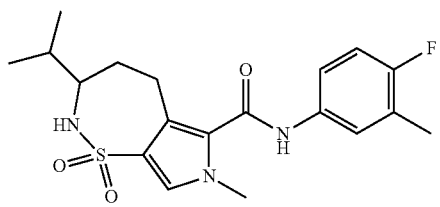 [SMILES: Cc1cc(NC(=O)c2c3c(cn2C)S(=O)(=O)NC(C(C)C)CC3)ccc1F]

Compound 109 (16.1 mg) was prepared similarly as described for compound 85, using 4-fluoro-3-methylaniline instead of 5-amino-2-fluoro-benzonitrile. $^1$H NMR (400 MHz, DMSO-$d_6$) δ ppm 0.89 (dd, J=6.82, 3.52 Hz, 6H) 1.38 (q, J=11.88 Hz, 1H) 1.62-1.74 (m, 1H) 1.86 (br dd, J=13.97, 6.71 Hz, 1H) 2.22 (d, J=1.32 Hz, 3H) 2.73-2.84 (m, 1H) 2.95-3.06 (m, 1H) 3.18-3.28 (m, 1H) 3.68 (s, 3H) 6.87 (br d, J=10.12 Hz, 1H) 7.10 (t, J=9.13 Hz, 1H) 7.39 (s, 1H) 7.45-7.54 (m, 1H) 7.58-7.66 (m, 1H) 10.23 (s, 1H); Method B; Rt: 1.03 min. m/z: 392 (M−H)$^-$ Exact mass: 393.1.

Compound 110: N-(3,4-difluorophenyl)-3-(dimethylaminomethyl)-7-methyl-1,1-dioxo-3,4-dihydro-2H-pyrrolo[3,4-b][1,4,5]oxathiazepine-6-carboxamide

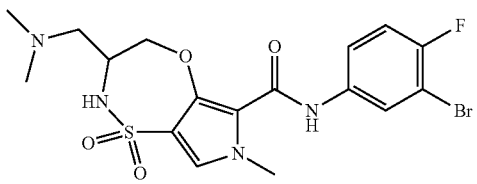 [SMILES: CN(C)CC1COc2c(cn(C)c2C(=O)Nc2ccc(F)c(Br)c2)S(=O)(=O)N1]

Compound 83 (105 mg, 0.27 mmol), MsCl (31 μL, 1.48 g/mL, 0.41 mmol) and TEA (150 μL, 0.73 g/mL, 1.08 mmol) were dissolved in DCM (10 mL) and stirred for 2 hours. Water was added and a precipitate appeared. This was filtered off, triturated with DIPE and dried to yield [6-[(3,4-difluorophenyl)carbamoyl]-7-methyl-1,1-dioxo-3,4-dihydro-2H-pyrrolo[3,4-b][1,4,5]oxathiazepin-3-yl]methyl methanesulfonate (64 mg) as a white powder.

[6-[(3,4-difluorophenyl)carbamoyl]-7-methyl-1,1-dioxo-3,4-dihydro-2H-pyrrolo[3,4-b]-[1,4,5]oxathiazepin-3-yl] methyl methanesulfonate (10 mg, 0.021 mmol) was dissolved in dimethylamine (3 mL, 2M in THF) and stirred for 4 hours at room temperature. The volatiles were removed under reduced pressure and the residue was purified on silica using a heptane to EtOAc gradient yielding compound 110 (2 mg). $^1$H NMR (400 MHz, DMSO-$d_6$) δ ppm 2.32 (s, 6H), 2.42 (dd, J=12.2, 5.8 Hz, 1H), 2.66 (dd, J=12.2, 9.6 Hz, 1H), 3.62-3.79 (m, 1H), 3.86-3.97 (m, 4H), 4.14 (dd, J=13.0, 5.7 Hz, 1H), 4.85 (dd, J=13.0, 2.4 Hz, 1H), 7.05 (s, 1H), 7.07-7.15 (m, 2H), 7.61-7.67 (m, 1H), 8.72 (s, 1H); Method B; Rt: 0.86 min. m/z: 413 (M−H)$^-$ Exact mass: 414.1.

Compound 111: (3R)—N-(2-bromo-4-pyridyl)-3-[(1S)-1-hydroxyethyl]-7-methyl-1,1-dioxo-2,3,4,5-tetrahydropyrrolo[3,4-f]thiazepine-6-carboxamide

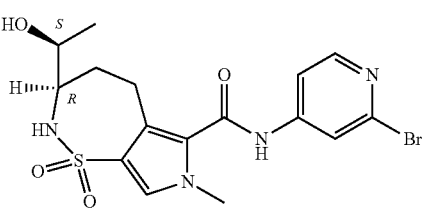

Compound 111 (20.5 mg) was prepared similarly as described for compound 90, using 4-amino-2-bromopyridine instead of 5-amino-2-fluoro-benzonitrile. $^1$H NMR (400 MHz, DMSO-$d_6$) δ ppm 1.13 (d, J=6.2 Hz, 3H), 1.22-1.34 (m, 1H), 2.18 (br dd, J=14.2, 6.7 Hz, 1H), 2.72-2.81 (m, 1H), 3.03 (br dd, J=14.7, 6.4 Hz, 1H), 3.16-3.28 (m, 1H), 3.47 (sxt, J=6.2 Hz, 1H), 3.70 (s, 3H), 4.68 (d, J=5.9 Hz, 1H), 6.92 (d, J=10.3 Hz, 1H), 7.47 (s, 1H), 7.62 (dd, J=5.6, 1.9 Hz, 1H), 7.96 (d, J=1.8 Hz, 1H), 8.27 (d, J=5.5 Hz, 1H), 10.78 (s, 1H); Method B; Rt: 0.67 min. m/z: 441 (M−H)⁻ Exact mass: 442.0.

Compound 112: (3R)—N-(4-fluoro-3-methyl-phenyl)-3-[(1S)-1-hydroxyethyl]-7-methyl-1,1-dioxo-2,3,4,5-tetrahydropyrrolo[3,4-f]thiazepine-6-carboxamide

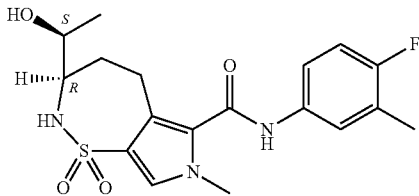

Compound 112 (56 mg) was prepared similarly as described for compound 90, using 4-fluoro-3-methylaniline instead of 5-amino-2-fluoro-benzonitrile. ¹H NMR (400 MHz, DMSO-d₆) δ ppm 1.13 (d, J=6.2 Hz, 3H), 1.29 (q, J=11.9 Hz, 1H), 2.13-2.24 (m, 4H), 2.70-2.79 (m, 1H), 3.02 (br dd, J=14.9, 6.5 Hz, 1H), 3.16-3.25 (m, 1H), 3.47 (sxt, J=6.2 Hz, 1H), 3.67 (s, 3H), 4.66 (d, J=5.7 Hz, 1H), 6.87 (d, J=10.1 Hz, 1H), 7.10 (t, J=9.2 Hz, 1H), 7.39 (s, 1H), 7.47-7.52 (m, 1H), 7.62 (dd, J=7.0, 2.2 Hz, 1H), 10.23 (s, 1H); Method B; Rt: 0.79 min. m/z: 394 (M−H)⁻ Exact mass: 395.1. MP: 287.3° C.

Compound 113: (3S)—N-(3,4-difluorophenyl)-3-(1-hydroxy-1-methyl-ethyl)-7-methyl-1,1-dioxo-2,3,4,5-tetrahydropyrrolo[3,4-f]thiazepine-6-carboxamide

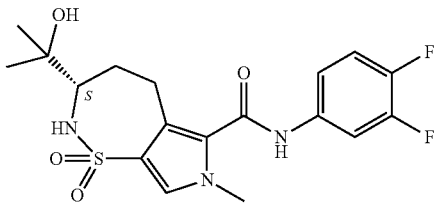

To a solution of methyl 3-acetyl-7-methyl-1,1-dioxo-2,3,4,5-tetrahydropyrrolo[3,4-f]-thiazepine-6-carboxylate (1000 mg, 3.33 mmol) in THF (15 mL) under nitrogen atmosphere at −78° C. was added methylmagnesium bromide (2.55 mL, 3 M in diethyl ether, 7.66 mmol). The reaction mixture was stirred 90 minutes at −78° C. methylmagnesium bromide (2.55 mL, 3 M in diethyl ether, 7.66 mmol) was added to the reaction mixture and the reaction was quenched with NH₄Cl (sat., aq., 4 mL) and allowed to reach room temperature. The reaction mixture was filtered and the solids were washed with THF (3×100 mL). The filtrate was washed with brine and dried (Na₂SO₄), and concentrated to afford a white foam. The residue was purified using silica gel column chromatography (EtOAc in heptane from 0 to 100%) to afford methyl 3-(1-hydroxy-1-methyl-ethyl)-7-methyl-1,1-dioxo-2,3,4,5-tetrahydropyrrolo[3,4-f]thiazepine-6-carboxylate (910 mg) as a white powder.

Methyl 3-(1-hydroxy-1-methyl-ethyl)-7-methyl-1,1-dioxo-2,3,4,5-tetrahydropyrrolo[3,4-f]thiazepine-6-carboxylate (220 mg, 0.63 mmol) and 3,4-difluoro-aniline (106 mg, 0.82 mmol) were dissolved in THF (5 mL). Lithium bis(trimethylsilyl)amide (4.11 mL, 1 M in THF, 4.11 mmol) was added and the reaction mixture was stirred 4 hours at room temperature. The reaction was quenched with NH₄Cl (sat., aq., 5 mL) and the organic layer was separated. The aqueous layer was extracted with 2-MeTHF (2×4 mL) and the combined organic layers were evaporated to dryness. The residue was purified using preparative HPLC (Stationary phase: RP XBridge Prep C18 OBD-10 μm, 50×150 mm, Mobile phase: 0.25% NH₄HCO₃ solution in water, ACN). The obtained product (222 mg) was separated into its enantiomers via preparative SFC (Stationary phase: Chiralpak Diacel AD 20×250 mm, Mobile phase: CO₂, EtOH+0.4 iPrNH₂) yielding compound 113 (105 mg), ¹H NMR (400 MHz, DMSO-d₆) δ ppm 1.03 (s, 3H), 1.17 (s, 3H), 1.24-1.39 (m, 1H), 2.16 (br dd, J=13.9, 6.8 Hz, 1H), 2.66-2.78 (m, 1H), 3.03 (br dd, J=14.6, 6.1 Hz, 1H), 3.22-3.35 (m, 1H), 3.69 (s, 3H), 4.39 (s, 1H), 6.83 (br d, J=10.1 Hz, 1H), 7.38-7.46 (m, 3H), 7.81-7.88 (m, 1H), 10.47 (br s, 1H); Method D; Rt: 1.60 min. m/z: 412 (M−H)⁻ Exact mass: 413.1; MP: 217.7° C. and compound 102 (105 mg). Method F; Rt: 113: 1.15 min, 102: 1.85 min.

Compound 114: N-(3,4-difluorophenyl)-3-(1-hydroxy-2-methyl-propyl)-7-methyl-1,1-dioxo-3,4-dihydro-2H-pyrrolo[3,4-b][1,4,5]oxathiazepine-6-carboxamide

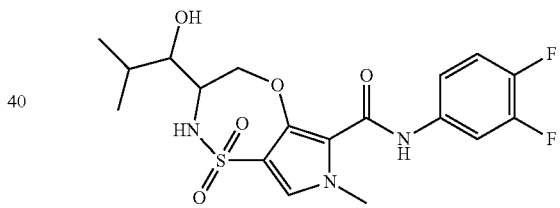

To a cooled solution (−78° C.) of ethyl 2-(dibenzylamino)acetate (2.0 g, 7.1 mmol) in dry THF was added dropwise lithium bis(trimethylsilyl)amide (24.7 mL, 1 M in THF, 24.7 mmol) while keeping the temperature below −50° C. The solution was stirred for 30 min at −78° C. The isobutyraldehyde (2.32 mL, 0.79 g/mL, 24.7 mmol) was added slowly keeping the temperature below −50° C. and the reaction mixture was stirred for 3 hours. The reaction mixture was warmed to 0° C. and then it was quenched with NH₄Cl (sat., aq.). Then EtOAc was added to extract the product. The combined organic layers were dried over Na₂SO₄, filtered and evaporated. The residue was purified and separated into its 2 diastereoisomers by silica gel column chromatography (0% to 50% EtOAc in heptane) yielding diastereoisomer 1 (492 mg); ¹H NMR (400 MHz, CHLOROFORM-d) δ ppm 0.60 (d, J=6.8 Hz, 3H), 0.87-1.02 (m, 3H), 1.39 (t, J=7.2 Hz, 3H), 1.50-1.62 (m, 1H), 3.27 (d, J=9.9 Hz, 1H), 3.41 (d, J=13.2 Hz, 2H), 3.84 (dd, J=9.9, 3.1 Hz, 1H), 4.04 (d, J=13.2 Hz, 2H), 4.21-4.40 (m, 2H), 7.18-7.39 (m, 10H); Method D; Rt: 2.54 min. m/z: 356 (M+H)⁺ Exact mass: 355.2 and diastereoisomer 2 (1.45 g); ¹H NMR (400 MHz, CHLOROFORM-d) δ ppm 0.35 (d, J=6.8 Hz, 3H), 0.92 (d, J=7.0 Hz, 3H), 1.43 (t, J=7.2 Hz, 3H), 2.08-2.20 (m, 2H), 3.32 (d, J=9.2 Hz, 1H), 3.44 (d, J=13.4 Hz, 2H), 3.83-3.87 (m, 1H), 3.90 (d, J=13.6 Hz, 2H), 4.23-4.45 (m, 2H), 7.20-7.28 (m, 2H), 7.29-7.38 (m, 8H); Method D; Rt: 2.47 min. m/z: 356 (M+H)$^+$ Exact mass: 355.2

To a solution of diastereoisomer 2 (1.35 g, 3.81 mmol) in dry THF (30 mL) was added LAH (2.29 mL, 1 M in THF, 4.57 mmol) at −70° C. The reaction mixture was warmed slowly to room temperature and stirred overnight. LAH (0.20 mL, 1 M in THF, 0.20 mmol) was added and the reaction mixture was stirred 4.5 hours. The reaction mixture was quenched carefully with EtOAc (30 mL) and it was stirred for 5 minutes. Then $Na_2SO_4.10H_2O$ was added and this was again stirred for 15 min. Then anhydrous $Na_2SO_4$ was added. The solids were filtered off and the filtrate was evaporated to dryness. The residue was purified on silica (0% to 50% EtOAc in DCM) yielding 2-(dibenzylamino)-4-methyl-pentane-1,3-diol (1.19 g) as a clear oil. $^1$H NMR (400 MHz, CHLOROFORM-d) δ ppm 0.65 (d, J=6.8 Hz, 3H), 0.89 (d, J=6.8 Hz, 3H), 1.44-1.73 (m, 2H), 1.99 (dtd, J=13.6, 6.8, 6.8, 4.8 Hz, 1H), 2.79 (q, J=5.9 Hz, 1H), 3.61-3.86 (m, 6H), 3.96 (dd, J=11.1, 6.3 Hz, 1H), 7.14-7.45 (m, 10H); Method D; Rt: 2.19 min. m/z: 314 (M+H)$^+$ Exact mass: 313.2.

Pd(OH)$_2$/C (50% w/w with respect to A) was added to a solution of 2-(dibenzylamino)-4-methyl-pentane-1,3-diol in degassed MeOH and the resulting suspension was stirred 1 hour at room temperature under a hydrogen atmosphere. The reaction mixture was filtered through a pad of dicalite and concentrated in vacuo to yield 2-amino-4-methyl-pentane-1,3-diol (485 mg)$^1$H NMR (400 MHz, CHLOROFORM-d) δ ppm 0.93 (d, J=6.6 Hz, 3H), 1.00 (d, J=6.6 Hz, 3H), 1.79 (dq, J=13.5, 6.8 Hz, 1H), 2.44 (br s, 4H), 3.00 (q, J=4.7 Hz, 1H), 3.28 (dd, J=7.2, 5.0 Hz, 1H), 3.65-3.81 (m, 2H).

2-amino-4-methyl-pentane-1,3-diol (485 mg, 3.64 mmol) was suspended in DCM (20 mL) and DIPEA (1.26 mL, 0.75 g/mL, 7.28 mmol) was added. The reaction mixture was stirred for 5 minutes. Ethyl 4-chlorosulfonyl-3-fluoro-1-methyl-pyrrole-2-carboxylate (982 mg, 3.64 mmol) was added. The suspension was stirred at room temperature for 5 hours. The reaction mixture was diluted with some DCM and then quenched with NaHCO$_3$ (aq. sat.). The water layer was extracted two times more with DCM. The combined organic layers were evaporated to dryness and the residue was purified by silica gel chromatography (0% to 100% EtOAc in DCM) yielding ethyl 3-fluoro-4-[[2-hydroxy-1-(hydroxymethyl)-3-methyl-butyl]sulfamoyl]-1-methyl-pyrrole-2-carboxylate (870 mg) as a white sticky solid. $^1$H NMR (400 MHz, DMSO-d$_6$) δ ppm 0.68 (d, J=6.6 Hz, 3H), 0.83 (d, J=6.8 Hz, 3H), 1.28 (t, J=7.0 Hz, 3H), 1.74-1.84 (m, 1H), 3.05-3.17 (m, 1H), 3.17-3.25 (m, 1H), 3.41-3.51 (m, 2H), 3.81 (s, 3H), 4.27 (q, J=7.0 Hz, 2H), 4.33 (t, J=5.5 Hz, 1H), 4.53 (d, J=5.7 Hz, 1H), 7.28 (br d, J=8.1 Hz, 1H), 7.52 (d, J=4.8 Hz, 1H); Method D; Rt: 1.45 min. m/z: 367 (M+H)$^+$ Exact mass: 366.1.

To a solution of ethyl 3-fluoro-4-[[2-hydroxy-1-(hydroxymethyl)-3-methyl-butyl]-sulfamoyl]-1-methyl-pyrrole-2-carboxylate (410 mg, 1.06 mmol) and 3,4-difluoro-aniline (0.13 mL, 1.29 g/mL, 1.28 mmol) in dry THF (10 mL) was added drop wise lithium bis(trimethylsilyl)amide (5.3 mL, 1 M in THF, 5.3 mmol) at room temperature under a nitrogen atmosphere. The reaction mixture was stirred at room temperature for 30 min. The reaction mixture was quenched with NH$_4$Cl (aq. sat.) and then diluted with EtOAc. The aqueous layer was extracted twice with EtOAc. The combined organic layers were dried over Na$_2$SO$_4$, filtered and concentrated under reduced pressure. The residue was triturated with diethylether to form N-(3,4-difluorophenyl)-3-fluoro-4-[[2-hydroxy-1-(hydroxymethyl)-3-methyl-butyl]sulfamoyl]-1-methyl-pyrrole-2-carboxamide (253 mg) as a white solid.

N-(3,4-difluorophenyl)-3-fluoro-4-[[2-hydroxy-1-(hydroxymethyl)-3-methyl-butyl]-sulfamoyl]-1-methyl-pyrrole-2-carboxamide (253 mg, 0.55 mmol) and cesium fluoride (335 mg, 2.21 mmol) were dissolved in dry DMF and heated overnight at 110° C. The reaction mixture was added slowly into an ice/water mixture. When the suspension had reached room temperature, the formed yellow solid was filtered off. The water layer was extracted with ether. The solid and the ether-crude were redissolved in MeOH and evaporated together with dicalite to be purified by silica gel chromatography (0% to 75% EtOAc in DCM) yielding compound 114. This racemic mixture was separated in enantiomers 114a (69 mg); $^1$H NMR (400 MHz, DMSO-d$_6$) δ ppm 0.83 (d, J=6.8 Hz, 3H), 0.92 (d, J=6.8 Hz, 3H), 2.01 (quind, J=6.8, 6.8, 6.8, 6.8, 3.0 Hz, 1H), 3.21-3.29 (m, 1H), 3.47-3.62 (m, 1H), 3.82 (s, 3H), 3.97 (dd, J=12.7, 8.9 Hz, 1H), 4.89 (dd, J=12.7, 1.9 Hz, 1H), 4.95 (d, J=6.4 Hz, 1H), 7.31-7.68 (m, 4H), 7.87 (ddd, J=13.1, 7.4, 2.5 Hz, 1H), 9.43 (s, 1H); Method D; Rt: 1.83 min. m/z: 430 (M+H)$^+$ Exact mass: 429.1; MP: 245.7° C. and 114b (62 mg)$^1$H NMR (400 MHz, DMSO-d$_6$) δ ppm 0.83 (d, J=6.8 Hz, 3H), 0.92 (d, J=7.0 Hz, 3H), 2.01 (quind, J=6.8, 6.8, 6.8, 6.8, 3.1 Hz, 1H), 3.23-3.30 (m, 1H), 3.49-3.62 (m, 1H), 3.82 (s, 3H), 3.97 (dd, J=12.7, 8.9 Hz, 1H), 4.89 (dd, J=12.5, 1.8 Hz, 1H), 4.95 (d, J=6.6 Hz, 1H), 7.33-7.51 (m, 3H), 7.52-7.65 (m, 1H), 7.87 (ddd, J=13.2, 7.5, 2.4 Hz, 1H), 9.43 (s, 1H); Method D; Rt: 1.84 min. m/z: 430 (M+H)$^+$ Exact mass: 429.1; MP: 247.3° C., by preparative SFC (Stationary phase: Chiralpak Diacel AD 20×250 mm, Mobile phase: CO$_2$, EtOH with 0.4% iPrNH$_2$). Method K; Rt: 114a: 1.18 min, 114b: 1.79 min.

Compound 115: (3R)-3-[cyclopropyl(hydroxy)methyl]-N-[3-(difluoromethyl)-4-fluoro-phenyl]-7-methyl-1,1-dioxo-3,4-dihydro-2H-pyrrolo[3,4-b][1,4,5]oxathiazepine-6-carboxamide

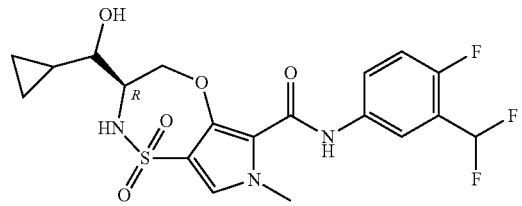

Compound 115 (541 mg) was prepared similarly as described for compound 105, using 3-(difluoromethyl)-4-fluoro-aniline instead of 3,4-difluoroaniline. This racemic mixture was separated in its epimers via preparative SFC (Stationary phase: Chiralpak Diacel AD 20×250 mm, Mobile phase: CO$_2$, EtOH+0.4 iPrNH$_2$) yielding 115a (130 mg) $^1$H NMR (400 MHz, DMSO-d$_6$) δ ppm 0.20-0.55 (m, 4H), 0.98-1.12 (m, 1H), 3.02-3.16 (m, 1H), 3.55-3.70 (m, 1H), 3.83 (s, 3H), 4.02 (dd, J=12.9, 9.1 Hz, 1H), 4.90 (dd, J=12.8, 1.8 Hz, 1H), 5.01 (br d, J=4.6 Hz, 1H), 7.02-7.40 (m, 2H), 7.47 (s, 1H), 7.60 (br s, 1H), 7.76-7.89 (m, 1H), 8.05 (dd, J=6.3, 2.5 Hz, 1H), 9.47 (s, 1H); Method D; Rt: 1.76 min. m/z: 458 (M−H)$^-$ Exact mass: 459.1 and 115b (44 mg) $^1$H NMR (400 MHz, DMSO-d$_6$) δ ppm 0.16-0.27 (m, 1H), 0.27-0.36 (m, 1H), 0.37-0.50 (m, 2H), 0.95-1.09 (m, 1H), 3.05-3.19 (m, 1H), 3.71-3.81 (m, 1H), 3.83 (s, 3H), 4.06 (dd, J=12.8, 9.2 Hz, 1H), 4.74 (dd, J=12.8, 1.3 Hz, 1H), 5.00 (br d, J=4.2 Hz, 1H), 7.02-7.57 (m, 4H), 7.75-7.86 (m, 1H), 8.03 (dd, J=6.4, 2.6 Hz, 1H), 9.48 (s, 1H); Method D; Rt: 1.76 min. m/z: 458 (M−H)⁻ Exact mass: 459.1; MP: 240.7° C. Method N; Rt: 115a: 1.75 min, 115b: 2.01 min.

Compound 116: N-(3-cyano-4-fluoro-phenyl)-3-(1-hydroxy-1-methyl-ethyl)-7-methyl-1,1-dioxo-2,3,4,5-tetrahydropyrrolo[3,4-f]thiazepine-6-carboxamide

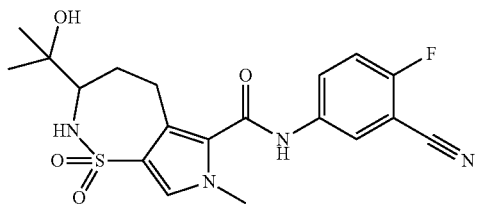 [SMILES: Cn1cc2c(c1C(=O)Nc1ccc(F)c(C#N)c1)CCC(C(C)(C)O)NS2(=O)=O]

Compound 116 (200 mg) was prepared similarly as described for compound 113, using 5-amino-2-fluoro-benzonitrile instead of 3,4-difluoroaniline. This racemic mixture was separated in its enantiomers via preparative SFC (Stationary phase: Chiralpak Diacel AD 20×250 mm, Mobile phase: CO₂, EtOH+0.4 iPrNH₂) yielding 116a (54 mg); ¹H NMR (400 MHz, DMSO-d₆) δ ppm 1.03 (s, 3H), 1.17 (s, 3H), 1.28-1.39 (m, 1H), 2.17 (br dd, J=14.0, 6.5 Hz, 1H), 2.66-2.79 (m, 1H), 3.06 (br dd, J=14.9, 6.3 Hz, 1H), 3.22-3.29 (m, 1H), 3.69 (s, 3H), 4.39 (s, 1H), 6.84 (br d, J=10.6 Hz, 1H), 7.45 (s, 1H), 7.54 (t, J=9.1 Hz, 1H), 7.96 (ddd, J=9.2, 4.9, 2.6 Hz, 1H), 8.19 (dd, J=5.9, 2.6 Hz, 1H), 10.59 (s, 1H); Method D; Rt: 1.49 min. m/z: 419 (M−H)⁻ Exact mass: 420.1 and 116b (52 mg); ¹H NMR (400 MHz, DMSO-d₆) δ ppm 1.03 (s, 3H), 1.17 (s, 3H), 1.34 (q, J=11.5 Hz, 1H), 2.17 (br dd, J=13.9, 6.8 Hz, 1H), 2.68-2.78 (m, 1H), 3.06 (br dd, J=14.5, 6.2 Hz, 1H), 3.23-3.29 (m, 1H), 3.69 (s, 3H), 4.39 (s, 1H), 6.84 (br d, J=10.6 Hz, 1H), 7.45 (s, 1H), 7.54 (t, J=9.1 Hz, 1H), 7.96 (ddd, J=9.1, 4.8, 2.8 Hz, 1H), 8.19 (dd, J=5.7, 2.6 Hz, 1H), 10.59 (s, 1H); Method D; Rt: 1.49 min. m/z: 419 (M−H)⁻ Exact mass: 420.1. Method F; Rt: 116a: 1.29 min, 116b: 2.03 min.

Compound 117: N-(3-cyano-4-fluoro-phenyl)-7-methyl-1,1-dioxo-3-(2,2,2-trifluoro-1-hydroxy-1-methyl-ethyl)-2,3,4,5-tetrahydropyrrolo[3,4-f]thiazepine-6-carboxamide

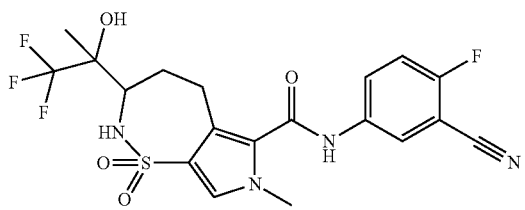 [SMILES: Cn1cc2c(c1C(=O)Nc1ccc(F)c(C#N)c1)CCC(C(C)(O)C(F)(F)F)NS2(=O)=O]

A DMF (5 ml) solution of methyl 3-acetyl-7-methyl-1,1-dioxo-2,3,4,5-tetrahydropyrrolo[3,4-f]thiazepine-6-carboxylate (156 mg, 0.52 mmol), (trifluoromethyl)-trimethylsilane (220 mg, 1.55 mmol) and TBAF (13.5 mg, 0.052 mmol) was stirred at 100° C. for 2 hours. (Trifluoromethyl) trimethylsilane (220 mg, 1.55 mmol) and CsF (79 mg. 0.52 mmol) were added to the reaction mixture. The reaction mixture was heated at 100° C. for 1 hour. Then the mixture was cooled to room temperature and HCl (aq., 1M. 2 ml) was added. After 18 hours, the mixture was quenched with NaHCO₃ (aq. sat., 20 mL), and the product was extracted with EtOAc (4×6 mL). The combined organic layers were dried over Na₂SO₄, evaporation and purification through silica gel column chromatography (EtOAc in heptane from 0 to 100%) yielded methyl 7-methyl-1,1-dioxo-3-(2,2,2-trifluoro-1-hydroxy-1-methyl-ethyl)-2,3,4,5-tetrahydropyrrolo[3,4-f]thiazepine-6-carboxylate (36 mg) as a yellow powder. Method B; Rt: 0.76 min. m/z: 369 (M−H)⁻ Exact mass: 370.1.

Methyl 7-methyl-1,1-dioxo-3-(2,2,2-trifluoro-1-hydroxy-1-methyl-ethyl)-2,3,4,5-tetrahydropyrrolo[3,4-f]thiazepine-6-carboxylate (36 mg, 0.097 mmol) and 5-amino-2-fluoro-benzonitrile (17 mg, 0.13 mmol) were dissolved in THF (5 mL). Lithium bis(trimethylsilyl)amide (0.63 mL, 1 M in THF, 0.63 mmol) was added and the reaction mixture was stirred at room temperature for 1 hour. The reaction was quenched with NH₄Cl (sat., aq., 5 mL) and the organic layer was separated. The aqueous layer was extracted with EtOAc (2×10 mL) and the combined organic layers were evaporated to dryness. The residue was purified using preparative HPLC (Stationary phase: RP XBridge Prep C18 OBD-10 μm, 50×150 mm, Mobile phase: 0.25% NH₄HCO₃ solution in water, ACN). The obtained product was purified using silica gel column chromatography (EtOAc in heptane from 0 to 100%) to afford compound 117 (18 mg) as a white powder. ¹H NMR (600 MHz, DMSO-d₆) δ ppm 1.20 (s, 3H), 1.38-1.46 (m, 1H), 2.13 (br dd, J=13.8, 7.0 Hz, 1H), 2.75-2.80 (m, 1H), 3.07-3.15 (m, 1H), 3.70 (s, 3H), 3.78 (br t, J=10.8 Hz, 1H), 6.16 (s, 1H), 7.23 (d, J=11.2 Hz, 1H), 7.49 (s, 1H), 7.55 (t, J=9.1 Hz, 1H), 7.96 (ddd, J=9.2, 4.8, 2.7 Hz, 1H), 8.19 (dd, J=5.7, 2.6 Hz, 1H), 10.63 (s, 1H); Method B; Rt: 0.86 min. m/z: 473 (M−H)⁻ Exact mass: 474.1.

Compound 118: N-(3-cyano-4-fluoro-phenyl)-3-(1,1-difluoroethyl)-7-methyl-1,1-dioxo-2,3,4,5-tetrahydropyrrolo[3,4-f]thiazepine-6-carboxamide

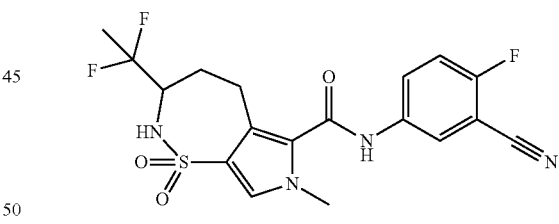

At room temperature to a solution of methyl 3-acetyl-7-methyl-1,1-dioxo-2,3,4,5-tetrahydropyrrolo[3,4-f]thiazepine-6-carboxylate (518 mg, 1.72 mmol) in DCM (7 mL) was added DAST (0.69 mL, 1.32 g/mL, 5.7 mmol). The reaction mixture was stirred for 18 hours. DAST (0.69 mL, 1.32 g/mL, 5.7 mmol) was added and the reaction mixture was stirred for 18 hours, cooled to 0° C. and quenched by addition of NaCl (aq. sat., 2 mL). The aqueous phase was separated and extracted with DCM (3×8 mL). The combined organic layers were dried over Na₂SO₄, filtered and concentrated. The residue was purified by silica gel column chromatography (EtOAc in heptane 0-50%) to give methyl 3-(1,1-difluoroethyl)-7-methyl-1,1-dioxo-2,3,4,5-tetrahydropyrrolo[3,4-f]-thiazepine-6-carboxylate (56 mg). Method B; Rt: 0.84 min. m/z: 321 (M−H)⁻ Exact mass: 322.1.

Methyl 3-(1,1-difluoroethyl)-7-methyl-1,1-dioxo-2,3,4,5-tetrahydropyrrolo[3,4-f]-thiazepine-6-carboxylate (56 mg, 0.15 mmol) and 5-amino-2-fluoro-benzonitrile (26 mg, 0.19 mmol) were dissolved in THF (3 mL). Lithium bis(trimethylsilyl)amide (1 mL, 1 M in THF, 1 mmol) was added and the reaction mixture was stirred at room temperature for 1 hour. The reaction was quenched with NH$_4$Cl (sat., aq., 5 mL) and the organic layer was separated. The aqueous layer was extracted with EtOAc (2×10 mL) and the combined organic layers were evaporated to dryness. The residue was purified using silica gel column chromatography (EtOAc in heptane from 0 to 100%). The obtained product was purified via HPLC (Stationary phase: RP XBridge Prep C18 OBD-10 μm, 50×150 mm, Mobile phase: 0.25% NH$_4$HCO$_3$ solution in water, ACN) to yield compound 118 (21 mg). $^1$H NMR (600 MHz, DMSO-d$_6$) δ ppm 1.48-1.59 (m, 1H), 1.64 (t, J=19.3 Hz, 3H), 2.04-2.11 (m, 1H), 2.77-2.88 (m, 1H), 3.09-3.19 (m, 1H), 3.69-3.86 (m, 4H), 7.50-7.70 (m, 3H), 7.96 (ddd, J=9.2, 4.8, 2.6 Hz, 1H), 8.19 (dd, J=5.8, 2.8 Hz, 1H), 10.64 (br s, 1H); Method B; Rt: 0.93 min. m/z: 425 (M–H)$^-$ Exact mass: 426.1.

Compound 119: N-(3-cyano-4-fluoro-phenyl)-3-(1-hydroxy-2-methyl-propyl)-7-methyl-1,1-dioxo-3,4-dihydro-2H-pyrrolo[3,4-b][1,4,5]oxathiazepine-6-carboxamide

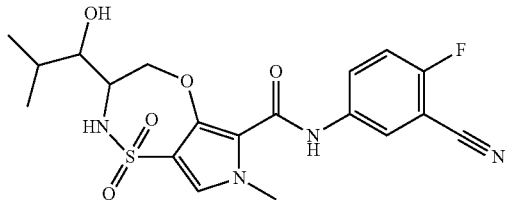

Compound 119 (165 mg) was prepared similarly as described for compound 114, using 5-amino-2-fluoro-benzonitrile instead of 3,4-difluoroaniline. This racemic mixture was separated in its epimers via preparative SFC (Stationary phase: Chiralpak Diacel AD 20×250 mm, Mobile phase: CO$_2$, EtOH+0.4 iPrNH$_2$) yielding 119a (49 mg); $^1$H NMR (400 MHz, DMSO-d$_6$) δ ppm 0.83 (d, J=6.8 Hz, 3H), 0.92 (d, J=6.8 Hz, 3H), 1.95-2.08 (m, 1H), 3.23-3.30 (m, 1H), 3.48-3.62 (m, 1H), 3.83 (s, 3H), 3.97 (dd, J=12.8, 9.0 Hz, 1H), 4.87-4.99 (m, 2H), 7.46-7.55 (m, 2H), 7.60 (d, J=9.9 Hz, 1H), 8.05 (ddd, J=9.1, 4.8, 2.8 Hz, 1H), 8.21 (dd, J=5.7, 2.6 Hz, 1H), 9.52 (s, 1H); Method D; Rt: 1.75 min. m/z: 435 (M–H)$^-$ Exact mass: 436.1; MP: 213.7° C. and 119b (44 mg); $^1$H NMR (400 MHz, DMSO-d$_6$) δ ppm 0.84 (d, J=6.8 Hz, 3H), 0.92 (d, J=7.0 Hz, 3H), 2.02 (quind, J=6.8, 6.8, 6.8, 6.8, 3.0 Hz, 1H), 3.24-3.30 (m, 1H), 3.56 (qd, J=9.4, 1.7 Hz, 1H), 3.83 (s, 3H), 3.97 (dd, J=12.8, 9.0 Hz, 1H), 4.86-5.01 (m, 2H), 7.45-7.55 (m, 2H), 7.60 (d, J=9.9 Hz, 1H), 8.05 (ddd, J=9.2, 4.9, 2.6 Hz, 1H), 8.21 (dd, J=5.8, 2.8 Hz, 1H), 9.52 (s, 1H); Method D; Rt: 1.75 min. m/z: 435 (M–H)$^-$ Exact mass: 436.1; MP: 213.7° C. Method N; Rt: 119a: 1.50 min, 119b: 2.78 min.

Compound 120: (3R)—N-(3-cyano-4-fluoro-phenyl)-3-[cyclopropyl(hydroxy)methyl]-7-methyl-1,1-dioxo-3,4-dihydro-2H-pyrrolo[3,4-b][1,4,5]oxathiazepine-6-carboxamide

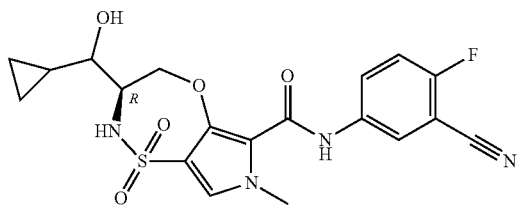

Compound 120 (225 mg) was prepared similarly as described for compound 105, using 5-amino-2-fluoro-benzonitrile instead of 3,4-difluoroaniline. This racemic mixture was separated in its epimers via preparative SFC (Stationary phase: Chiralpak Diacel AD 20×250 mm, Mobile phase: CO$_2$, EtOH+0.4 iPrNH$_2$) yielding 120a (84 mg) $^1$H NMR (400 MHz, DMSO-d$_6$) δ ppm 0.23-0.52 (m, 4H), 0.98-1.11 (m, 1H), 3.03-3.14 (m, 1H), 3.57-3.69 (m, 1H), 3.83 (s, 3H), 4.01 (dd, J=12.8, 9.2 Hz, 1H), 4.94 (dd, J=12.8, 1.8 Hz, 1H), 5.01 (d, J=5.5 Hz, 1H), 7.45-7.55 (m, 2H), 7.62 (d, J=9.9 Hz, 1H), 8.06 (ddd, J=9.2, 4.8, 2.9 Hz, 1H), 8.21 (dd, J=5.8, 2.8 Hz, 1H), 9.52 (s, 1H); Method D; Rt: 1.69 min. m/z: 433 (M–H)$^-$ Exact mass: 434.1 and 120b (36 mg) $^1$H NMR (400 MHz, DMSO-d$_6$) δ ppm 0.15-0.28 (m, 1H), 0.28-0.36 (m, 1H), 0.36-0.49 (m, 2H), 0.95-1.08 (m, 1H), 3.09-3.16 (m, 1H), 3.73-3.81 (m, 1H), 3.83 (s, 3H), 4.05 (dd, J=12.8, 9.2 Hz, 1H), 4.77 (dd, J=12.5, 1.3 Hz, 1H), 5.02 (d, J=5.1 Hz, 1H), 7.41-7.58 (m, 3H), 8.04 (ddd, J=9.2, 4.8, 2.9 Hz, 1H), 8.19 (dd, J=5.7, 2.6 Hz, 1H), 9.54 (s, 1H); Method D; Rt: 1.69 min. m/z: 433 (M–H)$^-$ Exact mass: 434.1; MP: 233.9° C. Method O; Rt: 120a: 1.81 min, 120b: 2.77 min.

Compound 121: (3S)—N-(3,4-difluorophenyl)-3-(1-fluoro-1-methyl-ethyl)-7-methyl-1,1-dioxo-3,4-dihydro-2H-pyrrolo[3,4-b][1,4,5]oxathiazepine-6-carboxamide

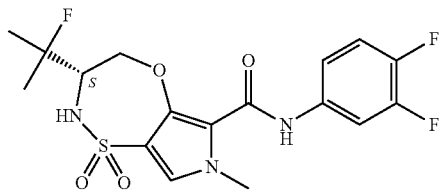

Diethylaminosulfur trifluoride (90 μL, 1 M, 0.09 mmol) was added dropwise to a solution of compound 94 (25 mg, 0.06 mmol) in DCM (0.46 mL, 1.33 g/mL, 7.2 mmol) at 0° C. under a nitrogen atmosphere. The reaction mixture was stirred at 0° C. for 15 minutes. The reaction mixture was allowed to reach room temperature and concentrated under reduced pressure. The residue was purified via preparative HPLC (Stationary phase: RP Vydac Denali C18-10 μm, 200 g, 5 cm, Mobile phase: 0.25% NH$_4$HCO$_3$ solution in water, MeOH). The obtained product was purified by preparative SFC (Stationary phase: Chiralpak Diacel AD 20 microhm 2000 gr, Mobile phase: CO$_2$, EtOH+0.4 iPrNH$_2$) yielding compound 121 (46.9 mg). $^1$H NMR (400 MHz, DMSO-d$_6$)

δ ppm 1.41 (dd, J=39.2, 22.2 Hz, 6H), 3.72-3.81 (m, 1H), 3.83 (s, 3H), 4.01 (dd, J=12.4, 9.1 Hz, 1H), 4.88 (d, J=11.4 Hz, 1H), 7.34-7.54 (m, 3H), 7.82-7.93 (m, 2H), 9.43 (s, 1H); $^{19}$F NMR (377 MHz, DMSO-d$_6$) δ ppm 144.56 (d, J=23.1 Hz, 1F), −141.28 (s, 1F), −137.61 (d, J=23.1 Hz, 1F); Method D; Rt: 1.96 min. m/z: 416 (M−H)$^−$ Exact mass: 417.1; MP: 239.8° C.

Compound 122: (3R)—N-(3-cyano-4-fluoro-phenyl)-3-(1-hydroxypropyl)-7-methyl-1,1-dioxo-3,4-dihydro-2H-pyrrolo[3,4-b][1,4,5]oxathiazepine-6-carboxamide

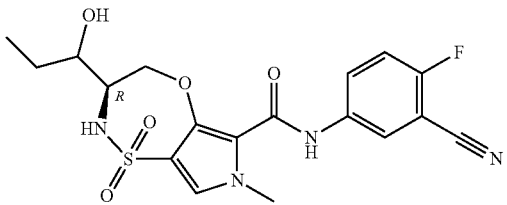

Compound 122 (262 mg) was prepared similarly as described for compound 105, using ethylmagnesium bromide instead of cyclopropylmagnesium bromide and 5-amino-2-fluoro-benzonitrile instead of 3,4-difluoroaniline. The racemic mixture was separated in its epimers via preparative SFC (Stationary phase: Kromasil (R,R) Whelk-O 1 10/100, Mobile phase: CO$_2$, EtOH+0.4% iPrNH$_2$) to yield compound 122a (113 mg); $^1$H NMR (400 MHz, DMSO-d$_6$) δ ppm 0.92 (t, J=7.4 Hz, 3H), 1.44 (dquin, J=14.2, 7.2, 7.2, 7.2, 7.2 Hz, 1H), 1.65-1.79 (m, 1H), 3.35-3.44 (m, 1H), 3.44-3.56 (m, 1H), 3.83 (s, 3H), 3.98 (dd, J=12.7, 8.9 Hz, 1H), 4.93 (dd, J=12.8, 1.8 Hz, 1H), 4.98 (br d, J=5.9 Hz, 1H), 7.44-7.55 (m, 2H), 7.61 (br d, J=9.0 Hz, 1H), 8.05 (ddd, J=9.2, 5.0, 2.8 Hz, 1H), 8.21 (dd, J=5.7, 2.6 Hz, 1H), 9.51 (s, 1H); Method D; Rt: 1.67 min. m/z: 421 (M−H)$^−$ Exact mass: 422.1; MP: 222.3° C., and 122b (102 mg); $^1$H NMR (400 MHz, DMSO-d$_6$) δ ppm 0.88 (t, J=7.4 Hz, 3H), 1.28-1.44 (m, 1H), 1.50-1.63 (m, 1H), 3.54-3.66 (m, 1H), 3.66-3.76 (m, 1H), 3.83 (s, 3H), 3.99 (dd, J=12.7, 9.1 Hz, 1H), 4.74 (dd, J=12.7, 1.0 Hz, 1H), 4.87 (d, J=5.3 Hz, 1H), 7.37 (br s, 1H), 7.49 (s, 1H), 7.52 (t, J=9.1 Hz, 1H), 8.05 (ddd, J=9.3, 4.9, 2.8 Hz, 1H), 8.19 (dd, J=5.7, 2.6 Hz, 1H), 9.54 (s, 1H); Method D; Rt: 1.69 min. m/z: 421 (M−H)$^−$ Exact mass: 422.1; MP: 252.2° C. Method L; Rt: 122a: 2.81 min, 122b: 3.50 min.

Compound 123: (3S)—N-(3,4-difluorophenyl)-7-methyl-1,1-dioxo-3-(2,2,2-trifluoro-1-hydroxy-ethyl)-3,4-dihydro-2H-pyrrolo[3,4-b][1,4,5]oxathiazepine-6-carboxamide

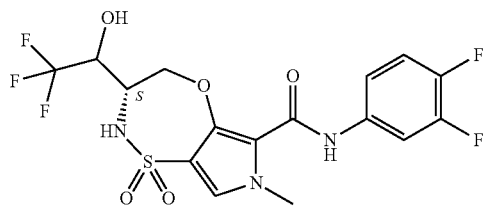

(Trifluoromethyl)trimethylsilane (0.82 mL, 0.96 g/mL, 5.6 mmol) was added to a solution of tert-butyl (4S)-4-formyl-2,2-dimethyl-oxazolidine-3-carboxylate (1.06 g, 4.62 mmol) and TBAF (0.11 mL, 1 M in THF, 0.11 mmol) in THF (28 mL) at room temperature under a nitrogen atmosphere. The reaction mixture was stirred overnight at room temperature. Tetrabutylammonium fluoride (9.25 mL, 1 M, 9.25 mmol) was added to the reaction mixture and stirring was continued overnight. The reaction mixture was quenched with NaHCO$_3$ (aq. sat.), and extracted with EtOAc (3 times). The combined organic layers were dried over Na$_2$SO$_4$, filtered and concentrated under reduced pressure. The residue was purified by silica gel column chromatography (heptane/ethyl acetate 100/0 to 0/100) to afford tert-butyl (4S)-2,2-dimethyl-4-(2,2,2-trifluoro-1-hydroxy-ethyl)oxazolidine-3-carboxylate (1.42 g) as an oil.

HCl (4.6 mL, 4 M in dioxane, 18 mmol) was added dropwise to a solution of tert-butyl (4S)-2,2-dimethyl-4-(2,2,2-trifluoro-1-hydroxy-ethyl)oxazolidine-3-carboxylate (1.38 g, 4.62 mmol) in 1,4-dioxane (40 mL). The reaction mixture was stirred at room temperature for 2 hours. The reaction mixture was concentrated under reduced pressure to yield (2S)-2-amino-4,4,4-trifluoro-butane-1,3-diol (735 mg).

Ethyl 4-chlorosulfonyl-3-fluoro-1-methyl-pyrrole-2-carboxylate (1.06 g, 3.93 mmol) was added portion wise to a solution of (2S)-2-amino-4,4,4-trifluoro-butane-1,3-diol (735 mg, 4.62 mmol) and DIPEA (4.78 mL, 0.75 g/mL, 27.7 mmol) in DCM (30 mL). The reaction mixture was stirred overnight at room temperature. The reaction mixture was quenched with NH$_4$Cl (sat., aq.) and diluted in DCM. The two layers were separated and the aqueous layer was extracted with DCM twice. The combined organic layers were dried over Na2SO4, filtered off and concentrated under reduced pressure and the residue was purified by silica gel column chromatography (heptane/ethyl acetate 100/0 to 0/100) to afford ethyl 3-fluoro-1-methyl-4-[[3,3,3-trifluoro-2-hydroxy-1-(hydroxymethyl)propyl]sulfamoyl]pyrrole-2-carboxylate (610 mg) as a beige solid. $^1$H NMR (400 MHz, DMSO-d$_6$) δ ppm 1.28 (s, 3H), 3.33-3.42 (m, 1H), 3.36 (s, 1H), 3.43-3.58 (m, 2H), 3.81 (s, 3H), 4.04 (dt, J=7.0, 3.7 Hz, 1H), 4.27 (d, J=7.0 Hz, 2H), 4.56 (br t, J=5.2 Hz, 1H), 6.51 (br d, J=6.6 Hz, 1H), 7.52 (d, J=4.6 Hz, 1H), 7.75 (br s, 1H); Method B; Rt: 0.73 min. m/z: 391 (M−H)$^−$ Exact mass: 392.1.

Lithium bis(trimethylsilyl)amide (7.8 mL, 1 M in THF, 7.8 mmol) was added dropwise to a solution of ethyl 3-fluoro-1-methyl-4-[[3,3,3-trifluoro-2-hydroxy-1-(hydroxyl-methyl)propyl]sulfamoyl]pyrrole-2-carboxylate (610 mg, 1.55 mmol) and 3,4-difluoroaniline (0.19 mL, 1.29 g/mL, 1.9 mmol) in THF (20 mL). The reaction mixture was stirred overnight at room temperature. Lithium bis(trimethylsilyl)amide (4.7 mL, 1 M in THF, 4.7 mmol) was added and the reaction mixture was stirred for 30 additional minutes. The reaction mixture was quenched with NH$_4$Cl (sat., aq.), and diluted with EtOAc. The two layers were separated and the aqueous layer was extracted with EtOAc twice. The combined organic layers were dried over Na$_2$SO$_4$, filtered and concentrated under reduced pressure. The residue was precipitated in DCM (small amount) and diethyl ether to afford N-(3,4-difluorophenyl)-3-fluoro-1-methyl-4-[[3,3,3-trifluoro-2-hydroxy-1-(hydroxymethyl)propyl]sulfamoyl]pyrrole-2-carboxamide (300 mg) as a beige solid. A second crop (280 mg) was obtained after purification of the filtrate via silica gel column chromatography (heptane/ethyl acetate 100/0 to 0/100).

Cesium fluoride (741 mg, 4.88 mmol) was added to a solution of N-(3,4-difluorophenyl)-3-fluoro-1-methyl-4-[[3,3,3-trifluoro-2-hydroxy-1-(hydroxyl-methyl)propyl]sulfamoyl]pyrrole-2-carboxamide (580 mg, 1.22 mmol) in DMF (13 mL). The reaction mixture was heated overnight at 105°

C. The reaction mixture was concentrated under reduced pressure and the residue was purified via silica gel column chromatography (heptane/ethyl acetate 100/0 to 0/100). The obtained product was purified via preparative SFC (Stationary phase: Chiralpak Diacel AS 20×250 mm, Mobile phase: $CO_2$, iPrOH+0.4 iPrNH$_2$) yielding 1 epimer of compound 123 (30.7 mg). $^1$H NMR (400 MHz, DMSO-d$_6$) δ ppm 3.82 (s, 3H), 3.83-3.88 (m, 1H), 4.08 (br s, 1H), 4.18 (dd, J=13.0, 9.5 Hz, 1H), 4.86 (dd, J=12.9, 2.5 Hz, 1H), 6.93 (br d, J=6.1 Hz, 1H), 7.35-7.44 (m, 1H), 7.44-7.50 (m, 1H), 7.50 (s, 1H), 7.87 (ddd, J=13.3, 7.5, 2.5 Hz, 1H), 8.00 (br s, 1H), 9.43 (s, 1H); Method D; Rt: 1.82 min. m/z: 454 (M–H)$^-$ Exact mass: 455.1.

Compound 124: (3R)—N-[3-(difluoromethyl)-4-fluoro-phenyl]-3-(1-hydroxypropyl)-7-methyl-1,1-dioxo-3,4-dihydro-2H-pyrrolo[3,4-b][1,4,5]oxathiazepine-6-carboxamide

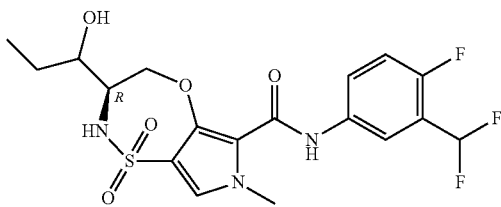

Compound 124 (445 mg) was prepared similarly as described for compound 122, using 3-(difluoromethyl)-4-fluoro-aniline instead of 5-amino-2-fluoro-benzonitrile. The racemic mixture was separated in its epimers via preparative SFC (Stationary phase: Kromasil (R,R) Whelk-O 1 10/100, Mobile phase: $CO_2$, EtOH+0.4% iPrNH$_2$) to yield compound 124a (209 mg); $^1$H NMR (400 MHz, DMSO-d$_6$) δ ppm 0.92 (t, J=7.3 Hz, 3H), 1.44 (dquin, J=14.2, 7.3, 7.3, 7.3, 7.3 Hz, 1H), 1.72 (dqd, J=14.1, 7.2, 7.2, 7.2, 3.1 Hz, 1H), 3.26-3.44 (m, 1H), 3.49 (br t, J=7.9 Hz, 1H), 3.83 (s, 3H), 3.99 (dd, J=12.7, 8.9 Hz, 1H), 4.89 (dd, J=12.7, 1.9 Hz, 1H), 4.98 (d, J=6.2 Hz, 1H), 7.03-7.40 (m, 2H), 7.47 (s, 1H), 7.58 (br s, 1H), 7.76-7.88 (m, 1H), 8.04 (dd, J=6.4, 2.6 Hz, 1H), 9.47 (s, 1H); Method D; Rt: 1.74 min. m/z: 446 (M–H)$^-$ Exact mass: 447.1, and 124b (159 mg); $^1$H NMR (400 MHz, DMSO-d$_6$) δ ppm 0.88 (t, J=7.4 Hz, 3H), 1.29-1.44 (m, 1H), 1.49-1.64 (m, 1H), 3.55-3.65 (m, 1H), 3.66-3.77 (m, 1H), 3.83 (s, 3H), 4.00 (dd, J=12.7, 9.1 Hz, 1H), 4.62-4.76 (m, 1H), 4.86 (br d, J=4.8 Hz, 1H), 7.04-7.41 (m, 3H), 7.46 (s, 1H), 7.77-7.87 (m, 1H), 8.03 (dd, J=6.3, 2.5 Hz, 1H), 9.49 (s, 1H); Method D; Rt: 1.77 min. m/z: 446 (M–H)$^-$ Exact mass: 447.1; MP: 224.5° C. Method M; Rt: 124a: 2.53 min, 124b: 3.56 min.

Compound 125: N-(3,4-difluorophenyl)-3,7-dimethyl-1,1-dioxo-3-phenyl-2,4-dihydropyrrolo[3,4-b][1,4,5]oxathiazepine-6-carboxamide

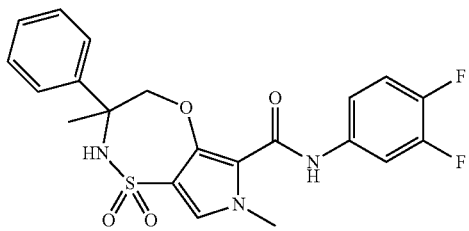 [SMILES: Cn1cc2c(c1C(=O)Nc1ccc(F)c(F)c1)OCC(C)(c1ccccc1)NS2(=O)=O]

Compound 125 (85 mg) was prepared similarly as described for compound 14, using 2-amino-2-phenylpropan-1-ol hydrochloride instead of DL-alaninol and DCM instead of THF as a solvent in the first step. The ring closure was obtained after heating 90 minutes at 110° C. in DMF and compound 125 was purified on silica using a gradient from heptane to EtOAc. $^1$H NMR (400 MHz, DMSO-d$_6$) δ ppm 1.60 (s, 3H), 3.82 (s, 3H), 4.89-5.00 (m, 2H), 7.25-7.49 (m, 6H), 7.58 (d, J=7.6 Hz, 2H), 7.82-7.89 (m, 1H), 8.35 (s, 1H), 9.43 (s, 1H); Method D; Rt: 2.05 min. m/z: 446 (M–H)$^-$ Exact mass: 447.1; MP: 256.6° C.

Compound 126: (3R)—N-(3,4-difluorophenyl)-3,7-dimethyl-1,1-dioxo-3-(2-pyridyl)-2,4-dihydropyrrolo[3,4-b][1,4,5]oxathiazepine-6-carboxamide

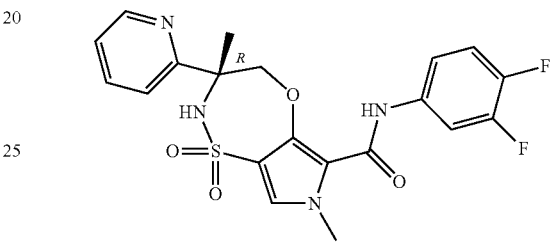

Compound 126 (115 mg) was prepared similarly as described for compound 125, using (2R)-2-amino-2-(2-pyridyl)propan-1-ol instead of 2-amino-2-phenylpropan-1-ol hydrochloride. The ring closure was obtained after heating 3 hours and compound 126 was purified on silica using a gradient from heptane to EtOAc:EtOH 3:1. $^1$H NMR (400 MHz, DMSO-d$_6$) δ ppm 1.59 (s, 3H), 3.82 (s, 3H), 4.99 (d, J=13.3 Hz, 1H), 5.21 (d, J=13.3 Hz, 1H), 7.29-7.51 (m, 4H), 7.78-7.92 (m, 3H), 8.46-8.54 (m, 2H), 9.39 (s, 1H); Method D; Rt: 1.97 min. m/z: 447 (M–H)$^-$ Exact mass: 448.1; MP: 270.5° C.

Compound 127: (3S)—N-(3,4-difluorophenyl)-3,7-dimethyl-1,1-dioxo-3-(2-pyridyl)-2,4-dihydropyrrolo[3,4-b][1,4,5]oxathiazepine-6-carboxamide

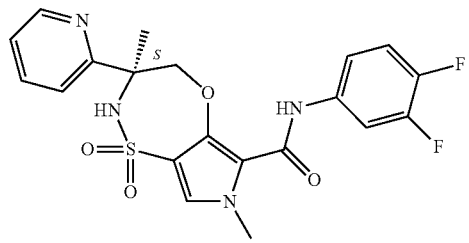

Compound 127 (145 mg) was prepared similarly as described for compound 126, using (2S)-2-amino-2-(2-pyridyl)propan-1-ol instead of (2R)-2-amino-2-(2-pyridyl)propan-1-ol hydrochloride. $^1$H NMR (400 MHz, DMSO-d$_6$) δ ppm 1.55-1.62 (m, 3H), 3.82 (s, 3H), 4.99 (d, J=13.3 Hz, 1H), 5.21 (d, J=13.3 Hz, 1H), 7.29-7.50 (m, 4H), 7.79-7.92 (m, 3H), 8.47-8.53 (m, 2H), 9.39 (s, 1H); Method D; Rt: 1.98 min. m/z: 447 (M–H)$^-$ Exact mass: 448.1; MP: 270.8° C.

Compound 128: (3S)—N-(3-cyano-4-fluoro-phenyl)-3,7-dimethyl-1,1-dioxo-3-(2-pyridyl)-2,4-dihydropyrrolo[3,4-b][1,4,5]oxathiazepine-6-carboxamide

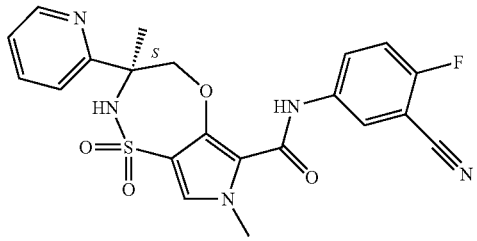

Compound 128 (55 mg) was prepared similarly as described for compound 127, using 5-amino-2-fluoro-benzonitrile instead of 3,4-difluoroaniline. $^1$H NMR (400 MHz, DMSO-d$_6$) δ ppm 1.59 (s, 3H), 3.83 (s, 3H), 4.99 (d, J=13.3 Hz, 1H), 5.25 (d, J=13.3 Hz, 1H), 7.31 (ddd, J=7.4, 4.8, 1.2 Hz, 1H), 7.48-7.55 (m, 2H), 7.78-7.84 (m, 1H), 7.84-7.90 (m, 1H), 8.08 (ddd, J=9.2, 4.9, 2.7 Hz, 1H), 8.21 (dd, J=5.7, 2.7 Hz, 1H), 8.47-8.51 (m, 1H), 8.53 (s, 1H), 9.47 (s, 1H); Method D; Rt: 1.89 min. m/z: 454 (M–H)$^-$ Exact mass: 455.1; MP: 235.0° C.

Compound 129: N-(3,4-difluorophenyl)-3-[methoxymethoxy(2-pyridyl)methyl]-7-methyl-1,1-dioxo-3,4-dihydro-2H-pyrrolo[3,4-b][1,4,5]oxathiazepine-6-carboxamide

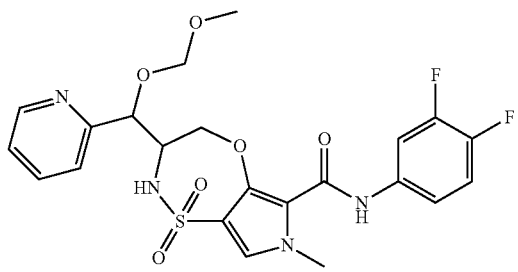

To a cooled solution of ethyl 2-(dibenzylamino)acetate (2.0 g, 7.1 mmol) in dry THF (40 mL) was added dropwise lithium bis(trimethylsilyl)amide (24.7 mL, 1 M in THF, 24.7 mmol) at –70° C. The solution was slowly warmed to –5° C. and it was stirred for 3 hours. Then the reaction mixture was cooled to –70° C. again and 2-pyridinecarboxaldehyde (2.36 mL, 24.7 mmol) was added slowly and it was stirred at –70° C. for 45 minutes. The reaction mixture was warmed slowly to room temperature and quenched with NH$_4$Cl (aq., sat., 50 mL). This was extracted with EtOAc (3×75 mL). The combined organic layers were dried over Na$_2$SO$_4$, filtered and evaporated to dryness. The residue was purified and separated into its 2 diastereoisomers by silica gel column chromatography (0% to 20% EtOAc in heptane) yielding diastereoisomer 1 (827 mg); Method B; Rt: 1.23 min. m/z: 391 (M+H)$^+$ Exact mass: 390.2 and diastereoisomer 2 (813 mg); Method B; Rt: 1.19 min. m/z: 391 (M+H)$^+$ Exact mass: 390.2.

To a solution of diastereoisomer 1 (827 mg, 0.72 mmol) in dry DCM (5 mL) was added DIPEA (1.12 mL, 6.48 mmol) followed by chloromethyl methyl ether (0.49 mL, 6.48 mmol) and the reaction mixture was stirred at room temperature for 3 days. DIPEA (1.12 mL, 6.48 mmol) and chloromethyl methyl ether (0.49 mL, 6.48 mmol) were added and the reaction mixture was stirred again for 3 days. The reaction mixture was quenched with NaHCO$_3$ (aq., sat., 25 mL) and extracted with EtOAc (3×25 mL). The combined organic layers were dried over Na$_2$SO$_4$, filtered and evaporated to dryness. The residue was purified on silica using a heptane to EtOAc gradient yielding ethyl 2-(dibenzylamino)-3-(methoxymethoxy)-3-(2-pyridyl)propanoate (418 mg) as a clear oil. Method B; Rt: 1.35 min. m/z: 435 (M+H)$^+$ Exact mass: 434.2.

To a solution of ethyl 2-(dibenzylamino)-3-(methoxymethoxy)-3-(2-pyridyl)propanoate (418 mg, 0.96 mmol) in dry THF was added LAH (0.72 mL, 2M in THF, 1.44 mmol) at –70° C. After addition the reaction mixture was slowly warmed to room temperature and stirred 4.5 hours. The reaction mixture was quenched carefully with EtOAc and the mixture was stirred for 5 min. Then Na$_2$SO$_4$.10H$_2$O was added and this was again stirred for 15 min. Then anhydrous Na$_2$SO$_4$ was added. The solids were filtered off and the filtrate was evaporated to dryness. The residue was purified on silica using a DCM to EtOAc gradient yielding 2-(dibenzylamino)-3-(methoxymethoxy)-3-(2-pyridyl)-propan-1-ol (316 mg) as a clear yellow oil.

Pd(OH)$_2$/C (150 mg) was added to a solution of 2-(dibenzylamino)-3-(methoxymethoxy)-3-(2-pyridyl)propan-1-ol (316 mg, 0.81 mmol) in degassed MeOH and the resulting suspension was stirred under H$_2$ at room temperature overnight. The reaction mixture was filtered through a pad of dicalite and concentrated in vacuo yielding 2-amino-3-(methoxymethoxy)-3-(2-pyridyl)propan-1-ol (119 mg).

2-amino-3-(methoxymethoxy)-3-(2-pyridyl)propan-1-ol (119 mg, 0.56 mmol) was dissolved in DCM (4 mL) and Hunig's base (0.193 mL, 1.12 mmol) was added followed by ethyl 4-chlorosulfonyl-3-fluoro-1-methyl-pyrrole-2-carboxylate (151 mg, 0.56 mmol). After 4 hours, the reaction mixture was diluted with DCM (5 mL) and then quenched with NaHCO$_3$ (aq., sat., 5 mL). The water layer was extracted with DCM (2×5 mL). The combined organic layers were evaporated to get a yellow foam. The crude was recrystallized/triturated in DCM and it was stirred for 3 days. The formed white solid was filtered off and washed with some DIPE to obtain ethyl 3-fluoro-4-[[1-(hydroxymethyl)-2-(methoxymethoxy)-2-(2-pyridyl)ethyl]sulfamoyl]-1-methyl-pyrrole-2-carboxylate (140 mg).

To a solution of ethyl 3-fluoro-4-[[1-(hydroxymethyl)-2-(methoxymethoxy)-2-(2-pyridyl)ethyl]sulfamoyl]-1-methyl-pyrrole-2-carboxylate (98 mg, 0.22 mmol) and 3,4-difluoroaniline (0.027 mL, 0.26 mmol) in dry THF (3 mL) was added dropwise lithium bis(trimethylsilyl)amide (0.88 mL, 1 M in THF, 0.88 mmol) in a nitrogen atmosphere and it was stirred at room temperature for 2.5 hours. Then the reaction mixture was quenched with NH$_4$Cl (aq., sat., 3 mL) and extracted with EtOAc (3×3 mL). The combined organic layers were dried over Na$_2$SO$_4$, filtered and evaporated to dryness. The residue was purified on silica using a DCM to EtOAc gradient yielding N-(3,4-difluorophenyl)-3-fluoro-4-[[1-(hydroxymethyl)-2-(methoxymethoxy)-2-(2-pyridyl)ethyl]sulfamoyl]-1-methyl-pyrrole-2-carboxamide (128 mg) as a brown solid.

N-(3,4-difluorophenyl)-3-fluoro-4-[[1-(hydroxymethyl)-2-(methoxymethoxy)-2-(2-pyridyl)ethyl]sulfamoyl]-1-methyl-pyrrole-2-carboxamide (128 mg, 0.24 mmol) and cesium fluoride (216 mg, 1.42 mmol) were dissolved in dry DMF (3 mL) and heated at 110° C. instantly. The mixture was stirred at 110° C. for 7 hours. The reaction mixture was quenched with water (3 mL) and the product was extracted with EtOAc (3×3 mL). The combined org layers were evaporated and the residue was purified on silica using a DCM to EtOAc gradient. The crude was purified via Prep HPLC (Stationary phase: RP XBridge Prep C18 OBD-10 µm, 30×150 mm, Mobile phase: 0.25% NH$_4$HCO$_3$ solution in water, ACN) yielding crude compound 129 and crude compound 141. The obtained crude compound 129 was purified on silica using a DCM to EtOAc gradient to obtain compound 129 (14 mg) as a beige solid. $^1$H NMR (400 MHz, CHLOROFORM-d) δ ppm 3.47 (s, 3H), 3.85-4.03 (m, 4H), 4.37-4.48 (m, 1H), 4.74 (dd, J=12.8, 2.0 Hz, 1H), 4.78-4.96 (m, 2H), 5.10 (d, J=4.0 Hz, 1H), 6.58-6.89 (m, 1H), 6.97-7.16 (m, 3H), 7.19-7.26 (m, 1H), 7.52-7.64 (m, 2H), 7.74 (td, J=7.7, 1.8 Hz, 1H), 8.42-8.53 (m, 1H), 8.64 (s, 1H); Method D; Rt: 1.88 min. m/z: 509 (M+H)$^+$ Exact mass: 508.1.

Compound 130: (3R)—N-(3,4-difluorophenyl)-3-(1-hydroxypropyl)-7-methyl-1,1-dioxo-3,4-dihydro-2H-pyrrolo[3,4-b][1,4,5]oxathiazepine-6-carboxamide

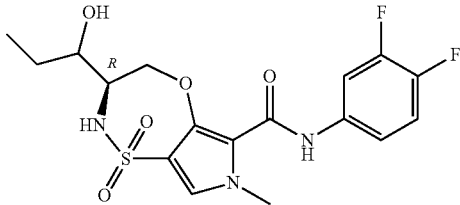

Compound 130 (414 mg) was prepared similarly as described for compound 122, using 3,4-difluoroaniline instead of 5-amino-2-fluoro-benzonitrile. The racemic mixture was separated in its epimers via preparative SFC (Stationary phase: Kromasil (R,R) Whelk-O 1 10/100, Mobile phase: CO$_2$, EtOH-iPrOH (50-50)+0.4% iPrNH$_2$) to yield compound 130a (130 mg); $^1$H NMR (400 MHz, DMSO-d$_6$) δ ppm 0.91 (t, J=7.4 Hz, 3H), 1.43 (dquin, J=14.2, 7.3, 7.3, 7.3, 7.3 Hz, 1H), 1.62-1.82 (m, 1H), 3.34-3.44 (m, 1H), 3.44-3.56 (m, 1H), 3.82 (s, 3H), 3.98 (dd, J=12.8, 9.0 Hz, 1H), 4.90 (dd, J=12.7, 1.9 Hz, 1H), 4.98 (d, J=6.4 Hz, 1H), 7.34-7.44 (m, 1H), 7.44-7.51 (m, 2H), 7.60 (d, J=9.7 Hz, 1H), 7.87 (ddd, J=13.3, 7.5, 2.5 Hz, 1H), 9.42 (s, 1H); Method D; Rt: 1.76 min. m/z: 414 (M−H)$^-$ Exact mass: 415.1; MP: 217.4° C., and 130b (104 mg); $^1$H NMR (400 MHz, DMSO-d$_6$) δ ppm 0.88 (t, J=7.4 Hz, 3H), 1.29-1.44 (m, 1H), 1.49-1.65 (m, 1H), 3.54-3.66 (m, 1H), 3.66-3.77 (m, 1H), 3.83 (s, 3H), 3.99 (dd, J=12.8, 9.0 Hz, 1H), 4.63-4.79 (m, 1H), 4.86 (d, J=5.3 Hz, 1H), 7.25-7.55 (m, 4H), 7.86 (ddd, J=13.1, 7.4, 2.5 Hz, 1H), 9.45 (s, 1H); Method D; Rt: 1.78 min. m/z: 414 (M−H)$^-$ Exact mass: 415.1; MP: 214.6° C. Method S; Rt: 130a: 2.65 min, 130b: 3.46 min.

Compound 131: N-(3,4-difluorophenyl)-7-methyl-1,1-dioxo-spiro[4,5-dihydro-2H-pyrrolo[3,4-f]thiazepine-3,3'-oxetane]-6-carboxamide

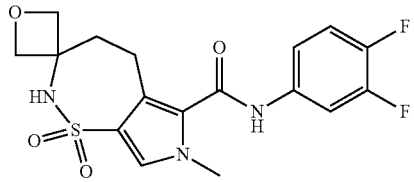 [SMILES: Cn1cc2c(c1C(=O)Nc1ccc(F)c(F)c1)CCC1(COC1)NS2(=O)=O]

Methyl 7-methyl-1,1-dioxo-spiro[2H-pyrrolo[3,4-f]thiazepine-3,3'-oxetane]-6-carboxylate (450 mg, 1.51 mmol) was dissolved in methanol (200 mL). Under a nitrogen atmosphere Et$_3$N (420 µL, 0.73 g/mL, 3 mmol) and Pd/C (10%) (161 mg, 0.15 mmol) were added. The reaction mixture was hydrogenated for 1 hour and then filtered over decalite and the solids were washed with THF (4×80 mL). The filtrate was evaporated to dryness to afford methyl 7-methyl-1,1-dioxo-spiro[4,5-dihydro-2H-pyrrolo[3,4-f]thiazepine-3,3'-oxetane]-6-carboxylate (430 mg) as a white powder.

Methyl 7-methyl-1,1-dioxo-spiro[4,5-dihydro-2H-pyrrolo[3,4-f]thiazepine-3,3'-oxetane]-6-carboxylate (107 mg, 0.36 mmol) and 3,4-difluoroaniline (51 mg, 0.39 mmol) were dissolved in THF (3 mL). Lithium bis(trimethylsilyl)amide (2.1 mL, 1 M in THF, 2.1 mmol) was added and the reaction mixture was stirred at room temperature for 30 minutes. The reaction was quenched with NH$_4$Cl (sat., aq., 5 mL) and the organic layer was separated. The aqueous layer was extracted with EtOAc (2×5 mL) and the combined organic layers were concentrated to dryness. The residue was purified using Prep HPLC (Stationary phase: RP XBridge Prep C18 OBD-10 µm, 50×150 mm, Mobile phase: 0.25% NH$_4$HCO$_3$ solution in water, ACN) yielding compound 131 (80 mg) after recrystallization from DCM as a white powder. $^1$H NMR (400 MHz, DMSO-d$_6$) δ ppm 2.13-2.25 (m, 2H), 2.84-2.99 (m, 2H), 3.69 (s, 3H), 4.29 (d, J=6.4 Hz, 2H), 4.64 (d, J=6.2 Hz, 2H), 7.39-7.46 (m, 3H), 7.78-7.89 (m, 2H), 10.49 (br s, 1H); Method B; Rt: 0.81 min. m/z: 396 (M−H)$^-$ Exact mass: 397.1.

Compound 132: N-(3,4-difluorophenyl)-7-methyl-1,1-dioxo-spiro[2H-pyrrolo[3,4-f]-thiazepine-3,3'-oxetane]-6-carboxamide

Compound 132 (84 mg) was prepared similarly as described for compound 84, using 3-vinyloxetan-3-amine hydrochloride instead of (2S,3R)-3-aminopent-4-en-2-ol hydrochloride. $^1$H NMR (400 MHz, DMSO-d$_6$) δ ppm 3.70 (s, 3H), 4.50 (d, J=6.4 Hz, 2H), 4.78 (d, J=6.2 Hz, 2H), 6.27 (d, J=12.8 Hz, 1H), 6.50 (d, J=12.8 Hz, 1H), 7.40-7.47 (m, 2H), 7.52 (s, 1H), 7.82-7.88 (m, 1H), 8.44 (br s, 1H), 10.76 (br s, 1H); Method B; Rt: 0.82 min. m/z: 394 (M−H)$^-$ Exact mass: 395.1.

Compound 133: N-(3,4-difluorophenyl)-3,3,7-trimethyl-1,1-dioxo-2,4-dihydropyrrolo-[3,4-b][1,4,5]oxathiazepine-6-carboxamide

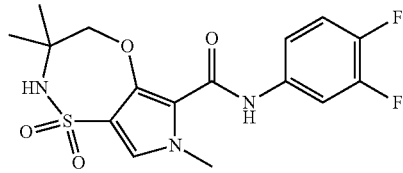 [SMILES: Cn1cc2c(c1C(=O)Nc1ccc(F)c(F)c1)OCC(C)(C)NS2(=O)=O]

Compound 133 (111 mg) was prepared similarly as described for compound 83, using 2-amino-2-methyl-1-propanol instead of 2-amino-1,3-propanediol and ACN instead of THF in the first step. The ring closure was obtained after heating 2 hours at 110° C. in DMF and compound 133 was purified on silica using a gradient from heptane to EtOAc. ¹H NMR (400 MHz, DMSO-d₆) δ ppm 1.29 (s, 6H), 3.81 (s, 3H), 4.40 (s, 2H), 7.37-7.45 (m, 3H), 7.76-7.88 (m, 2H), 9.38 (s, 1H); Method B; Rt: 1.01 min. m/z: 384 (M−H)⁻ Exact mass: 385.1.

Compound 134: N-(3,4-difluorophenyl)-3-ethyl-3,7-dimethyl-1,1-dioxo-2,4-dihydropyrrolo[3,4-b][1,4,5]oxathiazepine-6-carboxamide

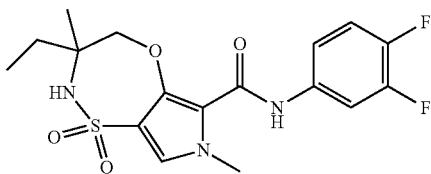 [SMILES: CCC1(C)COc2c(cn(C)c2C(=O)Nc2ccc(F)c(F)c2)S(=O)(=O)N1]

Compound 134 (121 mg) was prepared similarly as described for compound 133, using 2-amino-2-methylbutan-1-ol instead of 2-amino-2-methyl-1-propanol. ¹H NMR (400 MHz, DMSO-d₆) δ ppm 0.92 (t, J=7.4 Hz, 3H), 1.22 (s, 3H), 1.41-1.50 (m, 1H), 1.71-1.80 (m, 1H), 3.81 (s, 3H), 4.31-4.53 (m, 2H), 7.37-7.44 (m, 3H), 7.64 (s, 1H), 7.81-7.88 (m, 1H), 9.35 (s, 1H); Method B; Rt: 1.07 min. m/z: 398 (M−H)⁻ Exact mass: 399.1. This racemic mixture was separated in enantiomers 134a (49 mg) and 134b (52 mg) by preparative SFC (Stationary phase: Chiralpak Diacel AS 20×250 mat, Mobile phase: CO₂, EtOH with 0.4% iPrNH₂). Method T; Rt: 134a: 2.75 min, 134b: 2.92 min.

Compound 135: N-(3-cyano-4-fluoro-phenyl)-3,3,7-trimethyl-1,1-dioxo-2,4-dihydropyrrolo[3,4-b][1,4,5]oxathiazepine-6-carboxamide

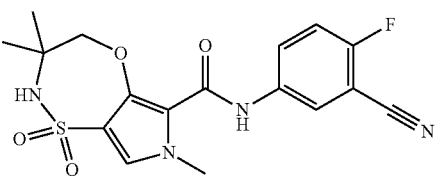 [SMILES: Cn1cc2c(c1C(=O)Nc1ccc(F)c(C#N)c1)OCC(C)(C)NS2(=O)=O]

Compound 135 (39 mg) was prepared similarly as described for compound 133, using 5-amino-2-fluoro-benzonitrile instead of 3,4-difluoroaniline. ¹H NMR (400 MHz, DMSO-d₆) δ ppm 1.30 (s, 6H), 3.82 (s, 3H), 4.41 (s, 2H), 7.45 (s, 1H), 7.53 (t, J=9.1 Hz, 1H), 7.80 (s, 1H), 8.03 (ddd, J=9.2, 4.8, 2.9 Hz, 1H), 8.16 (dd, J=5.7, 2.6 Hz, 1H), 9.46 (s, 1H); Method B; Rt: 0.94 min. m/z: 391 (M−H)⁻ Exact mass: 392.1.

Compound 136: 7-methyl-1,1-dioxo-N-(3,4,5-trifluorophenyl)spiro[4,5-dihydro-2H-pyrrolo[3,4-f]thiazepine-3,3'-oxetane]-6-carboxamide

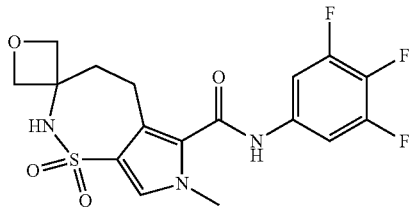 [SMILES: Cn1cc2c(c1C(=O)Nc1cc(F)c(F)c(F)c1)CCC1(COC1)NS2(=O)=O]

Compound 136 (41 mg) was prepared similarly as described for compound 131, using 3,4,5-trifluoroaniline instead of 3,4-difluoroaniline. ¹H NMR (400 MHz, DMSO-d₆) δ ppm 2.10-2.25 (m, 2H), 2.85-2.97 (m, 2H), 3.69 (s, 3H), 4.29 (d, J=6.4 Hz, 2H), 4.64 (d, J=6.2 Hz, 2H), 7.47 (s, 1H), 7.54-7.65 (m, 2H), 7.84 (s, 1H), 10.61 (s, 1H); Method D; Rt: 1.67 min. m/z: 414 (M−H)⁻ Exact mass: 415.1.

Compound 137: N-[3-(difluoromethyl)-4-fluoro-phenyl]-7-methyl-1,1-dioxo-spiro[4,5-dihydro-2H-pyrrolo[3,4-f]thiazepine-3,3'-oxetane]-6-carboxamide

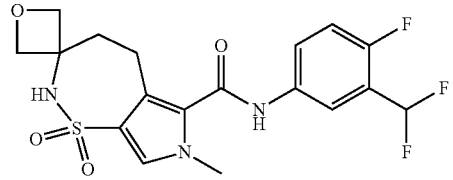 [SMILES: Cn1cc2c(c1C(=O)Nc1ccc(F)c(C(F)F)c1)CCC1(COC1)NS2(=O)=O]

Compound 137 (64 mg) was prepared similarly as described for compound 131, using 3-(difluoromethyl)-4-fluoro-aniline instead of 3,4-difluoroaniline. ¹H NMR (400 MHz, DMSO-d₆) δ ppm 2.10-2.33 (m, 2H), 2.86-3.00 (m, 2H), 3.70 (s, 3H), 4.29 (d, J=6.4 Hz, 2H), 4.65 (d, J=6.2 Hz, 2H), 7.23 (br t, J=54.2 Hz, 1H), 7.37 (t, J=9.5 Hz, 1H), 7.45 (s, 1H), 7.77-7.89 (m, 2H), 8.06 (dd, J=6.2, 2.4 Hz, 1H), 10.51 (s, 1H); Method D; Rt: 1.59 min. m/z: 428 (M−H)⁻ Exact mass: 429.1.

Compound 138: N-(3-cyano-4-fluoro-phenyl)-7-methyl-1,1-dioxo-spiro[4,5-dihydro-2H-pyrrolo[3,4-f]thiazepine-3,3'-oxetane]-6-carboxamide

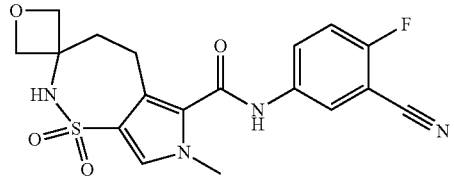 [SMILES: Cn1cc2c(c1C(=O)Nc1ccc(F)c(C#N)c1)CCC1(COC1)NS2(=O)=O]

Compound 138 (23 mg) was prepared similarly as described for compound 131, using 5-amino-2-fluoro-benzonitrile instead of 3,4-difluoroaniline. ¹H NMR (400 MHz, DMSO-d₆) δ ppm 2.14-2.27 (m, 2H), 2.87-2.99 (m, 2H), 3.70 (s, 3H), 4.29 (d, J=6.4 Hz, 2H), 4.64 (d, J=6.2 Hz, 2H), 7.46 (s, 1H), 7.55 (t, J=9.1 Hz, 1H), 7.84 (s, 1H), 7.97 (ddd, J=9.2, 4.8, 2.9 Hz, 1H), 8.19 (dd, J=5.8, 2.8 Hz, 1H), 10.61 (s, 1H); Method D; Rt: 1.48 min. m/z: 403 (M−H)⁻ Exact mass: 404.1.

Compound 139: N-[3-(difluoromethyl)-4-fluoro-phenyl]-7-methyl-1,1-dioxo-spiro[2H-pyrrolo[3,4-f]thiazepine-3,3'-oxetane]-6-carboxamide

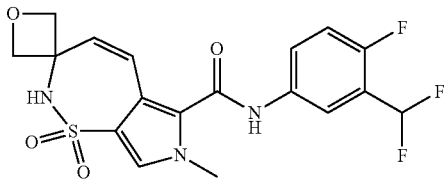 [SMILES: Cn1cc2c(c1C(=O)Nc1ccc(F)c(C(F)F)c1)C=CC1(COC1)NS2(=O)=O]

Compound 139 (108 mg) was prepared similarly as described for compound 132, using 3-(difluoromethyl)-4-fluoro-aniline instead of 3,4-difluoroaniline. ¹H NMR (400 MHz, DMSO-d₆) δ ppm 3.71 (s, 3H), 4.50 (d, J=6.2 Hz, 2H), 4.79 (d, J=6.4 Hz, 2H), 6.27 (d, J=12.8 Hz, 1H), 6.53 (d, J=12.8 Hz, 1H), 7.23 (t, J=54.2 Hz, 1H), 7.39 (t, J=9.6 Hz, 1H), 7.52 (s, 1H), 7.81-7.86 (m, 1H), 8.06 (dd, J=6.2, 2.4 Hz, 1H), 8.45 (br s, 1H), 10.78 (br s, 1H); Method B; Rt: 0.83 min. m/z: 426 (M−H)⁻ Exact mass: 427.1.

Compound 140: N-(3-cyano-4-fluoro-phenyl)-7-methyl-1,1-dioxo-spiro[2H-pyrrolo-[3,4-f]thiazepine-3,3'-oxetane]-6-carboxamide

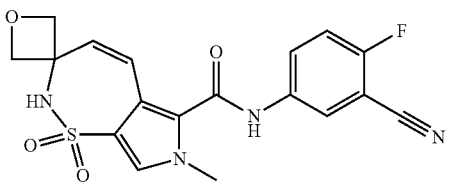 [SMILES: Cn1cc2c(c1C(=O)Nc1ccc(F)c(C#N)c1)C=CC1(COC1)NS2(=O)=O]

Compound 140 (23 mg) was prepared similarly as described for compound 132, using 5-amino-2-fluoro-benzonitrile instead of 3,4-difluoroaniline. ¹H NMR (400 MHz, DMSO-d₆) δ ppm 3.71 (s, 3H), 4.51 (d, J=6.4 Hz, 2H), 4.79 (d, J=6.4 Hz, 2H), 6.28 (d, J=12.8 Hz, 1H), 6.54 (d, J=12.8 Hz, 1H), 7.53-7.58 (m, 2H), 7.98 (ddd, J=9.2, 4.9, 2.6 Hz, 1H), 8.19 (dd, J=5.8, 2.8 Hz, 1H), 8.46 (br s, 1H), 10.88 (br s, 1H); Method D; Rt: 1.48 min. m/z: 401 (M−H)⁻ Exact mass: 402.1.

Compound 141: N-(3,4-difluorophenyl)-3-[hydroxy(2-pyridyl)methyl]-7-methyl-1,1-dioxo-3,4-dihydro-2H-pyrrolo[3,4-b][1,4,5]oxathiazepine-6-carboxamide

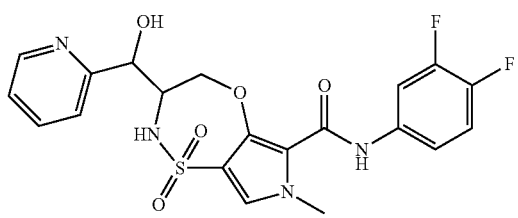

The crude compound 141 obtained in the synthesis of compound 129 was purified on silica eluting with a DCM to EtOAc gradient to obtain compound 141a (3 mg) as a beige solid. ¹H NMR (400 MHz, CHLOROFORM-d) δ ppm 3.87-4.04 (m, 3H), 4.25 (dd, J=12.8, 9.0 Hz, 1H), 4.40-4.53 (m, 1H), 4.82-4.97 (m, 1H), 5.00-5.12 (m, 1H), 6.96-7.21 (m, 3H), 7.27-7.37 (m, 1H), 7.42-7.49 (m, 1H), 7.58-7.73 (m, 1H), 7.76-7.88 (m, 1H), 8.49-8.60 (m, 1H), 8.80 (s, 1H); Method B; Rt: 0.91 min. m/z: 465 (M+H)⁺ Exact mass: 464.1.

Alternatively this compound can be synthesized as described in compound 129 using 6-bromopyridine-2-carbaldehyde instead of 2-pyridinecarboxaldehyde. During the synthesis diastereomers were separated in the final step using preparative HPLC (Stationary phase: RP XBridge Prep C18 OBD-10 μm, 30×150 mm, Mobile phase: 0.25% NH₄HCO₃ solution in water, MeOH) yielding compound 141a (5 mg); ¹H NMR (400 MHz, DMSO-d₆) δ ppm 3.87-4.04 (m, 3H), 4.25 (dd, J=12.8, 9.0 Hz, 1H), 4.40-4.53 (m, 1H), 4.82-4.97 (m, 1H), 5.00-5.12 (m, 1H), 6.96-7.21 (m, 3H), 7.27-7.37 (m, 1H), 7.42-7.49 (m, 1H), 7.58-7.73 (m, 1H), 7.76-7.88 (m, 1H), 8.49-8.60 (m, 1H), 8.80 (s, 1H); Method D; Rt: 1.76 min. m/z: 465 (M+H)⁺ Exact mass: 464.1 and compound 141b (14 mg); ¹H NMR (400 MHz, DMSO-d₆) δ ppm 3.81 (s, 3H), 4.03 (dd, J=12.6, 9.3 Hz, 1H), 4.13-4.21 (m, 1H), 4.82 (dd, J=12.3, 1.1 Hz, 1H), 4.90 (d, J=3.3 Hz, 1H), 5.91 (br s, 1H), 7.26-7.32 (m, 1H), 7.32-7.49 (m, 4H), 7.54 (d, J=7.7 Hz, 1H), 7.77-7.96 (m, 2H), 8.50-8.56 (m, 1H), 9.45 (s, 1H); Method D; Rt: 1.74 min. m/z: 465 (M+H)⁺ Exact mass: 464.1. Method AD; Rt: 141a: 5.75 min and 6.63 min, 141b: 5.13 min and 6.00 min.

Compound 142: N-(3,4-difluorophenyl)-3-(1-hydroxypropyl)-7-methyl-1,1-dioxo-3,4-dihydro-2H-pyrrolo[3,4-b][1,4,5]oxathiazepine-6-carboxamide

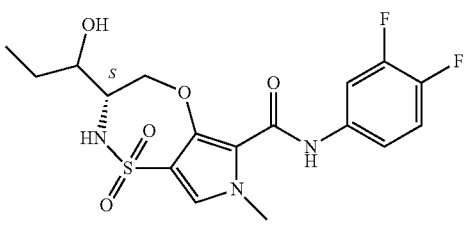

Compound 142 (387 mg) was prepared similarly as described for compound 92, using ethylmagnesium bromide instead of cyclopropylmagnesium bromide. The racemic mixture was separated in its epimers via preparative SFC (Stationary phase: Chiralpak Daicel ID 20×250 mm, Mobile phase: CO₂, EtOH+0.4 iPrNH₂) to yield compound 142a (141 mg); ¹H NMR (400 MHz, DMSO-d₆) δ ppm 0.91 (t, J=7.4 Hz, 3H), 1.44 (dquin, J=14.3, 7.3, 7.3, 7.3, 7.3 Hz, 1H), 1.64-1.79 (m, 1H), 3.34-3.44 (m, 1H), 3.44-3.55 (m, 1H), 3.82 (s, 3H), 3.98 (dd, J=12.8, 8.8 Hz, 1H), 4.90 (dd, J=12.5, 1.8 Hz, 1H), 4.98 (d, J=6.2 Hz, 1H), 7.34-7.44 (m, 1H), 7.44-7.51 (m, 2H), 7.60 (d, J=9.7 Hz, 1H), 7.87 (ddd, J=13.3, 7.5, 2.5 Hz, 1H), 9.42 (s, 1H); Method D; Rt: 1.75 min. m/z: 414 (M−H)⁻ Exact mass: 415.1; MP: 218.6° C., and 142b (136 mg); ¹H NMR (400 MHz, DMSO-d₆) δ ppm 0.88 (t, J=7.4 Hz, 3H), 1.29-1.43 (m, 1H), 1.49-1.63 (m, 1H), 3.55-3.64 (m, 1H), 3.66-3.75 (m, 1H), 3.82 (s, 3H), 3.99 (dd, J=12.7, 9.1 Hz, 1H), 4.68-4.75 (m, 1H), 4.86 (br d, J=4.2 Hz, 1H), 7.26-7.52 (m, 4H), 7.86 (ddd, J=13.2, 7.5, 2.4

Hz, 1H), 9.45 (s, 1H); Method D; Rt: 1.77 min. m/z: 414 (M−H)⁻ Exact mass: 415.1; MP: 212.6° C. Method U; Rt: 142a: 3.06 min, 142b: 3.64 min.

Compound 143: 7-methyl-1,1-dioxo-N-(3,4,5-trifluorophenyl)spiro[2H-pyrrolo[3,4-f]thiazepine-3,3'-oxetane]-6-carboxamide

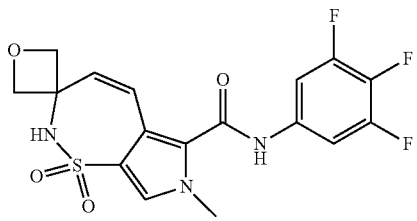 [SMILES: Cn1cc2c(c1C(=O)Nc1cc(F)c(F)c(F)c1)C=CC1(COC1)NS2(=O)=O]

Compound 143 (28 mg) was prepared similarly as described for compound 132, using 3,4,5-trifluoroaniline instead of 3,4-difluoroaniline. ¹H NMR (400 MHz, DMSO-d₆) δ ppm 3.70 (s, 3H), 4.51 (d, J=6.4 Hz, 2H), 4.78 (d, J=6.2 Hz, 2H), 6.28 (d, J=12.8 Hz, 1H), 6.50 (d, J=12.8 Hz, 1H), 7.54 (s, 1H), 7.56-7.66 (m, 2H), 8.45 (br s, 1H), 10.88 (br s, 1H); Method B; Rt: 0.88 min. m/z: 412 (M−H)⁻ Exact mass: 413.1.

Compound 144: N-[3-(difluoromethyl)-4-fluorophenyl]-3-(1-hydroxypropyl)-7-methyl-1,1-dioxo-3,4-dihydro-2H-pyrrolo[3,4-b][1,4,5]oxathiazepine-6-carboxamide

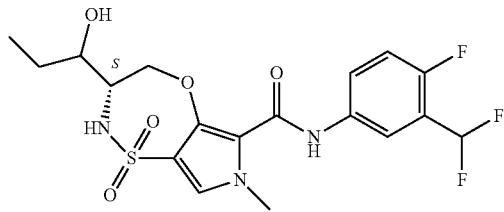

Compound 144 (420 mg) was prepared similarly as described for compound 142, using 3-(difluoromethyl)-4-fluoro-aniline instead of 3,4-difluoroaniline. The racemic mixture was separated in its epimers via preparative SFC (Stationary phase: Chiralpak Daicel ID 20×250 mm, Mobile phase: CO₂, EtOH+0.4 iPrNH₂) to yield compound 144a (176 mg); ¹H NMR (400 MHz, DMSO-d₆) δ ppm 0.92 (t, J=7.3 Hz, 3H), 1.44 (dquin, J=14.2, 7.1, 7.1, 7.1, 7.1 Hz, 1H), 1.64-1.79 (m, 1H), 3.35-3.44 (m, 1H), 3.44-3.56 (m, 1H), 3.83 (s, 3H), 3.99 (dd, J=12.7, 8.9 Hz, 1H), 4.89 (dd, J=12.8, 1.8 Hz, 1H), 4.98 (d, J=6.4 Hz, 1H), 7.03-7.41 (m, 2H), 7.47 (s, 1H), 7.59 (br s, 1H), 7.73-7.89 (m, 1H), 8.04 (dd, J=6.3, 2.5 Hz, 1H), 9.47 (s, 1H); Method D; Rt: 1.75 min. m/z: 446 (M−H)⁻ Exact mass: 447.1, and 144b (156 mg); ¹H NMR (400 MHz, DMSO-d₆) δ ppm 0.88 (t, J=7.4 Hz, 3H), 1.30-1.43 (m, 1H), 1.49-1.63 (m, 1H), 3.56-3.64 (m, 1H), 3.66-3.76 (m, 1H), 3.83 (s, 3H), 4.00 (dd, J=12.7, 9.1 Hz, 1H), 4.64-4.77 (m, 1H), 4.86 (d, J=5.5 Hz, 1H), 7.02-7.42 (m, 3H), 7.46 (s, 1H), 7.76-7.88 (m, 1H), 8.03 (dd, J=6.3, 2.5 Hz, 1H), 9.49 (s, 1H); Method D; Rt: 1.78 min. m/z: 446 (M−H)⁻ Exact mass: 447.1; MP: 224.6° C. Method U; Rt: 144a: 2.92 min, 144b: 3.49 min.

Synthesis of 2-amino-2-pyrazin-2-yl-propan-1-ol

A 100 ml flask was charged with acetylpyrazine (2.00 g, 16.4 mmol), NH₃ (33 mL, 7 M in MeOH, 229 mmol) and ammonium chloride (2.63 g, 49.1 mmol). Trimethylsilyl cyanide (6.2 mL, 0.793 g/mL, 49 mmol) was added and the mixture was stirred at room temperature for 16 hours. The mixture was concentrated in vacuo. The residue was was taken up in DCM and the precipitate was filtered off. The filtrate was concentrated in vacuo and the residue was purified by column chromatography using a gradient from 0 till 100% EtOAc-EtOH (3-1) in heptane. The product fractions were concentrated in vacuo to yield 2-amino-2-pyrazin-2-yl-propanenitrile (1.9 g) as a pale yellow oil.

2-amino-2-pyrazin-2-yl-propanenitrile (1.9 g, 12.8 mmol) was dissolved in acetic acid (6.3 mL). Hydrobromic acid in acetic acid (30 mL) was added carefully and the mixture was stirred at 80° C. for 1 hour. The mixture was cooled and poured out in EtOAc (400 mL). The precipitate was filtered off and washed with EtOAc and ACN and dried under vacuum to yield 2-amino-2-pyrazin-2-yl-propanamide trihydrobromide (5.2 g) as a yellow solid.

2-amino-2-pyrazin-2-yl-propanamide trihydrobromide (5.2 g, 12.7 mmol) was dissolved in MeOH (50 mL). H₂SO₄ (5 mL) was carefully added (exotherm) and the mixture was heated at reflux for 16 hours. The mixture was cooled and concentrated in vacuo. The residue was dissolved in water (50 mL) and washed with EtOAc. The water fraction was neutralized with Na₂CO₃, and extracted with Me-THF (2×50 mL). The combined organic layers were dried (MgSO4), filtered and concentrated in vacuo. The residue was purified by column chromatography using a gradient from 0 till 100% EtOAc-EtOH(3-1) in heptane. The product fractions were concentrated in vacuo to yield methyl 2-amino-2-pyrazin-2-yl-propanoate (371 mg) as a yellow oil.

Methyl 2-amino-2-pyrazin-2-yl-propanoate (371 mg, 2.05 mmol) was dissolved in MeOH (10 mL) under N₂ atmosphere. Sodium borohydride (155 mg, 4.10 mmol) was added and the mixture was stirred at room temperature for 16 hours. The mixture was concentrated in vacuo. The residue was dissolved in Me-THF, dried (MgSO₄), filtered and concentrated in vacuo yielding 2-amino-2-pyrazin-2-yl-propan-1-ol (285 mg).

Compound 145: N-(3,4-difluorophenyl)-3,7-dimethyl-1,1-dioxo-3-pyrazin-2-yl-2,4-dihydropyrrolo[3,4-b][1,4,5]oxathiazepine-6-carboxamide

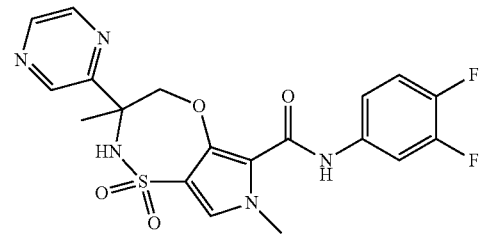 [SMILES: Cn1cc2c(c1C(=O)Nc1ccc(F)c(F)c1)OCC(C)(c1cnccn1)NS2(=O)=O]

Compound 145 (221 mg) was prepared similarly as described for compound 125, using 2-amino-2-pyrazin-2-yl-propan-1-ol instead of 2-amino-2-phenylpropan-1-ol hydrochloride. The ring closure was obtained after heating 3 hours and compound 145 was crystallized from ACN. ¹H NMR (400 MHz, DMSO-d$_6$) δ ppm 1.63 (s, 3H), 3.82 (s, 3H), 4.98-5.14 (m, 2H), 7.38-7.52 (m, 3H), 7.88 (ddd, J=13.2, 7.5, 2.5 Hz, 1H), 8.56-8.60 (m, 2H), 8.68 (s, 1H), 9.03 (d, J=1.1 Hz, 1H), 9.43 (s, 1H); Method B; Rt: 0.96 min. m/z: 448 (M−H)$^-$ Exact mass: 449.1. The racemic mixture was separated in its epimers via preparative SFC (Stationary phase: Chiralpak Daicel AS 20×250 mm, Mobile phase: CO$_2$, EtOH+0.4 iPrNH$_2$) to yield compound 145a (89 mg); Method D; Rt: 1.83 min. m/z: 448 (M−H)$^-$ Exact mass: 449.1, MP: 199.4° C., and 145b (156 mg); Method D; Rt: 1.83 min. m/z: 448 (M−H)$^-$ Exact mass: 449.1; MP: 199.4° C. Method T; Rt: 145a: 3.51 min, 145b: 4.34 min.

Compound 146: (3R)—N-(2-chloro-4-pyridyl)-3-(1-hydroxy-1-methyl-ethyl)-7-methyl-1,1-dioxo-3,4-dihydro-2H-pyrrolo[3,4-b][1,4,5]oxathiazepine-6-carboxamide

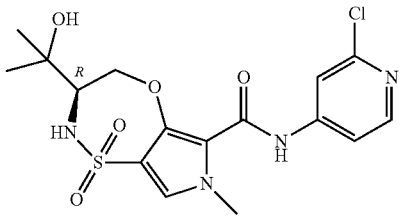

Compound 146 (214 mg) was prepared similarly as described for compound 93, using 4-amino-2-chloropyridine instead of 3,4-difluoroaniline. $^1$H NMR (400 MHz, DMSO-d$_6$) δ ppm 1.07 (s, 3H), 1.25 (s, 3H), 3.50-3.61 (m, 1H), 3.84 (s, 3H), 3.96 (dd, J=12.5, 8.8 Hz, 1H), 4.87 (s, 1H), 4.98 (dd, J=12.4, 1.0 Hz, 1H), 7.47-7.61 (m, 2H), 7.69 (dd, J=5.6, 1.9 Hz, 1H), 7.88 (d, J=1.8 Hz, 1H), 8.27 (d, J=5.7 Hz, 1H), 9.69 (s, 1H); Method D; Rt: 1.53 min. m/z: 413 (M−H)$^-$ Exact mass: 414.1, MP: 246.6° C.

Compound 147: (3R)-3-(1-hydroxy-1-methyl-ethyl)-7-methyl-1,1-dioxo-N-(3,4,5-trifluorophenyl)-3,4-dihydro-2H-pyrrolo[3,4-b][1,4,5]oxathiazepine-6-carboxamide

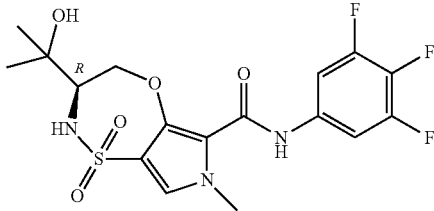

Compound 147 (259 mg) was prepared similarly as described for compound 93, using 3,4,5-trifluoroaniline instead of 3,4-difluoroaniline. $^1$H NMR (400 MHz, DMSO-d$_6$) δ ppm 1.07 (s, 3H), 1.25 (s, 3H), 3.50-3.60 (m, 1H), 3.83 (s, 3H), 3.92 (dd, J=12.4, 8.9 Hz, 1H), 4.86 (s, 1H), 4.95-5.04 (m, 1H), 7.43-7.59 (m, 2H), 7.65-7.79 (m, 2H), 9.49 (s, 1H); Method D; Rt: 1.84 min. m/z: 432 (M−H)$^-$ Exact mass: 433.1.

Compound 148: N-(3,4-difluorophenyl)-4,4-difluoro-7-methyl-1,1-dioxo-3,5-dihydro-2H-pyrrolo[3,4-f]thiazepine-6-carboxamide

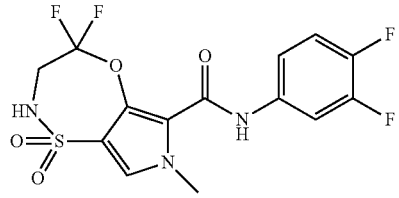 [SMILES: Cn1cc2c(c1C(=O)Nc1ccc(F)c(F)c1)OC(F)(F)CNS2(=O)=O]

2-iodoxybenzoic acid (3.71 g, 13.3 mmol) was added to a solution of ethyl 3-[3-(benzyloxycarbonylamino)-2-hydroxy-propyl]-1-methyl-pyrrole-2-carboxylate (2.12 g, 5.89 mmol) in EtOAc (50 mL) and stirred at reflux temperature for 5 hours and 30 minutes. The reaction mixture was filtered while still hot. The precipitate was washed with EtOAc (150 mL). The organic layer was washed with NaHCO$_3$ (aq., sat., 200 mL), dried over magnesium sulfate, filtered and concentrated. The residue was purified on silica using a gradient from 0 till 100% EtOAc in heptane yielding ethyl 3-[3-(benzyloxycarbonylamino)-2-oxo-propyl]-1-methyl-pyrrole-2-carboxylate (1.49 g) as a clear oil. $^1$H NMR (400 MHz, DMSO-d$_6$) δ ppm 1.24 (t, J=7.0 Hz, 3H), 3.76-3.93 (m, 7H), 4.16 (q, J=7.2 Hz, 2H), 5.03 (s, 2H), 6.00 (d, J=2.4 Hz, 1H), 7.01 (d, J=2.4 Hz, 1H), 7.27-7.50 (m, 6H); Method D; Rt: 1.90 min. m/z: 357 (M−H)$^-$ Exact mass: 358.2.

Diethylaminosulfur trifluoride (3.35 g, 20.8 mmol) was added to a solution of ethyl 3-[3-(benzyloxycarbonylamino)-2-oxo-propyl]-1-methyl-pyrrole-2-carboxylate (1.49 g, 4.16 mmol) in DCM (100 mL) and stirred overnight at room temperature. The reaction mixture was quenched by pouring in NaHCO$_3$ (aq., sat., 300 mL). The organic layer was dried over sodium sulfate, filtered and concentrated. The residue was purified on silica using a gradient from 0 till 100% EtOAc in heptane yielding ethyl 3-[3-(benzyloxycarbonylamino)-2,2-difluoro-propyl]-1-methyl-pyrrole-2-carboxylate (371 mg) as a clear oil. $^1$H NMR (400 MHz, DMSO-d$_6$) δ ppm 1.27 (t, J=7.0 Hz, 3H), 3.32-3.49 (m, 4H), 3.80 (s, 3H), 4.20 (q, J=7.0 Hz, 2H), 5.04 (s, 2H), 6.08 (d, J=2.2 Hz, 1H), 7.01 (d, J=2.6 Hz, 1H), 7.27-7.40 (m, 5H), 7.68 (br t, J=6.2 Hz, 1H); Method D; Rt: 2.07 min. m/z: 379 (M−H)$^-$ Exact mass: 380.2.

Chlorosulfonic acid (7.8 g, 67 mmol) was added to a solution of ethyl 3-[3-(benzyloxycarbonylamino)-2,2-difluoro-propyl]-1-methyl-pyrrole-2-carboxylate (365 mg, 0.96 mmol) in DCM (50 mL) and the reaction mixture was stirred for 20 minutes. The reaction mixture was poured in water (300 mL) and the organic layer was washed with NaHCO$_3$ (aq., sat., 250 mL), dried over magnesium sulfate, filtered and concentrated. The residue was purified on silica using a gradient from 0 till 100% EtOAc in heptane yielding ethyl 4,4-difluoro-7-methyl-1,1-dioxo-3,5-dihydro-2H-pyrrolo[3,4-f]thiazepine-6-carboxylate (17 mg) as white crystals. $^1$H NMR (400 MHz, DMSO-d$_6$) δ ppm 1.31 (t, J=7.2 Hz, 3H), 3.66 (td, J=11.6, 7.2 Hz, 2H), 3.76-3.89 (m, 5H), 4.30 (q, J=7.1 Hz, 2H), 7.65 (s, 1H), 8.18 (t, J=6.8 Hz, 1H); Method D; Rt: 1.65 min. m/z: 307 (M−H)$^-$ Exact mass: 308.1.

Lithium bis(trimethylsilyl)amide (0.33 mL, 1 M in THF, 0.33 mmol) was added to a solution of ethyl 4,4-difluoro-7-methyl-1,1-dioxo-3,5-dihydro-2H-pyrrolo[3,4-f]thiazepine-6-carboxylate (17 mg, 0.055 mmol) and 3,4-difluoroaniline (22 mg, 0.17 mmol) in THF (3 mL) and stirred for 30 minutes. The reaction mixture was quenched with NH₄Cl solution (aq., sat., 10 mL) and extracted with EtOAc (50 mL). The organic layer was dried over magnesium sulfate, filtered and concentrated. The residue was purified on silica using a gradient from 10 till 100% EtOAc in heptane yielding compound 148 (9.8 mg). $^1$H NMR (400 MHz, DMSO-d$_6$) δ ppm 3.39-3.50 (m, 2H), 3.61-3.70 (m, 2H), 3.72 (s, 3H), 7.39-7.49 (m, 2H), 7.55 (s, 1H), 7.81-7.88 (m, 1H), 8.14 (t, J=6.9 Hz, 1H), 10.62 (s, 1H); Method D; Rt: 1.72 min. m/z: 390 (M–H)⁻ Exact mass: 391.1.

Compound 149: 3-(1-hydroxy-1-methyl-ethyl)-7-methyl-1,1-dioxo-N-(3,4,5-trifluorophenyl)-2,3,4,5-tetrahydropyrrolo[3,4-f]thiazepine-6-carboxamide

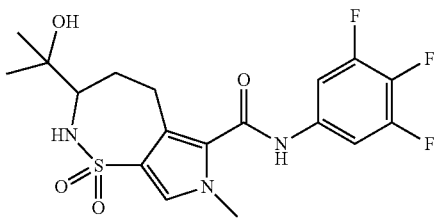 [SMILES: Cn1cc2c(c1C(=O)Nc1cc(F)c(F)c(F)c1)CCC(C(C)(C)O)NS2(=O)=O]

Compound 149 (140 mg) was prepared similarly as described for compound 113, using 3,4,5-trifluoroaniline instead of 3,4-difluoroaniline. The racemic mixture was separated in its enantiomers via preparative SFC (Stationary phase: Chiralpak Daicel AD 20×250 mm, Mobile phase: CO₂, EtOH+0.4 iPrNH₂) to yield compound 149a (66 mg); $^1$H NMR (400 MHz, DMSO-d$_6$) δ ppm 1.03 (s, 3H), 1.17 (s, 3H), 1.33 (br q, J=11.5 Hz, 1H), 2.17 (br dd, J=14.0, 6.9 Hz, 1H), 2.67-2.78 (m, 1H), 2.98-3.08 (m, 1H), 3.21-3.29 (m, 1H), 3.69 (s, 3H), 4.39 (s, 1H), 6.85 (d, J=10.8 Hz, 1H), 7.45 (s, 1H), 7.56-7.64 (m, 2H), 10.59 (s, 1H); Method D; Rt: 1.70 min. m/z: 430 (M–H)⁻ Exact mass: 431.1, and 149b (63 mg); $^1$H NMR (400 MHz, DMSO-d$_6$) δ ppm 1.03 (s, 3H), 1.17 (s, 3H), 1.27-1.38 (m, 1H), 2.17 (br dd, J=14.0, 6.9 Hz, 1H), 2.67-2.78 (m, 1H), 2.98-3.08 (m, 1H), 3.23-3.30 (m, 1H), 3.69 (s, 3H), 4.39 (s, 1H), 6.85 (d, J=10.6 Hz, 1H), 7.45 (s, 1H), 7.56-7.64 (m, 2H), 10.59 (s, 1H); Method D; Rt: 1.70 min. m/z: 430 (M–H)⁻ Exact mass: 431.1. Method R; Rt: 149a: 2.83 min, 149b: 3.64 min.

Compound 150: N-[3-(difluoromethyl)-4-fluorophenyl]-3-(1-hydroxy-1-methyl-ethyl)-7-methyl-1,1-dioxo-2,3,4,5-tetrahydropyrrolo[3,4-f]thiazepine-6-carboxamide

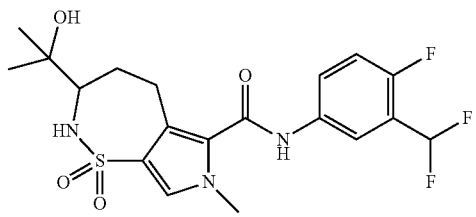 [SMILES: Cn1cc2c(c1C(=O)Nc1ccc(F)c(C(F)F)c1)CCC(C(C)(C)O)NS2(=O)=O]

Compound 150 (45 mg) was prepared similarly as described for compound 113, using 3-(difluoromethyl)-4-fluoro-aniline instead of 3,4-difluoroaniline. The racemic mixture was separated in its enantiomers via preparative SFC (Stationary phase: Chiralpak Daicel AD 20×250 mm, Mobile phase: CO₂, EtOH+0.4 iPrNH₂) to yield compound 150a (23 mg); $^1$H NMR (400 MHz, DMSO-d$_6$) δ ppm 1.03 (s, 3H), 1.17 (s, 3H), 1.34 (q, J=11.6 Hz, 1H), 2.17 (br dd, J=14.1, 6.8 Hz, 1H), 2.66-2.79 (m, 1H), 3.06 (br dd, J=14.4, 6.5 Hz, 1H), 3.21-3.30 (m, 1H), 3.69 (s, 3H), 4.39 (s, 1H), 6.83 (d, J=10.8 Hz, 1H), 7.22 (t, J=54.2 Hz, 1H), 7.37 (t, J=9.6 Hz, 1H), 7.43 (s, 1H), 7.78-7.84 (m, 1H), 8.06 (dd, J=6.3, 2.3 Hz, 1H), 10.49 (s, 1H); Method D; Rt: 1.61 min. m/z: 444 (M–H)⁻ Exact mass: 445.1, and 150b (22 mg); $^1$H NMR (400 MHz, DMSO-d$_6$) δ ppm 1.03 (s, 3H), 1.17 (s, 3H), 1.34 (br q, J=12.0 Hz, 1H), 2.17 (br dd, J=13.9, 6.8 Hz, 1H), 2.68-2.79 (m, 1H), 3.01-3.11 (m, 1H), 3.19-3.30 (m, 1H), 3.69 (s, 3H), 4.39 (s, 1H), 6.83 (br d, J=10.6 Hz, 1H), 7.22 (t, J=54.2 Hz, 1H), 7.37 (t, J=9.6 Hz, 1H), 7.43 (s, 1H), 7.78-7.84 (m, 1H), 8.06 (dd, J=6.2, 2.4 Hz, 1H), 10.49 (s, 1H); Method D; Rt: 1.61 min. m/z: 444 (M–H)⁻ Exact mass: 445.1. Method R; Rt: 150a: 2.92 min, 150b: 3.74 min.

Compound 151: (3R)—N-[2-(difluoromethyl)-4-pyridyl]-3-(1-hydroxy-1-methyl-ethyl)-7-methyl-1,1-dioxo-3,4-dihydro-2H-pyrrolo[3,4-b][1,4,5]oxathiazepine-6-carboxamide

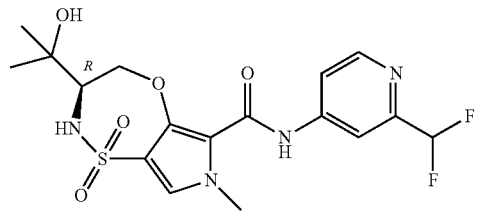

Compound 151 (359 mg) was prepared similarly as described for compound 93, using 2-(difluoromethyl)pyridin-4-amine instead of 3,4-difluoroaniline. $^1$H NMR (400 MHz, DMSO-d$_6$) δ ppm 1.06 (s, 3H), 1.25 (s, 3H), 3.49-3.61 (m, 1H), 3.85 (s, 3H), 3.97 (dd, J=12.5, 8.9 Hz, 1H), 4.88 (s, 1H), 4.97 (dd, J=12.9, 0.5 Hz, 1H), 6.91 (t, J=55.0 Hz, 1H), 7.48-7.61 (m, 2H), 7.77-7.85 (m, 1H), 8.09 (d, J=2.1 Hz, 1H), 8.53 (d, J=5.6 Hz, 1H), 9.75 (s, 1H); Method B; Rt: 0.73 min. m/z: 429 (M–H)⁻ Exact mass: 430.1.

Compound 152: (3S)—N-(3,4-difluorophenyl)-3,7,8-trimethyl-1,1-dioxo-2,3,4,5-tetrahydropyrrolo[3,4-f]thiazepine-6-carboxamide

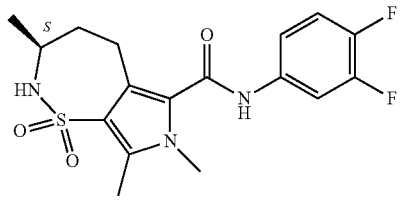

Methyl (3S)-3,7-dimethyl-1,1-dioxo-2,3,4,5-tetrahydropyrrolo[3,4-f]thiazepine-6-carboxylate (200 mg, 0.73 mmol) was dissolved in acetic acid (5 mL) and bromine (0.057 mL, 3.10 g/mL, 1.10 mmol) was added. The solution was then refluxed for 4 hours and stirred at room temperature 16 hours. The solution was then cooled to 0° C., quenched with NaHCO₃ and extracted with EtOAc. The combined organics were dried with Na₂SO₄, filtered and concentrated in vacuo. The crude was then purified on silica using heptane/EtOAc from 100/0 to 50/50 to give methyl (3S)-8-bromo-3,7-dimethyl-1,1-dioxo-2,3,4,5-tetrahydropyrrolo[3,4-f]thiazepine-6-carboxylate (202 mg).

Methyl (3S)-8-bromo-3,7-dimethyl-1,1-dioxo-2,3,4,5-tetrahydropyrrolo[3,4-f]thiazepine-6-carboxylate (202 mg, 0.58 mmol) and 3,4-difluoroaniline (0.069 mL, 1.29 g/mL, 0.69 mmol) are dissolved in THF (5 mL) and LiHMDS (1.7 mL, 1 M, 1.7 mmol) was added. After 2 hours the solution was quenched with NH₄Cl (aq., sat.) and stirred for 5 min. The solution was then diluted with EtOAc, extracted and the combined organics were dried with MgSO₄, filtered off and concentrated in vacuo. The crude was then purified on silica using heptane/EtOAc 100/0 to 0/100 to give (3S)-8-bromo-N-(3,4-difluorophenyl)-3,7-dimethyl-1,1-dioxo-2,3,4,5-tetrahydropyrrolo[3,4-f]thiazepine-6-carboxamide (228 mg). Method B; Rt: 0.97 min. m/z: 446 (M−H)⁻ Exact mass: 447.0.

(3S)-8-bromo-N-(3,4-difluorophenyl)-3,7-dimethyl-1,1-dioxo-2,3,4,5-tetrahydropyrrolo[3,4-f]thiazepine-6-carboxamide (54 mg, 0.12 mmol) was dissolved in DMF (2 mL). Tetramethyltin (0.025 mL, 0.18 mmol) was added and the solution was flushed with nitrogen during 5 minutes before tetrakis(triphenylphosphine)palladium(0) was added. The vial was then heated by microwave irradiation at 140° C. during 30 minutes. The solution was then filtered over dicalite and washed with EtOAc. The filtrate was concentrated in vacuo and purified on silica using heptane/EtOAc 100/0 to 80/20 and further triturated with diethylether to give compound 152 (37 mg) as a white solid. ¹H NMR (400 MHz, DMSO-d₆) δ ppm 1.12 (d, J=6.8 Hz, 3H) 1.15-1.39 (m, 1H) 1.83 (br dd, J=14.0, 7.2 Hz, 1H) 2.39-2.45 (m, 1H) 2.42 (s, 2H) 2.73-2.84 (m, 1H) 2.88-2.98 (m, 1H) 3.53 (s, 3H) 3.56-3.65 (m, 1H) 7.07 (d, J=9.5 Hz, 1H) 7.35-7.46 (m, 2H) 7.79-7.91 (m, 1H) 10.46 (s, 1H); Method B; Rt: 0.93 min. m/z: 382 (M−H)⁻ Exact mass: 383.1.

Compound 153: N-(3,4-difluorophenyl)-3,7-dimethyl-1,1-dioxo-3-pyrimidin-2-yl-2,4-dihydropyrrolo[3,4-b][1,4,5]oxathiazepine-6-carboxamide

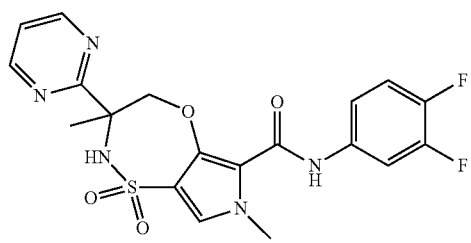 [SMILES: Cn1cc2c(c1C(=O)Nc1ccc(F)c(F)c1)OCC(C)(c1ncccn1)NS2(=O)=O]

Compound 153 (205 mg) was prepared similarly as described for compound 125, using 2-amino-2-pyrimidin-2-yl-propan-1-ol instead of 2-amino-2-phenylpropan-1-ol hydrochloride. 2-amino-2-pyrimidin-2-yl-propan-1-ol was synthesized as described for 2-amino-2-pyrazin-2-yl-propan-1-ol using 2-acetylpyrimidine instead of acetylpyrazine. The ring closure was obtained after heating 3 hours and compound 153 was crystallized from ACN. ¹H NMR (400 MHz, DMSO-d₆) δ ppm 1.63 (s, 3H), 3.80 (s, 3H), 5.07-5.20 (m, 2H), 7.36-7.43 (m, 2H), 7.43-7.48 (m, 2H), 7.80-7.87 (m, 1H), 8.30-8.36 (m, 1H), 8.86 (d, J=4.9 Hz, 2H), 9.38 (s, 1H); Method B; Rt: 1.01 min. m/z: 448 (M−H)⁻ Exact mass: 449.1. The racemic mixture was separated in its enantiomers via preparative SFC (Stationary phase: Chiralpak Daicel AD 20×250 mm, Mobile phase: CO₂, EtOH+0.4 iPrNH₂) to yield compound 153a (75 mg); Method D; Rt: 1.93 min. m/z: 448 (M−H)⁻ Exact mass: 449.1, MP: 228.3° C., and 153b (73 mg); Method D; Rt: 1.94 min. m/z: 448 (M−H)⁻ Exact mass: 449.1; MP: 228.6° C. Method R; Rt: 153a: 4.67 min, 153b: 5.97 min.

Synthesis of (2R)-2-amino-2-methyl-3-phenyl-propan-1-ol

A solution of Z-L-alanine (5 g, 22.4 mmol) and benzaldehyde dimethyl acetal (5.11 g, 33.6 mmol) in diethylether (50 mL) was cooled to −78° C. Boron trifluoride etherate (23.5 mL, 1.15 g/mL, 190 mmol) was added keeping the temperature below −70° C. After addition the reaction mixture was allowed to warm to −15° C. and stirring was continued over weekend at this temperature. The reaction mixture was quenched in cooled NaHCO₃ (sat., aq., 100 mL) and stirred for 30 minutes. The organic layer was removed and evaporated under reduced pressure. The residue was purified on silica using a heptane to heptane:EtOAc 1:1 yielding benzyl (2S,4S)-4-methyl-5-oxo-2-phenyl-oxazolidine-3-carboxylate (6.2 g) as an oil which solidified on standing. ¹H NMR (400 MHz, DMSO-d₆) δ ppm 1.52 (d, J=7.0 Hz, 3H), 4.56 (q, J=6.9 Hz, 1H), 5.10 (br s, 2H), 6.58 (s, 1H), 7.31 (br s, 4H), 7.40-7.50 (m, 6H).

A solution of benzyl (2S,4S)-4-methyl-5-oxo-2-phenyl-oxazolidine-3-carboxylate (1.5 g, 4.82 mmol) and benzyl bromide (572 µL, 1.44 g/mL, 4.82 mmol) was added dropwise to a solution of lithium bis(trimethylsilyl)amide (5.78 mL, 1 M in THF, 5.78 mmol) in THF (5 mL) and stirred for 1 hour. The reaction mixture was quenched with NH₄Cl (sat., aq., 10 mL) and the organic layer was removed. The aqueous layer was extracted with DCM (2×5 mL) and the combined organic layers were evaporated to dryness and the residue was purified on silica using a heptane to EtOAc gradient yielding benzyl (2S,4R)-4-benzyl-4-methyl-5-oxo-2-phenyl-oxazolidine-3-carboxylate (1.01 g). Method D; Rt: 2.38 min. m/z: 402 (M+H)⁺ Exact mass: 401.1.

LiOH (121 mg, 5.03 mmol) dissolved in water (1 mL) was added to a solution of benzyl (2S,4R)-4-benzyl-4-methyl-5-oxo-2-phenyl-oxazolidine-3-carboxylate (1.01 g, 2.52 mmol) in MeOH (10 mL). The reaction mixture was stirred for 2 hours. HCl (aq., 1M, 5 mL) was added and the volatiles were removed under reduced pressure. The residue was purified on silica using a heptane to EtOAc gradient yielding methyl (2R)-2-(benzyloxycarbonylamino)-2-methyl-3-phenyl-propanoate (691 mg). Method B; Rt: 1.13 min. m/z: 328 (M+H)⁺ Exact mass: 327.2.

Methyl (2R)-2-(benzyloxycarbonylamino)-2-methyl-3-phenyl-propanoate (560 mg, 1.71 mmol) was dissolved in THF (10 mL). Lithium aluminum hydride (5.13 mL, 1 M in THF, 5.13 mmol) was added and the reaction mixture was stirred for 2 hours. THF (100 mL) was added and then potassium sodium tartrate tetrahydrate (2.17 g, 7.7 mmol) dissolved in water (3 mL) was added and the reaction mixture was stirred for 15 minutes. Na₂SO₄ was added and the reaction mixture was stirred for 15 minutes. The precipitate was removed by filtration and the filtrate was evaporated to dryness. The residue was purified on silica using a heptane to EtOAc gradient yielding benzyl N-[(1R)-1-benzyl-2-hydroxy-1-methyl-ethyl]carbamate (186 mg).

Benzyl N-[(1R)-1-benzyl-2-hydroxy-1-methyl-ethyl]carbamate (186 mg, 0.62 mmol) and Pd/C (10%) (33 mg, 0.031 mmol) were dispensed in MeOH (40 mL) and set under a hydrogen atmosphere overnight. The reaction mixture was filtered and evaporated to dryness yielding (2R)-2-amino-2-methyl-3-phenyl-propan-1-ol which was used as such.

Compound 154: (3R)-3-benzyl-N-(3,4-difluorophenyl)-3,7-dimethyl-1,1-dioxo-2,4-dihydropyrrolo[3,4-b][1,4,5]oxathiazepine-6-carboxamide

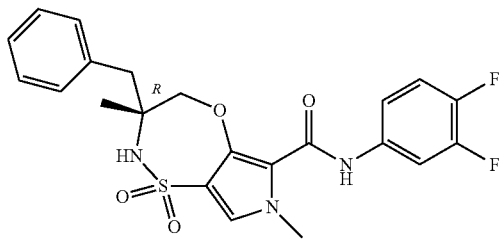

Compound 154 (111 mg) was prepared similarly as described for compound 133, using (2R)-2-amino-2-methyl-3-phenyl-propan-1-ol instead of 2-amino-2-methyl-1-propanol. $^1$H NMR (400 MHz, DMSO-$d_6$) δ ppm 1.15 (s, 3H), 2.80 (d, J=13.0 Hz, 1H), 3.00 (d, J=13.0 Hz, 1H), 3.82 (s, 3H), 4.40 (d, J=13.2 Hz, 1H), 4.57 (d, J=13.0 Hz, 1H), 7.24-7.38 (m, 5H), 7.38-7.46 (m, 2H), 7.47 (s, 1H), 7.57-7.80 (m, 1H), 7.81-7.90 (m, 1H), 9.40 (s, 1H); Method B; Rt: 1.19 min. m/z: 460 (M–H)$^-$ Exact mass: 461.1.

Compound 155: (3S)-3-benzyl-N-(3,4-difluorophenyl)-3,7-dimethyl-1,1-dioxo-2,4-dihydropyrrolo[3,4-b][1,4,5]oxathiazepine-6-carboxamide

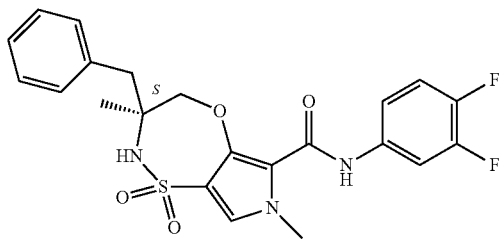

Compound 155 (92 mg) was prepared similarly as described for compound 133, using (2S)-2-amino-2-methyl-3-phenyl-propan-1-ol instead of 2-amino-2-methyl-1-propanol. (2S)-2-amino-2-methyl-3-phenyl-propan-1-ol was synthesized as described for (2S)-2-amino-2-methyl-3-phenyl-propan-1-ol using Z-D-alanine instead of Z-L-alanine. $^1$H NMR (400 MHz, DMSO-$d_6$) δ ppm 1.15 (s, 3H), 2.80 (d, J=13.0 Hz, 1H), 3.00 (d, J=13.2 Hz, 1H), 3.82 (s, 3H), 4.40 (d, J=13.2 Hz, 1H), 4.57 (d, J=13.2 Hz, 1H), 7.25-7.36 (m, 5H), 7.40-7.46 (m, 2H), 7.47 (s, 1H), 7.71-7.89 (m, 2H), 9.40 (s, 1H); Method B; Rt: 1.19 min. m/z: 460 (M–H)$^-$ Exact mass: 461.1.

Compound 156: (3S)-3-benzyl-N-(3-cyano-4-fluorophenyl)-3,7-dimethyl-1,1-dioxo-2,4-dihydropyrrolo[3,4-b][1,4,5]oxathiazepine-6-carboxamide

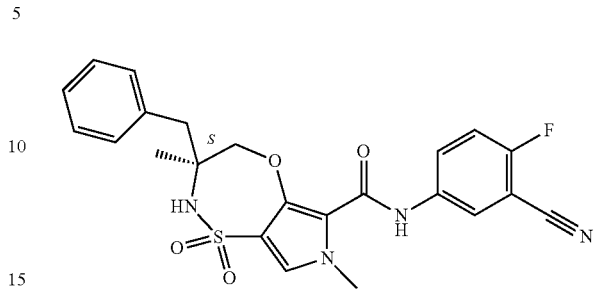

Compound 156 (41 mg) was prepared similarly as described for compound 155, using 5-amino-2-fluoro-benzonitrile instead of 3,4-difluoroaniline. $^1$H NMR (400 MHz, DMSO-$d_6$) δ ppm 1.16 (s, 3H), 2.79 (d, J=13.2 Hz, 1H), 3.01 (d, J=13.2 Hz, 1H), 3.83 (s, 3H), 4.40 (d, J=13.2 Hz, 1H), 4.59 (d, J=13.0 Hz, 1H), 7.24-7.36 (m, 5H), 7.49 (s, 1H), 7.55 (t, J=9.1 Hz, 1H), 7.75 (s, 1H), 8.02 (ddd, J=9.2, 4.8, 2.9 Hz, 1H), 8.18 (dd, J=5.7, 2.6 Hz, 1H), 9.49 (s, 1H); Method B; Rt: 1.13 min. m/z: 467 (M–H)$^-$ Exact mass: 468.1.

Synthesis of
(S)-2-(1-methylallyl)isoindoline-1,3-dione

DIBAL (11 mL, 1 M in heptane, 11 mmol) was added drop wise to an anhydrous solution of methyl (2S)-2-(benzyloxycarbonylamino)propanoate (2.50 g, 10.5 mmol) in THF (50 mL) at –78° C. After addition the solution was carefully quenched with NaF (aq., sat.) at –78° C. The resulting mixture was stirred while allowing warming to room temperature. More water was added and the reaction mixture was extracted with EtOAc (3×25 mL). The combined extracts were evaporated to dryness and the residue was purified on silica using a heptane to EtOAc gradient yielding benzyl N-[(1S)-1-methyl-2-oxo-ethyl]carbamate (1.13 g) as an oil.

Methyltriphenylphosphonium bromide (3.11 g, 8.69 mmol) was suspended in toluene (50 mL) and cooled to 0° C. Lithium bis(trimethylsilyl)amide (8.2 mL, 1 M in toluene, 8.2 mmol) was added. The reaction was stirred at 0° C. for 30 minutes, then cooled to –78° C. and a solution of benzyl N-[(1S)-1-methyl-2-oxo-ethyl]carbamate (1.13 g, 5.43 mmol) in toluene (5 mL) was added. The solution was allowed to warm to room temperature, stirred for 30 min, then quenched with sat NH$_4$Cl (aq., sat.) (20 mL). The layers were separated and the aqueous was washed with EtOAc (10 mL). The combined organic layers were evaporated to dryness and the residue was purified on silica using a heptane to EtOAc gradient yielding benzyl N-[(1 S)-1-methylallyl]carbamate (230 mg) as an oil which solidified on standing.

Benzyl N-[(1S)-1-methylallyl]carbamate (100 mg, 0.49 mmol) was dissolved in HCl (37% in H2O, 3 mL) and heated for 30 minutes at 100° C. The volatiles were removed under reduced pressure and the residue was dissolved in THF (5 mL). Hunig's base (0.84 mL, 0.75 g/mL, 4.9 mmol) and 1,3-isobenzofurandione (79 mg, 0.54 mmol) were added and the reaction mixture was stirred over weekend. Hunig's base (0.84 mL, 0.75 g/mL, 4.9 mmol) was added and the reaction mixture was heated at 50° C. for 2 hours. (S)-2-(1- methylallyl)isoindoline-1,3-dione formed in this reaction mixture was found identical to (*S)-2-(1-methylallyl)isoindoline-1,3-dione described in the synthesis of compound 29. Method Q; Rt: (*R)-2-(1-methylallyl)isoindoline-1,3-dione: 1.65 min, (*S)-2-(1-methylallyl)isoindoline-1,3-dione and (S)-2-(1-methylallyl)isoindoline-1,3-dione: 1.89 min.

Compound 157: (3S)—N-(3-cyano-2,4-difluorophenyl)-3,7-dimethyl-1,1-dioxo-2,3,4,5-tetrahydropyrrolo[3,4-f]thiazepine-6-carboxamide

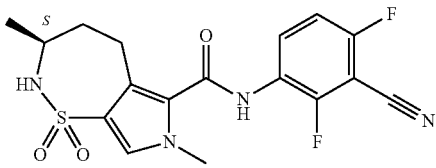

To methyl 3-bromo-1-methyl-pyrrole-2-carboxylate (10.0 g, 45.9 mmol) and 2-[(1S)-1-methylallyl]isoindoline-1,3-dione (10.2 g, 50.5 mmol) in DMF (50 mL) was added TEA (12.7 mL, 0.73 g/mL, 91.7 mmol) and this was stirred and purged with nitrogen for 5 minutes. Then bis(tri-tert-butylphosphine)palladium(0) (1.17 g, 2.29 mmol) was added and the mixture was stirred and heated in an oil bath at 110° C. for 90 minutes. The resulting mixture was filtered over a pad of dicalite, rinsed with EtOAc (300 mL) and concentrated in vacuo. The crude was purified on silica (gradient elution: EtOAc:heptane 0:100 to 100:0). The desired fractions were concentrated under reduced pressure yielding methyl 3-[(E,3S)-3-(1,3-dioxoisoindolin-2-yl)but-1-enyl]-1-methyl-pyrrole-2-carboxylate (15.1 g) as a yellow oil.

A hydrogenation flask was flushed with nitrogen and then charged with Pd/C (10%) (2.37 g, 2.22 mmol). To this was added under nitrogen methyl 3-[(E,3S)-3-(1,3-dioxoisoindolin-2-yl)but-1-enyl]-1-methyl-pyrrole-2-carboxylate (15.4 g, 44.5 mmol) in THF (200 mL). The resulting suspension was then stirred under a hydrogen atmosphere at room temperature for 2 hours. Then the mixture was filtered over a pad of dicalite under a constant nitrogen flow and this pad was rinsed with THF (250 mL). The filtrate was concentrated in vacuo to yield methyl 3-[(3S)-3-(1,3-dioxoisoindolin-2-yl)butyl]-1-methyl-pyrrole-2-carboxylate (15.0 g).

Methyl 3-[(3S)-3-(1,3-dioxoisoindolin-2-yl)butyl]-1-methyl-pyrrole-2-carboxylate (15.0 g, 44.1 mmol) was dissolved in n-butanol (150 mL). Ethylenediamine (118 mL) was added and stirred at room temperature for 5 minutes and then heated at 90° C. for 3 hours. The mixture was cooled and concentrated in vacuo. The residue was purified by column chromatography on silica using a gradient from 0 till 10% MeOH/NH$_3$ in DCM. The product fractions were concentrated in vacuo to yield methyl 3-[(3S)-3-aminobutyl]-1-methyl-pyrrole-2-carboxylate (9.1 g) as an oil. Method B; Rt: 0.52 min. m/z: 211 (M+H)$^+$ Exact mass: 210.1.

Chlorosulfonic acid (55 mL, 1.75 g/mL, 832 mmol) was stirred and cooled in an ice-acetone bath. A gentle nitrogen flow was maintained. To this was added dropwise methyl 3-[(3S)-3-aminobutyl]-1-methyl-pyrrole-2-carboxylate (3.50 g, 16.6 mmol) in DCM (65 mL). After addition the resulting mixture was added dropwise to an ice-cooled and stirring solution of Na$_2$CO$_3$ (176 g) in ice cold water (1 L). After addition the layers were separated and the water layer was extracted with DCM (2×500 mL). The combined extracts were dried on Na$_2$SO$_4$, filtered and concentrated in vacuo. The crude was purified on silica gel using gradient elution (heptane/iPrOH 100:0 to 20:80) yielding methyl (3S)-3,7-dimethyl-1,1-dioxo-2,3,4,5-tetrahydropyrrolo[3,4-f]thiazepine-6-carboxylate (1.95 g) as a clear oil. Method B; Rt: 0.73 min. m/z: 271 (M−H)$^−$ Exact mass: 272.1.

Methyl (3S)-3,7-dimethyl-1,1-dioxo-2,3,4,5-tetrahydropyrrolo[3,4-f]thiazepine-6-carboxylate (200 mg, 0.73 mmol) and 3-amino-2,6-difluoro-benzonitrile (0.16 g, 0.88 mmol) in dry THF (5 mL) was treated with lithium bis(trimethylsilyl)amide (2.2 mL, 1 M in THF, 2.2 mmol) and this was stirred overnight at room temperature. The resulting mixture was quenched with NH$_4$Cl (aq., sat., 5 mL). Then 5 mL of brine was added and the layers were separated. The water layer was extracted using EtOAc (2×30 mL). The combined extracts were concentrated in vacuo and the obtained crude was purified using silica gel column chromatography (gradient elution: EtOAc:heptane 0:100 to 100:0). The desired fractions were concentrated in vacuo and the obtained residue was purified via preparative HPLC (Stationary phase: RP XBridge Prep C18 OBD-10 µm, 30×150 mm, Mobile phase: 0.25% NH$_4$HCO$_3$ solution in water, ACN). The desired fractions were concentrated under reduced pressure, co-evaporated with methanol (2×25 mL) and dried in a vacuum oven at 55° C. for 18 hours yielding compound 157 (7.6 mg). $^1$H NMR (400 MHz, DMSO-d$_6$) δ ppm 1.14 (d, J=6.82 Hz, 3H) 1.31-1.45 (m, 1H) 1.81-1.91 (m, 1H) 2.77-2.89 (m, 1H) 3.07-3.18 (m, 1H) 3.58-3.67 (m, 1H) 3.70 (s, 3H) 7.03 (d, J=9.68 Hz, 1H) 7.40-7.51 (m, 2H) 8.06 (td, J=8.97, 6.05 Hz, 1H) 10.31 (s, 1H); Method B; Rt: 0.85 min. m/z: 393 (M−H)$^−$ Exact mass: 394.1, MP: 247.5° C.

Methyl (3S)-3,7-dimethyl-1,1-dioxo-2,3,4,5-tetrahydropyrrolo[3,4-f]thiazepine-6-carboxylate (140 mg, 0.51 mmol) and 5-amino-2-fluorobenzonitrile (77 mg, 0.57 mmol) in THF (8 mL) was treated with LiHMDS (1 mL, 1 M in THF, 1 mmol) and this was stirred for 2 hours at room temperature. The resulting mixture was quenched with NH$_4$Cl (aq., sat., 5 mL). Then brine (5 mL) was added and the layers were separated. The water layer was extracted with EtOAc (2×10 mL). The combined extracts were concentrated in vacuo and the obtained crude was purified using silica gel column chromatography (EtOAc:heptane 0:100 to 100:0). The desired fractions were concentrated in vacuo and the obtained residue was purified via preparative HPLC (Stationary phase: RP XBridge Prep C18 OBD-10 µm, 30×150 mm, Mobile phase: 0.25% NH$_4$HCO$_3$ solution in water, ACN) yielding (3S)—N-(3-cyano-4-fluoro-phenyl)-3,7-dimethyl-1,1-dioxo-2,3,4,5-tetrahydropyrrolo[3,4-f]thiazepine-6-carboxamide (41 mg) being identical to compound 56. $^1$H NMR (400 MHz, DMSO-d$_6$) δ ppm 1.13 (d, J=6.60 Hz, 3H) 1.28-1.42 (m, 1H) 1.77-1.92 (m, 1H) 2.77-2.90 (m, 1H) 2.92-3.04 (m, 1H) 3.56-3.66 (m, 1H) 3.69 (s, 3H) 7.02 (d, J=9.68 Hz, 1H) 7.43 (s, 1H) 7.54 (t, J=9.13 Hz, 1H) 7.95 (ddd, J=9.19, 4.90, 2.86 Hz, 1H) 8.19 (dd, J=5.72, 2.64 Hz, 1H) 10.59 (s, 1H); Method B; Rt: 0.85 min. m/z: 375 (M−H)$^−$ Exact mass: 376.1.

Compound 158: N-[2-(difluoromethyl)-4-pyridyl]-3,3,7-trimethyl-1,1-dioxo-2,4-dihydropyrrolo[3,4-b][1,4,5]oxathiazepine-6-carboxamide

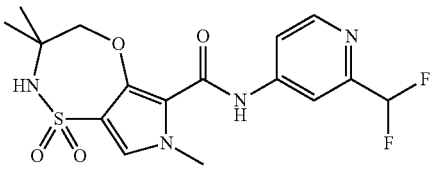 [SMILES: Cn1cc2c(c1C(=O)Nc1ccnc(C(F)F)c1)OCC(C)(C)NS2(=O)=O]

Compound 158 (610 mg) was prepared similarly as described for compound 133, using 2-(difluoromethyl)pyridin-4-amine instead of 3,4-difluoroaniline. $^1$H NMR (400 MHz, DMSO-$d_6$) δ ppm 1.30 (s, 6H), 3.82 (s, 3H), 4.43 (s, 2H), 6.91 (t, J=55.0 Hz, 1H), 7.49 (s, 1H), 7.77-7.81 (m, 1H), 7.82 (s, 1H), 8.03 (d, J=2.0 Hz, 1H), 8.54 (d, J=5.5 Hz, 1H), 9.69 (s, 1H); Method B; Rt: 0.82 min. m/z: 399 (M−H)$^-$ Exact mass: 400.1, MP: 229.9° C.

Compound 159: (3R)—N-(3-cyano-2,4-difluoro-phenyl)-3-[(1S)-1-hydroxyethyl]-7-methyl-1,1-dioxo-2,3,4,5-tetrahydropyrrolo[3,4-f]thiazepine-6-carboxamide

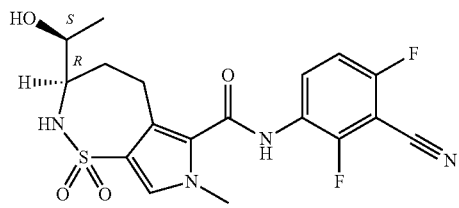

Compound 159 (7 mg) was prepared similarly as described for compound 88, using 3-amino-2,6-difluorobenzonitrile instead of 3,4-difluoroaniline. $^1$H NMR (400 MHz, DMSO-$d_6$) δ ppm 1.13 (d, J=6.2 Hz, 3H), 1.25-1.37 (m, 1H), 2.17-2.24 (m, 1H), 2.71-2.79 (m, 1H), 3.15-3.24 (m, 2H), 3.42-3.53 (m, 1H), 3.70 (s, 3H), 4.68 (d, J=5.7 Hz, 1H), 6.91 (d, J=10.1 Hz, 1H), 7.43-7.49 (m, 2H), 8.06 (td, J=8.9, 6.2 Hz, 1H), 10.31 (s, 1H); Method D; Rt: 1.71 min. m/z: 423 (M−H)$^-$ Exact mass: 424.1.

Compound 160: N-(3,4-difluorophenyl)-3,7-dimethyl-3-oxazol-2-yl-1,1-dioxo-2,4-dihydropyrrolo[3,4-b][1,4,5]oxathiazepine-6-carboxamide

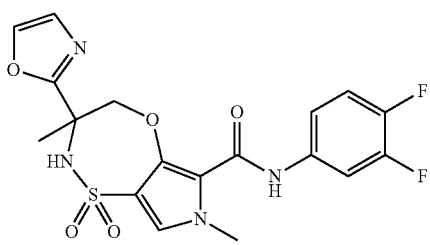 [SMILES: Cn1cc2c(c1C(=O)Nc1ccc(F)c(F)c1)OCC(C)(c1ncco1)NS2(=O)=O]

Compound 160 (240 mg) was prepared similarly as described for compound 153, using 1-(oxazol-2-yl)ethanone instead of 2-acetylpyrimidine. $^1$H NMR (400 MHz, DMSO-$d_6$) δ ppm 1.63 (s, 3H), 3.81 (s, 3H), 4.88 (d, J=13.3 Hz, 1H), 5.11 (d, J=13.3 Hz, 1H), 7.18 (d, J=0.8 Hz, 1H), 7.38-7.50 (m, 3H), 7.87 (ddd, J=13.2, 7.5, 2.4 Hz, 1H), 8.13 (d, J=0.8 Hz, 1H), 8.68 (s, 1H), 9.46 (s, 1H); Method B; Rt: 0.93 min. m/z: 439 (M+H)$^+$ Exact mass: 438.1. The racemic mixture was separated in its enantiomers via preparative SFC (Stationary phase: Chiralpak Daicel OD 20×250 mm, Mobile phase: CO$_2$, EtOH+0.4 iPrNH$_2$) to yield compound 160a (88 mg); MP: 239.5° C., and 160b (80 mg); MP: 240.2° C. Method Y; Rt: 160a: 3.43 min, 160b: 3.73 min.

Synthesis of 2-amino-3-(2,2,2-trifluoroethylamino)butan-1-ol

Tert-butyl 4-acetyl-2,2-dimethyloxazolidine-3-carboxylate (3.0 g, 12 mmol) and 2,2,2-trifluoroethylamine (1.47 mL, 1.24 g/mL, 18.5 mmol) were dissolved in DCM (50 mL) and stirred at room temperature for 30 min. Then NaBH(OAc)$_3$ (3.40 g, 16.0 mmol) was added and the reaction mixture was stirred overnight. The reaction mixture was diluted with DCM (40 mL) and quenched with Na$_2$CO$_3$ (aq., sat., 60 mL). The organic layer was separated, dried over Na$_2$SO$_4$, filtered and evaporated to dryness. The crude oil was purified on silica using a heptane to EtOAc gradient yielding tert-butyl 2,2-dimethyl-4-[1-(2,2,2-trifluoroethylamino)ethyl]oxazolidine-3-carboxylate (4.2 g) as a clear oil. $^1$H NMR (400 MHz, CHLOROFORM-d) δ ppm 1.04 (d, J=6.6 Hz, 3H), 1.35-1.57 (m, 15H), 3.00-4.21 (m, 6H).

tert-butyl 2,2-dimethyl-4-[1-(2,2,2-trifluoroethylamino)ethyl]oxazolidine-3-carboxylate (3.73 g, 11.43 mmol) was dissolved in 1,4-dioxane (50 mL) and HCl (17 mL, 4 M in 1,4-dioxane, 68.6 mmol) was added at room temperature. After stirring for 5 hours, the solvents were removed yielding crude 2-amino-3-(2,2,2-trifluoroethylamino)butan-1-ol hydrochloride which was used as such in the next step.

Compound 161: N-(3-cyano-4-fluoro-phenyl)-7-methyl-1,1-dioxo-3-[1-(2,2,2-trifluoroethylamino)ethyl]-3,4-dihydro-2H-pyrrolo[3,4-b][1,4,5]oxathiazepine-6-carboxamide

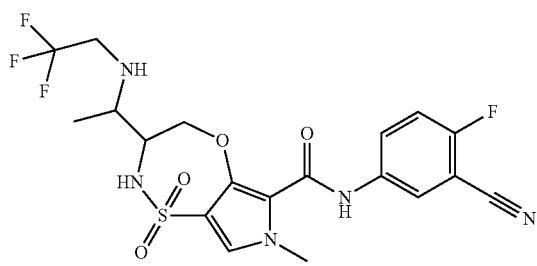

A mixture of 2-amino-3-(2,2,2-trifluoroethylamino)butan-1-ol hydrochloride (2.13 g, 11.4 mmol) and Hunig's base (12.4 mL, 0.75 g/mL, 72.2 mmol) in dry DCM (75 mL) was stirred for 15 min to get a clear yellow solution. Then ethyl 4-chlorosulfonyl-3-fluoro-1-methyl-pyrrole-2-carboxylate (3.08 g, 11.43 mmol) was added and the solution was stirred at room temperature for 4 hours. The reaction mixture was quenched with NaHCO$_3$ (aq., sat., 75 mL). The water layer was extracted with DCM (2×50 mL). The combined organic layers were dried over Na$_2$SO$_4$, filtered and evaporated to get a yellow oil. The crude was purified on silica using a DCM to EtOAc gradient to afford ethyl 3-fluoro-4-[[1-(hydroxymethyl)-2-(2,2,2-trifluoroethyl-amino)propyl]sulfamoyl]-1-methyl-pyrrole-2-carboxylate (4.55 g) as a yellow oil. ¹H NMR (400 MHz, DMSO-d₆) δ ppm 0.84-0.97 (m, 3H), 1.28 (t, J=7.0 Hz, 3H), 1.85-2.10 (m, 1H), 2.76-2.91 (m, 1H), 2.99-3.52 (m, 5H), 3.82 (s, 3H), 4.27 (q, J=7.0 Hz, 2H), 4.54-4.77 (m, 1H), 7.44 (br s, 1H), 7.51-7.60 (m, 1H); Method D; Rt: 1.64 min. m/z: 418 (M–H)⁻ Exact mass: 419.1.

To a solution of ethyl 3-fluoro-4-[[1-(hydroxymethyl)-2-(2,2,2-trifluoroethylamino)propyl]sulfamoyl]-1-methyl-pyrrole-2-carboxylate (1.00 g, 2.38 mmol) and 5-amino-2-fluoro-benzonitrile (389 mg, 2.86 mmol) in dry THF (25 mL) was added lithium bis(trimethylsilyl)amide (1M in THF) [4039-32-1] #JNJ-70824# (12 mL, 1 M in THF, 12 mmol). The reaction mixture was stirred at room temperature for 5 hours. Then NH₄Cl (aq., sat., 30 mL) was added followed by EtOAc (30 mL) and the mixture was stirred for 15 min. The two layers were separated and the aqueous layer was extracted with EtOAc (2×30 mL). The combined organic layers were dried over Na₂SO₄, filtered and concentrated under reduced pressure to get a brown oil. The crude was purified on silica using a DCM to EtOAc gradient yielding N-(3-cyano-4-fluoro-phenyl)-3-fluoro-4-[[1-(hydroxymethyl)-2-(2,2,2-trifluoroethylamino)propyl]sulfamoyl]-1-methyl-pyrrole-2-carboxamide (818 mg).

N-(3-cyano-4-fluoro-phenyl)-3-fluoro-4-[[1-(hydroxymethyl)-2-(2,2,2-trifluoroethylamino)propyl]sulfamoyl]-1-methyl-pyrrole-2-carboxamide (818 mg, 1.61 mmol) and cesium fluoride (976 mg, 6.42 mmol) were dissolved in dry DMF (12 mL) and heated at 110° C. for 18 hours. The reaction mixture was quenched with cold water (15 mL) and extracted with EtOAc (3×15 mL). The combined organic layers were evaporated and the residue was purified on silica using a DCM to EtOAc gradient to get a yellow foam. The 4 isomers were separated via Prep SFC (Stationary phase: Chiralpak Daicel AS 20 microhm 500 gr, Mobile phase: CO₂, EtOH+0.4 iPrNH₂) yielding compound 161a (89 mg); ¹H NMR (400 MHz, DMSO-d₆) δ ppm 1.08 (d, J=6.4 Hz, 3H), 2.30-2.43 (m, 1H), 2.71-2.84 (m, 1H), 3.12-3.41 (m, 2H), 3.53-3.63 (m, 1H), 3.83 (s, 3H), 4.00 (dd, J=12.7, 8.9 Hz, 1H), 4.84 (dd, J=12.8, 1.9 Hz, 1H), 7.44-7.56 (m, 2H), 7.60 (br s, 1H), 8.00 (ddd, J=9.2, 4.9, 2.7 Hz, 1H), 8.18 (dd, J=5.8, 2.7 Hz, 1H), 9.55 (s, 1H); Method D; Rt: 1.92 min. m/z: 488 (M–H)⁻ Exact mass: 489.1, compound 161b (70 mg); ¹H NMR (400 MHz, DMSO-d₆) ppm 1.08 (d, J=6.4 Hz, 3H), 2.31-2.43 (m, 1H), 2.70-2.85 (m, 1H), 3.13-3.41 (m, 2H), 3.53-3.64 (m, 1H), 3.83 (s, 3H), 4.00 (dd, J=12.7, 8.9 Hz, 1H), 4.84 (dd, J=12.7, 2.0 Hz, 1H), 7.47-7.57 (m, 2H), 7.62 (br s, 1H), 8.00 (ddd, J=9.2, 4.9, 2.8 Hz, 1H), 8.18 (dd, J=5.8, 2.7 Hz, 1H), 9.55 (s, 1H); Method D; Rt: 1.92 min. m/z: 488 (M–H)⁻ Exact mass: 489.1, compound 161c (15 mg); ¹H NMR (400 MHz, DMSO-d₆) δ ppm 1.07 (d, J=6.5 Hz, 3H), 2.35 (q, J=7.4 Hz, 1H), 2.88-3.02 (m, 1H), 3.12-3.44 (m, 2H), 3.62-3.72 (m, 1H), 3.83 (s, 3H), 4.01 (dd, J=12.8, 9.0 Hz, 1H), 4.72 (dd, J=12.8, 1.3 Hz, 1H), 7.42-7.56 (m, 2H), 7.59 (br s, 1H), 8.02 (ddd, J=9.2, 4.9, 2.7 Hz, 1H), 8.18 (dd, J=5.8, 2.7 Hz, 1H), 9.56 (s, 1H); Method D; Rt: 1.93 min. m/z: 488 (M–H)⁻ Exact mass: 489.1 and compound 161d (18 mg); ¹H NMR (400 MHz, DMSO-d₆) δ ppm 1.07 (d, J=6.5 Hz, 3H), 2.35 (q, J=7.3 Hz, 1H), 2.89-3.03 (m, 1H), 3.13-3.45 (m, 2H), 3.63-3.73 (m, 1H), 3.83 (s, 3H), 4.01 (dd, J=12.8, 9.0 Hz, 1H), 4.72 (dd, J=13.1, 1.2 Hz, 1H), 7.43-7.56 (m, 2H), 7.60 (br s, 1H), 8.02 (ddd, J=9.2, 4.9, 2.7 Hz, 1H), 8.18 (dd, J=5.8, 2.7 Hz, 1H), 9.56 (s, 1H); Method D; Rt: 1.93 min. m/z: 488 (M–H)⁻ Exact mass: 489.1. Method AA; Rt: 161a: 3.69 min, 161b: 3.61 min, 161c: 3.75 min, 161d: 4.02 min.

Compound 162: N-(3,4-difluorophenyl)-3,7-dimethyl-3-[(5-methylisoxazol-3-yl)methyl]-1,1-dioxo-2,4-dihydropyrrolo[3,4-b][1,4,5]oxathiazepine-6-carboxamide

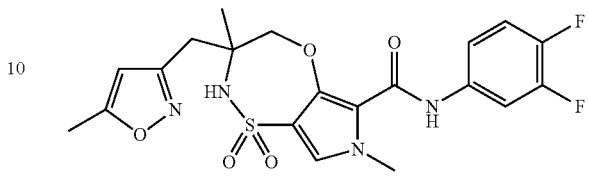

DL-alanine methyl ester hydrochloride (12.8 g, 91.7 mmol) was finely ground and added to DCM (250 mL). Benzophenone imine (14.4 g, 1.62 g/mL, 79.5 mmol) was added and the mixture was stirred overnight at room temperature. The mixture was filtered and the filtrate was washed with water. The organic layer was separated and concentrated in vacuo. The residue was purified on silica using a gradient from 0 till 50% EtOAc in heptane yielding methyl 2-(benzhydrylideneamino)propanoate (15.7 g) as a clear oil.

Potassium tert-butoxide (3.74 g, 33.3 mmol) was added to a cooled (−10° C.) solution of methyl 2-(benzhydrylideneamino)propanoate (7.42 g, 27.8 mmol) and 3-(chloromethyl)-5-methylisoxazole (3.77 g, 27.8 mmol) in NMP (20 mL). The reaction mixture was stirred 1 hour and HCl (67 mL, 1 M in H₂O, 67 mmol) was added and the reaction mixture was stirred overnight. The reaction mixture was then diluted with EtOAc (100 mL) and washed with brine (3×100 mL). The combined organic layers were evaporated to dryness and the residue was purified on silica using a heptane to EtOAc gradient yielding methyl 2-(benzhydrylideneamino)-2-methyl-3-(5-methylisoxazol-3-yl)propanoate (4.44 g) as an oil. ¹H NMR (400 MHz, DMSO-d₆) δ ppm 1.55 (s, 3H), 2.37-2.41 (m, 3H), 3.22 (s, 2H), 3.69-3.79 (m, 3H), 6.15 (s, 1H), 8.78 (br s, 3H).

Methyl 2-(benzhydrylideneamino)-2-methyl-3-(5-methylisoxazol-3-yl)propanoate (4.44 g, 18.9 mmol) was dissolved in MeOH (50 mL) cooled in an ice bath (−10° C.). Sodium borohydride (2.15 g, 56.8 mmol) was added and the reaction mixture was stirred overnight. Incomplete conversion was seen. The volatiles were removed under reduced pressure and the residue was redispensed in THF (100 mL) and lithium aluminum hydride (18.9 mL, 1 M in THF, 18.9 mmol) was added dropwise. The reaction mixture was stirred overnight. Sodium sulfate decahydrate (27.4 g, 85.1 mmol) was added followed by Na₂SO₄. The reaction mixture was filtered and the volatiles were removed under reduced pressure and the residue was purified on silica using a DCM to DCM:MeOH/NH₃ 9:1 gradient yielding 2-amino-2-methyl-3-(5-methylisoxazol-3-yl)propan-1-ol (1.41 g) as a clear oil. The filter cake was washed with MeOH and the volatiles were removed from the filtrate. The residue was purified on silica using a DCM to DCM:MeOH/NH₃ 9:1 gradient yielding a second crop of 2-amino-2-methyl-3-(5-methylisoxazol-3-yl)propan-1-ol (455 mg) as a light yellow oil.

Both fractions (1.44 g and 455 mg, 11.1 mmol), ethyl 4-chlorosulfonyl-3-fluoro-1-methyl-pyrrole-2-carboxylate (2.74 g, 10.2 mmol) and Hunig's base (4.37 mL, 0.75 g/mL, 25.4 mmol) were dissolved in ACN (25 mL) and the reaction mixture was stirred overnight. The volatiles were removed under reduced pressure and the residue was purified on silica using a heptane to EtOAc gradient yielding ethyl 3-fluoro-4-[[1-(hydroxymethyl)-1-methyl-2-(5-methylisoxazol-3-yl)ethyl]sulfamoyl]-1-methyl-pyrrole-2-carboxylate (2.42 g) as a yellow oil which solidified overnight.

Ethyl 3-fluoro-4-[[1-(hydroxymethyl)-1-methyl-2-(5-methylisoxazol-3-yl)ethyl]sulfamoyl]-1-methyl-pyrrole-2-carboxylate (484 mg, 1.20 mmol) and 3,4-difluoroaniline (0.12 mL, 1.29 g/mL, 1.2 mmol) were dispensed in THF (5 mL). Lithium bis(trimethylsilyl)amide (6 mL, 1 M in THF, 6 mmol) was added and the reaction mixture was stirred 3 hours at room temperature. The reaction mixture was quenched with NH$_4$Cl (sat., aq., 10 mL) and the organic layer was removed. The aqueous layer was extracted with DCM (2×5 mL) and the combined organic layers were evaporated to dryness and the residue was purified on silica using a heptane to EtOAc gradient yielding N-(3,4-difluorophenyl)-3-fluoro-4-[[1-(hydroxymethyl)-1-methyl-2-(5-methylisoxazol-3-yl)ethyl]sulfamoyl]-1-methyl-pyrrole-2-carboxamide (175 mg).

N-(3,4-difluorophenyl)-3-fluoro-4-[[1-(hydroxymethyl)-1-methyl-2-(5-methylisoxazol-3-yl)ethyl]sulfamoyl]-1-methyl-pyrrole-2-carboxamide (175 mg, 0.36 mmol) and cesium fluoride (219 mg, 1.44 mmol) were dispensed in DMF (3 mL) and heated in a microwave tube at 110° C. for 2 hours. The reaction mixture was directly loaded on a silica cartridge and a heptane to EtOAc gradient was applied yielding compound 162. This was separated into its enantiomers via preparative SFC (Stationary phase: Chiralpak Diacel AD 20×250 mm, Mobile phase: CO$_2$, MeOH+0.4 iPrNH$_2$) yielding compound 162a (32 mg); $^1$H NMR (400 MHz, DMSO-d$_6$) δ ppm 1.21 (s, 3H), 2.38-2.41 (m, 3H), 2.87 (d, J=13.9 Hz, 1H), 3.04 (d, J=13.9 Hz, 1H), 3.82 (s, 3H), 4.41 (d, J=13.0 Hz, 1H), 4.60 (d, J=13.0 Hz, 1H), 6.21 (d, J=0.9 Hz, 1H), 7.40-7.44 (m, 2H), 7.48 (s, 1H), 7.81-7.93 (m, 2H), 9.39 (s, 1H); Method B; Rt: 1.04 min. m/z: 465 (M–H)$^-$ Exact mass: 466.1 and compound 162b (33 mg); $^1$H NMR (400 MHz, DMSO-d$_6$) δ ppm 1.21 (s, 3H), 2.37-2.41 (m, 3H), 2.87 (d, J=13.9 Hz, 1H), 3.04 (d, J=13.9 Hz, 1H), 3.82 (s, 3H), 4.41 (d, J=13.2 Hz, 1H), 4.60 (d, J=13.0 Hz, 1H), 6.21 (d, J=0.9 Hz, 1H), 7.38-7.45 (m, 2H), 7.48 (s, 1H), 7.80-7.93 (m, 2H), 9.39 (s, 1H); Method B; Rt: 1.04 min. m/z: 465 (M–H)$^-$ Exact mass: 466.1, as white powders after crystallization from an EtOAc:DIPE mixture. Method V; Rt: 162a: 3.82 min, 162b: 4.21 min.

Compound 163: N-(3-cyano-4-fluoro-phenyl)-3-(1-hydroxypropyl)-7-methyl-1,1-dioxo-3,4-dihydro-2H-pyrrolo[3,4-b][1,4,5]oxathiazepine-6-carboxamide

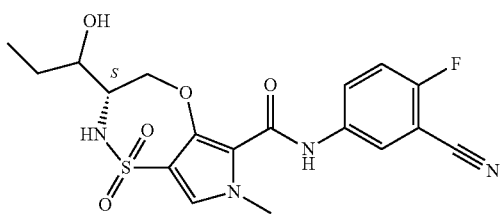

Compound 163 (132 mg) was prepared similarly as described for compound 142, using 5-amino-2-fluoro-benzonitrile instead of 3,4-difluoroaniline. The racemic mixture was separated in its epimers via preparative SFC (Stationary phase: Chiralpak Daicel AD 20×250 mm, Mobile phase: CO$_2$, EtOH+0.4 iPrNH$_2$) to yield compound 163a (41 mg); $^1$H NMR (400 MHz, DMSO-d$_6$) δ ppm 0.92 (t, J=7.4 Hz, 3H), 1.44 (dquin, J=14.2, 7.3, 7.3, 7.3, 7.3 Hz, 1H), 1.65-1.78 (m, 1H), 3.35-3.44 (m, 1H), 3.44-3.57 (m, 1H), 3.83 (s, 3H), 3.98 (dd, J=12.6, 8.8 Hz, 1H), 4.93 (dd, J=12.8, 2.0 Hz, 1H), 4.99 (d, J=6.2 Hz, 1H), 7.45-7.56 (m, 2H), 7.62 (br d, J=8.6 Hz, 1H), 8.05 (ddd, J=9.2, 4.9, 2.8 Hz, 1H), 8.21 (dd, J=5.8, 2.7 Hz, 1H), 9.51 (s, 1H); Method D; Rt: 1.69 min. m/z: 421 (M–H)$^-$ Exact mass: 422.1, and 163b (21 mg); $^1$H NMR (400 MHz, DMSO-d$_6$) δ ppm 0.88 (t, J=7.3 Hz, 3H), 1.29-1.43 (m, 1H), 1.50-1.63 (m, 1H), 3.55-3.64 (m, 1H), 3.67-3.76 (m, 1H), 3.83 (s, 3H), 3.99 (dd, J=12.7, 9.1 Hz, 1H), 4.74 (dd, J=13.1, 0.5 Hz, 1H), 4.88 (br d, J=5.3 Hz, 1H), 7.35 (br s, 1H), 7.49 (s, 1H), 7.52 (t, J=9.1 Hz, 1H), 8.05 (ddd, J=9.2, 4.9, 2.8 Hz, 1H), 8.19 (dd, J=5.8, 2.7 Hz, 1H), 9.54 (s, 1H); Method D; Rt: 1.70 min. m/z: 421 (M–H)$^-$ Exact mass: 422.1; MP: 247.0° C. Method R; Rt: 163a: 4.44 min, 163b: 4.60 min.

Compound 164: (3S)—N-[3-(difluoromethyl)-2,4-difluoro-phenyl]-3,7-dimethyl-1,1-dioxo-2,3,4,5-tetrahydropyrrolo[3,4-f]thiazepine-6-carboxamide

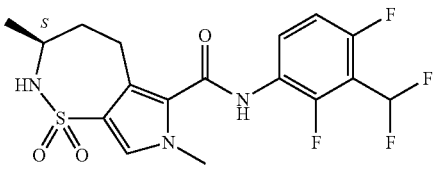

Compound 164 (87 mg) was prepared similarly as described for compound 157, using 3-(difluoromethyl)-2,4-difluoro-aniline instead of 3-amino-2,6-difluoro-benzonitrile. $^1$H NMR (400 MHz, DMSO-d$_6$) δ ppm 1.14 (d, J=6.82 Hz, 3H) 1.29-1.52 (m, 1H) 1.79-1.99 (m, 1H) 2.74-2.93 (m, 1H) 3.12 (br dd, J=15.07, 6.05 Hz, 1H) 3.55-3.67 (m, 1H) 3.70 (s, 3H) 7.02 (br d, J=9.02 Hz, 1H) 7.17-7.56 (m, 3H) 7.77-7.99 (m, 1H) 10.13 (br s, 1H); Method B; Rt: 0.89 min. m/z: 418 (M–H)$^-$ Exact mass: 419.1, MP: 227.7° C.

Compound 165: (3S)—N-[2-(difluoromethyl)-4-pyridyl]-3,7-dimethyl-1,1-dioxo-2,3,4,5-tetrahydropyrrolo[3,4-f]thiazepine-6-carboxamide

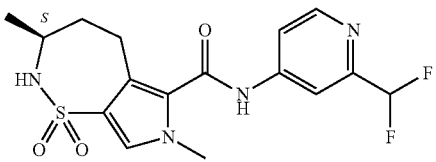

Compound 165 (84 mg) was prepared similarly as described for compound 157, using 2-(difluoromethyl)pyridin-4-amine instead of 3-amino-2,6-difluoro-benzonitrile. $^1$H NMR (400 MHz, DMSO-d$_6$) δ ppm 1.13 (d, J=6.82 Hz, 3H) 1.29-1.44 (m, 1H) 1.79-1.93 (m, 1H) 2.78-2.91 (m, 1H) 2.92-3.03 (m, 1H) 3.56-3.68 (m, 1H) 3.71 (s, 3H) 6.73-7.12 (m, 2H) 7.47 (s, 1H) 7.75 (dd, J=5.50, 1.76 Hz, 1H) 8.03 (d, J=1.76 Hz, 1H) 8.56 (d, J=5.50 Hz, 1H) 10.84 (s, 1H); Method B; Rt: 0.74 min. m/z: 385 (M–H)$^-$ Exact mass: 384.1.

Compound 166: (3S)—N-(2-chloro-4-pyridyl)-3,7-dimethyl-1,1-dioxo-2,3,4,5-tetrahydropyrrolo[3,4-f]thiazepine-6-carboxamide

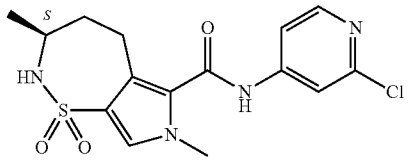

Compound 166 (107 mg) was prepared similarly as described for compound 157, using 2-chloropyridin-4-amine instead of 3-amino-2,6-difluoro-benzonitrile. $^1$H NMR (400 MHz, DMSO-$d_6$) δ ppm 1.13 (d, J=6.82 Hz, 3H) 1.27-1.47 (m, 1H) 1.79-1.91 (m, 1H) 2.78-2.90 (m, 1H) 2.91-3.04 (m, 1H) 3.55-3.67 (m, 1H) 3.70 (s, 3H) 7.04 (d, J=9.46 Hz, 1H) 7.47 (s, 1H) 7.58 (dd, J=5.72, 1.76 Hz, 1H) 7.80 (d, J=1.76 Hz, 1H) 8.29 (d, J=5.50 Hz, 1H) 10.81 (br s, 1H); Method B; Rt: 0.76 min. m/z: 367 (M−H)⁻ Exact mass: 368.1.

Compound 167: N-(3,4-difluorophenyl)-3,7-dimethyl-3-[(1-methylpyrazol-3-yl)methyl]-1,1-dioxo-2,4-dihydropyrrolo[3,4-b][1,4,5]oxathiazepine-6-carboxamide

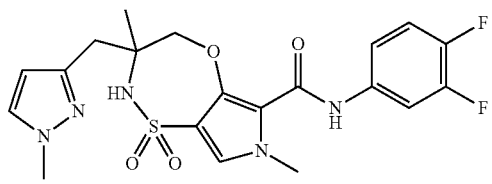 [SMILES: Cn1ccc(CC2(C)COc3c(cn(C)c3C(=O)Nc3ccc(F)c(F)c3)S(=O)(=O)N2)n1]

Compound 167 (435 mg) was prepared similarly as described for compound 162, using 3-(chloromethyl)-1-methyl-1H-pyrazole hydrochloride instead of 3-(chloromethyl)-5-methylisoxazole. The racemic mixture was separated in its enantiomers via preparative SFC (Stationary phase: Chiralpak Daicel AD 20×250 mm, Mobile phase: $CO_2$, MeOH+0.4 iPrNH$_2$) to yield compound 167a (154.1 mg); $^1$H NMR (400 MHz, DMSO-$d_6$) δ ppm 1.21 (s, 3H), 2.83 (d, J=13.9 Hz, 1H), 2.98 (d, J=13.9 Hz, 1H), 3.80 (s, 3H), 3.82 (s, 3H), 4.40 (d, J=13.0 Hz, 1H), 4.53 (d, J=13.2 Hz, 1H), 6.14 (d, J=2.2 Hz, 1H), 7.38-7.45 (m, 2H), 7.46 (s, 1H), 7.60 (d, J=2.0 Hz, 1H), 7.80 (s, 1H), 7.81-7.88 (m, 1H), 9.37 (s, 1H); Method B; Rt: 0.99 min. m/z: 464 (M−H)⁻ Exact mass: 465.1, and 167b (151.4 mg); $^1$H NMR (400 MHz, DMSO-$d_6$) δ ppm 1.21 (s, 3H), 2.83 (d, J=13.9 Hz, 1H), 2.98 (d, J=13.9 Hz, 1H), 3.80 (s, 3H), 3.82 (s, 3H), 4.40 (d, J=13.0 Hz, 1H), 4.53 (d, J=13.0 Hz, 1H), 6.14 (d, J=2.0 Hz, 1H), 7.38-7.45 (m, 2H), 7.46 (s, 1H), 7.60 (d, J=2.0 Hz, 1H), 7.80 (s, 1H), 7.81-7.87 (m, 1H), 9.37 (s, 1H); Method B; Rt: 0.99 min. m/z: 464 (M−H)⁻ Exact mass: 465.1. Method V; Rt: 167a: 3.93 min, 167b: 4.50 min.

Compound 168: N-(3,4-difluorophenyl)-3,7-dimethyl-3-(6-methyl-2-pyridyl)-1,1-dioxo-2,4-dihydropyrrolo[3,4-b][1,4,5]oxathiazepine-6-carboxamide

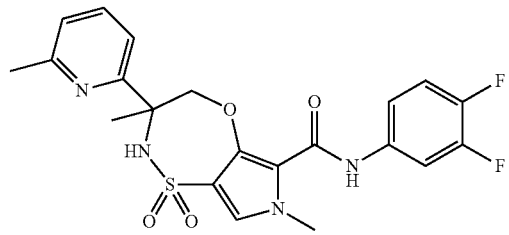 [SMILES: Cc1cccc(C2(C)COc3c(cn(C)c3C(=O)Nc3ccc(F)c(F)c3)S(=O)(=O)N2)n1]

Compound 168 (118 mg) was prepared similarly as described for compound 153, using 2-acetyl-6-methylpyridine instead of 2-acetylpyrimidine. $^1$H NMR (400 MHz, DMSO-$d_6$) δ ppm 1.54-1.59 (m, 3H), 2.44-2.47 (m, 3H), 3.79-3.84 (m, 3H), 4.97 (d, J=13.4 Hz, 1H), 5.21 (d, J=13.3 Hz, 1H), 7.16 (d, J=7.6 Hz, 1H), 7.37-7.51 (m, 3H), 7.60 (d, J=7.9 Hz, 1H), 7.75 (t, J=7.8 Hz, 1H), 7.89 (ddd, J=13.2, 7.5, 2.5 Hz, 1H), 8.47 (s, 1H), 9.40 (s, 1H); Method B; Rt: 1.26 min. m/z: 463 (M+H)⁺ Exact mass: 462.1. The racemic mixture was separated in its enantiomers via preparative SFC (Stationary phase: Chiralpak Daicel AS 20×250 mm, Mobile phase: $CO_2$, EtOH+0.4 iPrNH$_2$) to yield compound 168a (37 mg); MP: 221.9° C., and 168b (35 mg); MP: 221.5° C. Method T; Rt: 168a: 3.67 min, 168b: 4.66 min.

Compound 169: (3S)—N-[3-(difluoromethyl)-4-fluoro-phenyl]-3,7-dimethyl-1,1-dioxo-3-(2-pyridyl)-2,4-dihydropyrrolo[3,4-b][1,4,5]oxathiazepine-6-carboxamide

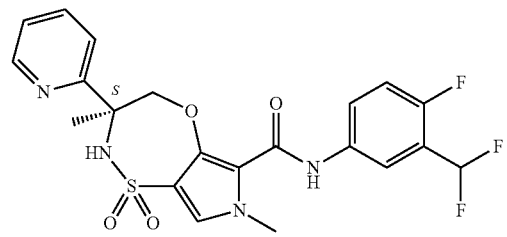

Compound 169 (131 mg) was prepared similarly as described for compound 127, using 3-(difluoromethyl)-4-fluoro-aniline instead of 3,4-difluoroaniline. $^1$H NMR (400 MHz, DMSO-$d_6$) δ ppm 1.55-1.62 (m, 3H), 3.82 (s, 3H), 4.99 (d, J=13.4 Hz, 1H), 5.20 (d, J=13.3 Hz, 1H), 7.04-7.41 (m, 3H), 7.47 (s, 1H), 7.79-7.89 (m, 3H), 8.05 (dd, J=6.3, 2.6 Hz, 1H), 8.48-8.52 (m, 2H), 9.44 (s, 1H); Method B; Rt: 1.07 min. m/z: 479 (M−H)⁻ Exact mass: 480.1; MP: 208.8° C.

Compound 170: 3,7-dimethyl-3-[(5-methylisoxazol-3-yl)methyl]-1,1-dioxo-N-(3,4,5-trifluorophenyl)-2,4-dihydropyrrolo[3,4-b][1,4,5]oxathiazepine-6-carboxamide

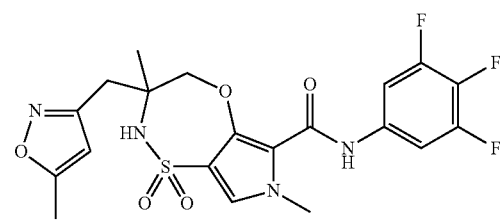 [SMILES: Cc1cc(CC2(C)COc3c(cn(C)c3C(=O)Nc3cc(F)c(F)c(F)c3)S(=O)(=O)N2)no1]

Compound 170 (102 mg) was prepared similarly as described for compound 162, using 3,4,5-trifluoroaniline instead of 3,4-difluoroaniline. This was separated into its enantiomers via preparative SFC (Stationary phase: Kromasil (R,R) Whelk-O 1 10/100, Mobile phase: $CO_2$, iPrOH+0.4 iPrNH$_2$) yielding compound 170a (18 mg), $^1$H NMR (400 MHz, DMSO-d$_6$) δ ppm 1.22 (s, 3H), 2.40 (s, 3H), 2.88 (d, J=14.1 Hz, 1H), 3.05 (d, J=13.9 Hz, 1H), 3.82 (s, 3H), 4.43 (d, J=13.2 Hz, 1H), 4.61 (d, J=13.2 Hz, 1H), 6.22 (s, 1H), 7.51 (s, 1H), 7.62-7.75 (m, 2H), 7.93 (s, 1H), 9.45 (s, 1H); Method B; Rt: 1.13 min. m/z: 483 (M−H)$^−$ Exact mass: 484.1 and compound 170b (29 mg), $^1$H NMR (400 MHz, DMSO-d$_6$) δ ppm 1.17-1.27 (m, 3H), 2.40 (s, 3H), 2.88 (d, J=13.9 Hz, 1H), 3.05 (d, J=14.1 Hz, 1H), 3.82 (s, 3H), 4.42 (d, J=13.0 Hz, 1H), 4.61 (d, J=13.2 Hz, 1H), 6.21 (d, J=0.9 Hz, 1H), 7.51 (s, 1H), 7.62-7.70 (m, 2H), 7.93 (s, 1H), 9.45 (s, 1H); Method B; Rt: 1.13 min. m/z: 483 (M−H)$^−$ Exact mass: 484.1. Method X; Rt: 170a: 4.81 min, 170b: 5.12 min.

Compound 171: 3-[(6-bromo-3-pyridyl)methyl]-N-(3,4-difluorophenyl)-3,7-dimethyl-1,1-dioxo-2,4-dihydropyrrolo[3,4-b][1,4,5]oxathiazepine-6-carboxamide

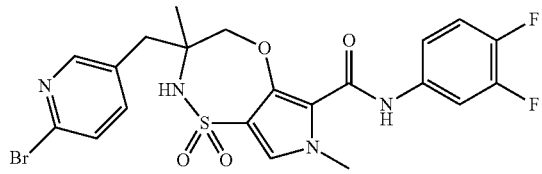 [SMILES: Cn1cc2c(c1C(=O)Nc1ccc(F)c(F)c1)OCC(C)(Cc1ccc(Br)nc1)NS2(=O)=O]

Compound 171 (102 mg) was prepared similarly as described for compound 162, using 2-bromo-5-(bromomethyl)pyridine instead of 3-(chloromethyl)-5-methylisoxazole. $^1$H NMR (400 MHz, DMSO-d$_6$) δ ppm 1.13 (s, 3H), 2.72 (d, J=13.2 Hz, 1H), 3.04 (d, J=13.2 Hz, 1H), 3.82 (s, 3H), 4.41 (d, J=13.2 Hz, 1H), 4.64 (d, J=13.2 Hz, 1H), 7.38-7.47 (m, 2H), 7.49 (s, 1H), 7.63-7.67 (m, 1H), 7.67-7.73 (m, 1H), 7.76 (s, 1H), 7.80-7.88 (m, 1H), 8.31 (d, J=2.2 Hz, 1H), 9.40 (s, 1H); Method B; Rt: 1.11 min. m/z: 539 (M−H)$^−$ Exact mass: 540.0, MP: 259.2° C.

Compound 172: N-(3,4-difluorophenyl)-3,7-dimethyl-3-[(6-methyl-2-pyridyl)methyl]-1,1-dioxo-2,4-dihydropyrrolo[3,4-b][1,4,5]oxathiazepine-6-carboxamide

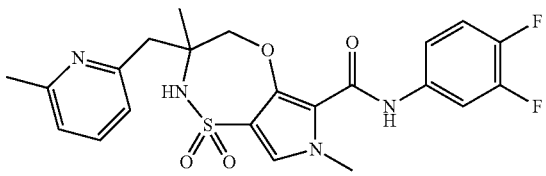 [SMILES: Cc1cccc(CC2(C)COc3c(cn(C)c3C(=O)Nc3ccc(F)c(F)c3)S(=O)(=O)N2)n1]

Compound 172 (196 mg) was prepared similarly as described for compound 162, using 2-(bromomethyl)-6-methyl-pyridine instead of 3-(chloromethyl)-5-methylisoxazole. $^1$H NMR (400 MHz, DMSO-d$_6$) δ ppm 1.23 (s, 3H), 2.42 (s, 3H), 2.99-3.11 (m, 2H), 3.81 (s, 3H), 4.49 (d, J=13.0 Hz, 1H), 4.62 (d, J=13.2 Hz, 1H), 7.12 (d, J=7.7 Hz, 1H), 7.20 (d, J=7.7 Hz, 1H), 7.38-7.45 (m, 2H), 7.46 (s, 1H), 7.62 (t, J=7.6 Hz, 1H), 7.79-7.86 (m, 1H), 8.02 (s, 1H), 9.30 (s, 1H); Method B; Rt: 1.13 min. m/z: 475 (M−H)$^−$ Exact mass: 476.1, MP: 206.0° C. This was separated into its enantiomers via preparative SFC (Stationary phase: Chiralpak Diacel AD 20×250 mm, Mobile phase: $CO_2$, iPrOH+0.4 iPrNH$_2$) yielding compound 172a (65 mg) and compound 172b (36 mg). Method W; Rt: 172a: 4.20 min, 172b: 4.40 min.

Compound 173: N-(3,4-difluorophenyl)-3,7-dimethyl-3-[(1-methylimidazol-2-yl)methyl]-1,1-dioxo-2,4-dihydropyrrolo[3,4-b][1,4,5]oxathiazepine-6-carboxamide

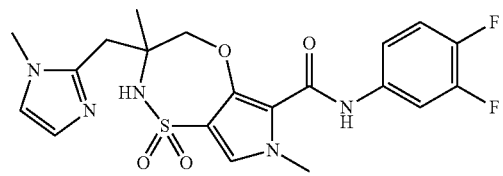 [SMILES: Cn1ccnc1CC1(C)COc2c(cn(C)c2C(=O)Nc2ccc(F)c(F)c2)S(=O)(=O)N1]

Compound 173 (109 mg) was prepared similarly as described for compound 162, using 2-chloromethyl-1-methyl-1H-imidazole instead of 3-(chloromethyl)-5-methylisoxazole. $^1$H NMR (400 MHz, DMSO-d$_6$) δ ppm 1.29-1.36 (m, 3H), 2.96-3.10 (m, 2H), 3.64 (s, 3H), 3.75-3.83 (m, 3H), 4.51-4.66 (m, 2H), 6.82 (d, J=1.1 Hz, 1H), 7.06 (d, J=1.1 Hz, 1H), 7.38-7.46 (m, 3H), 7.79-7.87 (m, 1H), 8.07 (br s, 1H), 9.37 (s, 1H); Method B; Rt: 0.92 min. m/z: 464 (M−H)$^−$ Exact mass: 465.1, MP: 297.1° C.

Compound 174: N-(3,4-difluorophenyl)-3,7-dimethyl-3-[(3-methylimidazol-4-yl)methyl]-1,1-dioxo-2,4-dihydropyrrolo[3,4-b][1,4,5]oxathiazepine-6-carboxamide

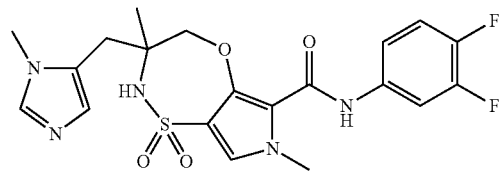 [SMILES: Cn1cncc1CC1(C)COc2c(cn(C)c2C(=O)Nc2ccc(F)c(F)c2)S(=O)(=O)N1]

Compound 174 (109 mg) was prepared similarly as described for compound 162, using 5-chloromethyl-1-methyl-1H-imidazole instead of 3-(chloromethyl)-5-methylisoxazole. $^1$H NMR (400 MHz, DMSO-d$_6$) δ ppm 1.03-1.24 (m, 3H), 2.83 (d, J=15.0 Hz, 1H), 2.97 (d, J=15.0 Hz, 1H), 3.60 (s, 3H), 3.81 (s, 3H), 4.38 (d, J=13.4 Hz, 1H), 4.65 (d, J=13.0 Hz, 1H), 6.80 (s, 1H), 7.38-7.45 (m, 2H), 7.46 (s, 1H), 7.53 (s, 1H), 7.79-7.91 (m, 2H), 9.39 (s, 1H); Method B; Rt: 0.87 min. m/z: 464 (M−H)$^−$ Exact mass: 465.1, MP: 265.5° C.

Compound 175: N-(3,4-difluorophenyl)-3-[(2,5-dimethylpyrazol-3-yl)methyl]-3,7-dimethyl-1,1-dioxo-2,4-dihydropyrrolo[3,4-b][1,4,5]oxathiazepine-6-carboxamide

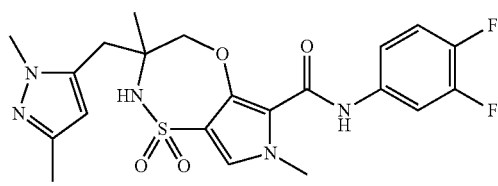 [SMILES: Cc1cc(CC2(C)COc3c(cn(C)c3C(=O)Nc3ccc(F)c(F)c3)S(=O)(=O)N2)n(C)n1]

Compound 175 (182 mg) was prepared similarly as described for compound 162, using 5-(chloromethyl)-1,3-dimethyl-1H-pyrazole instead of 3-(chloromethyl)-5-methylisoxazole. $^1$H NMR (400 MHz, DMSO-d$_6$) δ ppm 1.22 (s, 3H), 2.11 (s, 3H), 2.85 (d, J=14.5 Hz, 1H), 3.01 (d, J=14.7 Hz, 1H), 3.72 (s, 3H), 3.81 (s, 3H), 4.38 (d, J=13.2 Hz, 1H), 4.65 (d, J=13.2 Hz, 1H), 5.96 (s, 1H), 7.38-7.48 (m, 3H), 7.81-7.92 (m, 2H), 9.39 (s, 1H); Method B; Rt: 0.98 min. m/z: 478 (M−H)$^−$ Exact mass: 479.1. This was separated into its enantiomers via preparative SFC (Stationary phase: Chiralpak Diacel AD 20×250 mm, Mobile phase: CO$_2$, EtOH+0.4 iPrNH$_2$) yielding compound 175a (74 mg) and compound 175b (63 mg). Method R; Rt: 172a: 3.88 min, 172b: 5.31 min.

Compound 176: N-[3-(difluoromethyl)-4-fluoro-phenyl]-3-[(2,5-dimethylpyrazol-3-yl)methyl]-3,7-dimethyl-1,1-dioxo-2,4-dihydropyrrolo[3,4-b][1,4,5]oxathiazepine-6-carboxamide

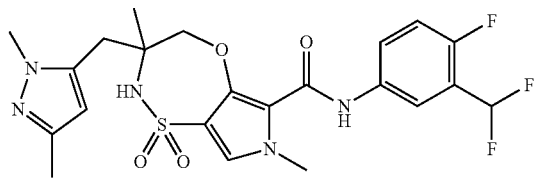 [SMILES: Cc1cc(CC2(C)COc3c(cn(C)c3C(=O)Nc3ccc(F)c(C(F)F)c3)S(=O)(=O)N2)n(C)n1]

Compound 176 was prepared similarly as described for compound 175, using 3-(difluoromethyl)-4-fluoro-aniline instead of 3,4-difluoroaniline. $^1$H NMR (400 MHz, DMSO-d$_6$) δ ppm 1.22 (s, 3H), 2.11 (s, 3H), 2.94 (dd, J=55.6, 14.6 Hz, 2H), 3.72 (s, 3H), 3.82 (s, 3H), 4.38 (d, J=13.2 Hz, 1H), 4.63 (d, J=13.6 Hz, 1H), 5.96 (s, 1H), 7.23 (t, J=54.8 Hz, 1H), 7.32-7.42 (m, 1H), 7.46 (s, 1H), 7.76-7.84 (m, 1H), 7.76-7.84 (m, 1H), 7.88 (s, 1H), 7.97-8.03 (m, 1H), 9.44 (s, 1H); Method B; Rt: 0.98 min. m/z: 510 (M−H)$^−$ Exact mass: 511.2. This was separated into its enantiomers via preparative SFC (Stationary phase: Chiralpak Diacel AD 20×250 mm, Mobile phase: CO$_2$, EtOH+0.4 iPrNH$_2$) yielding compound 176a (97 mg) and compound 176b (83 mg). Method R; Rt: 176a: 3.61 min, 176b: 5.13 min.

Compound 177: N-[3-(difluoromethyl)-4-fluoro-phenyl]-3,7-dimethyl-3-(6-methyl-2-pyridyl)-1,1-dioxo-2,4-dihydropyrrolo[3,4-b][1,4,5]oxathiazepine-6-carboxamide

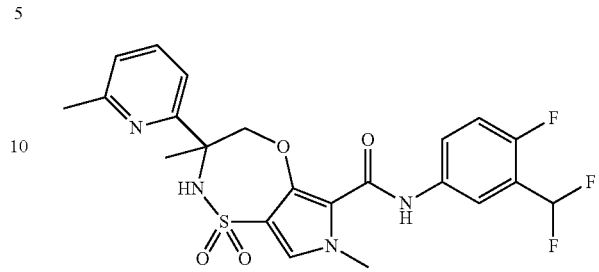

Compound 177 (273 mg) was prepared similarly as described for compound 168, using 3-(difluoromethyl)-4-fluoro-aniline instead of 3,4-difluoroaniline. $^1$H NMR (400 MHz, DMSO-d$_6$) δ ppm 1.52-1.62 (m, 3H), 2.44-2.48 (m, 3H), 3.78-3.86 (m, 3H), 4.97 (d, J=13.4 Hz, 1H), 5.20 (d, J=13.4 Hz, 1H), 7.04-7.42 (m, 2H), 7.47 (s, 1H), 7.60 (d, J=7.9 Hz, 1H), 7.75 (br t, J=7.7 Hz, 1H), 7.79-7.87 (m, 1H), 8.05 (dd, J=6.4, 2.7 Hz, 1H), 8.46 (s, 1H), 9.41-9.47 (m, 1H); Method B; Rt: 1.15 min. m/z: 493 (M−H)$^−$ Exact mass: 494.1; MP: 210.2° C. This was separated into it's enantiomers via Prep SFC (Stationary phase: Chiralpak Diacel AS 20×250 mm, Mobile phase: CO$_2$, EtOH+0.4 iPrNH$_2$) yielding compound 177a (66 mg) and compound 177b (86 mg). Method T; Rt: 177a: 3.09 min, 177b: 3.88 min.

Compound 178: (3R)—N-(3-cyano-2,4-difluoro-phenyl)-3-[(1S)-1-hydroxyethyl]-7-methyl-1,1-dioxo-2,3-dihydropyrrolo[3,4-f]thiazepine-6-carboxamide

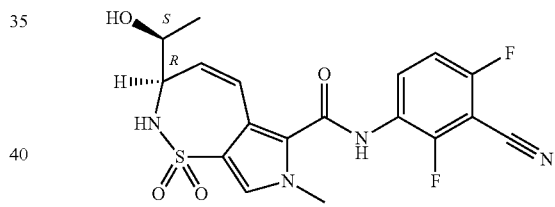

Compound 178 (26 mg) was prepared similarly as described for compound 84, using 3-amino-2,6-difluorobenzonitrile instead of 3,4-difluoroaniline. $^1$H NMR (400 MHz, DMSO-d$_6$) δ ppm 1.21 (d, J=6.2 Hz, 3H), 3.64-3.78 (m, 4H), 3.82 (ddt, J=10.1, 7.4, 2.7, 2.7 Hz, 1H), 4.98 (d, J=5.9 Hz, 1H), 5.98 (dd, J=12.5, 2.9 Hz, 1H), 6.70 (dd, J=12.5, 2.4 Hz, 1H), 7.41 (d, J=9.9 Hz, 1H), 7.47 (t, J=9.0 Hz, 1H), 7.59 (s, 1H), 8.06 (td, J=8.9, 6.2 Hz, 1H), 10.59 (br s, 1H); Method B; Rt: 0.73 min. m/z: 421 (M−H)$^−$ Exact mass: 422.1.

Compound 179: N-(3-bromo-2,4-difluoro-phenyl)-3-(1-hydroxy-1-methyl-ethyl)-7-methyl-1,1-dioxo-2,3,4,5-tetrahydropyrrolo[3,4-f]thiazepine-6-carboxamide

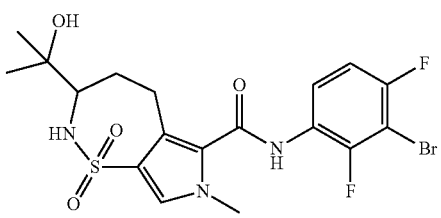

Compound 179 (274 mg) was prepared similarly as described for compound 113, using 3-bromo-2,4-difluoro-aniline instead of 3,4-difluoroaniline. $^1$H NMR (400 MHz, DMSO-d$_6$) δ ppm 1.04 (s, 3H), 1.17 (s, 3H), 1.37 (q, J=11.7 Hz, 1H), 2.18 (br dd, J=14.2, 7.2 Hz, 1H), 2.67-2.78 (m, 1H), 3.16-3.30 (m, 2H), 3.70 (s, 3H), 4.40 (s, 1H), 6.85 (br d, J=10.3 Hz, 1H), 7.31 (td, J=8.6, 1.9 Hz, 1H), 7.44 (s, 1H), 7.70 (td, J=8.7, 5.9 Hz, 1H), 10.15 (br s, 1H); Method B; Rt: 0.86 min. m/z: 490 (M–H)$^-$ Exact mass: 491.0, MP: 236.8° C.

Compound 180: (3R)—N-(3-chloro-4-fluoro-phenyl)-3-(1-hydroxy-1-methyl-ethyl)-7-methyl-1,1-dioxo-3,4-dihydro-2H-pyrrolo[3,4-b][1,4,5]oxathiazepine-6-carboxamide

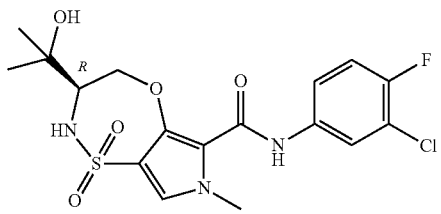

Compound 180 (289 mg) was prepared similarly as described for compound 93, using 3-chloro-4-fluoro-aniline instead of 3,4-difluoroaniline. $^1$H NMR (400 MHz, DMSO-d$_6$) δ ppm 1.06 (s, 3H), 1.25 (s, 3H), 3.55 (br t, J=8.5 Hz, 1H), 3.83 (s, 3H), 3.93 (dd, J=12.5, 8.9 Hz, 1H), 4.85 (s, 1H), 4.96 (d, J=12.4 Hz, 1H), 7.38 (t, J=9.1 Hz, 1H), 7.45-7.57 (m, 2H), 7.65 (ddd, J=9.0, 4.3, 2.6 Hz, 1H), 8.00 (dd, J=6.8, 2.6 Hz, 1H), 9.41 (s, 1H); Method D; Rt: 1.82 min. m/z: 430 (M–H)$^-$ Exact mass: 431.1, MP: 234.1° C.

Compound 181: N-[3-(difluoromethyl)-4-fluoro-phenyl]-3,7-dimethyl-3-(5-methylisoxazol-3-yl)-1,1-dioxo-2,4-dihydropyrrolo[3,4-b][1,4,5]oxathiazepine-6-carboxamide

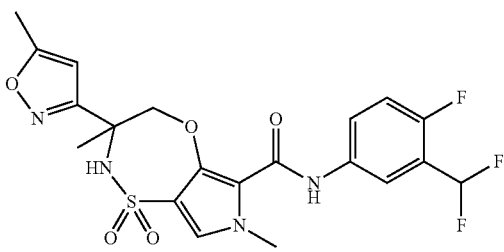 [SMILES: Cc1cc(C2(C)COc3c(cn(C)c3C(=O)Nc3ccc(F)c(C(F)F)c3)S(=O)(=O)N2)no1]

Compound 181 (151 mg) was prepared similarly as described for compound 153, using 1-(5-methylisoxazol-3-yl)ethanone instead of 2-acetylpyrimidine. $^1$H NMR (400 MHz, DMSO-d$_6$) δ ppm 1.60 (s, 3H), 2.39-2.43 (m, 3H), 3.82 (s, 3H), 4.83 (d, J=13.3 Hz, 1H), 4.99 (d, J=13.3 Hz, 1H), 6.34 (d, J=1.1 Hz, 1H), 7.22 (t, J=54.2 Hz, 1H), 7.37 (t, J=9.5 Hz, 1H), 7.47 (s, 1H), 7.80-7.85 (m, 1H), 8.05 (dd, J=6.4, 2.7 Hz, 1H), 8.56 (s, 1H), 9.47 (s, 1H); Method B; Rt: 1.03 min. m/z: 483 (M+H)$^+$ Exact mass: 484.1. The racemic mixture was separated in its epimers via preparative SFC (Stationary phase: Chiralpak Daicel OD 20×250 mm, Mobile phase: CO$_2$, EtOH+0.4 iPrNH$_2$) to yield compound 181a (47 mg) and 181b (48 mg). Method Y; Rt: 181a: 3.07 min, 181b: 3.53 min.

Compound 182: (3R)—N-[3-(difluoromethyl)-2,4-difluoro-phenyl]-3-(1-hydroxy-1-methyl-ethyl)-7-methyl-1,1-dioxo-3,4-dihydro-2H-pyrrolo[3,4-b][1,4,5]oxathiazepine-6-carboxamide

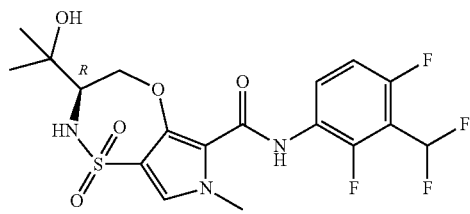

Compound 182 (153 mg) was prepared similarly as described for compound 93, using 3-(difluoromethyl)-2,4-difluoro-aniline instead of 3,4-difluoroaniline. $^1$H NMR (400 MHz, DMSO-d$_6$) δ ppm 1.04 (s, 3H), 1.25 (s, 3H), 3.53-3.63 (m, 1H), 3.87 (s, 3H), 3.99 (dd, J=12.5, 8.8 Hz, 1H), 4.83-5.03 (m, 2H), 7.15-7.78 (m, 4H), 8.17-8.34 (m, 1H), 9.36 (s, 1H); Method D; Rt: 1.79 min. m/z: 464 (M–H)$^-$ Exact mass: 465.1, MP: 182.1° C.

Compound 183: N-(3,4-difluorophenyl)-3-[hydroxy(4-pyridyl)methyl]-7-methyl-1,1-dioxo-3,4-dihydro-2H-pyrrolo[3,4-b][1,4,5]oxathiazepine-6-carboxamide

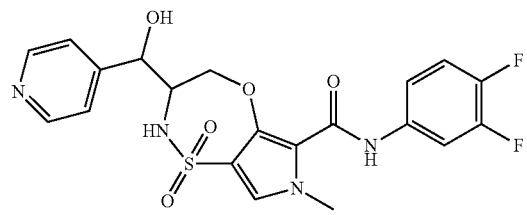

To a cooled solution of ethyl 2-(dibenzylamino)acetate (10 g, 35.3 mmol) in dry THF (200 mL) was added dropwise lithium bis(trimethylsilyl)amide (100 mL, 1 M in THF, 100 mmol) at −70° C. The solution was stirred for 1 hour. Then 4-pyridinecarboxaldehyde (6.6 mL, 1.137 g/mL, 70.6 mmol) was added slowly. After complete addition the reaction mixture was warmed to 0° C. over 1 hour. NH$_4$Cl-solution (aq., sat., 150 mL) was added and the product was extracted with EtOAc (3×200 mL). The combined organic layers were dried over Na$_2$SO$_4$, filtered and evaporated. The residue was purified on silica using a DCM to EtOAc gradient yielding ethyl 2-(dibenzylamino)-3-hydroxy-3-(4-pyridyl)propanoate (8.72 g) as a yellow oil.

To a solution of ethyl 2-(dibenzylamino)-3-hydroxy-3-(4-pyridyl)propanoate (1.30 g, 2.56 mmol) in dry DCM/pyridine was added imidazole (524 mg, 7.69 mmol) followed by TBDMS-Cl (1.16 g, 7.69 mmol) and the reaction mixture was stirred at room temperature for 2 hours. More imidazole (524 mg, 7.69 mmol) and TBDMS-Cl (1.16 g, 7.69 mmol) were added and the reaction mixture was stirred overnight. More imidazole (524 mg, 7.69 mmol) and TBDMS-Cl (1.16 g, 7.69 mmol) were added and the reaction mixture was stirred overnight. Pyridine (15 mL) was added and the reaction mixture was stirred overnight. The reaction mixture was quenched with NaHCO$_3$ (aq., sat.) and the product was extracted with DCM (3 times). The combined organic layers were dried over Na$_2$SO$_4$, filtered and evaporated to get a yellow oil, this was purified and separated into its 2 diastereoisomers by silica gel column chromatography (0% to 50% EtOAc in heptane) yielding diastereoisomer 1 (744 mg); $^1$H NMR (400 MHz, CHLOROFORM-d) δ ppm −0.30 (s, 3H), −0.02 (s, 3H), 0.72 (s, 9H), 1.42 (t, J=7.1 Hz, 3H), 3.31 (d, J=14.0 Hz, 2H), 3.53 (d, J=9.9 Hz, 1H), 3.91 (d, J=14.0 Hz, 2H), 4.20-4.43 (m, 2H), 4.97 (d, J=9.9 Hz, 1H), 6.89-7.02 (m, 6H), 7.15-7.24 (m, 6H), 8.48-8.57 (m, 2H); Method D; Rt: 3.11 min. m/z: 505 (M+H)$^+$ Exact mass: 504.3 and diastereoisomer 2 (40 mg); $^1$H NMR (400 MHz, CHLOROFORM-d) δ ppm −0.23 (s, 3H), 0.03 (s, 3H), 0.88 (s, 9H), 1.32 (t, J=7.1 Hz, 3H), 3.58 (d, J=4.5 Hz, 1H), 3.81 (d, J=14.3 Hz, 2H), 4.07-4.37 (m, 4H), 5.30 (d, J=4.5 Hz, 1H), 7.00-7.09 (m, 6H), 7.14-7.25 (m, 6H), 8.45-8.53 (m, 2H); Method D; Rt: 3.29 min. m/z: 505 (M+H)$^+$ Exact mass: 505.3.

To a cooled solution of diastereoisomer 1 (744 mg, 1.46 mmol) in dry DCM was added slowly DIBAL (3.5 mL, 1 M in heptane, 3.5 mmol) at −78° C. under nitrogen atmosphere and continuous stirring at this temperature for 4 hours. Extra DIBAL (3.5 mL, 1 M in heptane, 3.5 mmol) was added and the reaction was stirred for another 2 hours. The reaction mixture was quenched with MeOH (6 mL) followed by potassium sodium tartrate (15 mL) at −78° C. Then the cooling bath was removed and the reaction mixture was warmed slowly to room temperature. The product was extracted with DCM (3×20 mL). The combined organic layers were evaporated and purified on silica using a DCM to EtOAc gradient to yield 3-[tert-butyl(dimethyl)silyl]oxy-2-(dibenzylamino)-3-(4-pyridyl)propan-1-ol (611 mg) as a clear oil. Method B; Rt: 1.42 min. m/z: 463 (M+H)$^+$ Exact mass: 462.3.

Palladium hydroxide on carbon (91 mg, 0.65 mmol) was added to a solution of 3-[tert-butyl(dimethyl)silyl]oxy-2-(dibenzylamino)-3-(4-pyridyl)propan-1-ol (300 mg, 0.65 mmol) in degassed MeOH (6.5 mL) and the resulting suspension was stirred at room temperature under hydrogen atmosphere. After 18 hours the reaction mixture was filtered through a pad of dicalite (eluent MeOH) and concentrated in vacuo. The crude was used as such in the next step.

To a mixture of 2-amino-3-[tert-butyl(dimethyl)silyl]oxy-3-(4-pyridyl)propan-1-ol (162 mg, 0.57 mmol) and Hunig's base (0.62 mL, 0.75 g/mL, 3.6 mmol) in dry DCM (3.9 mL) was added ethyl 4-chlorosulfonyl-3-fluoro-1-methyl-pyrrole-2-carboxylate (0.16 g, 0.57 mmol), the reaction mixture was stirred for 1 hour. The reaction mixture was quenched with NaHCO$_3$ (aq., sat., 5 mL). The 2 layers were separated. The water layer was extracted with DCM (2×5 mL). The combined organic layers were evaporated and the crude was purified on silica using a DCM to EtOAc gradient to afford ethyl 4-[[2-[tert-butyl(dimethyl)silyl]oxy-1-(hydroxymethyl)-2-(4-pyridyl)ethyl]sulfamoyl]-3-fluoro-1-methyl-pyrrole-2-carboxylate (120 mg) as an orange oil.

To a solution of ethyl 4-[[2-[tert-butyl(dimethyl)silyl]oxy-1-(hydroxymethyl)-2-(4-pyridyl)ethyl]sulfamoyl]-3-fluoro-1-methyl-pyrrole-2-carboxylate (120 mg, 0.23 mmol) and 3,4-difluoroaniline (0.035 mL, 1.29 g/mL, 0.35 mmol) in dry THF (2.8 mL) was added slowly lithium bis(trimethylsilyl)amide (1.4 mL, 1 M in THF, 1.4 mmol). The mixture was stirred for 3 hours at room temperature. Then it was quenched with NH$_4$Cl-solution (aq., sat., 10 mL) and EtOAc was added (5 mL). The two layers were separated and the aqueous layer was extracted with EtOAc (2×10 mL). The combined organic layers were concentrated under reduced pressure. The crude was purified on silica using a DCM to EtOAc gradient to yield 4-[[2-[tert-butyl(dimethyl)silyl]oxy-1-(hydroxymethyl)-2-(4-pyridyl)ethyl]sulfamoyl]-N-(3,4-difluorophenyl)-3-fluoro-1-methyl-pyrrole-2-carboxamide (104 mg) as a brown solid.

4-[[2-[tert-butyl(dimethyl)silyl]oxy-1-(hydroxymethyl)-2-(4-pyridyl)ethyl]sulfamoyl]-N-(3,4-difluorophenyl)-3-fluoro-1-methyl-pyrrole-2-carboxamide (104 mg, 0.17 mmol) and cesium fluoride (106 mg, 0.70 mmol) were dissolved in DMF (2 mL) and heated at 110° C. for 18 hours. The reaction mixture was quenched with cold water (5 mL) and the product was extracted with EtOAc (3×5 mL). The combined organic layers were evaporated and the crude was purified on silica using a DCM to DCM:MeOH 9:1 gradient to obtain a brown foam. A second purification was performed via preparative HPLC (Stationary phase: RP XBridge Prep C18 OBD-10 μm, 30×150 mm, Mobile phase: 0.25% NH$_4$HCO$_3$ solution in water, ACN) to obtain compound 183 (8 mg) as a mixture of 2 enantiomers. $^1$H NMR (400 MHz, DMSO-d$_6$) δ ppm 3.73-3.80 (m, 1H), 3.81 (s, 3H), 4.17 (dd, J=12.8, 9.2 Hz, 1H), 4.57 (d, J=8.5 Hz, 1H), 4.93 (dd, J=12.9, 2.3 Hz, 1H), 6.10 (br s, 1H), 7.33-7.51 (m, 5H), 7.71 (br s, 1H), 7.87 (ddd, J=13.2, 7.5, 2.5 Hz, 1H), 8.53-8.62 (m, 2H), 9.42 (s, 1H); Method D; Rt: 1.62 min. m/z: 463 (M−H)$^−$ Exact mass: 464.1.

Compound 184: (3R)—N-[3-(difluoromethyl)-4-fluoro-phenyl]-3-(hydroxymethyl)-7-methyl-1,1-dioxo-2,3,4,5-tetrahydropyrrolo[3,4-f]thiazepine-6-carboxamide

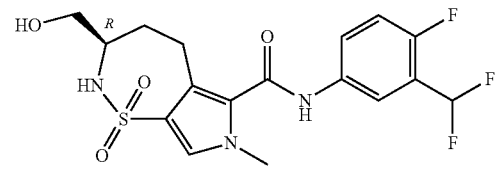

Diisobutylaluminum hydride (1.5 mL, 1 M in heptane, 1.5 mmol) was added dropwise during 5 minutes to a solution of 06-ethyl 03-methyl (3R)-7-methyl-1,1-dioxo-2,3,4,5-tetrahydropyrrolo[3,4-f]thiazepine-3,6-dicarboxylate (239 mg, 0.70 mmol) in 2-MeTHF (25 mL, 0.86 g/mL, 250 mmol) at −78° C. and stirred 1 hour. Another amount of diisobutylaluminum hydride (3 mL, 1 M, 3 mmol) was added and the reaction mixture was stirred 15 minutes at −78° C. The reaction mixture was allowed to reach room temperature in a water bath during 10 minutes and quenched with methanol (10 mL). The reaction mixture was diluted with HCl (aq., 1 M, 10 mL) and extracted with EtOAc (50 mL). The organic layer was separated, dried over magnesium sulfate, filtered and concentrated. The residue was purified on silica using a gradient from 0 till 100% EtOAc in heptane yielding ethyl (3R)-3-(hydroxymethyl)-7-methyl-1,1-dioxo-2,3,4,5-tetrahydropyrrolo[3,4-f]thiazepine-6-carboxylate (62 mg) as a white powder. Method D; Rt: 1.31 min. m/z: 301 (M−H)$^−$ Exact mass: 302.1.

Lithium bis(trimethylsilyl)amide in THF (1 mL, 1 M in THF, 1 mmol) was added to a solution of ethyl (3R)-3-(hydroxymethyl)-7-methyl-1,1-dioxo-2,3,4,5-tetrahydropyrrolo[3,4-f]thiazepine-6-carboxylate (62 mg, 0.205 mmol)

and 3-(difluoromethyl)-4-fluoro-aniline hydrochloride (51 mg, 0.26 mmol) in THF (3 mL) and stirred 3 hours. More 3-(difluoromethyl)-4-fluoro-aniline hydrochloride (102 mg, 0.52 mmol) and lithium bis(trimethylsilyl)amide in THF (2 mL, 1 M in THF, 2 mmol) were added and stirred 1 hour. The reaction mixture was quenched with NH₄Cl (aq., sat.), diluted with brine and extracted with EtOAc. The organic layer was dried over magnesium sulfate, filtered and concentrated. The residue was purified on silica using a gradient from 10 till 100% EtOAc in heptane and further via preparative HPLC (Stationary phase: RP XBridge Prep C18 OBD-10 μm, 30×150 mm, Mobile phase: 0.25% NH₄HCO₃ solution in water, ACN) yielding compound 184 (11 mg). $^1$H NMR (400 MHz, DMSO-$d_6$) δ ppm 1.22-1.36 (m, 1H), 2.02 (br dd, J=14.3, 6.6 Hz, 1H), 2.75-2.85 (m, 1H), 2.99-3.09 (m, 1H), 3.26 (dt, J=10.3, 6.8 Hz, 1H), 3.38-3.53 (m, 2H), 3.69 (s, 3H), 4.76 (t, J=5.7 Hz, 1H), 6.91 (d, J=9.7 Hz, 1H), 7.07-7.40 (m, 2H), 7.42 (s, 1H), 7.78-7.84 (m, 1H), 8.06 (dd, J=6.2, 2.4 Hz, 1H), 10.49 (s, 1H); Method D; Rt: 1.50 min. m/z: 416 (M–H)⁻ Exact mass: 417.1.

Compound 185: N-(3-cyano-2,4-difluoro-phenyl)-3-(1-hydroxy-1-methyl-ethyl)-7-methyl-1,1-dioxo-2,3,4,5-tetrahydropyrrolo[3,4-f]thiazepine-6-carboxamide

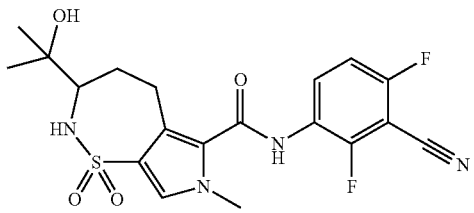 [SMILES: Cn1cc2c(c1C(=O)Nc1ccc(F)c(C#N)c1F)CCC(C(C)(C)O)NS2(=O)=O]

A microwave tube was loaded with compound 179 (248 mg, 0.5 mmol), zinc cyanide (41 mg, 0.35 mmol), and DMF (5 mL). This solution was purged with nitrogen for 10 minutes and 1,1'-bis(diphenylphosphino)ferrocenedichloropalladium(II) (37 mg, 0.05 mmol) was added. The tube was closed and stirred and heated under microwave irradiation at 160° C. for 30 minutes. The reaction mixture was cooled and purged with nitrogen for 10 minutes and Pd(PPh₃)₄ (58 mg, 0.05 mmol) was added. The tube was closed and stirred and heated under microwave irradiation at 160° C. for 50 minutes. The reaction mixture was filtered over a pad of dicalite, rinsed with 10 mL of acetonitrile and concentrated in vacuo. The residue was purified using preparative HPLC (Stationary phase: RP XBridge Prep C18 OBD-10 μm, 50×150 mm, Mobile phase: 0.25% NH₄HCO₃ solution in water, ACN) yielding compound 185 (17 mg). $^1$H NMR (400 MHz, DMSO-$d_6$) δ ppm 1.03 (s, 3H), 1.17 (s, 3H), 1.31-1.42 (m, 1H), 2.18 (br dd, J=13.5, 6.9 Hz, 1H), 2.67-2.78 (m, 1H), 3.15-3.29 (m, 2H), 3.70 (s, 3H), 4.40 (s, 1H), 6.85 (d, J=10.6 Hz, 1H), 7.42-7.48 (m, 2H), 8.07 (td, J=8.9, 6.1 Hz, 1H), 10.32 (br s, 1H); Method B; Rt: 0.76 min. m/z: 437 (M–H)⁻ Exact mass: 438.1.

Compound 186: (3R)—N-[3-(difluoromethyl)-2,4-difluoro-phenyl]-3-[(1S)-1-hydroxyethyl]-7-methyl-1,1-dioxo-2,3-dihydropyrrolo[3,4-f]thiazepine-6-carboxamide

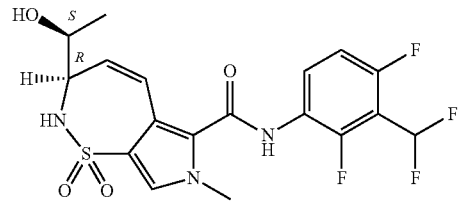

Compound 186 (72 mg) was prepared similarly as described for compound 84, using 3-(difluoromethyl)-2,4-difluoro-aniline instead of 3,4-difluoroaniline. $^1$H NMR (400 MHz, DMSO-$d_6$) δ ppm 1.21 (d, J=6.2 Hz, 3H), 3.64-3.74 (m, 1H), 3.75 (s, 3H), 3.78-3.85 (m, 1H), 4.98 (d, J=5.9 Hz, 1H), 5.98 (dd, J=12.5, 2.6 Hz, 1H), 6.69 (dd, J=12.7, 2.5 Hz, 1H), 7.35 (t, J=52.0 Hz, 1H), 7.29-7.48 (m, 2H), 7.58 (s, 1H), 7.84-7.91 (m, 1H), 10.41 (br s, 1H); Method B; Rt: 0.78 min. m/z: 446 (M–H)⁻ Exact mass: 447.1.

Compound 187: N-[3-(difluoromethyl)-4-fluoro-phenyl]-3,7-dimethyl-3-[(1-methylimidazol-2-yl)methyl]-1,1-dioxo-2,4-dihydropyrrolo[3,4-b][1,4,5]oxathiazepine-6-carboxamide

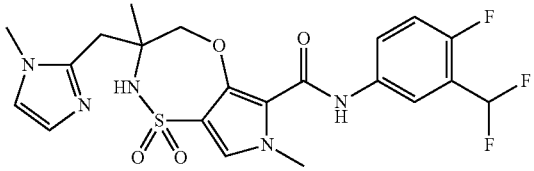 [SMILES: Cn1ccnc1CC1(C)COc2c(cn(C)c2C(=O)Nc2ccc(F)c(C(F)F)c2)S(=O)(=O)N1]

Compound 187 (75 mg) was prepared similarly as described for compound 173, using 3-(difluoromethyl)-4-fluoro-aniline instead of 3,4-difluoroaniline. $^1$H NMR (400 MHz, DMSO-$d_6$) δ ppm 1.33 (s, 3H), 3.01-3.06 (m, 2H), 3.64 (s, 3H), 3.81 (s, 3H), 4.54 (d, J=13.2 Hz, 1H), 4.64 (d, J=13.4 Hz, 1H), 6.82 (d, J=1.1 Hz, 1H), 7.05 (d, J=1.1 Hz, 1H), 7.22 (t, J=54.4 Hz, 1H), 7.36 (t, J=9.5 Hz, 1H), 7.45 (s, 1H), 7.76-7.81 (m, 1H), 8.00 (dd, J=6.3, 2.5 Hz, 1H), 8.08 (br s, 1H), 9.41 (s, 1H); Method B; Rt: 0.93 min. m/z: 496 (M–H)⁻ Exact mass: 497.1, MP: 282.8° C.

Compound 188: (3R)—N-[3-(difluoromethyl)-2,4-difluoro-phenyl]-3-[(1S)-1-hydroxyethyl]-7-methyl-1,1-dioxo-2,3,4,5-tetrahydropyrrolo[3,4-f]thiazepine-6-carboxamide

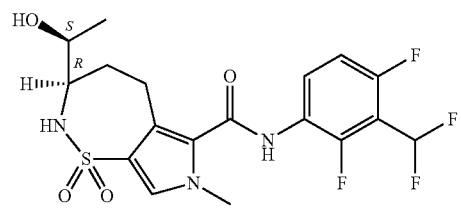

Compound 188 (96 mg) was prepared similarly as described for compound 88, using 3-(difluoromethyl)-2,4-difluoro-aniline instead of 3,4-difluoroaniline. $^1$H NMR (400 MHz, DMSO-d$_6$) δ ppm 1.13 (d, J=6.2 Hz, 3H), 1.27-1.38 (m, 1H), 2.21 (br dd, J=14.0, 6.9 Hz, 1H), 2.66-2.80 (m, 1H), 3.16-3.27 (m, 2H), 3.44-3.52 (m, 1H), 3.70 (s, 3H), 4.67 (d, J=5.7 Hz, 1H), 6.90 (br d, J=10.1 Hz, 1H), 7.34 (br t, J=52.2 Hz, 1H), 7.30 (br t, J=9.5 Hz, 1H), 7.43 (s, 1H), 7.85-7.92 (m, 1H), 10.14 (br s, 1H); Method B; Rt: 0.88 min. m/z: 448 (M–H)$^-$ Exact mass: 449.1, MP: 277.1° C.

Compound 189: N-(3-cyano-4-fluoro-phenyl)-3-(difluoromethyl)-7-methyl-1,1-dioxo-2,3-dihydropyrrolo[3,4-f]thiazepine-6-carboxamide

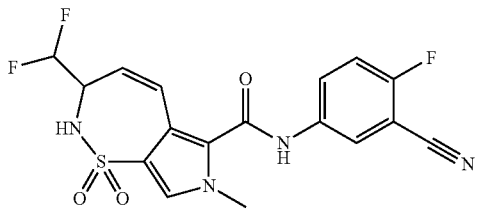 [SMILES: Cn1cc2c(c1C(=O)Nc1ccc(F)c(C#N)c1)C=CC(C(F)F)NS2(=O)=O]

(S)-(–)-2-methyl-2-propanesulfinamide (21.2 g, 175 mmol) was mixed with 1-ethoxy-2,2-difluoroethanol (20.1 g, 159 mmol). Titanium(IV)ethoxide (50 mL, 1.09 g/mL, 238 mmol) was added to form a clear, thick solution which was heated to 80° C. with a reflux condenser under nitrogen for 2 days. The mixture was cooled to room temperature and diluted using EtOAc (500 mL). This was poured into brine (500 mL) under vigorous stirring. This biphasic mixture was filtered over a pad of dicalite which was rinsed with EtOAc (500 mL). The layers of the filtrate were separated and the organic layer was dried on Na$_2$SO$_4$, filtered and concentrated in vacuo. The crude was purified on silica using gradient elution (EtOAc:heptane 0:100 to 100:0) yielding N-(1-ethoxy-2,2-difluoro-ethyl)-2-methyl-propane-2-sulfinamide (18.3 g). Method B; Rt: 0.69 min. m/z: 230 (M+H)$^+$ Exact mass: 229.1.

N-(1-ethoxy-2,2-difluoro-ethyl)-2-methyl-propane-2-sulfinamide (18.0 g, 78.5 mmol) in DCM (300 mL) was cooled under a nitrogen flow to –50° C. To this was added vinylmagnesium bromide (118 mL, 1 M, 118 mmol) drop wise under nitrogen and stirring, maintaining the temperature below –47° C. After complete addition stirring was continued for 3 hours, allowed to reach 0° C. and stirred for 2 hours. The reaction mixture was quenched with NH$_4$Cl (aq., sat.) and diluted with EtOAc (500 mL). The layers were separated and the aqueous layer was extracted with EtOAc (2×250 mL). The combined organics were dried on Na$_2$SO$_4$, filtered and concentrated in vacuo. The residue was purified on silica using a gradient from heptane to EtOAc to yield N-[1-(difluoromethyl)allyl]-2-methyl-propane-2-sulfinamide (8.86 g). Method B; Rt: 0.71 min. m/z: 212 (M+H)$^+$ Exact mass: 211.1.

N-[1-(difluoromethyl)allyl]-2-methyl-propane-2-sulfinamide (8.86 g, 42.0 mmol) was dissolved in MeOH (100 mL) and cooled to 0° C. This was treated with HCl (21 mL, 4 M in dioxane, 84 mmol). The resulting mixture was stirred for 2 hours. The mixture was concentrated in vacuo. The obtained residue was triturated with diethylether, filtered, rinsed with diethylether (100 mL) and dried in a vacuum oven to yield 1,1-difluorobut-3-en-2-amine hydrochloride (5.4 g) as a white solid.

Methyl 3-bromo-4-chlorosulfonyl-1-methyl-pyrrole-2-carboxylate (3.68 g, 11.6 mmol) was dissolved in pyridine (10 mL). 1,1-difluorobut-3-en-2-amine hydrochloride (2 g, 13.9 mmol) was added and the mixture was stirred at room temperature for 19 hours. The resulting mixture was concentrated in vacuo and the residue was purified on silica (gradient elution: EtOAc:heptane 0:100 to 100:0) yielding methyl 3-bromo-4-[1-(difluoromethyl)allylsulfamoyl]-1-methyl-pyrrole-2-carboxylate (1200 mg). Method B; Rt: 0.84 min. m/z: 385 (M–H)$^-$ Exact mass: 386.0.

Methyl 3-bromo-4-[1-(difluoromethyl)allylsulfamoyl]-1-methyl-pyrrole-2-carboxylate (200 mg, 0.52 mmol) and 5-amino-2-fluoro-benzonitrile (84 mg, 0.62 mmol) in dry THF (5 mL) was treated with lithium bis(trimethylsilyl)amide (1.6 mL, 1 M in THF, 1.6 mmol) at room temperature. After 1 hour at room temperature, lithium bis(trimethylsilyl)amide (1 mL, 1 M in THF, 1 mmol) was added and the mixture was stirred at room temperature for 1 hour. The mixture was quenched with NH$_4$Cl (aq., sat., 10 mL) and brine (10 mL). The layers were separated and the water layer was extracted with EtOAc (3×20 mL). The combined extracts were dried on Na$_2$SO$_4$, filtered and concentrated in vacuo. The crude was purified on silica (gradient elution: EtOAc:heptane 0:100 to 100:0) yielding 3-bromo-N-(3-cyano-4-fluoro-phenyl)-4-[1-(difluoromethyl)allylsulfamoyl]-1-methyl-pyrrole-2-carboxamide (210 mg).

3-bromo-N-(3-cyano-4-fluoro-phenyl)-4-[1-(difluoromethyl)allylsulfamoyl]-1-methyl-pyrrole-2-carboxamide (210 mg, 0.43 mmol) in DMF (1 mL) with TEA (0.12 mL, 0.73 g/mL, 0.85 mmol) was purged with nitrogen for 5 minutes. Then bis(tri-tert-butylphosphine)palladium(0) (11 mg, 0.021 mmol) was added and the mixture was heated under nitrogen in a sealed tube at 90° C. for 2 hours. The mixture was poured on a silica plug as such and a gradient from heptane to EtOAc was applied yielding compound 189 (86 mg). $^1$H NMR (400 MHz, DMSO-d$_6$) δ ppm 3.74 (s, 3H) 4.38-4.59 (m, 1H) 5.74 (dd, J=12.54, 2.86 Hz, 1H) 6.07-6.49 (m, 1H) 6.76 (dd, J=12.54, 2.64 Hz, 1H) 7.56 (t, J=9.13 Hz, 1H) 7.68 (s, 1H) 7.98 (ddd, J=9.19, 4.90, 2.64 Hz, 1H) 8.03-8.34 (m, 2H) 10.93 (br s, 1H); Method B; Rt: 0.88 min. m/z: 409 (M–H)$^-$ Exact mass: 410.1.

Compound 190: 3-[(2-chloro-4-pyridyl)methyl]-N-(3,4-difluorophenyl)-3,7-dimethyl-1,1-dioxo-2,4-dihydropyrrolo[3,4-b][1,4,5]oxathiazepine-6-carboxamide

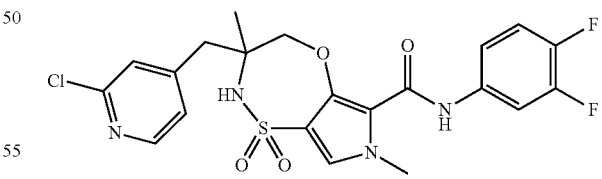

Compound 190 (90 mg) was prepared similarly as described for compound 162, using 2-chloro-4-(chloromethyl)pyridine instead of 3-(chloromethyl)-5-methylisoxazole. $^1$H NMR (400 MHz, DMSO-d$_6$) δ ppm 1.37 (s, 3H) 2.65 (d, J=12.9 Hz, 1H) 3.35 (d, J=13.2 Hz, 1H) 3.97 (s, 3H) 4.38 (d, J=13.2 Hz, 1H) 4.65 (s, 1H) 4.98 (br d, J=13.4 Hz, 1H) 7.07 (s, 1H) 7.09-7.18 (m, 2H) 7.26 (d, J=1.3 Hz, 1H) 7.32 (s, 1H) 7.61-7.69 (m, 1H) 8.39 (d, J=5.1 Hz, 1H) 8.61 (s, 1H); Method B; Rt: 1.07 min. m/z: 495 (M–H)$^-$ Exact mass: 496.1, MP: 225.0° C.

Compound 191: N-(3,4-difluorophenyl)-3,7-dimethyl-1,1-dioxo-3-(4-pyridylmethyl)-2,4-dihydropyrrolo[3,4-b][1,4,5]oxathiazepine-6-carboxamide

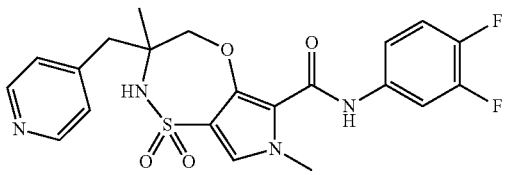 [SMILES: Cn1cc2c(c1C(=O)Nc1ccc(F)c(F)c1)OCC(C)(Cc1ccncc1)NS2(=O)=O]

Compound 190 (70 mg, 0.14 mmol) was dissolved in MeOH (25 mL) and Pd/C (10%) (15 mg, 0.014 mmol) was added and the reaction mixture was set under a hydrogen atmosphere. After 2 hours the solution was filtered over dicalite, concentrated in vacuo, redissolved in DCM (30 mL), neutralized with NaHCO$_3$ (aq., sat.) and the combined organics were concentrated in vacuo and purified on silica using DCM/MeOH 100/0 to 90/10 to yield compound 191 (23 mg). $^1$H NMR (400 MHz, DMSO-d$_6$) δ ppm 1.15 (s, 3H) 2.74 (d, J=13.0 Hz, 1H) 3.07 (d, J=12.8 Hz, 1H) 3.82 (s, 3H) 4.40 (d, J=13.2 Hz, 1H) 4.63 (d, J=13.6 Hz, 1H) 7.30-7.36 (m, 2H) 7.40-7.46 (m, 2H) 7.49 (s, 1H) 7.78 (br s, 1H) 7.82-7.90 (m, 1H) 8.51-8.53 (m, 2H) 9.41 (s, 1H); Method B; Rt: 0.96 min. m/z: 461 (M−H)$^−$ Exact mass: 462.1, MP: 276.0° C.

Synthesis of
2-amino-2-(1-methylpyrazol-3-yl)propan-1-ol

A 30 ml tube was charged with ethyl N-(diphenylmethylene)glycinate (2.5 g, 9.35 mmol), 3-bromo-1-methyl-1h-pyrazole (1.51 g, 9.35 mmol), potassium phosphate tribasic (6 g, 27.7 mmol) in toluene (15 mL) and the mixture was purged with N$_2$ for 5 minutes. Bis(tri-tert-butylphosphine)palladium(0) (526 mg, 1.03 mmol) was added and the vial was capped and the mixture was stirred at 100° C. for 16 hours. The mixture was cooled and filtered over decalite. The filtrate was concentrated in vacuo. The residue was purified by column chromatography using a gradient from 0 till 100% EtOAc in heptane. The product fractions were concentrated in vacuo to yield ethyl 2-(benzhydrylideneamino)-2-(1-methylpyrazol-3-yl)acetate (1.95 g) as a pale yellow oil.

Ethyl 2-(benzhydrylideneamino)-2-(1-methylpyrazol-3-yl)acetate (1.95 g, 5.61 mmol) was dissolved in DMF (30 mL) under N$_2$ atmosphere. The mixture was cooled on a ice bath and NaH (60% dispersion in mineral oil) (269 mg, 6.74 mmol) was added portionwise. The mixture was stirred at 5° C. for 30 minutes. MeI (0.42 mL, 2.28 g/mL, 6.74 mmol) was added dropwise and the mixture was stirred at 5° C. for 15 minutes and was then allowed to rise to room temperature. The mixture was stirred at room temperature for 16 hours. The mixture was quenched with water and the mixture was concentrated in vacuo. The residue was partitioned between water and EtOAc and the organic layer was separated, washed with brine, dried (MgSO4), filtered and concentrated in vacuo. The residue was purified by column chromatography using a gradient from 0 till 50% EtOAc in heptane. The product fractions were concentrated in vacuo to yield ethyl 2-(benzhydrylideneamino)-2-(1-methylpyrazol-3-yl)propanoate (1.1 g) as a yellow oil.

Ethyl 2-(benzhydrylideneamino)-2-(1-methylpyrazol-3-yl)propanoate (1.1 g, 3.04 mmol) was dissolved in diethylether (20 mL). HCl (3.7 mL, 1 M in H$_2$O, 3.7 mmol) was added and the mixture was stirred at room temperature for 3 hours. The organic layer was separated and the water layer was neutralized with NaHCO$_3$. The water layer was extracted with 2-MeTHF and the organic layer was dried (MgSO4), filtered and concentrated in vacuo. The residue was purified by column chromatography using a gradient from 0 till 100% MeOH/NH3 (90/10) in DCM. The product fractions were concentrated in vacuo to yield ethyl 2-amino-2-(1-methylpyrazol-3-yl)propanoate (382 mg) as a clear oil. Method B; Rt: 0.52 min. m/z: 198 (M+H)$^+$ Exact mass: 197.1.

Ethyl 2-amino-2-(1-methylpyrazol-3-yl)propanoate (382 mg, 1.94 mmol) was dissolved in MeOH (10 mL) under N$_2$. Sodium borohydride (147 mg, 3.87 mmol) was added and the mixture was stirred at room temperature for 16 hours. The mixture was concentrated in vacuo. The residue was purified by column chromatography using a gradient from 0 till 100% MeOH/NH3 (90/10) in DCM. The product fractions were concentrated in vacuo to yield 2-amino-2-(1-methylpyrazol-3-yl)propan-1-ol (230 mg) as a clear oil.

Compound 192: N-(3,4-difluorophenyl)-3,7-dimethyl-3-(1-methylpyrazol-3-yl)-1,1-dioxo-2,4-dihydropyrrolo[3,4-b][1,4,5]oxathiazepine-6-carboxamide

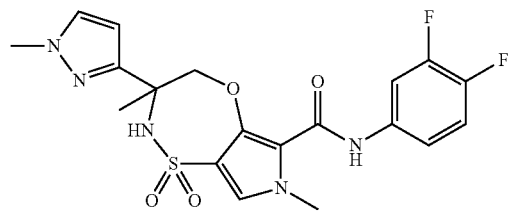 [SMILES: Cn1ccc(C2(C)COc3c(cn(C)c3C(=O)Nc3ccc(F)c(F)c3)S(=O)(=O)N2)n1]

Compound 192 (223 mg) was prepared similarly as described for compound 125, using 2-amino-2-(1-methylpyrazol-3-yl)propan-1-ol instead of 2-amino-2-phenylpropan-1-ol hydrochloride. $^1$H NMR (400 MHz, DMSO-d$_6$) δ ppm 1.59 (s, 3H), 3.79 (s, 3H), 3.82 (s, 3H), 4.81-4.92 (m, 2H), 6.33 (d, J=2.2 Hz, 1H), 7.36-7.50 (m, 3H), 7.60 (d, J=2.2 Hz, 1H), 7.87 (ddd, J=13.2, 7.5, 2.5 Hz, 1H), 8.16 (s, 1H), 9.33-9.38 (m, 1H); Method B; Rt: 1.05 min. m/z: 450 (M−H)$^−$ Exact mass: 451.1. The racemic mixture was separated in its enantiomers via preparative SFC (Stationary phase: Chiralpak Daicel AD 20×250 mm, Mobile phase: CO$_2$, EtOH+0.4 iPrNH$_2$) to yield compound 192a (85 mg); Method D; Rt: 1.85 min. m/z: 450 (M−H)$^−$ Exact mass: 451.1, MP: 208.7° C., and 192b (85 mg); Method D; Rt: 1.86 min. m/z: 450 (M−H)$^−$ Exact mass: 451.1; MP: 209.2° C. Method R; Rt: 192a: 4.17 min, 192b: 4.96 min.

Compound 193: (3R)—N-(3-chloro-4-fluoro-phenyl)-3-[(1S)-1-hydroxyethyl]-7-methyl-1,1-dioxo-2,3,4,5-tetrahydropyrrolo[3,4-f]thiazepine-6-carboxamide

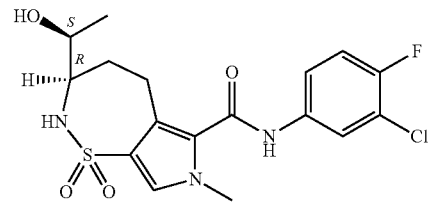

Compound 193 (101 mg) was prepared similarly as described for compound 88, using 3-chloro-4-fluoro-aniline instead of 3,4-difluoroaniline. ¹H NMR (400 MHz, DMSO-$d_6$) δ ppm 1.13 (d, J=6.4 Hz, 3H), 1.21-1.35 (m, 1H), 2.19 (br dd, J=14.3, 6.8 Hz, 1H), 2.70-2.81 (m, 1H), 3.03 (br dd, J=14.9, 6.5 Hz, 1H), 3.15-3.26 (m, 1H), 3.47 (sxt, J=6.3 Hz, 1H), 3.69 (s, 3H), 4.69 (d, J=5.7 Hz, 1H), 6.91 (d, J=10.1 Hz, 1H), 7.38-7.45 (m, 2H), 7.61 (ddd, J=9.0, 4.4, 2.6 Hz, 1H), 8.00 (dd, J=6.9, 2.5 Hz, 1H), 10.46 (s, 1H); Method B; Rt: 0.92 min. m/z: 414 (M−H)⁻ Exact mass: 415.1, MP: 290.8° C.

Compound 194: (3R)—N-(3-chloro-4-fluoro-phenyl)-3-[(1S)-1-hydroxyethyl]-7-methyl-1,1-dioxo-2,3-dihydropyrrolo[3,4-f]thiazepine-6-carboxamide

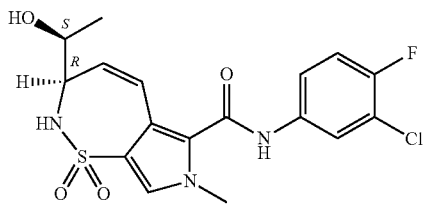

Compound 194 (89 mg) was prepared similarly as described for compound 84, using 3-chloro-4-fluoro-aniline instead of 3,4-difluoroaniline. ¹H NMR (400 MHz, DMSO-$d_6$) δ ppm 1.20 (d, J=6.2 Hz, 3H), 3.62-3.74 (m, 4H), 3.76-3.88 (m, 1H), 4.96 (d, J=5.7 Hz, 1H), 5.96 (dd, J=12.5, 2.6 Hz, 1H), 6.55 (dd, J=12.5, 2.4 Hz, 1H), 7.34-7.46 (m, 2H), 7.57 (s, 1H), 7.62 (ddd, J=9.0, 4.3, 2.5 Hz, 1H), 8.00 (dd, J=6.8, 2.6 Hz, 1H), 10.71 (s, 1H); Method D; Rt: 1.63 min. m/z: 412 (M−H)⁻ Exact mass: 413.1; MP: 211.3° C.

Compound 195: (3R)—N-(4-fluoro-3-methyl-phenyl)-3-(1-hydroxy-1-methyl-ethyl)-7-methyl-1,1-dioxo-3,4-dihydro-2H-pyrrolo[3,4-b][1,4,5]oxathiazepine-6-carboxamide

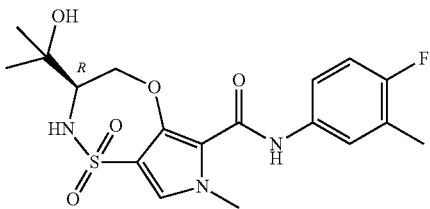

Compound 195 (274 mg) was prepared similarly as described for compound 93, using 4-fluoro-3-methyl-aniline instead of 3,4-difluoroaniline. ¹H NMR (400 MHz, DMSO-$d_6$) δ ppm 1.06 (s, 3H), 1.25 (s, 3H), 2.23 (d, J=2.0 Hz, 3H), 3.47-3.61 (m, 1H), 3.83 (s, 3H), 3.93 (dd, J=12.5, 8.9 Hz, 1H), 4.85 (s, 1H), 4.90-5.00 (m, 1H), 7.09 (t, J=9.2 Hz, 1H), 7.46 (s, 1H), 7.47-7.55 (m, 2H), 7.57 (dd, J=7.0, 2.6 Hz, 1H), 9.22 (s, 1H); Method D; Rt: 1.75 min. m/z: 410 (M−H)⁻ Exact mass: 411.1.

Synthesis of ethyl 4-chlorosulfonyl-3-hydroxy-1-methyl-pyrrole-2-carboxylate

Chlorosulfonic acid (2 mL, 1.753 g/mL, 30 mmol) was cooled to 0° C. and to this stirring liquid was added ethyl 3-hydroxy-1-methyl-pyrrole-2-carboxylate (1 g, 5.9 mmol) portion wise. After addition the mixture was allowed to reach room temperature and then stirred for another hour. The resulting mixture was added dropwise to a stirred ice-water mixture (100 mL) keeping the temperature below 5° C. The mixture was extracted with Me-THF, dried (Na₂SO₄), filtered and concentrated in vacuo. The obtained crude was triturated in cyclohexane, filtered and dried to yield ethyl 4-chlorosulfonyl-3-hydroxy-1-methyl-pyrrole-2-carboxylate (1.1 g).

Compound 196: (3S)—N-(3,4-difluorophenyl)-3-(1-hydroxycyclopropyl)-7-methyl-1,1-dioxo-3,4-dihydro-2H-pyrrolo[3,4-b][1,4,5]oxathiazepine-6-carboxamide

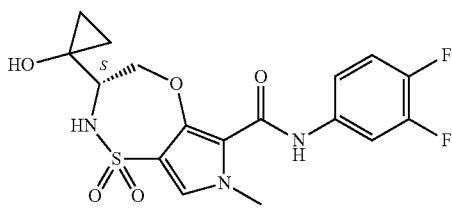

(S)-(−)-3-tert-butoxycarbonyl-4-methoxycarbonyl-2,2-dimethyl-1,3-oxazolidine (5 g, 19.3 mmol) was dissolved in THF (100 mL) and cooled to 0° C. before titanium(IV) isopropoxide (2.9 mL, 0.96 g/mL, 9.6 mmol) was added while stirred over 10 minutes. Then ethylmagnesium bromide (16 mL, 3 M, 48 mmol) was slowly added over 10 minutes to obtain a dark brown solution, and the solution was stirred at 0° C. and then allowed to reach room temperature. After 16 hours the solution was quenched with NH₄Cl (aq., sat.) and extracted with EtOAc, dried over MgSO₄, filtered and concentrated in vacuo. The obtained crude was purified on silica using heptane/EtOAc: 100/0 to 80/20 to yield tert-butyl (4S)-4-(1-hydroxycyclopropyl)-2,2-dimethyl-oxazolidine-3-carboxylate (4.0 g) as light oil. ¹H NMR (400 MHz, DMSO-$d_6$) δ ppm 0.29-0.73 (m, 4H) 1.35-1.49 (m, 15H) 3.74 (br d, J=81.0 Hz, 1H) 3.93-4.09 (m, 2H) 5.30 (br s, 1H).

NaH (933 mg, 60% dispersion in mineral oil, 23.3 mmol) was dissolved in DMF (45 mL) and cooled to 0° C. before a solution of tert-butyl (4S)-4-(1-hydroxycyclopropyl)-2,2-dimethyl-oxazolidine-3-carboxylate (3.0 g, 11.7 mmol) in THF (10 mL) was added. The solution was stirred for 30 minutes and then benzyl bromide (1.5 mL, 1.44 g/mL, 13 mmol) was added. The solution was allowed to reach room temperature and stirred for 16 hours. The solution was quenched with NH₄Cl (aq., sat.) and stirred for 10 minutes before being extracted with EtOAc and washed three times with brine. The combined organic layers were dried over MgSO₄, filtered off and concentrated in vacuo. The obtained crude was purified on silica using heptane/EtOac from 100/0 to 50/50 to yield tert-butyl (4S)-4-(1-benzyloxycyclopropyl)-2,2-dimethyl-oxazolidine-3-carboxylate (2.8 g).

tert-butyl (4S)-4-(1-benzyloxycyclopropyl)-2,2-dimethyl-oxazolidine-3-carboxylate (2.8 g, 8.1 mmol) was dissolved in a mixture of MeOH (30 mL) and THF (65 mL). HCl (25 mL, 1 M in H₂O, 24.176 mmol) was added dropwise and the solution was heated to 50° C. and stirred for 48 hours. The solution was then basified with K₂CO₃ and concentrated in vacuo. The crude was then diluted with DCM and washed with water. The combined organic layers were concentrated in vacuo and purified on silica using a gradient from DCM to DCM/MeOH(NH₃ 7N) 9/1 to yield (2S)-2-amino-2-(1-benzyloxycyclopropyl)ethanol (1.2 g). Method B; Rt: 0.52 min. m/z: 208 (M+H)+ Exact mass: 207.1.

(2S)-2-amino-2-(1-benzyloxycyclopropyl)ethanol (950 mg, 4.6 mmol) was dissolved in dry DCM and 2 g molecular sieves (4 Å) was added at room temperature under inert atmosphere. 4-methoxybenzaldehyde (0.69 mL, 1.119 g/mL, 5.5 mmol) was then added and the solution was stirred at room temperature for 16 hours. The solution was rapidly filtered, concentrated in vacuo and redissolved in MeOH (18 mL) and cooled to 0° C. before sodium borohydride (433 mg, 11.46 mmol) was added and the solution then allowed to reach room temperature. After 2 hours the solution was quenched with water, extracted with DCM, dried over $Na_2SO_4$, filtered, concentrated and purified on silica using heptane/EtOAc 100/0 to 10/90 to yield (2S)-2-(1-benzyloxycyclopropyl)-2-[(4-methoxyphenyl)methylamino]ethanol (1.38 g). $^1$H NMR (400 MHz, DMSO-$d_6$) δ ppm 0.59-0.71 (m, 2H) 0.87-1.03 (m, 2H) 2.68 (dd, J=7.0, 4.6 Hz, 1H) 3.56 (dd, J=10.8, 7.0 Hz, 1H) 3.74 (dd, J=10.8, 4.6 Hz, 1H) 3.78-3.84 (m, 4H) 3.91-3.98 (m, 1H) 4.47-4.62 (m, 2H) 6.86 (d, J=7.7 Hz, 2H) 7.22-7.34 (m, 7H); Method B; Rt: 0.94 min. m/z: 328 (M+H)+ Exact mass: 327.2.

(2S)-2-(1-benzyloxycyclopropyl)-2-[(4-methoxyphenyl) methylamino]ethanol (1.13 g, 3.451 mmol) was dissolved in ACN (20 mL) and Hunig's base (1.78 mL, 0.75 g/mL, 10.4 mmol) was added followed by ethyl 4-chlorosulfonyl-3-hydroxy-1-methyl-pyrrole-2-carboxylate (924 mg, 3.45 mmol). After 16 hours, the solution was quenched with NaHCO₃ (aq., sat., 50 mL) and stirred for 10 minutes. The solution was then extracted with EtOAc (3×50 mL). The combined organics were dried over $Na_2SO_4$, filtered, concentrated in vacuo and purified on silica using heptane/EtOAc 100/0 to 20/80 to yield ethyl 4-[[(1S)-1-(1-benzyloxycyclopropyl)-2-hydroxy-ethyl]-[(4-methoxyphenyl) methyl]sulfamoyl]-3-hydroxy-1-methyl-pyrrole-2-carboxylate (800 mg).

Ethyl 4-[[(1S)-1-(1-benzyloxycyclopropyl)-2-hydroxy-ethyl]-[(4-methoxyphenyl)methyl]sulfamoyl]-3-hydroxy-1-methyl-pyrrole-2-carboxylate (800 mg, 1.43 mmol) was dissolved in THF (15 mL). Triphenylphosphine (413 mg, 1.58 mmol) and di-tert-butyl azodicarboxylate (363 mg, 1.58 mmol) were added. After 16 hours, the solution was extracted with EtOAc, washed with water and the combined organics dried over $MgSO_4$, filtered and concentrated in vacuo. The crude was purified on silica using heptane/EtOAc 100/to 0/100 to yield ethyl (3S)-3-(1-benzyloxycyclopropyl)-2-[(4-methoxyphenyl)methyl]-7-methyl-1,1-dioxo-3,4-dihydropyrrolo[3,4-b][1,4,5]oxathiazepine-6-carboxylate (774 mg).

Ethyl (3 S)-3-(1-benzyloxycyclopropyl)-2-[(4-methoxyphenyl)methyl]-7-methyl-1,1-dioxo-3,4-dihydropyrrolo[3,4-b][1,4,5]oxathiazepine-6-carboxylate (774 mg, 1.43 mmol) was dissolved in THF (20 mL) and 3,4-difluoroaniline (0.16 mL, 1.29 g/mL, 1.58 mmol) and LiHMDS (7 mL, 1 M in THF, 7 mmol) were added. After 2 hours at room temperature the solution was quenched with $NH_4Cl$ (aq., sat.) and extracted with EtOAc, the combined organic layers were dried with $MgSO_4$, filtered, concentrated in vacuo and the crude purified on silica using heptane/EtOAc: 100/0 to 0/100 gradient elution. The obtained crude was partitioned between EtOAc (50 ml), 10 mL HCl (aq., 1M) and water (20 mL) and stirred during 10 minutes. After extraction, the combined organic layers were dried over $MgSO_4$, filtered and concentrated in vacuo to yield (3S)-3-(1-benzyloxycyclopropyl)-N-(3,4-difluorophenyl)-2-[(4-methoxyphenyl) methyl]-7-methyl-1,1-dioxo-3,4-dihydropyrrolo[3,4-b][1,4,5]oxathiazepine-6-carboxamide (621 mg) Method B; Rt: 1.41 min. m/z: 624 (M+H)+ Exact mass: 623.1.

(3S)-3-(1-benzyloxycyclopropyl)-N-(3,4-difluorophenyl)-2-[(4-methoxyphenyl)methyl]-7-methyl-1,1-dioxo-3,4-dihydropyrrolo[3,4-b][1,4,5]oxathiazepine-6-carboxamide (100 mg, 0.16 mmol) was dissolved in DCM (2 mL) and TFA (1.23 mL, 1.49 g/mL, 16.0 mmol) was added at room temperature. After 16 hours, the reaction was quenched with water and NaHCO₃ (aq., sat.) and extracted with DCM. The combined organic layers were dried over $MgSO_4$, filtered, concentrated in vacuo and purified on silica yielding (3S)-3-(1-benzyloxycyclopropyl)-N-(3,4-difluorophenyl)-7-methyl-1,1-dioxo-3,4-dihydro-2H-pyrrolo[3,4-b][1,4,5]oxathiazepine-6-carboxamide (70 mg). Method B; Rt: 1.21 min. m/z: 504 (M+H)+ Exact mass: 503.1.

(3S)-3-(1-benzyloxycyclopropyl)-N-(3,4-difluorophenyl)-7-methyl-1,1-dioxo-3,4-dihydro-2H-pyrrolo[3,4-b][1,4,5]oxathiazepine-6-carboxamide (70 mg, 0.139 mmol) was dissolved in MeOH (20 mL) and HOAc (0.4 mL, 1.049 g/mL, 7.0 mmol) and 5 droplets 0.4% thiophene in THF were added. Pd/C (10%) (15 mg, 0.014 mmol) was added. The solution was hydrogenated at room temperature during 1 hour. The reaction mixture was filtered over dicalite, concentrated in vacuo, purified on silica using heptane/EtOAc 100/0 to 50/50 to yield compound 196 (12 mg). $^1$H NMR (400 MHz, DMSO-$d_6$) δ ppm 0.57-0.80 (m, 4H) 3.46-3.53 (m, 1H) 3.83 (s, 3H) 3.99-4.09 (m, 1H) 4.92 (dd, J=12.5, 1.3 Hz, 1H) 5.50 (s, 1H) 7.36-7.53 (m, 4H) 7.87 (ddd, J=13.1, 7.5, 2.4 Hz, 1H) 9.43 (s, 1H); Method B; Rt: 0.89 min. m/z: 412 (M−H)− Exact mass: 413.1.

Compound 197: 3-[(6-chloro-3-pyridyl)methyl]-N-(3,4-difluorophenyl)-3,7-dimethyl-1,1-dioxo-2,4-dihydropyrrolo[3,4-b][1,4,5]oxathiazepine-6-carboxamide

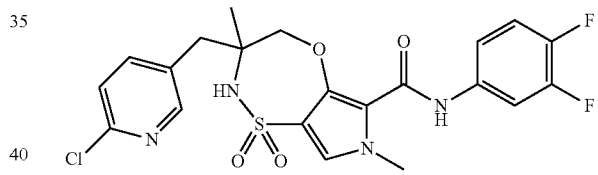

Compound 197 (331 mg) was prepared similarly as described for compound 162, using 2-chloro-5-(chloromethyl)pyridine instead of 3-(chloromethyl)-5-methylisoxazole. $^1$H NMR (400 MHz, DMSO-$d_6$) δ ppm 1.13 (s, 3H), 2.75 (d, J=13.2 Hz, 1H), 3.06 (d, J=13.2 Hz, 1H), 3.82 (s, 3H), 4.41 (d, J=13.0 Hz, 1H), 4.64 (d, J=13.2 Hz, 1H), 7.38-7.46 (m, 2H), 7.49 (s, 1H), 7.52 (d, J=8.1 Hz, 1H), 7.74-7.88 (m, 3H), 8.33 (d, J=2.2 Hz, 1H), 9.40 (s, 1H); Method B; Rt: 1.08 min. m/z: 495 (M−H)− Exact mass: 496.1.

Compound 198: N-(3-chloro-4-fluoro-phenyl)-3-[(6-chloro-3-pyridyl)methyl]-3,7-dimethyl-1,1-dioxo-2,4-dihydropyrrolo[3,4-b][1,4,5]oxathiazepine-6-carboxamide

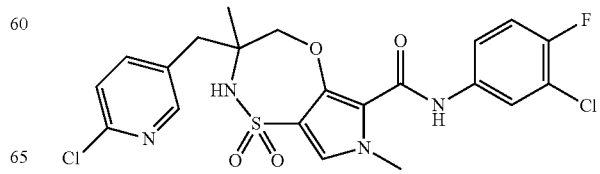

Compound 198 (109 mg) was prepared similarly as described for compound 197, using 3-chloro-4-fluoro-aniline instead of 3,4-difluoroaniline. ¹H NMR (400 MHz, DMSO-d₆) δ ppm 1.14 (s, 3H), 2.74 (d, J=13.2 Hz, 1H), 3.07 (d, J=13.4 Hz, 1H), 3.82 (s, 3H), 4.42 (d, J=13.2 Hz, 1H), 4.64 (d, J=13.2 Hz, 1H), 7.41 (t, J=9.0 Hz, 1H), 7.49 (s, 1H), 7.51 (d, J=8.5 Hz, 1H), 7.63 (ddd, J=9.0, 4.4, 2.6 Hz, 1H), 7.76 (s, 1H), 7.80 (dd, J=8.4, 2.4 Hz, 1H), 7.97 (dd, J=6.8, 2.6 Hz, 1H), 8.33 (d, J=2.4 Hz, 1H), 9.38 (s, 1H); Method B; Rt: 1.13 min. m/z: 511 (M−H)⁻ Exact mass: 512.1.

Compound 199: N-(3,4-difluorophenyl)-3,7-dimethyl-1,1-dioxo-3-(3-pyridylmethyl)-2,4-dihydropyrrolo[3,4-b][1,4,5]oxathiazepine-6-carboxamide

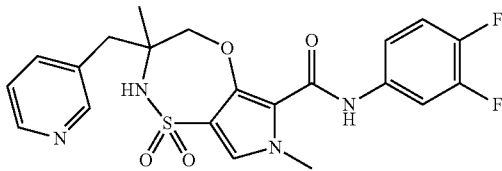 [SMILES: Cn1cc2c(c1C(=O)Nc1ccc(F)c(F)c1)OCC(C)(Cc1cccnc1)NS2(=O)=O]

Compound 197 (389 mg, 0.78 mmol), Pd/C (10%) (42 mg, 0.039 mmol) and TEA (0.22 mL, 0.73 g/mL, 1.57 mmol) were dispensed in THF (50 mL) and set under a hydrogen atmosphere for 2 hours. The reaction mixture was filtered and the residue was triturated in DIPE yielding compound 199 as an off-white powder. This was separated into its enantiomers via preparative SFC (Stationary phase: Chiralpak Diacel AD 20×250 mm, Mobile phase: CO₂, EtOH+0.4 iPrNH₂) yielding compound 199a (141 mg), ¹H NMR (400 MHz, DMSO-d₆) δ ppm 1.14 (s, 3H), 2.74 (d, J=13.2 Hz, 1H), 3.06 (d, J=13.4 Hz, 1H), 3.82 (s, 3H), 4.42 (d, J=13.2 Hz, 1H), 4.63 (d, J=13.2 Hz, 1H), 7.37 (dd, J=7.7, 5.3 Hz, 1H), 7.40-7.45 (m, 2H), 7.48 (s, 1H), 7.71-7.75 (m, 1H), 7.76 (s, 1H), 7.82-7.89 (m, 1H), 8.47 (d, J=5.0 Hz, 1H), 8.52 (s, 1H), 9.41 (s, 1H); Method B; Rt: 0.94 min. m/z: 461 (M−H)⁻ Exact mass: 462.1, MP: 267.1° C. and compound 199b (136 mg), ¹H NMR (400 MHz, DMSO-d₆) δ ppm 1.14 (s, 3H), 2.74 (d, J=13.2 Hz, 1H), 3.06 (d, J=13.2 Hz, 1H), 3.82 (s, 3H), 4.42 (d, J=13.2 Hz, 1H), 4.63 (d, J=13.2 Hz, 1H), 7.37 (dd, J=7.8, 5.2 Hz, 1H), 7.40-7.47 (m, 2H), 7.49 (s, 1H), 7.71-7.75 (m, 1H), 7.76 (s, 1H), 7.82-7.89 (m, 1H), 8.46-8.53 (m, 2H), 9.41 (s, 1H); Method B; Rt: 0.94 min. m/z: 461 (M−H)⁻ Exact mass: 462.1, MP: 268.3° C. after trituration from DIPE. Method R; Rt: 197a: 4.57 min, 197b: 5.09 min.

Compound 200: (3R)—N-(4-fluoro-3-methyl-phenyl)-3-[(1S)-1-hydroxyethyl]-7-methyl-1,1-dioxo-3,4-dihydro-2H-pyrrolo[3,4-b][1,4,5]oxathiazepine-6-carboxamide

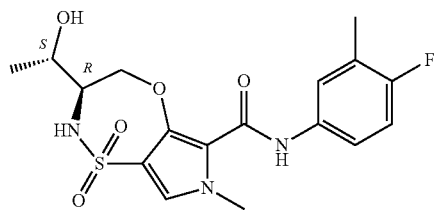

Compound 200 (241 mg) was prepared similarly as described for compound 35, using 4-fluoro-3-methyl-aniline instead of 3,4-difluoroaniline and heating 8 hours at 110° C. The crude product was purified via preparative HPLC (Stationary phase: RP XBridge Prep C18 ODB-5 μm, 30×250 mm, Mobile phase: 0.1% TFA solution in water+5% ACN, ACN) yielding compound 200 (241 mg). ¹H NMR (400 MHz, DMSO-d₆) δ ppm 1.21 (d, J=6.2 Hz, 3H), 2.23 (d, J=2.0 Hz, 3H), 3.36-3.46 (m, 1H), 3.55-3.66 (m, 1H), 3.83 (s, 3H), 3.98 (dd, J=12.7, 8.9 Hz, 1H), 4.88 (dd, J=12.7, 2.0 Hz, 1H), 5.04 (d, J=5.9 Hz, 1H), 7.09 (t, J=9.2 Hz, 1H), 7.44 (s, 1H), 7.48-7.55 (m, 1H), 7.55-7.67 (m, 2H), 9.21 (s, 1H); Method Z; Rt: 7.32 min. m/z: 396 (M−H)⁻ Exact mass: 397.1.

Compound 201: N-(3,4-difluorophenyl)-3,3-bis(hydroxymethyl)-7-methyl-1,1-dioxo-4,5-dihydro-2H-pyrrolo[3,4-f]thiazepine-6-carboxamide

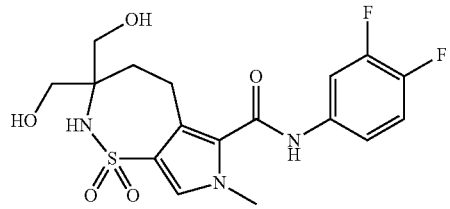 [SMILES: Cn1cc2c(c1C(=O)Nc1ccc(F)c(F)c1)CCC(CO)(CO)NS2(=O)=O]

Compound 131 (55 mg, 0.14 mmol), water (0.200 ml), MeOH (3 mL), PTSA (0.57 mg, 0.003 mmol) and 2,6-ditert-butyl-4-methyl-phenol (0.5 mg, 0.002 mmol) were placed in a sealed tube. The reaction was carried out by heating and stirring for 132 hours at 80° C. The reaction mixture was purified via preparative HPLC (Stationary phase: RP XBridge Prep C18 OBD-10 μm, 50×150 mm, Mobile phase: 0.25% NH₄HCO₃ solution in water, ACN) yielding compound 201 (10 mg); ¹H NMR (400 MHz, DMSO-d₆) δ ppm 1.84-1.96 (m, 2H), 2.86-2.97 (m, 2H), 3.40-3.55 (m, 4H), 3.69 (s, 3H), 4.91 (br s, 1H), 7.35-7.46 (m, 3H), 7.80-7.87 (m, 1H); Method B; Rt: 0.71 min. m/z: 414 (M−H)⁻ Exact mass: 415.1, and crude compound 202 (18 mg).

Compound 202: N-(3,4-difluorophenyl)-3-(hydroxymethyl)-3-(methoxymethyl)-7-methyl-1,1-dioxo-4,5-dihydro-2H-pyrrolo[3,4-f]thiazepine-6-carboxamide

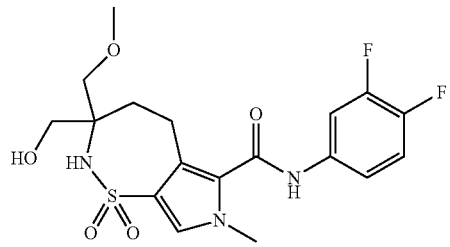 [SMILES: COCC1(CO)CCc2c(cn(C)c2C(=O)Nc2ccc(F)c(F)c2)S(=O)(=O)N1]

The crude compound 202 (18 mg) obtained in the synthesis of compound 201 was purified on silica using a heptane to EtOAc gradient to yield compound 202 (12 mg); ¹H NMR (400 MHz, DMSO-d₆) δ ppm 1.82-1.97 (m, 2H), 2.86-2.98 (m, 2H), 3.27-3.29 (m, 3H), 3.35-3.53 (m, 4H), 3.69 (s, 3H), 4.72 (br s, 1H), 6.94 (br s, 1H), 7.37-7.46 (m, 3H), 7.79-7.87 (m, 1H), 10.36 (br s, 1H); Method B; Rt: 0.81 min. m/z: 428 (M–H)⁻ Exact mass: 429.1.

Compound 203: N-(3,4-difluorophenyl)-3-(hydroxymethyl)-3,7-dimethyl-1,1-dioxo-2,4-dihydropyrrolo[3,4-b][1,4,5]oxathiazepine-6-carboxamide

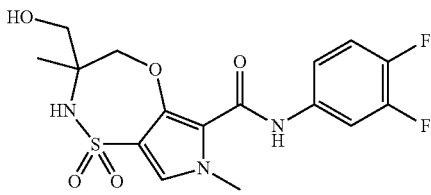 [SMILES: Cn1cc2c(c1C(=O)Nc1ccc(F)c(F)c1)OCC(C)(CO)NS2(=O)=O]

Compound 203 (196 mg) was prepared similarly as described for compound 133, using 2-amino-2-methyl-propane-1,3-diol instead of 2-amino-1,3-propanediol. This racemic mixture was separated into its enantiomers using preparative SFC (Stationary phase: Chiralpak Diacel AD 20×250 mm, Mobile phase: CO₂, EtOH with 0.4% iPrNH₂) yielding compound 203a (46.6 mg); ¹H NMR (400 MHz, DMSO-d₆) δ ppm 1.26 (s, 3H), 3.19-3.29 (m, 1H), 3.68 (dd, J=10.9, 6.1 Hz, 1H), 3.81 (s, 3H), 4.47 (d, J=13.2 Hz, 1H), 4.56 (d, J=13.2 Hz, 1H), 5.06 (t, J=5.8 Hz, 1H), 7.37-7.45 (m, 3H), 7.70 (s, 1H), 7.81-7.88 (m, 1H), 9.33 (s, 1H); Method B; Rt: 0.85 min. m/z: 400 (M–H)⁻ Exact mass: 401.1; and compound 203b (44.7 mg); ¹H NMR (400 MHz, DMSO-d₆) δ ppm 1.26 (s, 3H), 3.22-3.28 (m, 1H), 3.68 (dd, J=10.7, 6.1 Hz, 1H), 3.81 (s, 3H), 4.44-4.59 (m, 2H), 5.06 (t, J=5.8 Hz, 1H), 7.37-7.45 (m, 3H), 7.71 (s, 1H), 7.81-7.88 (m, 1H), 9.33 (s, 1H); Method B; Rt: 0.85 min. m/z: 400 (M–H)⁻ Exact mass: 401.1 as white powders after crystallization from a EtOAc:DIPE mixture. Method R; Rt: 203a: 3.86 min, 203b: 4.39 min.

Compound 204: N-(2-chloro-4-pyridyl)-3-(hydroxymethyl)-3,7-dimethyl-1,1-dioxo-2,4-dihydropyrrolo[3,4-b][1,4,5]oxathiazepine-6-carboxamide

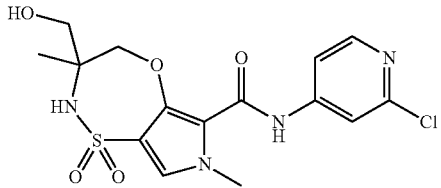 [SMILES: Cn1cc2c(c1C(=O)Nc1ccnc(Cl)c1)OCC(C)(CO)NS2(=O)=O]

Compound 204 (205 mg) was prepared similarly as described for compound 203, using 2-chloropyridin-4-amine instead of 3,4-difluoroaniline. The crude product was purified via preparative HPLC (Stationary phase: RP XBridge Prep C18 ODB-5 μm, 50×150 mm, Mobile phase: 0.25% NH₄HCO₃ solution in water, MeOH) yielding compound 204. This racemic mixture was separated into its enantiomers using preparative SFC (Stationary phase: Chiralpak Diacel AD 20×250 mm, Mobile phase: CO₂, EtOH with 0.4% iPrNH₂) yielding compound 204a (44.2 mg); ¹H NMR (400 MHz, DMSO-d₆) δ ppm 1.27 (s, 3H), 3.26-3.29 (m, 1H), 3.68 (dd, J=10.8, 5.9 Hz, 1H), 3.82 (s, 3H), 4.48-4.61 (m, 2H), 5.08 (t, J=5.8 Hz, 1H), 7.50 (s, 1H), 7.67 (dd, J=5.7, 2.0 Hz, 1H), 7.75 (s, 1H), 7.83 (d, J=1.5 Hz, 1H), 8.28 (d, J=5.7 Hz, 1H), 9.58 (s, 1H); Method B; Rt: 0.72 min. m/z: 399 (M–H)⁻ Exact mass: 400.1; and compound 203b (48.7 mg); ¹H NMR (400 MHz, DMSO-d₆) δ ppm 1.27 (s, 3H), 3.25-3.29 (m, 1H), 3.64-3.72 (m, 1H), 3.82 (s, 3H), 4.48-4.61 (m, 2H), 5.03-5.13 (m, 1H), 7.50 (s, 1H), 7.67 (dd, J=5.6, 1.9 Hz, 1H), 7.75 (br s, 1H), 7.83 (d, J=1.8 Hz, 1H), 8.28 (d, J=5.5 Hz, 1H), 9.58 (br s, 1H); Method B; Rt: 0.85 min. m/z: 399 (M–H)⁻ Exact mass: 400.1 as white powders after crystallization from a EtOAc:DIPE mixture. Method R; Rt: 204a: 4.58 min, 204b: 5.15 min.

Compound 205: 3-but-2-ynyl-N-(3,4-difluorophenyl)-7-methyl-1,1-dioxo-3,4-dihydro-2H-pyrrolo[3,4-b][1,4,5]oxathiazepine-6-carboxamide

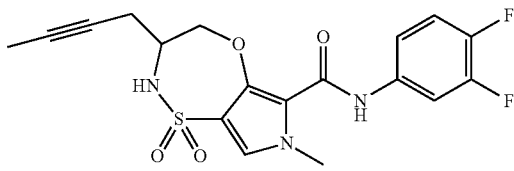 [SMILES: CC#CCC1COc2c(cn(C)c2C(=O)Nc2ccc(F)c(F)c2)S(=O)(=O)N1]

Compound 205 (243 mg) was prepared similarly as described for compound 14, using 2-aminohex-4-yn-1-ol instead of DL-alaninol and ACN instead of THF as a solvent in the first step. The ring closure was obtained after heating overnight at 110° C. in DMF. ¹H NMR (400 MHz, DMSO-d₆) δ ppm 1.78 (t, J=2.4 Hz, 3H), 2.32-2.47 (m, 2H), 3.68-3.78 (m, 1H), 3.81 (s, 3H), 3.95 (dd, J=13.0, 9.0 Hz, 1H), 4.67 (dd, J=12.8, 2.0 Hz, 1H), 7.36-7.48 (m, 3H), 7.77 (d, J=9.2 Hz, 1H), 7.82-7.88 (m, 1H), 9.45 (s, 1H); Method B; Rt: 1.03 min. m/z: 408 (M–H)⁻ Exact mass: 409.1.

Compound 206: 3-[cyclopropyl(hydroxy)methyl]-N-(4-fluoro-3-methyl-phenyl)-7-methyl-1,1-dioxo-3,4-dihydro-2H-pyrrolo[3,4-b][1,4,5]oxathiazepine-6-carboxamide

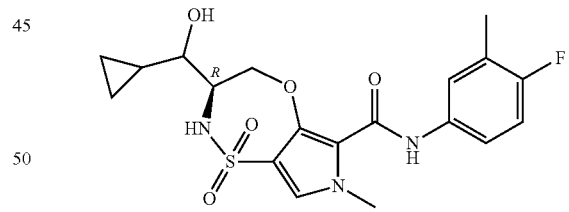

Compound 206 (361 mg) was prepared similarly as described for compound 105, using 4-fluoro-3-methyl-aniline instead of 3,4-difluoroaniline. This racemic mixture was separated in its epimers via preparative SFC (Stationary phase: Chiralpak Diacel ID 20×250 mm, Mobile phase: CO₂, EtOH+0.4 iPrNH₂) yielding 206a (163 mg); ¹H NMR (400 MHz, DMSO-d₆) δ ppm 0.23-0.51 (m, 4H), 1.00-1.12 (m, 1H), 2.23 (d, J=2.0 Hz, 3H), 3.09 (q, J=6.5 Hz, 1H), 3.57-3.69 (m, 1H), 3.83 (s, 3H), 4.01 (dd, J=12.8, 9.1 Hz, 1H), 4.90 (dd, J=12.7, 2.0 Hz, 1H), 5.00 (d, J=5.6 Hz, 1H), 7.09 (t, J=9.2 Hz, 1H), 7.44 (s, 1H), 7.47-7.55 (m, 1H), 7.55-7.64 (m, 2H), 9.22 (s, 1H); Method D; Rt: 1.80 min. m/z: 422 (M–H)⁻ Exact mass: 423.1 and 206b (32 mg); ¹H NMR (400 MHz, DMSO-d₆) δ ppm 0.17-0.48 (m, 4H), 0.96-1.09 (m, 1H), 2.23 (d, J=2.0 Hz, 3H), 3.05-3.18 (m, 1H), 3.71-3.81 (m, 1H), 3.83 (s, 3H), 4.05 (dd, J=12.7, 9.2 Hz, 1H), 4.74 (dd, J=13.2, 0.7 Hz, 1H), 4.90-5.08 (m, 1H), 7.09 (t, J=9.2 Hz, 1H), 7.35-7.47 (m, 2H), 7.47-7.54 (m, 1H), 7.56 (dd, J=6.9, 2.8 Hz, 1H), 9.24 (s, 1H); Method D; Rt: 1.81 min. m/z: 422 (M−H)⁻ Exact mass: 423.1; MP: 234.7° C. Method U; Rt: 206a: 4.19 min, 206b: 5.11 min.

Compound 207: N-(3-chloro-4-fluoro-phenyl)-3-[cyclopropyl(hydroxy)methyl]-7-methyl-1,1-dioxo-3,4-dihydro-2H-pyrrolo[3,4-b][1,4,5]oxathiazepine-6-carboxamide

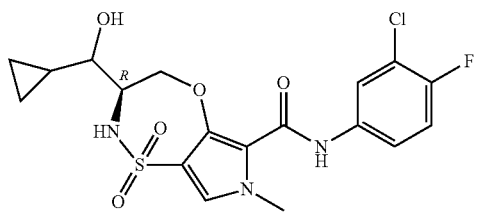

Compound 207 (260 mg) was prepared similarly as described for compound 105, using 3-chloro-4-fluoro-aniline instead of 3,4-difluoroaniline. This racemic mixture was separated in its epimers via preparative SFC (Stationary phase: Chiralpak Diacel ID 20×250 mm, Mobile phase: CO₂, EtOH+0.4 iPrNH₂) yielding 207a (148 mg); ¹H NMR (400 MHz, DMSO-d₆) δ ppm 0.20-0.55 (m, 4H), 0.96-1.12 (m, 1H), 3.09 (q, J=6.5 Hz, 1H), 3.56-3.69 (m, 1H), 3.83 (s, 3H), 4.00 (dd, J=12.8, 9.2 Hz, 1H), 4.91 (dd, J=12.7, 2.0 Hz, 1H), 5.00 (d, J=5.6 Hz, 1H), 7.38 (t, J=9.1 Hz, 1H), 7.47 (s, 1H), 7.60 (d, J=9.9 Hz, 1H), 7.65 (ddd, J=9.1, 4.3, 2.6 Hz, 1H), 8.00 (dd, J=6.8, 2.6 Hz, 1H), 9.41 (s, 1H); Method D; Rt: 1.88 min. m/z: 442 (M−H)⁻ Exact mass: 443.1 and 207b (45 mg); ¹H NMR (400 MHz, DMSO-d₆) δ ppm 0.16-0.49 (m, 4H), 0.95-1.09 (m, 1H), 3.08-3.17 (m, 1H), 3.71-3.81 (m, 1H), 3.83 (s, 3H), 4.04 (dd, J=12.7, 9.2 Hz, 1H), 4.75 (dd, J=12.9, 1.1 Hz, 1H), 5.00 (d, J=4.9 Hz, 1H), 7.39 (t, J=9.1 Hz, 1H), 7.42-7.50 (m, 2H), 7.64 (ddd, J=9.0, 4.3, 2.6 Hz, 1H), 7.99 (dd, J=6.8, 2.6 Hz, 1H), 9.43 (s, 1H); Method D; Rt: 1.81 min. m/z: 442 (M−H)⁻ Exact mass: 443.1; MP: 215.8° C. Method U; Rt: 206a: 4.30 min, 206b: 5.41 min.

Compound 208: 3-[cyclopropyl(hydroxy)methyl]-7-methyl-1,1-dioxo-N-(3,4,5-trifluorophenyl)-3,4-dihydro-2H-pyrrolo[3,4-b][1,4,5]oxathiazepine-6-carboxamide

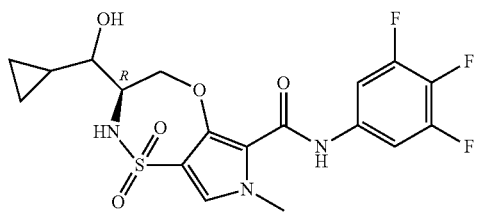

Compound 208 (289 mg) was prepared similarly as described for compound 105, using 3,4,5-trifluoroaniline instead of 3,4-difluoroaniline. This racemic mixture was separated in its epimers via preparative SFC (Stationary phase: Chiralpak Diacel ID 20×250 mm, Mobile phase: CO₂, EtOH+0.4 iPrNH₂) yielding 208a (124 mg); ¹H NMR (400 MHz, DMSO-d₆) δ ppm 0.25-0.53 (m, 4H), 0.99-1.11 (m, 1H), 3.08 (q, J=6.5 Hz, 1H), 3.63 (q, J=8.4 Hz, 1H), 3.82 (s, 3H), 3.99 (dd, J=12.8, 9.2 Hz, 1H), 4.94 (dd, J=12.8, 1.8 Hz, 1H), 5.02 (d, J=5.6 Hz, 1H), 7.50 (s, 1H), 7.62 (br d, J=9.5 Hz, 1H), 7.66-7.77 (m, 2H), 9.49 (s, 1H); Method D; Rt: 1.91 min. m/z: 444 (M−H)⁻ Exact mass: 445.1 and 208b (43 mg); ¹H NMR (400 MHz, DMSO-d₆) δ ppm 0.16-0.50 (m, 4H), 0.95-1.08 (m, 1H), 3.08-3.16 (m, 1H), 3.72-3.81 (m, 1H), 3.82 (s, 3H), 4.04 (dd, J=12.7, 9.2 Hz, 1H), 4.77 (dd, J=12.5, 1.1 Hz, 1H), 5.02 (d, J=4.9 Hz, 1H), 7.41-7.53 (m, 2H), 7.64-7.75 (m, 2H), 9.51 (s, 1H); Method D; Rt: 1.88 min. m/z: 444 (M−H)⁻ Exact mass: 445.1. Method U; Rt: 208a: 3.49 min, 208b: 4.27 min.

Compound 209: N-[2-(difluoromethyl)-4-pyridyl]-3,7-dimethyl-3-[(5-methylisoxazol-3-yl)methyl]-1,1-dioxo-2,4-dihydropyrrolo[3,4-b][1,4,5]oxathiazepine-6-carboxamide

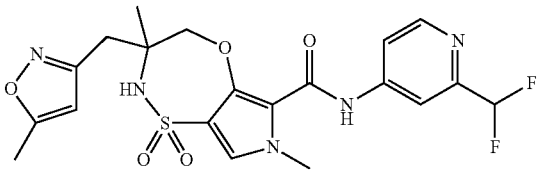 [SMILES: Cc1cc(CC2(C)COc3c(cn(C)c3C(=O)Nc3ccnc(C(F)F)c3)S(=O)(=O)N2)no1]

Compound 209 (92 mg) was prepared similarly as described for compound 162, using 2-(difluoromethyl)pyridin-4-amine instead of 3,4-difluoroaniline. This was separated into its enantiomers via preparative SFC (Stationary phase: Kromasil (R,R) Whelk-O 1 10/100, Mobile phase: CO₂, EtOH+0.4 iPrNH₂) yielding compound 209a (23 mg), ¹H NMR (400 MHz, DMSO-d₆) δ ppm 1.22 (s, 3H), 2.40 (s, 3H), 2.89 (d, J=13.9 Hz, 1H), 3.04 (d, J=14.1 Hz, 1H), 3.83 (s, 3H), 4.44 (d, J=13.2 Hz, 1H), 4.62 (d, J=13.2 Hz, 1H), 6.21 (d, J=0.9 Hz, 1H), 6.91 (t, J=55.0 Hz, 1H), 7.54 (s, 1H), 7.79 (br d, J=5.6 Hz, 1H), 7.95 (br s, 1H), 8.03 (d, J=1.8 Hz, 1H), 8.55 (d, J=5.5 Hz, 1H), 9.71 (s, 1H); Method B; Rt: 0.88 min. m/z: 480 (M−H)⁻ Exact mass: 481.1 and compound 209b (19 mg), ¹H NMR (400 MHz, DMSO-d₆) δ ppm 1.22 (s, 3H), 2.40 (s, 3H), 2.91 (s, 1H), 3.04 (d, J=14.1 Hz, 1H), 3.83 (s, 3H), 4.44 (d, J=13.2 Hz, 1H), 4.61 (s, 1H), 6.21 (s, 1H), 6.91 (t, J=55.0 Hz, 1H), 7.54 (s, 1H), 7.79 (d, J=5.4 Hz, 1H), 7.95 (br s, 1H), 8.03 (d, J=1.8 Hz, 1H), 8.55 (d, J=5.7 Hz, 1H), 9.71 (s, 1H); Method B; Rt: 0.86 min. m/z: 480 (M−H)⁻ Exact mass: 481.1. Method X; Rt: 209a: 5.56 min, 209b: 5.91 min.

Compound 210: N-(3-cyano-4-fluoro-phenyl)-3-(hydroxymethyl)-3,7-dimethyl-1,1-dioxo-2,4-dihydropyrrolo[3,4-b][1,4,5]oxathiazepine-6-carboxamide

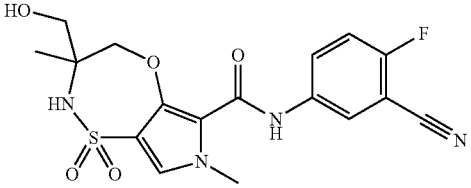 [SMILES: Cn1cc2c(c1C(=O)Nc1ccc(F)c(C#N)c1)OCC(C)(CO)NS2(=O)=O]

Compound 210 (354 mg) was prepared similarly as described for compound 203, using 5-amino-2-fluoro-benzonitrile instead of 3,4-difluoroaniline. This racemic mixture was separated into its enantiomers using preparative SFC (Stationary phase: Chiralpak Diacel AD 20×250 mm, Mobile phase: CO$_2$, EtOH with 0.4% iPrNH$_2$) yielding compound 210a (96.6 mg); $^1$H NMR (400 MHz, DMSO-d$_6$) δ ppm 1.27 (s, 3H), 3.19-3.28 (m, 1H), 3.68 (dd, J=10.6, 6.2 Hz, 1H), 3.82 (s, 3H), 4.49 (d, J=13.2 Hz, 1H), 4.57 (d, J=13.0 Hz, 1H), 5.07 (t, J=5.8 Hz, 1H), 7.45 (s, 1H), 7.52 (t, J=9.1 Hz, 1H), 7.73 (s, 1H), 8.03 (ddd, J=9.2, 5.0, 2.8 Hz, 1H), 8.17 (dd, J=5.7, 2.6 Hz, 1H), 9.42 (s, 1H); Method B; Rt: 0.79 min. m/z: 407 (M−H)$^−$ Exact mass: 408.1; and compound 210b (73.4 mg); $^1$H NMR (400 MHz, DMSO-d$_6$) δ ppm 1.27 (s, 3H), 3.21-3.29 (m, 1H), 3.64-3.71 (m, 1H), 3.82 (s, 3H), 4.49 (d, J=13.2 Hz, 1H), 4.57 (d, J=13.2 Hz, 1H), 5.07 (t, J=5.8 Hz, 1H), 7.45 (s, 1H), 7.52 (t, J=9.1 Hz, 1H), 7.73 (s, 1H), 8.01-8.05 (m, 1H), 8.16-8.19 (m, 1H), 9.42 (s, 1H); Method B; Rt: 0.80 min. m/z: 407 (M−H)$^−$ Exact mass: 408.1 as white powders after crystallization from a EtOAc:DIPE mixture. Method R; Rt: 210a: 4.21 min, 210b: 4.67 min.

Compound 211: N-(3-chloro-4-fluoro-phenyl)-3,7-dimethyl-1,1-dioxo-3-(3-pyridylmethyl)-2,4-dihydropyrrolo[3,4-b][1,4,5]oxathiazepine-6-carboxamide

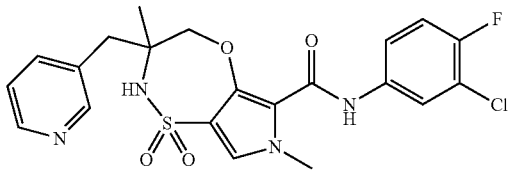 [SMILES: Cn1cc2c(c1C(=O)Nc1ccc(F)c(Cl)c1)OCC(C)(Cc1cccnc1)NS2(=O)=O]

Compound 198 (252 mg, 0.49 mmol), Pd/C (10%) (26 mg, 0.025 mmol), TEA (0.14 mL, 0.73 g/mL, 0.98 mmol) and thiofene (2.15 mL, 0.72 g/mL, 0.4% in DIPE, 0.074 mmol) were dispensed in THF (100 mL) and set under a hydrogen atmosphere for 2 hours. More Pt/C (5%) (96 mg, 0.025 mmol) was added and the reaction mixture was stirred overnight under a hydrogen atmosphere. Pd/C (10%) (52 mg, 0.049 mmol) was added and the reaction mixture was stirred overnight under a hydrogen atmosphere. More Pd/C (10%) (52 mg, 0.049 mmol) was added and the reaction mixture was stirred 2 days under a hydrogen atmosphere. The reaction mixture was filtered and the residue was purified on silica using a heptane to EtOAc gradient and again via preparative HPLC (Stationary phase: RP XBridge Prep C18 OBD-10 μm, 30×150 mm, Mobile phase: 0.25% NH$_4$HCO$_3$ solution in water, ACN) yielding compound 211 (87 mg) as a white powder. $^1$H NMR (400 MHz, DMSO-d$_6$) δ ppm 1.14 (s, 3H), 2.74 (d, J=13.0 Hz, 1H), 3.06 (d, J=13.2 Hz, 1H), 3.82 (s, 3H), 4.42 (d, J=13.0 Hz, 1H), 4.63 (d, J=13.2 Hz, 1H), 7.35-7.44 (m, 2H), 7.48 (s, 1H), 7.61-7.66 (m, 1H), 7.73 (br d, J=7.7 Hz, 2H), 7.97 (dd, J=6.8, 2.6 Hz, 1H), 8.47 (dd, J=4.7, 1.7 Hz, 1H), 8.52 (d, J=1.5 Hz, 1H), 9.39 (s, 1H); Method B; Rt: 1.00 min. m/z: 477 (M−H)$^−$ Exact mass: 478.1, MP: 211.5° C.

Compound 212: N-(3-chloro-4-fluoro-phenyl)-7-methyl-1,1-dioxo-spiro[2,4-dihydropyrrolo[3,4-b][1,4,5]oxathiazepine-3,3'-tetrahydrofuran]-6-carboxamide

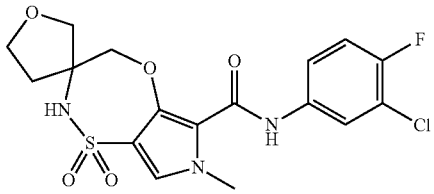 [SMILES: Cn1cc2c(c1C(=O)Nc1ccc(F)c(Cl)c1)OCC1(CCOC1)NS2(=O)=O]

Compound 212 (243 mg) was prepared similarly as described for compound 205, using (3-aminotetrahydrofuran-3-yl)methanol instead of 2-aminohex-4-yn-1-ol. The ring closure was obtained after heating 2 hours at 110° C. in DMF. $^1$H NMR (400 MHz, DMSO-d$_6$) δ ppm 1.99-2.19 (m, 2H), 3.73-3.89 (m, 7H), 4.40-4.53 (m, 2H), 7.40 (t, J=9.1 Hz, 1H), 7.49 (s, 1H), 7.66 (ddd, J=9.1, 4.2, 2.5 Hz, 1H), 7.98 (dd, J=6.8, 2.6 Hz, 1H), 8.24 (br s, 1H), 9.36 (s, 1H); Method B; Rt: 0.96 min. m/z: 428 (M−H)$^−$ Exact mass: 429.1. This was separated into its enantiomers via preparative SFC (Stationary phase: Chiralpak Diacel IC 20×250 mm, Mobile phase: CO$_2$, EtOH+0.4 iPrNH$_2$) yielding compound 212a (97 mg) and compound 212b (14 mg). Method AA; Rt: 212a: 4.78 min, 212b: 5.55 min.

Compound 213: N-(2-chloro-4-pyridyl)-3,7-dimethyl-3-[(5-methylisoxazol-3-yl)methyl]-1,1-dioxo-2,4-dihydropyrrolo[3,4-b][1,4,5]oxathiazepine-6-carboxamide

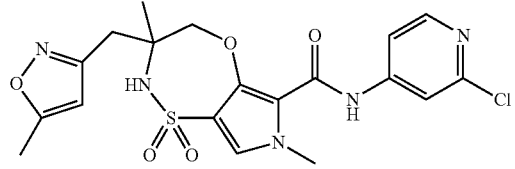 [SMILES: Cc1cc(CC2(C)COc3c(cn(C)c3C(=O)Nc3ccnc(Cl)c3)S(=O)(=O)N2)no1]

Compound 213 (92 mg) was prepared similarly as described for compound 162, using 4-amino-2-chloropyridine instead of 3,4-difluoroaniline. This was separated into its enantiomers via preparative SFC (Stationary phase: Chiralpak Diacel AD 20×250 mm, Mobile phase: CO$_2$, EtOH+ 0.4 iPrNH$_2$) yielding compound 213a (25 mg), $^1$H NMR (400 MHz, DMSO-d$_6$) δ ppm 1.22 (s, 3H), 2.38-2.41 (m, 3H), 2.88 (d, J=13.9 Hz, 1H), 3.04 (d, J=13.9 Hz, 1H), 3.82 (s, 3H), 4.44 (d, J=13.0 Hz, 1H), 4.62 (d, J=13.2 Hz, 1H), 6.21 (d, J=0.9 Hz, 1H), 7.55 (s, 1H), 7.66 (dd, J=5.7, 1.8 Hz, 1H), 7.82 (d, J=1.8 Hz, 1H), 7.95 (br s, 1H), 8.28 (d, J=5.5 Hz, 1H), 9.65 (br s, 1H); Method B; Rt: 0.92 min. m/z: 464 (M−H)$^−$ Exact mass: 465.1 and compound 213b (23 mg), $^1$H NMR (400 MHz, DMSO-d$_6$) δ ppm 1.19-1.24 (m, 3H), 2.37-2.43 (m, 3H), 2.88 (d, J=14.1 Hz, 1H), 3.04 (d, J=14.1 Hz, 1H), 3.82 (s, 3H), 4.44 (d, J=13.2 Hz, 1H), 4.62 (d, J=13.2 Hz, 1H), 6.21 (s, 1H), 7.55 (s, 1H), 7.67 (dd, J=5.7, 1.8 Hz, 1H), 7.82 (d, J=1.8 Hz, 1H), 7.95 (br s, 1H), 8.28 (d, J=5.7 Hz, 1H), 9.65 (s, 1H); Method B; Rt: 0.93 min. m/z: 464 (M−H)$^−$ Exact mass: 465.1. Method R; Rt: 213a: 4.57 min, 213b: 4.87 min.

Compound 214: 3-(hydroxymethyl)-3,7-dimethyl-1,1-dioxo-N-(3,4,5-trifluorophenyl)-2,4-dihydropyrrolo[3,4-b][1,4,5]oxathiazepine-6-carboxamide

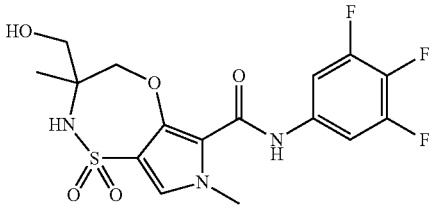 [SMILES: Cn1cc2c(c1C(=O)Nc1cc(F)c(F)c(F)c1)OCC(C)(CO)NS2(=O)=O]

Compound 214 (474 mg) was prepared similarly as described for compound 203, using 3,4,5-trifluoroaniline instead of 3,4-difluoroaniline. This racemic mixture was separated into its enantiomers using preparative SFC (Stationary phase: Chiralpak Diacel AS 20×250 mm, Mobile phase: $CO_2$, iPrOH with 0.4% $iPrNH_2$) yielding compound 214a (80 mg); $^1$H NMR (400 MHz, DMSO-$d_6$) δ ppm 1.27 (s, 3H), 3.18-3.28 (m, 1H), 3.68 (dd, J=10.9, 6.3 Hz, 1H), 3.81 (s, 3H), 4.49 (d, J=13.2 Hz, 1H), 4.57 (d, J=13.2 Hz, 1H), 5.07 (t, J=5.8 Hz, 1H), 7.46 (s, 1H), 7.64-7.74 (m, 3H), 9.39 (s, 1H); Method B; Rt: 0.94 min. m/z: 418 (M–H)$^-$ Exact mass: 419.1; and compound 214b (75 mg); $^1$H NMR (400 MHz, DMSO-$d_6$) δ ppm 1.27 (s, 3H), 3.21-3.30 (m, 1H), 3.68 (dd, J=10.8, 6.2 Hz, 1H), 3.81 (s, 3H), 4.47-4.60 (m, 2H), 5.07 (t, J=5.8 Hz, 1H), 7.46 (s, 1H), 7.64-7.74 (m, 3H), 9.39 (s, 1H); Method B; Rt: 0.95 min. m/z: 418 (M–H)$^-$ Exact mass: 419.1 as white powders after crystallization from a EtOAc:DIPE mixture. Method T; Rt: 214a: 2.90 min, 214b: 3.19 min.

Compound 215: N-[2-(difluoromethyl)-4-pyridyl]-3-(hydroxymethyl)-3,7-dimethyl-1,1-dioxo-2,4-dihydropyrrolo[3,4-b][1,4,5]oxathiazepine-6-carboxamide

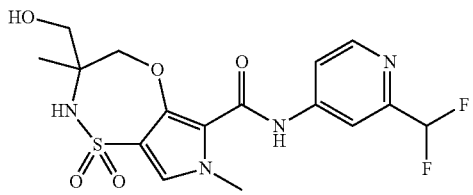 [SMILES: Cn1cc2c(c1C(=O)Nc1ccnc(C(F)F)c1)OCC(C)(CO)NS2(=O)=O]

Compound 215 was prepared similarly as described for compound 203, using 2-(difluoromethyl)pyridin-4-amine instead of 3,4-difluoroaniline. This racemic mixture was separated into its enantiomers using preparative SFC (Stationary phase: Chiralpak Diacel AD 20×250 mm, Mobile phase: $CO_2$, EtOH with 0.4% $iPrNH_2$) yielding compound 215a (78.3 mg); $^1$H NMR (400 MHz, DMSO-$d_6$) δ ppm 1.27 (s, 3H), 3.23-3.29 (m, 1H), 3.68 (dd, J=10.8, 6.2 Hz, 1H), 3.82 (s, 3H), 4.46-4.62 (m, 2H), 5.08 (t, J=5.7 Hz, 1H), 6.91 (t, J=55.0 Hz, 1H), 7.50 (s, 1H), 7.71-7.80 (m, 2H), 8.05 (d, J=2.0 Hz, 1H), 8.54 (d, J=5.5 Hz, 1H), 9.65 (s, 1H); Method B; Rt: 0.72 min. m/z: 415 (M–H)$^-$ Exact mass: 416.1; and compound 215b (79.3 mg); $^1$H NMR (400 MHz, DMSO-$d_6$) δ ppm 1.27 (s, 3H), 3.24-3.29 (m, 1H), 3.68 (dd, J=10.7, 6.1 Hz, 1H), 3.82 (s, 3H), 4.46-4.62 (m, 2H), 5.08 (t, J=5.8 Hz, 1H), 6.91 (t, J=55.0 Hz, 1H), 7.50 (s, 1H), 7.71-7.81 (m, 2H), 8.05 (d, J=2.0 Hz, 1H), 8.54 (d, J=5.5 Hz, 1H), 9.65 (s, 1H); Method B; Rt: 0.72 min. m/z: 415 (M–H)$^-$ Exact mass: 416.1 as white powders after crystallization from a EtOAc:DIPE mixture. Method R; Rt: 215a: 3.83 min, 215b: 4.26 min.

Compound 216: 1'-benzyl-N-(3,4-difluorophenyl)-7-methyl-1,1-dioxo-spiro[2,4-dihydropyrrolo[3,4-b][1,4,5]oxathiazepine-3,3'-pyrrolidine]-6-carboxamide

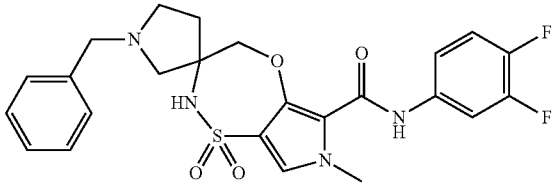 [SMILES: Cn1cc2c(c1C(=O)Nc1ccc(F)c(F)c1)OCC1(CCN(Cc3ccccc3)C1)NS2(=O)=O]

Compound 216 (265 mg) was prepared similarly as described for compound 212, using (3-amino-1-benzyl-pyrrolidin-3-yl)methanol instead of (3-aminotetrahydrofuran-3-yl)methanol. $^1$H NMR (400 MHz, DMSO-$d_6$) ppm 1.93-2.05 (m, 2H), 2.45-2.48 (m, 1H), 2.54 (s, 1H), 2.68 (br d, J=8.1 Hz, 1H), 2.86 (br d, J=9.7 Hz, 1H), 3.61 (q, J=13.1 Hz, 2H), 3.81 (s, 3H), 4.37-4.55 (m, 2H), 7.25 (br d, J=4.0 Hz, 1H), 7.32 (d, J=4.2 Hz, 4H), 7.38-7.48 (m, 3H), 7.80-7.88 (m, 1H), 8.12 (s, 1H), 9.34 (s, 1H); Method B; Rt: 1.19 min. m/z: 501 (M–H)$^-$ Exact mass: 502.2.

Compound 217: N-[2-(difluoromethyl)-4-pyridyl]-3,7-dimethyl-3-[(1-methylpyrazol-3-yl)methyl]-1,1-dioxo-2,4-dihydropyrrolo[3,4-b][1,4,5]oxathiazepine-6-carboxamide

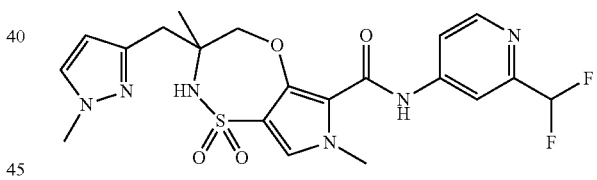

Compound 217 (269 mg) was prepared similarly as described for compound 167, using 2-(difluoromethyl)pyridin-4-amine instead of 3,4-difluoroaniline. This was separated into it's enantiomers via Prep SFC (Stationary phase: Chiralpak Diacel IC 20×250 mm, Mobile phase: $CO_2$, EtOH+0.4 $iPrNH_2$) yielding compound 176a (62.2 mg); $^1$H NMR (400 MHz, DMSO-$d_6$) δ ppm 1.21 (s, 3H), 2.83 (d, J=13.9 Hz, 1H), 2.99 (d, J=13.9 Hz, 1H), 3.80 (s, 3H), 3.83 (s, 3H), 4.42 (d, J=13.2 Hz, 1H), 4.56 (d, J=13.4 Hz, 1H), 6.15 (d, J=2.2 Hz, 1H), 6.92 (t, J=55.1 Hz, 1H), 7.52 (s, 1H), 7.59 (s, 1H), 7.75-7.87 (m, 2H), 8.02 (d, J=2.0 Hz, 1H), 8.55 (d, J=5.5 Hz, 1H), 9.68 (s, 1H); Method B; Rt: 0.85 min. m/z: 479 (M–H)$^-$ Exact mass: 480.1. and compound 176b (59.4 mg); $^1$H NMR (400 MHz, DMSO-$d_6$) δ ppm 1.22 (s, 3H), 2.83 (d, J=13.9 Hz, 1H), 2.99 (d, J=14.1 Hz, 1H), 3.80 (s, 3H), 3.83 (s, 3H), 4.42 (d, J=13.2 Hz, 1H), 4.56 (d, J=13.2 Hz, 1H), 6.15 (d, J=2.2 Hz, 1H), 6.92 (t, J=55.1 Hz, 1H), 7.52 (s, 1H), 7.59 (s, 1H), 7.78 (br d, J=3.7 Hz, 1H), 7.84 (s, 1H), 8.02 (d, J=2.0 Hz, 1H), 8.55 (d, J=5.5 Hz, 1H), 9.68 (s, 1H); Method B; Rt: 0.85 min. m/z: 479 (M–H)$^-$ Exact mass: 480.1. Method AA; Rt: 217a: 5.76 min, 217b: 6.29 min.

Compound 218: 7-methyl-1,1-dioxo-3-[1-(2,2,2-trifluoroethylamino)ethyl]-N-(3,4,5-trifluorophenyl)-2,3,4,5-tetrahydropyrrolo[3,4-f]thiazepine-6-carboxamide

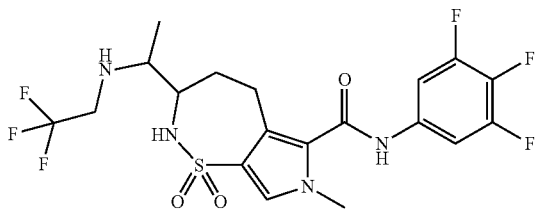 [SMILES: CC(NCC(F)(F)F)C1CCc2c(cn(C)c2C(=O)Nc2cc(F)c(F)c(F)c2)S(=O)(=O)N1]

Methyl 3-acetyl-7-methyl-1,1-dioxo-2,3,4,5-tetrahydropyrrolo[3,4-f]thiazepine-6-carboxylate (550 mg, 1.83 mmol) and 2,2,2-trifluoroethylamine (7.31 mL, 1.24 g/mL, 91.6 mmol) were dissolved in methanol (70 mL) and thiophene (1 mL, 4% in DiPE) and Pd/C (10%) (390 mg, 0.37 mmol) were added successively. The reaction mixture was hydrogenated for 38 hours. Pd/C (10%) (390 mg, 0.37 mmol) was added to the reaction mixture under a nitrogen atmosphere and was hydrogenated for 20 hours. Pd/C (10%) (390 mg, 0.37 mmol) was added to the reaction mixture under a nitrogen atmosphere and was hydrogenated for 120 hours more. The reaction mixture was filtered over decalite and the solids were washed with THF (3×100 mL). The filtrate was concentrated to afford methyl 7-methyl-1,1-dioxo-3-[1-(2,2,2-trifluoroethylamino)ethyl]-2,3,4,5-tetrahydropyrrolo[3,4-f]thiazepine-6-carboxylate (1.50 g). This was separated into its 4 isomers via preparative SFC (Stationary phase: Chiralpak Diacel AS 20×250 mm, Mobile phase: $CO_2$, EtOH+0.4 $iPrNH_2$). The obtained 4 isomers were reacted with 3,4,5-trifluoroaniline using LiHMDS as a base in THF yielding compound 218a (33 mg); $^1$H NMR (400 MHz, DMSO-$d_6$) δ ppm 1.00 (d, J=6.6 Hz, 3H), 1.33 (br d, J=13.2 Hz, 1H), 2.01-2.13 (m, 2H), 2.53-2.67 (m, 1H), 2.74-2.82 (m, 1H), 3.01 (br dd, J=15.0, 6.6 Hz, 1H), 3.16-3.28 (m, 2H), 3.37-3.47 (m, 1H), 3.69 (s, 3H), 6.91 (d, J=10.3 Hz, 1H), 7.46 (s, 1H), 7.56-7.64 (m, 2H), 10.60 (s, 1H); Method D; Rt: 1.99 min. m/z: 497 (M−H)⁻ Exact mass: 498.1, compound 218b (78 mg); $^1$H NMR (400 MHz, DMSO-$d_6$) δ ppm 0.99 (d, J=6.6 Hz, 3H), 1.38-1.48 (m, 1H), 1.92 (br dd, J=14.4, 6.5 Hz, 1H), 2.20-2.30 (m, 1H), 2.67-2.82 (m, 2H), 3.00 (br dd, J=14.4, 6.1 Hz, 1H), 3.15-3.36 (m, 2H), 3.37-3.47 (m, 1H), 3.69 (s, 3H), 6.94 (d, J=10.3 Hz, 1H), 7.47 (s, 1H), 7.55-7.64 (m, 2H), 10.61 (br s, 1H); Method D; Rt: 2.00 min. m/z: 497 (M−H)⁻ Exact mass: 498.1, compound 218c (38 mg); $^1$H NMR (400 MHz, DMSO-$d_6$) δ ppm 0.99 (d, J=6.6 Hz, 3H), 1.38-1.48 (m, 1H), 1.88-1.95 (m, 1H), 2.24 (q, J=7.4 Hz, 1H), 2.67-2.82 (m, 2H), 3.01 (br dd, J=15.3, 5.8 Hz, 1H), 3.15-3.35 (m, 2H), 3.37-3.47 (m, 1H), 3.69 (s, 3H), 6.94 (d, J=10.3 Hz, 1H), 7.47 (s, 1H), 7.56-7.64 (m, 2H), 10.61 (s, 1H); Method D; Rt: 2.00 min. m/z: 497 (M−H)⁻ Exact mass: 498.1; MP: 216.2° C. and compound 218d (34 mg); $^1$H NMR (400 MHz, DMSO-$d_6$) δ ppm 1.00 (d, J=6.6 Hz, 3H), 1.28-1.38 (m, 1H), 2.01-2.13 (m, 2H), 2.54-2.67 (m, 1H), 2.73-2.82 (m, 1H), 3.01 (br dd, J=15.2, 5.7 Hz, 1H), 3.16-3.29 (m, 2H), 3.39-3.48 (m, 1H), 3.69 (s, 3H), 6.91 (d, J=10.3 Hz, 1H), 7.47 (s, 1H), 7.56-7.64 (m, 2H), 10.60 (s, 1H); Method D; Rt: 1.99 min. m/z: 497 (M−H)⁻ Exact mass: 498.1, after purification via preparative HPLC (Stationary phase: RP XBridge Prep C18 OBD-10 μm, 50×150 mm, Mobile phase: 0.25% $NH_4HCO_3$ solution in water, MeOH). Method AB; Rt: 218a: 3.49 min, 218b: 3.15 min, 218c: 2.09 min, 218d: 2.26 min.

Compound 219: 3-[(6-chloro-3-pyridyl)methyl]-N-(3,4-difluorophenyl)-3,7-dimethyl-1,1-dioxo-2H-pyrrolo[3,4-f]thiazepine-6-carboxamide

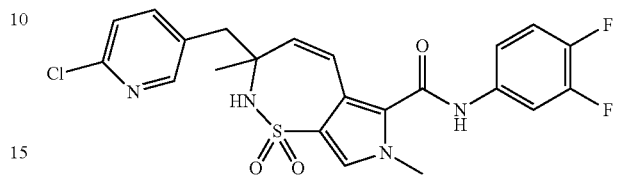

2-amino-3-(6-chloro-3-pyridyl)-2-methyl-propan-1-ol (1.00 g, 4.98 mmol), methyl 3-bromo-4-chlorosulfonyl-1-methyl-pyrrole-2-carboxylate (1.58 mg, 4.98 mmol) and Hunig's base (2.58 mL, 0.75 g/mL, 15 mmol) were dissolved in ACN (20 mL) and the reaction mixture was stirred overnight. The volatiles were removed under reduced pressure and the residue was purified on silica using a heptane to EtOAc gradient yielding methyl 3-bromo-4-[[1-[(6-chloro-3-pyridyl)methyl]-2-hydroxy-1-methyl-ethyl]sulfamoyl]-1-methyl-pyrrole-2-carboxylate (777 mg) as a white powder.

Methyl 3-bromo-4-[[1-[(6-chloro-3-pyridyl)methyl]-2-hydroxy-1-methyl-ethyl]sulfamoyl]-1-methyl-pyrrole-2-carboxylate (777 mg, 1.62 mmol) and 3,4-difluoroaniline (162 μL, 1.29 g/mL, 1.62 mmol) were dissolved in THF (5 mL). Lithium bis(trimethylsilyl)amide (1M in THF) (8 mL, 1 M in THF, 8 mmol) was added and the reaction mixture was stirred overnight at room temperature. The reaction mixture was quenched with $NH_4Cl$ (sat., aq., 10 mL) and the organic layer was removed. The aqueous layer was extracted with DCM (2×5 mL) and the combined organic layers were filtered and evaporated to dryness yielding crude 3-bromo-4-[[1-[(6-chloro-3-pyridyl)methyl]-2-hydroxy-1-methyl-ethyl]sulfamoyl]-N-(3,4-difluorophenyl)-1-methyl-pyrrole-2-carboxamide (833 mg).

3-bromo-4-[[1-[(6-chloro-3-pyridyl)methyl]-2-hydroxy-1-methyl-ethyl]sulfamoyl]-N-(3,4-difluorophenyl)-1-methyl-pyrrole-2-carboxamide (833 mg, 1.44 mmol) was dissolved in ACN (15 mL). 2-iodoxybenzoic acid (606 mg, 2.16 mmol) was added and the reaction mixture was heated at 80° C. for 90 minutes. The reaction mixture was filtered while still hot, evaporated to dryness and the residue was purified on silica using a heptane to EtOAc gradient yielding 3-bromo-4-[[1-[(6-chloro-3-pyridyl)methyl]-1-methyl-2-oxo-ethyl]sulfamoyl]-N-(3,4-difluorophenyl)-1-methyl-pyrrole-2-carboxamide (721 mg). $^1$H NMR (400 MHz, DMSO-$d_6$) δ ppm 1.07 (s, 3H), 2.96-3.04 (m, 2H), 3.74 (s, 3H), 7.41-7.49 (m, 3H), 7.67 (s, 1H), 7.72 (dd, J=8.1, 2.4 Hz, 1H), 7.80-7.88 (m, 1H), 8.24 (s, 1H), 8.27 (d, J=2.2 Hz, 1H), 9.57 (s, 1H), 10.60 (s, 1H).

KOtBu (73.1 mg, 0.65 mmol) was added to a stirred suspension of methyltriphenylphosphonium bromide (233 mg, 0.65 mmol) in THF (5 mL) at 0° C. The suspension was stirred at 0° C. for 10 min and then at room temperature for 1 hour. 3-bromo-4-[[1-[(6-chloro-3-pyridyl)methyl]-1-methyl-2-oxo-ethyl]sulfamoyl]-N-(3,4-difluorophenyl)-1-methyl-pyrrole-2-carboxamide (150 mg, 0.26 mmol) in THF (5 mL) was added dropwise to this solution at 0° C. The reaction mixture was allowed to warm to room temperature and stirred overnight. LCMS showed product formed. The volatiles were removed under reduced pressure and the residue was purified on silica using a heptane to EtOAc gradient yielding 3-bromo-4-[[1-[(6-chloro-3-pyridyl)methyl]-1-methyl-allyl]sulfamoyl]-N-(3,4-difluorophenyl)-1-methyl-pyrrole-2-carboxamide (118 mg) as a white powder.

3-bromo-4-[[1-[(6-chloro-3-pyridyl)methyl]-1-methyl-allyl]sulfamoyl]-N-(3,4-difluorophenyl)-1-methyl-pyrrole-2-carboxamide (118 mg, 0.21 mmol), bis(tri-tert-butylphosphine)palladium(0) (5 mg, 0.01 mmol) and Hunig's base (39 µL, 0.75 g/mL, 0.23 mmol) were dissolved in DMF (1 mL) and heated in the microwave at 150° C. for 5 minutes. Bis(tri-tert-butylphosphine)palladium(0) (5 mg, 0.01 mmol) was added and the reaction mixture was and heated in the microwave at 150° C. for 5 minutes. The reaction mixture was directly loaded on a silica cartridge and a gradient from heptane to EtOAc was applied yielding compound 219 (54 mg) after crystallization from a DCM:DIPE mixture. $^1$H NMR (400 MHz, DMSO-$d_6$) δ ppm 1.13 (s, 3H), 2.83 (d, J=13.4 Hz, 1H), 3.42 (d, J=13.4 Hz, 1H), 3.70 (s, 3H), 5.61 (d, J=13.0 Hz, 1H), 6.40 (d, J=13.0 Hz, 1H), 7.40-7.55 (m, 4H), 7.61 (s, 1H), 7.80-7.88 (m, 2H), 8.36 (d, J=2.2 Hz, 1H), 10.70 (s, 1H); Method B; Rt: 1.06 min. m/z: 491 (M−H)$^-$ Exact mass: 492.1.

Compound 220: N-(3-cyano-4-fluoro-phenyl)-3,7-dimethyl-3-[(5-methylisoxazol-3-yl)methyl]-1,1-dioxo-2,4-dihydropyrrolo[3,4-b][1,4,5]oxathiazepine-6-carboxamide

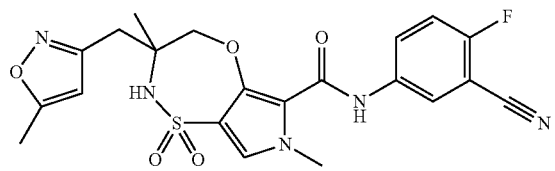 [SMILES: Cc1cc(CC2(C)COc3c(cn(C)c3C(=O)Nc3ccc(F)c(C#N)c3)S(=O)(=O)N2)no1]

Compound 220 (124 mg) was prepared similarly as described for compound 162, using 5-amino-2-fluoro-benzonitrile instead of 3,4-difluoroaniline. This was separated into its enantiomers via preparative SFC (Stationary phase: Chiralpak Diacel AS 20×250 mm, Mobile phase: $CO_2$, iPrOH+0.4 iPrNH$_2$) yielding compound 220a (28 mg), $^1$H NMR (400 MHz, DMSO-$d_6$) δ ppm 1.22 (s, 3H), 2.40 (s, 3H), 2.88 (d, J=13.9 Hz, 1H), 3.05 (d, J=13.9 Hz, 1H), 3.75-3.88 (m, 3H), 4.42 (d, J=13.2 Hz, 1H), 4.62 (d, J=13.0 Hz, 1H), 6.22 (s, 1H), 7.49-7.56 (m, 2H), 7.93 (s, 1H), 8.02 (ddd, J=9.2, 4.8, 2.9 Hz, 1H), 8.16 (dd, J=5.7, 2.6 Hz, 1H), 9.47 (s, 1H); Method B; Rt: 1.01 min. m/z: 472 (M−H)$^-$ Exact mass: 473.1 and compound 2210 (21 mg), $^1$H NMR (400 MHz, DMSO-$d_6$) δ ppm 1.23 (s, 3H), 2.40 (s, 3H), 2.88 (d, J=13.9 Hz, 1H), 3.05 (d, J=13.9 Hz, 1H), 3.83 (s, 3H), 4.42 (d, J=13.0 Hz, 1H), 4.62 (d, J=13.2 Hz, 1H), 6.22 (d, J=0.9 Hz, 1H), 7.49-7.56 (m, 2H), 7.93 (s, 1H), 8.02 (ddd, J=9.2, 4.8, 2.9 Hz, 1H), 8.16 (dd, J=5.7, 2.6 Hz, 1H), 9.47 (s, 1H); Method B; Rt: 1.00 min. m/z: 472 (M−H)$^-$ Exact mass: 473.1. Method AC; Rt: 220a: 4.96 min, 220b: 5.40 min.

Compound 221: N-(3,4-difluorophenyl)-3,7-dimethyl-1,1-dioxo-3-(3-pyridylmethyl)-4,5-dihydro-2H-pyrrolo[3,4-f]thiazepine-6-carboxamide

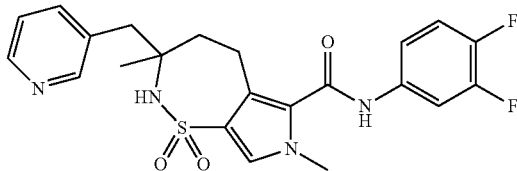 [SMILES: Cn1cc2c(c1C(=O)Nc1ccc(F)c(F)c1)CCC(C)(Cc1cccnc1)NS2(=O)=O]

Compound 219 (48 mg, 0.097 mmol), Pd/C (10%) (5 mg, 0.005 mmol) and TEA (0.027 mL, 0.73 g/mL, 0.19 mmol) were dispensed in MeOH (25 mL) and set under a hydrogen atmosphere for 2 hours. The reaction mixture was filtered and evaporated to dryness. The residue was purified on silica using a heptane to EtOAc gradient yielding compound 221 (25 mg) as a white powder after crystallisation from a DCM:DIPE mixture. $^1$H NMR (400 MHz, DMSO-$d_6$) δ ppm 1.02-1.09 (m, 5H), 2.64-2.68 (m, 1H), 3.00 (br s, 2H), 3.19-3.29 (m, 1H), 3.71 (s, 3H), 7.29 (s, 1H), 7.34 (t, J=6.2 Hz, 1H), 7.40-7.46 (m, 3H), 7.73 (br d, J=7.3 Hz, 1H), 7.80-7.91 (m, 1H), 8.44 (dd, J=4.7, 1.7 Hz, 1H), 8.51 (d, J=1.5 Hz, 1H), 10.38 (s, 1H); Method B; Rt: 0.94 min. m/z: 459 (M−H)$^-$ Exact mass: 460.1.

Compound 222: 3-(1-aminoethyl)-7-methyl-1,1-dioxo-N-(3,4,5-trifluorophenyl)-2,3,4,5-tetrahydropyrrolo[3,4-f]thiazepine-6-carboxamide

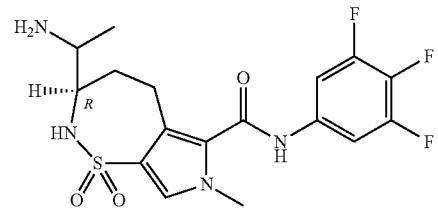

To a suspension of compound 104 (740 mg, 1.42 mmol) in EtOAc (200 mL) was added 2-iodoxybenzoic acid (477 mg, 1.70 mmol). The suspension was heated at reflux for 2 hours. The reaction mixture was filtered and the solids were washed with THF. The filtrate was concentrated. To the residue in EtOAc (200 mL) was added 2-iodoxybenzoic acid (1.99 g, 7.09 mmol). The suspension was heated at reflux for 20 hours. The reaction mixture was filtered and the solids were washed with THF. The filtrate was concentrated in vacuo. The residue was triturated in boiling DCM (20 mL) and the white solid was filtered and washed with DCM (3 mL) yielding (3R)-3-acetyl-7-methyl-1,1-dioxo-N-(3,4,5-trifluorophenyl)-2,3,4,5-tetrahydropyrrolo[3,4-f]thiazepine-6-carboxamide (350 mg). Method B; Rt: 0.93 min. m/z: 414 (M−H)$^-$ Exact mass: 415.1.

To a stirred solution of (3R)-3-acetyl-7-methyl-1,1-dioxo-N-(3,4,5-trifluorophenyl)-2,3,4,5-tetrahydropyrrolo[3,4-f]thiazepine-6-carboxamide (150 mg, 0.36 mmol) in dry MeOH (2 mL) and dry THF (2 mL), under nitrogen, was added zinc chloride (0.071 mL, 1 M in diethylether, 0.071 mmol). After stirring at ambient temperature for 30 minutes, this mixture was treated with ammonium formate (274 mg, 4.30 mmol). After stirring another hour at ambient temperature molecular sieves (1 g) were added followed by sodium cyanoborohydride (47 mg, 0.71 mmol). The reaction was then stirred at ambient temperature overnight. The reaction mixture was filtered over decalite and the solids were washed with 2-MeTHF (3×20 mL). The filtrate was washed with water, Brine, dried (Na₂SO₄), filtered and concentrated. The residue was purified using preparative HPLC (Stationary phase: RP XBridge Prep C18 OBD-10 μm, 50×150 mm, Mobile phase: 0.25% NH₄HCO₃ solution in water, ACN) yielding compound 222a (17 mg); ¹H NMR (400 MHz, DMSO-d₆) δ ppm 0.99 (d, J=6.6 Hz, 3H), 1.30 (q, J=12.0 Hz, 1H), 2.01 (br dd, J=14.0, 6.7 Hz, 1H), 2.66-2.81 (m, 2H), 3.02 (br dd, J=15.1, 6.5 Hz, 1H), 3.16-3.25 (m, 1H), 3.69 (s, 3H), 7.44 (s, 1H), 7.55-7.64 (m, 2H), 10.07-11.08 (m, 1H); Method B; Rt: 0.75 min. m/z: 415 (M−H)⁻ Exact mass: 416.1; MP: 227.5° C. and compound 222b (43 mg); ¹H NMR (400 MHz, DMSO-d₆) δ ppm 0.97 (d, J=6.4 Hz, 3H), 1.35-1.46 (m, 1H), 1.87 (br s, 1H), 2.75-2.86 (m, 2H), 2.95-3.04 (m, 1H), 3.23-3.29 (m, 1H), 3.69 (s, 3H), 7.45 (s, 1H), 7.56-7.64 (m, 2H), 10.60 (br s, 1H); Method B; Rt: 0.76 min. m/z: 415 (M−H)⁻ Exact mass: 416.1; MP: 281.2° C.

Compound 223: 3-[(2-chloro-4-pyridyl)methyl]-N-(3,4-difluorophenyl)-3,7-dimethyl-1,1-dioxo-2H-pyrrolo[3,4-f]thiazepine-6-carboxamide

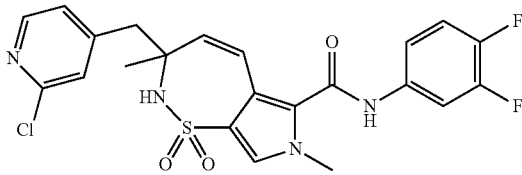 [SMILES: Cn1cc2c(c1C(=O)Nc1ccc(F)c(F)c1)C=CC(C)(Cc1ccnc(Cl)c1)NS2(=O)=O]

2-amino-3-(2-chloro-4-pyridyl)-2-methyl-propan-1-ol (an intermediate used in the synthesis of compound 190) (1047 mg, 5.22 mmol), methyl 3-bromo-4-chlorosulfonyl-1-methyl-pyrrole-2-carboxylate (1.65 g, 5.22 mmol) and Hunig's base (2.7 mL, 0.75 g/mL, 15.7 mmol) were dissolved in ACN (20 mL) and the reaction mixture was stirred overnight. The volatiles were removed under reduced pressure and the residue was purified on silica using a heptane to EtOAc gradient yielding methyl 3-bromo-4-[[1-[(2-chloro-4-pyridyl)methyl]-2-hydroxy-1-methyl-ethyl]sulfamoyl]-1-methyl-pyrrole-2-carboxylate (880 mg) as a white powder.

Methyl 3-bromo-4-[[1-[(2-chloro-4-pyridyl)methyl]-2-hydroxy-1-methyl-ethyl]sulfamoyl]-1-methyl-pyrrole-2-carboxylate (150 mg, 0.31 mmol) was dissolved in ACN (15 mL). 2-iodoxybenzoic acid (131 mg, 0.47 mmol) was added and the reaction mixture was heated at 80° C. for 90 minutes. The reaction mixture was filtered while still hot, evaporated to dryness and the residue was purified on silica using a heptane to EtOAc gradient yielding methyl 3-bromo-4-[[1-[(2-chloro-4-pyridyl)methyl]-1-methyl-2-oxo-ethyl]sulfamoyl]-1-methyl-pyrrole-2-carboxylate (107 mg).

KOtBu (251 mg, 2.23 mmol) was added to a stirred suspension of methyltriphenylphosphonium bromide (798 mg, 2.23 mmol) in THF (10 mL) at 0° C. The suspension was stirred at 0° C. for 10 min and then at room temperature for 1 hour. methyl 3-bromo-4-[[1-[(2-chloro-4-pyridyl)methyl]-1-methyl-2-oxo-ethyl]sulfamoyl]-1-methyl-pyrrole-2-carboxylate (107 mg, 0.22 mmol) in THF (5 mL) was added dropwise to this solution at 0° C. The reaction mixture was allowed to warm to room temperature and stirred overnight. The volatiles were removed under reduced pressure and the residue was purified on silica using a heptane to EtOAc gradient yielding methyl 3-bromo-4-[[1-[(2-chloro-4-pyridyl)methyl]-1-methyl-allyl]sulfamoyl]-1-methyl-pyrrole-2-carboxylate (78 mg).

Methyl 3-bromo-4-[[1-[(2-chloro-4-pyridyl)methyl]-1-methyl-allyl]sulfamoyl]-1-methyl-pyrrole-2-carboxylate (78 mg, 0.16 mmol), bis(tri-tert-butylphosphine)palladium (0) (4 mg, 0.008 mmol) and Hunig's base (0.031 mL, 0.75 g/mL, 0.18 mmol) were dissolved in DMF (3 mL) and heated in the microwave at 150° C. for 10 minutes. The reaction mixture was directly loaded on a silica cartridge and a gradient from heptane to EtOAc was applied yielding methyl 3-[(2-chloro-4-pyridyl)methyl]-3,7-dimethyl-1,1-dioxo-2H-pyrrolo[3,4-f]thiazepine-6-carboxylate (51 mg).

Methyl 3-[(2-chloro-4-pyridyl)methyl]-3,7-dimethyl-1,1-dioxo-2H-pyrrolo[3,4-f]thiazepine-6-carboxylate (51 mg, 0.13 mmol) and 3,4-difluoroaniline (0.014 mL, 1.29 g/mL, 0.14 mmol) were dissolved in THF (5 mL). Lithium bis(trimethylsilyl)amide (0.64 mL, 1 M in THF, 0.64 mmol) was added and the reaction mixture was stirred overnight at room temperature. The reaction mixture was quenched with NH₄Cl (sat., aq., 10 mL) and the organic layer was removed. The aqueous layer was extracted with DCM (2×5 mL) and the combined organic layers were filtered and evaporated to dryness. The residue was purified via preparative HPLC (Stationary phase: RP XBridge Prep C18 OBD-10 μm, 30×150 mm, Mobile phase: 0.25% NH₄HCO₃ solution in water, ACN) yielding compound 223 (11 mg). ¹H NMR (400 MHz, DMSO-d₆) δ ppm 1.15 (s, 3H), 2.84 (d, J=12.8 Hz, 1H), 3.46 (d, J=12.8 Hz, 1H), 3.71 (s, 3H), 5.59 (d, J=13.0 Hz, 1H), 6.43 (br d, J=13.9 Hz, 1H), 7.38-7.51 (m, 5H), 7.66 (br s, 1H), 7.81-7.88 (m, 1H), 8.35 (d, J=4.8 Hz, 1H), 10.72 (br s, 1H); Method B; Rt: 1.02 min. m/z: 491 (M−H)⁻ Exact mass: 492.1

Compound 224: N-(3,4-difluorophenyl)-3-methyl-1,1-dioxo-2,3-dihydrothieno[3,4-f]thiazepine-6-carboxamide

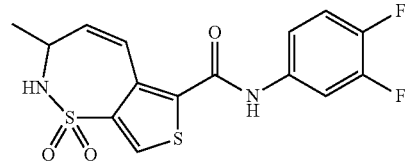 [SMILES: CC1C=Cc2c(csc2C(=O)Nc2ccc(F)c(F)c2)S(=O)(=O)N1]

Methyl 3-bromothiophene-2-carboxylate (5 g, 22.6 mmol) was added portion wise to chlorosulfonic acid (7.6 mL, 1.73 g/mL, 113 mmol) at 0° C. The reaction mixture was allowed to warm to room temperature and was heated at 120° C. for 3 hours. The resulting mixture was added dropwise to a stirred ice-water mixture (250 mL) keeping the temperature below 5° C. The precipitate was filtered and dissolved in 2-MeTHF, dried (MgSO₄), filtered and concentrated in vacuo to yield 3-bromo-4-chlorosulfonyl-thiophene-2-carboxylic acid (6.9 g) as a brown oil.

Oxalyl chloride (10 mL) was added to 3-bromo-4-chlorosulfonyl-thiophene-2-carboxylic acid (6.9 g, 22.582 mmol), DMF (87 μL, 0.944 g/mL, 1.13 mmol) in DCM (350 mL) and stirred overnight. The reaction mixture was concentrated yielding 3-bromo-4-chlorosulfonyl-thiophene-2-carbonyl chloride (7.5 g) as a yellow resin which was used as such.

3-bromo-4-chlorosulfonyl-thiophene-2-carbonyl chloride (7.5 g, 23.1 mmol) was dissolved in toluene (180 mL). The mixture was brought to reflux and 3,4-difluoroaniline (2.34 mL, 1.29 g/mL, 23.1 mmol) was added. The mixture was heated at reflux for 45 minutes. The mixture was cooled and concentrated in vacuo. The residue was purified by column chromatography using a gradient from 0 till 100% EtOAc in heptane yielding 4-bromo-5-[(3,4-difluorophenyl)carbamoyl]thiophene-3-sulfonyl chloride (5.7 g).

3-buten-2-amine hydrochloride (762 mg, 7.08 mmol) was added to ACN (20 mL) and the mixture was cooled on an ice bath. DIPEA (3.66 mL, 0.75 g/mL, 21.2 mmol) was added and the mixture was stirred until a clear solution was obtained. 4-bromo-5-[(3,4-difluorophenyl)carbamoyl]thiophene-3-sulfonyl chloride (2.95 g, 7.08 mmol) was added and the mixture was stirred at room temperature for 16 hours. The mixture was concentrated in vacuo and the residue was partioned between water and DCM. The organic layer was separated, dried (MgSO$_4$), filtered and concentrated in vacuo. The residue was recrystallized from ACN and the precipitate was filtered off to yield 3-bromo-N-(3,4-difluorophenyl)-4-(1-methylallylsulfamoyl)thiophene-2-carboxamide (800 mg). Method B; Rt: 1.04 min. m/z: 451 (M+H)$^+$ Exact mass: 450.0.

A microwave vial was charged with 3-bromo-N-(3,4-difluorophenyl)-4-(1-methylallylsulfamoyl)thiophene-2-carboxamide (200 mg, 0.443 mmol), Hunig's base (0.084 mL, 0.75 g/mL, 0.49 mmol) and DMF (5 mL) and purged with N$_2$ for 5 minutes. Bis(tri-tert-butylphosphine)palladium (0) (11 mg, 0.022 mmol) was added and the vial was capped. The mixture was irradiated for 10 minutes at 150° C. The mixture was concentrated in vacuo and the residue was purified via preparative HPLC (Stationary phase: RP XBridge Prep C18 OBD-10 µm, 50×150 mm, Mobile phase: 0.25% NH$_4$HCO$_3$ solution in water, MeOH) yielding compound 224 (65 mg) as a white solid after crystallization from ACN. $^1$H NMR (400 MHz, DMSO-d$_6$) δ ppm 1.33 (d, J=7.3 Hz, 3H), 4.31 (br s, 1H), 5.79 (dd, J=13.1, 2.3 Hz, 1H), 6.82 (dd, J=13.1, 2.3 Hz, 1H), 7.43-7.44 (m, 1H), 7.44-7.46 (m, 1H), 7.79-7.84 (m, 1H), 8.07-8.11 (m, 1H), 8.30 (s, 1H), 10.76 (br s, 1H); Method B; Rt: 0.96 min. m/z: 369 (M–H)$^-$ Exact mass: 370.0; MP: 220.8° C.

Compound 225: N-(3,4-difluorophenyl)-3,7-dimethyl-1,1-dioxo-3,4-dihydro-2H-thieno[3,2-b][1,4,5]oxathiazepine-6-carboxamide

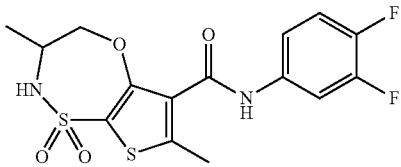 [SMILES: Cc1sc2c(c1C(=O)Nc1ccc(F)c(F)c1)OCC(C)NS2(=O)=O]

Chlorosulfonic acid (1 mL, 1.73 g/mL, 16.109 mmol) was added to chloroform (15 mL) and cooled on an ice bath. Ethyl 4-hydroxy-2-methylthiophene-3-carboxylate (1 g, 5.37 mmol) dissolved in chloroform (5 mL) was added dropwise to the cooled solution. The mixture was allowed to rise to r.t. and was stirred at r.t. for 1 hour. The mixture was poured out in ice water and the organic layer was separated. The organic layer was dried (MgSO$_4$), filtered and concentrated in vacuo. The residue was purified by column chromatography using a gradient from 0 till 100% EtOAc in heptane to yield ethyl 5-chlorosulfonyl-4-hydroxy-2-methyl-thiophene-3-carboxylate (523 mg).

2-[(4-methoxyphenyl)methylamino]propan-1-ol (286 mg, 1.46 mmol) and Hunig's base (0.757 mL, 0.75 g/mL, 4.39 mmol) was dissolved in ACN (7 mL). Ethyl 5-chlorosulfonyl-4-hydroxy-2-methyl-thiophene-3-carboxylate (417 mg, 1.46 mmol) was added and the mixture was stirred at room temperature for 16 hours. The mixture was concentrated in vacuo and the residue was purified by column chromatography using a gradient from 0 till 100% EtOAc in heptane yielding ethyl 4-hydroxy-5-[(2-hydroxy-1-methyl-ethyl)-[(4-methoxyphenyl)methyl]sulfamoyl]-2-methyl-thiophene-3-carboxylate (359 mg). Method B; Rt: 1.20 min. m/z: 442 (M–H)$^-$ Exact mass: 443.1.

Ethyl 4-hydroxy-5-[(2-hydroxy-1-methyl-ethyl)-[(4-methoxyphenyl)methyl]sulfamoyl]-2-methyl-thiophene-3-carboxylate (359 mg, 0.81 mmol) was dissolved in dry THF (8 mL). Triphenylphosphine (234 mg, 0.89 mmol) and di-tert-butyl azodicarboxylate (205 mg, 0.89 mmol) were added at room temperature. The mixture was stirred for 30 minutes and then concentrated in vacuo. The residue was purified by column chromatography using a gradient from 0 till 100% EtOAc in heptane to yield ethyl 2-[(4-methoxyphenyl)methyl]-3,7-dimethyl-1,1-dioxo-3,4-dihydrothieno[3,2-b][1,4,5]oxathiazepine-6-carboxylate (275 mg).

Ethyl 2-[(4-methoxyphenyl)methyl]-3,7-dimethyl-1,1-dioxo-3,4-dihydrothieno[3,2-b][1,4,5]oxathiazepine-6-carboxylate (275 mg, 0.65 mmol) and 3,4-difluoroaniline (0.078 mL, 1.29 g/mL, 0.78 mmol) was dissolved in THF (5 mL). Lithium bis(trimethylsilyl)amide (1.9 mL, 1 M in THF, 1.9 mmol) was added dropwise and the mixture was stirred at room temperature for 2 hours. The mixture was quenched with NH$_4$Cl (aq., sat.). The mixture was diluted with 2-MeTHF and the organic layer was separated, dried (MgSO$_4$), filtered and concentrated in vacuo. The product was purified by column chromatography using a gradient from 0 till 50% EtOAc in heptane yielding N-(3,4-difluorophenyl)-2-[(4-methoxyphenyl)methyl]-3,7-dimethyl-1,1-dioxo-3,4-dihydrothieno[3,2-b][1,4,5]oxathiazepine-6-carboxamide (232 mg).

N-(3,4-difluorophenyl)-2-[(4-methoxyphenyl)methyl]-3,7-dimethyl-1,1-dioxo-3,4-dihydrothieno[3,2-b][1,4,5]oxathiazepine-6-carboxamide (116 mg, 0.23 mmol) was dissolved in dry DCM (3 mL) and TFA (3 mL, 1.49 g/mL, 39 mmol) was added under N$_2$. The mixture was stirred at room temperature for 16 hours. The mixture was concentrated in vacuo and the residue was purified by column chromatography using a gradient from 0 till 50% EtOAc in heptane yielding compound 225 (63 mg). $^1$H NMR (400 MHz, DMSO-d$_6$) δ ppm 1.19 (d, J=7.0 Hz, 3H), 2.50 (s, 3H), 3.79 (q, J=7.5 Hz, 1H), 4.05 (dd, J=12.8, 8.3 Hz, 1H), 4.50 (dd, J=12.8, 2.6 Hz, 1H), 7.33-7.44 (m, 2H), 7.77-7.85 (m, 1H), 8.02 (d, J=8.2 Hz, 1H), 10.18 (s, 1H); Method D; Rt: 1.90 min. m/z: 387 (M–H)$^-$ Exact mass: 388.0. MP: 221.5° C.

Compound 226: N-(3,4-difluorophenyl)-3,7-dimethyl-1,1-dioxo-2,3-dihydropyrazolo[4,3-f]thiazepine-6-carboxamide

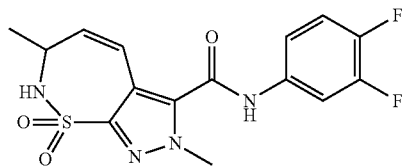 [SMILES: CC1C=Cc2c(nn(C)c2C(=O)Nc2ccc(F)c(F)c2)S(=O)(=O)N1]

Methyl 5-amino-2-methyl-pyrazole-3-carboxylate (2.00 g, 12.9 mmol) was dissolved in THF (50 mL) and N-bromosuccinimide (2.52 g, 14.2 mmol) was added and stirred for 2 hours. The solution was concentrated in vacuo, redissolved in DCM and washed with water. The combined organics are evaporated till dryness and the crude purified on silica using DCM/MeOH 100/0 to 90/10. The obtained crude was redissolved in DIPE, and the remaining salts removed by filtration. The filtrate was then concentrated in vacuo to yield methyl 5-amino-4-bromo-2-methyl-pyrazole-3-carboxylate (2.0 g) as a light orange solid.

To a cooled (0° C.) solution of water (3.5 mL) was added $SOCl_2$ (0.642 mL, 1.64 g/mL, 8.84 mmol) and allowed to warm to room temperature and stirred for 1 h. Then cuprous chloride (19 mg, 0.20 mmol) was added and the solution cooled to −5° C.

In another solution of HCl (1.97 mL, 37% in $H_2O$, 1.18 g/mL, 23.6 mmol) was added methyl 5-amino-4-bromo-2-methyl-pyrazole-3-carboxylate (500 mg, 1.97 mmol) and cooled to −5° C. before a solution of sodium nitrite (149 mg, 2.16 mmol) in water (1 mL) was added to it. This solution was then added to the first solution dropwise and cooling was maintained at −5° C. The solution was then allowed to warm to 0° C. and stirring was continued at this temperature for 2 hours, before it was allowed to warm to room temperature. EtOAc (20 mL) was added and the organic layer was concentrated in vacuo. The residue was purified on silica using a heptane to EtOAc gradient yielding methyl 4-bromo-5-chlorosulfonyl-2-methyl-pyrazole-3-carboxylate (544 mg).

Methyl 4-bromo-5-chlorosulfonyl-2-methyl-pyrazole-3-carboxylate (383 mg, 1.04 mmol) was dissolved in ACN (5 mL, 0.786 g/mL, 104 mmol). DIPEA (0.715 mL, 0.75 g/mL, 4.15 mmol) and but-3-en-2-amine hydrochloride (223 mg, 2.08 mmol) were added and the reaction mixture was stirred 5 hours. The solution was then concentrated in vacuo and directly purified on silica using heptane/EtOAc 100 to 50/50 to yield methyl 4-bromo-2-methyl-5-(1-methylallylsulfamoyl)pyrazole-3-carboxylate (98 mg).

Methyl 4-bromo-2-methyl-5-(1-methylallylsulfamoyl)pyrazole-3-carboxylate (98 mg, 0.278 mmol) was dissolved in THF (5 mL) and 3,4-difluoroaniline (0.030 mL, 1.302 g/mL, 0.31 mmol) and LiHMDS (0.835 mL, 1 M in THF, 0.84 mmol) was added at room temperature. After 2 hours the solution was diluted with EtOAc and washed with water. The combined organic layers were dried with $MgSO_4$, filtered, concentrated in vacuo and purified on silica using heptane/EtOAc 100/0 to 50/50 yielding 4-bromo-N-(3,4-difluorophenyl)-2-methyl-5-(1-methylallylsulfamoyl)pyrazole-3-carboxamide (70 mg).

To a solution of 4-bromo-N-(3,4-difluorophenyl)-2-methyl-5-(1-methylallylsulfamoyl)pyrazole-3-carboxamide (70 mg, 0.16 mmol) in DMF (2 mL) was added Hunig's base (0.054 mL, 0.75 g/mL, 0.31 mmol) and flushed under nitrogen. The mixture was first heated to 100° C. before bis(tri-tert-butylphosphine)palladium(0) (8 mg, 0.016 mmol) was added and the solution was then heated to 150° C. for 5 minutes in the microwave. The reaction mixture was directly purified on preparative HPLC (Stationary phase: RP XBridge Prep C18 ODB-5 µm, 30×250 mm, Mobile phase: 0.25% $NH_4HCO_3$ solution in water, ACN) yielding compound 226 (26 mg). $^1$H NMR (400 MHz, DMSO-$d_6$) δ ppm 1.36 (d, J=7.3 Hz, 3H) 3.97 (s, 3H) 4.20-4.29 (m, 1H) 5.75 (dd, J=12.2, 2.5 Hz, 1H) 6.40 (dd, J=12.1, 2.6 Hz, 1H) 7.41-7.50 (m, 2H) 8.02 (br s, 1H) 7.81-7.90 (m, 1H) 11.14 (br s, 1H); Method B; Rt: 0.90 min. m/z: 367 (M−H)⁻ Exact mass: 368.1.

The following compounds were also synthesized according to the procedures described above:

Compound 227

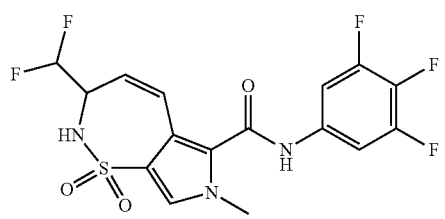

Compound 228

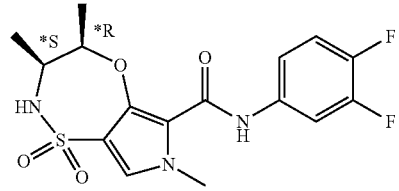

Compound 229

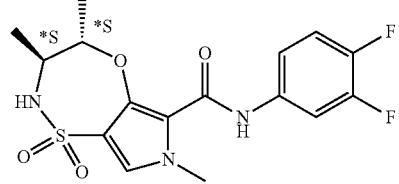

Compound 230

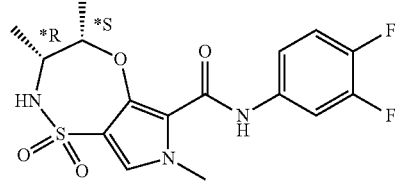

Compound 231

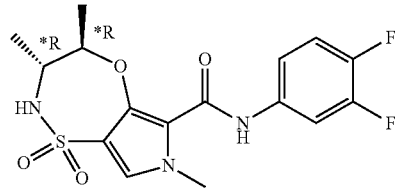

Compound 232

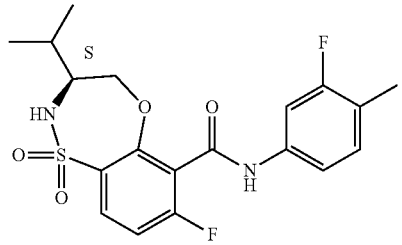

Compound 233

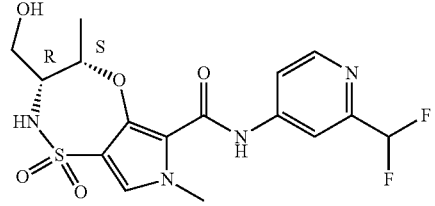

Compound 234
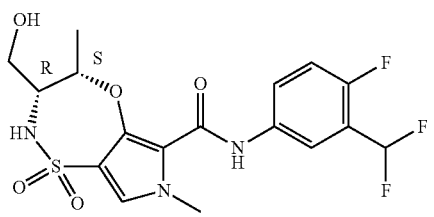
Compound 235
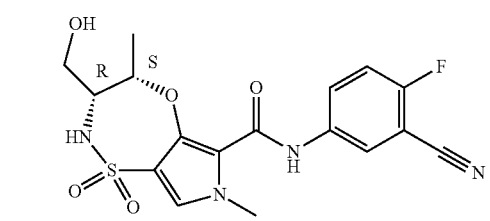
Compound 236
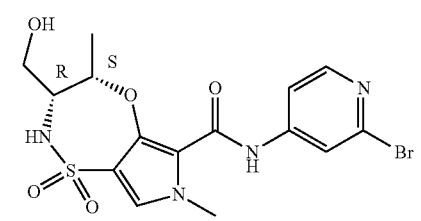
Compound 237
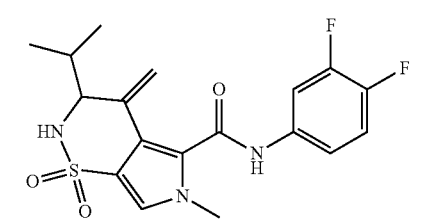
Compound 238
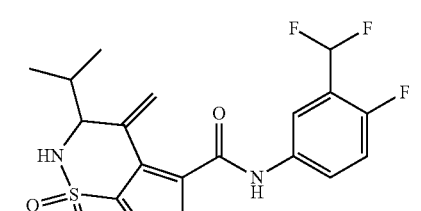
Compound 239
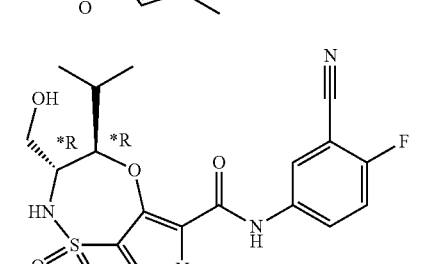
Compound 240
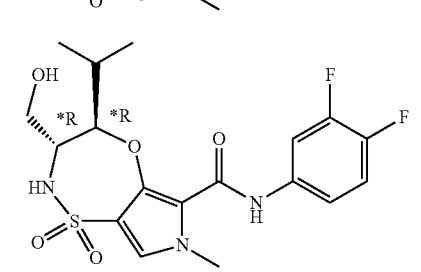
Compound 241
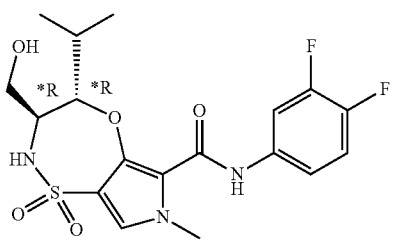
Compound 242
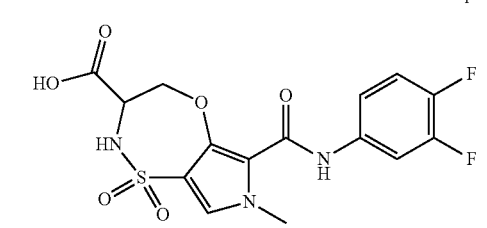
Compound 243
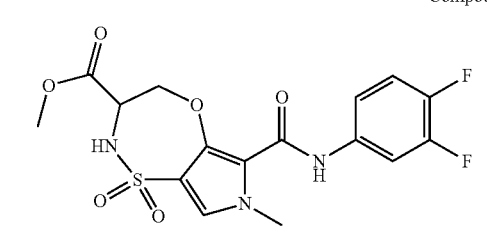
Compound 244
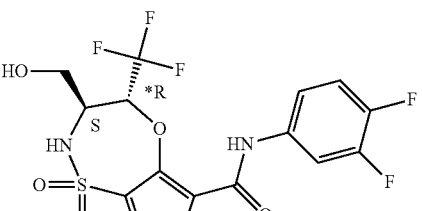
Compound 245
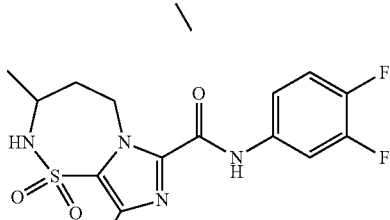
Compound 246
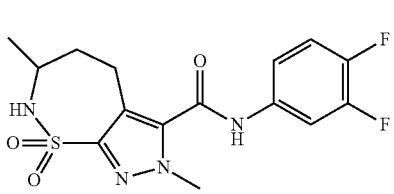
Compound 247
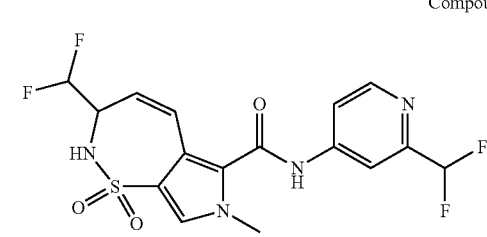

-continued

Compound 248

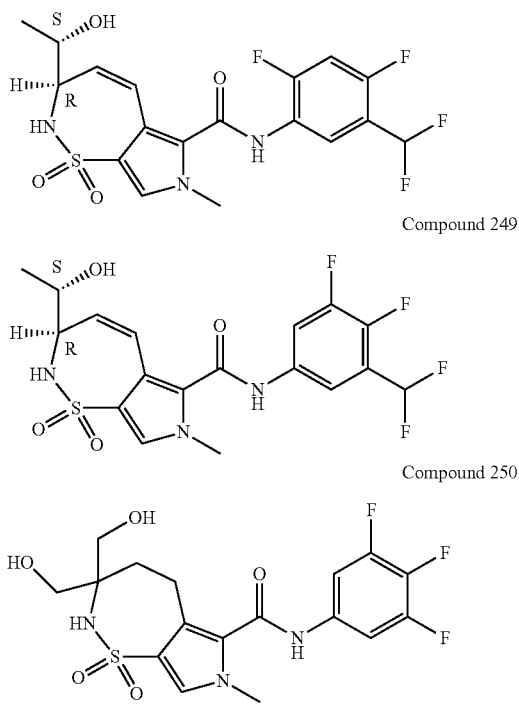

Compound 249

Compound 250

Biological Examples—Anti-HBV Activity of Compounds of Formula (A)

The anti HBV activity was measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1 anti HBV activity and cytotoxicity

| Compound # | HBV-AVE-HepG2.117 EC50 (μM) | TOX-HepG2-4 d CC50 (μM) |
|---|---|---|
| 1 | 2.74 | >25 |
| 2a | 0.28 | >25 |
| 2b | 0.49 | >25 |
| 3 | >0.5 | >25 |
| 4 | 1.09 | >25 |
| 5 | 0.18 | >25 |
| 6 | 3.98 | >25 |
| 7a | 0.13 | >25 |
| 7b | 0.007 | >25 |
| 8 | 0.047 | >25 |
| 9 | 0.036 | >25 |
| 10a | 0.22 | >25 |
| 10b | 0.006 | >25 |
| 11 | 0.077 | >25 |
| 12 | 0.35 | >25 |
| 13 | 0.11 | >25 |
| 14a | 0.25 | >25 |
| 14b | 0.078 | >25 |
| 15a | 0.078 | >25 |
| 15b | >0.5 | >25 |
| 16 | 0.23 | >25 |
| 17 | <0.098 | >25 |
| 18 | 0.71 | >25 |
| 19 | 0.19 | >25 |
| 20 | 0.058 | >25 |
| 21 | 0.15 | >25 |
| 22 | 0.009 | >25 |
| 23 | 0.005 | 10.62 |
| 24 | 0.068 | >25 |
| 25 | 0.022 | >25 |
| 26 | 0.027 | >25 |
| 27 | 0.11 | >25 |
| 28 | 0.89 | >25 |
| 29 | 0.005 | >25 |
| 30 | 0.013 | >25 |
| 31 | 0.009 | >25 |
| 32 | 0.003 | >25 |
| 33 | 0.053 | >25 |
| 34 | 0.056 | >25 |
| 35 | 0.012 | >25 |
| 36 | 0.005 | >25 |
| 37 | 0.20 | >25 |
| 38 | 0.005 | >25 |
| 39 | 0.003 | >25 |
| 40 | 0.022 | >25 |
| 41 | 0.008 | >25 |
| 42 | 0.081 | >25 |
| 43 | 0.056 | >25 |
| 44 | 0.17 | >25 |
| 45 | 0.23 | >25 |
| 46 | 0.33 | >25 |
| 47 | 0.017 | >25 |
| 48 | 0.084 | >25 |
| 49 | 0.31 | >25 |
| 50 | 0.002 | >25 |
| 51 | <0.002 | >25 |
| 52 | 0.056 | >25 |
| 53 | 0.19 | >25 |
| 54 | 0.004 | >25 |
| 55 | 0.003 | >25 |
| 56 | 0.010 | >25 |
| 57 | 0.013 | >25 |
| 58 | 0.29 | >25 |
| 59 | 0.24 | >25 |
| 59a | >0.5 | >25 |
| 59b | 0.14 | >25 |
| 60 | 0.013 | >25 |
| 60a | 0.055 | >25 |
| 60b | 0.005 | >25 |
| 61 | 0.074 | >25 |
| 62 | 0.009 | >25 |
| 63 | 0.24 | >25 |
| 64 | 0.008 | >25 |
| 65 | 0.007 | >25 |
| 66 | 0.047 | >25 |
| 67 | 0.069 | >25 |
| 68 | 0.23 | >25 |
| 69 | 0.033 | >25 |
| 70 | 0.014 | >25 |
| 71 | 0.003 | >25 |
| 72 | 0.050 | >25 |
| 73 | 0.48 | >25 |
| 74 | 0.052 | >25 |
| 75 | 0.007 | >25 |
| 76 | 0.22 | >25 |
| 77 | 0.23 | >25 |
| 78 | 0.056 | >25 |
| 79a | 0.043 | >25 |

TABLE 1-continued anti HBV activity and cytotoxicity

| Compound # | HBV-AVE-HepG2.117 EC50 (μM) | TOX-HepG2-4 d CC50 (μM) |
|---|---|---|
| 79b | 0.002 | >25 |
| 80 | 0.018 | >25 |
| 81 | 0.002 | >25 |
| 82 | 0.004 | >25 |
| 83 | 0.058 | >25 |
| 84 | 0.010 | >25 |
| 85 | 0.007 | >25 |
| 86 | 0.005 | >25 |
| 87 | 0.018 | >25 |
| 88 | 0.011 | >25 |
| 89a | 0.19 | >25 |
| 89b | 0.017 | >25 |
| 90 | 0.019 | >25 |
| 91 | 0.13 | >25 |
| 92a | 0.031 | >24 |
| 92b | 0.17 | >25 |
| 93 | 0.012 | >25 |
| 94 | 0.080 | >25 |
| 95 | 0.022 | >25 |
| 96 | 0.005 | >25 |
| 97 | 0.055 | >25 |
| 98 | 0.008 | >25 |
| 99 | 0.004 | >25 |
| 100 | 0.003 | >25 |
| 101 | 0.014 | >25 |
| 102 | 0.009 | >25 |
| 103 | 0.006 | >25 |
| 104 | 0.007 | >25 |
| 105a | 0.007 | >25 |
| 105b | 0.011 | >25 |
| 106 | 0.008 | >25 |
| 107 | 0.080 | >25 |
| 108 | 0.016 | >25 |
| 109 | 0.003 | >25 |
| 110 | 0.20 | >25 |
| 111 | 0.089 | >25 |
| 112 | 0.003 | >25 |
| 113 | 0.12 | >25 |
| 114a | 0.022 | >25 |
| 114b | 0.008 | >25 |
| 115a | 0.008 | >25 |
| 115b | 0.007 | >25 |
| 116a | 0.022 | >25 |
| 116b | >0.35 | >25 |
| 117 | 0.010 | >25 |
| 118 | 0.013 | >25 |
| 119a | 0.011 | >25 |
| 119b | 0.006 | >25 |
| 120a | 0.007 | >25 |
| 120b | 0.011 | >25 |
| 121 | 0.029 | >25 |
| 122a | 0.012 | >25 |
| 122b | 0.009 | >25 |
| 123 | 0.019 | >25 |
| 124a | 0.005 | >25 |
| 124b | 0.004 | >25 |
| 125 | 0.007 | >25 |
| 126 | 0.062 | >25 |
| 127 | 0.013 | >25 |
| 128 | 0.024 | >25 |
| 129 | 0.012 | >25 |
| 130a | 0.018 | >25 |
| 130b | 0.012 | >25 |
| 131 | 0.023 | >25 |
| 132 | 0.019 | >25 |
| 133 | 0.011 | >25 |
| 134a | 0.008 | >25 |
| 134b | 0.007 | >25 |
| 135 | 0.005 | >25 |
| 136 | 0.016 | >25 |
| 137 | 0.006 | >25 |
| 138 | 0.029 | >25 |
| 139 | 0.016 | >25 |
| 140 | 0.062 | >25 |
| 141a | 0.030 | >25 |
| 141b | NA | >25 |
| 142a | 0.065 | >25 |
| 142b | >0.125 | >25 |
| 143 | 0.024 | >25 |
| 144a | 0.019 | >25 |
| 144b | 0.063 | >25 |
| 145 | 0.037 | >25 |
| 145a | 0.014 | >25 |
| 145b | 0.06 | >25 |
| 146 | 0.055 | >25 |
| 147 | 0.013 | >25 |
| 148 | 0.077 | >25 |
| 149a | >0.125 | >25 |
| 149b | 0.010 | >25 |
| 150a | >0.125 | >25 |
| 150b | 0.005 | >25 |
| 151 | 0.076 | >25 |
| 152 | 0.014 | >25 |
| 153 | 0.068 | >25 |
| 153a | >0.125 | >25 |
| 153b | 0.060 | >25 |
| 154 | 0.008 | >25 |
| 155 | 0.025 | >25 |
| 156 | 0.009 | >25 |
| 157 | 0.017 | >25 |
| 158 | 0.031 | >25 |
| 159 | 0.014 | >25 |
| 160 | 0.0145 | >25 |
| 160a | 0.077 | >25 |
| 160b | 0.021 | >25 |
| 161a | 0.049 | >25 |
| 161b | >0.125 | >25 |
| 161c | 0.011 | >25 |
| 161d | 0.011 | >25 |
| 162 | 0.003 | >25 |
| 162a | 0.033 | >25 |
| 162b | 0.011 | >25 |
| 163 | >0.125 | >25 |
| 164 | 0.012 | >25 |
| 165 | 0.068 | >25 |
| 166 | 0.056 | >25 |
| 167 | 0.041 | >25 |
| 168 | 0.025 | >25 |
| 168a | >0.125 | >25 |
| 168b | 0.015 | >25 |
| 169 | 0.017 | >25 |
| 170a | NA | >25 |
| 170b | 0.007 | >25 |
| 171 | 0.008 | >25 |
| 172 | 0.074 | >25 |
| 172a | 0.072 | >25 |
| 172b | 0.064 | >25 |
| 173 | 0.017 | >25 |
| 174 | 0.007 | >25 |
| 175 | 0.004 | >25 |
| 175a | 0.021 | >22.9 |
| 175b | 0.003 | >25 |
| 176 | 0.004 | >25 |
| 176a | 0.012 | >25 |
| 176b | NA | >25 |
| 177 | 0.008 | >25 |
| 177a | NA | >25 |
| 177b | 0.004 | >25 |
| 178 | 0.016 | >25 |
| 179 | 0.021 | >25 |
| 180 | 0.005 | >25 |
| 181 | 0.008 | >25 |
| 181a | 0.035 | >25 |
| 181b | 0.006 | >25 |
| 182 | 0.010 | >25 |
| 183 | 0.002 | >25 |
| 184 | 0.020 | >25 |
| 185 | 0.041 | >25 |

TABLE 1-continued anti HBV activity and cytotoxicity

| Compound # | HBV-AVE-HepG2.117 EC50 (μM) | TOX-HepG2-4 d CC50 (μM) |
|---|---|---|
| 186 | 0.011 | >25 |
| 187 | 0.003 | >25 |
| 188 | 0.011 | >25 |
| 189 | 0.11 | >25 |
| 190 | 0.006 | >25 |
| 191 | 0.010 | >25 |
| 192 | 0.056 | >25 |
| 192a | 0.036 | >25 |
| 192b | 0.024 | >25 |
| 193 | 0.006 | >25 |
| 194 | 0.006 | >25 |
| 195 | 0.007 | >25 |
| 196 | 0.065 | >25 |
| 197 | 0.011 | >25 |
| 198 | 0.011 | >25 |
| 199 | 0.015 | >25 |
| 199a | 0.030 | >25 |
| 199b | 0.008 | >25 |
| 200 | 0.084 | >25 |
| 201 | 0.11 | >25 |
| 202 | 0.025 | >25 |
| 203a | 0.094 | >25 |
| 203b | 0.059 | >25 |
| 204a | >0.125 | >25 |
| 204b | >0.125 | >25 |
| 205 | 0.050 | >25 |
| 206a | 0.013 | >25 |
| 206b | 0.012 | >25 |
| 207a | 0.008 | >25 |
| 207b | 0.005 | >25 |
| 208a | 0.008 | >25 |
| 208b | 0.011 | >25 |
| 209a | 0.060 | >25 |
| 209b | 0.018 | >25 |
| 210a | 0.037 | >25 |
| 210b | 0.034 | >25 |
| 211 | 0.007 | >25 |
| 212 | 0.007 | >25 |
| 213a | 0.048 | >25 |
| 213b | 0.016 | >25 |
| 214a | 0.12 | >25 |
| 214b | 0.022 | >25 |
| 215a | 0.062 | >25 |
| 215b | >0.125 | >25 |
| 216 | 0.034 | >25 |
| 217a | 0.025 | >25 |
| 217b | 0.10 | >25 |
| 218a | >0.125 | >25 |
| 218b | 0.079 | >25 |
| 218c | 0.006 | >25 |
| 218d | 0.021 | >25 |
| 219 | NA | >25 |
| 220a | 0.007 | >25 |
| 220b | 0.034 | >25 |
| 228 | >0.5 | >25 |
| 229 | >0.5 | >25 |
| 230 | >0.5 | >25 |
| 231 | >0.5 | >25 |
| 232 | >0.5 | >25 |
| 233 | >0.5 | >25 |
| 234 | >0.5 | >25 |
| 235 | >0.5 | >25 |
| 236 | 0.34 | >25 |
| 237 | >0.5 | >25 |
| 238 | 0.077 | >25 |
| 239 | >0.5 | >25 |
| 240 | >0.25 | >25 |
| 241 | >0.25 | >25 |
| 242 | >0.13 | >25 |
| 243 | >0.5 | >25 |
| 244 | >0.5 | >25 |
| 245 | >25 | >25 |
| 246 | >0.13 | >25 |
| 247 | >0.13 | >25 |

The invention claimed is:

1. A compound of Formula (I-A)

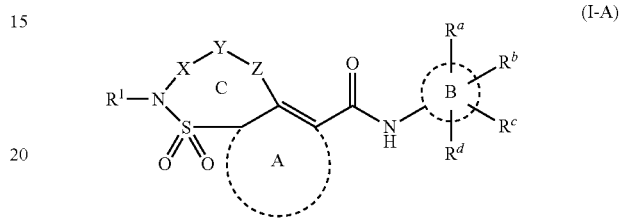

or a stereoisomer or tautomeric form thereof, wherein

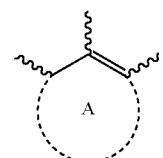

represents

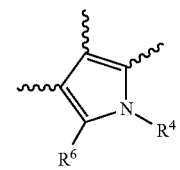

wherein $R^4$ is selected the group consisting of hydrogen, $C_1$-$C_3$alkyl and $C_3$-$C_4$-cycloalkyl, and $R^6$ is selected from the group consisting of hydrogen, methyl, —CN and halogen;

represents a 6 membered aryl optionally containing one nitrogen atom;

X represents —$CR^2R^3$—;

Y represents $C_1$-$C_7$alkanediyl or $C_2$-$C_7$alkenediyl, each optionally substituted with one or more substituents each independently selected from the group consisting of $C_1$-$C_4$alkyl, fluoro, and —OH;

Z represents a heteroatom or a single bond;

$R^a$, $R^b$, $R^c$ and $R^d$ are each independently selected from the group consisting of hydrogen, halogen, —$CHF_2$, —$CF_2$-methyl, —$CH_2F$, —$CF_3$, —$OCF_3$, —CN, $C_3$-$C_4$cycloalkyl and —$C_1$-$C_4$alkyl;

$R^1$ is hydrogen or $C_1$-$C_{10}$alkyl optionally substituted with one or more substituents each independently selected from the group consisting of —OH, fluoro and oxo;

$R^2$ is selected from the group consisting of hydrogen; $C_1$-$C_{10}$alkyl optionally substituted with one or more substituents each independently selected from the group consisting of —OH, fluoro, methoxy, oxo and —C(=O)OC_1-$C_4$alkyl; $C_1$-$C_3$alkyl-$R^7$; $C_2$-$C_4$alkynyl; a 3-7 membered saturated ring optionally containing one or more heteroatoms each independently selected from the group consisting of O, S and N: and monocyclic aryl optionally containing one or two heteroatoms, wherein $C_1$-$C_3$alkyl-$R^7$, 3-7 membered saturated ring and monocyclic aryl are each optionally substituted with one or more $R^8$ substituents;

$R^3$ is hydrogen or $C_{1-6}$alkyl optionally substituted with —OH, or $R^2$ and $R^3$ taken together with the carbon atom to which they are attached form a 3-7 membered saturated ring optionally containing one or more heteroatoms each independently selected from the group consisting of O, S and N, wherein said ring is optionally substituted with one or more substituents each independently selected from the group consisting of —OH, fluoro, methoxy, oxo, —C(=O)OC_1-$C_4$alkyl, benzyl, and $C_1$-$C_4$alkyl optionally substituted with one or more substituents each independently selected from fluoro and —OH;

$R^7$ is a monocyclic aryl optionally containing one or two heteroatoms, wherein said aryl is optionally substituted with one or two substituents each independently selected from the group consisting of halo and $C_{1-3}$alkyl; a 3-7 membered saturated ring optionally containing one or more heteroatoms each independently selected from the group consisting of O, S and N; or —NR^9R^{10}, wherein $R^9$ and $R^{10}$ are each independently selected from hydrogen and $C_1$-$C_3$alkyl optionally substituted with one or more fluoro substituent;

each $R^8$ is independently selected from the group consisting of —OH, fluoro, methoxy, oxo, C(=O)OC_1-$C_4$alkyl, $C_1$-$C_4$alkyloxyC_1-$C_4$alkyloxy, and $C_1$-$C_4$alkyl optionally substituted with one or more substituents each independently selected from fluoro and —OH;

or a pharmaceutically acceptable salt or a solvate thereof.

2. The compound according to claim 1, wherein
Y represents $C_1$-$C_2$alkanediyl or $C_2$alkenediyl each optionally substituted with one or more substituents each independently selected from $C_1$-$C_4$alkyl and —OH; and
Z represents oxygen or a single bond.

3. The compound according to claim 2, wherein
Y represents a $C_1$alkanediyl optionally substituted with one or more $C_1$-$C_4$alkyl or —OH; and
Z represents O.

4. The compound according to claim 1, wherein

represents phenyl, and $R^a$, $R^b$ and $R^d$ are each independently hydrogen or halogen; and $R^c$ is selected from the group consisting of hydrogen, halogen, $CH_3$, $CHF_2$, $CF_3$ and —CN.

5. The compound according to claim 1, wherein ring C consists of 6 to 8 atoms.

6. The compound according to claim 1, wherein $R^4$ is methyl, and $R^6$ is hydrogen.

7. The compound according to claim 1, wherein $R^2$ is $C_1$-$C_6$alkyl.

8. The compound according to claim 7, wherein $R^2$ is methyl.

9. The compound according to claim 7, wherein $R^2$ is optionally substituted with one or more substituents each independently selected from the group consisting of —OH, fluoro, and methoxy.

10. The compound according to claim 1, wherein $R^2$ is $C_1$-$C_4$alkyl optionally substituted with one or more fluoro.

11. The compound according to claim 1, wherein $R^2$ is $C_1$-$C_6$alkyl optionally substituted with one or more —OH.

12. The compound according to claim 1, wherein $R^1$ is hydrogen.

13. The compound according to claim 1, wherein said compound is selected from the group consisting of:

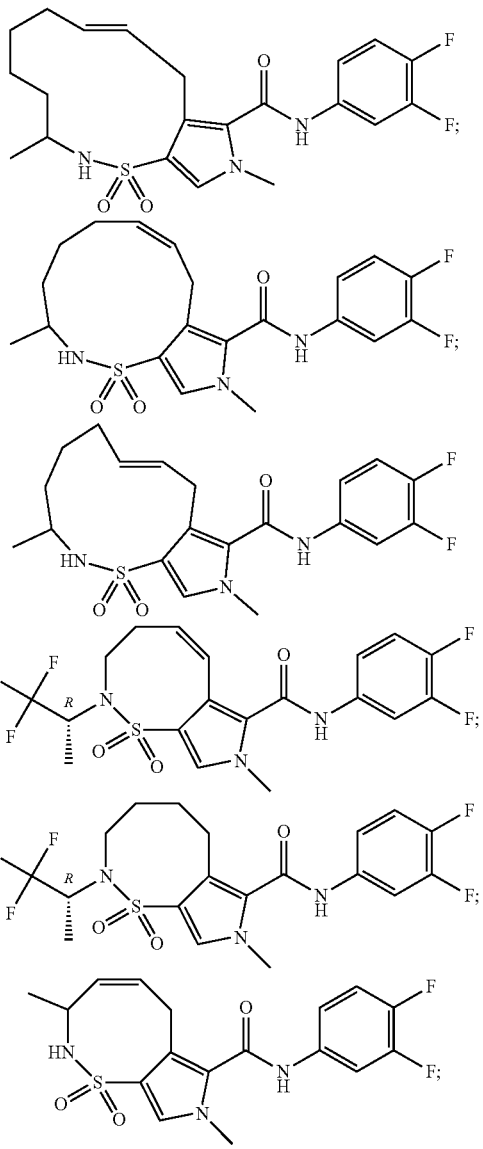

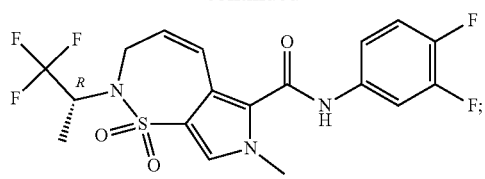
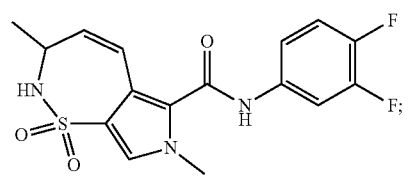
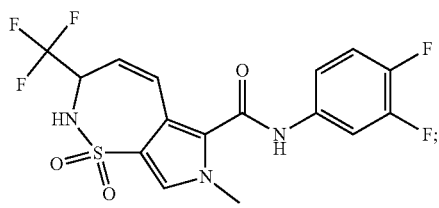
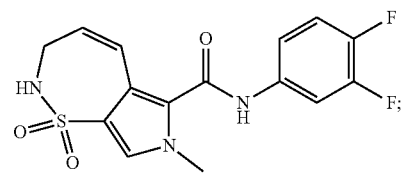
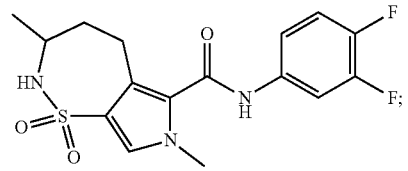
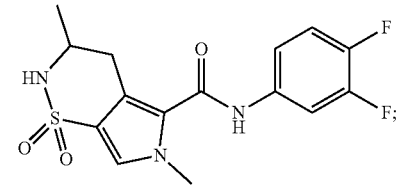
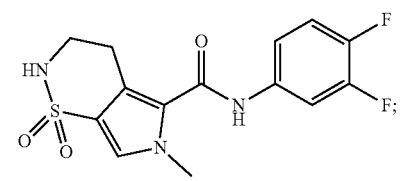
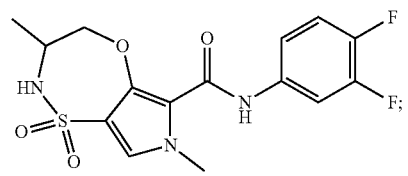
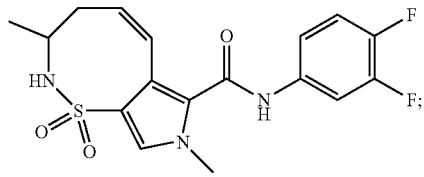
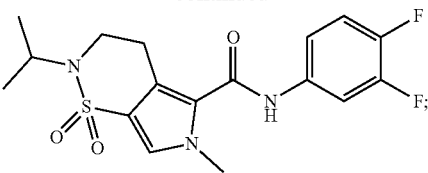
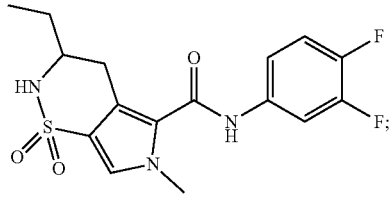
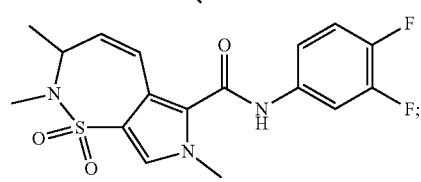
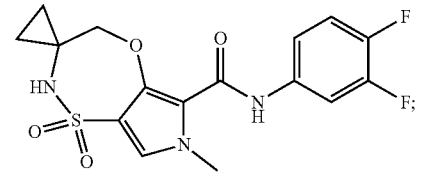
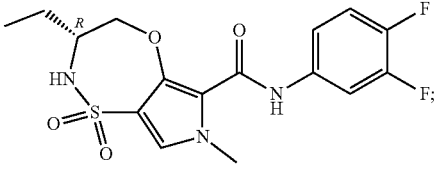
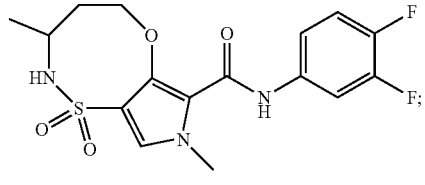
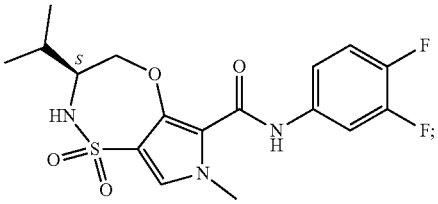
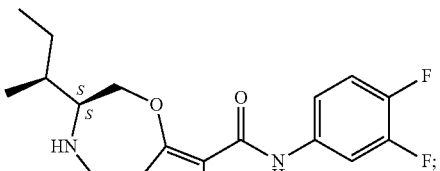
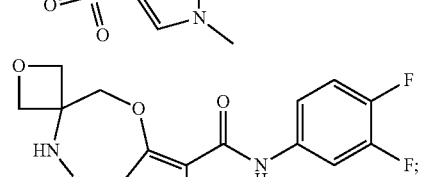

207
-continued
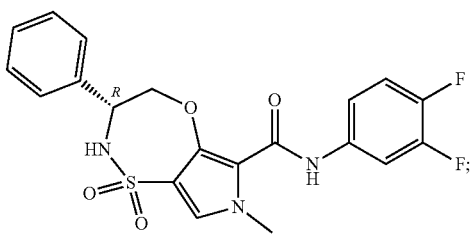
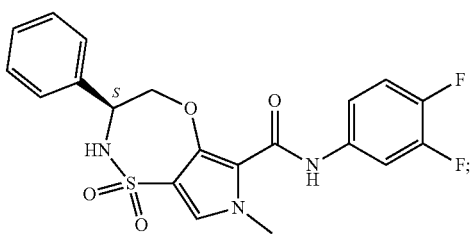
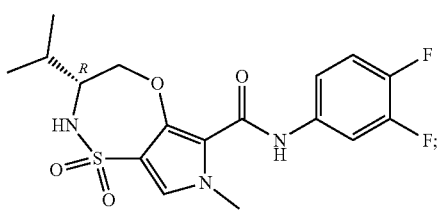
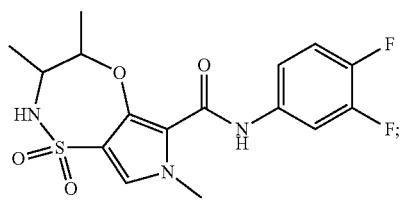
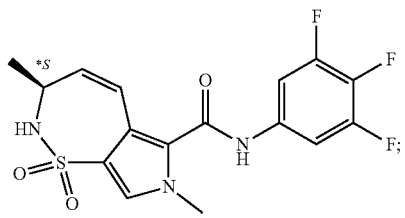
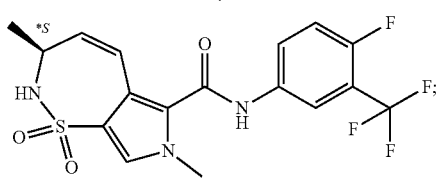
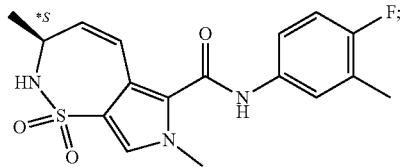
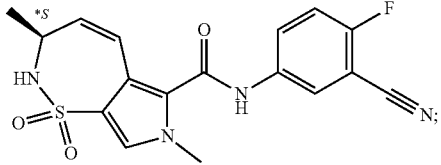
208
-continued
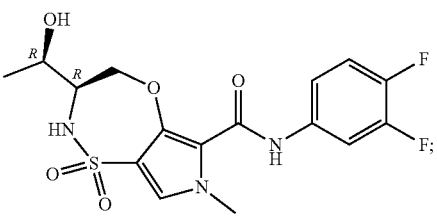
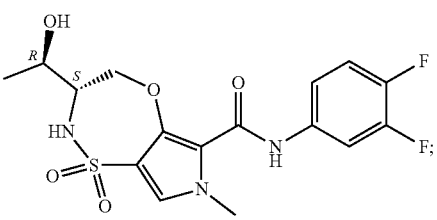
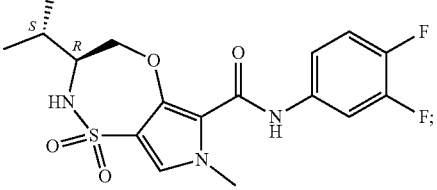
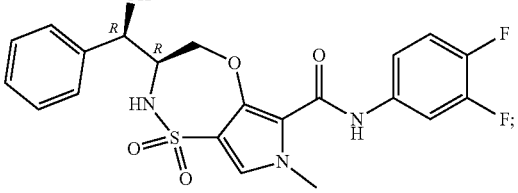
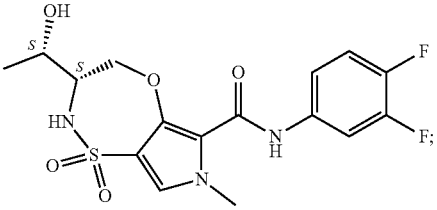
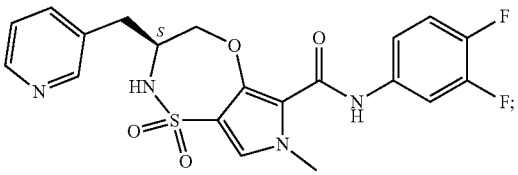
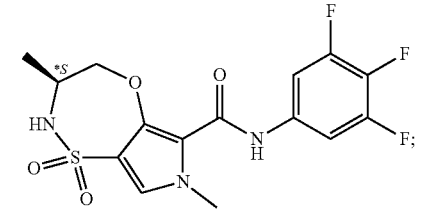
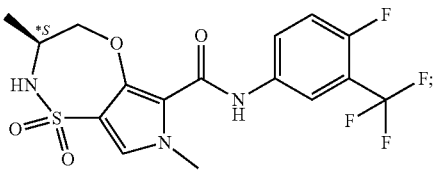

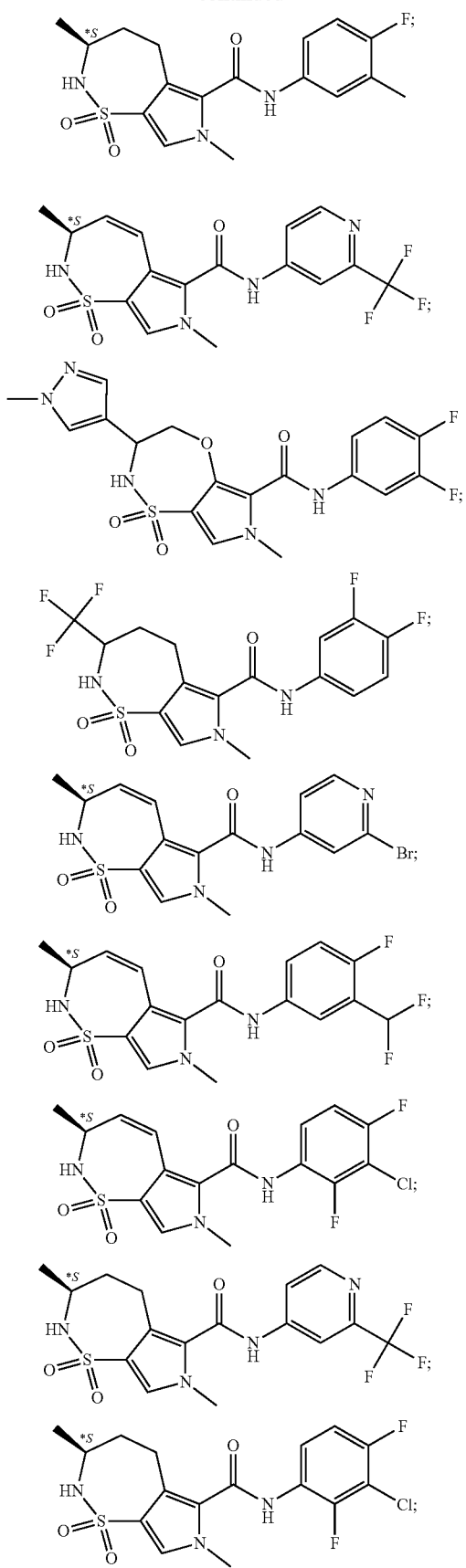
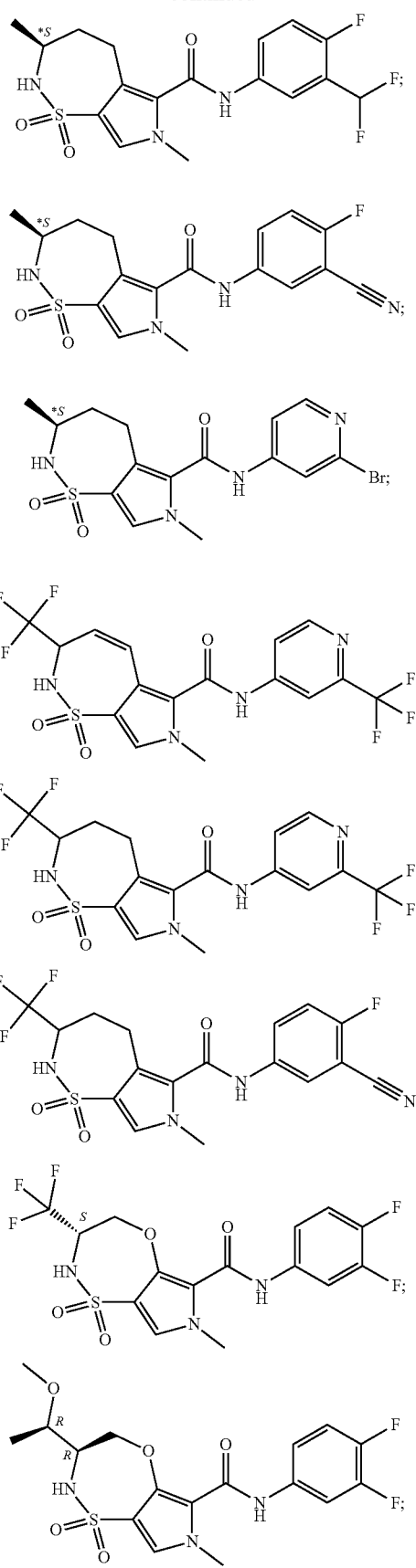

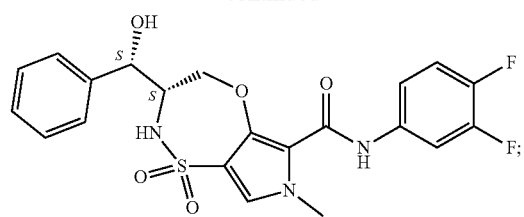
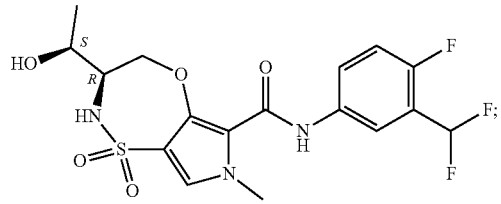
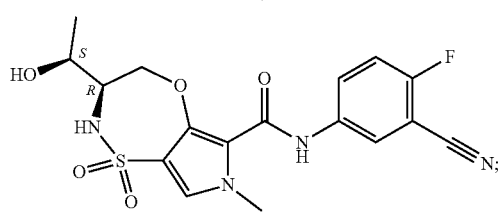
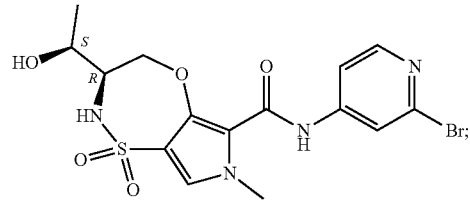
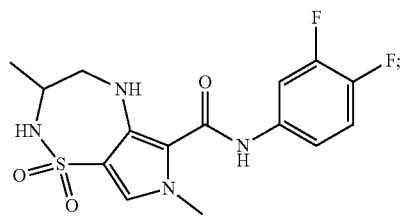
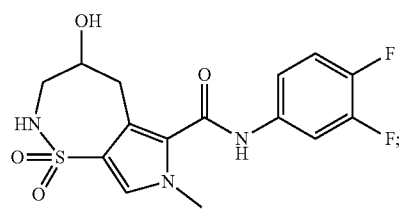
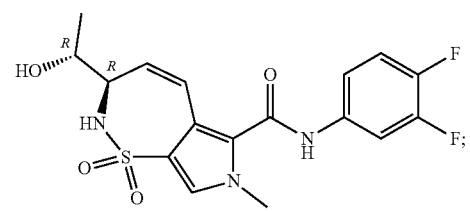
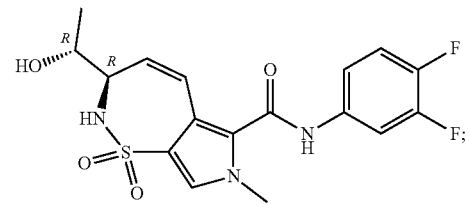
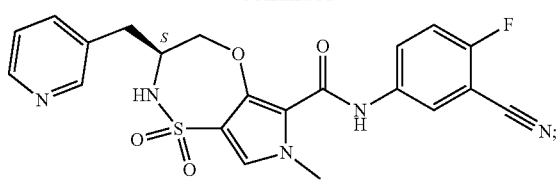
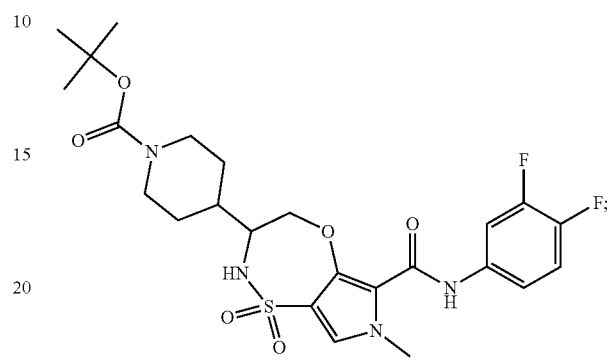
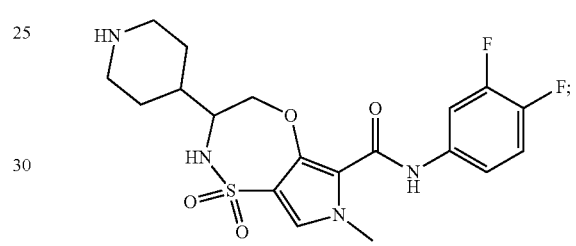
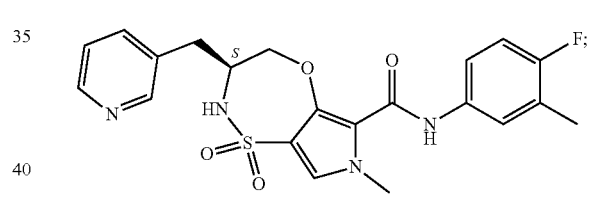
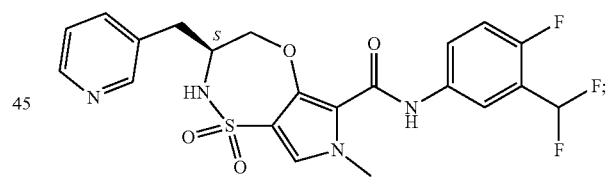
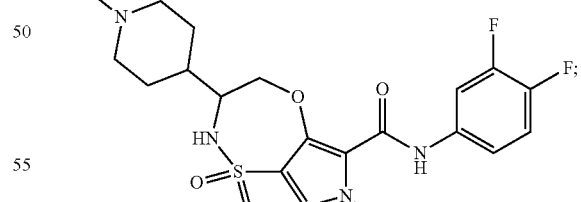
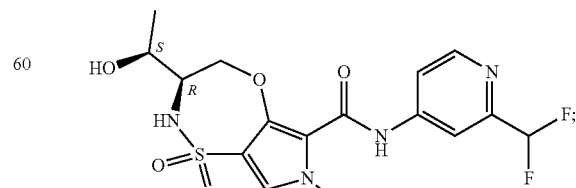

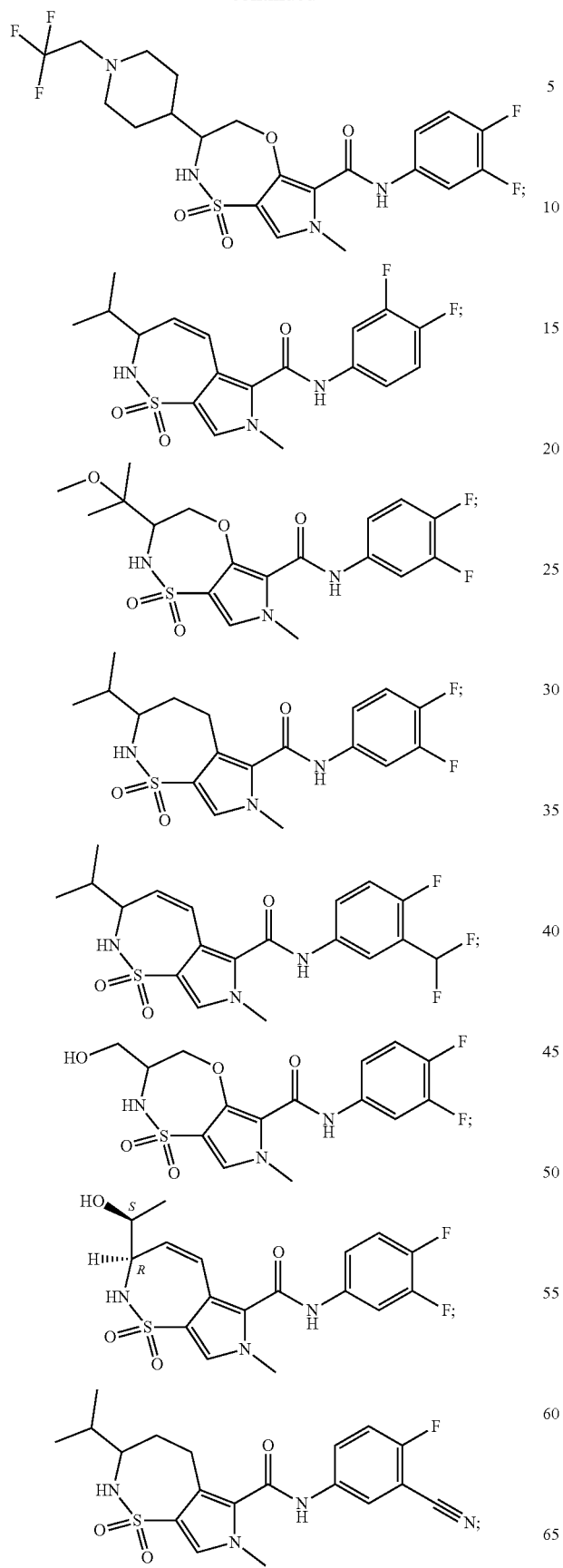
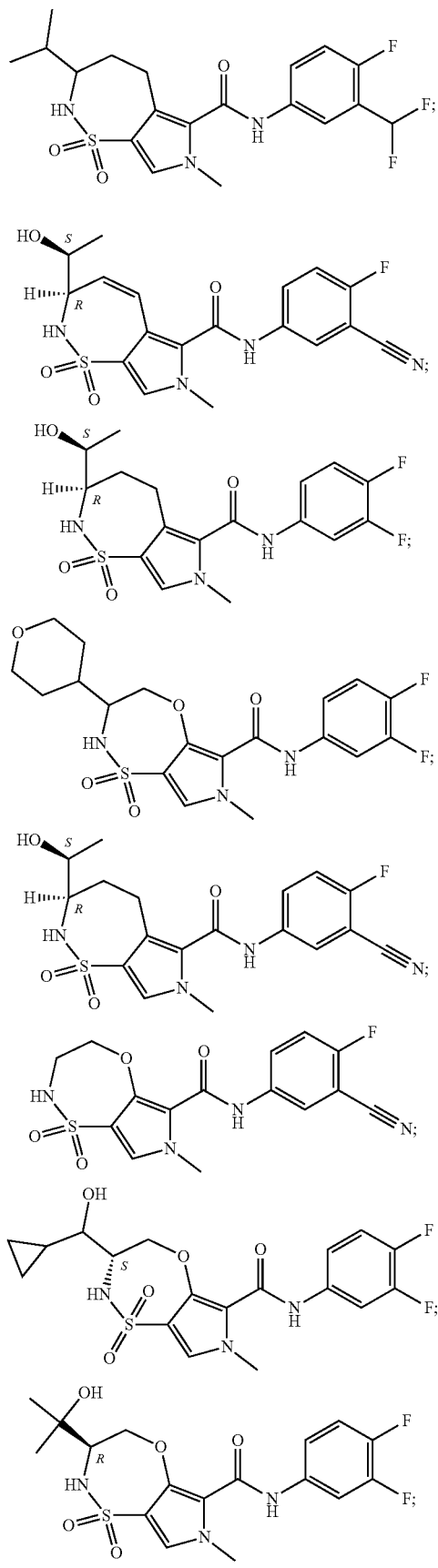

215
-continued
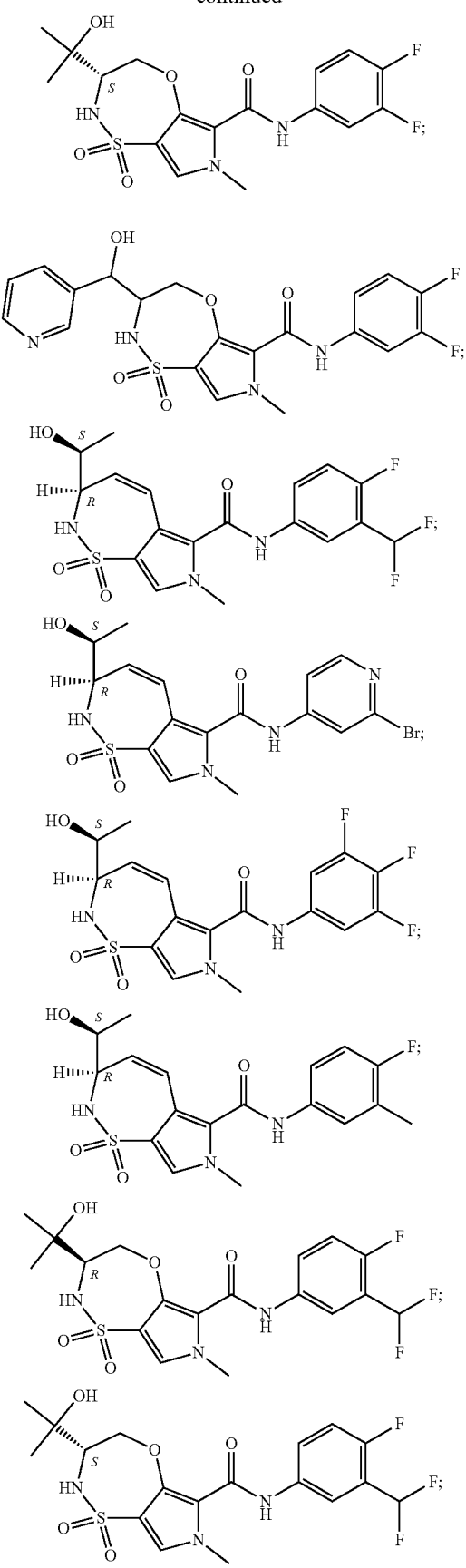
216
-continued
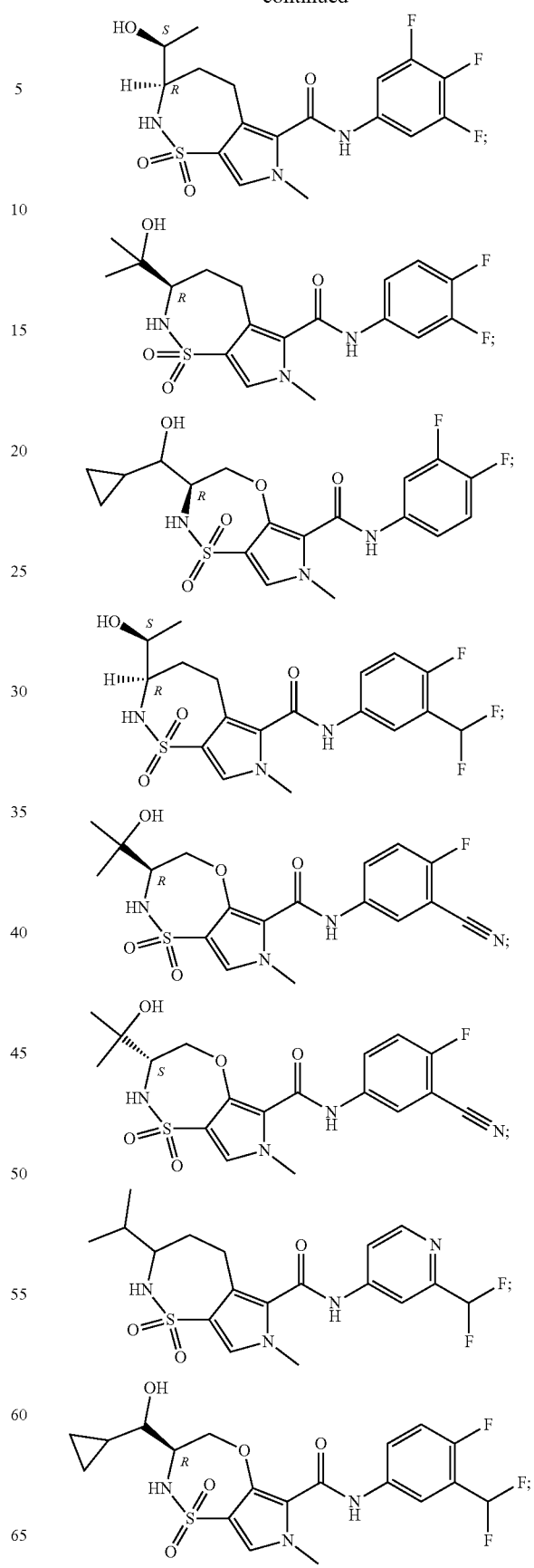

217
-continued
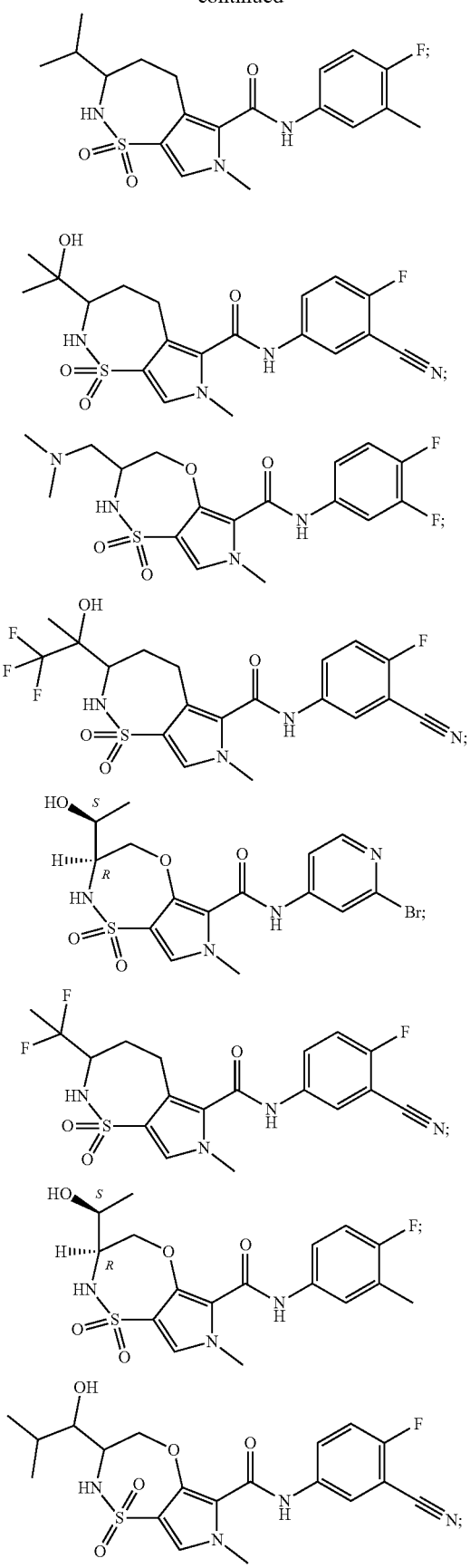
218
-continued
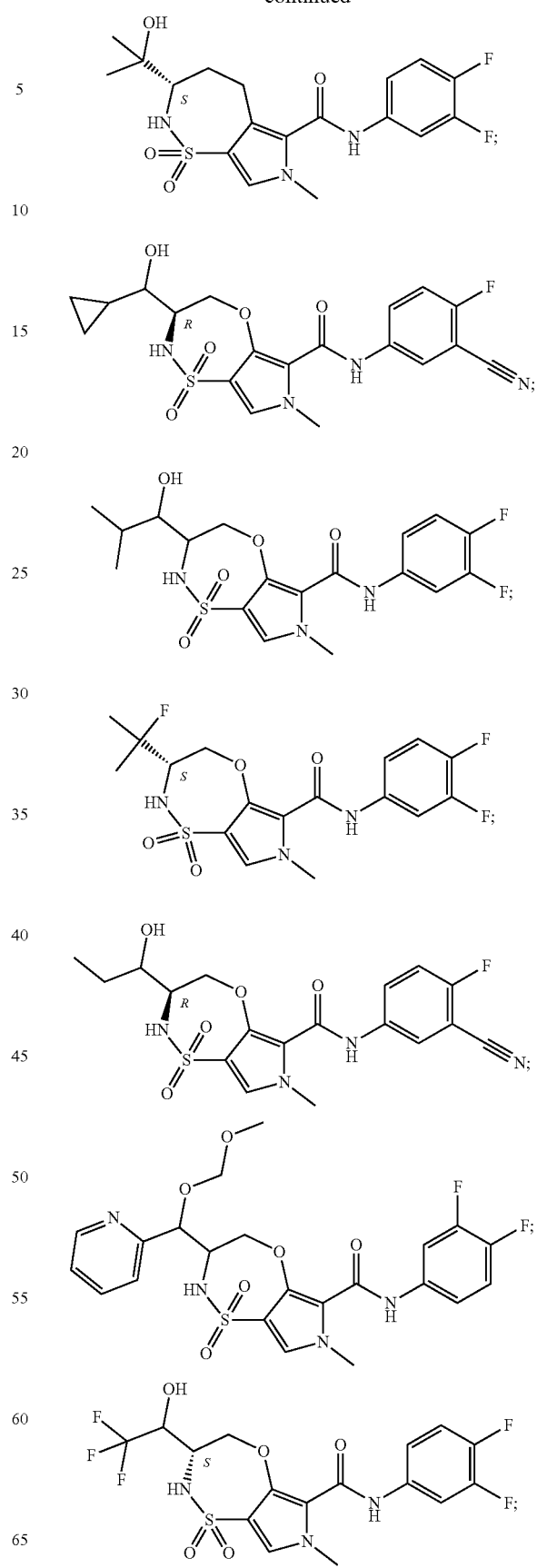

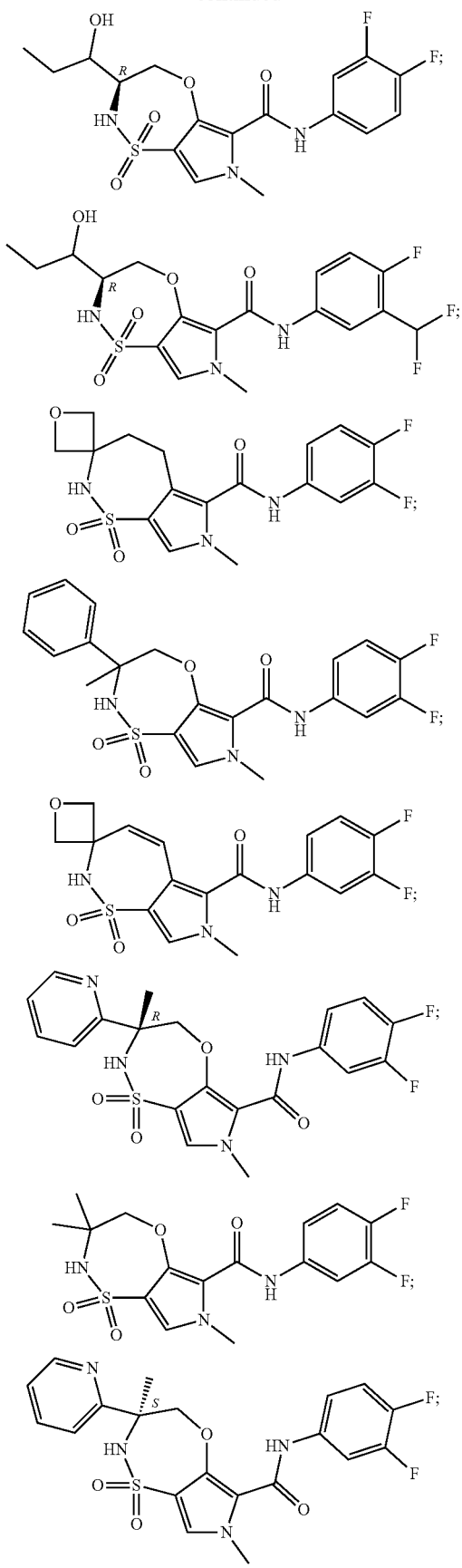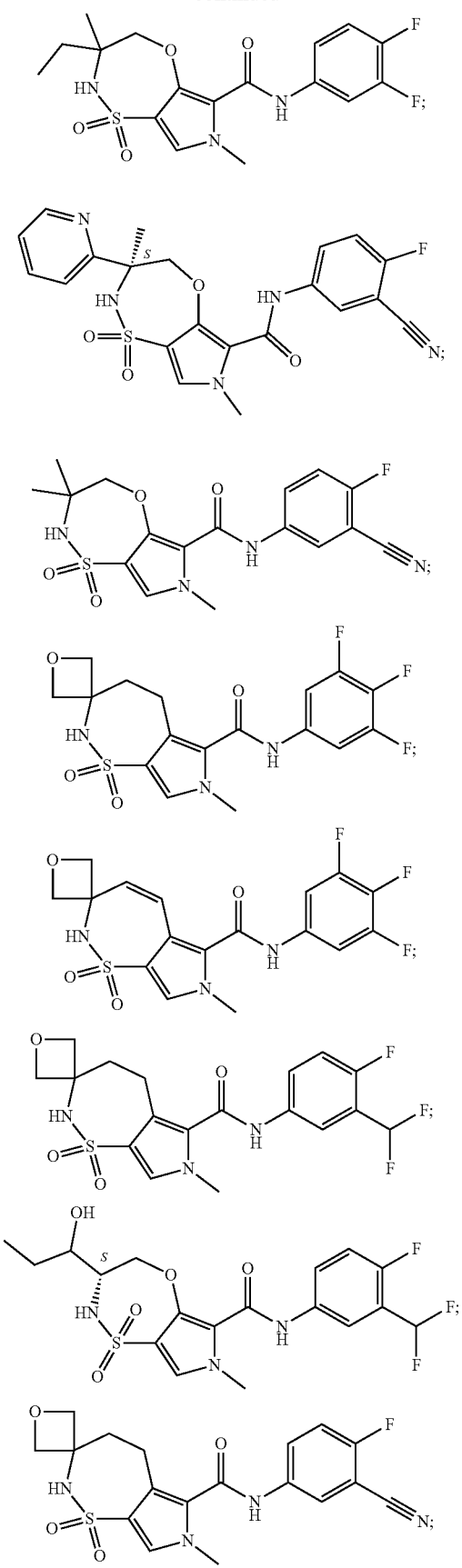

-continued
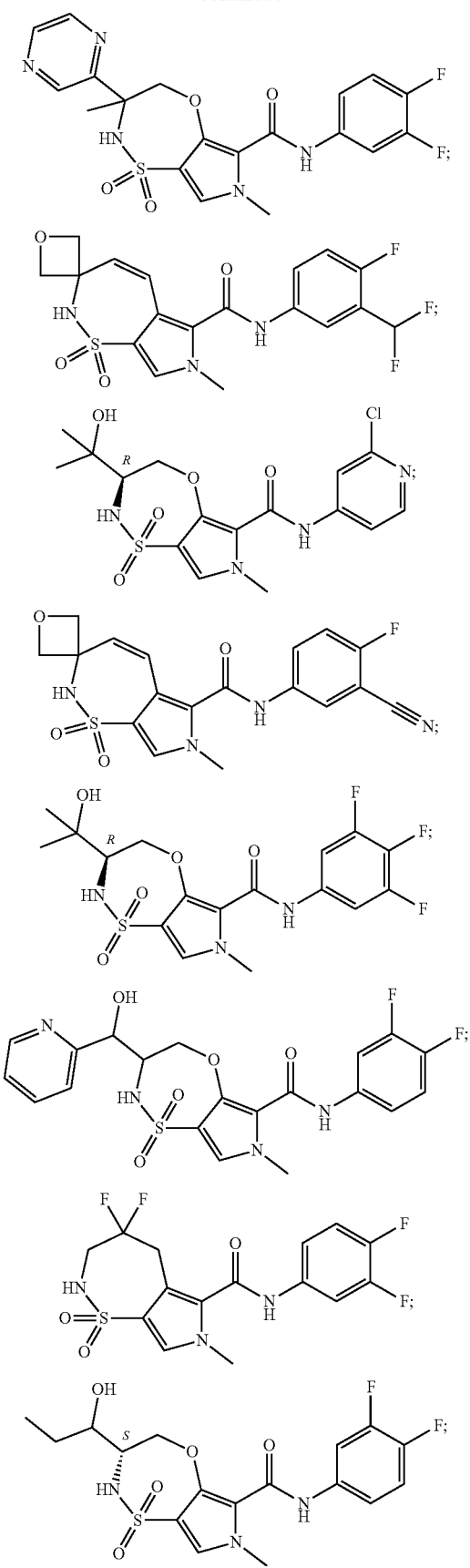
-continued
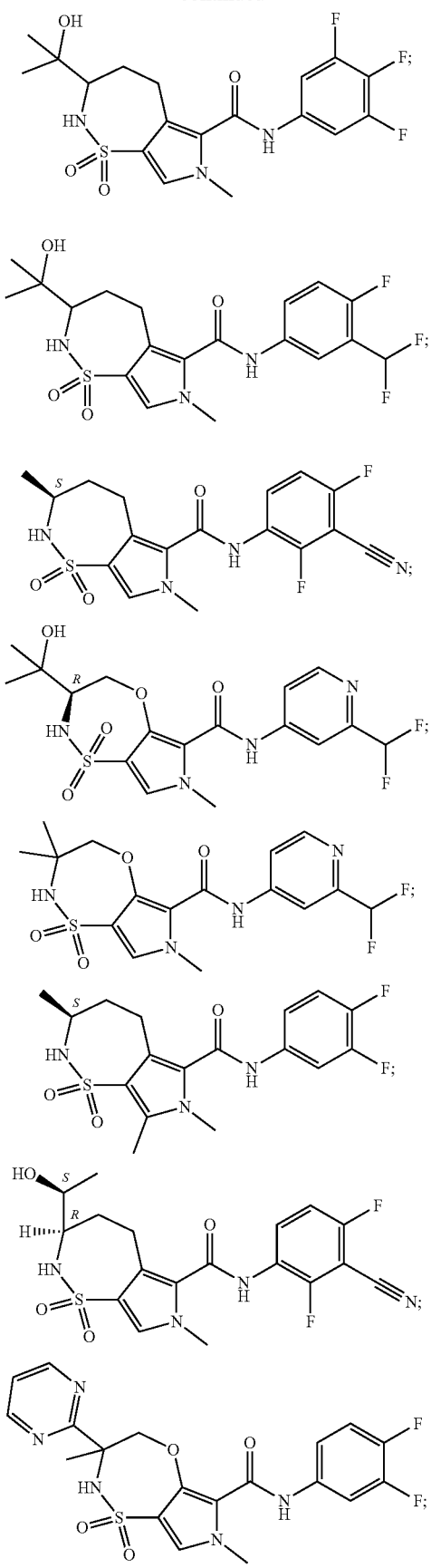

223
-continued
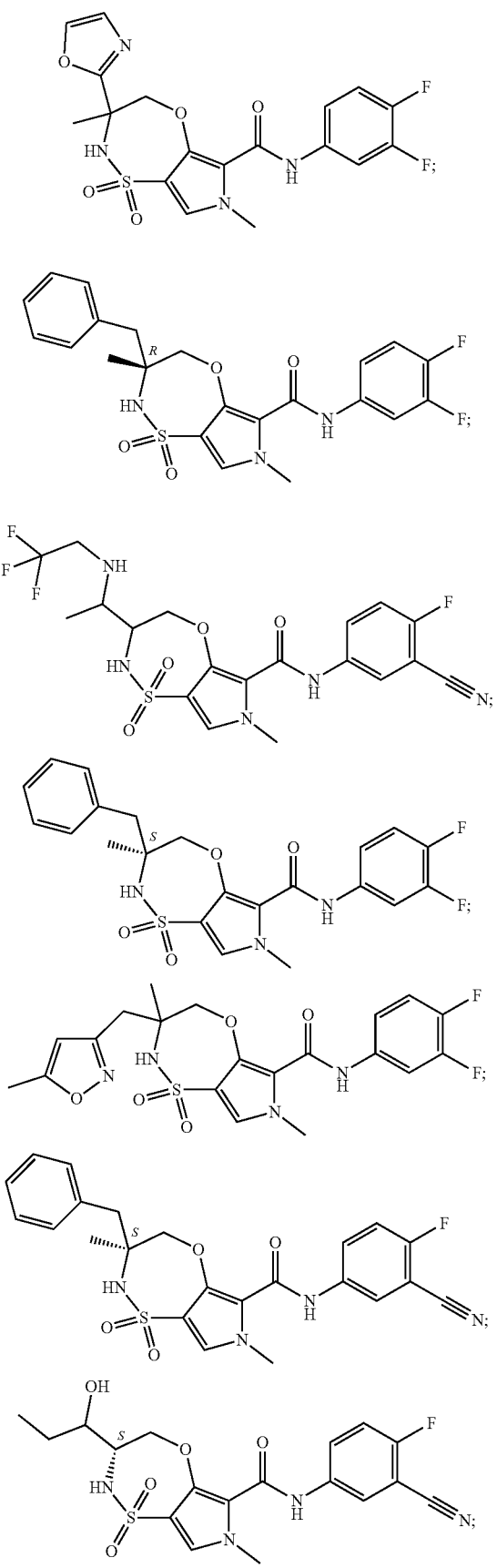
224
-continued
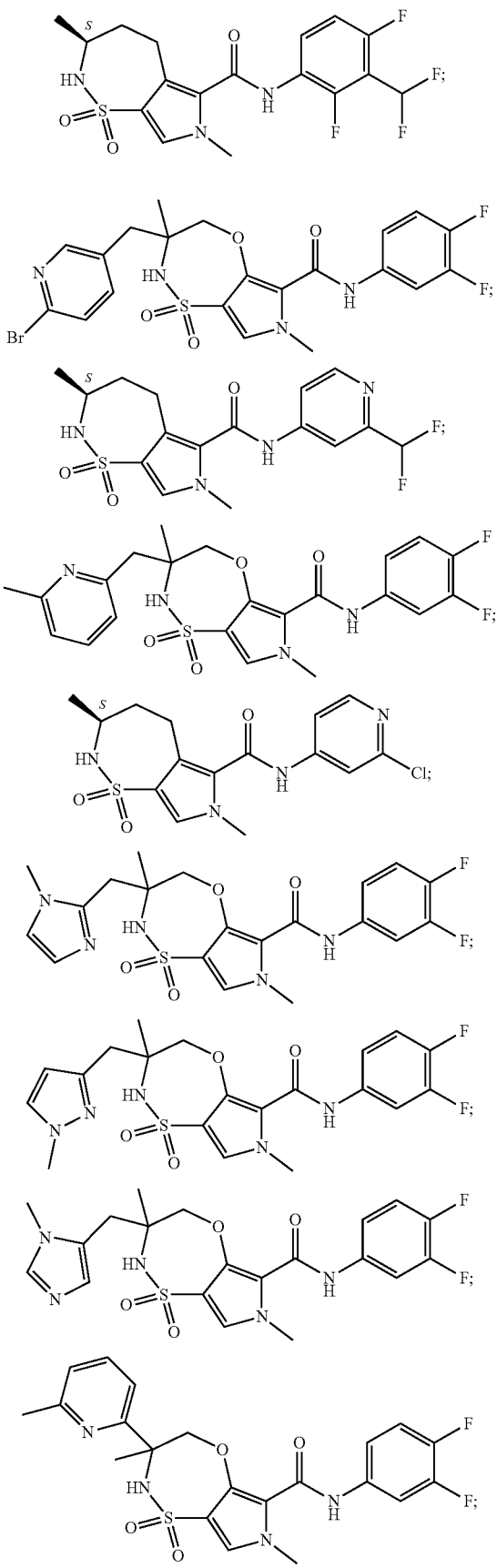

225
-continued
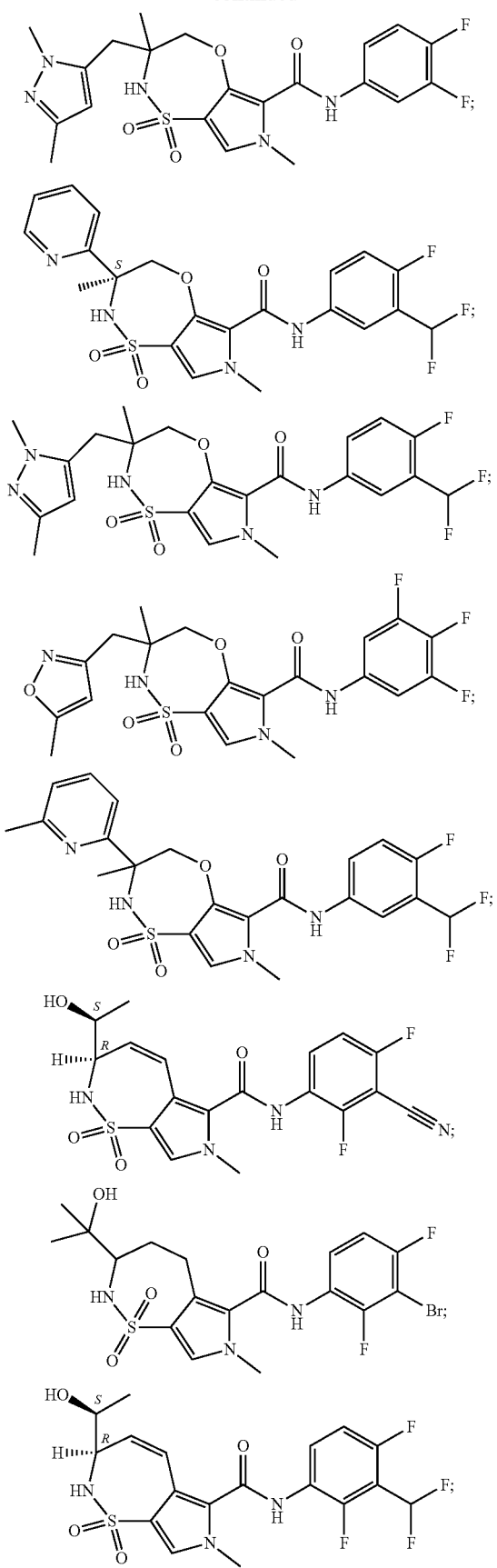
226
-continued
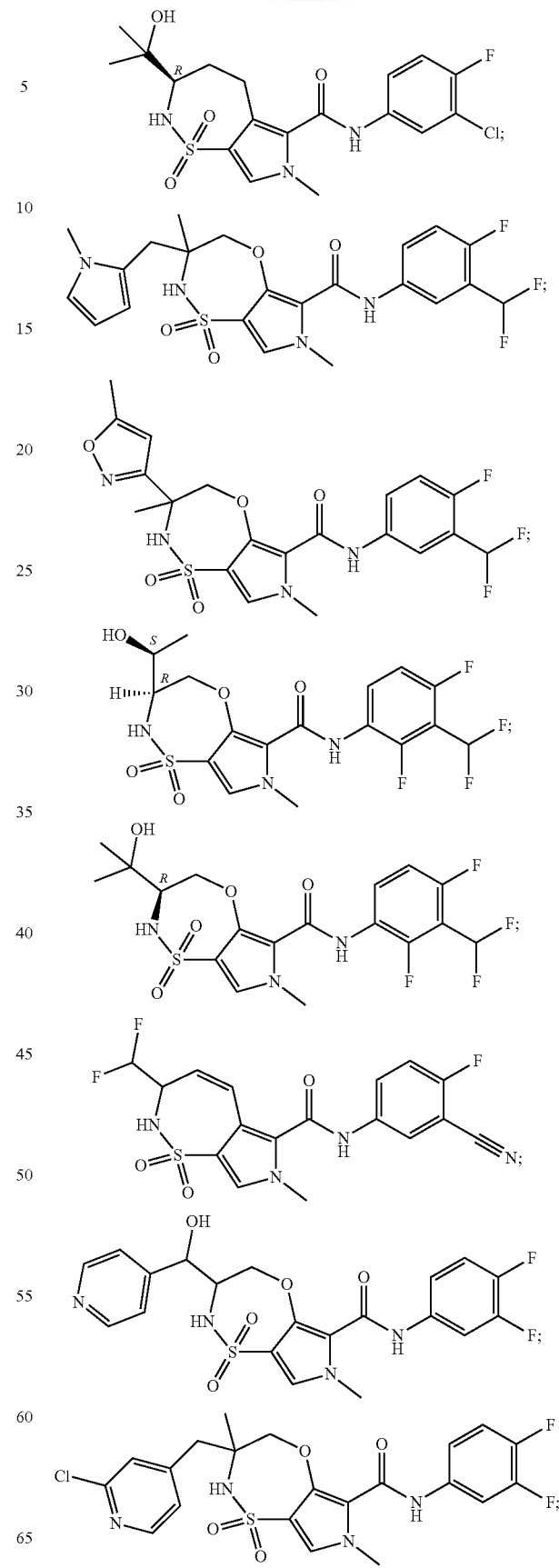

227
-continued
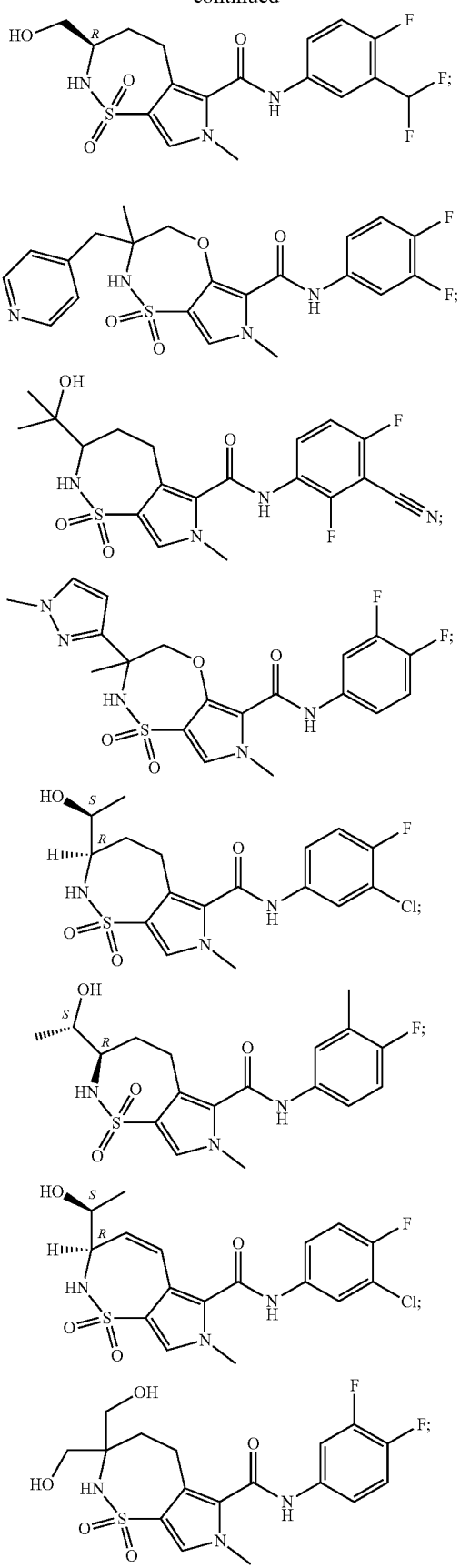
228
-continued
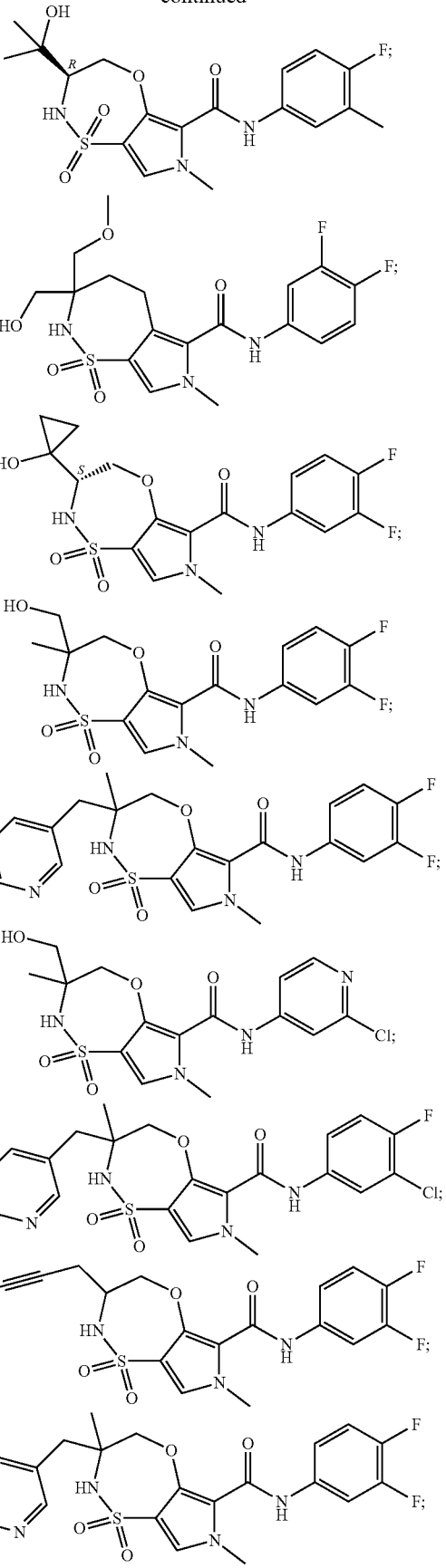

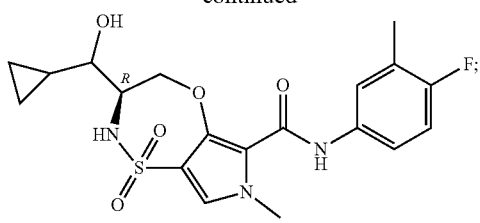
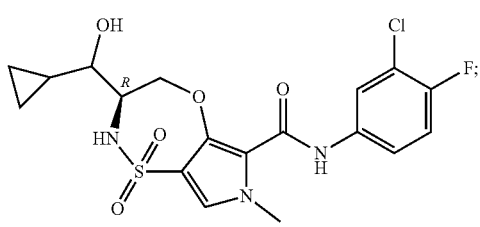
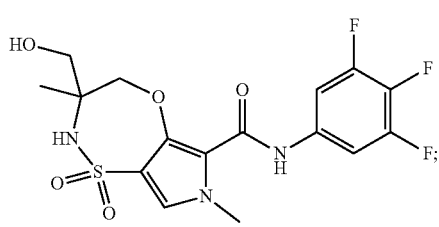
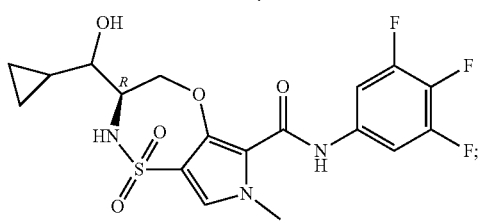
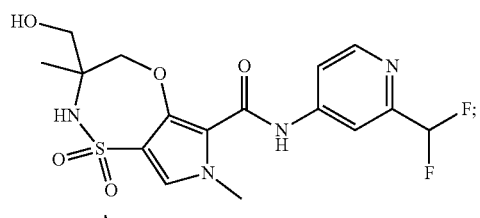
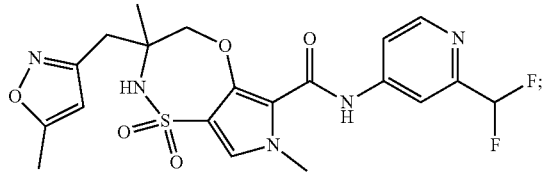
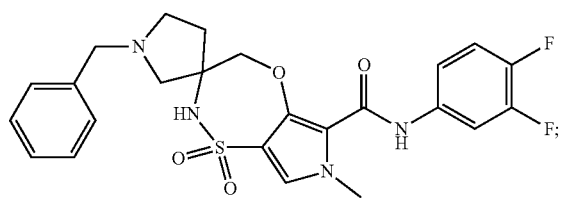
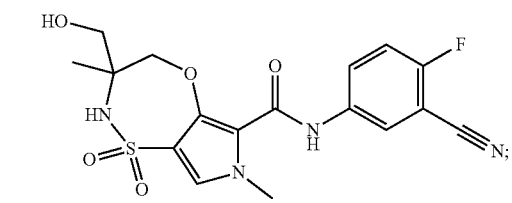
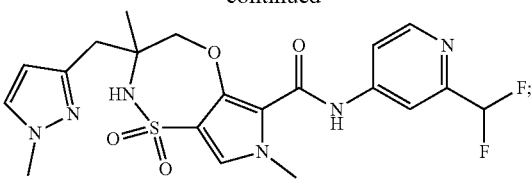
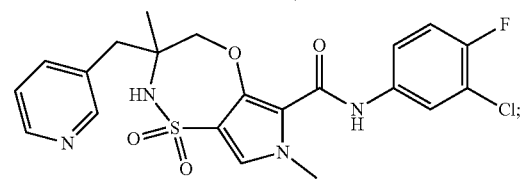
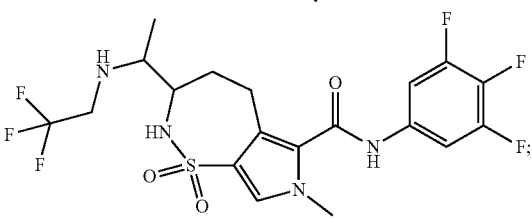
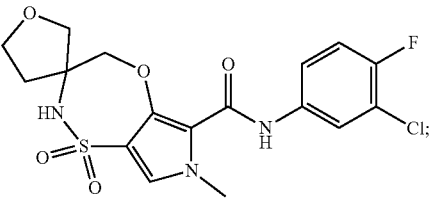
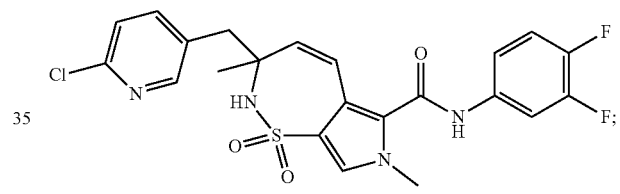
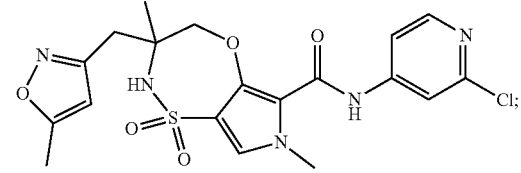
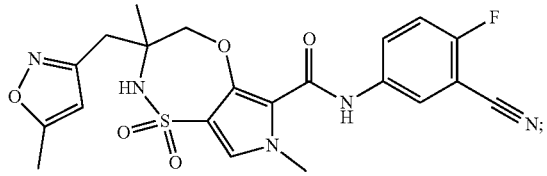
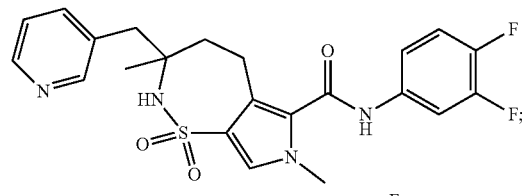
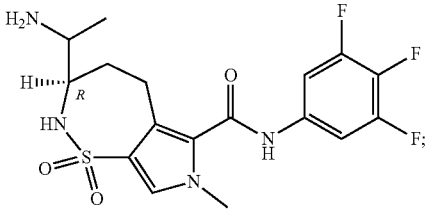

231
-continued
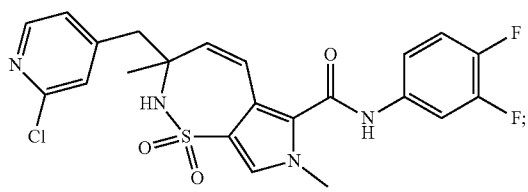
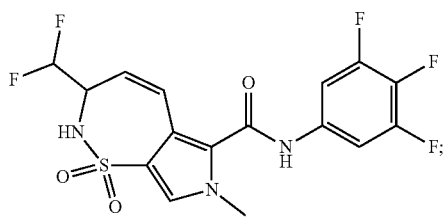
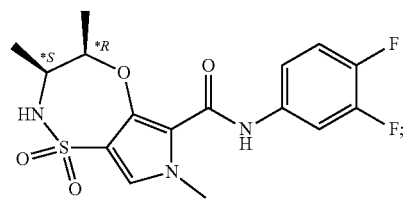
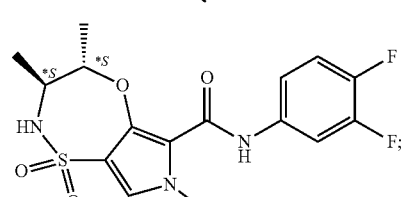
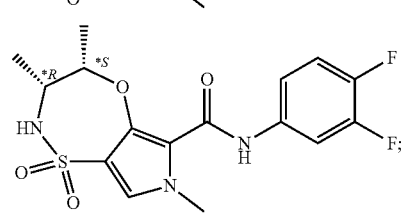
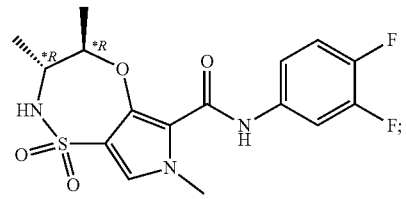
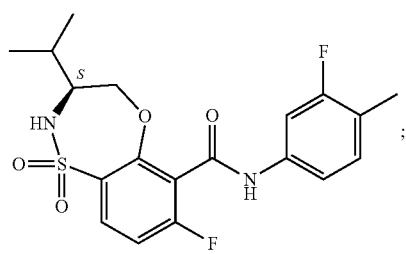
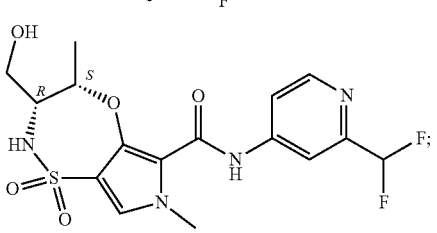
232
-continued
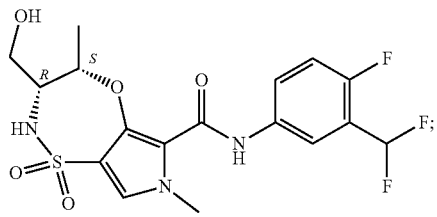
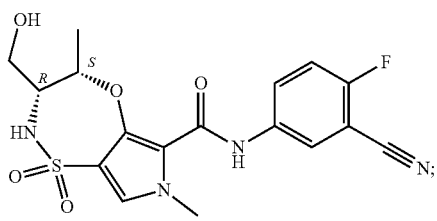
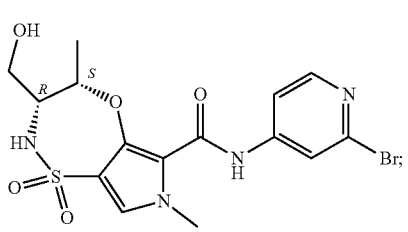
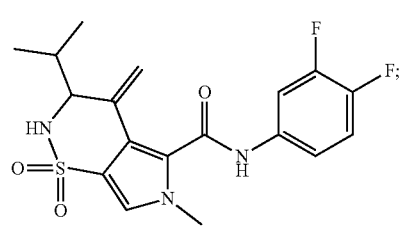
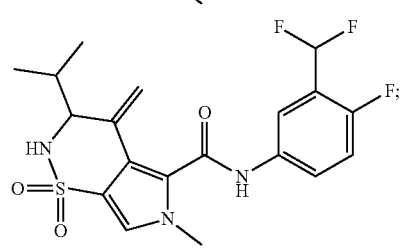
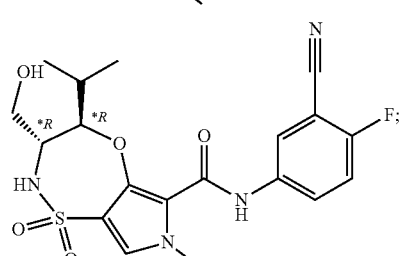
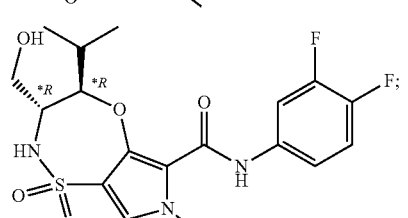

233
-continued

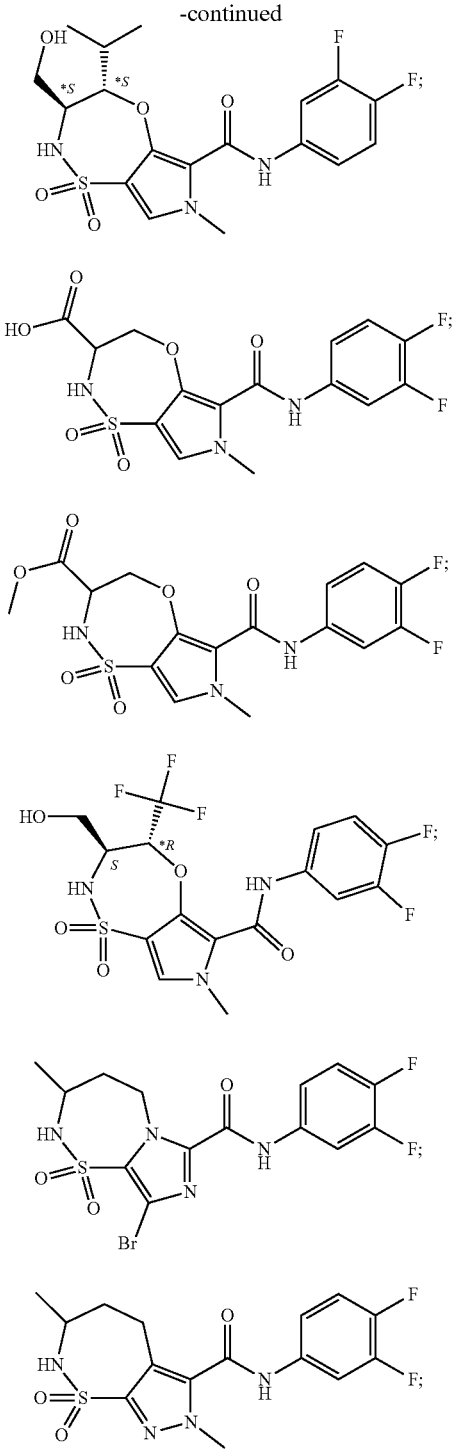

234
-continued

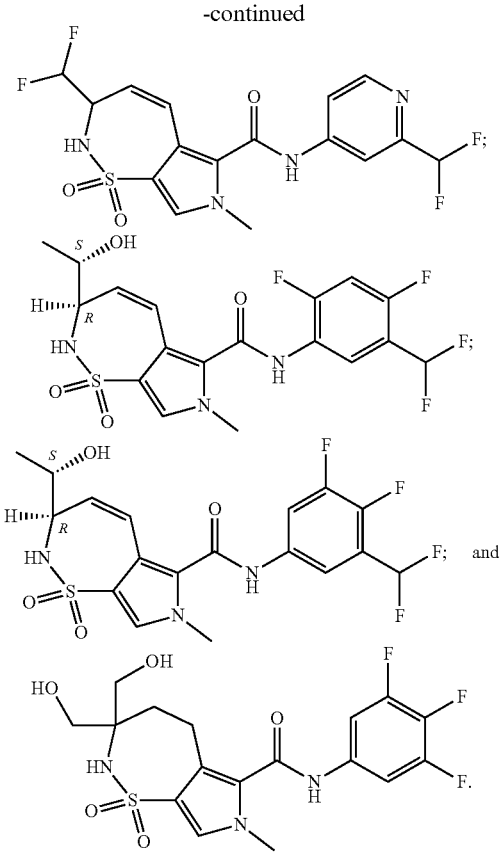

14. The compound according to claim 2, wherein
    Y represents C$_2$alkanediyl optionally substituted with one or more substituents each independently selected from the group consisting of C$_1$-C$_4$alkyl and —OH; and
    Z represents a single bond.

15. The compound according to claim 2, wherein
    Y represents C$_2$alkenediyl optionally substituted with one or more substituents each independently selected from C$_1$-C$_4$alkyl and —OH; and
    Z represents a single bond.

16. A pharmaceutical composition comprising a compound of claim 1, and a pharmaceutically acceptable carrier.

17. A product containing (a) a compound of claim 1, and (b) an HBV inhibitor, as a combined preparation for simultaneous, separate or sequential use in the treatment of HBV infections.

18. A method of treating a subject infected by HBV, or at risk of infection by HBV, said method comprising the administration of a therapeutically effective amount of a compound of claim 1.

* * * * *